(12) United States Patent
Yang et al.

(10) Patent No.: US 12,410,179 B2
(45) Date of Patent: Sep. 9, 2025

(54) MODULATORS OF TNF ALPHA ACTIVITY AND USES THEREOF

(71) Applicant: RayThera, Inc., San Diego, CA (US)

(72) Inventors: Pengyu Yang, San Diego, CA (US); Lynnie Trzoss, San Diego, CA (US); Venkat Bollu, San Diego, CA (US); Junhu Zhang, San Diego, CA (US); Qing Dong, San Diego, CA (US)

(73) Assignee: RAYTHERA, INC., San Diego, CA (US)

( * ) Notice: Subject to any disclaimer, the term of this patent is extended or adjusted under 35 U.S.C. 154(b) by 0 days.

(21) Appl. No.: 18/812,527

(22) Filed: Aug. 22, 2024

(65) Prior Publication Data

US 2025/0066375 A1    Feb. 27, 2025

Related U.S. Application Data

(63) Continuation of application No. PCT/US2024/042661, filed on Aug. 16, 2024.

(60) Provisional application No. 63/650,626, filed on May 22, 2024, provisional application No. 63/613,206, filed on Dec. 21, 2023, provisional application No. 63/519,990, filed on Aug. 16, 2023.

(51) Int. Cl.

| | | |
|---|---|---|
| *C07D 487/22* | (2006.01) | |
| *A61K 31/55* | (2006.01) | |
| *A61K 31/675* | (2006.01) | |
| *C07D 471/22* | (2006.01) | |
| *C07F 9/6561* | (2006.01) | |

(52) U.S. Cl.
CPC ............ *C07D 487/22* (2013.01); *A61K 31/55* (2013.01); *A61K 31/675* (2013.01); *C07D 471/22* (2013.01); *C07F 9/6561* (2013.01)

(58) Field of Classification Search
None
See application file for complete search history.

(56) References Cited

FOREIGN PATENT DOCUMENTS

| EP | 1081144 A2 * | 3/2001 | ............ C07D 231/12 |
|---|---|---|---|
| WO | WO-2007084451 A1 * | 7/2007 | ............ C07D 401/06 |
| WO | WO-2016050975 A1 | 4/2016 | |
| WO | WO-2017167993 A1 | 10/2017 | |
| WO | WO-2017167994 A1 | 10/2017 | |
| WO | WO-2017167995 A1 | 10/2017 | |
| WO | WO-2017167996 A1 | 10/2017 | |
| WO | WO-2018167176 A1 | 9/2018 | |
| WO | WO-2018197503 A1 | 11/2018 | |
| WO | WO-2020084008 A1 | 4/2020 | |
| WO | WO-2024112796 A1 | 5/2024 | |
| WO | WO-2024129763 A1 | 6/2024 | |
| WO | WO-2024148191 A1 | 7/2024 | |
| WO | WO-2024223740 A1 | 10/2024 | |
| WO | WO-2024251282 A1 | 12/2024 | |
| WO | WO-2025038927 A1 | 2/2025 | |

OTHER PUBLICATIONS

Gold, Joann. Cisplatin. StatPearls, NCBI Bookshelf. Retrieved from the Internet on Oct. 15, 2024, https://www.ncbi.nlm.nih.gov/books/NBK547695/#:~:text=Cisplatin%20is%20FDA%20approved%20for,risks%20of%20adverse%20drug%20effects. Published May 2023. (Year: 2023).*
Deepak K. Dalvie, Amit S. Kalgutkar, S. Cyrus Khojasteh-Bakht, R. Scott Obach, and John P. O'Donnell Chemical Research in Toxicology 2002 15 (3), 269-299 (Year: 2002).*
Coe, Samuel. Metabolism of five membered nitrogen containing heterocycles, HyphaDiscovery. Retrieved from WayBack Machine on Nov. 16, 2024, https://web.archive.org/web/20230307015207/https://www.hyphadiscovery.com/blog/metabolism-of-five-membered-nitrogen-containing-heterocycles/. Published Mar. 7, 2023 (Year: 2023).*
PCT/US2024/042661 International Search Report and Written Opinion dated Oct. 23, 2024.
Chédotal et al. Small-molecule modulators of tumor necrosis factor signaling. Drug Discov today 28(6):103575 (2023).
Dietrich et al., Development of Orally Efficacious Allosteric Inhibitors of TNFα via Fragment-Based Drug Design. J Med Chem 64:417-429 (2021).
Vulger et al. An orally available small molecule that targets soluble TNF to deliver anti-TNF biologic-like efficacy in rheumatoid arthritis. Front Pharmacol 13:1037983 (2022).
Xiao et al., Biologic-like In Vivo Efficacy with Small Molecule Inhibitors of TNFα Identified Using Scaffold Hopping and Structure-Based Drug Design Approaches. J Med Chem 63(23):15050-15071 (2020).

* cited by examiner

*Primary Examiner* — James H Alstrum-Acevedo
*Assistant Examiner* — Lauren Wells
(74) *Attorney, Agent, or Firm* — WILSON SONSINI GOODRICH & ROSATI

(57) ABSTRACT

Described herein are modulators of TNF alpha activity and pharmaceutical compositions comprising said inhibitors. The subject compounds and compositions are useful for the treatment of TNF alpha-mediated disorders or diseases.

16 Claims, 2 Drawing Sheets

1: DMSO Control
2: Dofetilide
3: Comp. Ex. 1
4: Ex. 15

1: DMSO Control
2: Dofetilide
3: Comp. Ex. 1
4: Ex. 15

1: DMSO Control
2: Dofetilide
3: Comp. Ex. 1
4: Ex. 15

MODULATORS OF TNF ALPHA ACTIVITY AND USES THEREOF

CROSS-REFERENCE

This patent application is a continuation of International Application No. PCT/US2024/042661, filed Aug. 16, 2024, which claims the benefit of U.S. Provisional Application Ser. No. 63/519,990 filed Aug. 16, 2023, U.S. Provisional Application Ser. No. 63/613,206 filed Dec. 21, 2023, and U.S. Provisional Application Ser. No. 63/650,626 filed May 22, 2024; which are hereby incorporated by reference in their entirety.

BACKGROUND OF THE INVENTION

TNF alpha is the protottypical member of the Tumor Necrosis Factor (TNT) superfamily of proteins that share a primary function of regulating cell survival and cell death. One structural feature common to all known members of the TNF superfamily is the formation of trimeric complexes that bind to, and activate specific TNF superfamily receptors. By way of example, TNF alpha exists in soluble and transmembrane forms and signals through two receptors, known as TNFR1 and TNFR2, with distinct functional endpoints.

TNF superfamily members, including TNF alpha itself are implicated in a variety of physiological and pathological functions that are believed to play a part in a range of conditions of significant medical importance. Various products capable of modulating TNF alpha activity are already commercially available. All currently approved products are macromolecular and act by inhibiting the binding of human TNF alpha to its receptor. Typical macromolecular TNF alpha inhibitors include anti-TNF alpha antibodies and soluble TNF alpha receptor fusion proteins. All are approved for the treatment of inflammatory and autoimmune disorders such as rheumatoid arthritis and Crohn's disease.

As such there is a need for new potent small molecule modulators of human TNF alpha activity beneficial in the treatment of various disorders including autoimmune and inflammatory disorders: neurological and neurodegenerative disorders; pain and nociceptive disorders; cardiovascular disorders: metabolic disorders; ocular disorders; and oncological disorders.

SUMMARY OF THE INVENTION

Disclosed herein is a compound of Formula (I*), or a pharmaceutically acceptable salt, solvate, or stereoisomer thereof:

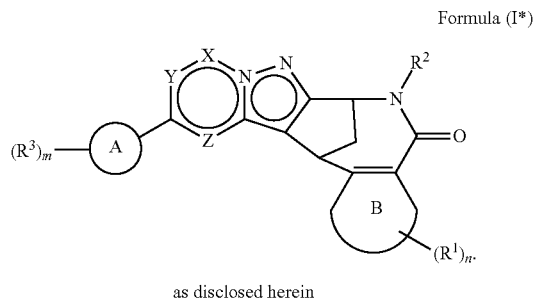

Formula (I*)

as disclosed herein

Also disclosed herein is a pharmaceutical composition comprising a compound disclosed herein, or a pharmaceutically acceptable salt or solvate thereof, and at least one pharmaceutically acceptable excipient.

Also disclosed herein is a method for the treatment of disorders for which the administration of a modulator of TNF alpha function is indicated which comprises administering to a patient in need of such treatment an effective amount of a compound disclosed herein, or a pharmaceutically acceptable salt or solvate thereof.

Also disclosed herein is a method for the treatment of an inflammatory or autoimmune disorder, a neurological, a neuro-degenerative disorder, pain, a nociceptive disorder, a cardiovascular disorder, a metabolic disorder, an ocular disorder, or an oncological disorder, which comprises administering to a patient in need of such treatment an effective amount of a compound disclosed herein, or a pharmaceutically acceptable salt or solvate thereof.

INCORPORATION BY REFERENCE

Figure 1:
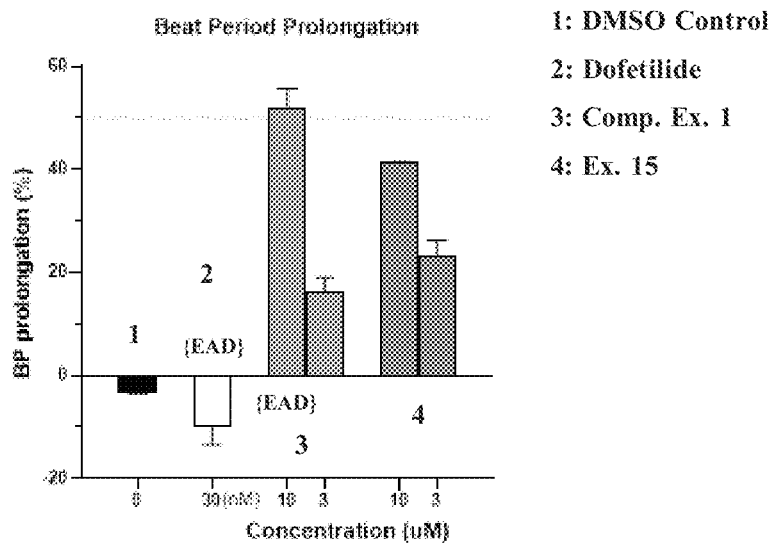
FIG. 1 depicts the Beat Period Prolongation for Comp. Ex. 1 and Ex. 15.

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or"

is generally employed in its sense including "and/or" unless the content clearly dictates otherwise.

The terms below, as used herein, have the following meanings, unless indicated otherwise:

"oxo" refers to =O.

"Amine" refers to —NH$_2$.

"hydroxy" refers to —OH.

"Carboxyl" refers to —COOH.

"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl. In some embodiments, the alkyl is a $C_1$-$C_6$ alkyl. In some embodiments, the alkyl is a $C_1$-$C_5$ alkyl. In some embodiments, the alkyl is a $C_1$-$C_4$ alkyl. In some embodiments, the alkyl is a $C_1$-$C_3$ alkyl. Unless stated otherwise specifically in the specification, an alkyl group may be optionally substituted, for example, with one or more oxo, halogen, amino, nitrile, nitro, hydroxyl, haloalkyl, alkoxy, carboxyl, carboxylate, aryl, cycloalkyl, heterocycloalkyl, or heteroaryl, and the like. In some embodiments, the alkyl is optionally substituted with one or more oxo, halogen, —CN, —COOH, —COOMe, —OH, —OMe, —NH$_2$, or —NO$_2$. In some embodiments, the alkyl is optionally substituted with one or more halogen, —CN, —OH, or —OMe. In some embodiments, the alkyl is optionally substituted with halogen.

"Alkenyl" refers to a straight-chain or branched-chain hydrocarbon monoradical having one or more carbon-carbon double-bonds and having from two to about ten carbon atoms, more preferably two to about six carbon atoms. The group may be in either the cis or trans or Z or E conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkenyl is optionally substituted with one or more oxo, halogen, —CN, —COOH, —COOMe, —OH, —OMe, —NH$_2$, or —NO$_2$. In some embodiments, the alkenyl is optionally substituted with one or more halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkynyl is optionally substituted with one or more oxo, halogen, —CN, —COOH, —COOMe, —OH, —OMe, —NH$_2$, or —NO$_2$. In some embodiments, the alkynyl is optionally substituted with one or more halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkylene is optionally substituted with one or more oxo, halogen, —CN, —COOH, —COOMe, —OH, —OMe, —NH$_2$, or —NO$_2$. In some embodiments, the alkylene is optionally substituted with one or more halogen, —CN, —OH, or —OMe. In some embodiments, the alkylene is optionally substituted with halogen.

"Alkoxy" refers to a radical of the formula-Oalkyl where alkyl is defined as above. Unless stated otherwise specifically in the specification, an alkoxy group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkoxy is optionally substituted with one or more halogen, —CN, —COOH, —COOMe, —OH, —OMe, —NH$_2$, or —NO$_2$. In some embodiments, the alkoxy is optionally substituted with one or more halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to anthracenyl, naphthyl, phenanthrenyl, azulenyl, phenyl, chrysenyl, fluoranthenyl, fluorenyl, as-indacenyl, s-indacenyl, indanyl, indenyl, phenalenyl, phenanthrenyl, pleiadenyl, pyrenyl, and triphenylenyl. Unless stated otherwise specifically in the specification, an aryl may be optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the aryl is optionally substituted with one or more halogen, methyl, ethyl, —CN, —COOH, —COOMe, —CF$_3$, —OH, —OMe, —NH$_2$, or —NO$_2$. In some embodiments, the aryl is optionally substituted with one or more halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, and/or bridged ring systems. In some embodiments, the cycloalkyl is fully saturated. Representative cycloalkyls include, but are not limited to, cycloalkyls having from three to fifteen carbon atoms (e.g., $C_3$-$C_{15}$ fully saturated cycloalkyl or $C_3$-$C_{15}$ cycloalkenyl), from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), from three to five carbon atoms (e.g., $C_3$-$C_5$ fully saturated cycloalkyl or $C_3$-$C_5$ cycloalkenyl), or three to four carbon atoms (e.g., $C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octyl, bicyclo[4.3.0]nonyl, cis-decalinyl, trans-decalinyl, bicyclo[2.1.1]hexyl, bicyclo[2.2.1]heptyl, bicyclo[2.2.2]octyl, bicyclo[3.2.1]octyl, bicyclo[3.2.2]nonyl, and bicyclo[3.3.2]decyl, bicyclo[1.1.1]pentyl, bicyclo[3.1.0]hexyl, bicyclo[3.1.1]heptyl, 7,7-dimethyl-bicyclo[2.2.1]heptanyl, Spiro[4.2]heptyl, spiro[4.3]octyl, spiro[5.2]octyl, spiro[3.3]heptyl, and spiro[5.3]nonyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, a cycloalkyl is optionally substituted with one or more oxo, halogen, methyl, ethyl, —CN, —COOH, —COOMe, —CF$_3$, —OH, —OMe, —NH$_2$, or —NO$_2$. In some embodiments, a cycloalkyl is optionally substituted with one or more oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 2-fluoroethyl, 3-bromo-2-fluoropropyl, 1,2-dibromoethyl, and the like.

"Haloalkoxy" refers to —O-haloalkyl, with haloalkyl as defined above.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl includes, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl includes, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl includes, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Heteroalkyl" refers to an alkyl group in which one or more skeletal atoms of the alkyl are selected from an atom other than carbon, e.g., oxygen, nitrogen, sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen, sulfur, phosphorus, or combinations thereof wherein the heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or two atoms selected from the group consisting of oxygen, nitrogen, and sulfur wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with one or more oxo, halogen, amino, nitrile, nitro, hydroxyl, alkyl, alkenyl, alkynyl, haloalkyl, alkoxy, aryl, cycloalkyl, heterocycloalkyl, or heteroaryl, and the like. In some embodiments, a heteroalkyl is optionally substituted with one or more oxo, halogen, methyl, ethyl, —CN, —CF$_3$, —OH, —OMe, —NH$_2$, or —NO$_2$. In some embodiments, a heteroalkyl is optionally substituted with one or more oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl is C-linked. In some embodiments, the heterocycloalkyl is N-linked. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through anon-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_5$ fully saturated heterocycloalkyl or $C_2$-$C_5$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_6$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with one or more oxo, halogen, methyl, ethyl, —CN, —COOH, —COOMe, —CF$_3$, —OH, —OMe, —NH$_2$, or —NO$_2$. In some embodiments, the heterocycloalkyl is optionally substituted with one or more halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. In some embodiments, the heteroaryl is C-linked. In some embodiments, the heteroaryl is N-linked. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl comprising 1, 2, or 3 heteroatoms selected from the group consisting of oxygen, nitrogen, and sulfur. In some embodiments, the heteroaryl is a 5- to 6-membered heteroaryl comprising 1, 2, or 3 heteroatoms selected from the group consisting of oxygen, nitrogen, and sulfur. In some embodiments, the heteroaryl is a 6-membered heteroaryl comprising 1, 2, or 3 heteroatoms selected from the group consisting of oxygen, nitrogen, and sulfur. In some embodiments, the heteroaryl is a 5-membered heteroaryl comprising 1, 2, or 3 heteroatoms selected from the group consisting of oxygen, nitrogen, and sulfur. Examples include, but are not limited to, azepinyl, acridinyl, benzimidazolyl, benzothiazolyl, benzindolyl, benzodioxolyl, benzofuranyl, benzoxazolyl, benzothiadiazolyl, benzo[b][1,4]dioxepinyl, 1,4-benzodioxanyl, benzonaphthofuranyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the heteroaryl is optionally substituted with one or more halogen, methyl, ethyl, —CN, —COOH, —COOMe, —CF₃, —OH, —OMe, —NH₂, or —NO₂. In some embodiments, the heteroaryl is optionally substituted with one or more halogen, methyl, ethyl, —CN, —CF₃, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH₂CH₃), fully substituted (e.g., —CF₂CF₃), mono-substituted (e.g., —CH₂CH₂F) or substituted at a level anywhere in-between fully substituted and mono-substituted (e.g., —CH₂CHF₂, —CH₂CF₃, —CF₂CH₃, —CFHCHF₂, etc.).

The term "one or more" when referring to an optional substituent means that the subject group is optionally substituted with one, two, three, or four, or more substituents. In some embodiments, the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents. In some embodiments, the subject group is optionally substituted with three substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with TNF alpha" or, alternatively, "a TNF alpha-mediated disease or disorder" means any disease or other deleterious condition in which TRPML1 or a mutant thereof, is known or suspected to play a role.

Compounds

Described herein are compounds, or a pharmaceutically acceptable salt, solvate, or stereoisomer thereof useful in the treatment of a TNF alpha-mediated disease or disorder.

In some embodiments, the compounds described herein, or a pharmaceutically acceptable salt, solvate, or stereoisomer thereof, are more potent than corresponding compounds with a benzimidazole core. In some embodiments, the compounds described herein, or a pharmaceutically acceptable salt, solvate, or stereoisomer thereof, are 5%, 6%, 7%, 8%, 9%, 10%, 15%, 20%, 25%, 30%, 35%, 40%, 45%, 50%, 55%, 60%, 65%, 70%, 75%, or 80% more potent than corresponding compounds with a benzimidazole core.

In some embodiments, the compounds described herein, or a pharmaceutically acceptable salt, solvate, or stereoisomer thereof, have less cardiac toxicity than corresponding compounds with a benzimidazole core. In some embodiments, the compounds described herein, or a pharmaceutically acceptable salt, solvate, or stereoisomer thereof, have 5%, 6%, 7%, 8%, 9%, 10%, 15%, 20%, 25%, 30%, 35%, 40%, 45%, 50%, 55%, 60%, 65%, 70%, 75%, or 80% less cardiac toxicity than corresponding compounds with a benzimidazole core.

In some embodiments, the compounds described herein, or a pharmaceutically acceptable salt, solvate, or stereoisomer thereof, have better cell permeability than corresponding compounds with a benzimidazole core. In some embodiments, the compounds described herein, or a pharmaceutically acceptable salt, solvate, or stereoisomer thereof, have 5%, 6%, 7%, 8%, 9%, 10%, 15%, 20%, 25%, 30%, 35%, 40%, 45%, 50%, 55% 60%, 65%, 70%, 75%, or 80% better cell permeability than corresponding compounds with a benzimidazole core.

In some embodiments, the compounds described herein, or a pharmaceutically acceptable salt, solvate, or stereoisomer thereof, have better physical properties than corresponding compounds with a benzimidazole core.

In some embodiments, the compounds described herein, or a pharmaceutically acceptable salt, solvate, or stereoisomer thereof, have better pharmacokinetic properties than corresponding compounds with a benzimidazole core.

In some embodiments, the compounds described herein, or a pharmaceutically acceptable salt, solvate, or stereoisomer thereof, have better pharmacodynamic properties than corresponding compounds with a benzimidazole core.

The compounds with a benzimidazole core comprise the following ring system:

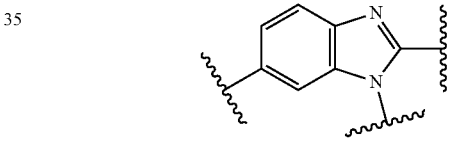

in their central core.

Disclosed herein is a compound of Formula (I'), or a pharmaceutically acceptable salt, solvate, or stereoisomer thereof:

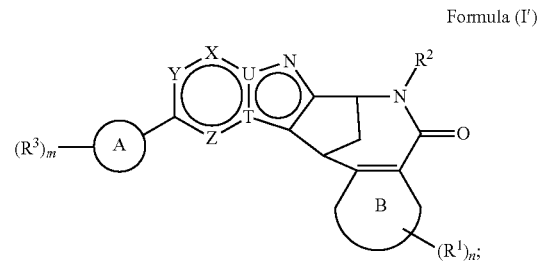

Formula (I')

wherein:

Ring B is phenyl or a 6-membered heteroaryl comprising one or two nitrogen; each $R^1$ is independently halogen, —CN, —NO₂, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R;
or two $R^1$ on the same atom are taken together to form an oxo;
n is 1, 2, 3, or 4;
$R^2$ is hydrogen, $C_1$-$C_6$alkyl, $C_1$-$C_6$haloalkyl, $C_1$-$C_6$deuteroalkyl, or cycloalkyl;
X is N or $CR^X$;
$R^X$ is hydrogen, halogen, —CN, —OH, —$OR^a$, —$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl;
Y is N or $CR^Y$;
$R^Y$ is hydrogen, halogen, —CN, —OH, —$OR^a$, —$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;
Z is N or $CR^Z$;
$R^Z$ is hydrogen, halogen, —CN, —OH, —$OR^a$, —$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl;
U is N and T is C or U is C and T is N;
Ring A is cycloalkyl, heterocycloalkyl, aryl, or heteroaryl;
each $R^3$ is independently halogen, -L-CN, -L-$NO_2$, -L-OH, -L-$OR^a$, -L-OC(=O)$R^a$, -L-OC(=O)$OR^b$, -L-OC(=O)$NR^cR^d$, -L-SH, -L-$SR^a$, -L-S(=O)$R^a$, -L-S(=O)$_2 R^a$, -L-S(=O)(=NH)$R^a$, -L-S(=O)$_2OR^b$, -L-S(=O)$_2NR^cR^d$, -L-$NR^cR^d$, -L-$NR^bC$(=O)$NR^cR^d$, -L-$NR^bC$(=O)$R^a$, -L-$NR^bC$(=O)$OR^b$, -L-$NR^bS$(=O)$_2 R^a$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
or two $R^3$ on the same atom are taken together to form an oxo;
or two $R^3$ on adjacent atoms are taken together to form a cycloalkyl, heterocycloalkyl, aryl, or heteroaryl;
each independently optionally substituted with one or more R;
m is 0, 1, 2, 3, or 4;
each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
or $R^c$ and $R^d$ are taken together with the atom to which they are attached to form a heterocycloalkyl independently optionally substituted with one or more R; and
L is absent or $C_1$-$C_3$alkylene optionally substituted with one or more R;
each R is independently halogen, —CN, —OH, —$OC_1$-$C_3$alkyl, —S(=O)$C_1$-$C_3$alkyl, —S(=O)$_2C_1$-$C_3$alkyl, —S(=O)$_2NH_2$, —S(=O)$_2NHC_1$-$C_3$alkyl, —S(=O)$_2$N($C_1$-$C_3$alkyl)$_2$, —$NH_2$, —$NHC_1$-$C_3$alkyl, —N($C_1$-$C_3$alkyl)$_2$, —NHC(=O)$OC_1$-$C_3$alkyl, —C(=O)$C_1$-$C_3$alkyl, —C(=O)OH, —C(=O)$OC_1$-$C_3$alkyl, —C(=O)$NH_2$, —C(=O)N($C_1$-$C_3$alkyl)$_2$, —C(=O)$NHC_1$-$C_3$alkyl, —P(=O)($C_1$-$C_3$alkyl)$_2$, —P(=O)(O$C_1$-$C_3$alkyl)$_2$, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl;
or two R on the same atom are taken together to form an oxo.
In some embodiments, the compound of Formula (I') is:

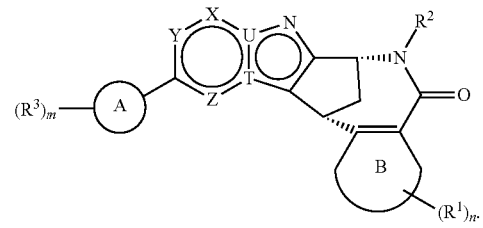

In some embodiments, the compound of Formula (I') is:

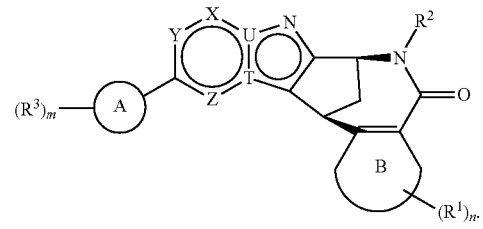

Disclosed herein is a compound of Formula (I*), or a pharmaceutically acceptable salt, solvate, or stereoisomer thereof:

Formula (I*)

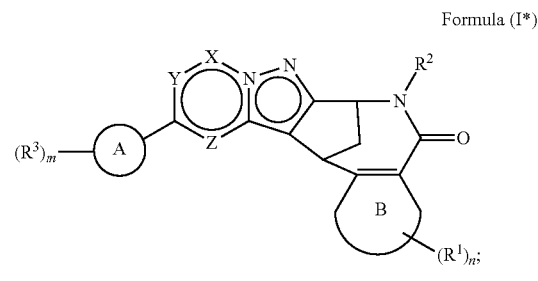

wherein:

Ring B is phenyl or a 6-membered heteroaryl comprising one or two nitrogen;

each $R^1$ is independently halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R;

or two $R^1$ on the same atom are taken together to form an oxo;

n is 0, 1, 2, 3, or 4;

$R^2$ is hydrogen, C$_1$-C$_6$alkyl, C$_1$-C$_6$haloalkyl, C$_1$-C$_6$deuteroalkyl, or cycloalkyl;

X is N or CR$^X$;

$R^X$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl;

Y is N or CR$^Y$;

$R^Y$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

Z is N or CR$^Z$;

$R^Z$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

Ring A is cycloalkyl, heterocycloalkyl, aryl, or heteroaryl;

each $R^3$ is independently halogen, -L-CN, -L-NO$_2$, -L-OH, -L-OR$^a$, -L-OC(=O)R$^a$, -L-OC(=O)OR$^b$, -L-OC(=O)NR$^c$R$^d$, -L-SH, -L-SR$^a$, -L-S(=O)R$^a$, -L-S(=O)$_2$R$^a$, -L-S(=O)(=NH)R$^a$, -L-S(=O)$_2$OR$^b$, -L-S(=O)$_2$NR$^c$R$^d$, -L-NR$^c$R$^d$, -L-NR$^b$C(=O)NR$^c$R$^d$, -L-NR$^b$C(=O)R$^a$, -L-NR$^b$C(=O)OR$^b$, -L-NR$^b$S(=O)$_2$R$^a$, -L-C(=O)R$^a$, -L-C(=O)OR$^b$, -L-C(=O)NR$^c$R$^d$, -L-P(=O)R$^c$R$^d$, -L-P(=O)OR$^c$OR$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

or two $R^3$ on the same atom are taken together to form an oxo;

or two $R^3$ on adjacent atoms are taken together to form a cycloalkyl, heterocycloalkyl, aryl, or heteroaryl; each independently optionally substituted with one or more R;

m is 0, 1, 2, 3, or 4;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

each $R^c$ and $R^d$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl independently optionally substituted with one or more R; and L is absent or C$_1$-C$_3$alkylene optionally substituted with one or more R;

each R is independently halogen, —CN, —OH, —OC$_1$-C$_3$alkyl, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —NH$_2$, —NHC$_1$-C$_3$alkyl, —N(C$_1$-C$_3$alkyl)$_2$, —NHC(=O)OC$_1$-C$_3$alkyl, —C(=O)C$_1$-C$_3$alkyl, —C(=O)OH, —C(=O)OC$_1$-C$_3$alkyl, —C(=O)NH$_2$, —C(=O)N(C$_1$-C$_3$alkyl)$_2$, —C(=O)NHC$_1$-C$_3$alkyl, —P(=O)(C$_1$-C$_3$alkyl)$_2$, —P(=O)(OC$_1$-C$_3$alkyl)$_2$, C$_1$-C$_3$alkyl, C$_1$-C$_3$haloalkyl, C$_1$-C$_3$hydroxyalkyl, C$_1$-C$_3$aminoalkyl, C$_1$-C$_3$heteroalkyl, C$_1$-C$_6$cycloalkyl, or 3- to 6-membered heterocycloalkyl;

or two R on the same atom are taken together to form an oxo.

In some embodiments, the compound of Formula (I*) is:

In some embodiments, the compound of Formula (I*) is:

In some embodiments of a compound of Formula (I') or (I*), Ring B is phenyl. In some embodiments of a compound of Formula (I') or (I*), Ring B is pyridinyl. In some embodiments of a compound of Formula (I') or (I*), Ring B is pyrimidinyl.

In some embodiments of a compound of Formula (I') or (I*),

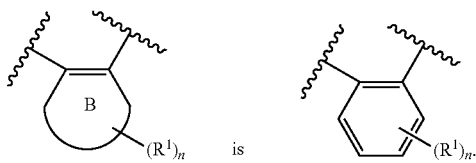

In some embodiments of a compound of Formula (I') or (I*),

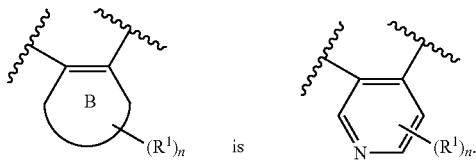

In some embodiments of a compound of Formula (I') or (I*),

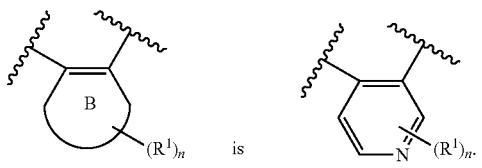

In some embodiments of a compound of Formula (I') or (I*),

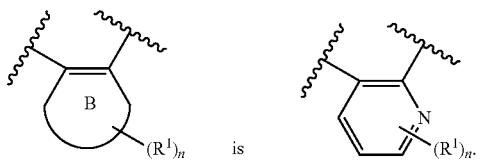

Disclosed herein is a compound of Formula (I) or (I*), or a pharmaceutically acceptable salt, solvate, or stereoisomer thereof:

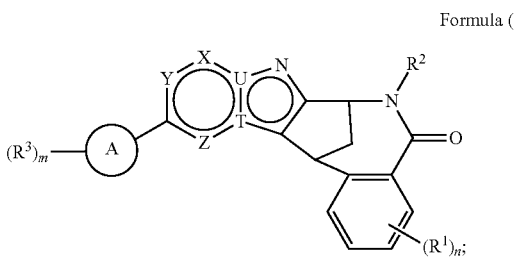

Formula (I)

wherein:
each $R^1$ is independently halogen, —CN, —NO$_2$, —OH, —OR$^a$, —NR$^c$R$^d$, —C(=O)R$^a$, —C(=O)OR$^b$, —C(=O)NR$^c$R$^d$ C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R;
or two $R^1$ on the same atom are taken together to form an oxo;
n is 1, 2, 3, or 4;
$R^2$ is hydrogen, C$_1$-C$_6$alkyl, C$_1$-C$_6$haloalkyl, or cycloalkyl;
X is N or CR$^X$;
$R^X$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl;
Y is N or CR$^Y$;
$R^Y$ is hydrogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
Z is N or CR$^Z$;
$R^Z$ is hydrogen, halogen, —CN, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
U is N and T is C or U is C and T is N;
Ring A is cycloalkyl, heterocycloalkyl, aryl, or heteroaryl;
each $R^3$ is independently halogen, -L-CN, -L-NO$_2$, -L-OH, -L-OR$^a$, -L-OC(=O)R$^a$, -L-OC(=O)OR$^b$, -L-OC(=O)NR$^c$R$^d$, -L-SH, -L-SR$^a$, -L-S(=O)R$^a$, -L-S(=O)$_2$R$^a$, -L-S(=O)(=NH)R$^a$, -L-S(=O)$_2$OR$^b$, -L-S(=O)$_2$NR$^c$R$^d$, -L-NR$^c$R$^d$, -L-NR$^b$C(=O)NR$^c$R$^d$, -L-NR$^b$C(=O)R$^a$, -L-NR$^b$C(=O)OR$^b$, -L-NR$^b$S(=O)$_2$R$^a$, -L-C(=O)R$^a$, -L-C(=O)OR$^b$, -L-C(=O)NR$^c$R$^d$, -L-P(=O)R$^c$R$^d$, -L-P(=O)OR$^c$OR$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R;
or two $R^3$ on the same atom are taken together to form an oxo;
or two $R^3$ on adjacent atoms are taken together to form a cycloalkyl, heterocycloalkyl, aryl, or heteroaryl;
each independently optionally substituted with one or more R;
m is 0, 1, 2, 3, or 4;
each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;
each $R^c$ and $R^d$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, -L-cycloalkyl, -L-heterocycloalkyl, -L- aryl, or -L-heteroaryl; wherein each alkyl, heteroalkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl independently optionally substituted with one or more R; and L is absent or $C_1$-$C_3$alkylene optionally substituted with one or more R;

each R is independently halogen, —CN, —OH, —O$C_1$-$C_3$alkyl, —S(=O)$C_1$-$C_3$alkyl, —S(=O)$_2$$C_1$-$C_3$alkyl, —S(=O)$_2$NH$_2$, —S(=O)$_2$NH$C_1$-$C_3$alkyl, —S(=O)$_2$N($C_1$-$C_3$alkyl)$_2$, —NH$_2$, —NH$C_1$-$C_3$alkyl, —N($C_1$-$C_3$alkyl)$_2$, —NHC(=O)O$C_1$-$C_3$alkyl, —C(=O)$C_1$-$C_3$alkyl, —C(=O)OH, —C(=O)O$C_1$-$C_3$alkyl, —C(=O)NH$_2$, —C(=O)N($C_1$-$C_3$alkyl)$_2$, —C(=O)NH$C_1$-$C_3$alkyl, —P(=O)($C_1$-$C_3$alkyl)$_2$, —P(=O)(O$C_1$-$C_3$alkyl)$_2$, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl;

or two R on the same atom are taken together to form an oxo.

In some embodiments, the compound of Formula (I) or (I*) is:

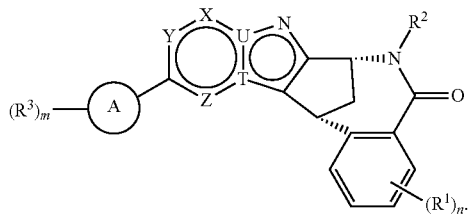

In some embodiments, the compound of Formula (I) or (I*) is:

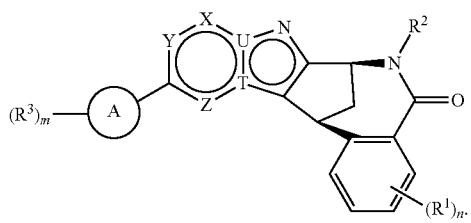

In some embodiments of a compound of Formula (I) or (I')

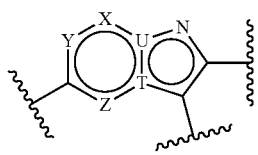

is fully aromatic.

In some embodiments of a compound of Formula (I*)

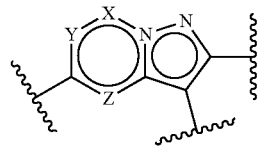

is fully aromatic.

In some embodiments of a compound of Formula (I') or (I) or (I*), X is N. In some embodiments of a compound of Formula (I') or (I) or (I*), X is $CR^X$.

In some embodiments of a compound of Formula (I') or (I) or (I*), Y is N. In some embodiments of a compound of Formula (I') or (I) or (I*), Y is $CR^Y$.

In some embodiments of a compound of Formula (I') or (I) or (I*), Z is N. In some embodiments of a compound of Formula (I') or (I) or (I*), Z is $CR^Z$.

In some embodiments of a compound of Formula (I') or (I), U is N and T is C. In some embodiments of a compound of Formula (I') or (I), U is C and T is N.

In some embodiments of a compound of Formula (I') or (I), U is N and T is C; X is $CR^X$, Y is $CR^Y$, and Z is $CR^Z$. In some embodiments of a compound of Formula (I') or (I), U is N and T is C; X is $CR^X$, Y is N, and Z is $CR^Z$. In some embodiments of a compound of Formula (I') or (I), U is N and T is C; X is $CR^X$, Y is $CR^Y$, and Z is N. In some embodiments of a compound of Formula (I') or (I), U is N and T is C; X is $CR^X$, Y is N, and Z is N.

In some embodiments of a compound of Formula (I') or (I), U is N and T is C; X is N, Y is $CR^Y$, and Z is $CR^Z$. In some embodiments of a compound of Formula (I') or (I), U is N and T is C; X is N, Y is $CR^Y$, and Z is N.

In some embodiments of a compound of Formula (I') or (I), U is C and T is N; X is $CR^X$, Y is $CR^Y$, and Z is $CR^Z$. In some embodiments of a compound of Formula (I') or (I), U is C and T is N; X is N, Y is $CR^Y$, and Z is $CR^Z$. In some embodiments of a compound of Formula (I') or (I), U is C and T is N; X is $CR^X$, Y is N, and Z is $CR^Z$. In some embodiments of a compound of Formula (I') or (I), U is C and T is N; X is $CR^X$, Y is $CR^Y$, and Z is N. In some embodiments of a compound of Formula (I') or (I), U is C and T is N; X is $CR^X$, Y is N, and Z is N.

In some embodiments of a compound of Formula (I')

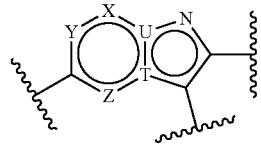

is not

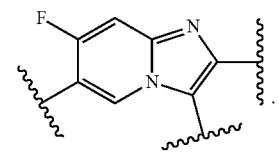 [SMILES: *c1cn2c(*)c(*)nc2cc1F]

.

In some embodiments of a compound of Formula (I') or (I) or (I*), the compound is of Formula (Ia):

Formula (Ia)

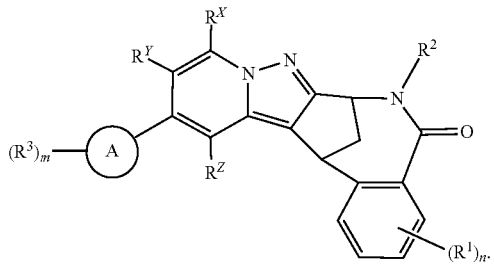

In some embodiments of a compound of Formula (I') or (I) or (I*), the compound is of Formula (Ib):

Formula (Ib)

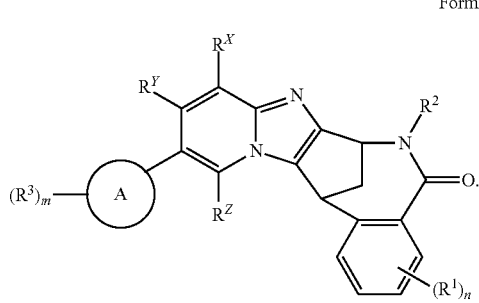

In some embodiments of a compound of Formula (I') or (I) or (I*), the compound is of Formula (Ic):

Formula (Ic)

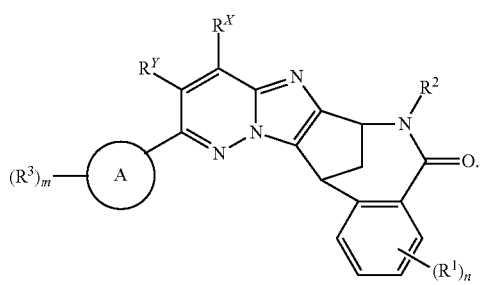

In some embodiments of a compound of Formula (I') or (I) or (I*), the compound is of Formula (Id):

Formula (Id)

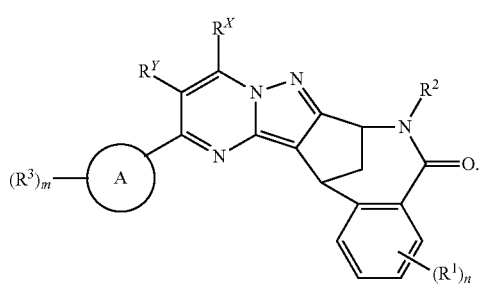

In some embodiments of a compound of Formula (I') or (I) or (I*), the compound is of Formula (Ie):

Formula (Ie)

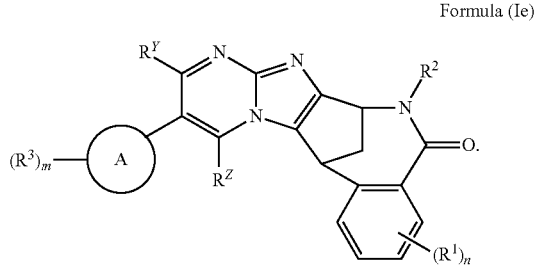

In some embodiments of a compound of Formula (I') or (I) or (I*), the compound is of Formula (If):

Formula (If)

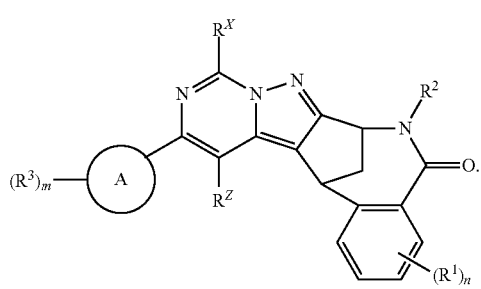

In some embodiments of Formula (I'), (I), (I*), (Ia)-(If), n is 1, 2, or 3. In some embodiments of Formula (I'), (I), (I*), (Ia)-(If), n is 1 or 2. In some embodiments of Formula (I'), (I), (I*), (Ia)-(If), n is 1. In some embodiments of Formula (I'), (I), (I*), (Ia)-(If), n is 2. In some embodiments of Formula (I'), (I), (I*), (Ia)-(If), n is 3. In some embodiments of Formula (I*), n is 0 or 1. In some embodiments of Formula (I*), n is 0.

In some embodiments of Formula (I'), (I), (I*), (Ia)-(If), each $R^1$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of Formula (I'), (I), (I*), (Ia)-(If), each $R^1$ is independently halogen, —CN, —OH, —OR$^a$, —NR$^c$R$^d$, $C_1$-$C_6$alkyl, or $C_1$-$C_6$haloalkyl. In some embodiments of Formula (I'), (I), (I*), (Ia)-(If), each $R^1$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl. In some embodiments of Formula (I'), (I), (I*), (Ia)-(If), each $R^1$ is independently halogen, —CN, —OH, —OR$^a$, —NR$^c$R$^d$, $C_1$-$C_6$alkyl, or $C_1$-$C_6$haloalkyl. In some embodiments of Formula (I'), (I), (I*), (Ia)-(If), each $R^1$ is independently —OR$^a$. In some embodiments of Formula (I'), (I), (I*), (Ia)-(If), each $R^1$ is —OCHF$_2$. In some embodiments of Formula (I'), (I), (I*), (Ia)-(If), each $R^1$ is -Ocyclopropyl. In some embodiments of Formula (I'), (I), (I*), (Ia)-(If), each $R^1$ is —CN. In some embodiments of Formula (I'), (I), (I*), (Ia)-(If), each $R^1$ is independently —CN or —OCHF$_2$.

In some embodiments of Formula (I'), (I), (I*), (Ia)-(Id), or (If), $R^X$ is hydrogen, halogen, —CN, —OH, —OR$^a$, —NR$^c$R$^d$, $C_1$-$C_6$alkyl, or $C_1$-$C_6$haloalkyl. In some embodiments of Formula (I'), (I), (I*), (Ia)-(Id), or (If), $R^X$ is hydrogen, halogen, $C_1$-$C_6$alkyl, or $C_1$-$C_6$haloalkyl. In some embodiments of Formula (I'), (I), (I*), (Ia)-(Id), or (If), $R^X$ is hydrogen.

In some embodiments of Formula (I'), (I), (I*), (Ia)-(Ie), $R^Y$ is hydrogen, —CN, —OH, —OR$^a$, —NR$^c$R$^d$, $C_1$-$C_6$alkyl, or $C_1$-$C_6$haloalkyl. In some embodiments of Formula (I'), (I), (I*), (Ia)-(Ie), $R^Y$ is hydrogen, $C_1$-$C_6$alkyl, or $C_1$-$C_6$haloalkyl. In some embodiments of Formula (I'), (I), (I*), (Ia)-(Ie), $R^Y$ is hydrogen.

In some embodiments of Formula (I'), (Ia)-(Ie), $R^Y$ is hydrogen, halogen, —CN, —OH, —OR$^a$, —NR$^c$R$^d$, $C_1$-$C_6$alkyl, or $C_1$-$C_6$haloalkyl. In some embodiments of Formula (I'), (Ia)-(Ie), $R^Y$ is hydrogen, halogen, $C_1$-$C_6$alkyl, or $C_1$-$C_6$haloalkyl. In some embodiments of Formula (I'), (Ia)-(Ie), $R^Y$ is hydrogen or halogen. In some embodiments of Formula (I'), (Ia)-(Ie), $R^Y$ is hydrogen. In some embodiments of Formula (I'), (Ia)-(Ie), $R^Y$ is halogen.

In some embodiments of Formula (I'), (I), (I*), (Ia), (Ib), (Ie), or (If), $R^Z$ is hydrogen, halogen, —CN, —OH, —OR$^a$, —NR$^c$R$^d$, $C_1$-$C_6$alkyl, or $C_1$-$C_6$haloalkyl. In some embodiments of Formula (I'), (I), (I*), (Ia), (Ib), (Ie), or (If), $R^Z$ is hydrogen, halogen, $C_1$-$C_6$alkyl, or $C_1$-$C_6$haloalkyl. In some embodiments of Formula (I'), (I), (I*), (Ia), (Ib), (Ie), or (If), $R^Z$ is hydrogen.

In some embodiments of Formula (I'), (I), (I*), or (Ia), the compound is of Formula (Ia-1):

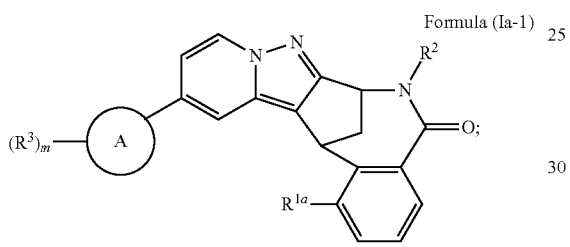

Formula (Ia-1)

wherein $R^{1a}$ is hydrogen or $R^1$.

In some embodiments of Formula (I'), (I), or (Ib), the compound is of Formula (Ib-1):

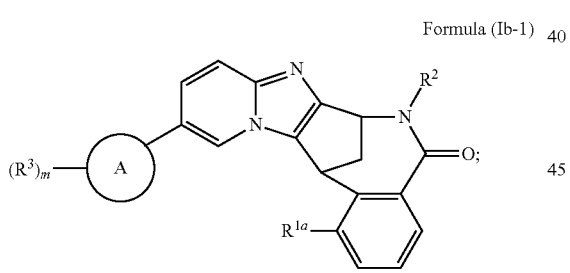

Formula (Ib-1)

wherein $R^{1a}$ is hydrogen or $R^1$.

In some embodiments of Formula (I'), (I), or (Ic), the compound is of Formula (Ic-1):

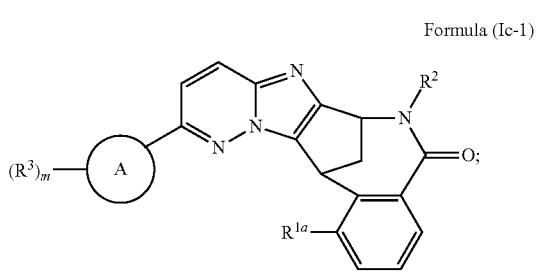

Formula (Ic-1)

wherein $R^{1a}$ is hydrogen or $R^1$.

In some embodiments of a compound of Formula (I'), (I), (I*), or (Id), the compound is of Formula (Id-1):

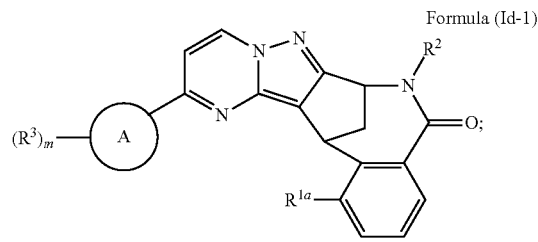

Formula (Id-1)

wherein $R^{1a}$ is hydrogen or $R^1$.

In some embodiments of a compound of Formula (I'), (I), or (Ie), the compound is of Formula (Ie-1):

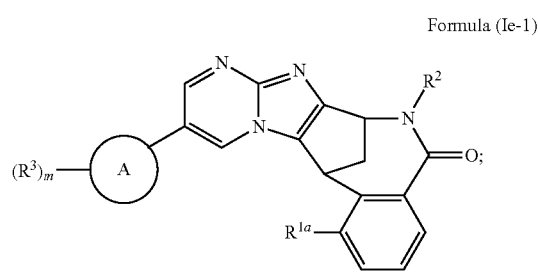

Formula (Ie-1)

wherein $R^{1a}$ is hydrogen or $R^1$.

In some embodiments of a compound of Formula (I'), (I), (I*), or (If), the compound is of Formula (If-1):

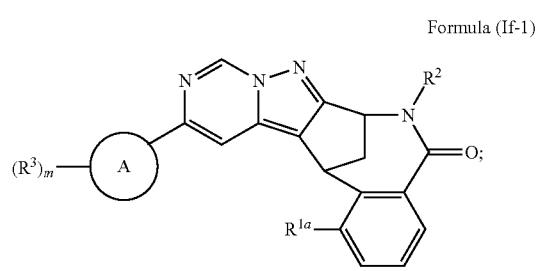

Formula (If-1)

wherein $R^{1a}$ is hydrogen or $R^1$.

In some embodiments of Formula (I'), (I), (I*), (Ia)-(If), or (Ia-1)-(If-1), $R^2$ is hydrogen, $C_1$-$C_6$alkyl, or $C_1$-$C_6$haloalkyl.

In some embodiments of Formula (I'), (I), (I*), (Ia)-(If), or (Ia-1)-(If-1), $R^2$ is hydrogen, $C_1$-$C_6$alkyl, $C_1$-$C_6$haloalkyl, or cycloalkyl.

In some embodiments of Formula (I'), (I), (I*), (Ia)-(If), or (Ia-1)-(If-1), $R^2$ is $C_1$-$C_6$alkyl or $C_1$-$C_6$haloalkyl. In some embodiments of Formula (I'), (I), (I*), (Ia)-(If), or (Ia-1)-(If-1), $R^2$ is hydrogen or $C_1$-$C_6$alkyl. $R^2$ is $C_1$-$C_6$alkyl, $C_1$-$C_6$haloalkyl, or cycloalkyl. In some embodiments of Formula (I'), (I), (I*), (Ia)-(If), or (Ia-1)-(If-1), $R^2$ is $C_1$-$C_6$alkyl or $C_1$-$C_6$deuteroalkyl. In some embodiments of Formula (I'), (I), (I*), (Ia)-(If), or (Ia-1)-(If-1), $R^2$ is $C_1$-$C_6$alkyl. In some embodiments of Formula (I'), (I), (I*), (Ia)-(If), or (Ia-1)-(If-1), $R^2$ is $C_1$-$C_6$deuteroalkyl.

In some embodiments of Formula (I'), (I), (I*), (Ia)-(If), or (Ia-1)-(If-1), $R^2$ is $C_1$-$C_6$alkyl. In some embodiments of Formula (I'), (I), (I*), (Ia)-(If), or (Ia-1)-(If-1), $R^2$ is $C_1$-$C_6$deuteroalkyl. In some embodiments of Formula (I'), (I), (I*), (Ia)-(If), or (Ia-1)-(If-1), $R^2$ is —$CH_3$ or -$CD_3$. In some embodiments of Formula (I'), (I), (I*), (Ia)-(If), or (Ia-1)-(If-1), $R^2$ is hydrogen.

In some embodiments of Formula (Ia-1)-(If-1), $R^{1a}$ is hydrogen, halogen, —CN, —OH, —$OR^a$, —$NR^cR^d$, $C_1$-$C_6$alkyl, or $C_1$-$C_6$haloalkyl. In some embodiments of Formula (Ia-1)-(If-1), $R^{1a}$ is —$OR^a$. In some embodiments of Formula (Ia-1)-(If-1), $R^{1a}$ is —$OCHF_2$. In some embodiments of Formula (Ia-1)-(If-1), $R^{1a}$ is —Ocyclopropyl. In some embodiments of Formula (Ia-1)-(If-1), $R^{1a}$ is —CN. In some embodiments of Formula (Ia-1)-(If-1), $R^{1a}$ is —CN or —$OCHF_2$ In some embodiments of Formula (I'), (I), (I*), (Ia)-(If), or (Ia-1)-(If-1), Ring A is aryl or heteroaryl.

In some embodiments of Formula (I'), (I), (I*), (Ia)-(If), or (Ia-1)-(If-1), Ring A is heteroaryl.

In some embodiments of Formula (I'), (I), (I*), (Ia)-(If), or (Ia-1)-(If-1), Ring A is 5- or 6-membered heteroaryl. In some embodiments of Formula (I'), (I), (I*), (Ia)-(If), or (Ia-1)-(If-1), Ring A is 6-membered heteroaryl. In some embodiments of Formula (I'), (I), (I*), (Ia)-(If), or (Ia-1)-(If-1), Ring A is pyridinyl or pyrimidinyl. In some embodiments of Formula (I'), (I), (I*), (Ia)-(If), or (Ia-1)-(If-1), Ring A is pyridinyl. In some embodiments of Formula (I'), (I), (I*), (Ia)-(If), or (Ia-1)-(If-1), Ring A is pyrimidinyl. In some embodiments of Formula (I'), (I), (I*), (Ia)-(If), or (Ia-1)-(If-1), Ring A is 5-membered heteroaryl.

In some embodiments of Formula (I'), (I), (I*), (Ia)-(If), or (Ia-1)-(If-1), Ring A is cycloalkyl or heterocycloalkyl.

In some embodiments of Formula (I'), (I), (I*), (Ia)-(If), or (Ia-1)-(If-1), Ring A is fully saturated cycloalkyl or fully saturated heterocycloalkyl.

In some embodiments of Formula (I'), (I), (I*), (Ia)-(If), or (Ia-1)-(If-1), Ring A is fully saturated cycloalkyl.

In some embodiments of Formula (I'), (I), (I*), (Ia)-(If), or (Ia-1)-(If-1), Ring A is fully saturated heterocycloalkyl.

In some embodiments of Formula (I'), (I), (I*), (Ia)-(If), or (Ia-1)-(If-1), Ring A is cycloalkenyl or heterocycloalkenyl.

In some embodiments of Formula (I'), (I), (I*), (Ia)-(If), or (Ia-1)-(If-1), Ring A is cycloalkenyl.

In some embodiments of Formula (I'), (I), (I*), (Ia)-(If), or (Ia-1)-(If-1), Ring A is heterocycloalkenyl.

In some embodiments of Formula (I'), (I), (I*), (Ia)-(If), or (Ia-1)-(If-1), Ring A is 1,2,3,6-tetrahydropyridinyl, 3,6-dihydro-2H-pyranyl or tetrahydro-2H-pyranyl.

In some embodiments of Formula (I'), (I), (I*), (Ia)-(If), or (Ia-1)-(If-1), Ring A is cyclohexenyl.

In some embodiments of Formula (I'), (I), (I*), (Ia)-(If), or (Ia-1)-(If-1), Ring A is cyclohexyl.

In some embodiments of Formula (I'), (I), (I*), (Ia)-(If), or (Ia-1)-(If-1), each $R^3$ is independently halogen, -L-CN, -L-$NO_2$, -L-OH, -L-$OR^a$, -L-OC(=O)$R^a$, -L-OC(=O)$OR^b$, -L-OC(=O)$NR^cR^d$, -L-SH, -L-$SR^a$, -L-S(=O)$R^a$, -L-S(=O)$_2R^a$, -L-S(=O)$_2OR^b$, -L-S(=O)$_2NR^cR^d$, -L-$NR^cR^d$, -L-$NR^bC$(=O)$NR^cR^d$, -L-$NR^bC$(=O)$R^a$, -L-$NR^bC$(=O)$OR^b$, -L-$NR^bS$(=O)$_2R^a$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R.

In some embodiments of Formula (I'), (I), (I*), (Ia)-(If), or (Ia-1)-(If-1), each $R^3$ is independently halogen, -L-CN, -L-$NO_2$, -L-OH, -L-$OR^a$, -L-OC(=O)$R^a$, -L-OC(=O)$OR^b$, -L-OC(=O)$NR^cR^d$, -L-SH, -L-$SR^a$, -L-S(=O)$R^a$, -L-S(=O)$_2R^a$, -L-S(=O)(=NH)$R^a$, -L-S(=O)$_2OR^b$, -L-S(=O)$_2NR^cR^d$, -L-$NR^WR^d$, -L-$NR^bC$(=O)$NR^cR^d$, -L-$NR^bC$(=O)$R^a$, -L-$NR^bC$(=O)$OR^b$, -L-$NR^bS$(=O)$_2R^a$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, heteroalkyl, alkenyl, alkynyl, cycloalkyl, heterocycloalkyl, aryl, and heteroaryl is independently optionally substituted with one or more R;

In some embodiments of Formula (I'), (I), (I*), (Ia)-(If), or (Ia-1)-(If-1), each $R^3$ is independently halogen, -L-S(=O)$R^a$, -L-S(=O)$_2R^a$, -L-S(=O)$_2NR^cR^d$, -L-$NR^cR^d$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, -L-cycloalkyl, or -L-heterocycloalkyl; wherein each alkyl, heteroalkyl, cycloalkyl, heterocycloalkyl is independently optionally substituted with one or more R.

In some embodiments of Formula (I'), (I), (I*), (Ia)-(If), or (Ia-1)-(If-1), each $R^3$ is independently halogen, -L-S(=O)$_2R^a$, -L-$NR^cR^d$, -L-C(=O)$R^a$, -L-C(=O)$OR^b$, $C_1$-$C_6$alkyl, $C_1$-$C_6$haloalkyl, $C_1$-$C_6$hydroxyalkyl, $C_1$-$C_6$aminoalkyl, -L-cycloalkyl, or -L-heterocycloalkyl; wherein each alkyl, cycloalkyl, heterocycloalkyl is independently optionally substituted with one or more R.

In some embodiments of Formula (I'), (I), (I*), (Ia)-(If), or (Ia-1)-(If-1), each $R^3$ is independently halogen, -L-$OR^a$, -L-$NR^cR^d$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, $C_1$-$C_6$haloalkyl, -L-cycloalkyl, -L-heterocycloalkyl, -L-aryl, or -L-heteroaryl; wherein each alkyl, cycloalkyl, heterocycloalkyl, aryl, and heteroaryl is independently optionally substituted with one or more R.

In some embodiments of Formula (I'), (I), (I*), (Ia)-(If), or (Ia-1)-(If-1), each $R^3$ is independently halogen, -L-$OR^a$, -L-$NR^cR^d$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, -L-cycloalkyl, or -L-heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently halogen, -L-$OR^a$, -L-$NR^cR^d$, $C_1$-$C_6$alkyl, $C_1$-$C_6$haloalkyl, -L-cycloalkyl, or -L-heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently halogen, -L-$NR^cR^d$, $C_1$-$C_6$alkyl, -L-cycloalkyl, or -L-heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently -L-cycloalkyl or -L-heterocycloalkyl; wherein each cycloalkyl and heterocycloalkyl is independently optionally substituted with one or more R.

In some embodiments of Formula (I'), (I), (I*), (Ia)-(If), or (Ia-1)-(If-1), each $R^3$ is independently halogen or -L-cycloalkyl independently optionally substituted with one or more R.

In some embodiments of Formula (I'), (I), (I*), (Ia)-(If), or (Ia-1)-(If-1), each $R^3$ is independently -L-cycloalkyl independently optionally substituted with one or more R.

In some embodiments of Formula (I'), (I), (I*), (Ia)-(If), or (Ia-1)-(If-1), each $R^3$ is independently halogen or -L-heterocycloalkyl independently optionally substituted with one or more R.

In some embodiments of Formula (I'), (I), (I*), (Ia)-(If), or (Ia-1)-(If-1), each $R^3$ is independently -L-heterocycloalkyl independently optionally substituted with one or more R.

In some embodiments of Formula (I'), (I), (I*), (Ia)-(If), or (Ia-1)-(If-1), each $R^3$ is independently halogen, -L-S(=O)$R^a$, -L-S(=O)$_2R^a$, -L-S(=O)$_2NR^cR^d$, -L-NR$^cR^d$, -L-C(=O)$R^a$, -L-C(=O)OR$^b$, -L-C(=O)NR$^cR^d$, -L-P(=O)$R^cR^d$, -L-P(=O)OR$^c$OR$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, heteroalkyl, cycloalkyl, heterocycloalkyl is independently optionally substituted with one or more R.

In some embodiments of Formula (I'), (I), (I*), (Ia)-(If), or (Ia-1)-(If-1), each $R^3$ is independently halogen, -L-S(=O)$_2R^a$, -L-NR$^cR^d$, -L-C(=O)$R^a$, -L-C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, heterocycloalkyl is independently optionally substituted with one or more R.

In some embodiments of Formula (I'), (I), (I*), (Ia)-(If), or (Ia-1)-(If-1), each $R^3$ is independently halogen, -L-OR$^a$, -L-NR$^cR^d$, -L-C(=O)$R^a$, -L-C(=O)OR$^b$, -L-C(=O)NR$^cR^d$, -L-P(=O)$R^cR^d$, -L-P(=O)OR$^c$OR$^d$, $C_1$-$C_6$alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one or more R.

In some embodiments of Formula (I'), (I), (I*), (Ia)-(If), or (Ia-1)-(If-1), each $R^3$ is independently halogen, -L-OR$^a$, -L-NR$^cR^d$, -L-C(=O)$R^a$, -L-C(=O)OR$^b$, -L-C(=O)NR$^cR^d$, -L-P(=O)$R^cR^d$, -L-P(=O)OR$^c$OR$^d$, $C_1$-$C_6$alkyl, cycloalkyl, or heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently halogen, -L-OR$^a$, -L-NR$^cR^d$, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently halogen, -L-NR$^cR^d$, $C_1$-$C_6$alkyl, cycloalkyl, or heterocycloalkyl; wherein each alkyl, cycloalkyl, and heterocycloalkyl is independently optionally substituted with one or more R.

In some embodiments of Formula (I'), (I), (I*), (Ia)-(If), or (Ia-1)-(If-1), each $R^3$ is independently cycloalkyl or heterocycloalkyl; wherein each cycloalkyl and heterocycloalkyl is independently optionally substituted with one or more R.

In some embodiments of Formula (I'), (I), (I*), (Ia)-(If), or (Ia-1)-(If-1), each $R^3$ is independently halogen or cycloalkyl independently optionally substituted with one or more R.

In some embodiments of Formula (I'), (I), (I*), (Ia)-(If), or (Ia-1)-(If-1), each $R^3$ is independently cycloalkyl independently optionally substituted with one or more R.

In some embodiments of Formula (I'), (I), (I*), (Ia)-(If), or (Ia-1)-(If-1), each $R^3$ is independently halogen or heterocycloalkyl independently optionally substituted with one or more R.

In some embodiments of Formula (I'), (I), (I*), (Ia)-(If), or (Ia-1)-(If-1), each $R^3$ is independently heterocycloalkyl independently optionally substituted with one or more R.

In some embodiments of Formula (I'), (I), (I*), (Ia)-(If), or (Ia-1)-(If-1), each $R^3$ is independently halogen or -L-NR$^cR^d$.

In some embodiments of Formula (I'), (I), (I*), (Ia)-(If), or (Ia-1)-(If-1), each $R^3$ is independently -L-NR$^cR^d$.

In some embodiments of Formula (I'), (I), (I*), (Ia)-(If), or (Ia-1)-(If-1), each $R^3$ is independently

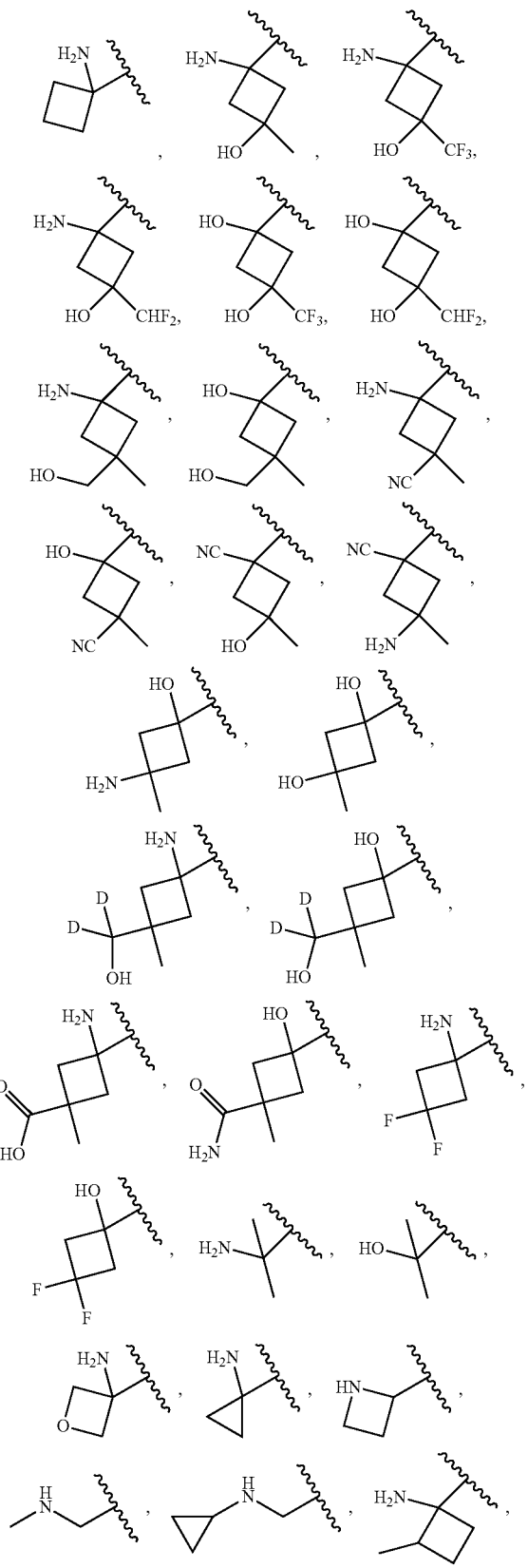

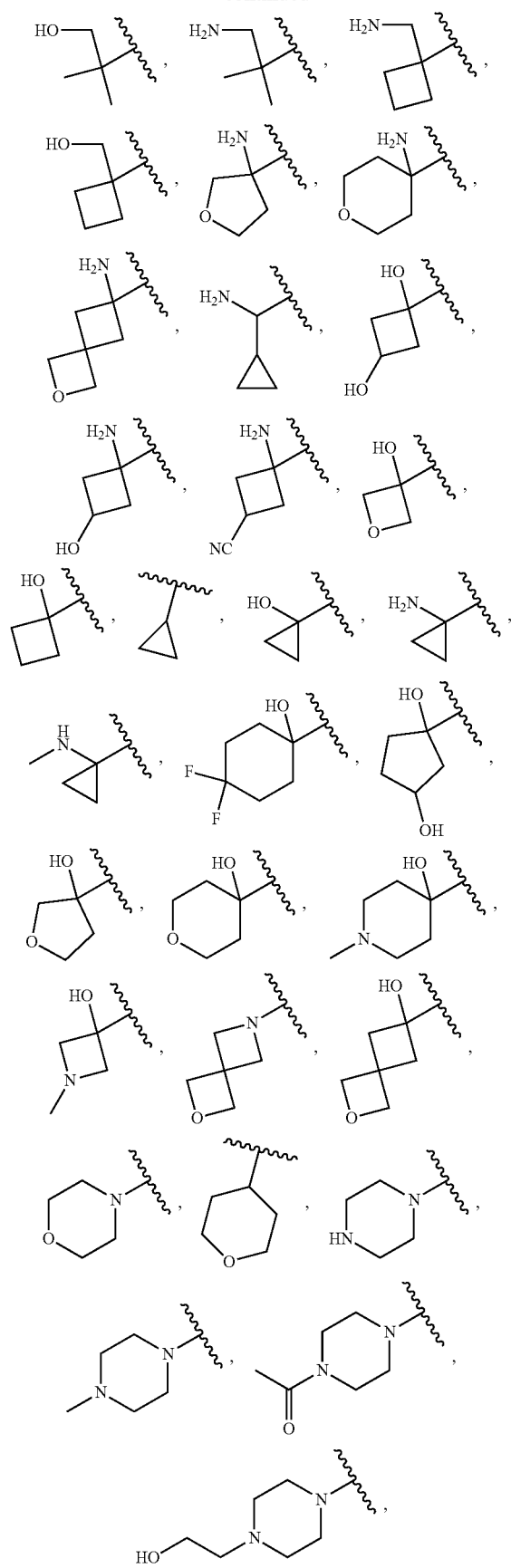
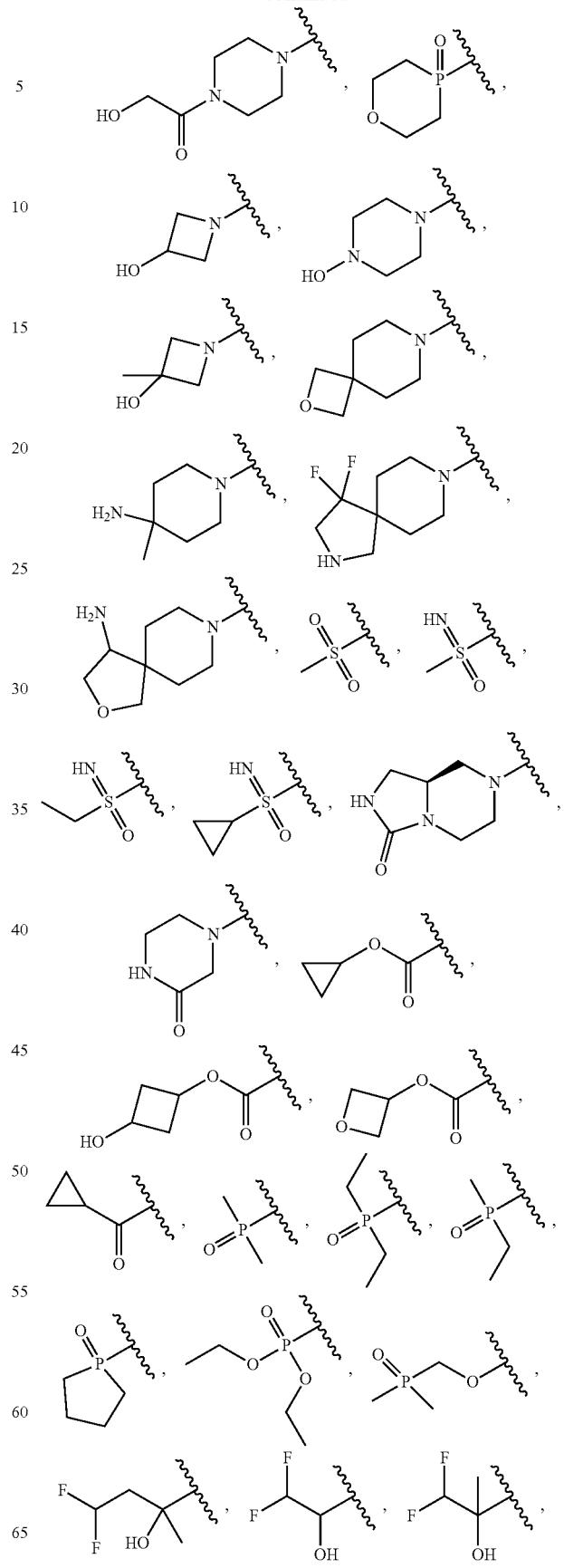

-continued
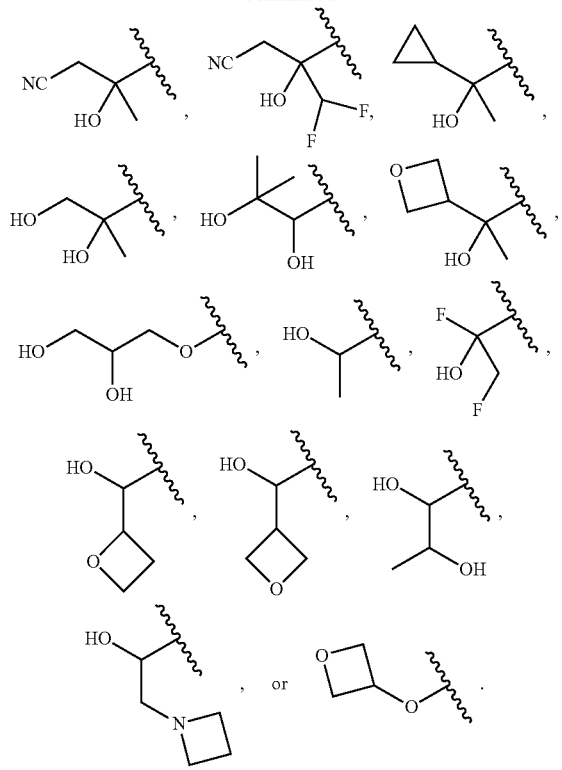
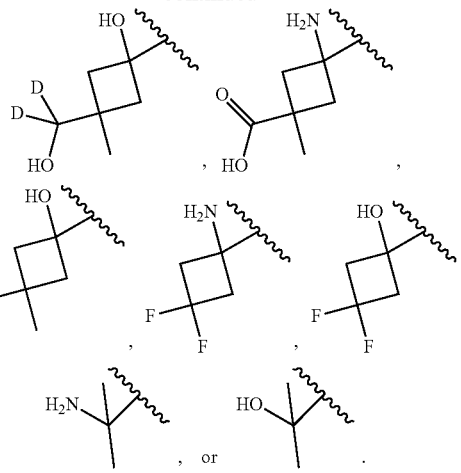
In some embodiments of Formula (I'), (I), (I*), (Ia)-(If), or (Ia-1)-(If-1), each R³ is independently
In some embodiments of Formula (I'), (I), (I*), (Ia)-(If), or (Ia-1)-(If-1), each R³ is independently
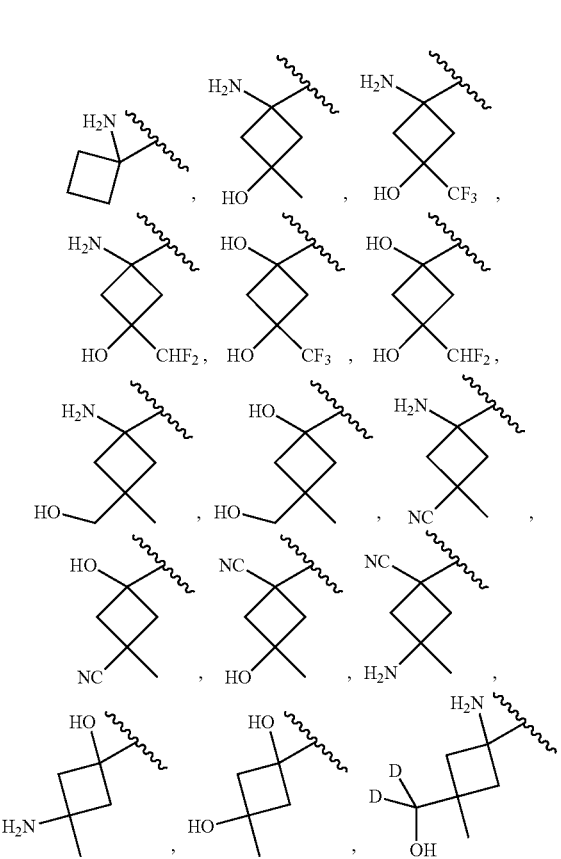
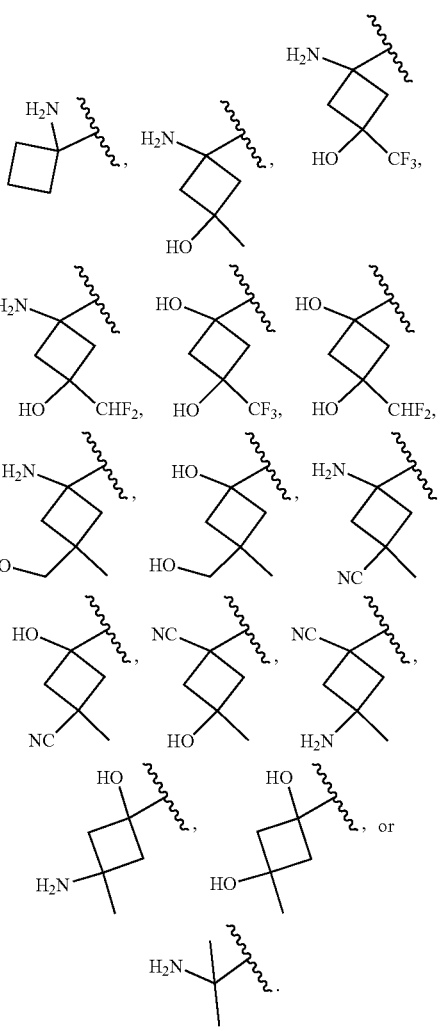
In some embodiments of Formula (I'), (I), (I*), (Ia)-(If), or (Ia-1)-(If-1), each R³ is independently

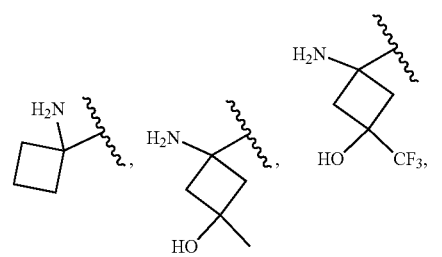
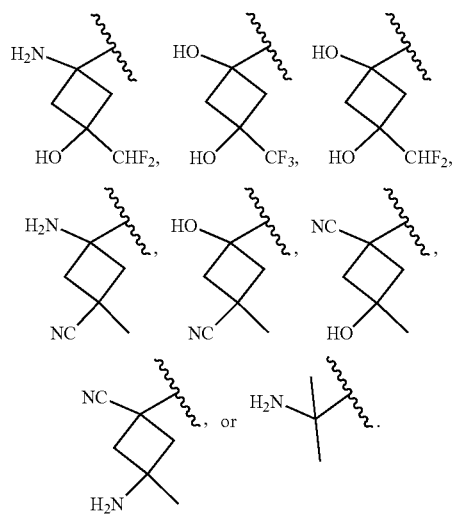
In some embodiments of Formula (I'), (I), (I*), (Ia)-(If), or (Ia-1)-(If-1), each R³ is independently
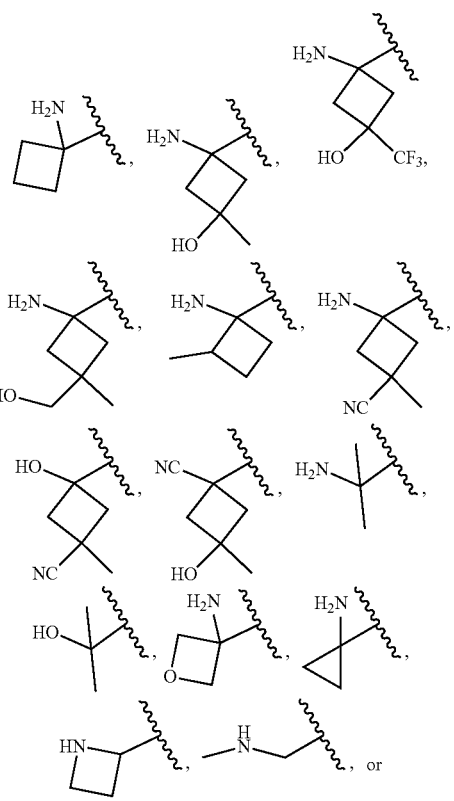
-continued
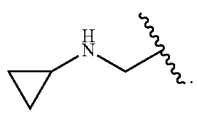
In some embodiments of Formula (I'), (I), (I*), (Ia)-(If), or (Ia-1)-(If-1), each R³ is independently
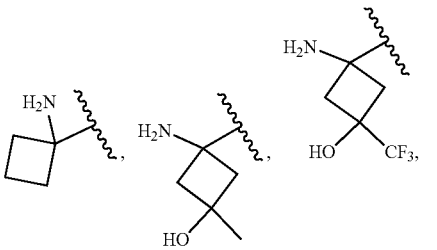
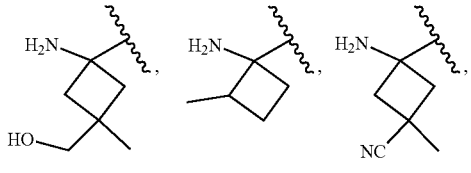
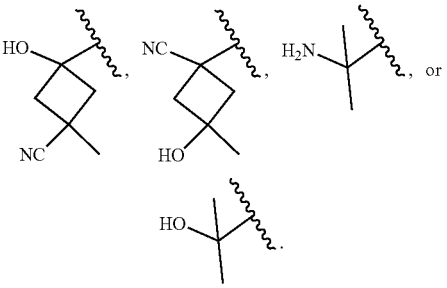
In some embodiments of Formula (I'), (I), (I*), (Ia)-(If), or (Ia-1)-(If-1), each R³ is independently
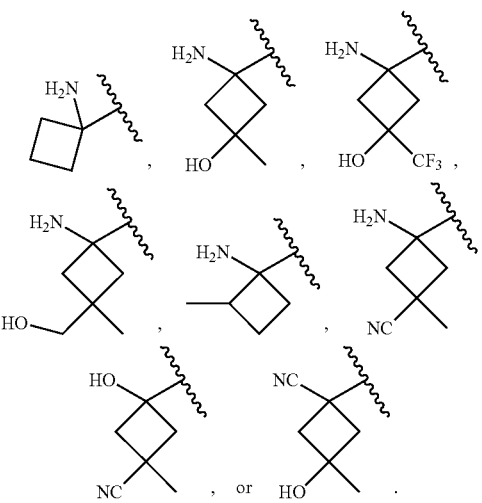
In some embodiments of Formula (I'), (I), (I*), (Ia)-(If), or (Ia-1)-(If-1), each R³ is independently

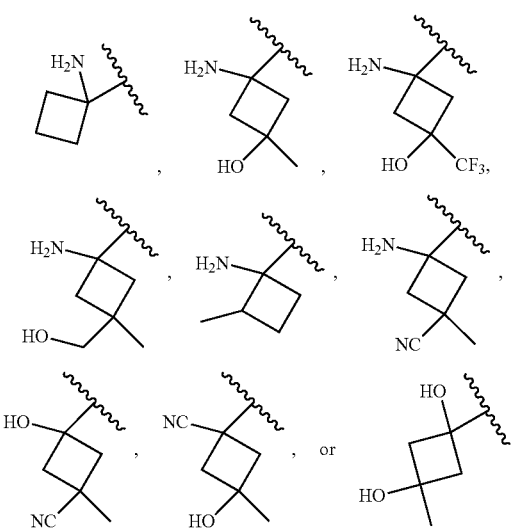

In some embodiments of Formula (I'), (I), (I*), (Ia)-(If), or (Ia-1)-(If-1), each R³ is independently

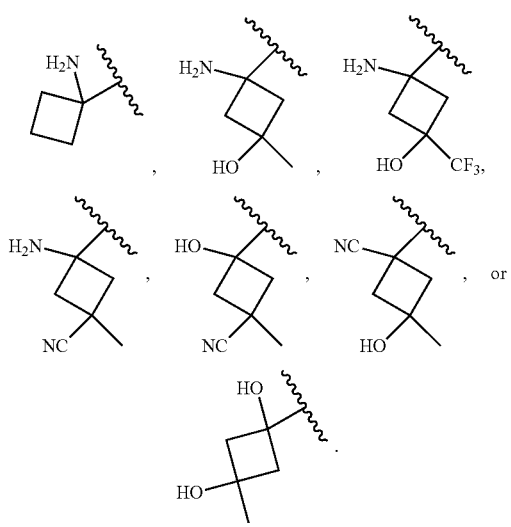

In some embodiments of Formula (I'), (I), (I*), (Ia)-(If), or (Ia-1)-(If-1), each R³ is independently

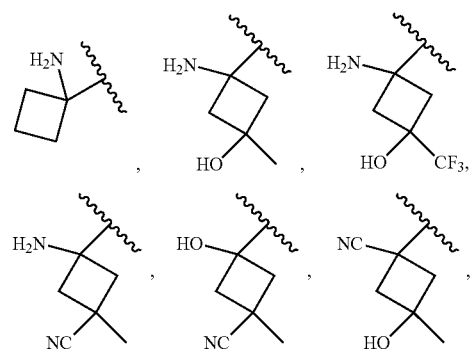

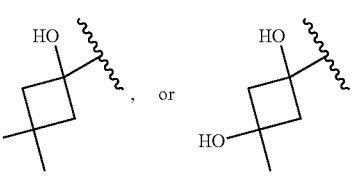

In some embodiments of Formula (I'), (I), (I*), (Ia)-(If), or (Ia-1)-(If-1), each R³ is independently

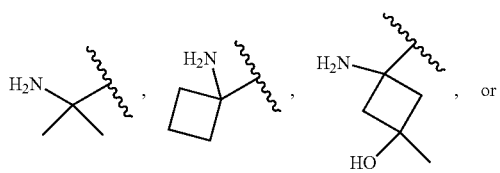

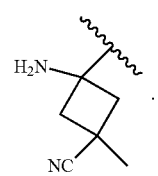

In some embodiments of Formula (I'), (I), (I*), (Ia)-(If), or (Ia-1)-(If-1), each R³ is independently

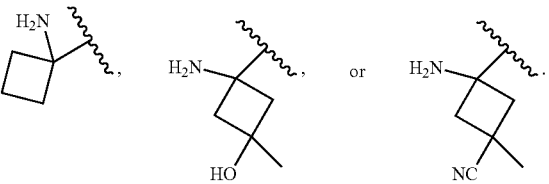

In some embodiments of Formula (I'), (I), (I*), (Ia)-(If), or (Ia-1)-(If-1), each R³ is independently

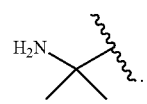

In some embodiments of Formula (I'), (I), (I*), (Ia)-(If), or (Ia-1)-(If-1), each R³ is

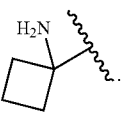

In some embodiments of Formula (I'), (I), (I*), (Ia)-(If), or (Ia-1)-(If-1), each R³ is

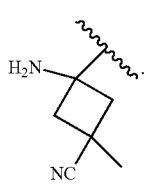
In some embodiments of Formula (I'), (I), (I*), (Ia)-(If), or (Ia-1)-(If-1), each R³ is
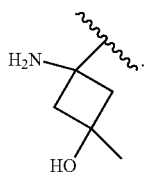
In some embodiments of Formula (I'), (I), (I*), (Ia)-(If), or (Ia-1)-(If-1), each R³ is independently
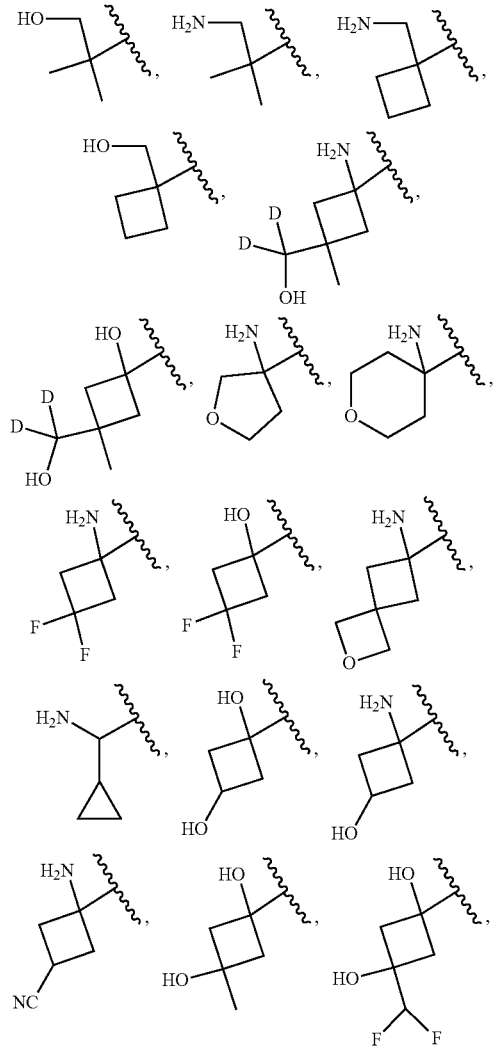
-continued
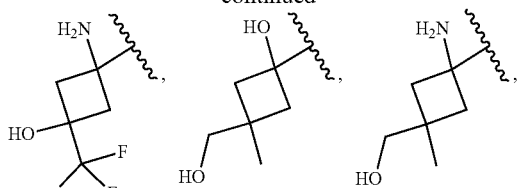
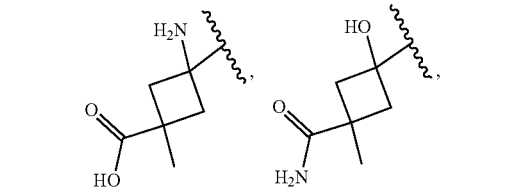
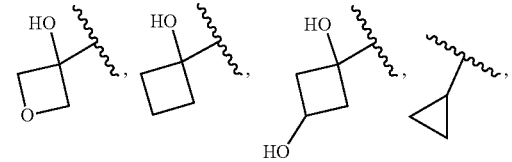
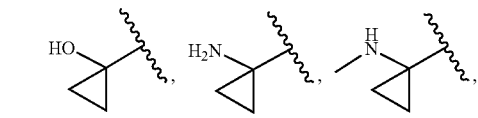
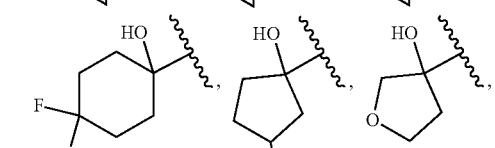
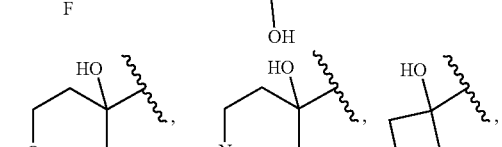
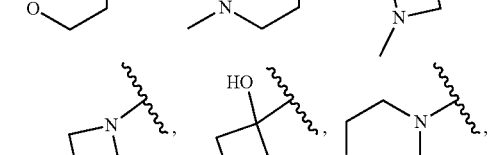
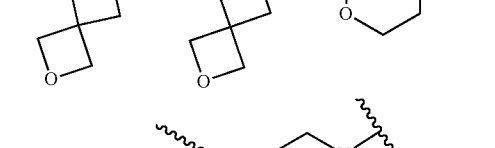

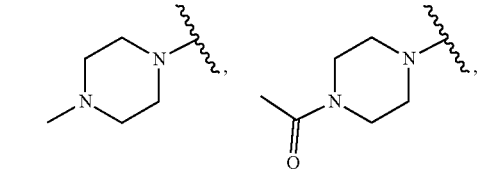
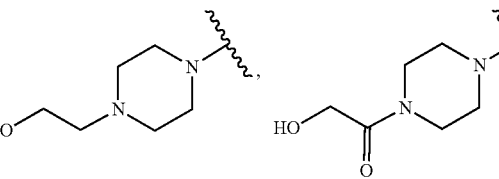

-continued

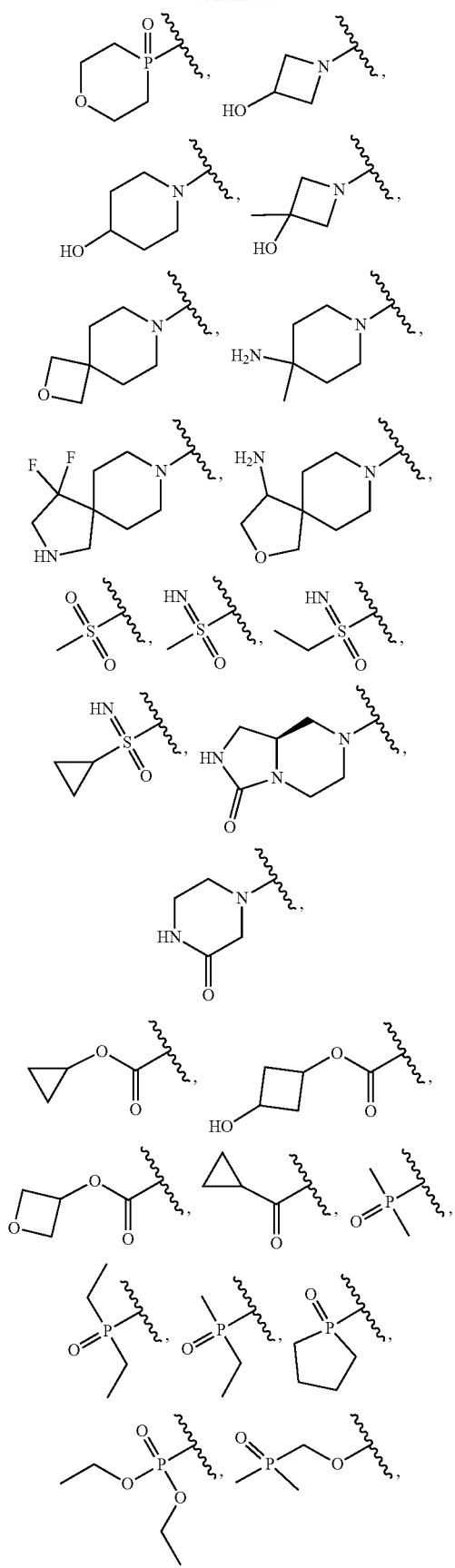

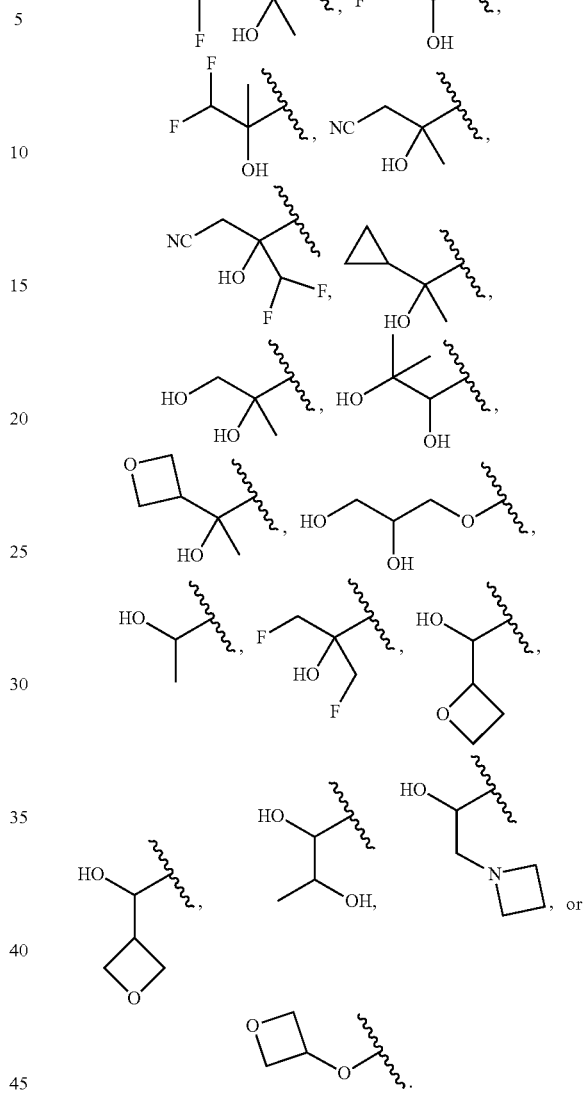

In some embodiments of Formula (I'), (I), (I*), (Ia)-(If), or (Ia-1)-(If-1), two $R^3$ on adjacent atoms are taken together to form a cycloalkyl or heterocycloalkyl; each independently optionally substituted with one or more R.

In some embodiments of Formula (I'), (I), (I*), (Ia)-(If), or (Ia-1)-(If-1), two $R^3$ on adjacent atoms are taken together to form a cycloalkyl independently optionally substituted with one or more R.

In some embodiments of Formula (I'), (I), (I*), (Ia)-(If), or (Ia-1)-(If-1), two $R^3$ on adjacent atoms are taken together to form a heterocycloalkyl independently optionally substituted with one or more R.

In some embodiments of Formula (I'), (I), (I*), (Ia)-(If), or (Ia-1)-(If-1), m is 0, 1, 2, or 3. In some embodiments of Formula (I'), (I), (I*), (Ia)-(If), or (Ia-1)-(If-1), m is 0, 1, or 2. In some embodiments of Formula (I'), (I), (I*), (Ia)-(If), or (Ia-1)-(If-1), m is 0 or 1. In some embodiments of Formula (I'), (I), (I*), (Ia)-(If), or (Ia-1)-(If-1), m is 1 or 2.

In some embodiments of Formula (I'), (I), (I*), (Ia)-(If), or (Ia-1)-(If-1), is

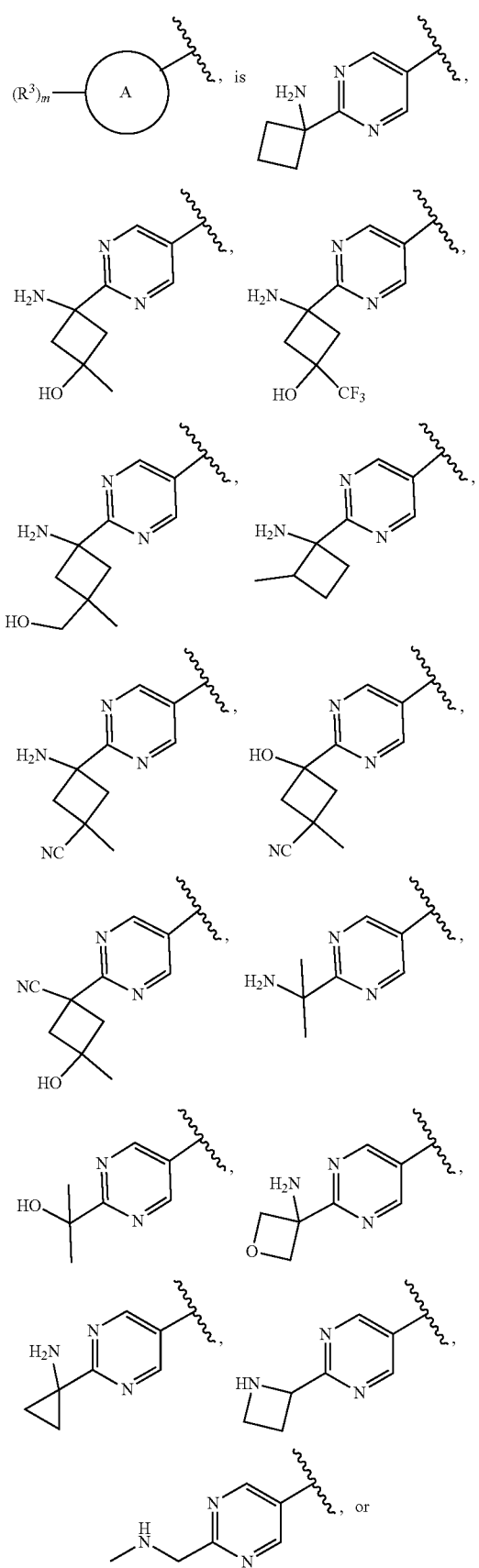
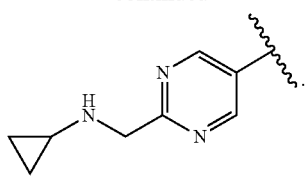
In some embodiments of Formula (I') (I) (I*), (Ia)-(If), or (Ia-1)-(If-1) is
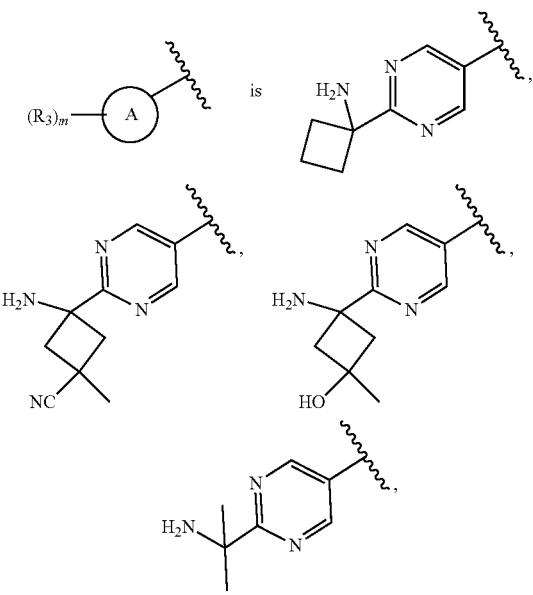
In some embodiments of Formula (I'), (I), (I*), (Ia)-(If), or (Ia-1)-(If-1), is
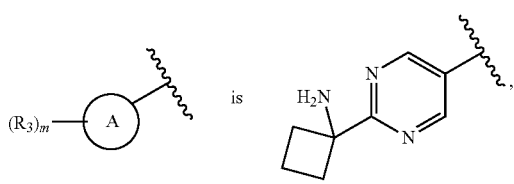
In some embodiments of Formula (I'), (I), (I*), (Ia)-(If), or (Ia-1)-(If-1),
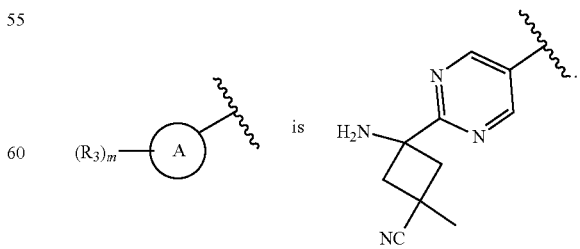
In some embodiments of Formula (I'), (I), (I*), (Ia)-(If), or (Ia-1)-(If-1),

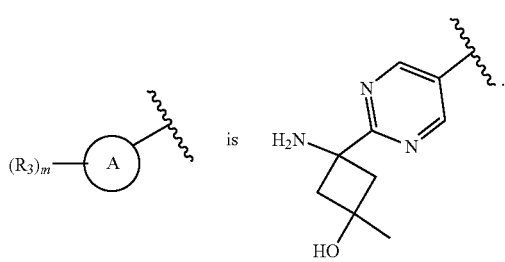
In some embodiments of Formula (I'), (I), (I*), (Ia)-(If), or (Ia-1)-(If-1),
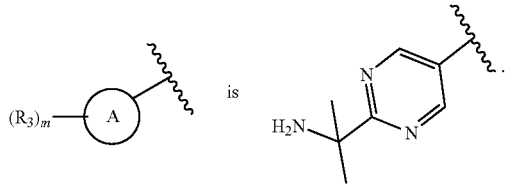
In some embodiments of Formula (I'), (I), (I*), (Ia)-(If), or (Ia-1)-(If-1),
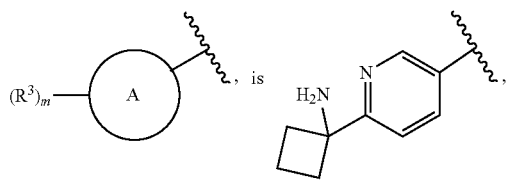
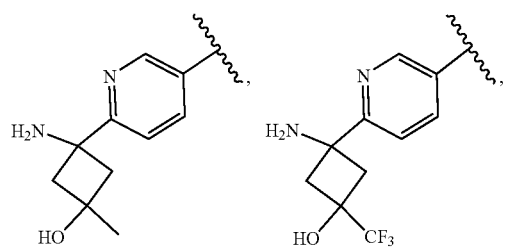
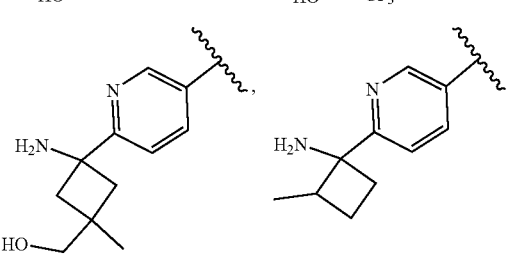
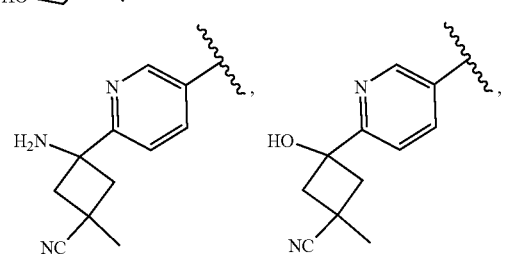
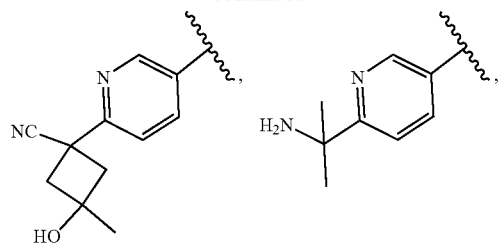
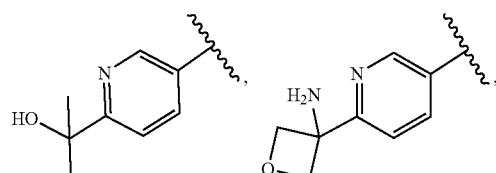
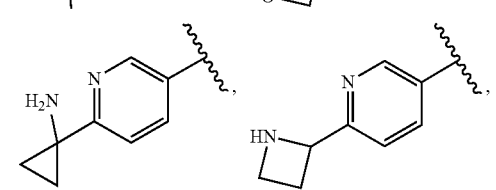
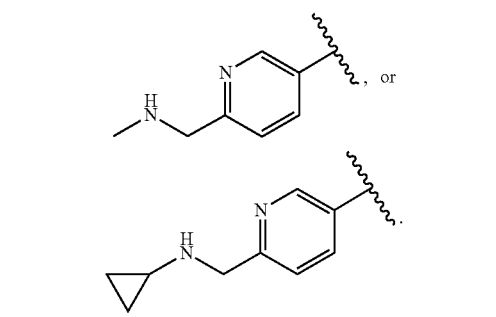
In some embodiments of Formula (I'), (I), (I*), (Ia)-(If), or (Ia-1)-(If-1),
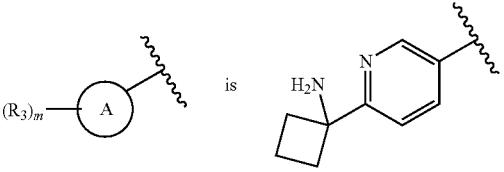
In some embodiments of Formula (I'), (I), (I*), (Ia)-(If), or (Ia-1)-(If-1),
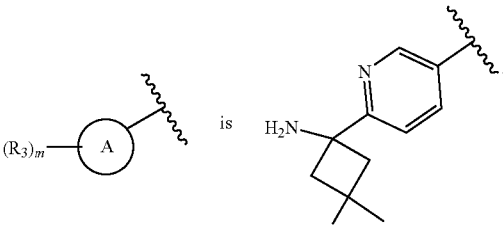
In some embodiments of Formula (I'), (I), (I*), (Ia)-(If), or (Ia-1)-(If-1),

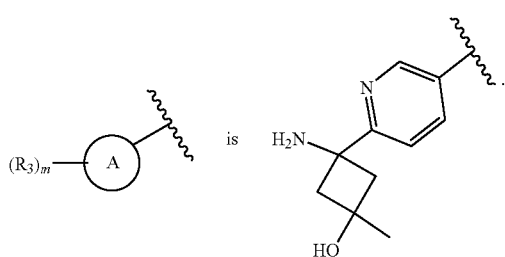
In some embodiments of Formula (I'), (I), (I*), (Ia)-(If), or (Ia-1)-(If-1), is
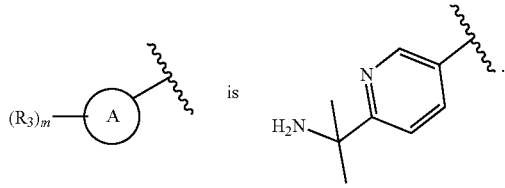
In some embodiments of Formula (I'), (I), (I*), (Ia)-(If), or (Ia-1)-(If-1), is
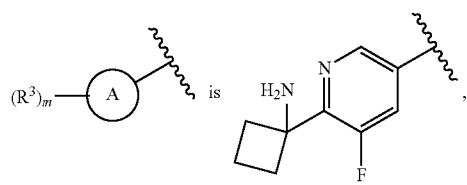
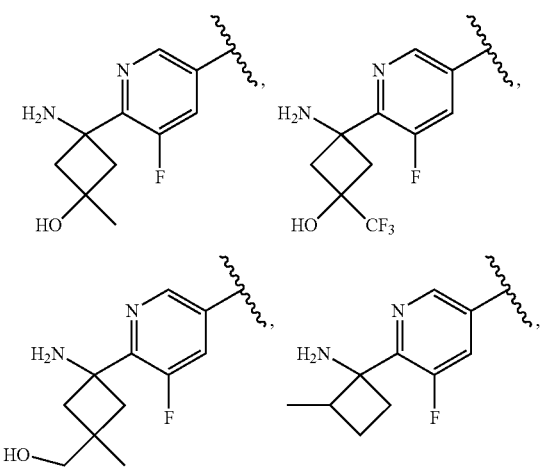
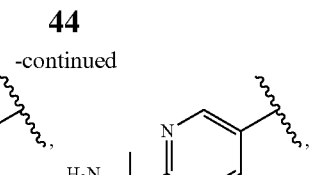
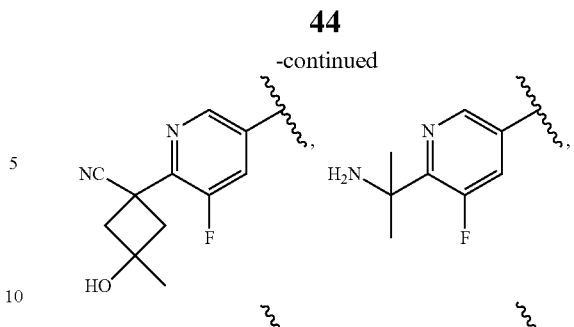
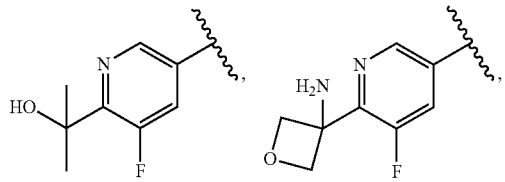
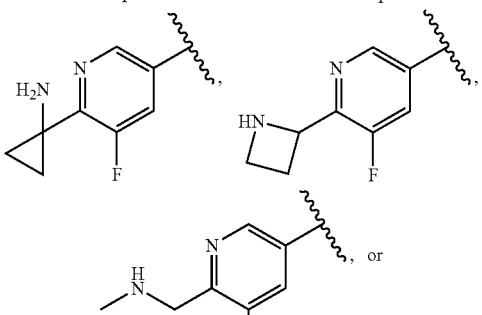
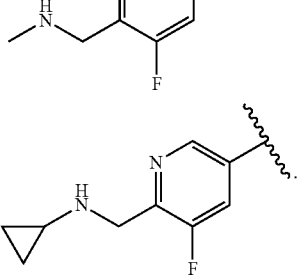
In some embodiments of Formula (I'), (I), (I*), (Ia)-(If), or (Ia-1)-(If-1),
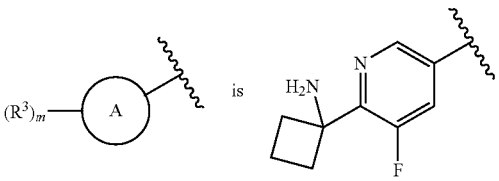
In some embodiments of Formula (I'), (I), (I*), (Ia)-(If), or (Ia-1)-(If-1),
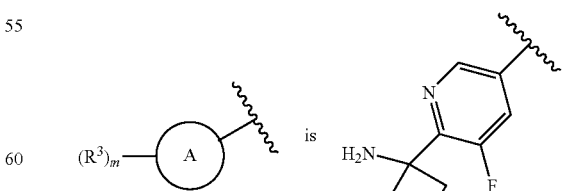
In some embodiments of Formula (I'), (I), (I*), (Ia)-(If), or (Ia-1)-(If-1),

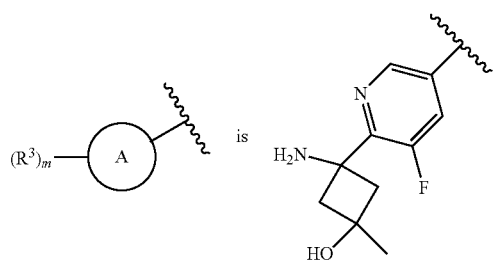 is 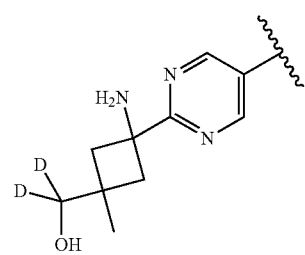
In some embodiments of Formula (I'), (I), (I*), (Ia)-(If), or (Ia-1)-(If-1),
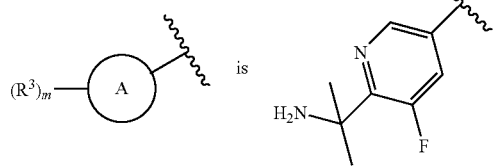 is 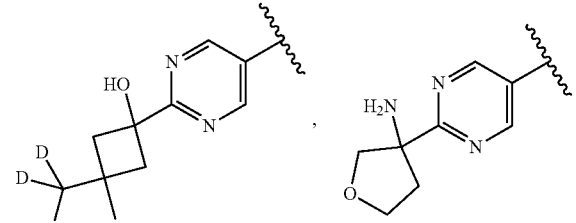
In some embodiments of Formula (I'), (I), (I*), (Ia)-(If), or (Ia-1)-(If-1), is
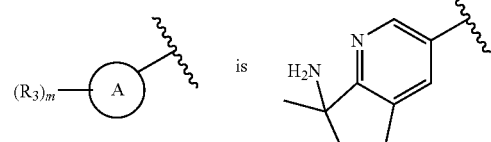
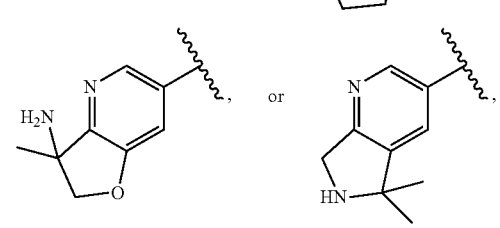 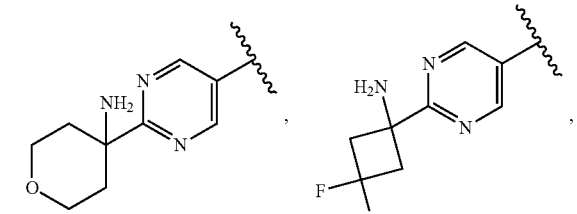
In some embodiments of Formula (I'), (I), (I*), (Ia)-(If), or (Ia-1)-(If-1) is
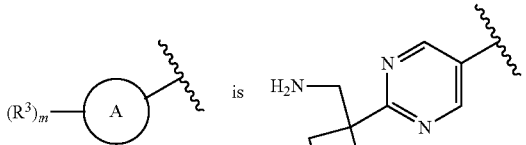 is 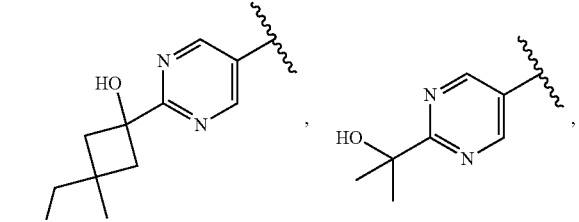
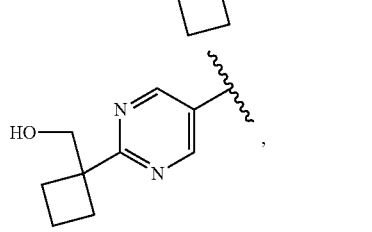
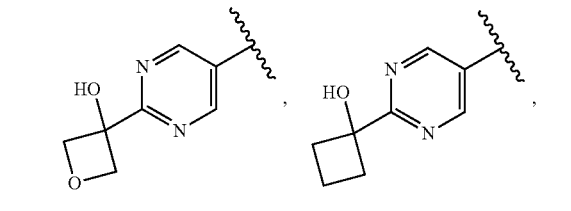

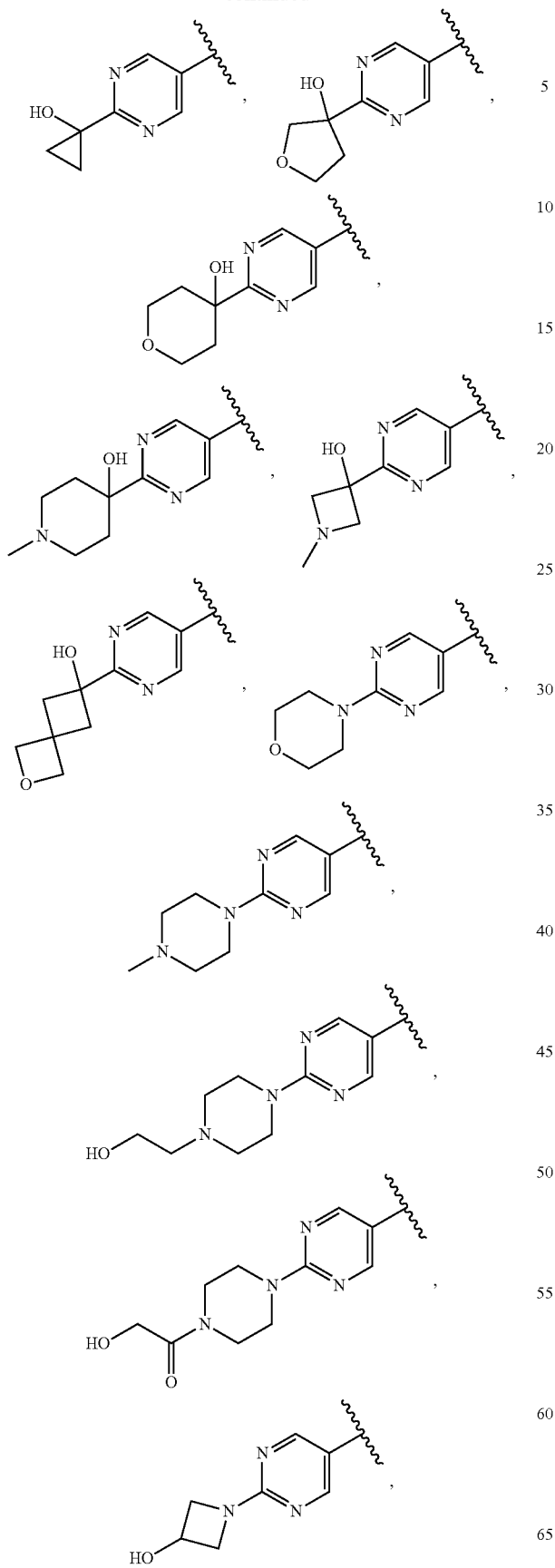
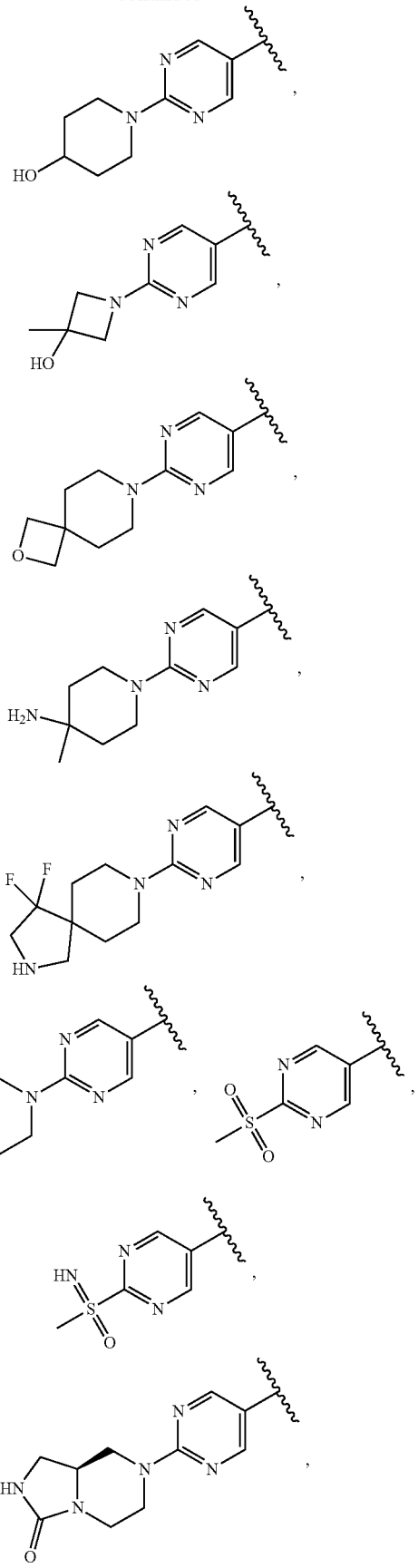

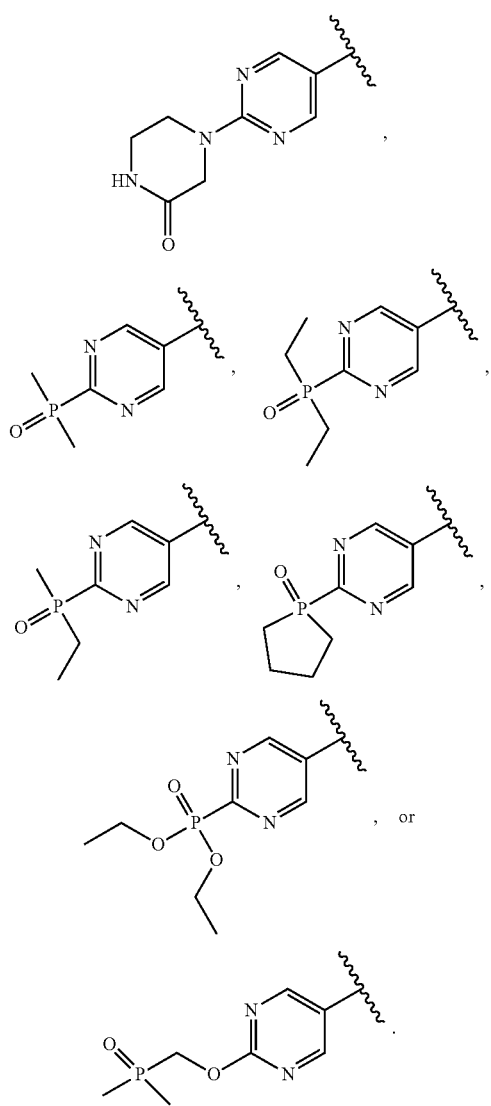
In some embodiments of Formula (P), (I), (I*), (Ia)-(If), or (Ia-1)-(If-1), is
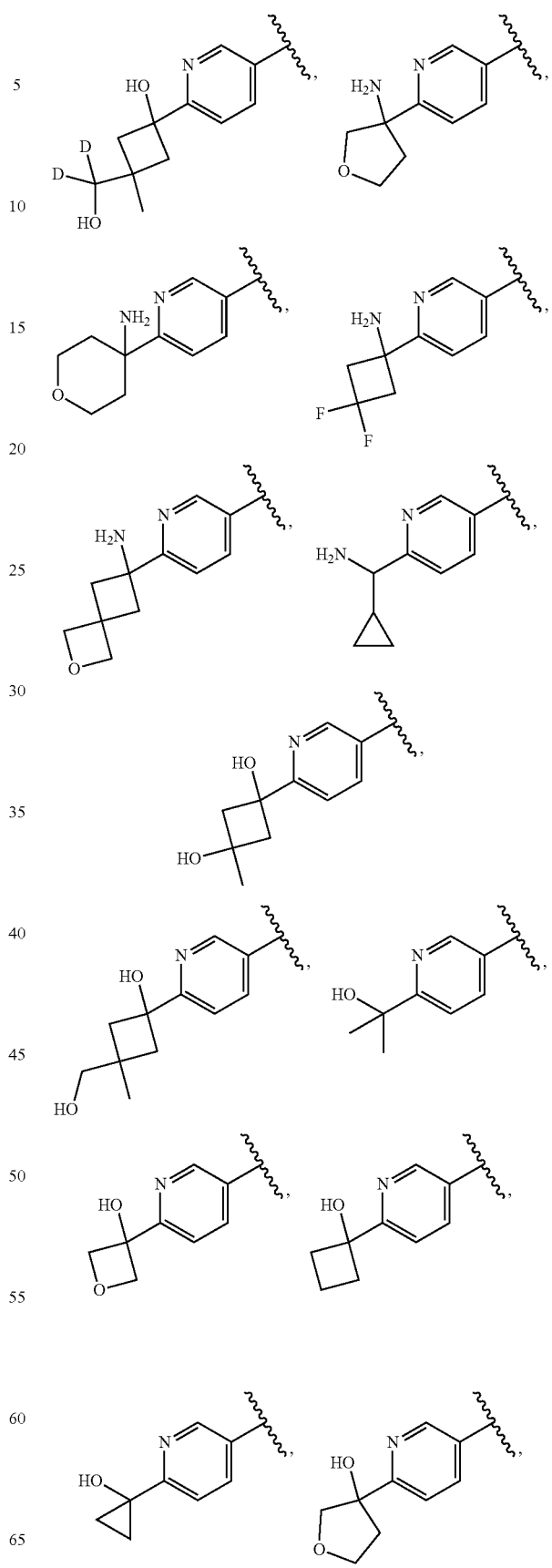

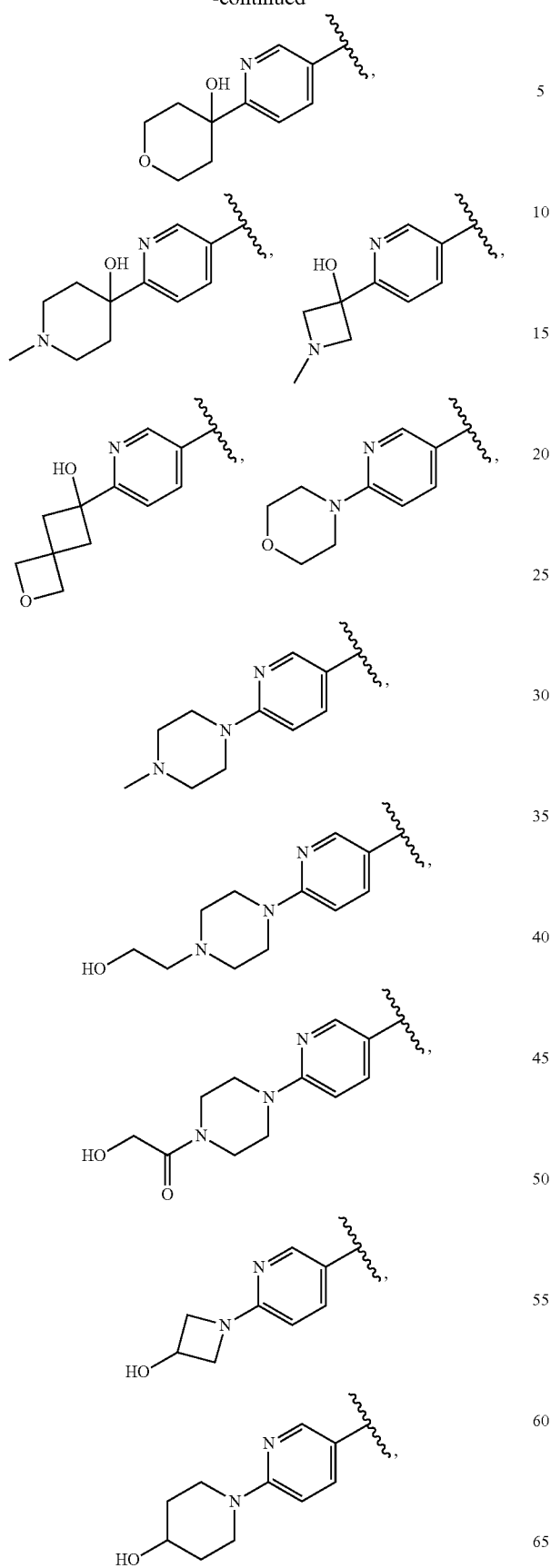
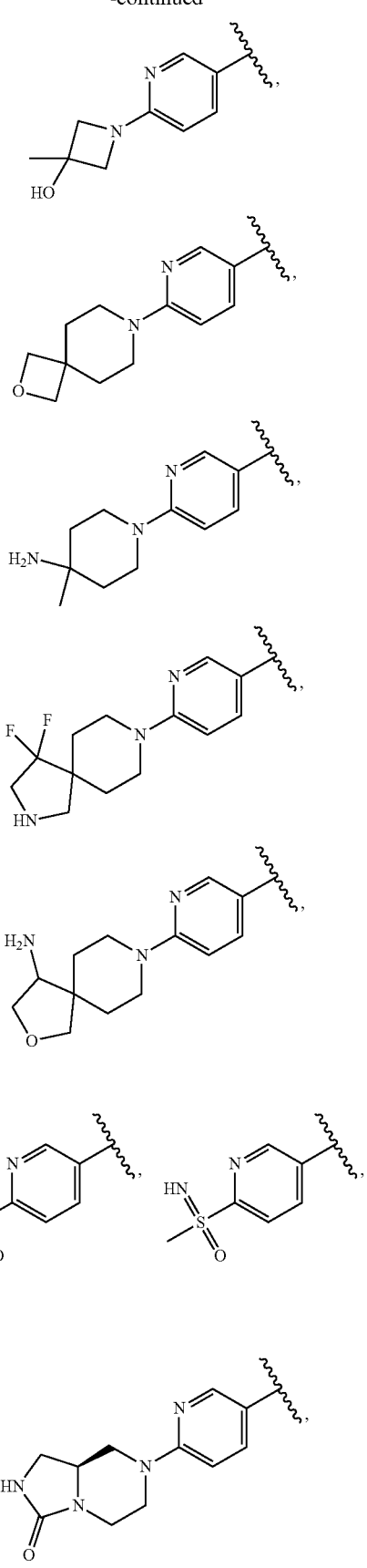

-continued
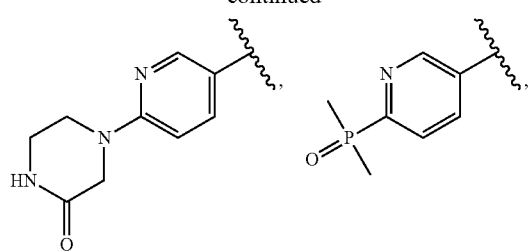
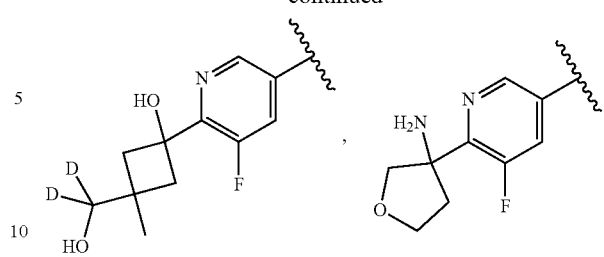
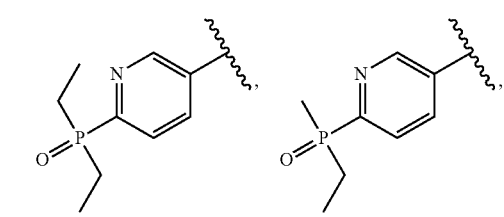
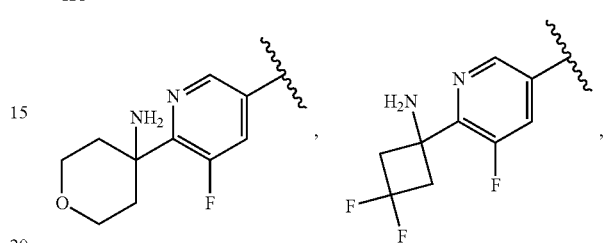
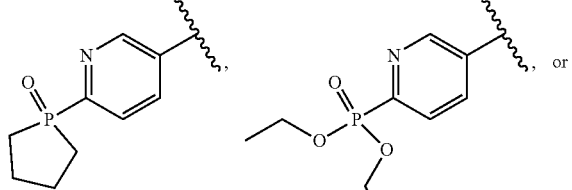, or
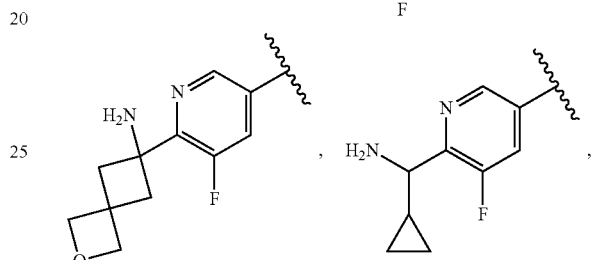
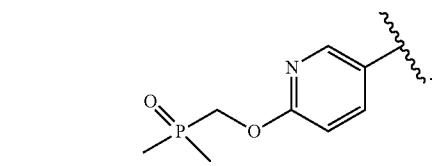
In some embodiments of Formula (P), (I), (I*), (Ia)-(If), or (Ia-1)-(If-1),
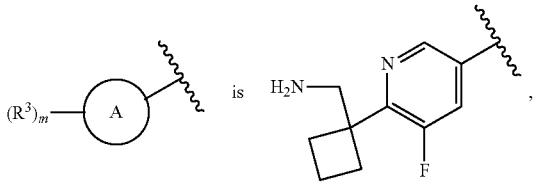 is 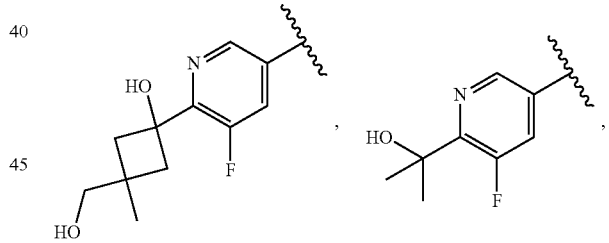
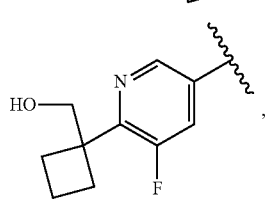
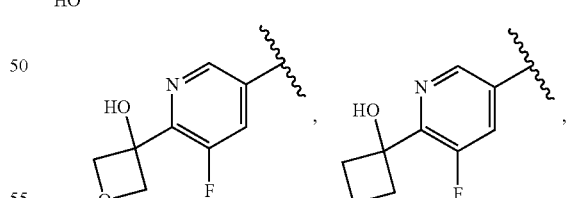
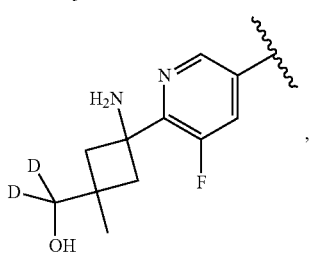
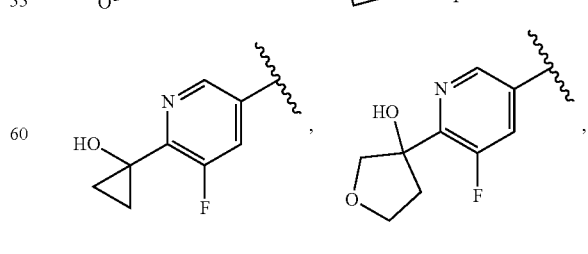

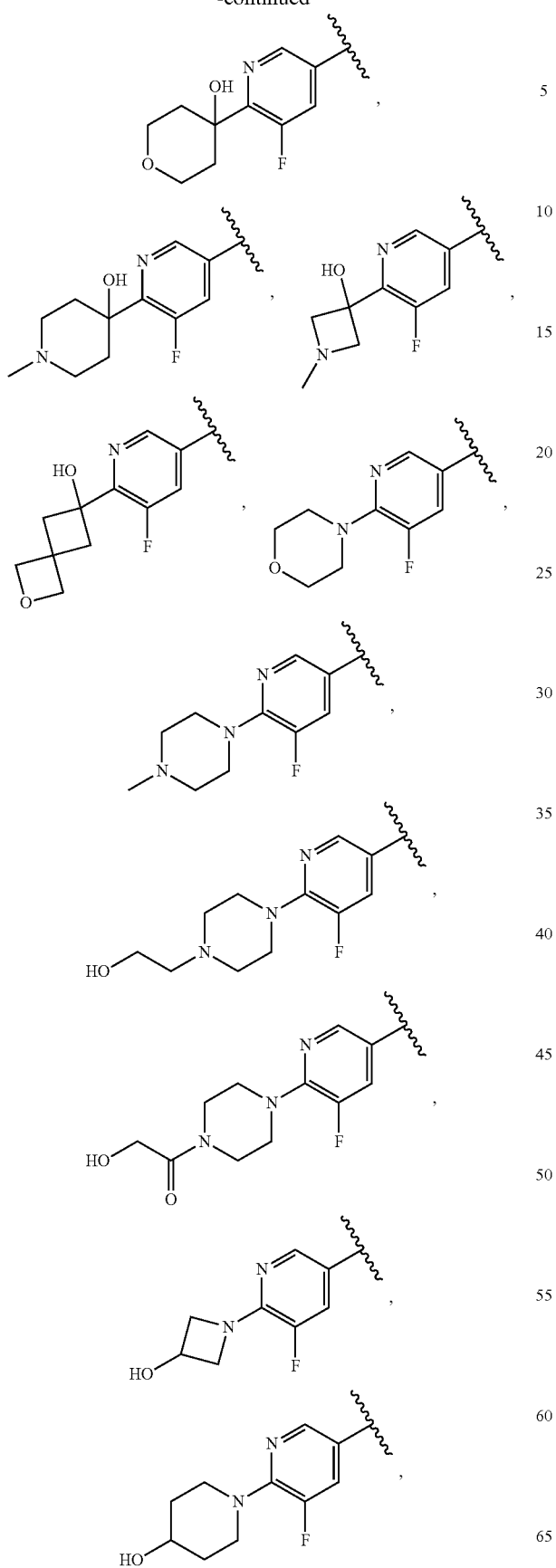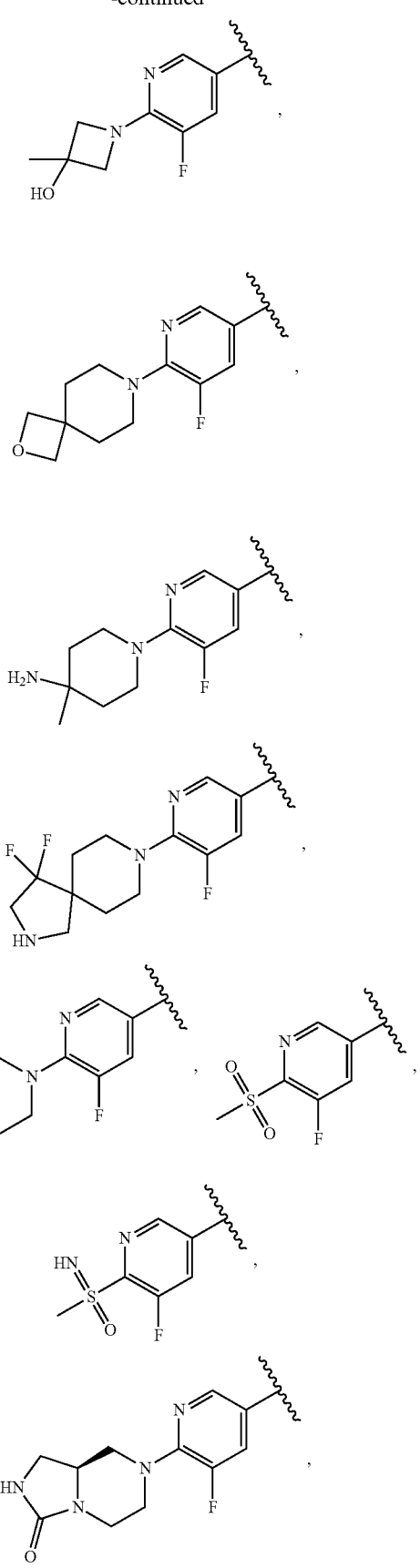

-continued

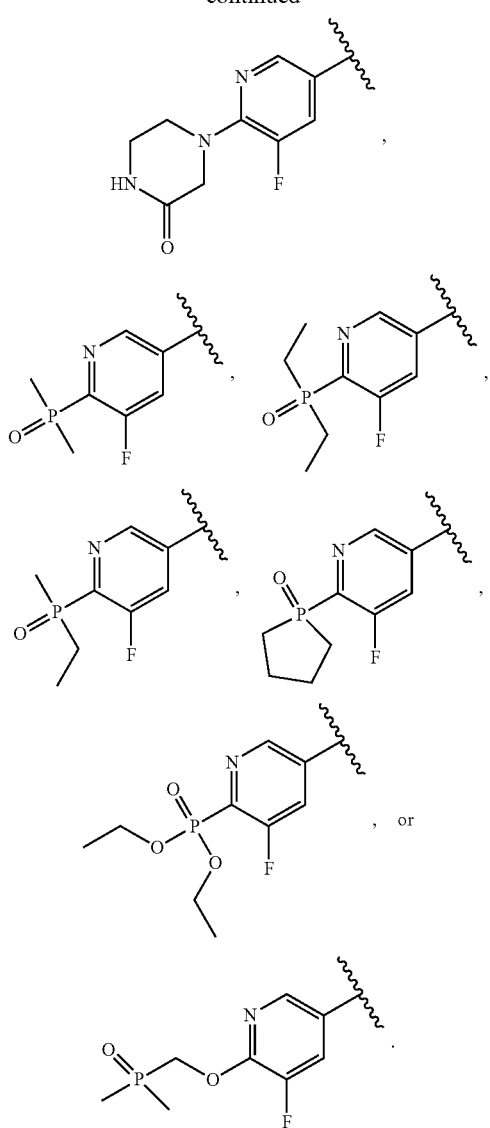

In some embodiments of Formula (I'), (I), (I*), (Ia)-(If), or (Ia-1)-(If-1),

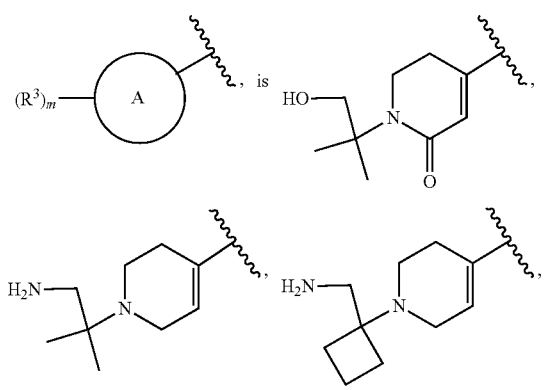

-continued

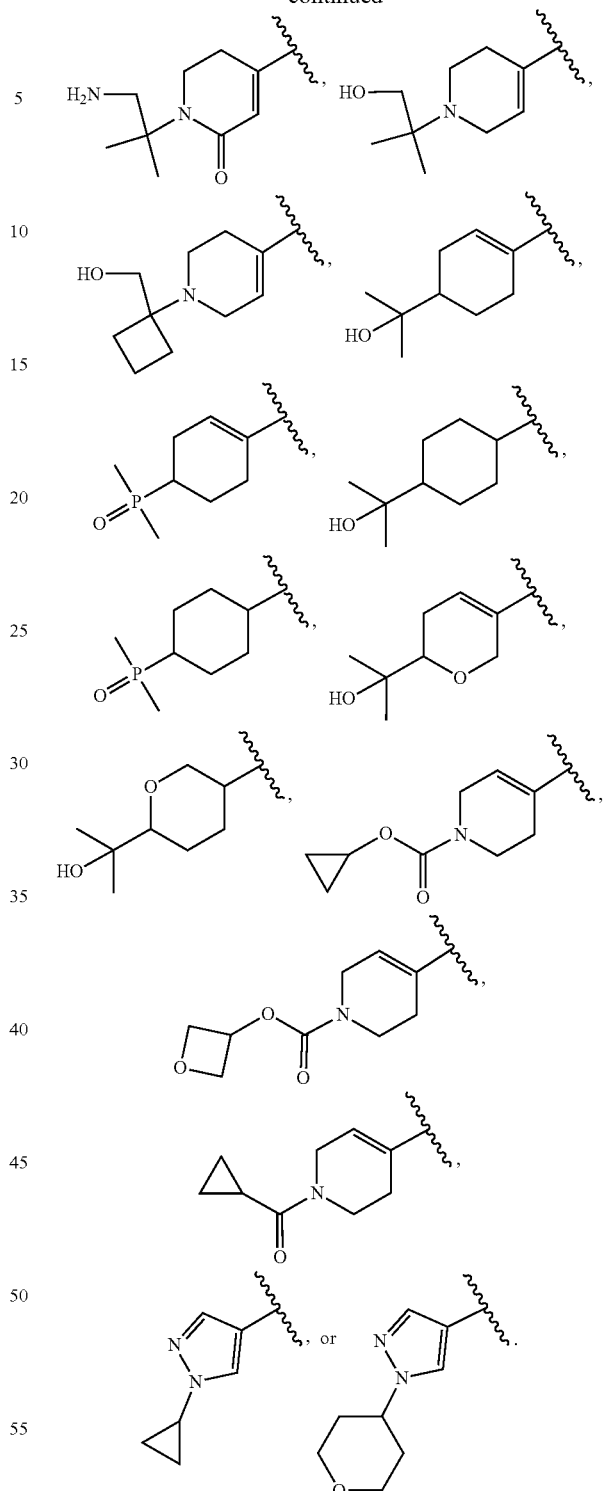

In some embodiments of a compound disclosed herein, each $R^a$ is independently $C_1$-$C_6$alkyl, $C_1$-$C_6$haloalkyl, $C_1$-$C_6$heteroalkyl, -L-cycloalkyl, or -L-heterocycloalkyl; wherein each alkyl, heteroalkyl, cycloalkyl, heterocycloalkyl is independently optionally substituted with one or more R. In some embodiments of a compound disclosed herein, each $R^a$ is independently $C_1$-$C_6$alkyl, $C_1$-$C_6$haloalkyl, or $C_1$-$C_6$heteroalkyl; wherein each alkyl and heteroalkyl is independently optionally substituted with one or more R. In some embodiments of a compound disclosed herein, each $R^a$ is independently $C_1$-$C_6$alkyl, $C_1$-$C_6$haloalkyl, $C_1$-$C_6$heteroalkyl, -L-cycloalkyl, or -L-heterocycloalkyl. In some embodiments of a compound disclosed herein, each $R^a$ is independently $C_1$-$C_6$alkyl, $C_1$-$C_6$haloalkyl, or $C_1$-$C_6$heteroalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$heteroalkyl, -L-cycloalkyl, or -L-heterocycloalkyl; wherein each alkyl, heteroalkyl, cycloalkyl, heterocycloalkyl is independently optionally substituted with one or more R. In some embodiments of a compound disclosed herein, each $R^b$ is independently hydrogen, $C_1$-$C_6$alkyl, $C_1$-$C_6$haloalkyl, or $C_1$-$C_6$heteroalkyl; wherein each alkyl and heteroalkyl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$heteroalkyl, -L-cycloalkyl, or -L-heterocycloalkyl. In some embodiments of a compound disclosed herein, each $R^b$ is independently hydrogen, $C_1$-$C_6$alkyl, $C_1$-$C_6$haloalkyl, or $C_1$-$C_6$heteroalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is hydrogen. In some embodiments of a compound disclosed herein, each $R^b$ is independently $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$heteroalkyl, -L-cycloalkyl, or -L-heterocycloalkyl; wherein each alkyl, heteroalkyl, cycloalkyl, heterocycloalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, or $C_1$-$C_6$heteroalkyl; wherein each alkyl and heteroalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, $C_1$-$C_6$heteroalkyl, -L-cycloalkyl, or -L-heterocycloalkyl. In some embodiments of a compound disclosed herein, each $R^c$ and $R^d$ are independently hydrogen, $C_1$-$C_6$alkyl, $C_1$-$C_6$haloalkyl, or $C_1$-$C_6$heteroalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl. In some embodiments of a compound disclosed herein, each $R^c$ and $R^d$ are hydrogen. In some embodiments of a compound disclosed herein, each $R^c$ and $R^d$ are independently $C_1$-$C_6$alkyl.

In some embodiments of a compound disclosed herein, $R^c$ and $R^d$ are taken together with the atom to which they are attached to form a heterocycloalkyl independently optionally substituted with one or more R.

In some embodiments of a compound disclosed herein, L is absent. In some embodiments of a compound disclosed herein, L is $C_1$-$C_3$alkylene optionally substituted with one or more R. In some embodiments of a compound disclosed herein, L is $C_1$-$C_3$alkylene. In some embodiments of a compound disclosed herein, L is $C_1$alkylene. In some embodiments of a compound disclosed herein, L is $C_2$alkylene. In some embodiments of a compound disclosed herein, L is $C_3$alkylene. In some embodiments of a compound disclosed herein, L is —$CH_2$—. In some embodiments of a compound disclosed herein, L is —$CH_2CH_2$—. In some embodiments of a compound disclosed herein, L is —$CH_2CH_2CH_2$—.

In some embodiments of a compound disclosed herein, each R is independently halogen, —CN, —OH, —$OC_1$-$C_3$alkyl, —S(=O)$C_1$-$C_3$alkyl, —S(=O)$_2C_1$-$C_3$alkyl, —S(=O)$_2NH_2$, —S(=O)$_2NHC_1$-$C_3$alkyl, —S(=O)$_2N(C_1$-$C_3$alkyl)$_2$, —$NH_2$, —$NHC_1$-$C_3$alkyl, —N($C_1$-$C_3$alkyl)$_2$, —NHC(=O)$OC_1$-$C_3$alkyl, —C(=O)$C_1$-$C_3$alkyl, —C(=O)OH, —C(=O)$OC_1$-$C_3$alkyl, —C(=O)$NH_2$, —C(=O)N($C_1$-$C_3$alkyl)$_2$, —C(=O)$NHC_1$-$C_3$alkyl, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl.

In some embodiments of a compound disclosed herein, each R is independently halogen, —CN, —OH, —$OC_1$-$C_3$alkyl, —$NH_2$, —$NHC_1$-$C_3$alkyl, —N($C_1$-$C_3$alkyl)$_2$, —NHC(=O)$OC_1$-$C_3$alkyl, —C(=O)$C_1$-$C_3$alkyl, —C(=O)OH, —C(=O)$OC_1$-$C_3$alkyl, —C(=O)$NH_2$, —C(=O)N($C_1$-$C_3$alkyl)$_2$, —C(=O)$NHC_1$-$C_3$alkyl, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl; or two R on the same atom are taken together to form an oxo. In some embodiments of a compound disclosed herein, each R is independently halogen, —CN, —OH, —$OC_1$-$C_3$alkyl, —$NH_2$, —$NHC_1$-$C_3$alkyl, —N($C_1$-$C_3$alkyl)$_2$, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl; or two R on the same atom are taken together to form an oxo. In some embodiments of a compound disclosed herein, each R is independently halogen, —CN, —OH, —$OC_1$-$C_3$alkyl, —$NH_2$, —$NHC_1$-$C_3$alkyl, —N($C_1$-$C_3$alkyl)$_2$, —NHC(=O)$OC_1$-$C_3$alkyl, —C(=O)$C_1$-$C_3$alkyl, —C(=O)OH, —C(=O)$OC_1$-$C_3$alkyl, —C(=O)$NH_2$, —C(=O)N($C_1$-$C_3$alkyl)$_2$, —C(=O)$NHC_1$-$C_3$alkyl, $C_1$-$C_3$alkyl, $C_1$-$C_3$haloalkyl, $C_1$-$C_3$hydroxyalkyl, $C_1$-$C_3$aminoalkyl, or $C_1$-$C_3$heteroalkyl; or two R on the same atom are taken together to form an oxo. In some embodiments of a compound disclosed herein, each R is independently halogen, —CN, —OH, —$OC_1$-$C_3$alkyl, —$NH_2$, —$NHC_1$-$C_3$alkyl, —N($C_1$-$C_3$alkyl)$_2$, $C_1$-$C_3$alkyl, $C_1$-$C_3$haloalkyl, $C_1$-$C_3$hydroxyalkyl, $C_1$-$C_3$aminoalkyl, or $C_1$-$C_3$heteroalkyl; or two R on the same atom are taken together to form an oxo. In some embodiments of a compound disclosed herein, each R is independently halogen, —CN, —OH, —$OC_1$-$C_3$alkyl, —$NH_2$, —$NHC_1$-$C_3$alkyl, —N($C_1$-$C_3$alkyl)$_2$, $C_1$-$C_3$alkyl, $C_1$-$C_3$haloalkyl, or $C_1$-$C_3$hydroxyalkyl; or two R on the same atom are taken together to form an oxo. In some embodiments of a compound disclosed herein, each R is independently halogen, —CN, —OH, —$NH_2$, $C_1$-$C_3$alkyl, $C_1$-$C_3$haloalkyl, or $C_1$-$C_3$hydroxyalkyl; or two R on the same atom are taken together to form an oxo. In some embodiments of a compound disclosed herein, each R is independently halogen, —CN, —OH, —$NH_2$, $C_1$-$C_3$alkyl, or $C_1$-$C_3$haloalkyl. In some embodiments of a compound disclosed herein, each R is independently halogen, —CN, —OH, —$NH_2$, or $C_1$-$C_3$alkyl. In some embodiments of a compound disclosed herein, each R is independently halogen or $C_1$-$C_3$alkyl. In some embodiments of a compound disclosed herein, each R is independently halogen. In some embodiments of a compound disclosed herein, each R is independently $C_1$-$C_3$alkyl.

Any combination of the groups described above for the various variables is contemplated herein. Throughout the specification, groups and substituents thereof are chosen by one skilled in the field to provide stable moieties and compounds.

In some embodiments, the compound is selected from a compound found in Table 1.

TABLE 1

| Ex. | Structure |
|---|---|
| 1 | 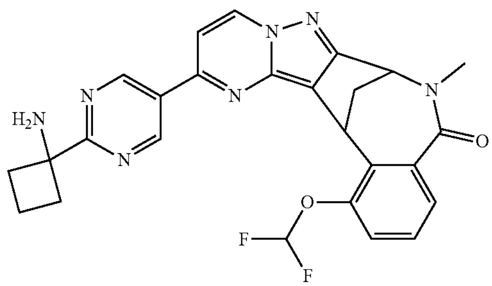 [SMILES: CN1C(=O)c2cccc(OC(F)F)c2C2CC1c1nn3ccc(-c4cnc(C5(N)CCC5)nc4)nc3c12] |
| 2 | 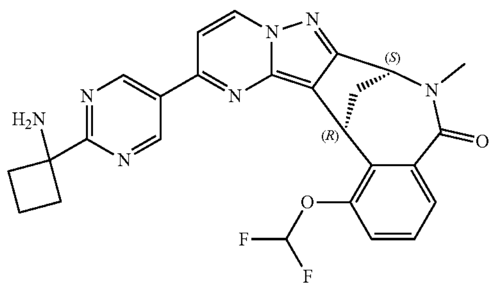 |
| 3 | 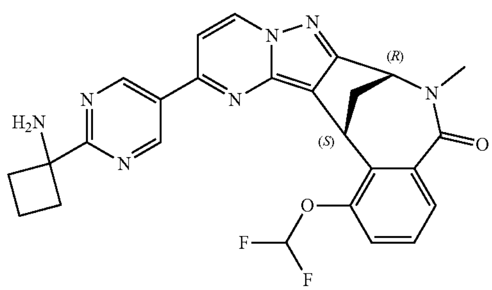 |
| 4 | 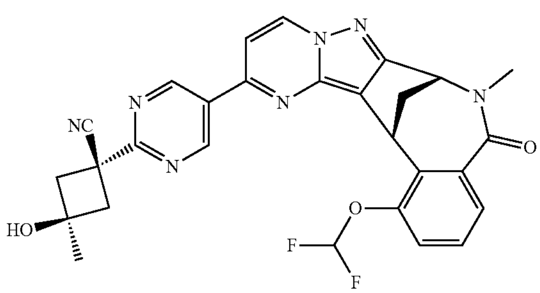 |
| 5 | 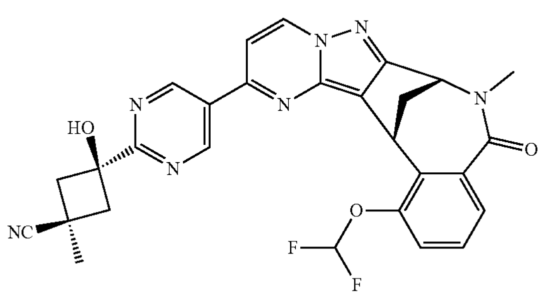 [SMILES: CN1C(=O)c2cccc(OC(F)F)c2[C@H]2C[C@@H]1c1nn3ccc(-c4cnc([C@]5(O)C[C@@](C)(C#N)C5)nc4)nc3c12] |

TABLE 1-continued

| Ex. | Structure |
| --- | --- |
| 6 | 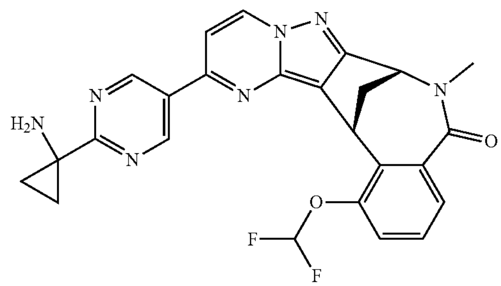 [SMILES: CN1C(=O)c2cccc(OC(F)F)c2[C@H]2C[C@@H]1c1nn3ccc(-c4cnc(C5(N)CC5)nc4)nc3c12] |
| 7 | 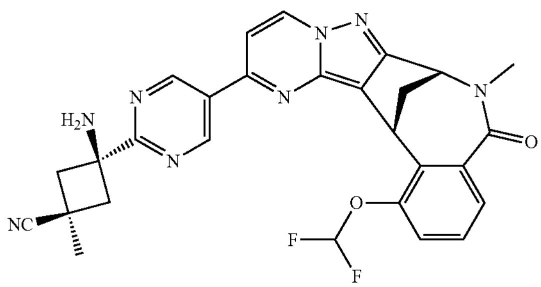 [SMILES: CN1C(=O)c2cccc(OC(F)F)c2[C@H]2C[C@@H]1c1nn3ccc(-c4cnc([C@]5(N)C[C@@](C)(C#N)C5)nc4)nc3c12] |
| 8 | 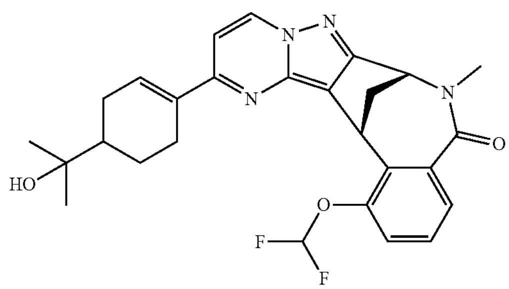 [SMILES: CN1C(=O)c2cccc(OC(F)F)c2[C@H]2C[C@@H]1c1nn3ccc(C4=CCC(C(C)(C)O)CC4)nc3c12] |
| 9 | 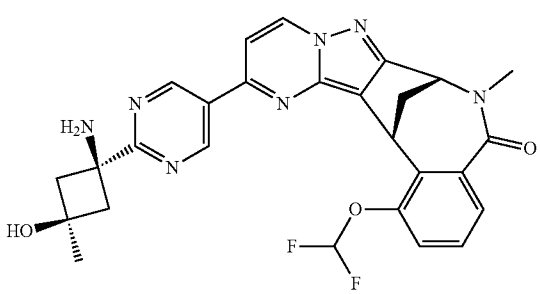 |
| 10 | 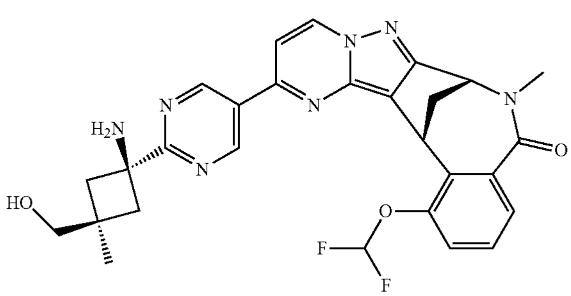 [SMILES: CN1C(=O)c2cccc(OC(F)F)c2[C@H]2C[C@@H]1c1nn3ccc(-c4cnc([C@]5(N)C[C@@](C)(CO)C5)nc4)nc3c12] |

TABLE 1-continued

| Ex. | Structure |
|---|---|
| 11 | 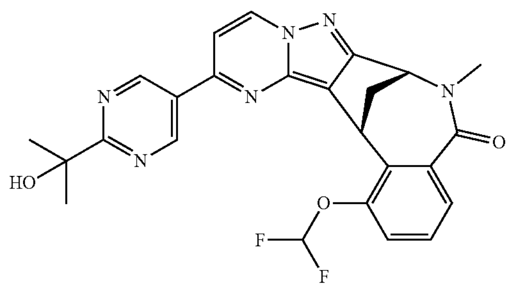 [SMILES: CN1C(=O)c2cccc(OC(F)F)c2[C@H]2C[C@@H]1c1nn3ccc(-c4cnc(C(C)(C)O)nc4)nc3c12] |
| 12 | 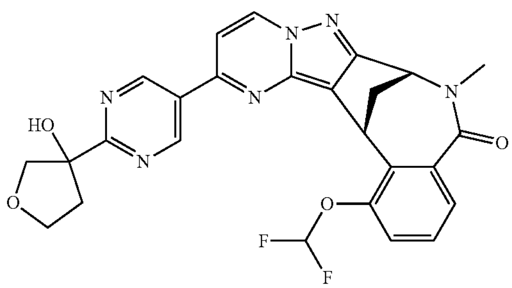 [SMILES: CN1C(=O)c2cccc(OC(F)F)c2[C@H]2C[C@@H]1c1nn3ccc(-c4cnc(C5(O)CCOC5)nc4)nc3c12] |
| 13 | 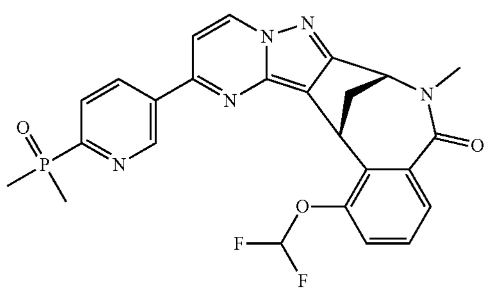 [SMILES: CN1C(=O)c2cccc(OC(F)F)c2[C@H]2C[C@@H]1c1nn3ccc(-c4ccc(P(C)(C)=O)nc4)nc3c12] |
| 14 | 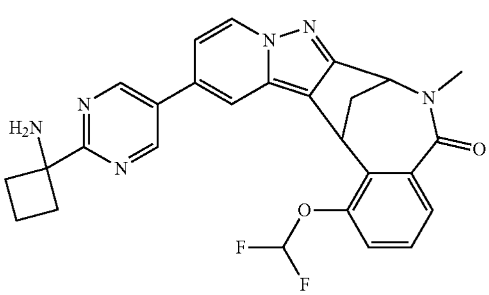 |
| 15 | 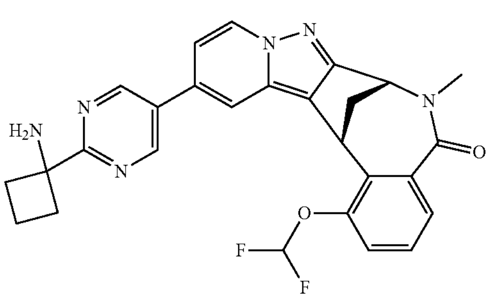 [SMILES: CN1C(=O)c2cccc(OC(F)F)c2[C@H]2C[C@@H]1c1nn3ccc(-c4cnc(C5(N)CCC5)nc4)cc3c12] |

TABLE 1-continued

| Ex. | Structure |
|---|---|
| 16 | 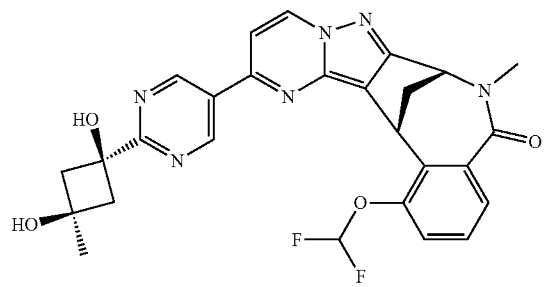 |
| 17 | 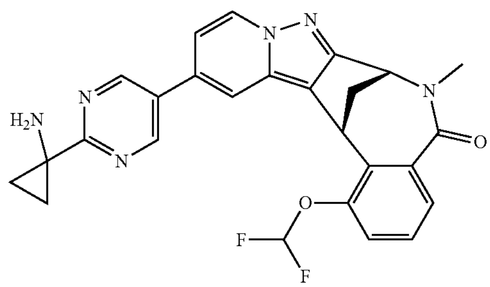 [SMILES: CN1C(=O)c2cccc(OC(F)F)c2[C@H]2C[C@@H]1c1nn3ccc(-c4cnc(C5(N)CC5)nc4)cc3c12] |
| 18 | 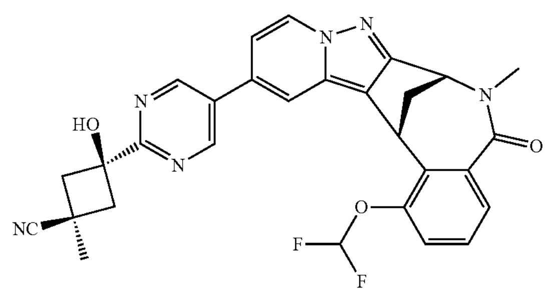 [SMILES: CN1C(=O)c2cccc(OC(F)F)c2[C@H]2C[C@@H]1c1nn3ccc(-c4cnc([C@]5(O)C[C@@](C)(C#N)C5)nc4)cc3c12] |
| 19 | 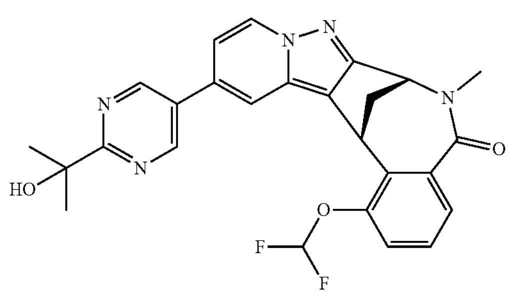 [SMILES: CN1C(=O)c2cccc(OC(F)F)c2[C@H]2C[C@@H]1c1nn3ccc(-c4cnc(C(C)(C)O)nc4)cc3c12] |
| 20 | 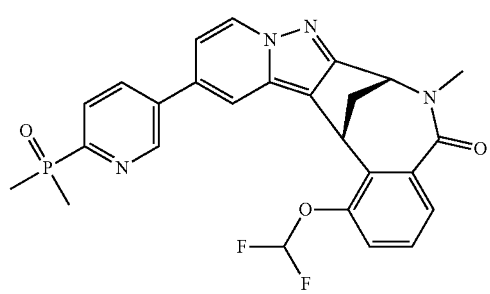 [SMILES: CN1C(=O)c2cccc(OC(F)F)c2[C@H]2C[C@@H]1c1nn3ccc(-c4ccc(P(C)(C)=O)nc4)cc3c12] |

TABLE 1-continued

| Ex. | Structure |
|---|---|
| 21 | 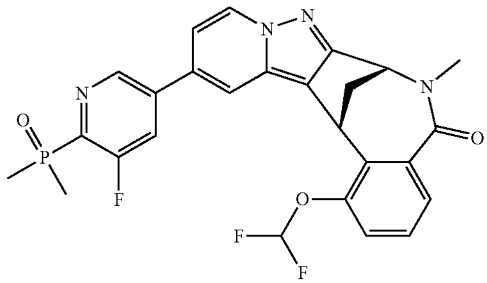 [SMILES: CN1C(=O)c2cccc(OC(F)F)c2[C@H]2C[C@@H]1c1nn3ccc(-c4cnc(P(C)(C)=O)c(F)c4)cc3c12] |
| 22 | 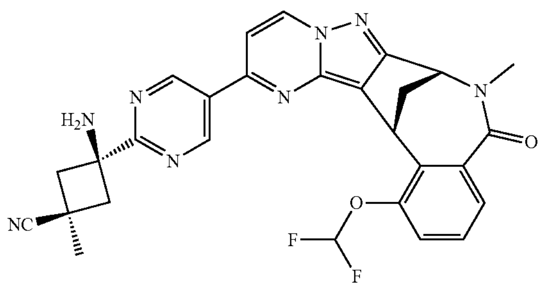 [SMILES: CN1C(=O)c2cccc(OC(F)F)c2[C@H]2C[C@@H]1c1nn3ccc(-c4cnc([C@]5(N)C[C@@](C)(C#N)C5)nc4)nc3c12] |
| 23 | 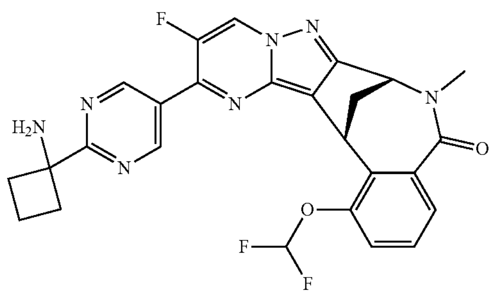 [SMILES: CN1C(=O)c2cccc(OC(F)F)c2[C@H]2C[C@@H]1c1nn3cc(F)c(-c4cnc(C5(N)CCC5)nc4)nc3c12] |
| 24 | 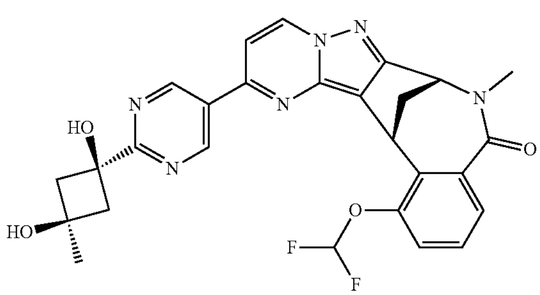 |
| 25 | 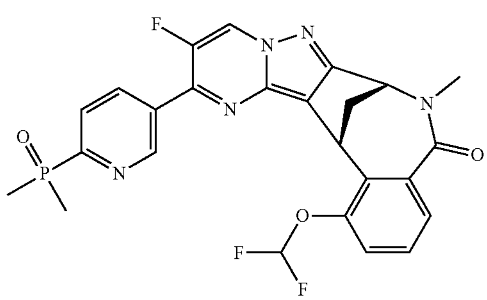 [SMILES: CN1C(=O)c2cccc(OC(F)F)c2[C@H]2C[C@@H]1c1nn3cc(F)c(-c4ccc(P(C)(C)=O)nc4)nc3c12] |

TABLE 1-continued

| Ex. | Structure |
|---|---|
| 26 | 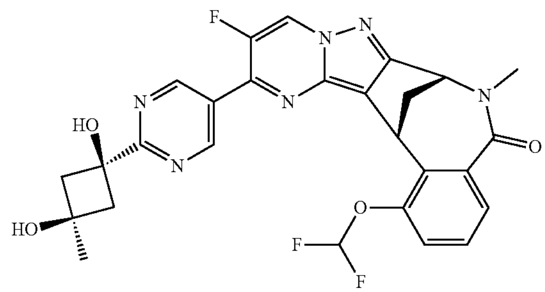 [SMILES: CN1C(=O)c2cccc(OC(F)F)c2[C@H]2C[C@@H]1c1nn3cc(F)c(-c4cnc([C@]5(O)C[C@@](C)(O)C5)nc4)nc3c12] |
| 27 | 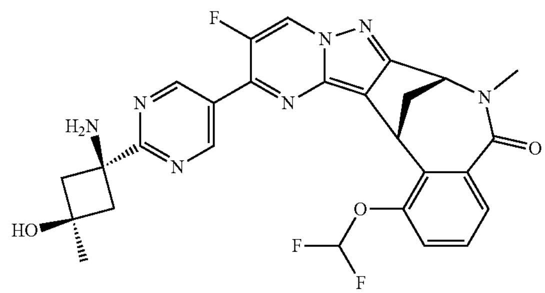 [SMILES: CN1C(=O)c2cccc(OC(F)F)c2[C@H]2C[C@@H]1c1nn3cc(F)c(-c4cnc([C@]5(N)C[C@@](C)(O)C5)nc4)nc3c12] |
| 28 | 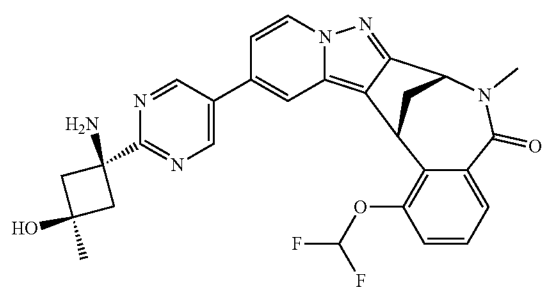 |
| 29 | 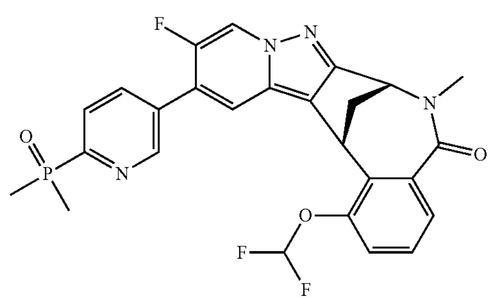 [SMILES: CN1C(=O)c2cccc(OC(F)F)c2[C@H]2C[C@@H]1c1nn3cc(F)c(-c4ccc(P(C)(C)=O)nc4)cc3c12] |
| 30 | 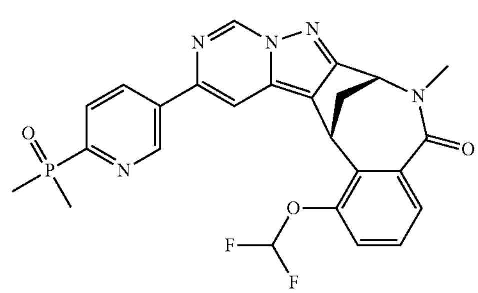 [SMILES: CN1C(=O)c2cccc(OC(F)F)c2[C@H]2C[C@@H]1c1nn3cnc(-c4ccc(P(C)(C)=O)nc4)cc3c12] |

TABLE 1-continued

| Ex. | Structure |
|---|---|
| 31 | 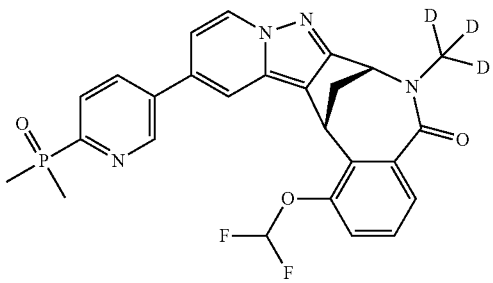 [SMILES: [2H]C([2H])([2H])N1C(=O)c2cccc(OC(F)F)c2[C@H]2C[C@@H]1c1nn3ccc(-c4ccc(P(C)(C)=O)nc4)cc3c12] |
| 32 | 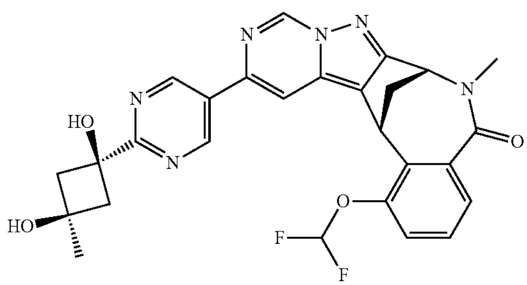 |
| 33 | 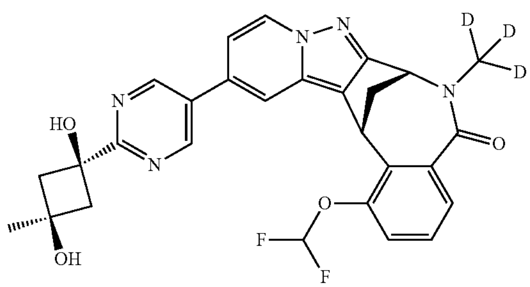 [SMILES: [2H]C([2H])([2H])N1C(=O)c2cccc(OC(F)F)c2[C@H]2C[C@@H]1c1nn3ccc(-c4cnc([C@]5(O)C[C@@](C)(O)C5)nc4)cc3c12] |
| 34 | 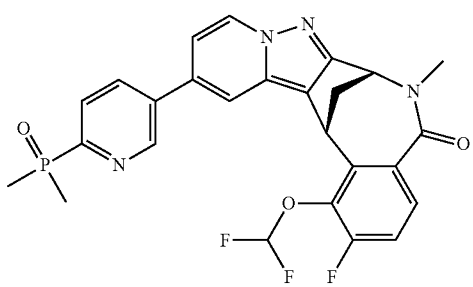 [SMILES: CN1C(=O)c2ccc(F)c(OC(F)F)c2[C@H]2C[C@@H]1c1nn3ccc(-c4ccc(P(C)(C)=O)nc4)cc3c12] |
| 35 | 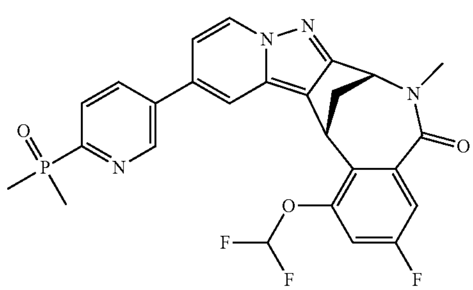 [SMILES: CN1C(=O)c2cc(F)cc(OC(F)F)c2[C@H]2C[C@@H]1c1nn3ccc(-c4ccc(P(C)(C)=O)nc4)cc3c12] |

TABLE 1-continued

| Ex. | Structure |
|---|---|
| 36 | (structure) |
| 37 | (structure) |
| 38 | (structure) |
| 39 | (structure) |
| 40 | (structure) |

TABLE 1-continued

| Ex. | Structure |
|---|---|
| 41 | 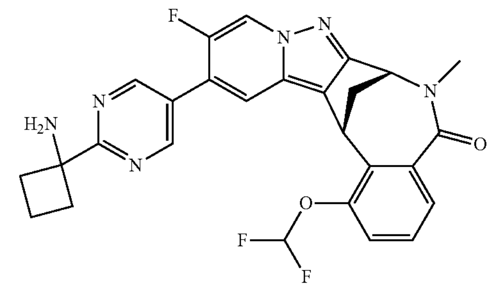 [SMILES: CN1C(=O)c2cccc(OC(F)F)c2[C@H]2C[C@@H]1c1nn3cc(F)c(-c4cnc(C5(N)CCC5)nc4)cc3c12] |
| 42 | 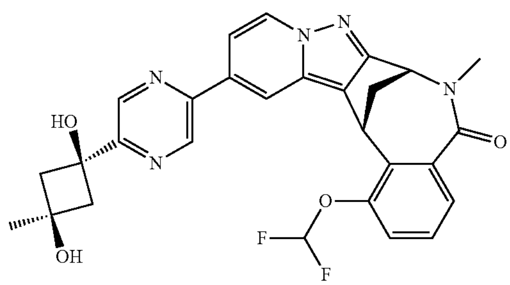 [SMILES: CN1C(=O)c2cccc(OC(F)F)c2[C@H]2C[C@@H]1c1nn3ccc(-c4cnc([C@]5(O)C[C@@](C)(O)C5)cn4)cc3c12] |
| 43 | 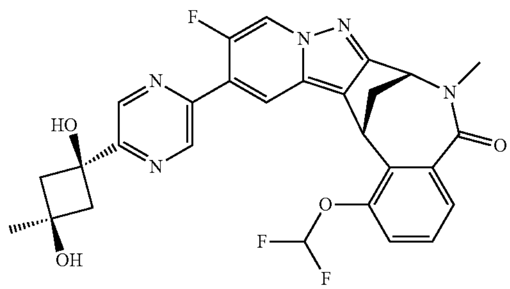 [SMILES: CN1C(=O)c2cccc(OC(F)F)c2[C@H]2C[C@@H]1c1nn3cc(F)c(-c4cnc([C@]5(O)C[C@@](C)(O)C5)cn4)cc3c12] |
| 44 | 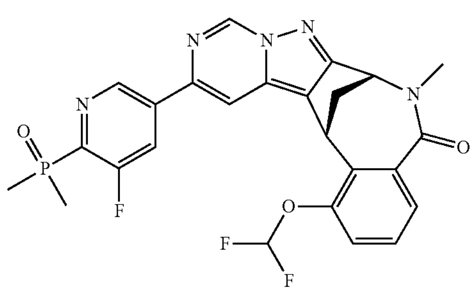 [SMILES: CN1C(=O)c2cccc(OC(F)F)c2[C@H]2C[C@@H]1c1nn3cnc(-c4cnc(P(C)(C)=O)c(F)c4)cc3c12] |
| 45 | 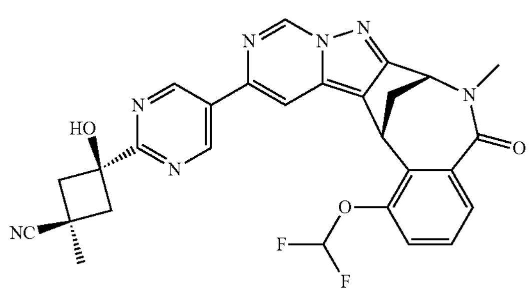 [SMILES: CN1C(=O)c2cccc(OC(F)F)c2[C@H]2C[C@@H]1c1nn3cnc(-c4cnc([C@]5(O)C[C@@](C)(C#N)C5)nc4)cc3c12] |

TABLE 1-continued

| Ex. | Structure |
|---|---|
| 46 | 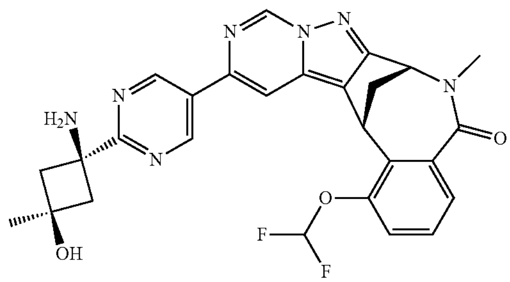 [SMILES: CN1C(=O)c2cccc(OC(F)F)c2[C@H]2C[C@@H]1c1nn3cnc(-c4cnc([C@]5(N)C[C@@](C)(O)C5)nc4)cc3c12] |
| 47 | 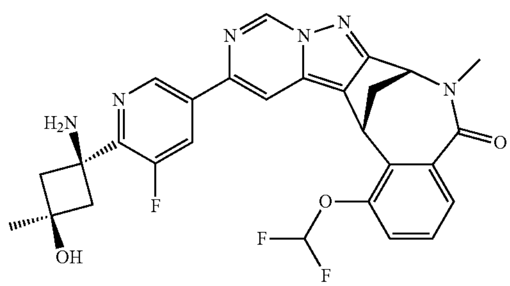 [SMILES: CN1C(=O)c2cccc(OC(F)F)c2[C@H]2C[C@@H]1c1nn3cnc(-c4cnc([C@]5(N)C[C@@](C)(O)C5)c(F)c4)cc3c12] |
| 48 | 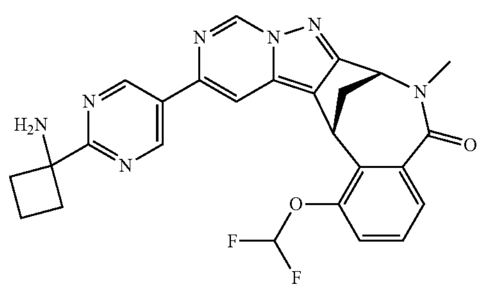 [SMILES: CN1C(=O)c2cccc(OC(F)F)c2[C@H]2C[C@@H]1c1nn3cnc(-c4cnc(C5(N)CCC5)nc4)cc3c12] |
| 49 | 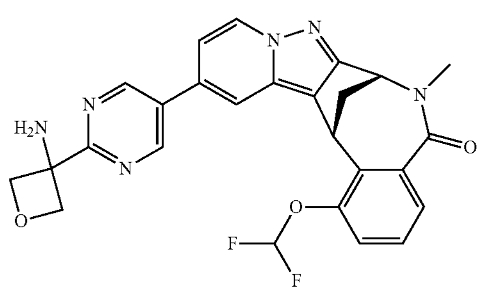 [SMILES: CN1C(=O)c2cccc(OC(F)F)c2[C@H]2C[C@@H]1c1nn3ccc(-c4cnc(C5(N)COC5)nc4)cc3c12] |
| 50 | 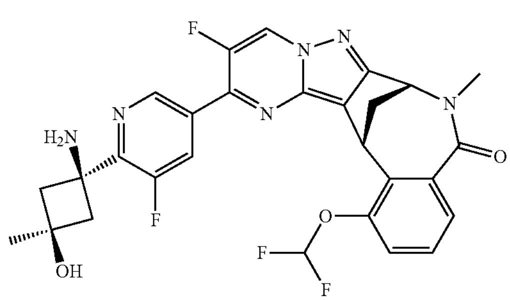 [SMILES: CN1C(=O)c2cccc(OC(F)F)c2[C@H]2C[C@@H]1c1nn3cc(F)c(-c4cnc([C@]5(N)C[C@@](C)(O)C5)c(F)c4)nc3c12] |

TABLE 1-continued

| Ex. | Structure |
|---|---|
| 51 | 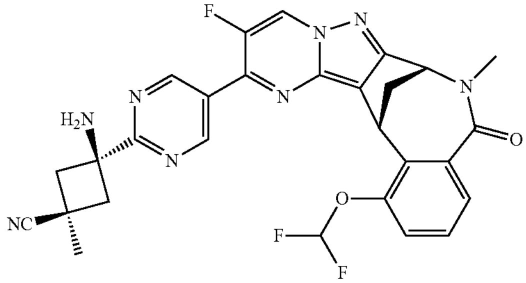 [SMILES: CN1C(=O)c2cccc(OC(F)F)c2[C@H]2C[C@@H]1c1nn3cc(F)c(-c4cnc([C@]5(N)C[C@@](C)(C#N)C5)nc4)nc3c12] |
| 52 | 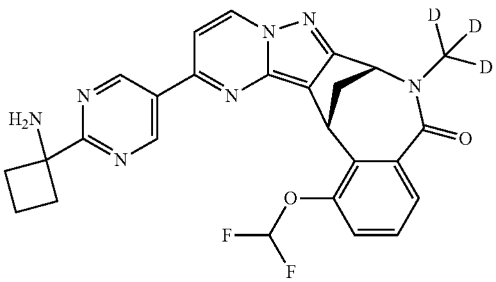 [SMILES: [2H]C([2H])([2H])N1C(=O)c2cccc(OC(F)F)c2[C@H]2C[C@@H]1c1nn3ccc(-c4cnc(C5(N)CCC5)nc4)nc3c12] |
| 53 | 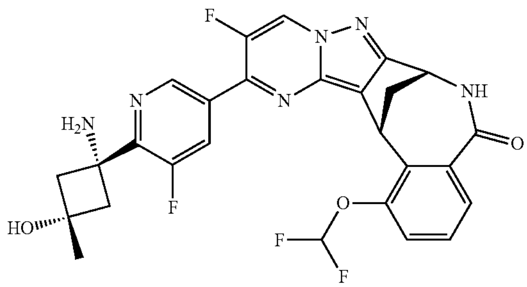 |
| 54 | 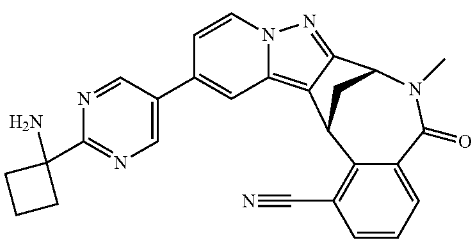 [SMILES: CN1C(=O)c2cccc(C#N)c2[C@H]2C[C@@H]1c1nn3ccc(-c4cnc(C5(N)CCC5)nc4)cc3c12] |
| 55 | 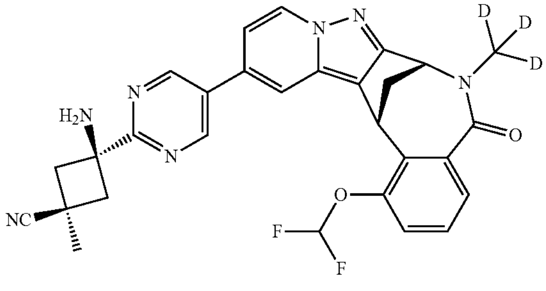 [SMILES: [2H]C([2H])([2H])N1C(=O)c2cccc(OC(F)F)c2[C@H]2C[C@@H]1c1nn3ccc(-c4cnc([C@]5(N)C[C@@](C)(C#N)C5)nc4)cc3c12] |

TABLE 1-continued
| Ex. | Structure |
|---|---|
| 56 | 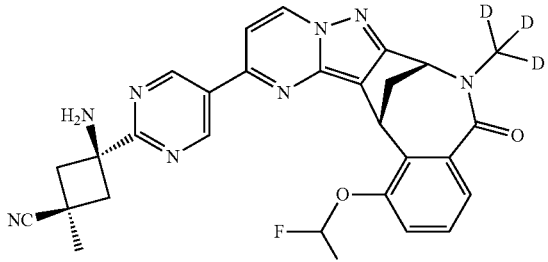 |
| 57 | 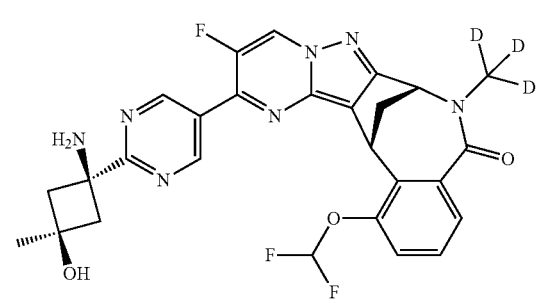 [SMILES: [2H]C([2H])([2H])N1C(=O)c2cccc(OC(F)F)c2[C@H]2C[C@@H]1c1nn3cc(F)c(-c4cnc([C@]5(N)C[C@@](C)(O)C5)nc4)nc3c12] |
| 58 | 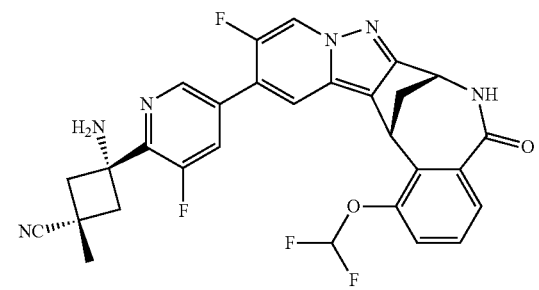 [SMILES: C[C@]1(C#N)C[C@](N)(c2ncc(-c3cc4c5c(nn4cc3F)[C@H]3C[C@@H]5c4c(OC(F)F)cccc4C(=O)N3)cc2F)C1] |
| 59 | 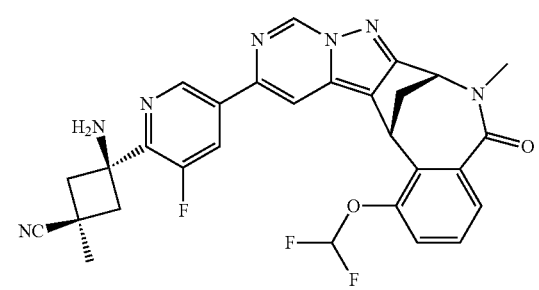 [SMILES: CN1C(=O)c2cccc(OC(F)F)c2[C@H]2C[C@@H]1c1nn3cnc(-c4cnc([C@]5(N)C[C@@](C)(C#N)C5)c(F)c4)cc3c12] |
| 60 | 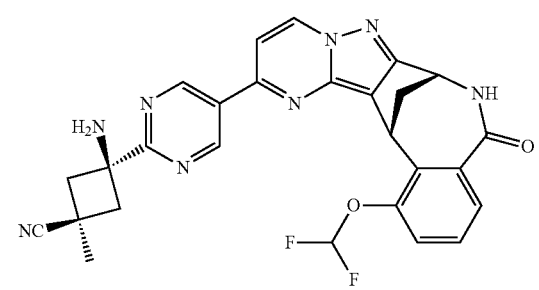 [SMILES: C[C@]1(C#N)C[C@](N)(c2ncc(-c3ccn4nc5c(c4n3)[C@@H]3C[C@H]5NC(=O)c4cccc(OC(F)F)c43)cn2)C1] |

TABLE 1-continued

| Ex. | Structure |
|---|---|
| 61 | 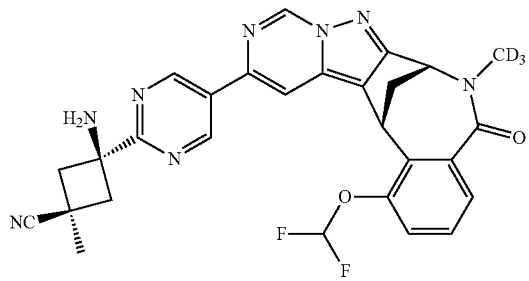 [SMILES: [2H]C([2H])([2H])N1C(=O)c2cccc(OC(F)F)c2[C@H]2C[C@@H]1c1nn3cnc(-c4cnc([C@]5(N)C[C@@](C)(C#N)C5)nc4)cc3c12] |
| 62 | 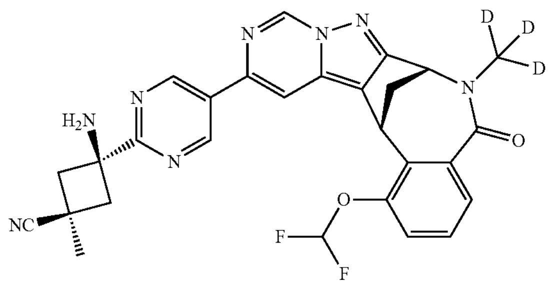 [SMILES: [2H]C([2H])([2H])N1C(=O)c2cccc(OC(F)F)c2[C@H]2C[C@@H]1c1nn3cnc(-c4cnc([C@]5(N)C[C@@](C)(C#N)C5)nc4)cc3c12] |
| 63 | 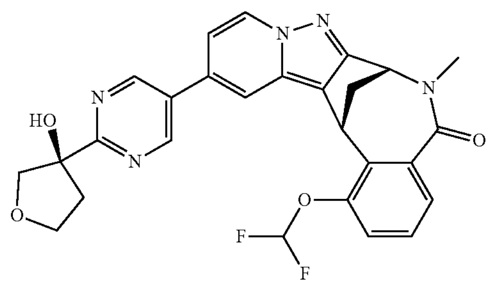 [SMILES: CN1C(=O)c2cccc(OC(F)F)c2[C@H]2C[C@@H]1c1nn3ccc(-c4cnc([C@]5(O)CCOC5)nc4)cc3c12] |
| 64 | 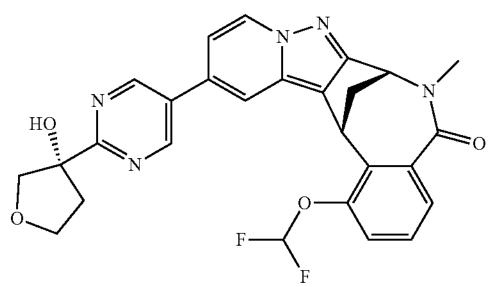 [SMILES: CN1C(=O)c2cccc(OC(F)F)c2[C@H]2C[C@@H]1c1nn3ccc(-c4cnc([C@@]5(O)CCOC5)nc4)cc3c12] |
| 65 | 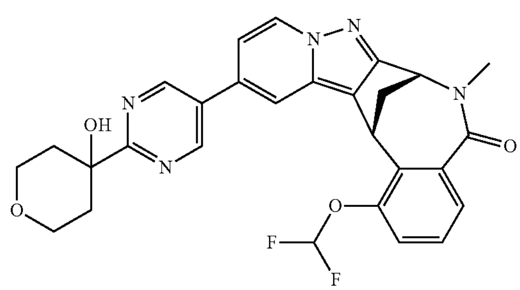 [SMILES: CN1C(=O)c2cccc(OC(F)F)c2[C@H]2C[C@@H]1c1nn3ccc(-c4cnc(C5(O)CCOCC5)nc4)cc3c12] |

TABLE 1-continued

| Ex. | Structure |
|---|---|
| 66 | 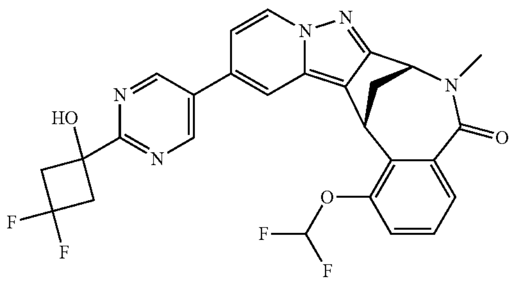 [SMILES: CN1C(=O)c2cccc(OC(F)F)c2[C@H]2C[C@@H]1c1nn3ccc(-c4cnc(C5(O)CC(F)(F)C5)nc4)cc3c12] |
| 67 | 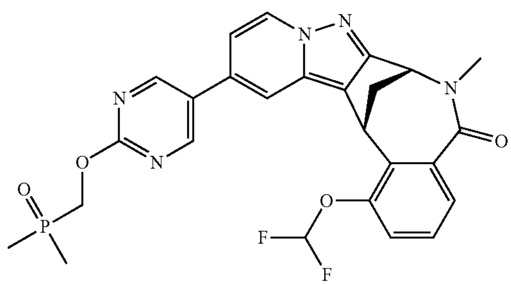 [SMILES: CN1C(=O)c2cccc(OC(F)F)c2[C@H]2C[C@@H]1c1nn3ccc(-c4cnc(OCP(C)(C)=O)nc4)cc3c12] |
| 68 | 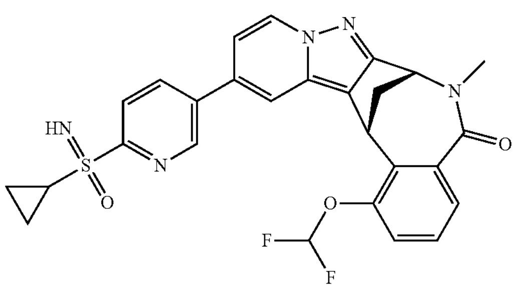 [SMILES: CN1C(=O)c2cccc(OC(F)F)c2[C@H]2C[C@@H]1c1nn3ccc(-c4ccc(S(=N)(=O)C5CC5)nc4)cc3c12] |
| 69 | 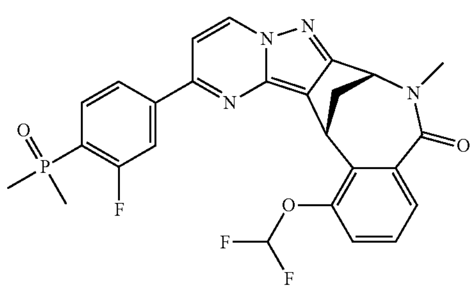 [SMILES: CN1C(=O)c2cccc(OC(F)F)c2[C@H]2C[C@@H]1c1nn3ccc(-c4ccc(P(C)(C)=O)c(F)c4)nc3c12] |
| 70 | 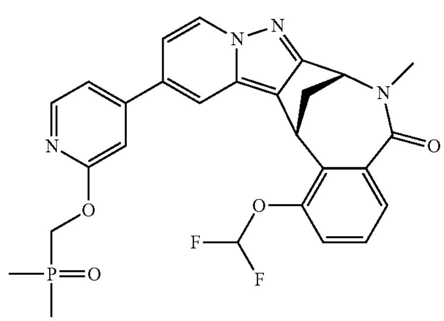 [SMILES: CN1C(=O)c2cccc(OC(F)F)c2[C@H]2C[C@@H]1c1nn3ccc(-c4ccnc(OCP(C)(C)=O)c4)cc3c12] |

TABLE 1-continued
| Ex. | Structure |
|---|---|
| 71 | 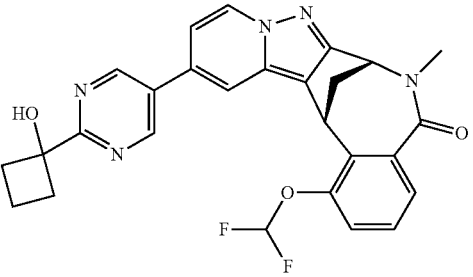 [SMILES: CN1C(=O)c2cccc(OC(F)F)c2[C@H]2C[C@@H]1c1nn3ccc(-c4cnc(C5(O)CCC5)nc4)cc3c12] |
| 72 | 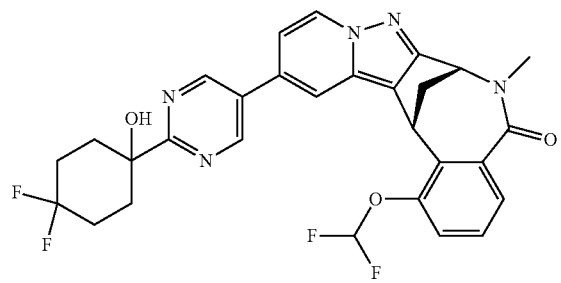 [SMILES: CN1C(=O)c2cccc(OC(F)F)c2[C@H]2C[C@@H]1c1nn3ccc(-c4cnc(C5(O)CCC(F)(F)CC5)nc4)cc3c12] |
| 73 | 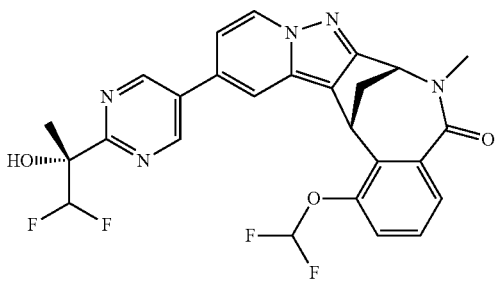 [SMILES: CN1C(=O)c2cccc(OC(F)F)c2[C@H]2C[C@@H]1c1nn3ccc(-c4cnc([C@@](C)(O)C(F)F)nc4)cc3c12] |
| 74 | 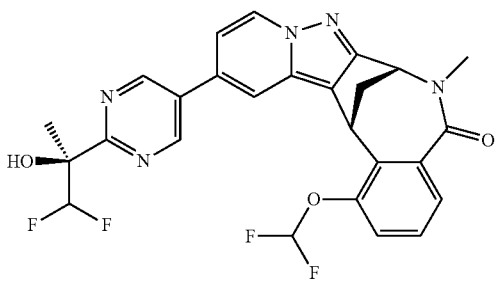 [SMILES: CN1C(=O)c2cccc(OC(F)F)c2[C@H]2C[C@@H]1c1nn3ccc(-c4cnc([C@](C)(O)C(F)F)nc4)cc3c12] |
| 75 | 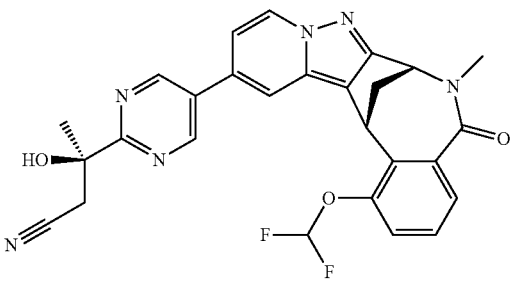 [SMILES: CN1C(=O)c2cccc(OC(F)F)c2[C@H]2C[C@@H]1c1nn3ccc(-c4cnc([C@](C)(O)CC#N)nc4)cc3c12] |

TABLE 1-continued

| Ex. | Structure |
|---|---|
| 76 | 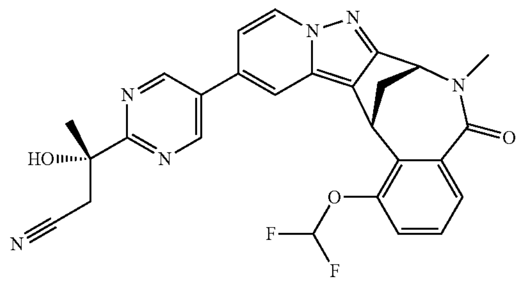 [SMILES: CN1C(=O)c2cccc(OC(F)F)c2[C@H]2C[C@@H]1c1nn3ccc(-c4cnc([C@@](C)(O)CC#N)nc4)cc3c12] |
| 77 | 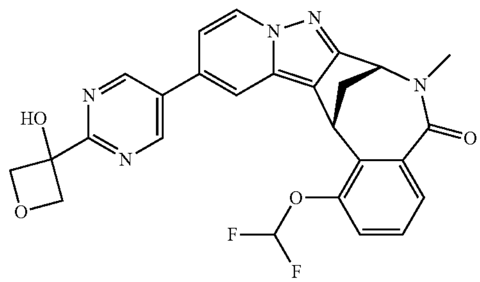 [SMILES: CN1C(=O)c2cccc(OC(F)F)c2[C@H]2C[C@@H]1c1nn3ccc(-c4cnc(C5(O)COC5)nc4)cc3c12] |
| 78 | 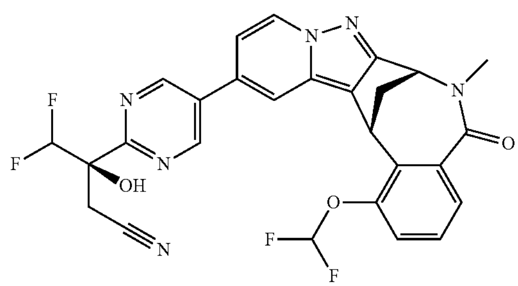 [SMILES: CN1C(=O)c2cccc(OC(F)F)c2[C@H]2C[C@@H]1c1nn3ccc(-c4cnc([C@](O)(CC#N)C(F)F)nc4)cc3c12] |
| 79 | 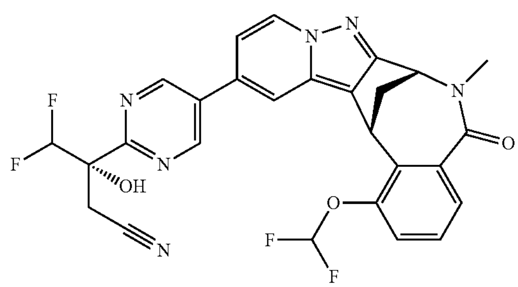 [SMILES: CN1C(=O)c2cccc(OC(F)F)c2[C@H]2C[C@@H]1c1nn3ccc(-c4cnc([C@@](O)(CC#N)C(F)F)nc4)cc3c12] |
| 80 | 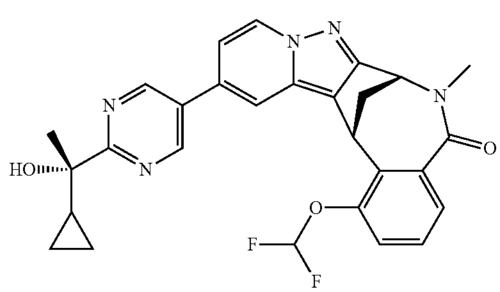 [SMILES: CN1C(=O)c2cccc(OC(F)F)c2[C@H]2C[C@@H]1c1nn3ccc(-c4cnc([C@@](C)(O)C5CC5)nc4)cc3c12] |

TABLE 1-continued
| Ex. | Structure |
|---|---|
| 81 | 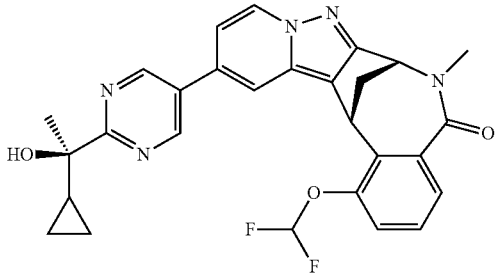 [SMILES: CN1C(=O)c2cccc(OC(F)F)c2[C@H]2C[C@@H]1c1nn3ccc(-c4cnc([C@](C)(O)C5CC5)nc4)cc3c12] |
| 82 | 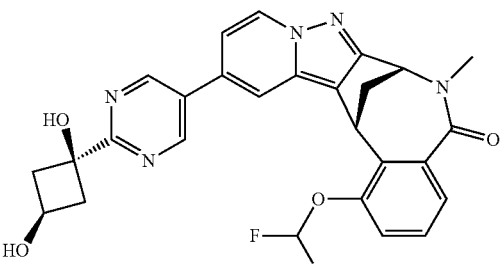 |
| 83 | 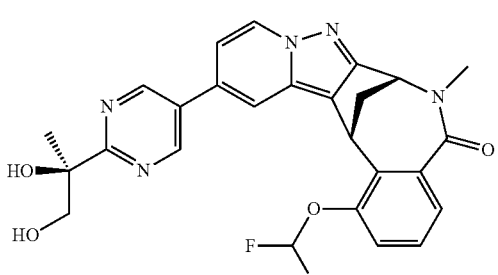 |
| 84 | 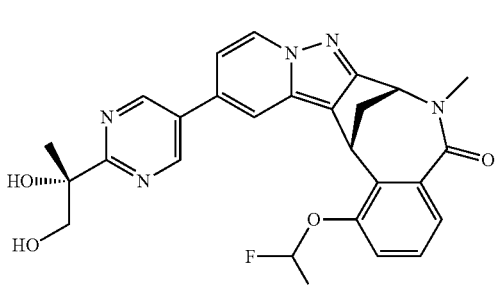 |
| 85 | 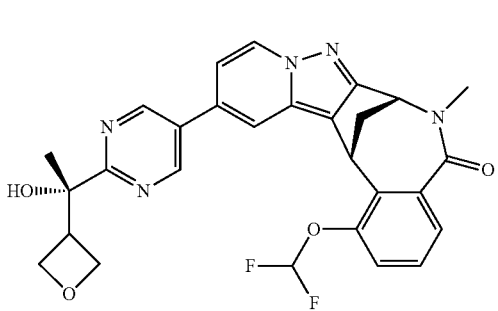 [SMILES: CN1C(=O)c2cccc(OC(F)F)c2[C@H]2C[C@@H]1c1nn3ccc(-c4cnc([C@@](C)(O)C5COC5)nc4)cc3c12] |

TABLE 1-continued

| Ex. | Structure |
| --- | --- |
| 86 | 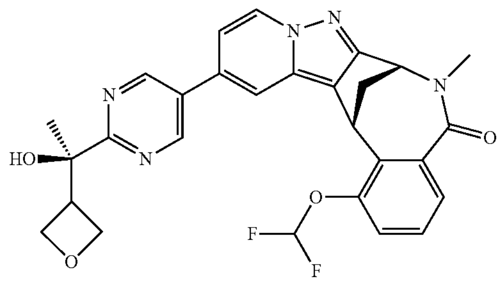 [SMILES: CN1C(=O)c2cccc(OC(F)F)c2[C@H]2C[C@@H]1c1nn3ccc(-c4cnc([C@](C)(O)C5COC5)nc4)cc3c12] |
| 87 | 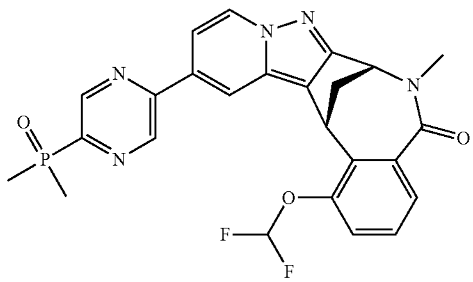 [SMILES: CN1C(=O)c2cccc(OC(F)F)c2[C@H]2C[C@@H]1c1nn3ccc(-c4cnc(P(C)(C)=O)cn4)cc3c12] |
| 88 | 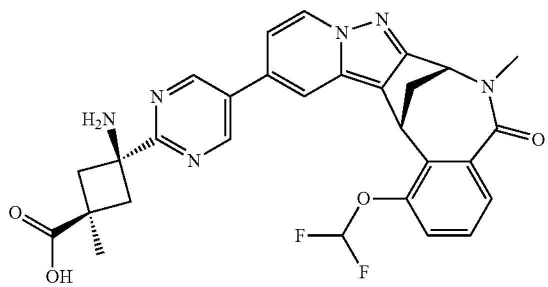 [SMILES: CN1C(=O)c2cccc(OC(F)F)c2[C@H]2C[C@@H]1c1nn3ccc(-c4cnc([C@]5(N)C[C@@](C)(C(=O)O)C5)nc4)cc3c12] |
| 89 | 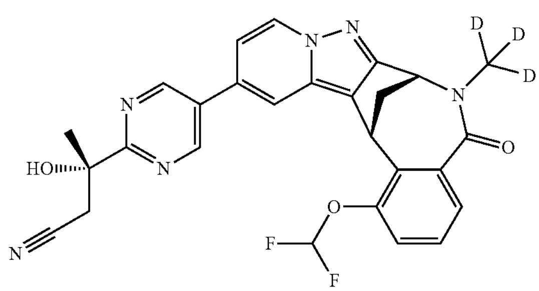 [SMILES: [2H]C([2H])([2H])N1C(=O)c2cccc(OC(F)F)c2[C@H]2C[C@@H]1c1nn3ccc(-c4cnc([C@@](C)(O)CC#N)nc4)cc3c12] |
| 90 | 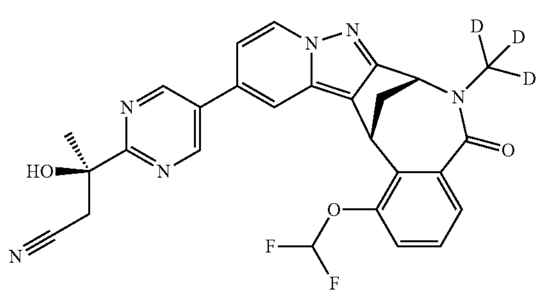 [SMILES: [2H]C([2H])([2H])N1C(=O)c2cccc(OC(F)F)c2[C@H]2C[C@@H]1c1nn3ccc(-c4cnc([C@](C)(O)CC#N)nc4)cc3c12] |

TABLE 1-continued

| Ex. | Structure |
|---|---|
| 91 | 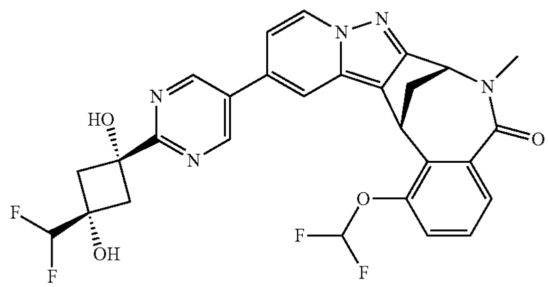 [SMILES: CN1C(=O)c2cccc(OC(F)F)c2[C@H]2C[C@@H]1c1nn3ccc(-c4cnc([C@]5(O)C[C@](O)(C(F)F)C5)nc4)cc3c12] |
| 92 | 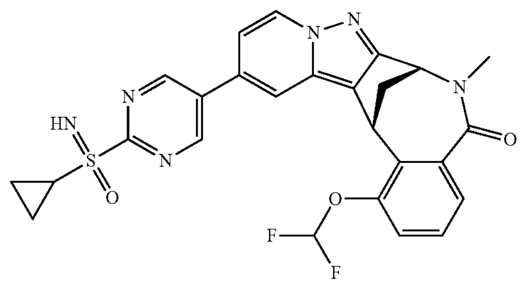 [SMILES: CN1C(=O)c2cccc(OC(F)F)c2[C@H]2C[C@@H]1c1nn3ccc(-c4cnc(S(=N)(=O)C5CC5)nc4)cc3c12] |
| 93 | 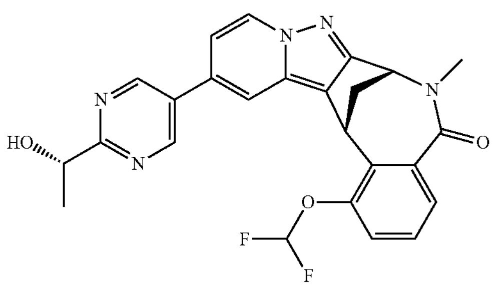 [SMILES: C[C@H](O)c1ncc(-c2ccn3nc4c(c3c2)[C@@H]2C[C@H]4N(C)C(=O)c3cccc(OC(F)F)c32)cn1] |
| 94 | 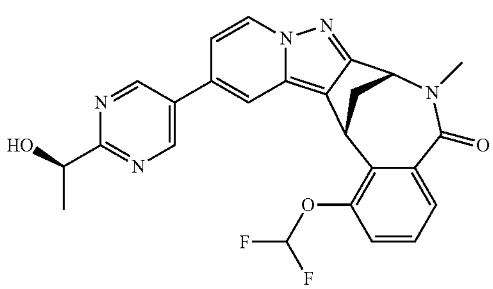 [SMILES: C[C@@H](O)c1ncc(-c2ccn3nc4c(c3c2)[C@@H]2C[C@H]4N(C)C(=O)c3cccc(OC(F)F)c32)cn1] |
| 95 | 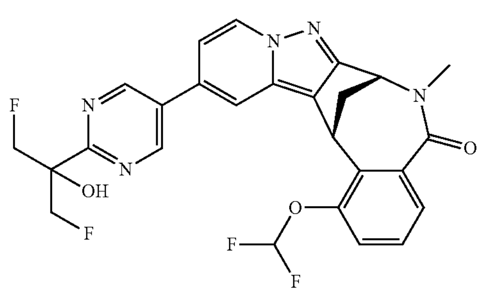 [SMILES: CN1C(=O)c2cccc(OC(F)F)c2[C@H]2C[C@@H]1c1nn3ccc(-c4cnc(C(O)(CF)CF)nc4)cc3c12] |

TABLE 1-continued

| Ex. | Structure |
|---|---|
| 96 | 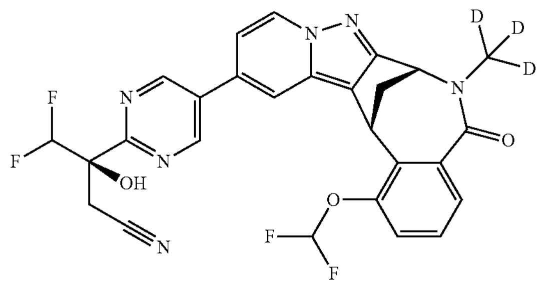 [SMILES: [2H]C([2H])([2H])N1C(=O)c2cccc(OC(F)F)c2[C@H]2C[C@@H]1c1nn3ccc(-c4cnc([C@](O)(CC#N)C(F)F)nc4)cc3c12] |
| 97 | 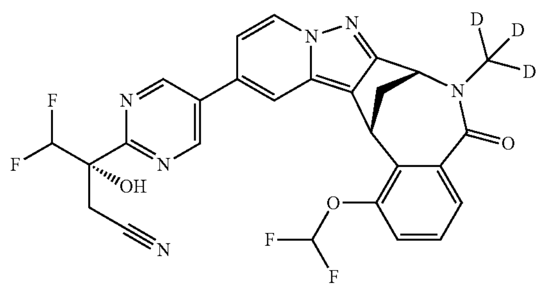 [SMILES: [2H]C([2H])([2H])N1C(=O)c2cccc(OC(F)F)c2[C@H]2C[C@@H]1c1nn3ccc(-c4cnc([C@@](O)(CC#N)C(F)F)nc4)cc3c12] |
| 98 | 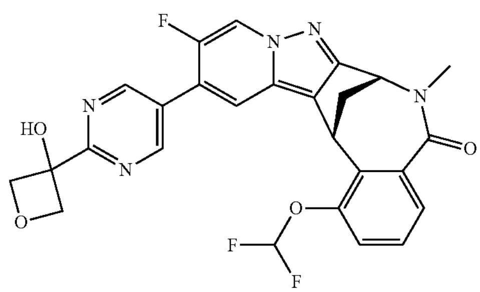 [SMILES: CN1C(=O)c2cccc(OC(F)F)c2[C@H]2C[C@@H]1c1nn3cc(F)c(-c4cnc(C5(O)COC5)nc4)cc3c12] |
| 99 | 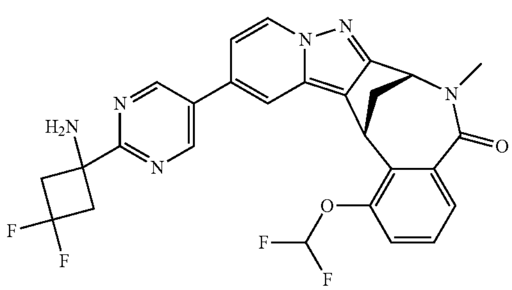 [SMILES: CN1C(=O)c2cccc(OC(F)F)c2[C@H]2C[C@@H]1c1nn3ccc(-c4cnc(C5(N)CC(F)(F)C5)nc4)cc3c12] |
| 100 | 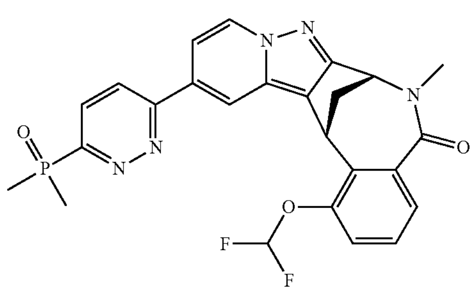 [SMILES: CN1C(=O)c2cccc(OC(F)F)c2[C@H]2C[C@@H]1c1nn3ccc(-c4ccc(P(C)(C)=O)nn4)cc3c12] |

TABLE 1-continued

| Ex. | Structure |
|---|---|
| 101 | 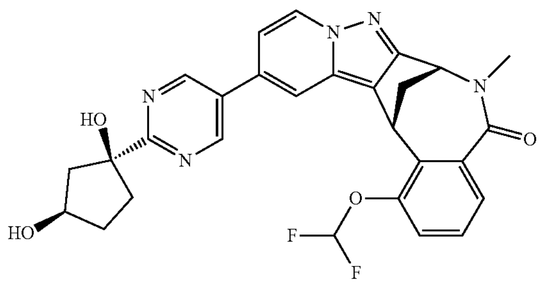 [SMILES: CN1C(=O)c2cccc(OC(F)F)c2[C@H]2C[C@@H]1c1nn3ccc(-c4cnc([C@]5(O)CC[C@@H](O)C5)nc4)cc3c12] |
| 102 | 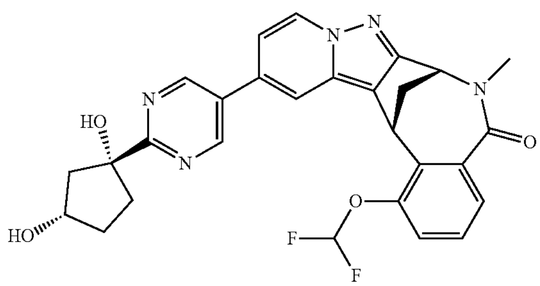 [SMILES: CN1C(=O)c2cccc(OC(F)F)c2[C@H]2C[C@@H]1c1nn3ccc(-c4cnc([C@@]5(O)CC[C@H](O)C5)nc4)cc3c12] |
| 103 | 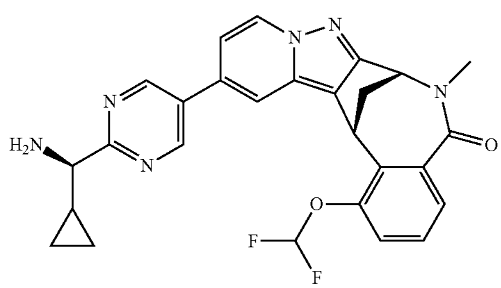 [SMILES: CN1C(=O)c2cccc(OC(F)F)c2[C@H]2C[C@@H]1c1nn3ccc(-c4cnc([C@H](N)C5CC5)nc4)cc3c12] |
| 104 | 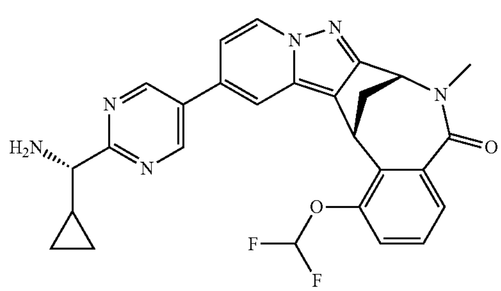 [SMILES: CN1C(=O)c2cccc(OC(F)F)c2[C@H]2C[C@@H]1c1nn3ccc(-c4cnc([C@@H](N)C5CC5)nc4)cc3c12] |
| 105 | 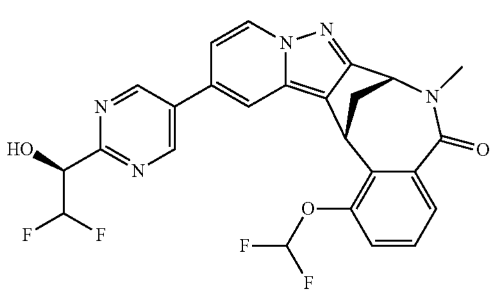 [SMILES: CN1C(=O)c2cccc(OC(F)F)c2[C@H]2C[C@@H]1c1nn3ccc(-c4cnc([C@H](O)C(F)F)nc4)cc3c12] |

TABLE 1-continued

| Ex. | Structure |
|---|---|
| 106 | 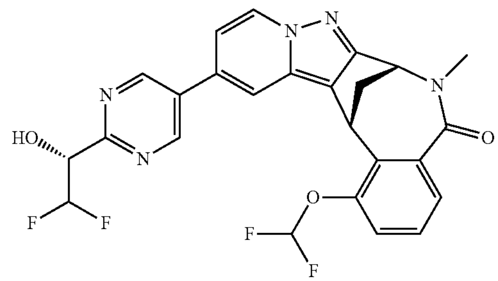 [SMILES: CN1C(=O)c2cccc(OC(F)F)c2[C@H]2C[C@@H]1c1nn3ccc(-c4cnc([C@@H](O)C(F)F)nc4)cc3c12] |
| 107 | 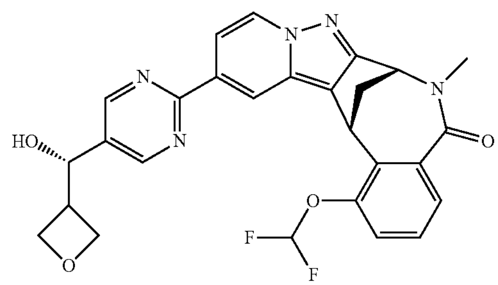 [SMILES: CN1C(=O)c2cccc(OC(F)F)c2[C@H]2C[C@@H]1c1nn3ccc(-c4ncc([C@@H](O)C5COC5)cn4)cc3c12] |
| 108 | 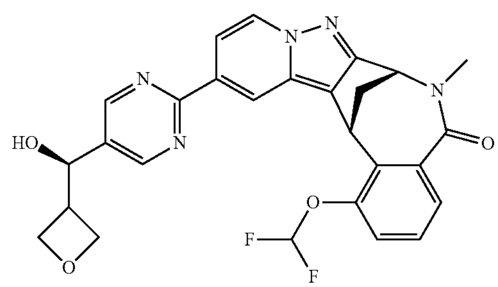 [SMILES: CN1C(=O)c2cccc(OC(F)F)c2[C@H]2C[C@@H]1c1nn3ccc(-c4ncc([C@H](O)C5COC5)cn4)cc3c12] |
| 109 | 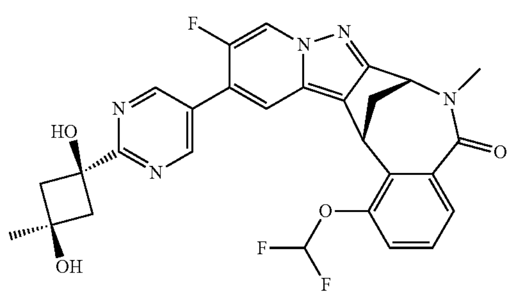 [SMILES: CN1C(=O)c2cccc(OC(F)F)c2[C@H]2C[C@@H]1c1nn3cc(F)c(-c4cnc([C@]5(O)C[C@@](C)(O)C5)nc4)cc3c12] |
| 110 | 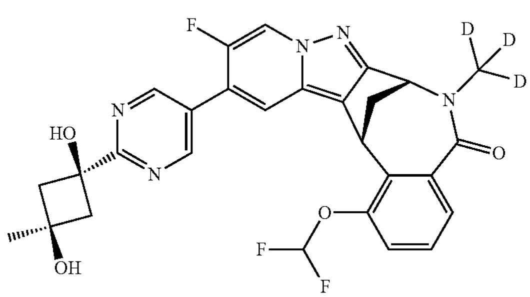 [SMILES: [2H]C([2H])([2H])N1C(=O)c2cccc(OC(F)F)c2[C@H]2C[C@@H]1c1nn3cc(F)c(-c4cnc([C@]5(O)C[C@@](C)(O)C5)nc4)cc3c12] |

TABLE 1-continued

| Ex. | Structure |
|---|---|
| 111 | 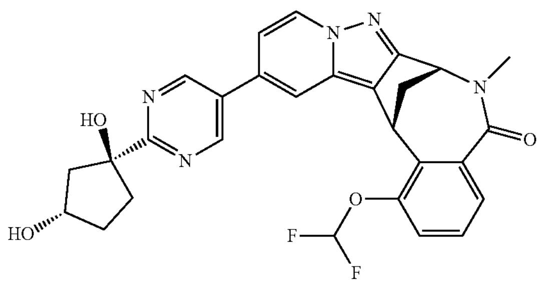 [SMILES: CN1C(=O)c2cccc(OC(F)F)c2[C@H]2C[C@@H]1c1nn3ccc(-c4cnc([C@]5(O)CC[C@H](O)C5)nc4)cc3c12] |
| 112 | 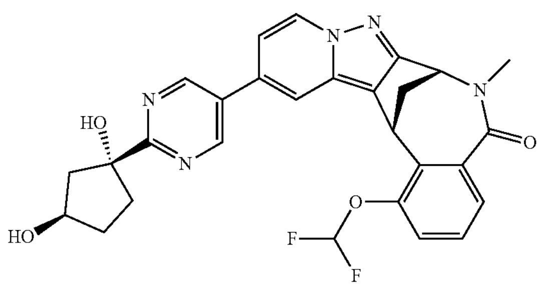 [SMILES: CN1C(=O)c2cccc(OC(F)F)c2[C@H]2C[C@@H]1c1nn3ccc(-c4cnc([C@@]5(O)CC[C@@H](O)C5)nc4)cc3c12] |
| 113 | 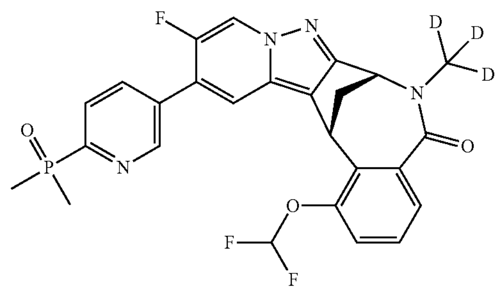 [SMILES: [2H]C([2H])([2H])N1C(=O)c2cccc(OC(F)F)c2[C@H]2C[C@@H]1c1nn3cc(F)c(-c4ccc(P(C)(C)=O)nc4)cc3c12] |
| 114 | 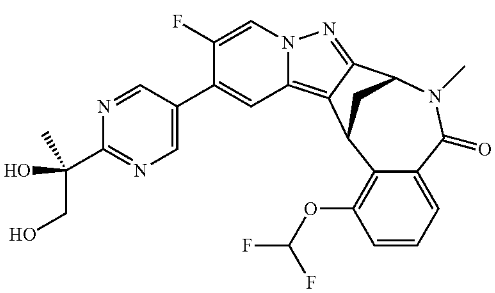 [SMILES: CN1C(=O)c2cccc(OC(F)F)c2[C@H]2C[C@@H]1c1nn3cc(F)c(-c4cnc([C@](C)(O)CO)nc4)cc3c12] |
| 115 | 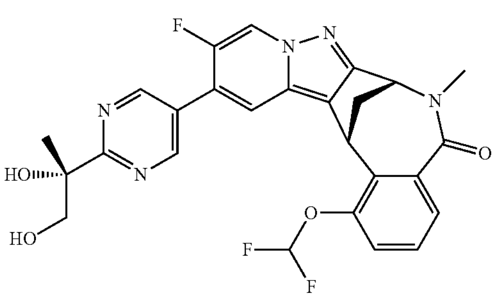 [SMILES: CN1C(=O)c2cccc(OC(F)F)c2[C@H]2C[C@@H]1c1nn3cc(F)c(-c4cnc([C@@](C)(O)CO)nc4)cc3c12] |

TABLE 1-continued
| Ex. | Structure |
|---|---|
| 116 | 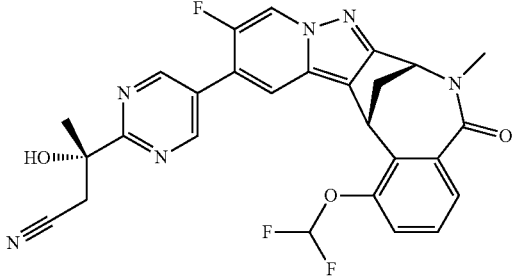 [SMILES: CN1C(=O)c2cccc(OC(F)F)c2[C@H]2C[C@@H]1c1nn3cc(F)c(-c4cnc([C@@](C)(O)CC#N)nc4)cc3c12] |
| 117 | 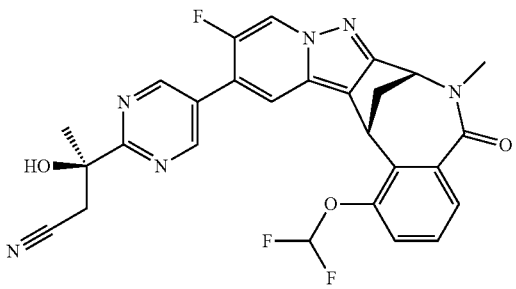 [SMILES: CN1C(=O)c2cccc(OC(F)F)c2[C@H]2C[C@@H]1c1nn3cc(F)c(-c4cnc([C@](C)(O)CC#N)nc4)cc3c12] |
| 118 | 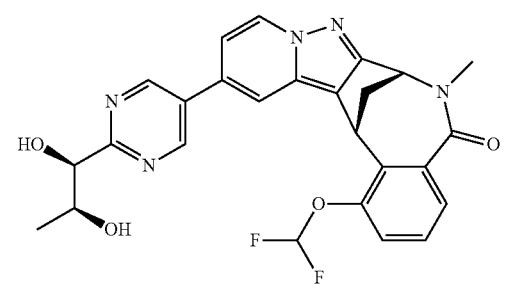 [SMILES: C[C@H](O)[C@@H](O)c1ncc(-c2ccn3nc4c(c3c2)[C@@H]2C[C@H]4N(C)C(=O)c3cccc(OC(F)F)c32)cn1] |
| 119 | 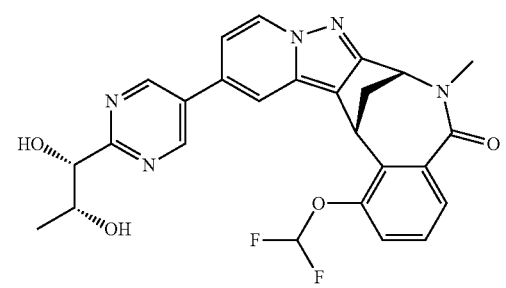 [SMILES: C[C@@H](O)[C@H](O)c1ncc(-c2ccn3nc4c(c3c2)[C@@H]2C[C@H]4N(C)C(=O)c3cccc(OC(F)F)c32)cn1] |
| 120 | 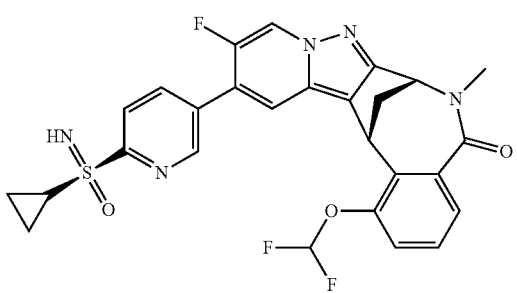 [SMILES: CN1C(=O)c2cccc(OC(F)F)c2[C@H]2C[C@@H]1c1nn3cc(F)c(-c4ccc([S@@](=N)(=O)C5CC5)nc4)cc3c12] |

TABLE 1-continued

| Ex. | Structure |
|---|---|
| 121 | 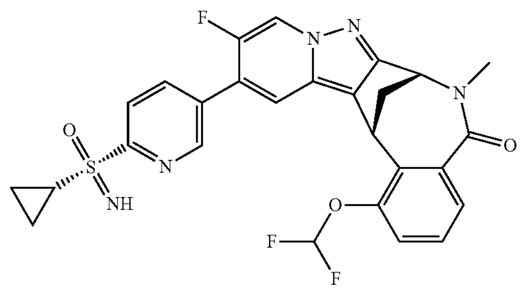 [SMILES: CN1C(=O)c2cccc(OC(F)F)c2[C@H]2C[C@@H]1c1nn3cc(F)c(-c4ccc([S@@](=N)(=O)C5CC5)nc4)cc3c12] |
| 122 | 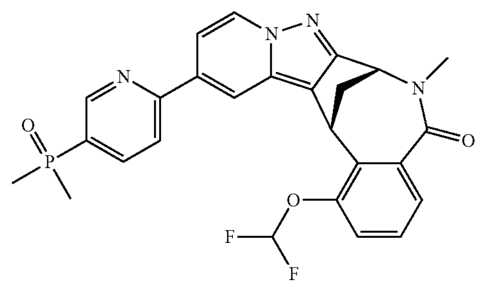 |
| 123 | 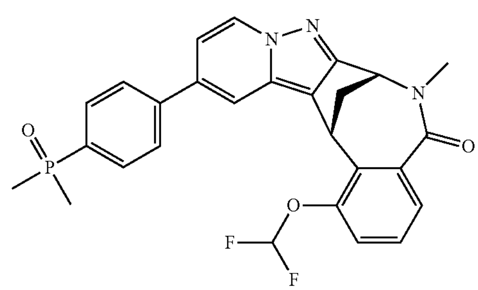 [SMILES: CN1C(=O)c2cccc(OC(F)F)c2[C@H]2C[C@@H]1c1nn3ccc(-c4ccc(P(C)(C)=O)cc4)cc3c12] |
| 124 | 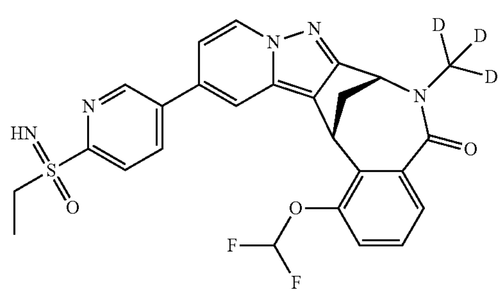 [SMILES: [2H]C([2H])([2H])N1C(=O)c2cccc(OC(F)F)c2[C@H]2C[C@@H]1c1nn3ccc(-c4ccc(S(=N)(=O)CC)nc4)cc3c12] |
| 125 | 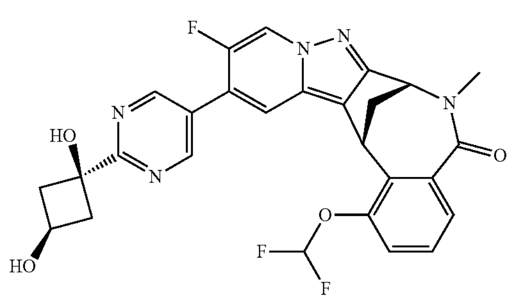 [SMILES: CN1C(=O)c2cccc(OC(F)F)c2[C@H]2C[C@@H]1c1nn3cc(F)c(-c4cnc([C@]5(O)C[C@@H](O)C5)nc4)cc3c12] |

TABLE 1-continued

| Ex. | Structure |
|---|---|
| 126 | 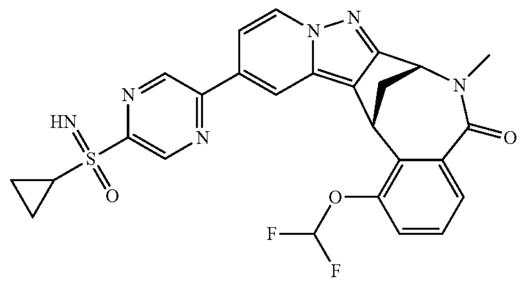 [SMILES: CN1C(=O)c2cccc(OC(F)F)c2[C@H]2C[C@@H]1c1nn3ccc(-c4cnc(S(=N)(=O)C5CC5)cn4)cc3c12] |
| 127 | 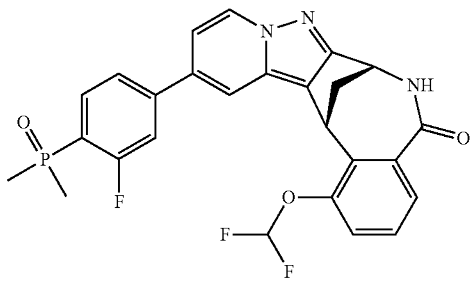 [SMILES: CP(C)(=O)c1ccc(-c2ccn3nc4c(c3c2)[C@@H]2C[C@H]4NC(=O)c3cccc(OC(F)F)c32)cc1F] |
| 128 | 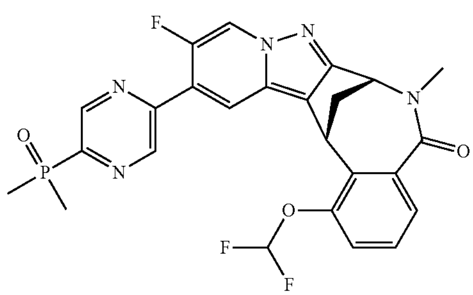 [SMILES: CN1C(=O)c2cccc(OC(F)F)c2[C@H]2C[C@@H]1c1nn3cc(F)c(-c4cnc(P(C)(C)=O)cn4)cc3c12] |
| 129 | 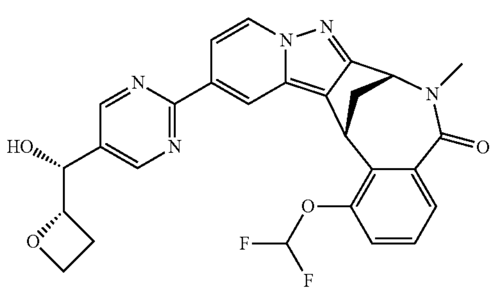 |
| 130 | 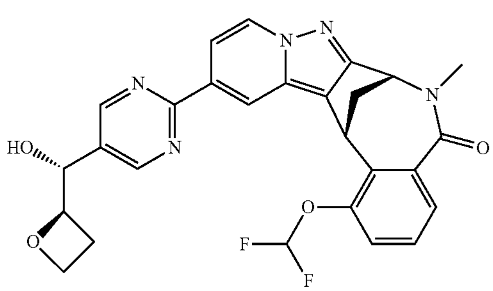 [SMILES: CN1C(=O)c2cccc(OC(F)F)c2[C@H]2C[C@@H]1c1nn3ccc(-c4ncc([C@@H](O)[C@H]5CCO5)cn4)cc3c12] |

TABLE 1-continued

| Ex. | Structure |
|---|---|
| 131 | 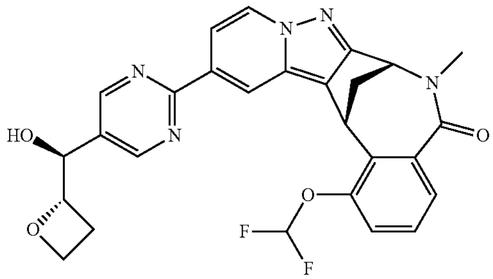 |
| 132 | 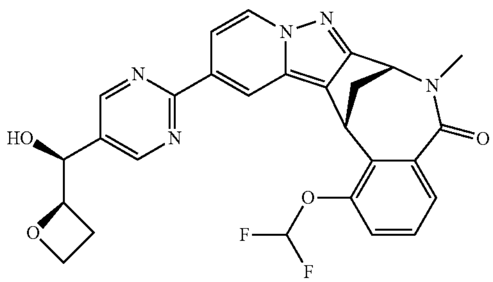 [SMILES: CN1C(=O)c2cccc(OC(F)F)c2[C@H]2C[C@@H]1c1nn3ccc(-c4ncc([C@H](O)[C@H]5CCO5)cn4)cc3c12] |
| 133 | 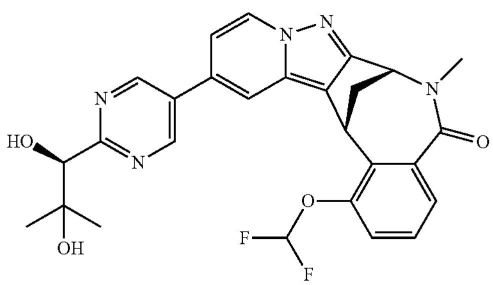 [SMILES: CN1C(=O)c2cccc(OC(F)F)c2[C@H]2C[C@@H]1c1nn3ccc(-c4cnc([C@H](O)C(C)(C)O)nc4)cc3c12] |
| 134 | 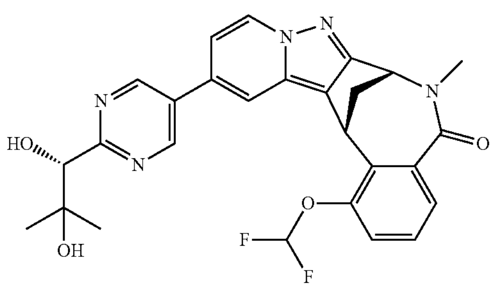 [SMILES: CN1C(=O)c2cccc(OC(F)F)c2[C@H]2C[C@@H]1c1nn3ccc(-c4cnc([C@@H](O)C(C)(C)O)nc4)cc3c12] |
| 135 | 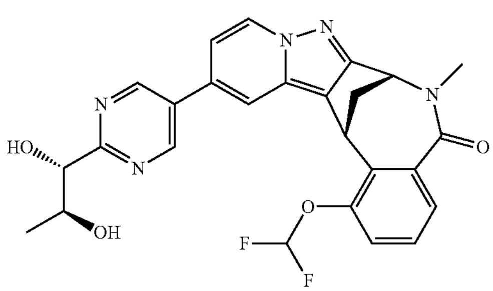 [SMILES: C[C@H](O)[C@H](O)c1ncc(-c2ccn3nc4c(c3c2)[C@@H]2C[C@H]4N(C)C(=O)c3cccc(OC(F)F)c32)cn1] |

TABLE 1-continued

| Ex. | Structure |
|---|---|
| 136 | 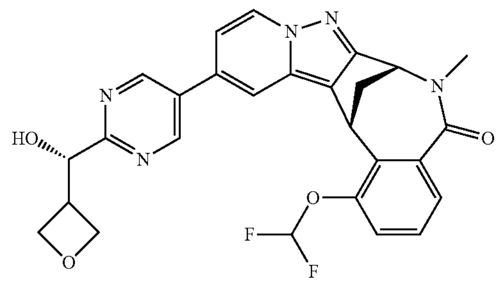 [SMILES: CN1C(=O)c2cccc(OC(F)F)c2[C@H]2C[C@@H]1c1nn3ccc(-c4cnc([C@@H](O)C5COC5)nc4)cc3c12] |
| 137 | 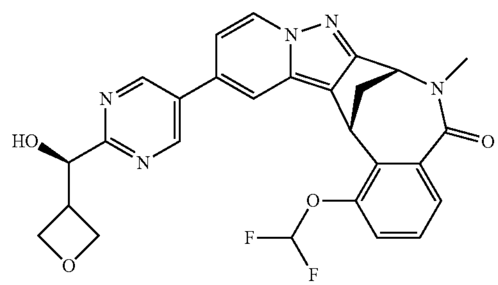 [SMILES: CN1C(=O)c2cccc(OC(F)F)c2[C@H]2C[C@@H]1c1nn3ccc(-c4cnc([C@H](O)C5COC5)nc4)cc3c12] |
| 138 | 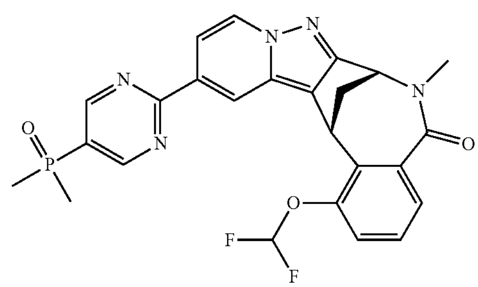 [SMILES: CN1C(=O)c2cccc(OC(F)F)c2[C@H]2C[C@@H]1c1nn3ccc(-c4ncc(P(C)(C)=O)cn4)cc3c12] |
| 139 | 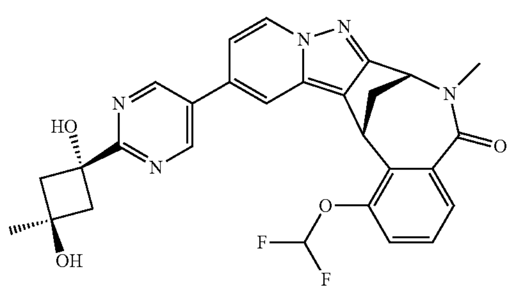 [SMILES: CN1C(=O)c2cccc(OC(F)F)c2[C@H]2C[C@@H]1c1nn3ccc(-c4cnc([C@]5(O)C[C@](C)(O)C5)nc4)cc3c12] |
| 140 | 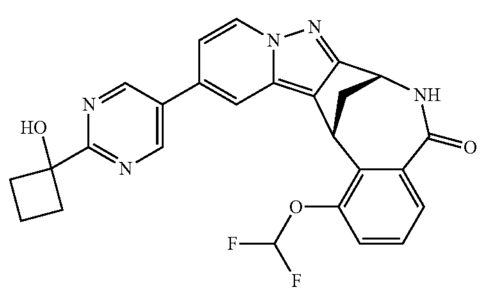 [SMILES: O=C1N[C@@H]2C[C@H](c3c(OC(F)F)cccc31)c1c2nn2ccc(-c3cnc(C4(O)CCC4)nc3)cc12] |

TABLE 1-continued

| Ex. | Structure |
|---|---|
| 141 | 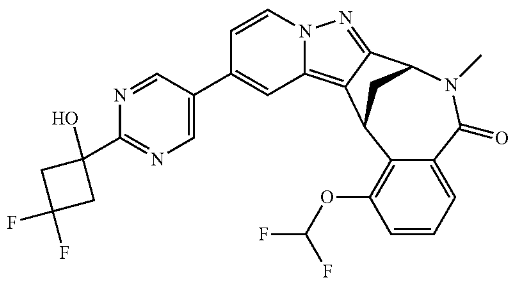 [SMILES: CN1C(=O)c2cccc(OC(F)F)c2[C@H]2C[C@@H]1c1nn3ccc(-c4cnc(C5(O)CC(F)(F)C5)nc4)cc3c12] |
| 142 | 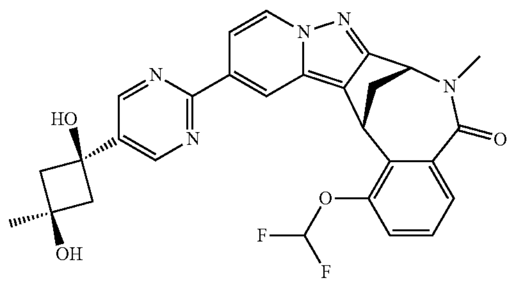 [SMILES: CN1C(=O)c2cccc(OC(F)F)c2[C@H]2C[C@@H]1c1nn3ccc(-c4ncc([C@]5(O)C[C@@](C)(O)C5)cn4)cc3c12] |
| 143 | 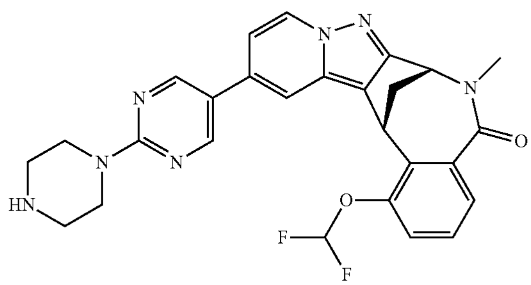 [SMILES: CN1C(=O)c2cccc(OC(F)F)c2[C@H]2C[C@@H]1c1nn3ccc(-c4cnc(N5CCNCC5)nc4)cc3c12] |
| 144 | 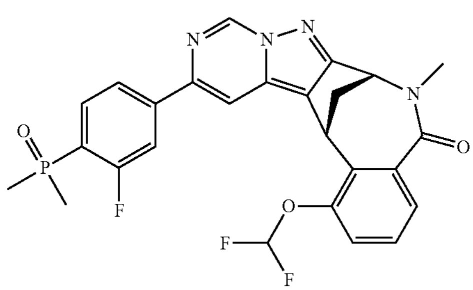 [SMILES: CN1C(=O)c2cccc(OC(F)F)c2[C@H]2C[C@@H]1c1nn3cnc(-c4ccc(P(C)(C)=O)c(F)c4)cc3c12] |
| 145 | 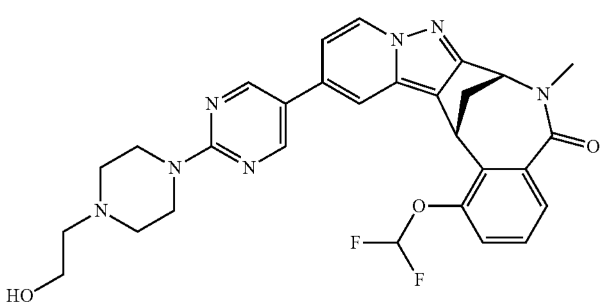 [SMILES: CN1C(=O)c2cccc(OC(F)F)c2[C@H]2C[C@@H]1c1nn3ccc(-c4cnc(N5CCN(CCO)CC5)nc4)cc3c12] |

TABLE 1-continued

| Ex. | Structure |
|---|---|
| 146 | 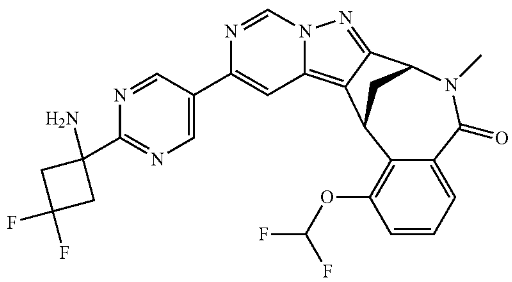 [SMILES: CN1C(=O)c2cccc(OC(F)F)c2[C@H]2C[C@@H]1c1nn3cnc(-c4cnc(C5(N)CC(F)(F)C5)nc4)cc3c12] |
| 147 | 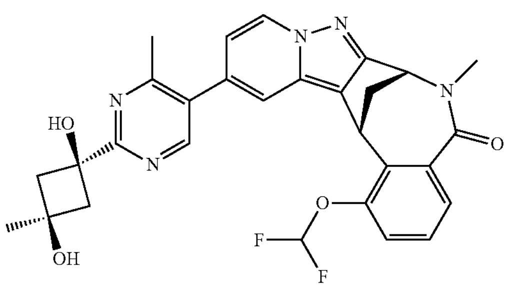 [SMILES: Cc1nc([C@]2(O)C[C@@](C)(O)C2)ncc1-c1ccn2nc3c(c2c1)[C@@H]1C[C@H]3N(C)C(=O)c2cccc(OC(F)F)c21] |
| 148 | 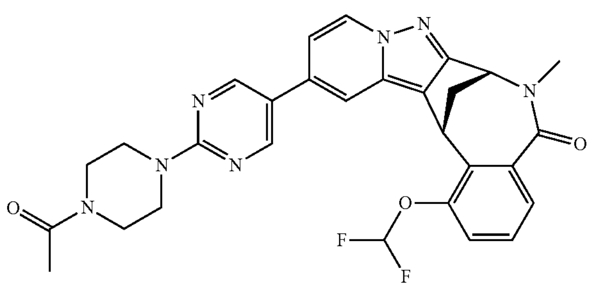 [SMILES: CC(=O)N1CCN(c2ncc(-c3ccn4nc5c(c4c3)[C@@H]3C[C@H]5N(C)C(=O)c4cccc(OC(F)F)c43)cn2)CC1] |
| 149 | 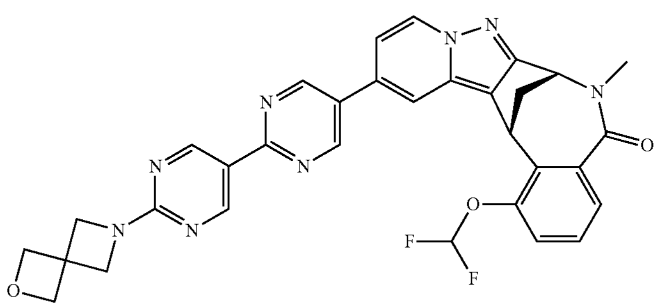 [SMILES: CN1C(=O)c2cccc(OC(F)F)c2[C@H]2C[C@@H]1c1nn3ccc(-c4cnc(-c5cnc(N6CC7(COC7)C6)nc5)nc4)cc3c12] |
| 150 | 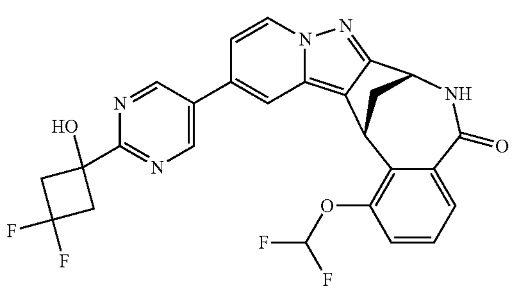 [SMILES: O=C1N[C@@H]2C[C@H](c3c(OC(F)F)cccc31)c1c2nn2ccc(-c3cnc(C4(O)CC(F)(F)C4)nc3)cc12] |

TABLE 1-continued

| Ex. | Structure |
|---|---|
| 151 | 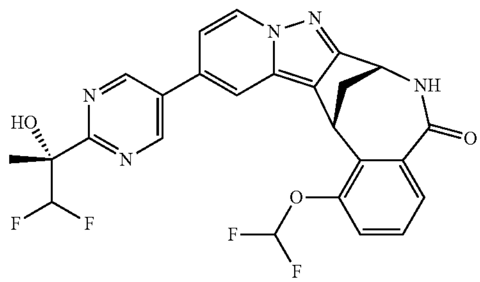 [SMILES: C[C@@](O)(c1ncc(-c2ccn3nc4c(c3c2)[C@@H]2C[C@H]4NC(=O)c3cccc(OC(F)F)c32)cn1)C(F)F] |
| 152 | 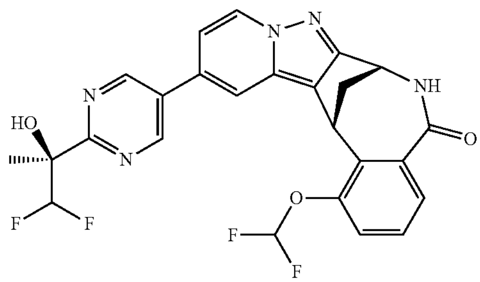 [SMILES: C[C@](O)(c1ncc(-c2ccn3nc4c(c3c2)[C@@H]2C[C@H]4NC(=O)c3cccc(OC(F)F)c32)cn1)C(F)F] |
| 153 | 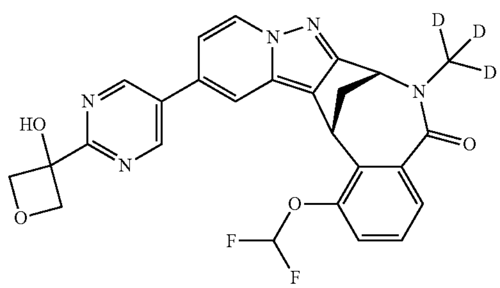 [SMILES: [2H]C([2H])([2H])N1C(=O)c2cccc(OC(F)F)c2[C@H]2C[C@@H]1c1nn3ccc(-c4cnc(C5(O)COC5)nc4)cc3c12] |
| 154 | 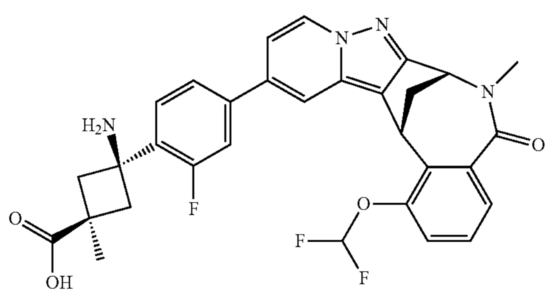 [SMILES: CN1C(=O)c2cccc(OC(F)F)c2[C@H]2C[C@@H]1c1nn3ccc(-c4ccc([C@]5(N)C[C@@](C)(C(=O)O)C5)c(F)c4)cc3c12] |
| 155 | 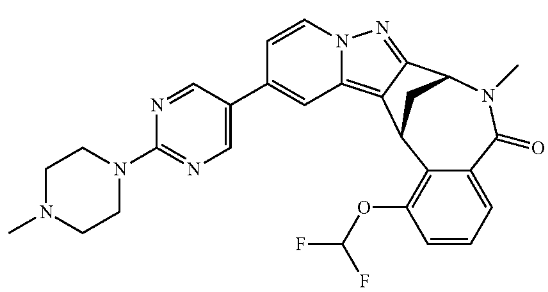 [SMILES: CN1CCN(c2ncc(-c3ccn4nc5c(c4c3)[C@@H]3C[C@H]5N(C)C(=O)c4cccc(OC(F)F)c43)cn2)CC1] |

TABLE 1-continued

| Ex. | Structure |
|---|---|
| 156 | 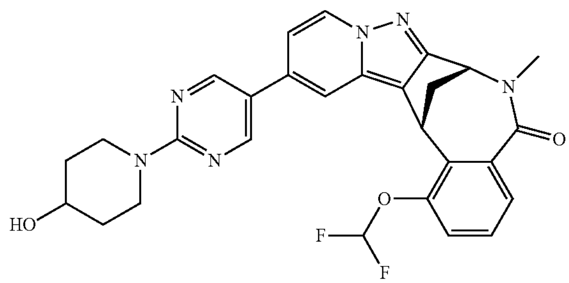 [SMILES: CN1C(=O)c2cccc(OC(F)F)c2[C@H]2C[C@@H]1c1nn3ccc(-c4cnc(N5CCC(O)CC5)nc4)cc3c12] |
| 157 | 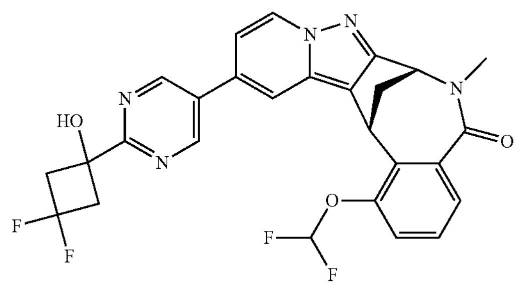 [SMILES: CN1C(=O)c2cccc(OC(F)F)c2[C@H]2C[C@@H]1c1nn3ccc(-c4cnc(C5(O)CC(F)(F)C5)nc4)cc3c12] |
| 158 | 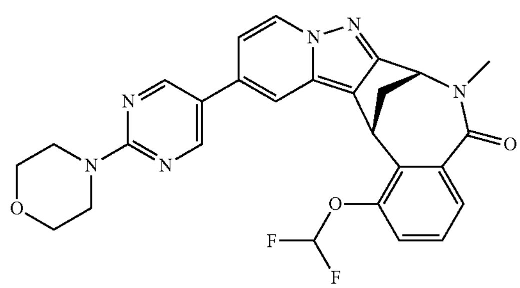 [SMILES: CN1C(=O)c2cccc(OC(F)F)c2[C@H]2C[C@@H]1c1nn3ccc(-c4cnc(N5CCOCC5)nc4)cc3c12] |
| 159 | 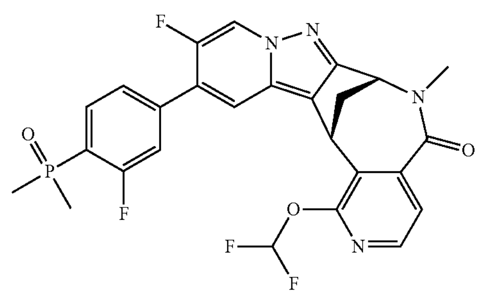 [SMILES: CN1C(=O)c2ccnc(OC(F)F)c2[C@H]2C[C@@H]1c1nn3cc(F)c(-c4ccc(P(C)(C)=O)c(F)c4)cc3c12] |
| 160 | 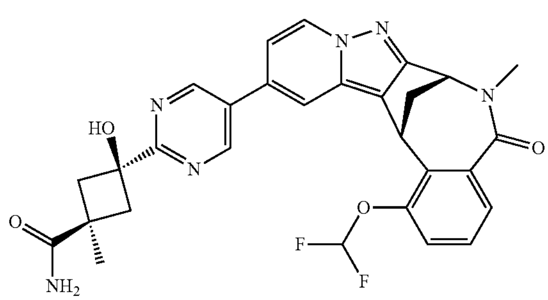 [SMILES: CN1C(=O)c2cccc(OC(F)F)c2[C@H]2C[C@@H]1c1nn3ccc(-c4cnc([C@]5(O)C[C@@](C)(C(N)=O)C5)nc4)cc3c12] |

TABLE 1-continued

| Ex. | Structure |
|---|---|
| 161 | 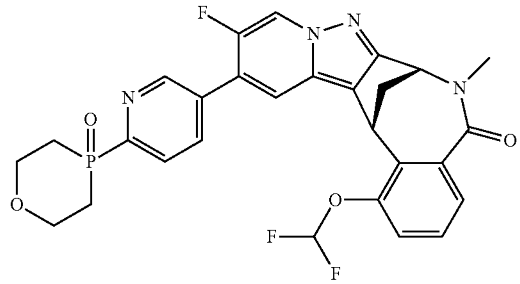 [SMILES: CN1C(=O)c2cccc(OC(F)F)c2[C@H]2C[C@@H]1c1nn3cc(F)c(-c4ccc(P5(=O)CCOCC5)nc4)cc3c12] |
| 162 | 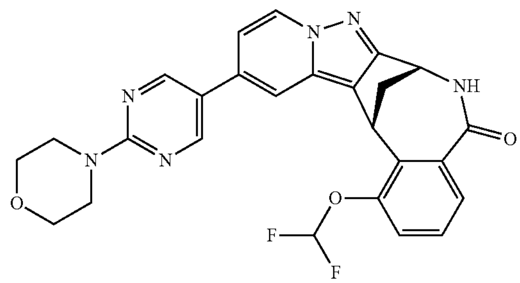 [SMILES: O=C1N[C@@H]2C[C@H](c3c(OC(F)F)cccc31)c1c2nn2ccc(-c3cnc(N4CCOCC4)nc3)cc12] |
| 163 | 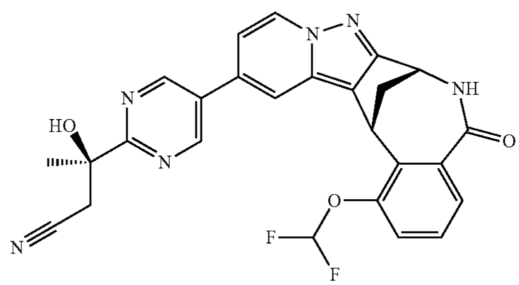 [SMILES: C[C@@](O)(CC#N)c1ncc(-c2ccn3nc4c(c3c2)[C@@H]2C[C@H]4NC(=O)c3cccc(OC(F)F)c32)cn1] |
| 164 | 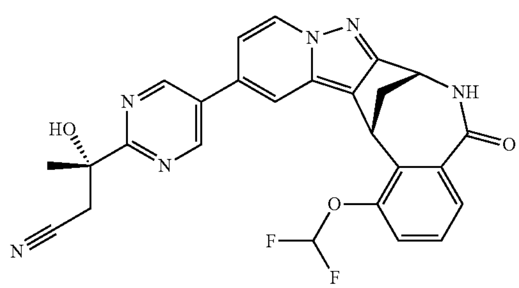 [SMILES: C[C@](O)(CC#N)c1ncc(-c2ccn3nc4c(c3c2)[C@@H]2C[C@H]4NC(=O)c3cccc(OC(F)F)c32)cn1] |
| 165 | 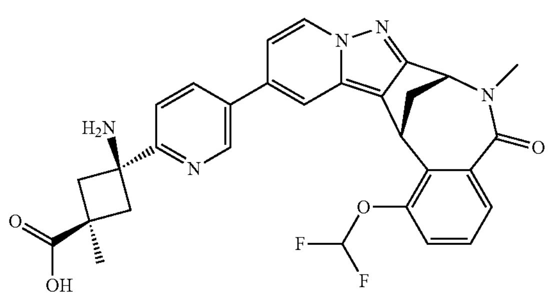 [SMILES: CN1C(=O)c2cccc(OC(F)F)c2[C@H]2C[C@@H]1c1nn3ccc(-c4ccc([C@]5(N)C[C@@](C)(C(=O)O)C5)nc4)cc3c12] |

TABLE 1-continued

| Ex. | Structure |
|---|---|
| 166 | 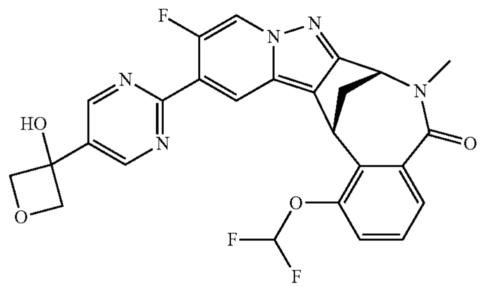 [SMILES: CN1C(=O)c2cccc(OC(F)F)c2[C@H]2C[C@@H]1c1nn3cc(F)c(-c4ncc(C5(O)COC5)cn4)cc3c12] |
| 167 | 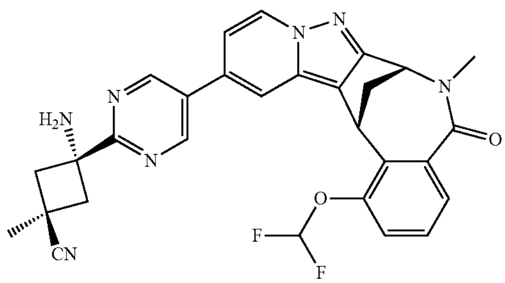 [SMILES: CN1C(=O)c2cccc(OC(F)F)c2[C@H]2C[C@@H]1c1nn3ccc(-c4cnc([C@]5(N)C[C@](C)(C#N)C5)nc4)cc3c12] |
| 168 | 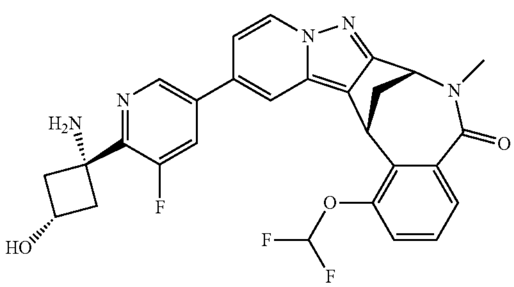 [SMILES: CN1C(=O)c2cccc(OC(F)F)c2[C@H]2C[C@@H]1c1nn3ccc(-c4cnc([C@]5(N)C[C@@H](O)C5)c(F)c4)cc3c12] |
| 169 | 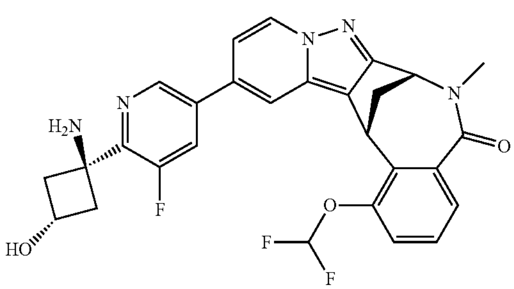 [SMILES: CN1C(=O)c2cccc(OC(F)F)c2[C@H]2C[C@@H]1c1nn3ccc(-c4cnc([C@]5(N)C[C@H](O)C5)c(F)c4)cc3c12] |
| 170 | 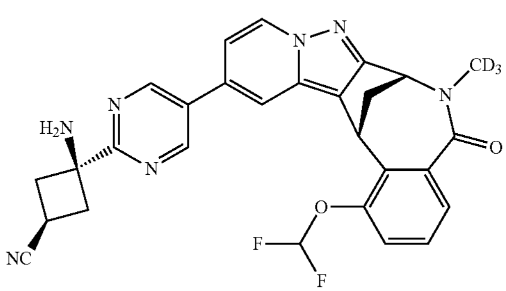 [SMILES: [2H]C([2H])([2H])N1C(=O)c2cccc(OC(F)F)c2[C@H]2C[C@@H]1c1nn3ccc(-c4cnc([C@]5(N)C[C@@H](C#N)C5)nc4)cc3c12] |

TABLE 1-continued

| Ex. | Structure |
|---|---|
| 171 | 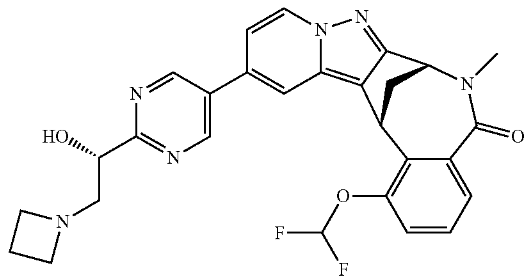 [SMILES: CN1C(=O)c2cccc(OC(F)F)c2[C@H]2C[C@@H]1c1nn3ccc(-c4cnc([C@@H](O)CN5CCC5)nc4)cc3c12] |
| 172 | 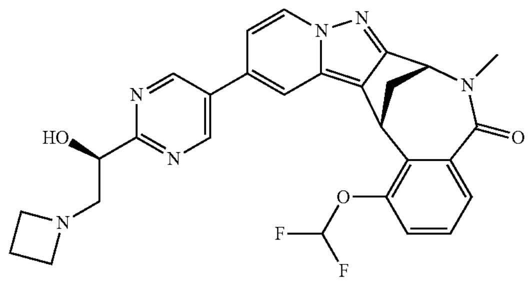 [SMILES: CN1C(=O)c2cccc(OC(F)F)c2[C@H]2C[C@@H]1c1nn3ccc(-c4cnc([C@H](O)CN5CCC5)nc4)cc3c12] |
| 173 | 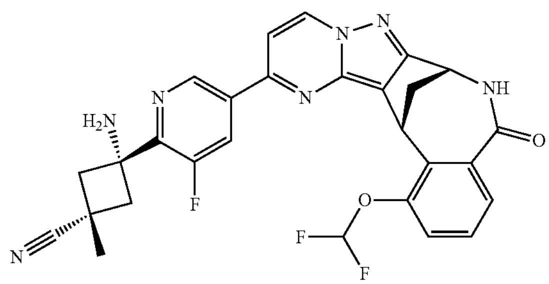 [SMILES: C[C@]1(C#N)C[C@](N)(c2ncc(-c3ccn4nc5c(c4n3)[C@@H]3C[C@H]5NC(=O)c4cccc(OC(F)F)c43)cc2F)C1] |
| 174 | 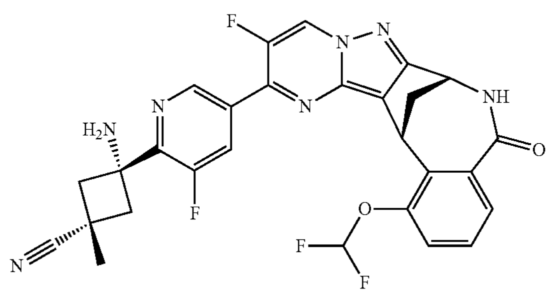 [SMILES: C[C@]1(C#N)C[C@](N)(c2ncc(-c3nc4c5c(nn4cc3F)[C@H]3C[C@@H]5c4c(OC(F)F)cccc4C(=O)N3)cc2F)C1] |
| 175 | 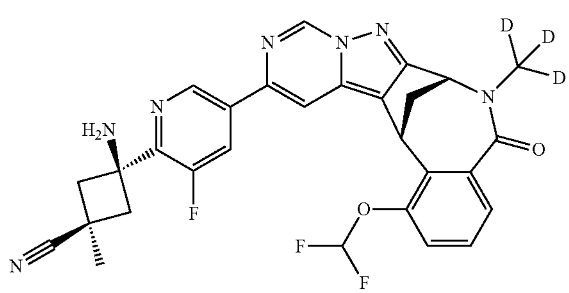 [SMILES: [2H]C([2H])([2H])N1C(=O)c2cccc(OC(F)F)c2[C@H]2C[C@@H]1c1nn3cnc(-c4cnc([C@]5(N)C[C@@](C)(C#N)C5)c(F)c4)cc3c12] |

TABLE 1-continued

| Ex. | Structure |
|---|---|
| 176 | 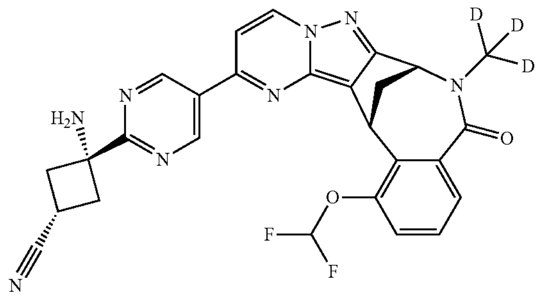 [SMILES: [2H]C([2H])([2H])N1C(=O)c2cccc(OC(F)F)c2[C@H]2C[C@@H]1c1nn3ccc(-c4cnc([C@]5(N)C[C@@H](C#N)C5)nc4)nc3c12] |
| 177 | 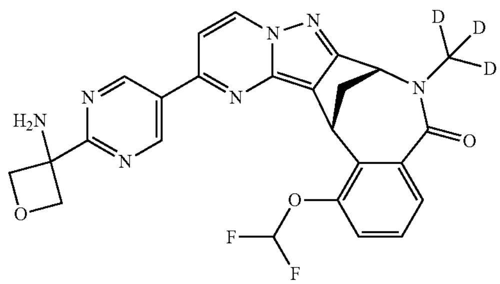 [SMILES: [2H]C([2H])([2H])N1C(=O)c2cccc(OC(F)F)c2[C@H]2C[C@@H]1c1nn3ccc(-c4cnc(C5(N)COC5)nc4)nc3c12] |
| 178 | 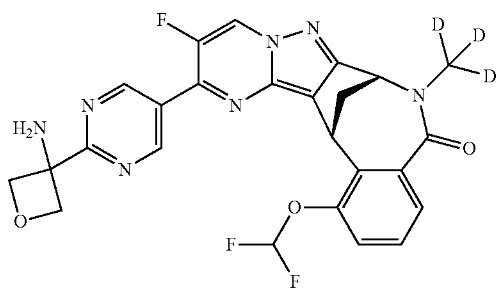 [SMILES: [2H]C([2H])([2H])N1C(=O)c2cccc(OC(F)F)c2[C@H]2C[C@@H]1c1nn3cc(F)c(-c4cnc(C5(N)COC5)nc4)nc3c12] |
| 179 | 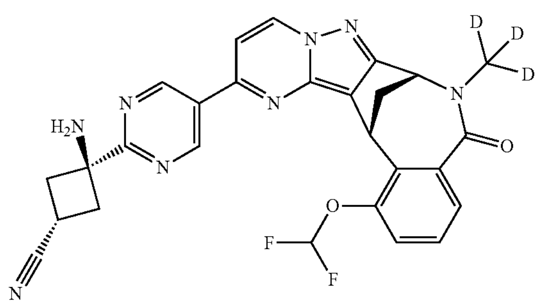 [SMILES: [2H]C([2H])([2H])N1C(=O)c2cccc(OC(F)F)c2[C@H]2C[C@@H]1c1nn3ccc(-c4cnc([C@]5(N)C[C@H](C#N)C5)nc4)nc3c12] |
| 180 | 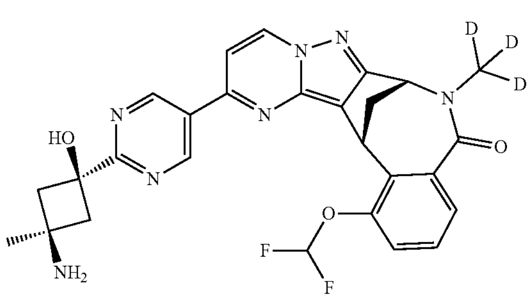 |

TABLE 1-continued
| Ex. | Structure |
|---|---|
| 181 | 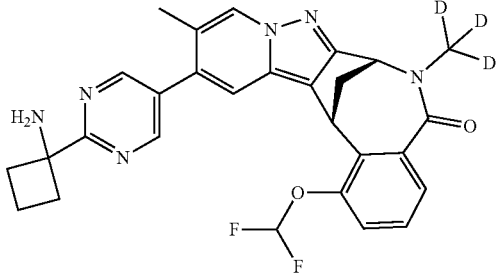 |
| 182 | 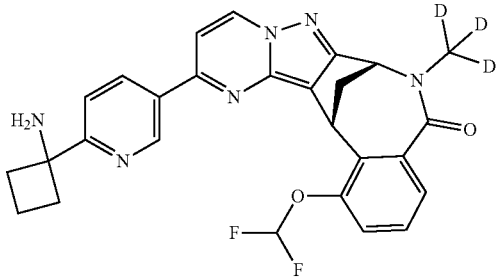 |
| 183 | 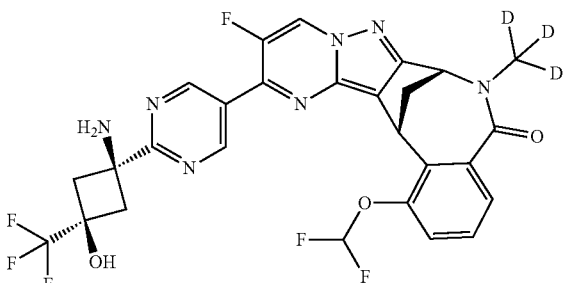 |
| 184 | 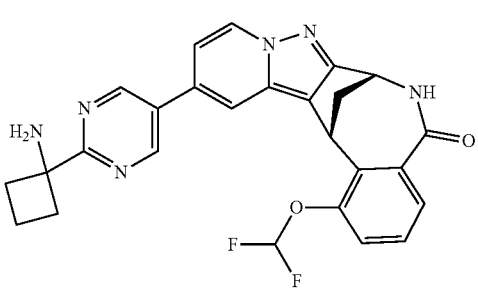 |
| 185 | 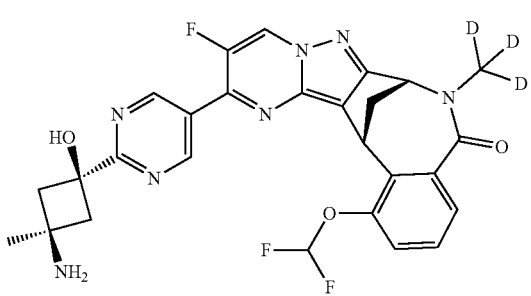 |

TABLE 1-continued

| Ex. | Structure |
|---|---|
| 186 | 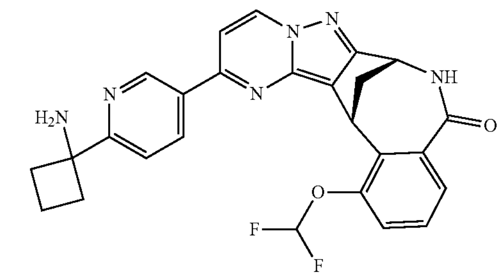 [SMILES: NC1(c2ccc(-c3ccn4nc5c(c4n3)[C@@H]3C[C@H]5NC(=O)c4cccc(OC(F)F)c43)cn2)CCC1] |
| 187 | 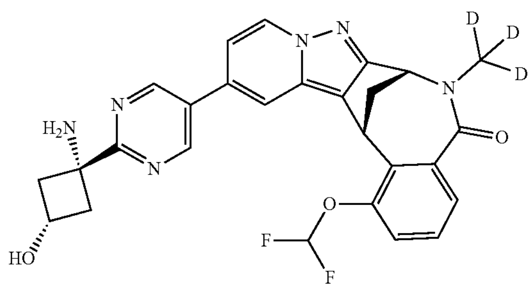 |
| 188 | 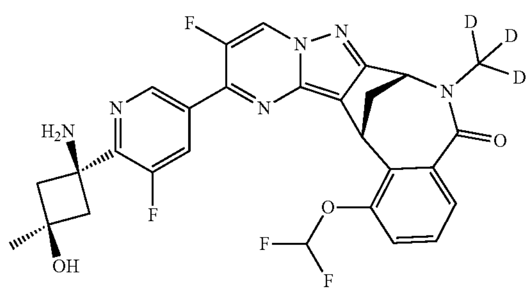 |
| 189 | 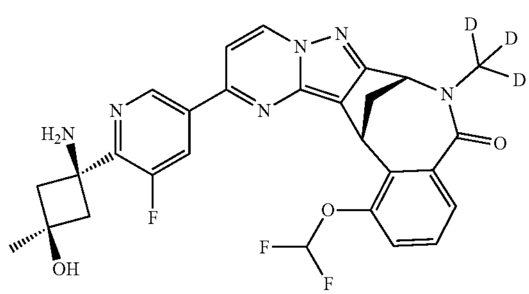 |
| 190 | 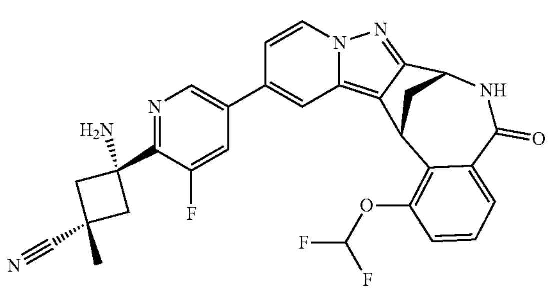 |

TABLE 1-continued
| Ex. | Structure |
|---|---|
| 191 | 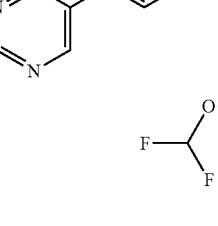 |
| 192 | 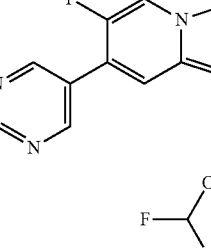 |
| 193 | 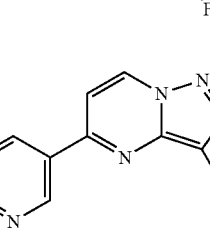 |
| 194 | 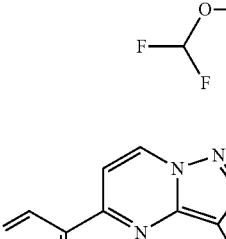 |
| 195 | 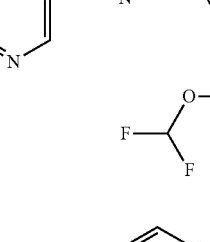 |

139
140
TABLE 1-continued
| Ex. | Structure |
|---|---|
| 196 | 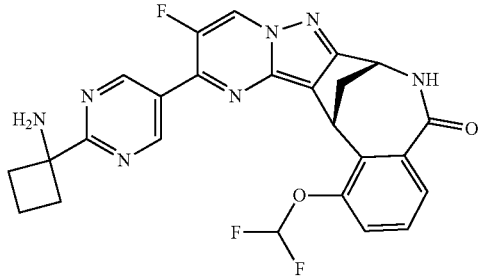 |
| 197 | 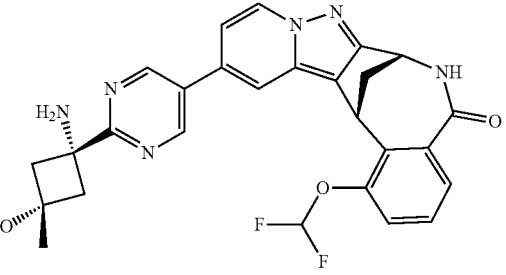 |
| 198 | 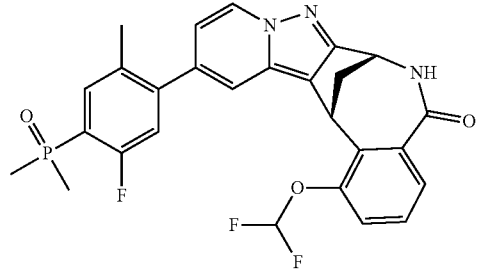 |
| 199 | 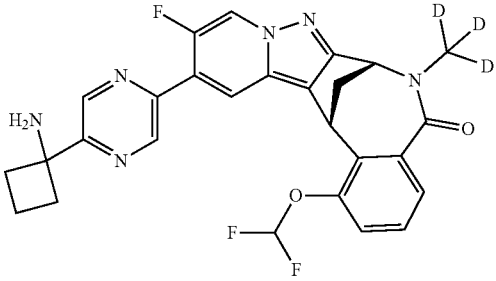 |
| 200 | 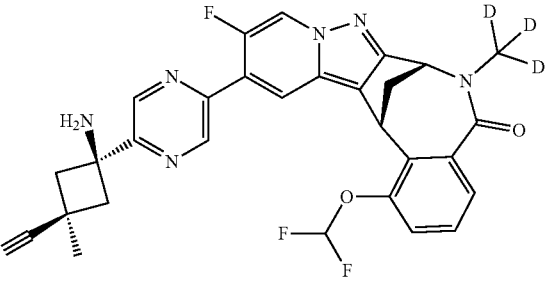 |

TABLE 1-continued

| Ex. | Structure |
|---|---|
| 201 | 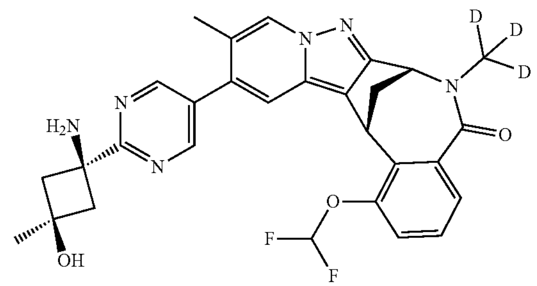 |
| 202 | 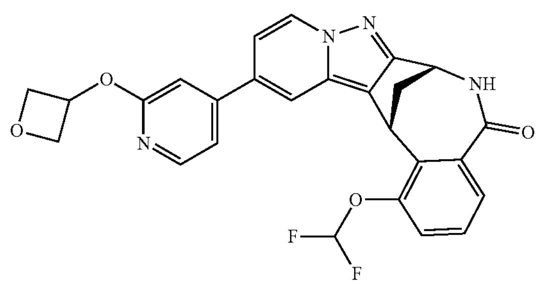 |
| 203 | 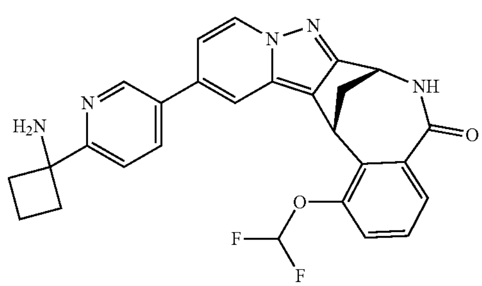 |
| 204 | 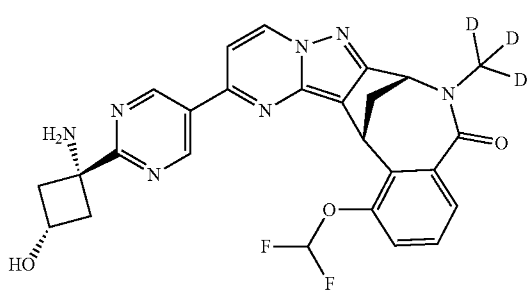 |
| 205 | 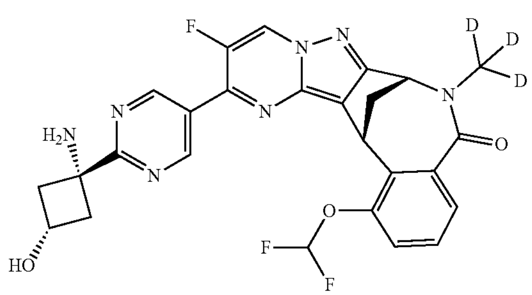 |

TABLE 1-continued

| Ex. | Structure |
|---|---|
| 206 | 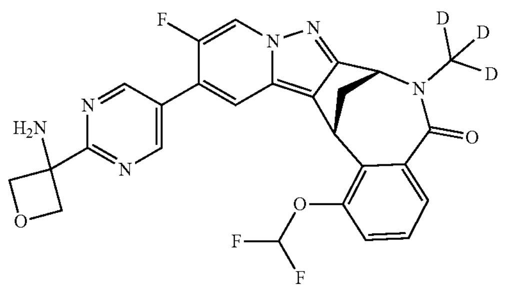 |
| 207 | 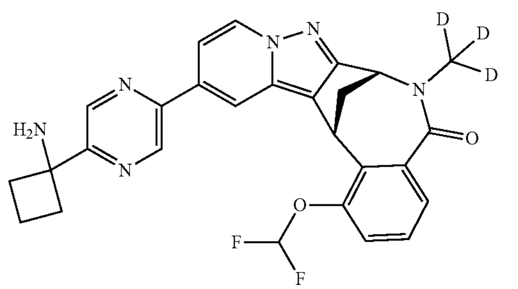 |
| 208 | 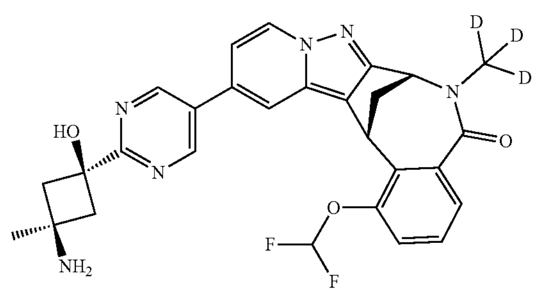 |
| 209 | 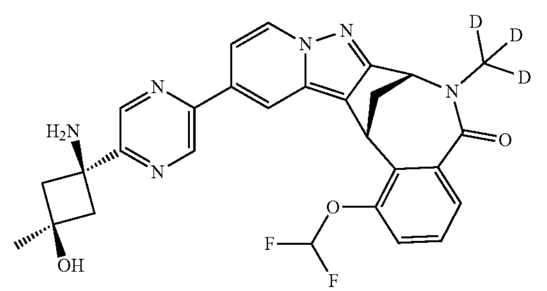 |
| 210 | 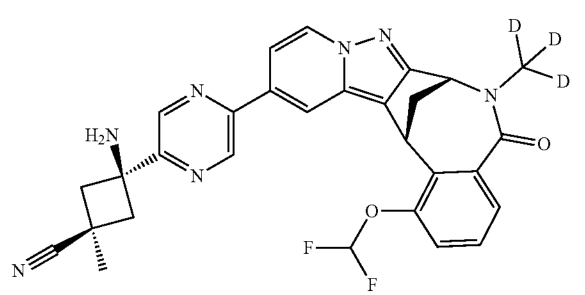 |

TABLE 1-continued

| Ex. | Structure |
|---|---|
| 211 | 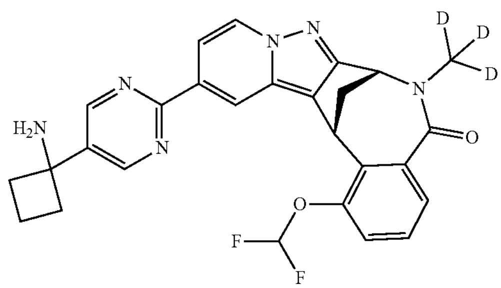 |
| 212 | 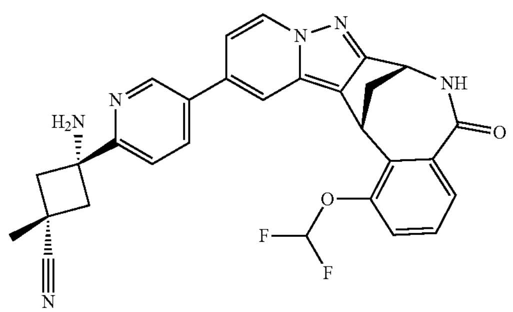 |
| 213 | 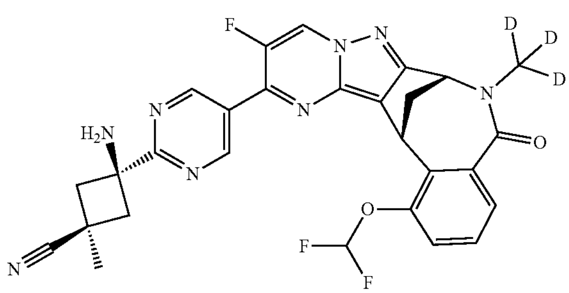 |
| 214 | 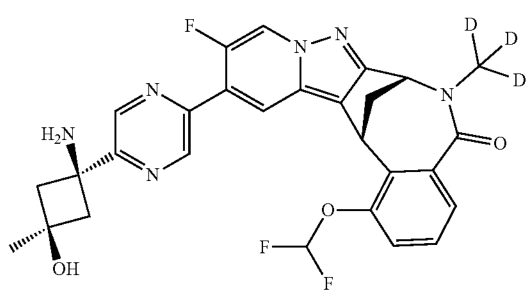 |
| 215 | 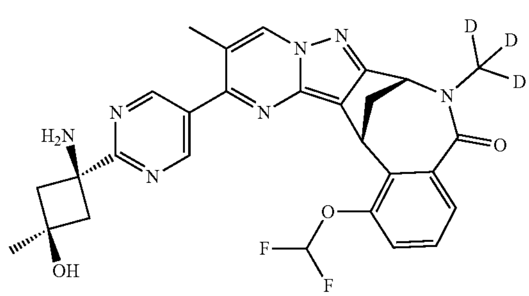 |

TABLE 1-continued

| Ex. | Structure |
|---|---|
| 216 | 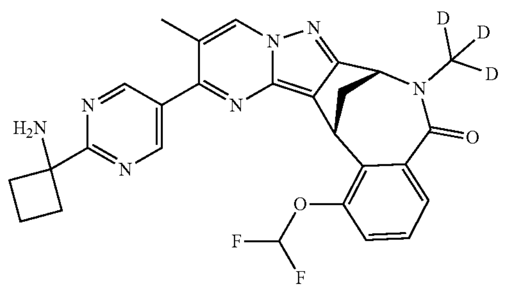 |
| 217 | 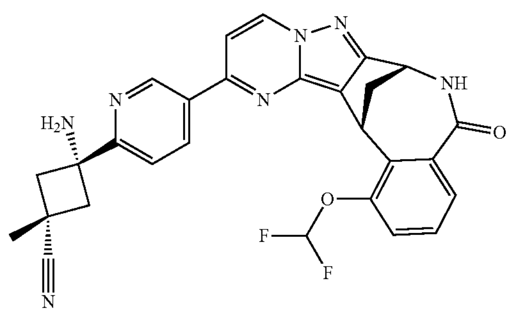 |
| 218 | 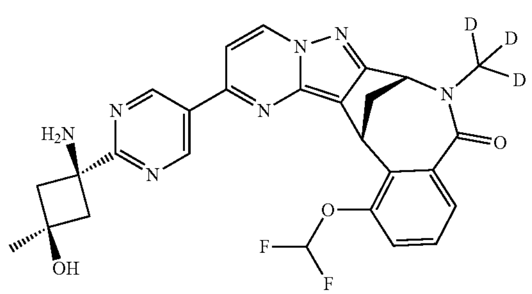 |
| 219 | 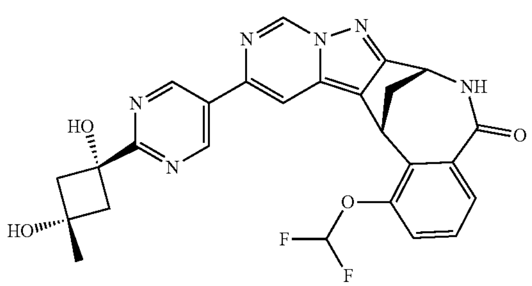 |
| 220 | 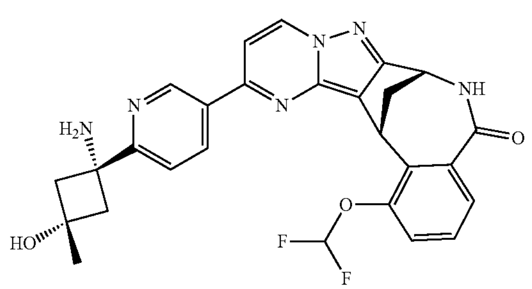 |

TABLE 1-continued
| Ex. | Structure |
|---|---|
| 221 | 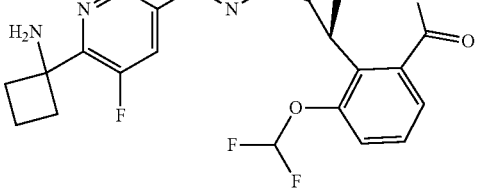 |
| 222 | 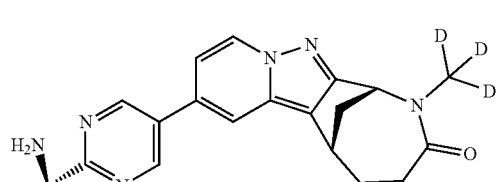 |
| 223 | 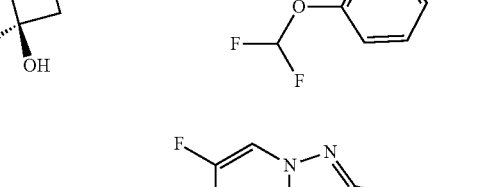 |
| 224 | 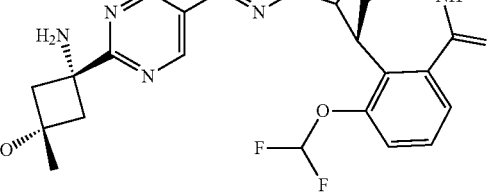 |
| 225 | 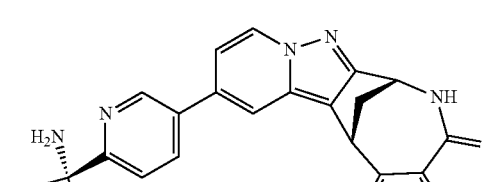 |

TABLE 1-continued

| Ex. | Structure |
|---|---|
| 226 | 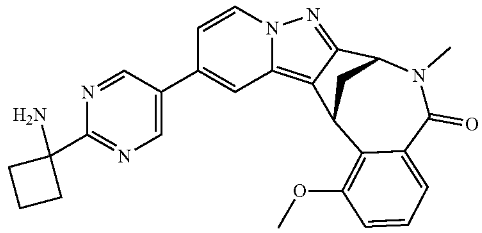 |
| 227 | 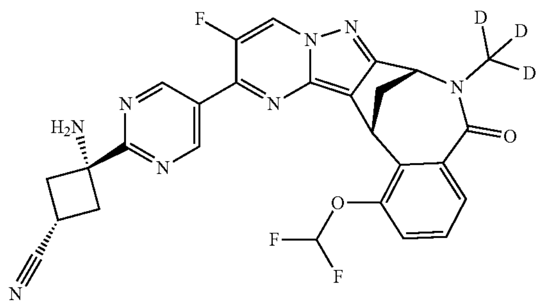 |
| 228 | 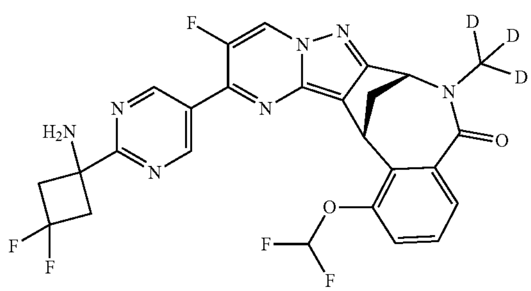 |
| 229 | 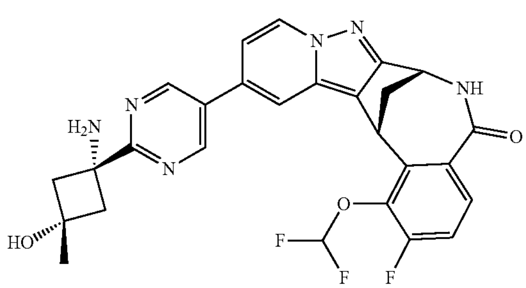 |
| 230 | 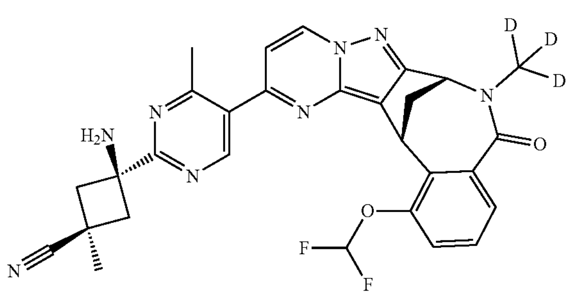 |

TABLE 1-continued

| Ex. | Structure |
|---|---|
| 231 | 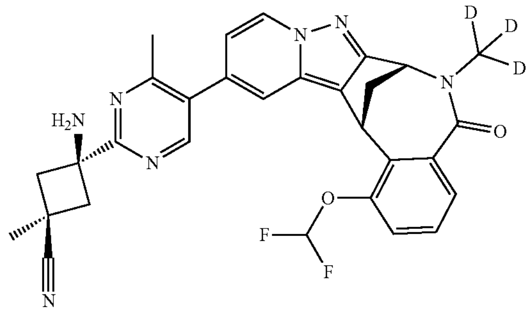 |
| 232 | 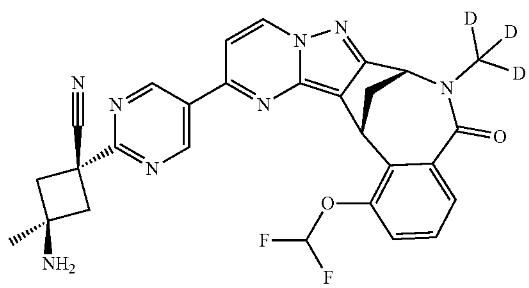 |
| 233 | 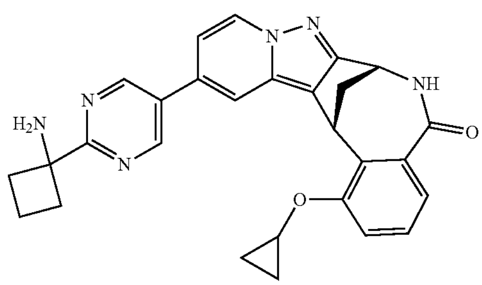 |
| 234 | 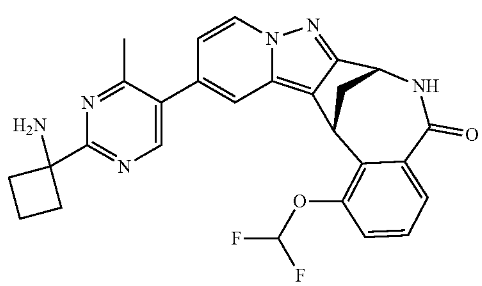 |
| 235 | 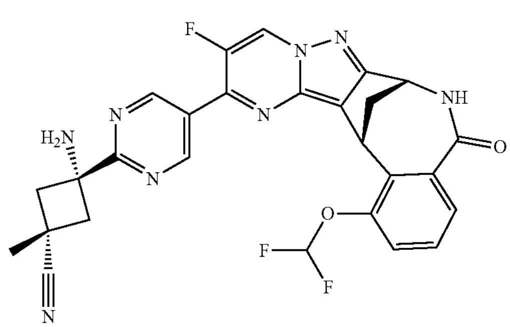 |

TABLE 1-continued

| Ex. | Structure |
|---|---|
| 236 | 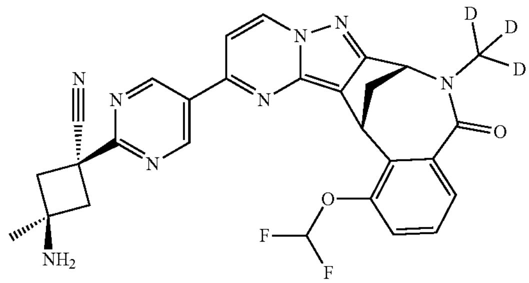 |
| 237 | 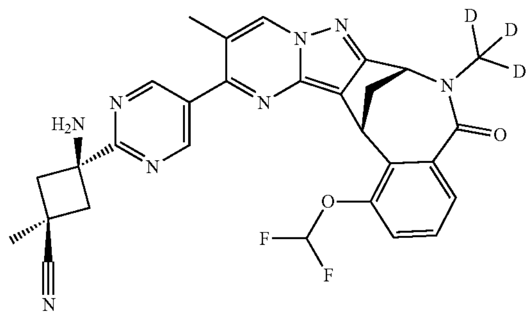 |
| 238 | 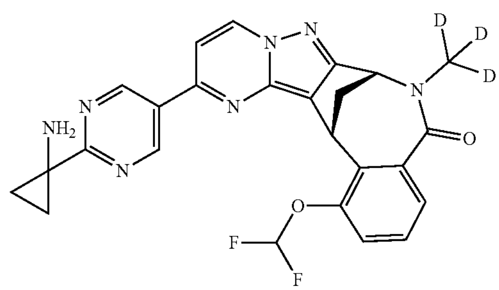 |
| 239 | 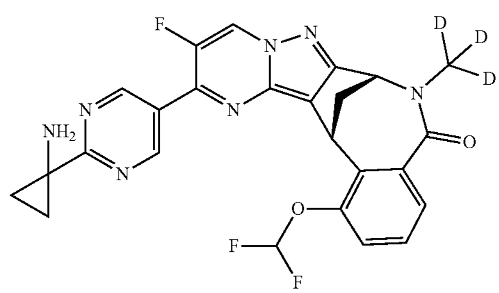 |
| 240 | 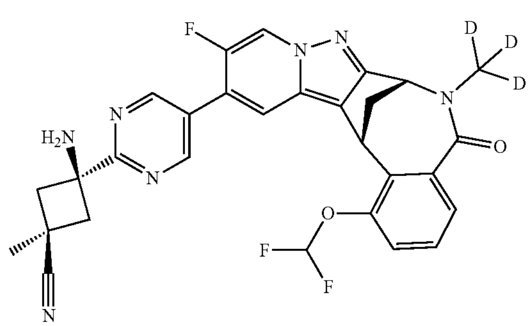 |

TABLE 1-continued
| Ex. | Structure |
|---|---|
| 241 | 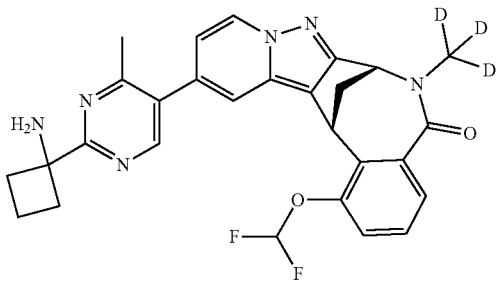 |
| 242 | 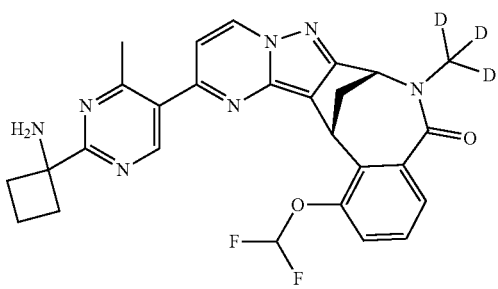 |
| 243 | 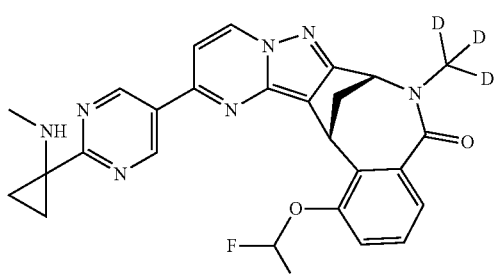 |
| 244 | 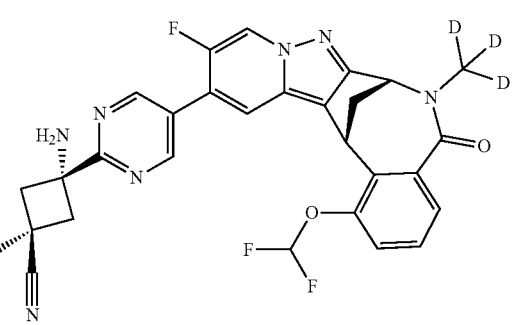 |
| 245 | 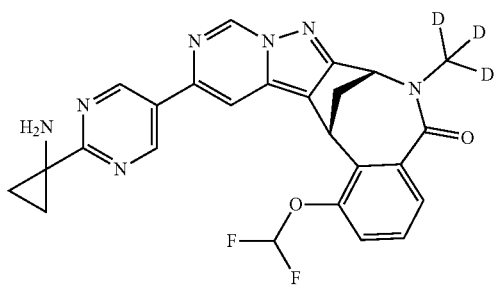 |

TABLE 1-continued

| Ex. | Structure |
|---|---|
| 246 | 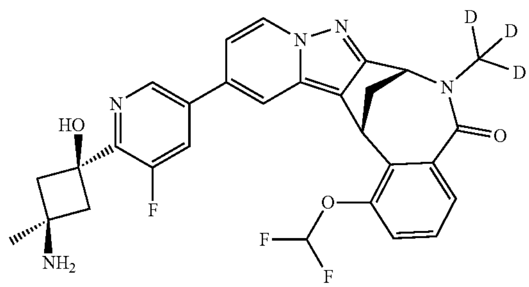 |
| 247 | 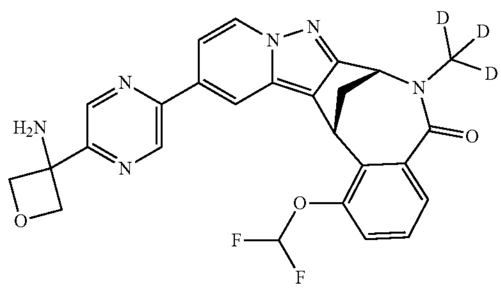 |
| 248 | 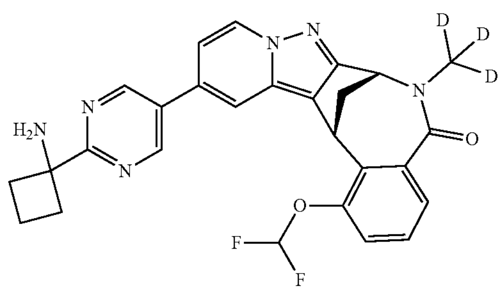 |
| 249 | 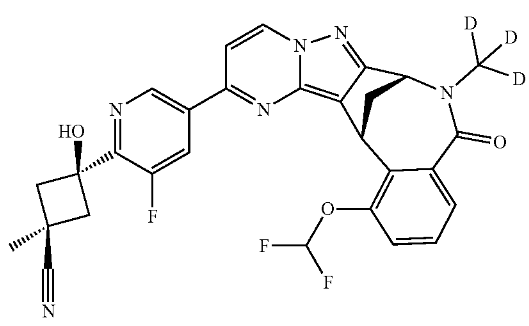 |
| 250 | 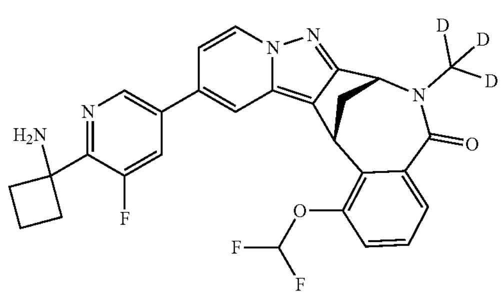 |

TABLE 1-continued

| Ex. | Structure |
|---|---|
| 251 | 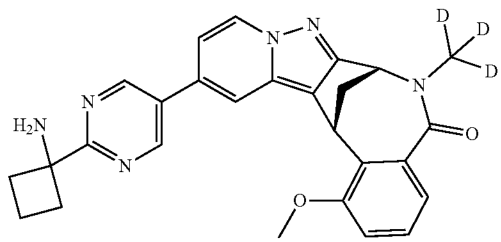 |
| 252 | 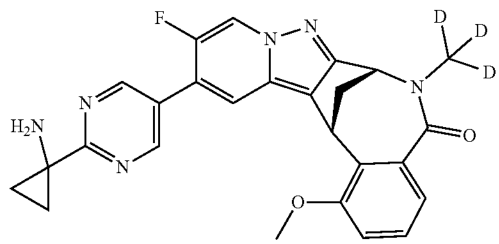 |
| 253 | 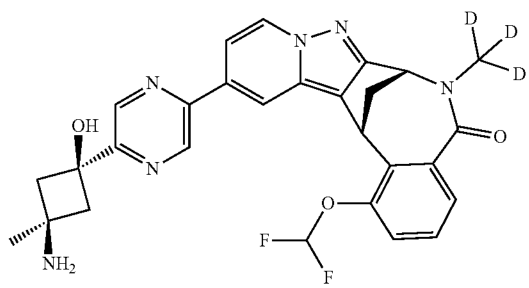 |
| 254 | 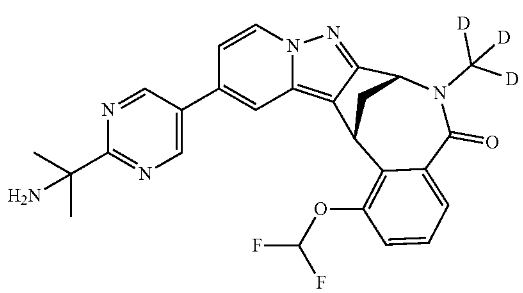 |
| 255 | 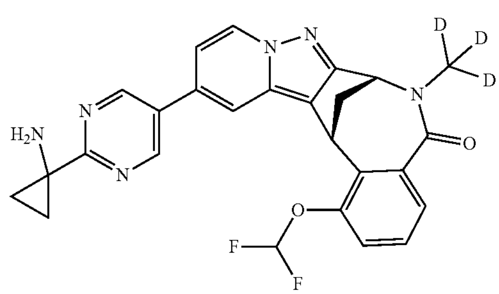 |

TABLE 1-continued

| Ex. | Structure |
|---|---|
| 256 | 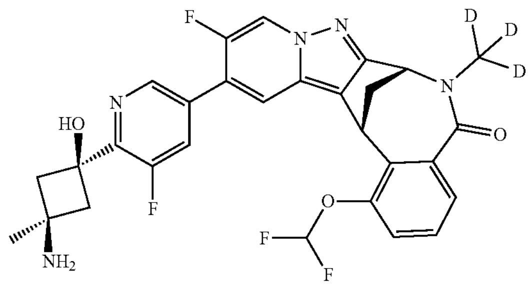 |
| 257 | 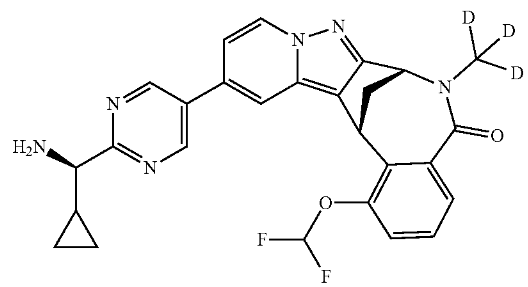 |
| 258 | 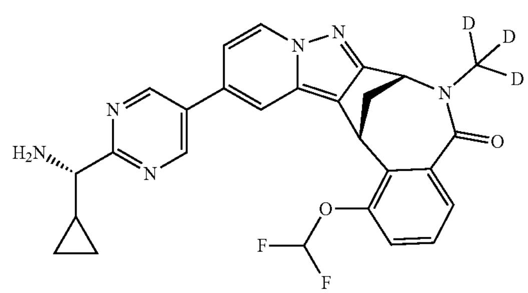 |
| 259 | 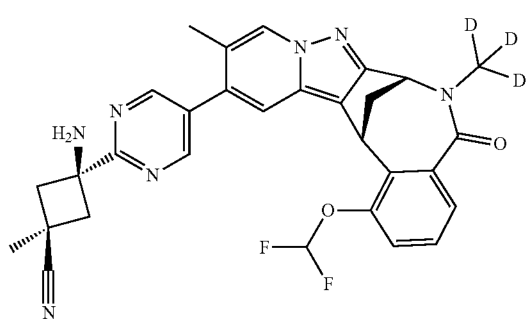 |
| 260 | 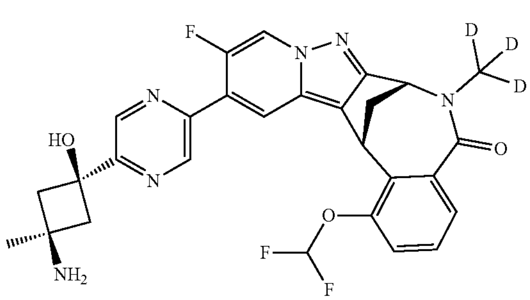 |

TABLE 1-continued

| Ex. | Structure |
|---|---|
| 261 | 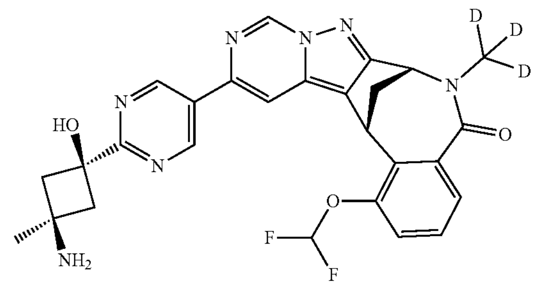 |
| 262 | 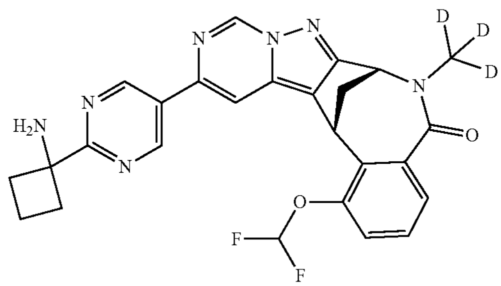 |
| 263 | 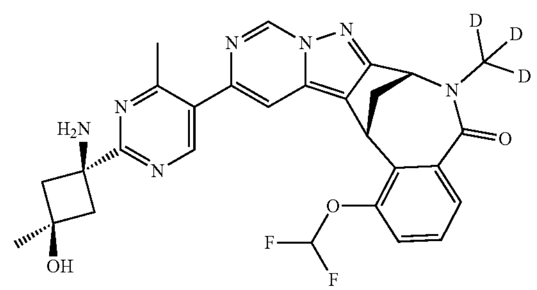 |
| 264 | 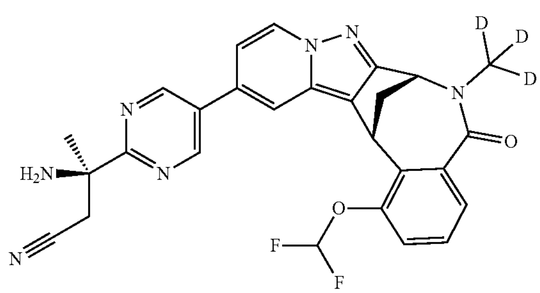 |
| 265 | 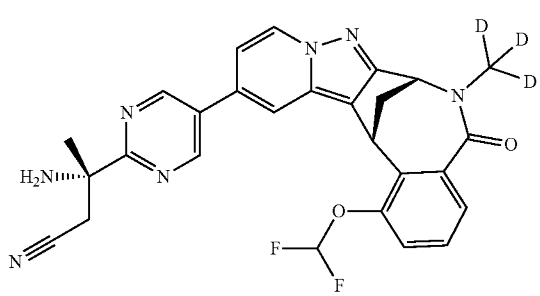 |

TABLE 1-continued

| Ex. | Structure |
|---|---|
| 266 | 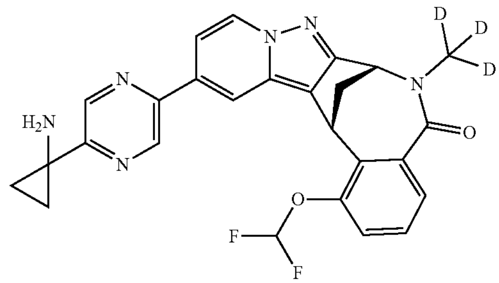 |
| 267 | 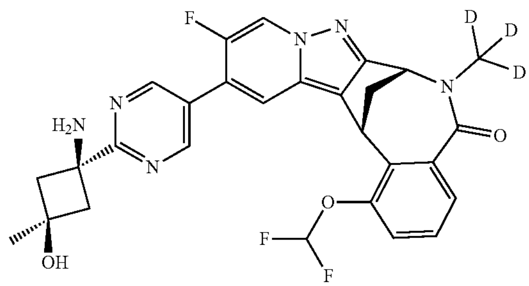 |
| 268 | 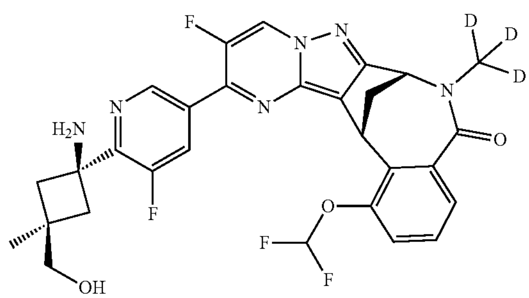 |
| 269 | 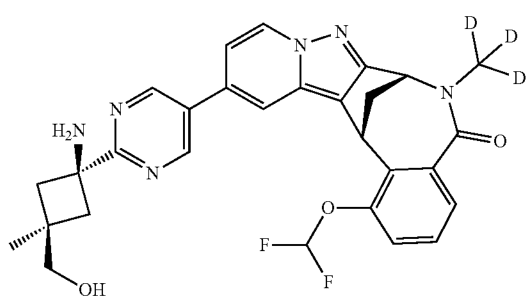 |
| 270 | 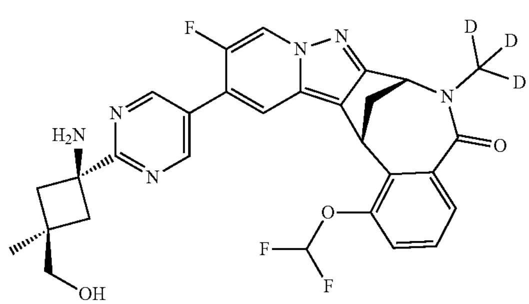 |

TABLE 1-continued

| Ex. | Structure |
|---|---|
| 271 | 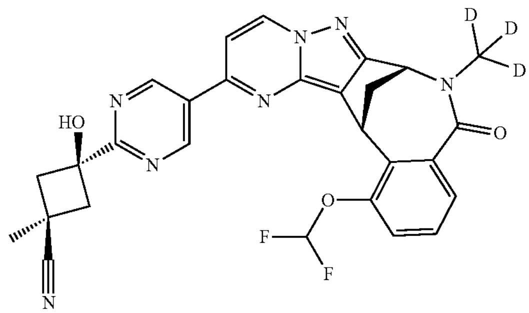 |
| 272 | 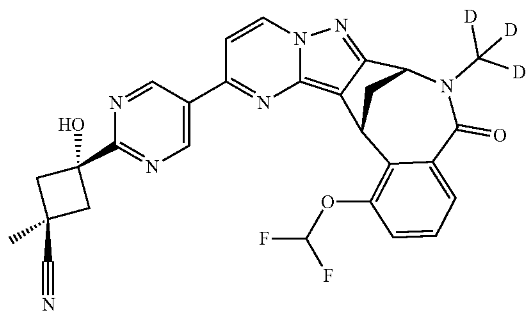 |
| 273 | 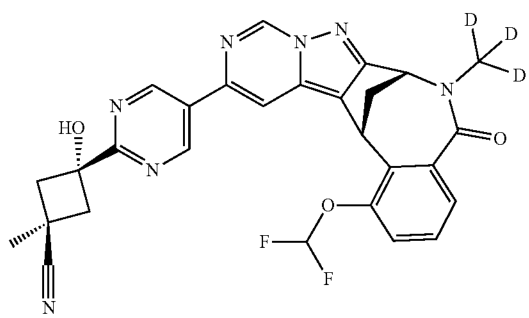 |
| 274 | 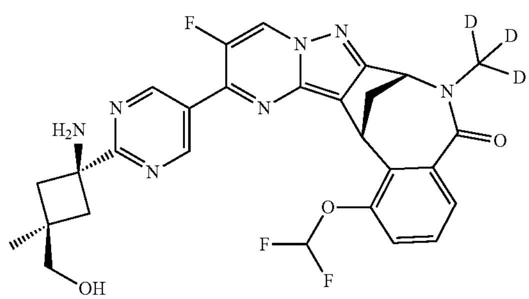 |
| 275 | 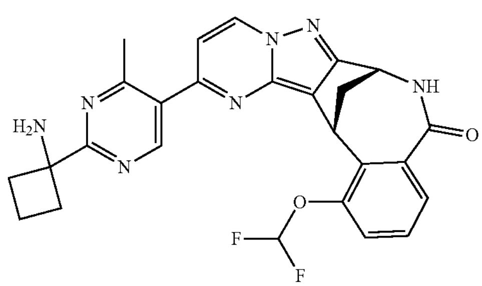 |

TABLE 1-continued

| Ex. | Structure |
|---|---|
| 276 | 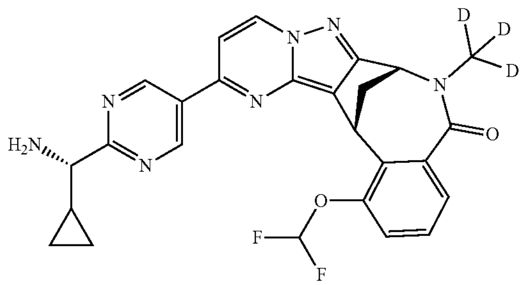 |
| 277 | 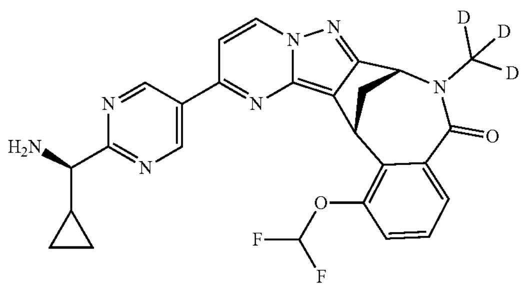 |
| 278 | 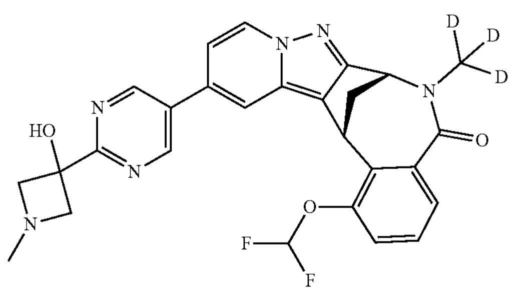 |
| 279 | 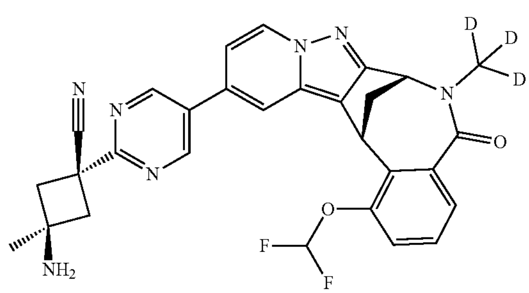 |
| 280 | 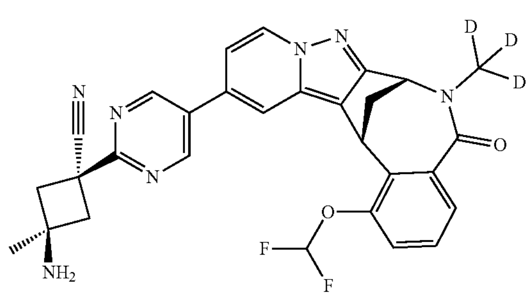 |

TABLE 1-continued

| Ex. | Structure |
|---|---|
| 281 | 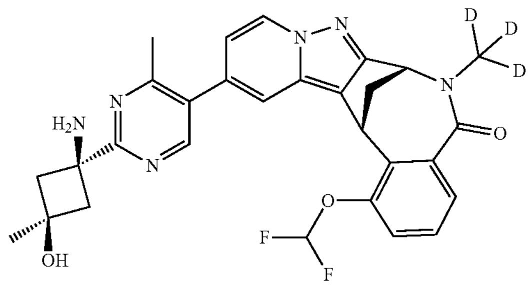 |
| 282 | 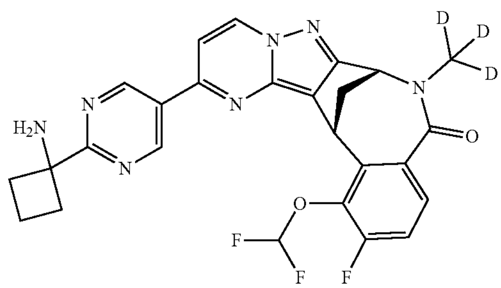 |
| 283 | 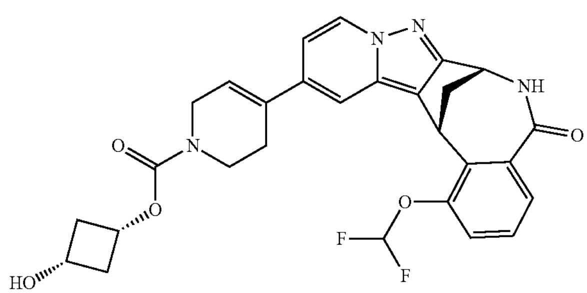 |
| 284 | 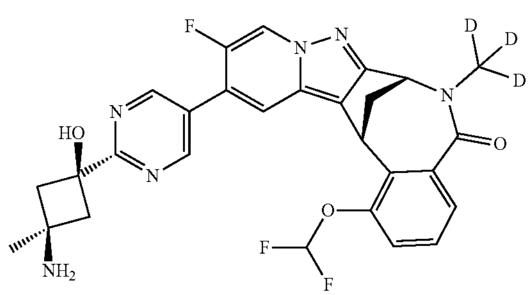 |
| 285 | 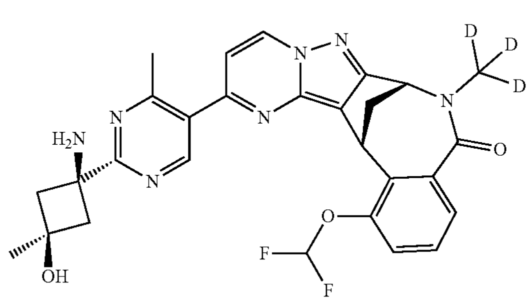 |

TABLE 1-continued

| Ex. | Structure |
|---|---|
| 286 | 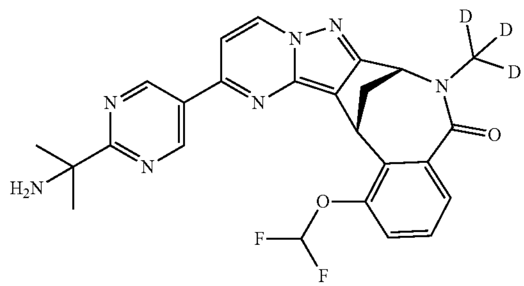 |
| 287 | 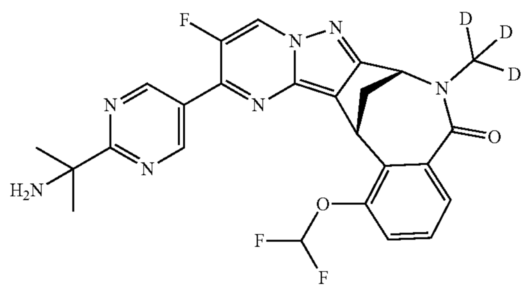 |
| 288 | 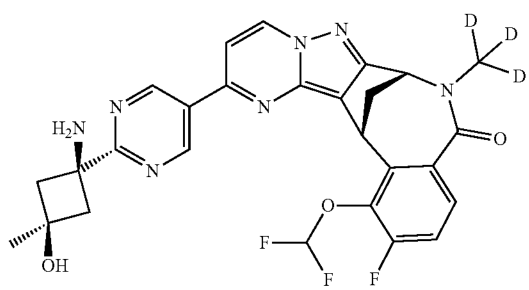 |
| 289 | 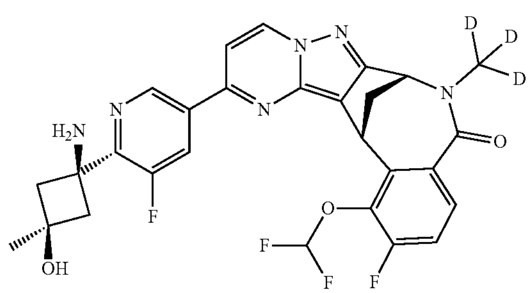 |
| 290 | 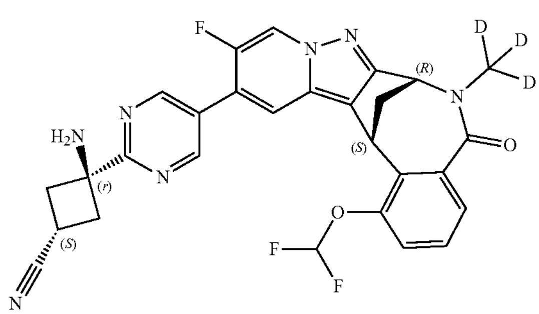 |

TABLE 1-continued

| Ex. | Structure |
|---|---|
| 291 | 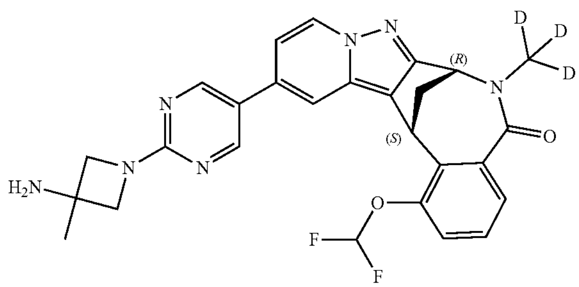 |
| 292 | 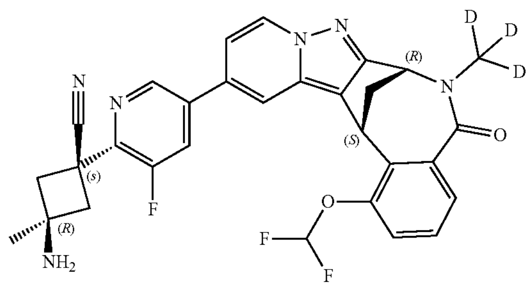 |
| 293 | 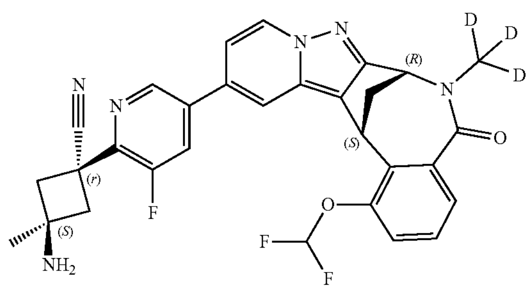 |
| 294 | 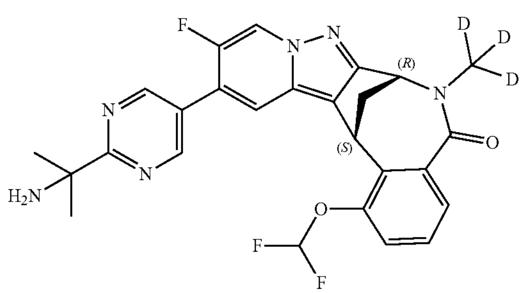 |
| 295 | 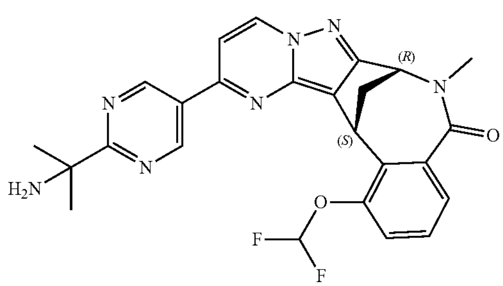 |

TABLE 1-continued

| Ex. | Structure |
|---|---|
| 296 | 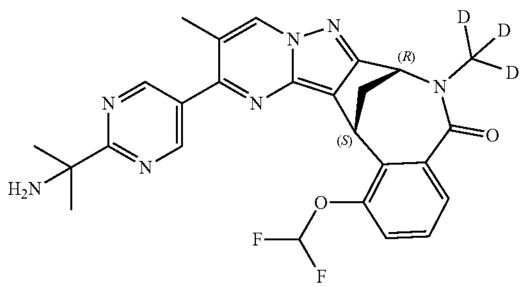 |
| 297 | 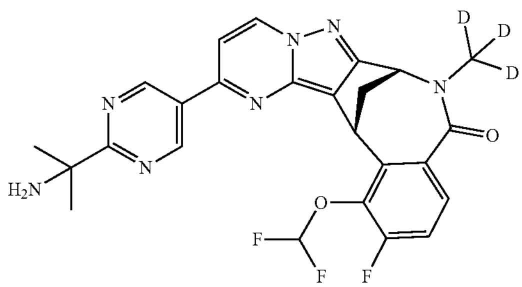 |
| 298 | 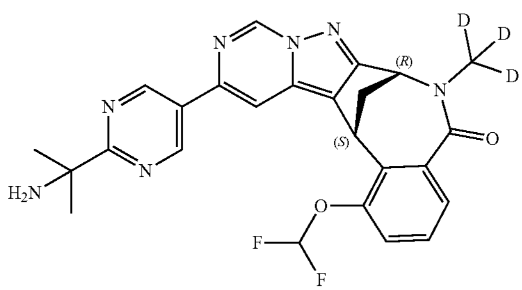 |
| 299 | 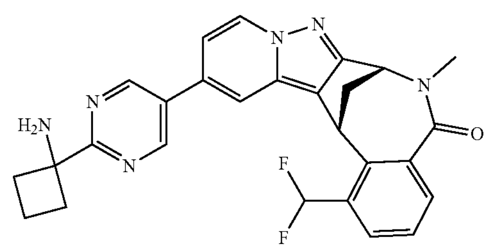 |
| 300 | 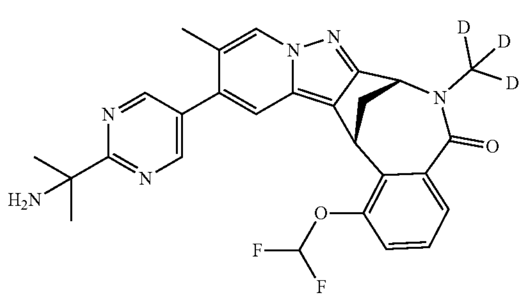 |

TABLE 1-continued

| Ex. | Structure |
|---|---|
| 301 | 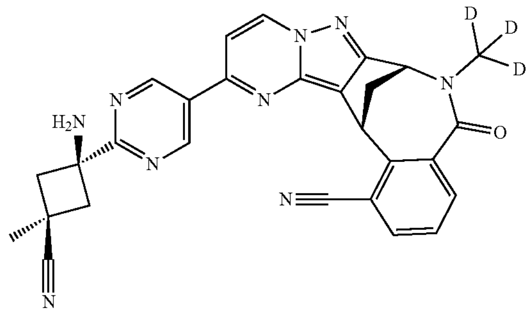 |
| 302 | 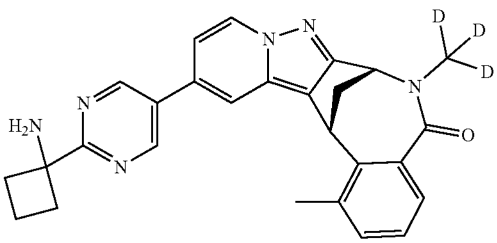 |
| 303 | 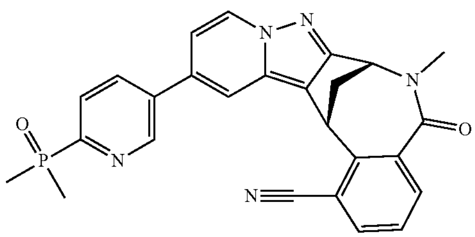 |
| 304 | 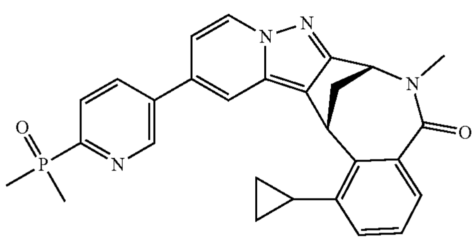 |
| 305 | 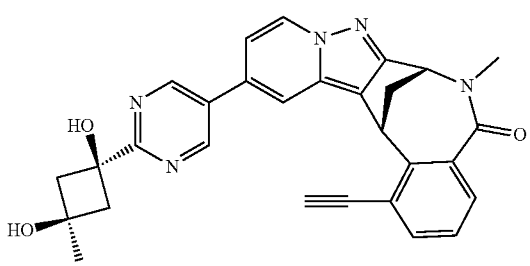 |
| 306 | 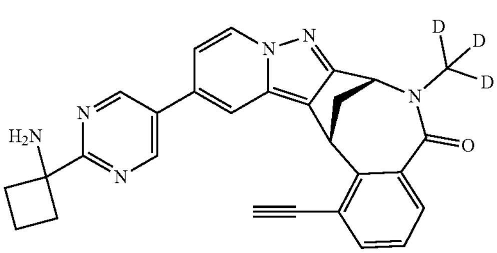 |

TABLE 1-continued

| Ex. | Structure |
|-----|-----------|
| 307 | 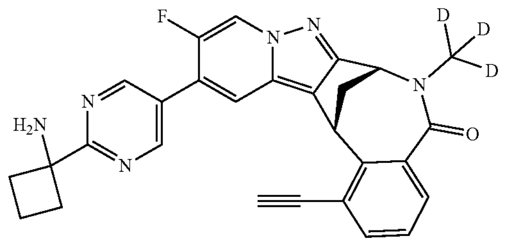 |
| 308 | 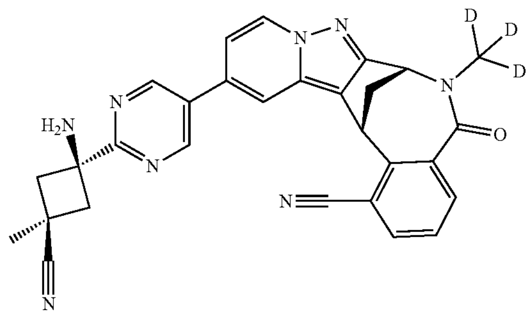 |
| 309 | 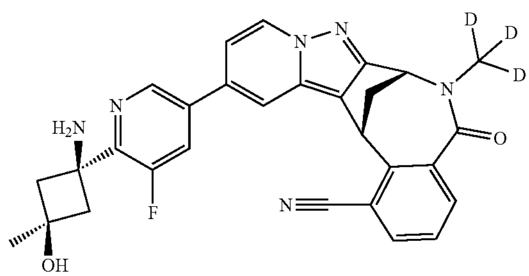 |
| 310 | 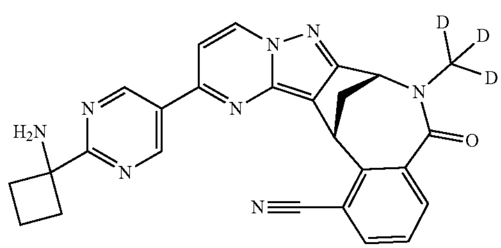 |
| 311 | 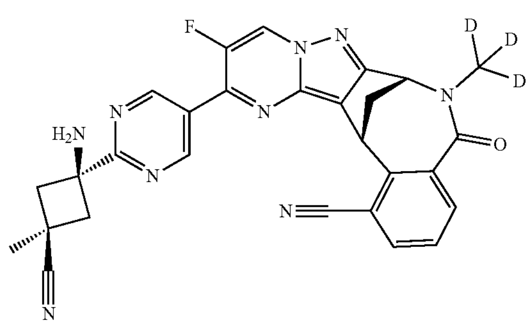 |

TABLE 1-continued

| Ex. | Structure |
|---|---|
| 312 | 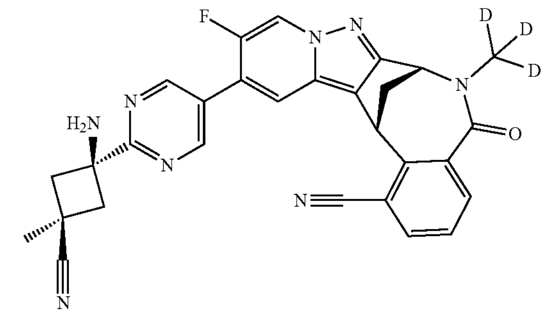 |
| 313 | 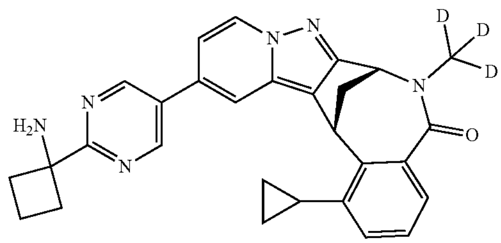 |
| 314 | 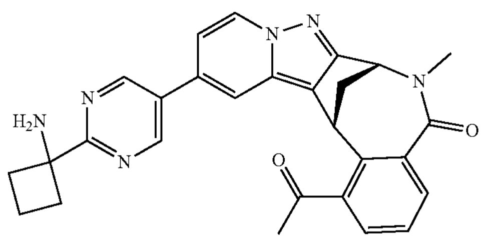 |
| 315 | 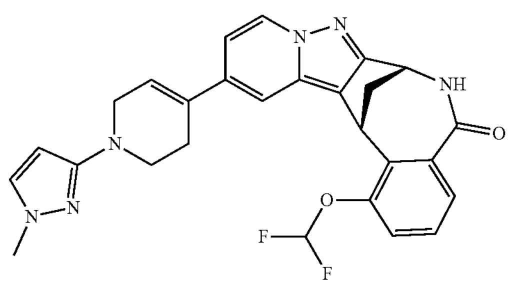 |
| 316 | 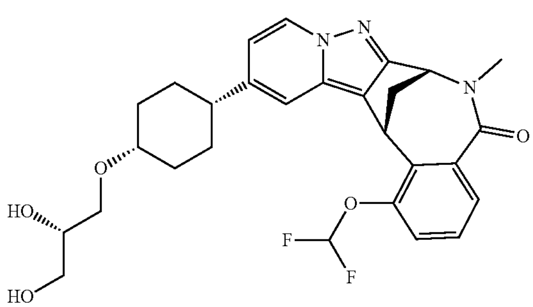 |

TABLE 1-continued

| Ex. | Structure |
|---|---|
| 317 | 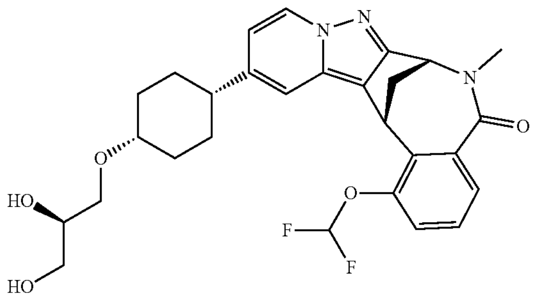 |
| 318 | 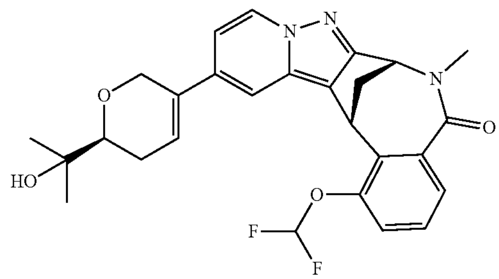 |
| 319 | 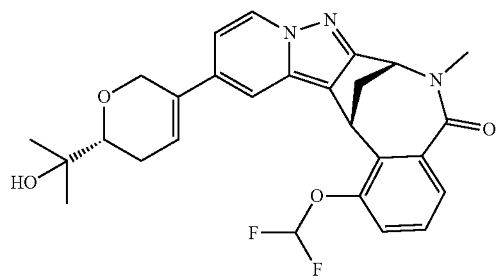 |
| 320 | 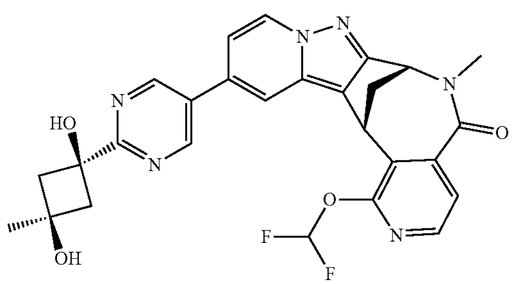 |
| 321 | 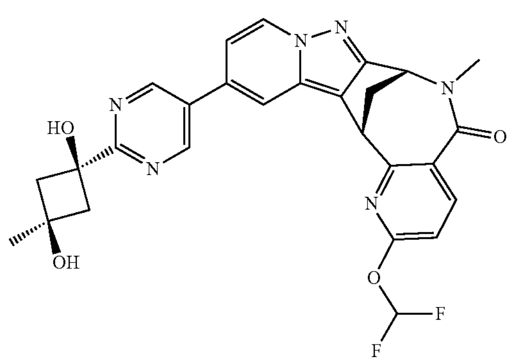 |

TABLE 1-continued

| Ex. | Structure |
|---|---|
| 322 | 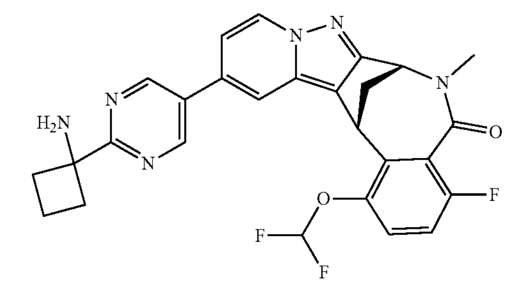 |
| 323 | 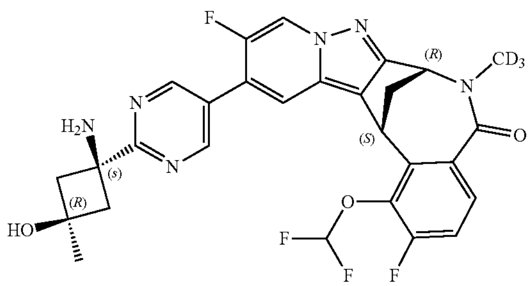 |
| 324 | 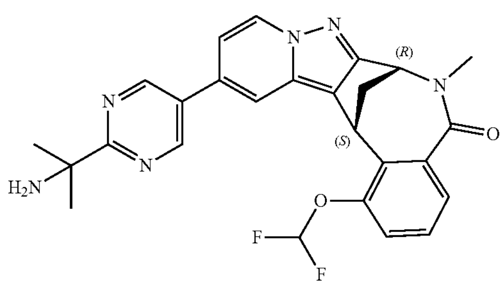 |
| 325 | 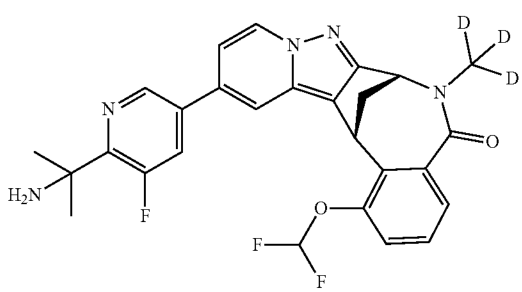 |
| 326 | 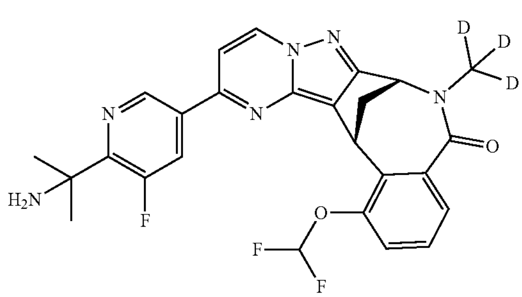 |

TABLE 1-continued

| Ex. | Structure |
|---|---|
| 327 | 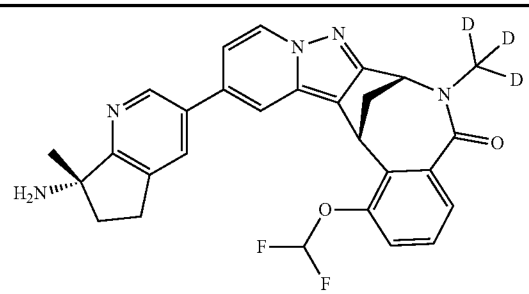 |
| 328 | 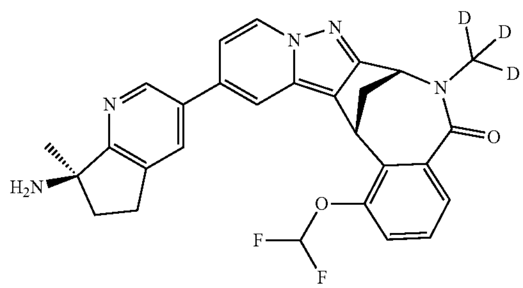 |
| 329 | 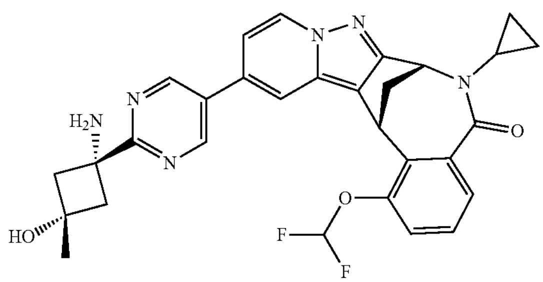 |

In some embodiments, the compound is selected from a compound found in Table 2.

TABLE 2

TABLE 2-continued

193
TABLE 2-continued
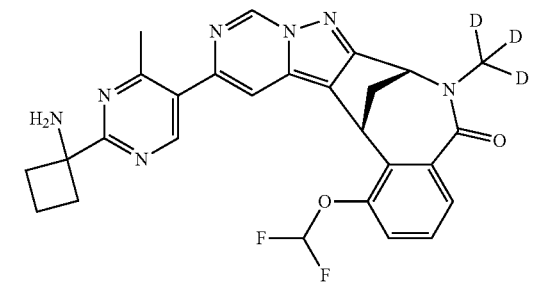 [SMILES: [2H]C([2H])([2H])N1C(=O)c2cccc(OC(F)F)c2[C@H]2C[C@@H]1c1nn3cnc(-c4cnc(C5(N)CCC5)nc4C)cc3c12]
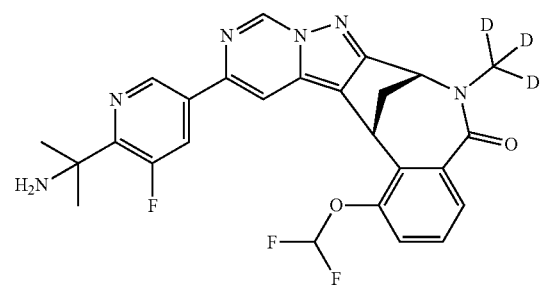 [SMILES: [2H]C([2H])([2H])N1C(=O)c2cccc(OC(F)F)c2[C@H]2C[C@@H]1c1nn3cnc(-c4cnc(C(C)(C)N)c(F)c4)cc3c12]
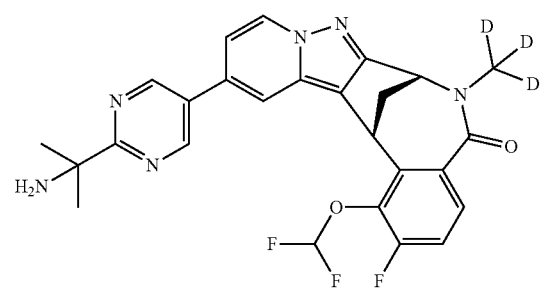 [SMILES: [2H]C([2H])([2H])N1C(=O)c2ccc(F)c(OC(F)F)c2[C@H]2C[C@@H]1c1nn3ccc(-c4cnc(C(C)(C)N)nc4)cc3c12]
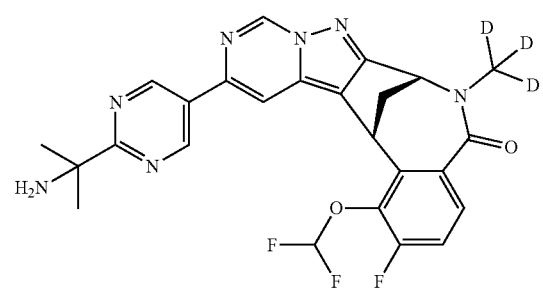 [SMILES: [2H]C([2H])([2H])N1C(=O)c2ccc(F)c(OC(F)F)c2[C@H]2C[C@@H]1c1nn3cnc(-c4cnc(C(C)(C)N)nc4)cc3c12]
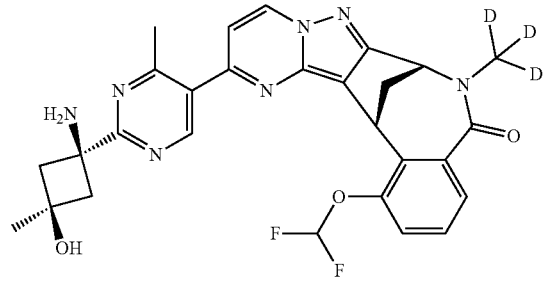 [SMILES: [2H]C([2H])([2H])N1C(=O)c2cccc(OC(F)F)c2[C@H]2C[C@@H]1c1nn3ccc(-c4cnc([C@]5(N)C[C@@](C)(O)C5)nc4C)nc3c12]
194
TABLE 2-continued
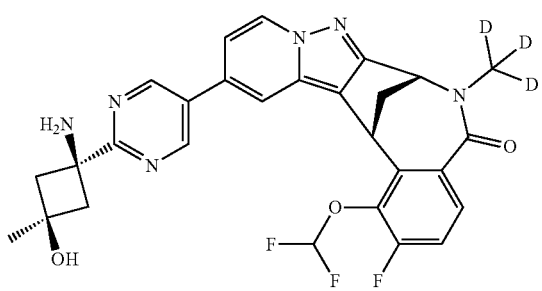 [SMILES: [2H]C([2H])([2H])N1C(=O)c2ccc(F)c(OC(F)F)c2[C@H]2C[C@@H]1c1nn3ccc(-c4cnc([C@]5(N)C[C@@](C)(O)C5)nc4)cc3c12]
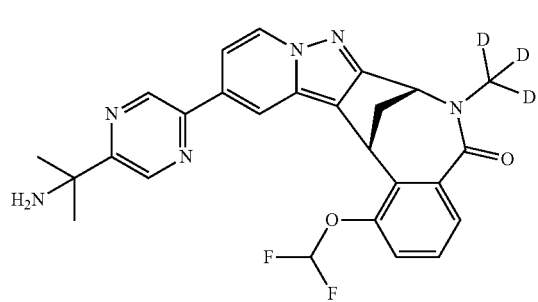 [SMILES: [2H]C([2H])([2H])N1C(=O)c2cccc(OC(F)F)c2[C@H]2C[C@@H]1c1nn3ccc(-c4cnc(C(C)(C)N)cn4)cc3c12]
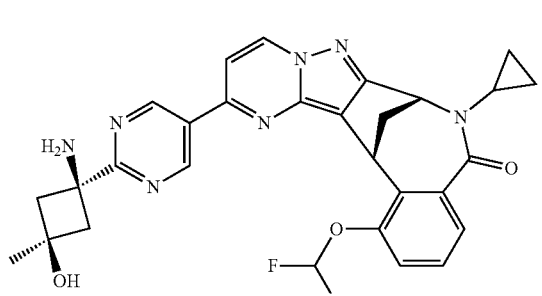
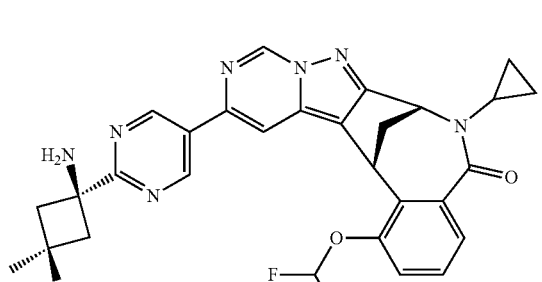
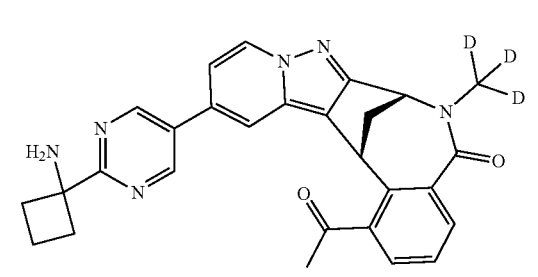 [SMILES: [2H]C([2H])([2H])N1C(=O)c2cccc(C(C)=O)c2[C@H]2C[C@@H]1c1nn3ccc(-c4cnc(C5(N)CCC5)nc4)cc3c12]

TABLE 2-continued
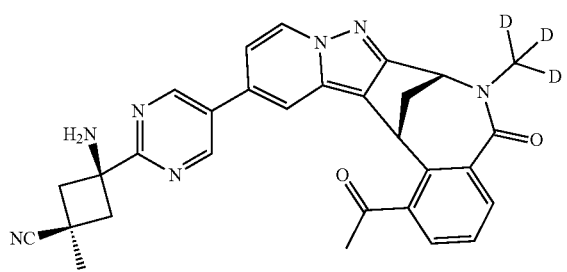 [SMILES: [2H]C([2H])([2H])N1C(=O)c2cccc(C(C)=O)c2[C@H]2C[C@@H]1c1nn3ccc(-c4cnc([C@]5(N)C[C@@](C)(C#N)C5)nc4)cc3c12]
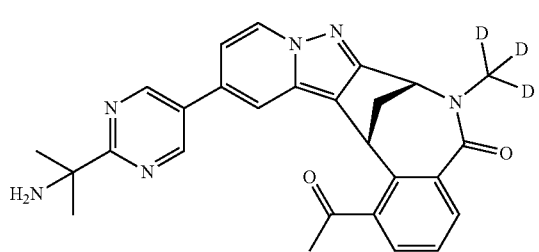 [SMILES: [2H]C([2H])([2H])N1C(=O)c2cccc(C(C)=O)c2[C@H]2C[C@@H]1c1nn3ccc(-c4cnc(C(C)(C)N)nc4)cc3c12]
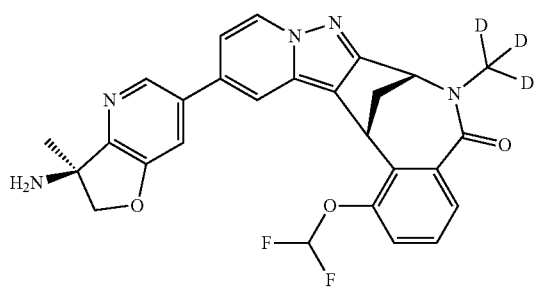 [SMILES: [2H]C([2H])([2H])N1C(=O)c2cccc(OC(F)F)c2[C@H]2C[C@@H]1c1nn3ccc(-c4cnc5c(c4)OC[C@@]5(C)N)cc3c12]
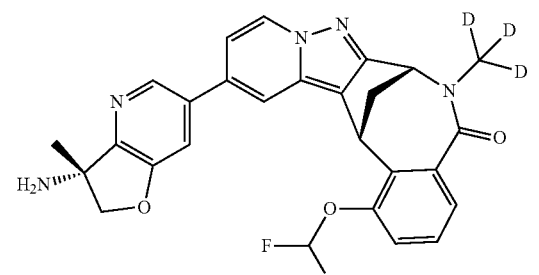
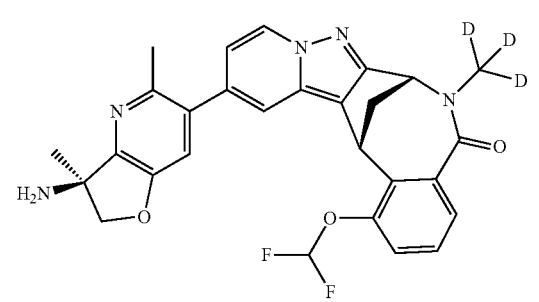 [SMILES: [2H]C([2H])([2H])N1C(=O)c2cccc(OC(F)F)c2[C@H]2C[C@@H]1c1nn3ccc(-c4cc5c(nc4C)[C@](C)(N)CO5)cc3c12]
TABLE 2-continued
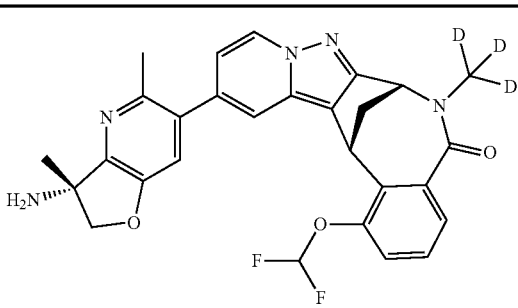
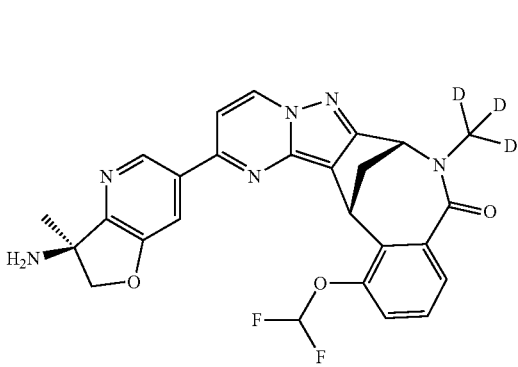 [SMILES: [2H]C([2H])([2H])N1C(=O)c2cccc(OC(F)F)c2[C@H]2C[C@@H]1c1nn3ccc(-c4cnc5c(c4)OC[C@@]5(C)N)nc3c12]
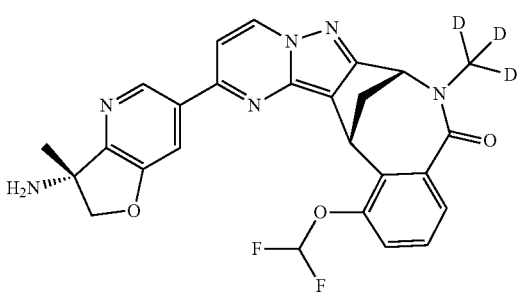 [SMILES: [2H]C([2H])([2H])N1C(=O)c2cccc(OC(F)F)c2[C@H]2C[C@@H]1c1nn3ccc(-c4cnc5c(c4)OC[C@]5(C)N)nc3c12]
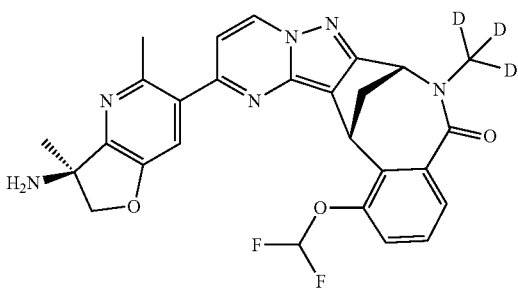
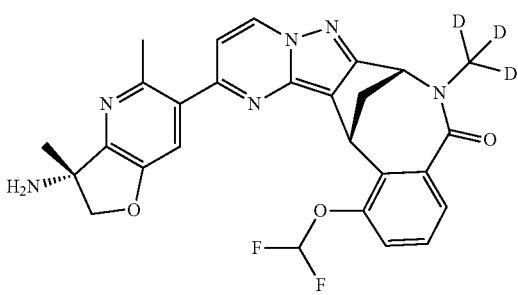 [SMILES: [2H]C([2H])([2H])N1C(=O)c2cccc(OC(F)F)c2[C@H]2C[C@@H]1c1nn3ccc(-c4cc5c(nc4C)[C@@](C)(N)CO5)nc3c12]

TABLE 2-continued
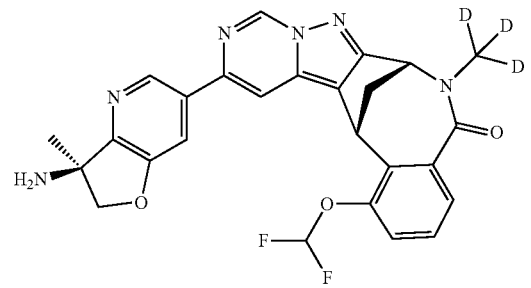
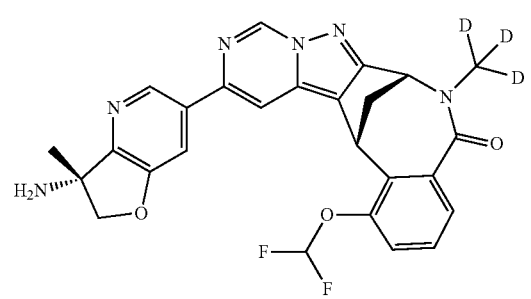 [SMILES: [2H]C([2H])([2H])N1C(=O)c2cccc(OC(F)F)c2[C@H]2C[C@@H]1c1nn3cnc(-c4cnc5c(c4)OC[C@]5(C)N)cc3c12]
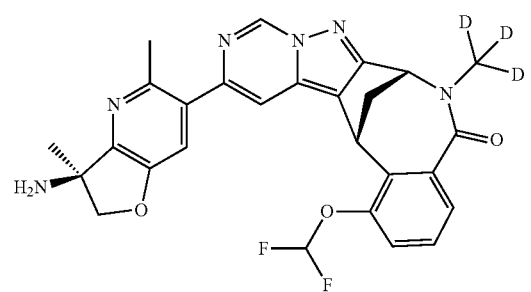 [SMILES: [2H]C([2H])([2H])N1C(=O)c2cccc(OC(F)F)c2[C@H]2C[C@@H]1c1nn3cnc(-c4cc5c(nc4C)[C@](C)(N)CO5)cc3c12]
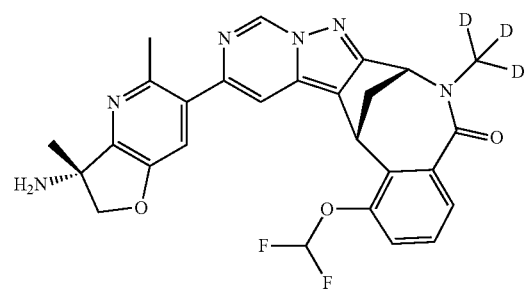 [SMILES: [2H]C([2H])([2H])N1C(=O)c2cccc(OC(F)F)c2[C@H]2C[C@@H]1c1nn3cnc(-c4cc5c(nc4C)[C@@](C)(N)CO5)cc3c12]
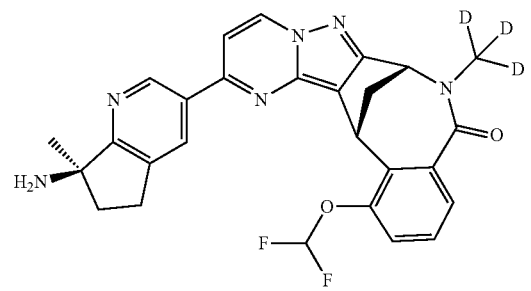
TABLE 2-continued
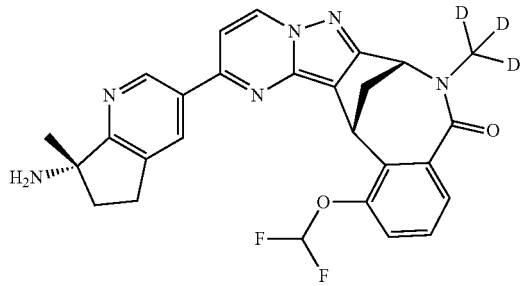 [SMILES: [2H]C([2H])([2H])N1C(=O)c2cccc(OC(F)F)c2[C@H]2C[C@@H]1c1nn3ccc(-c4cnc5c(c4)CC[C@]5(C)N)nc3c12]
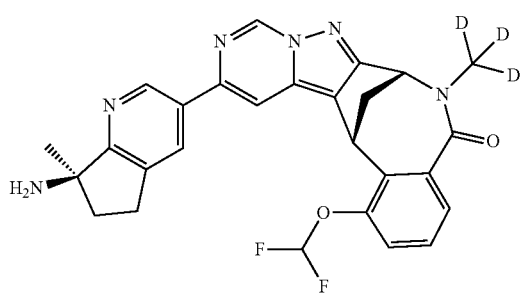 [SMILES: [2H]C([2H])([2H])N1C(=O)c2cccc(OC(F)F)c2[C@H]2C[C@@H]1c1nn3cnc(-c4cnc5c(c4)CC[C@@]5(C)N)cc3c12]
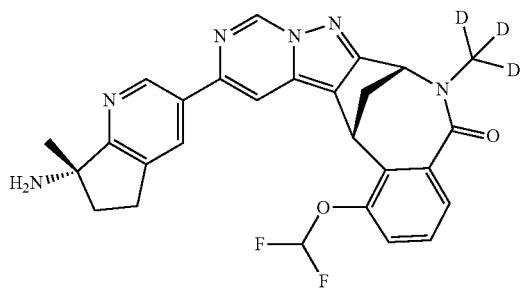 [SMILES: [2H]C([2H])([2H])N1C(=O)c2cccc(OC(F)F)c2[C@H]2C[C@@H]1c1nn3cnc(-c4cnc5c(c4)CC[C@]5(C)N)cc3c12]
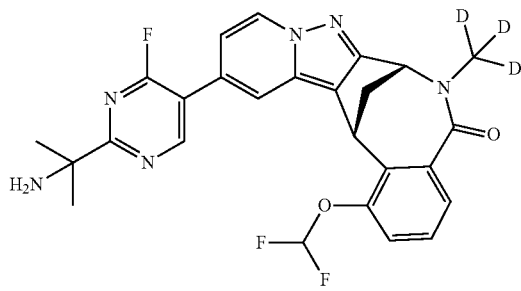 [SMILES: [2H]C([2H])([2H])N1C(=O)c2cccc(OC(F)F)c2[C@H]2C[C@@H]1c1nn3ccc(-c4cnc(C(C)(C)N)nc4F)cc3c12]
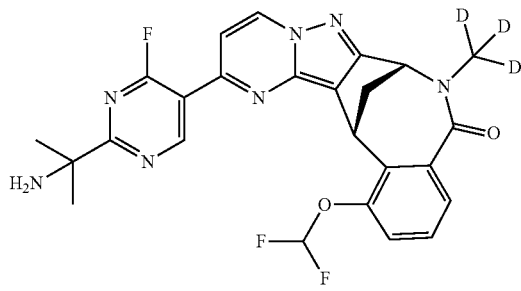 [SMILES: [2H]C([2H])([2H])N1C(=O)c2cccc(OC(F)F)c2[C@H]2C[C@@H]1c1nn3cnc(-c4cnc(C(C)(C)N)nc4F)cc3c12]

TABLE 2-continued
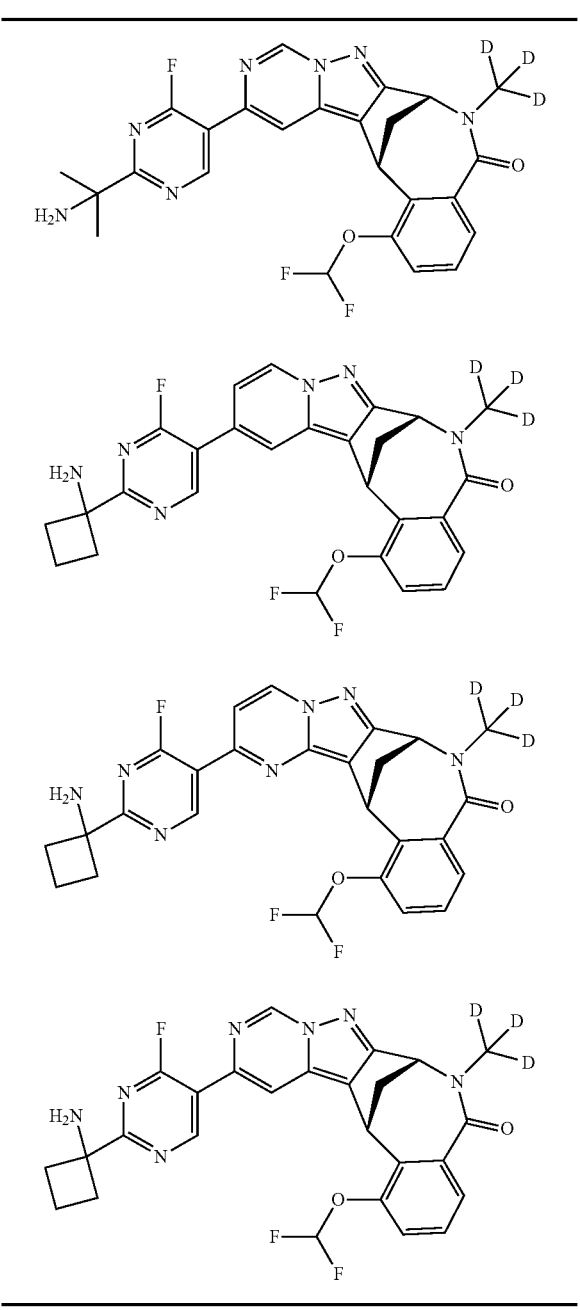
In some embodiments, the compound is selected from the group consisting of:
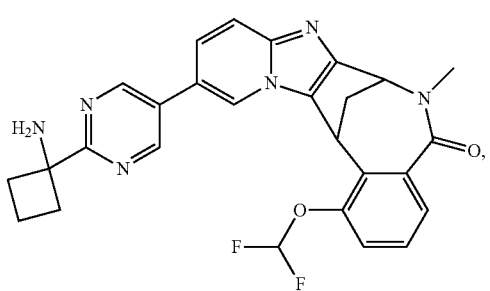
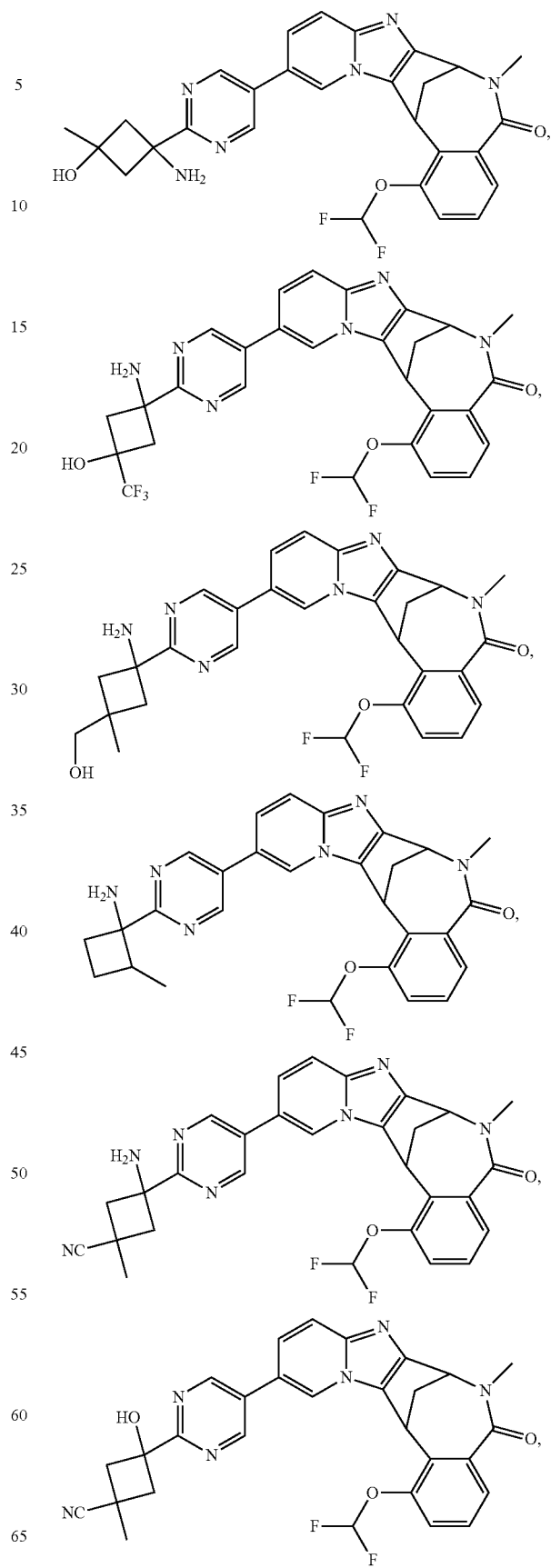

201
-continued
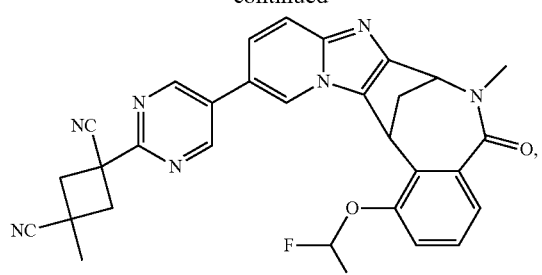
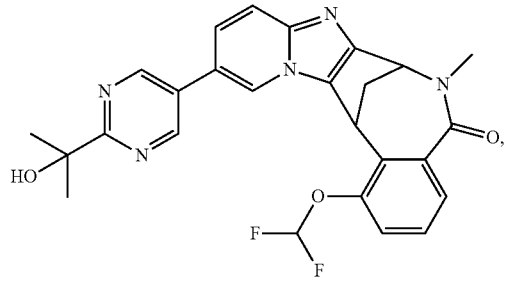
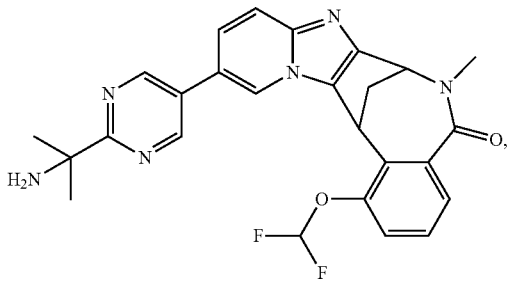
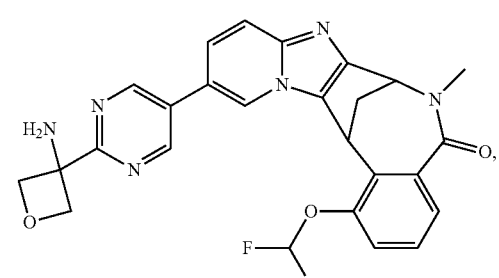
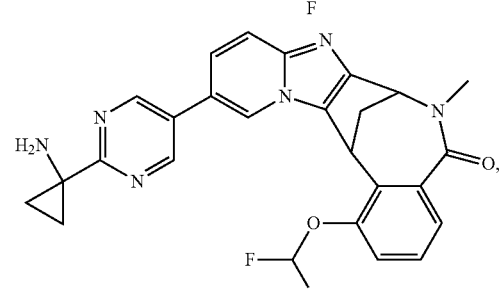
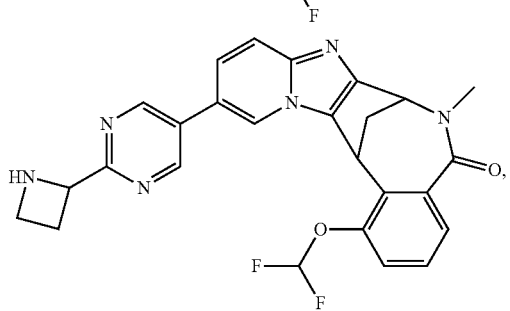
202
-continued
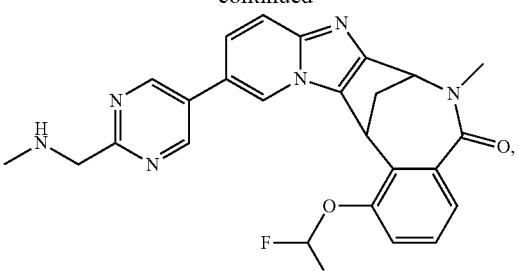
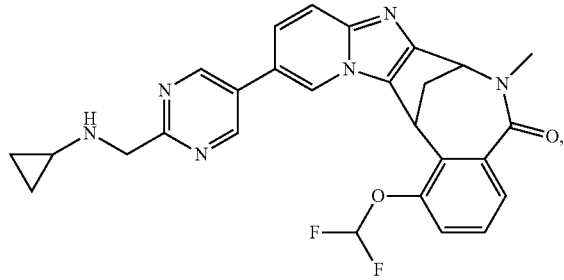
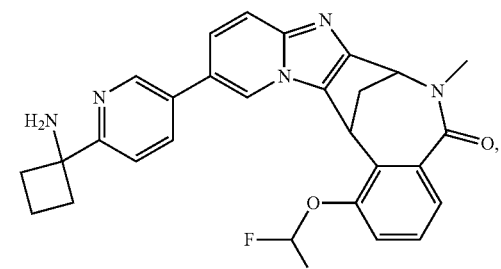
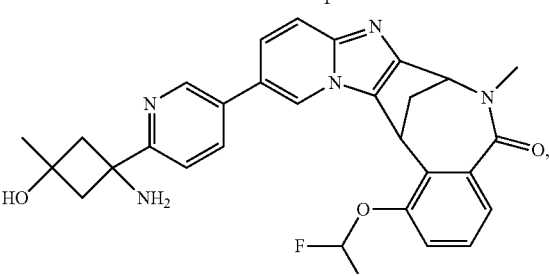
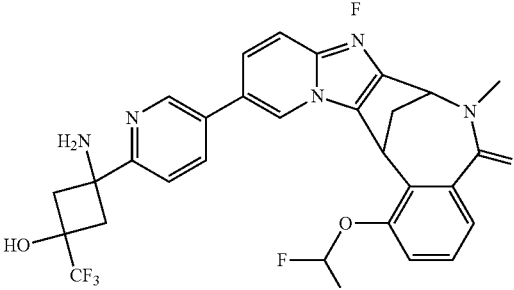
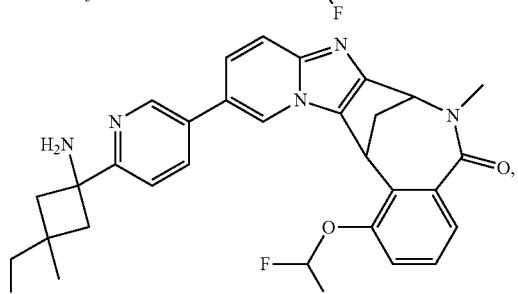

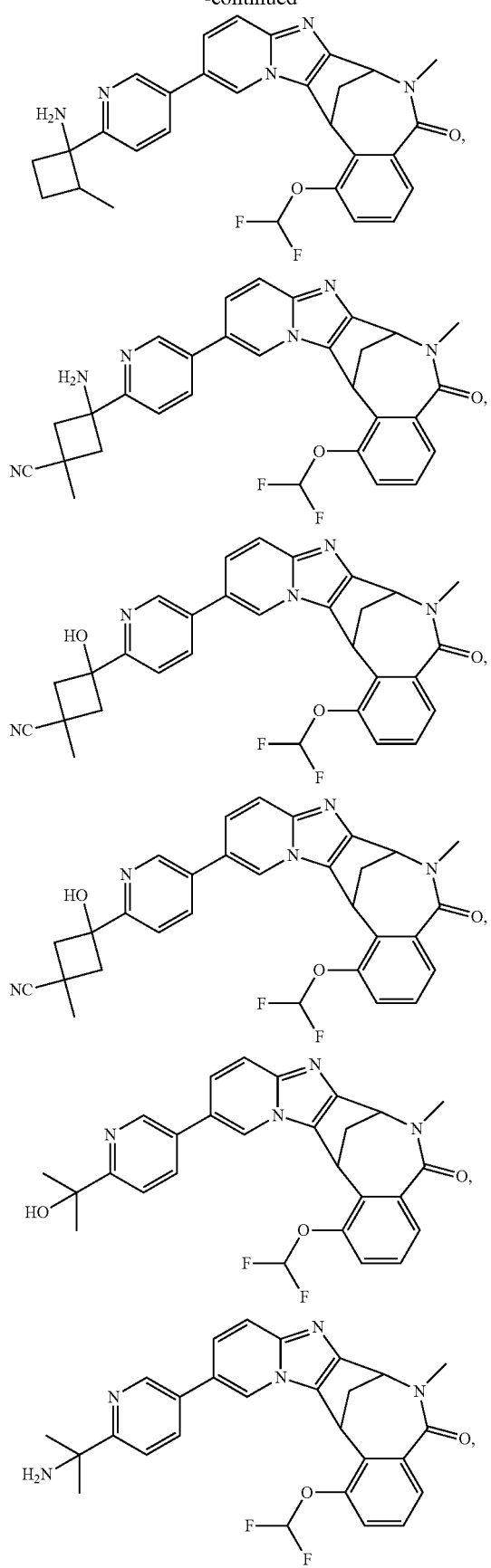
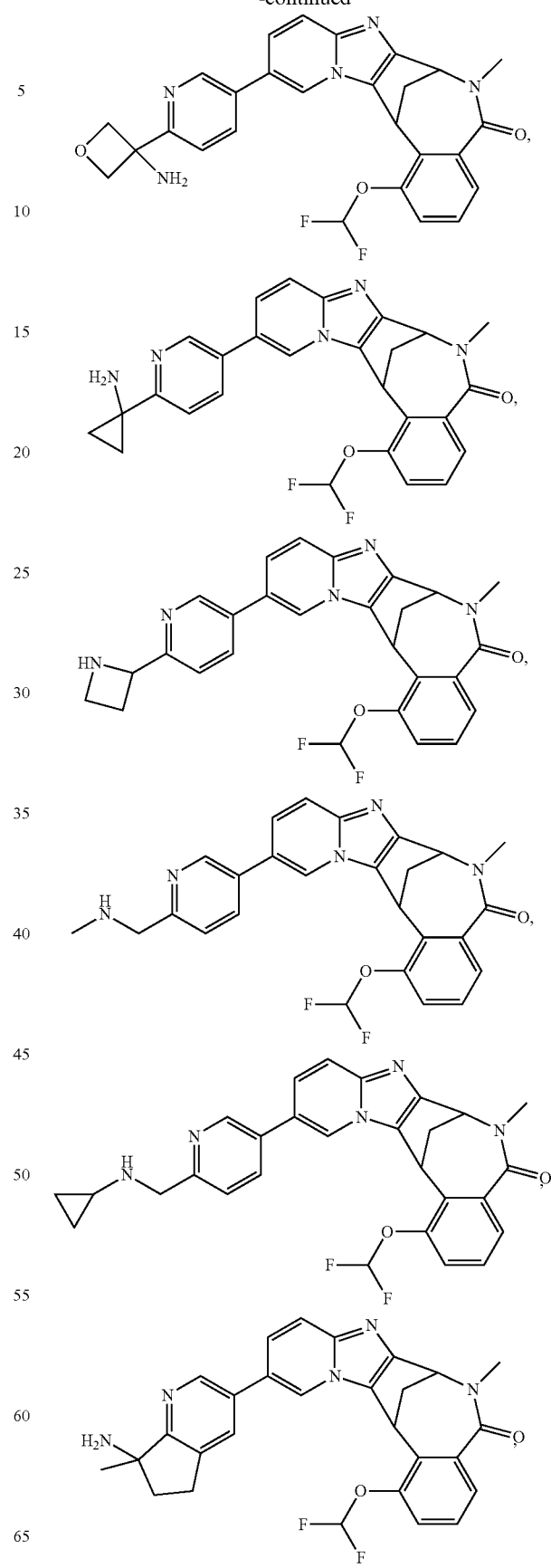

205
-continued
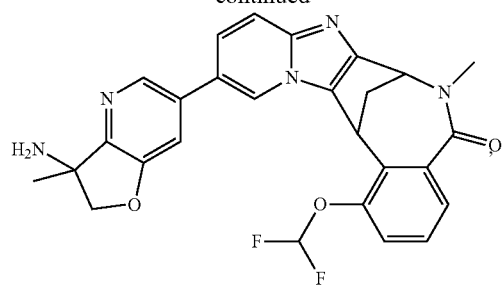
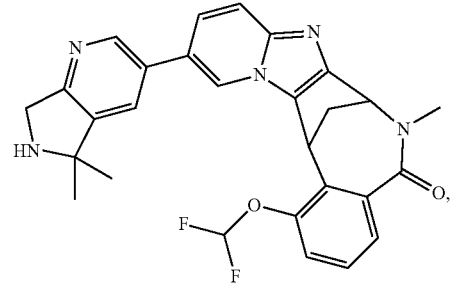
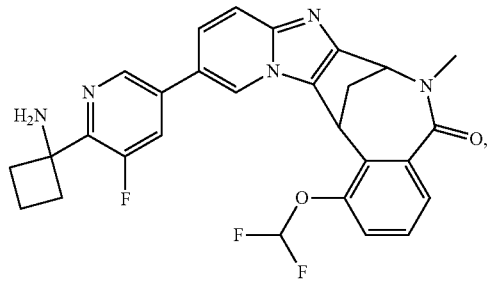
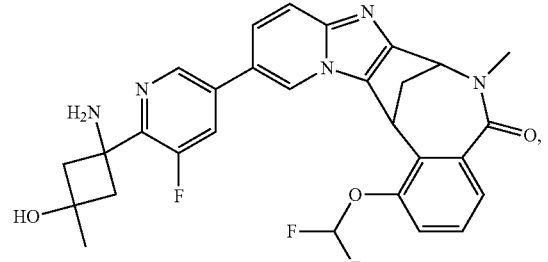
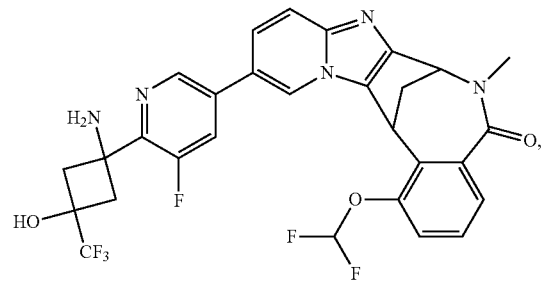
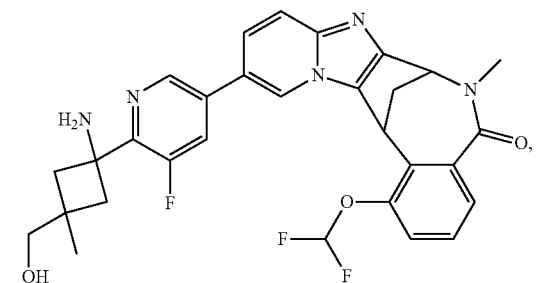
206
-continued
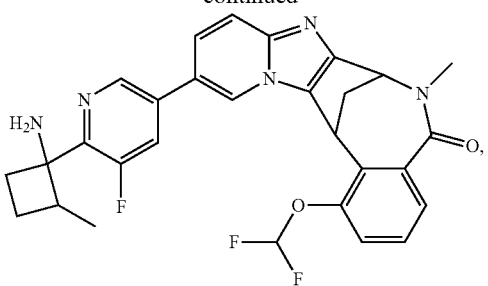
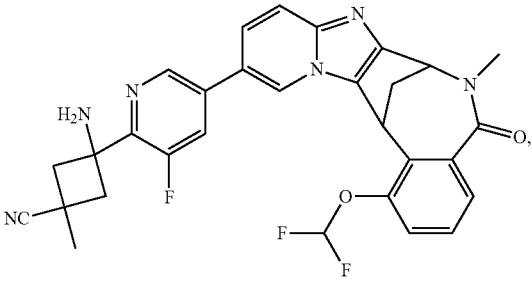
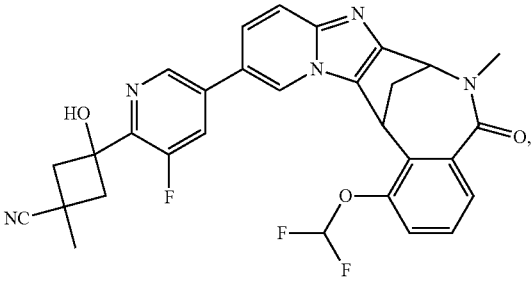
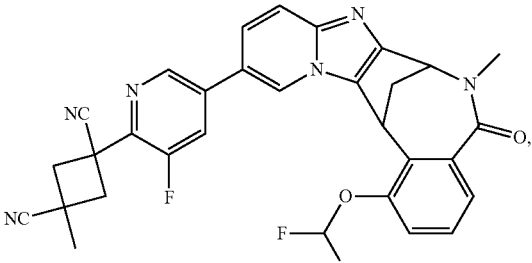
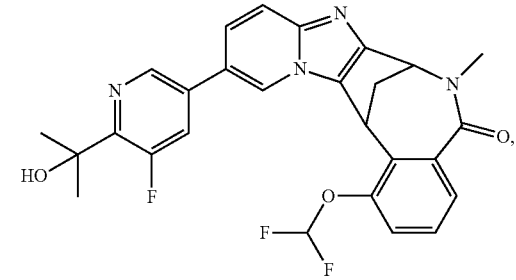
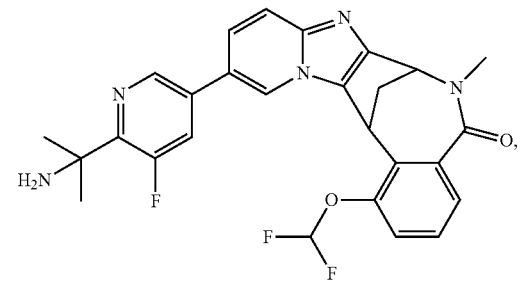

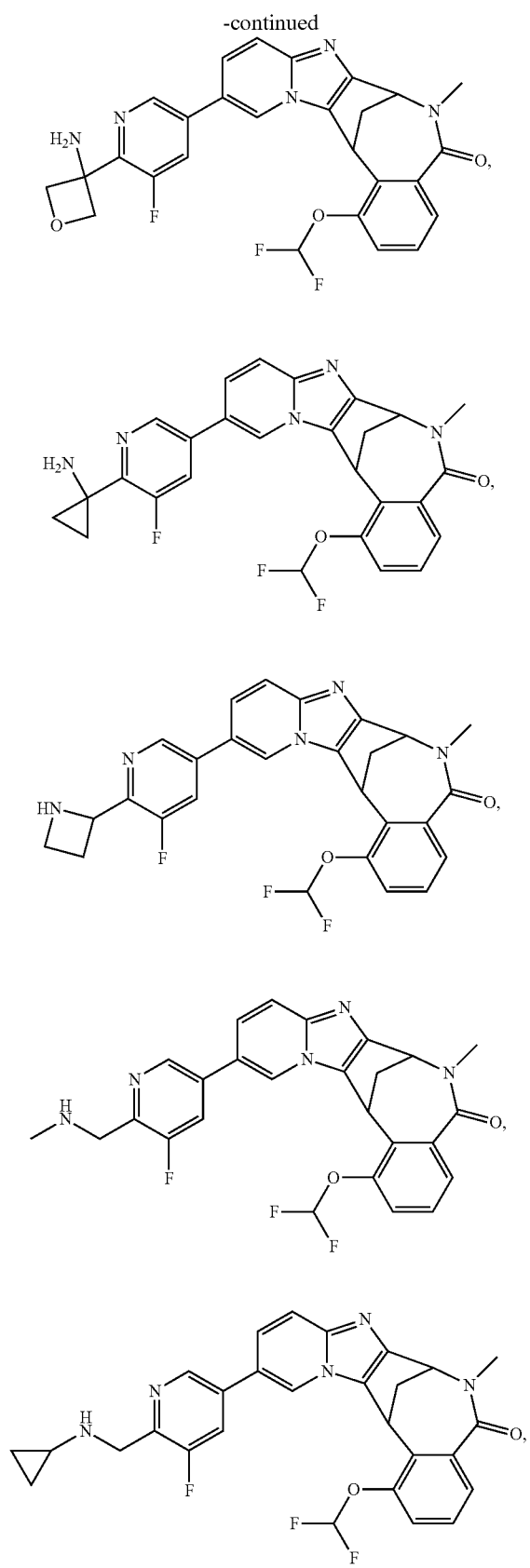
or a pharmaceutically acceptable salt, solvate, or stereoisomer thereof.
In some embodiments of the compounds disclosed above,
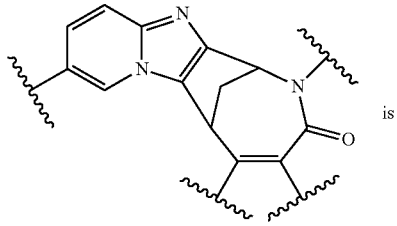
is
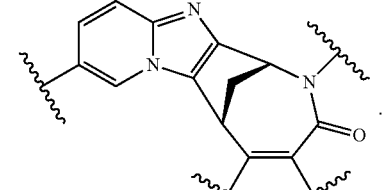
In some embodiments, the compound is selected from the group consisting of:
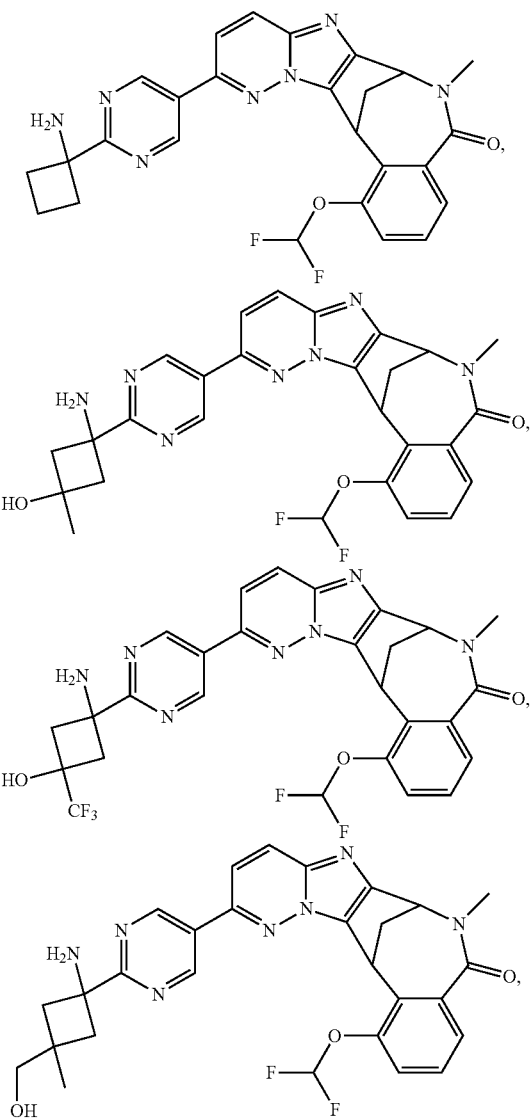

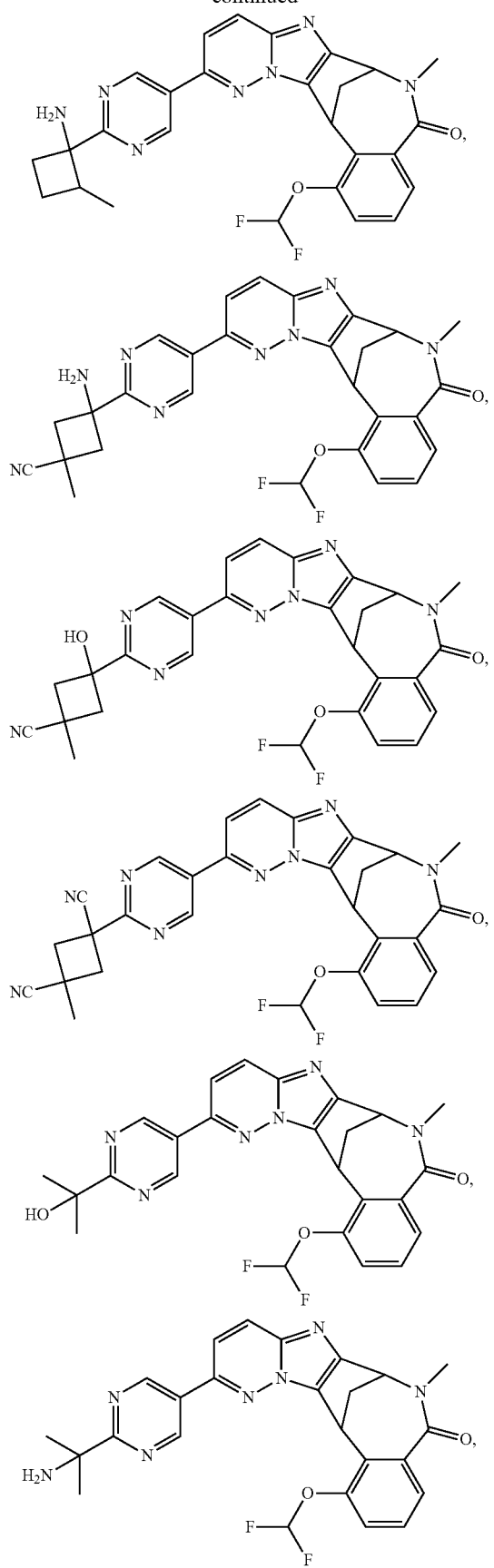
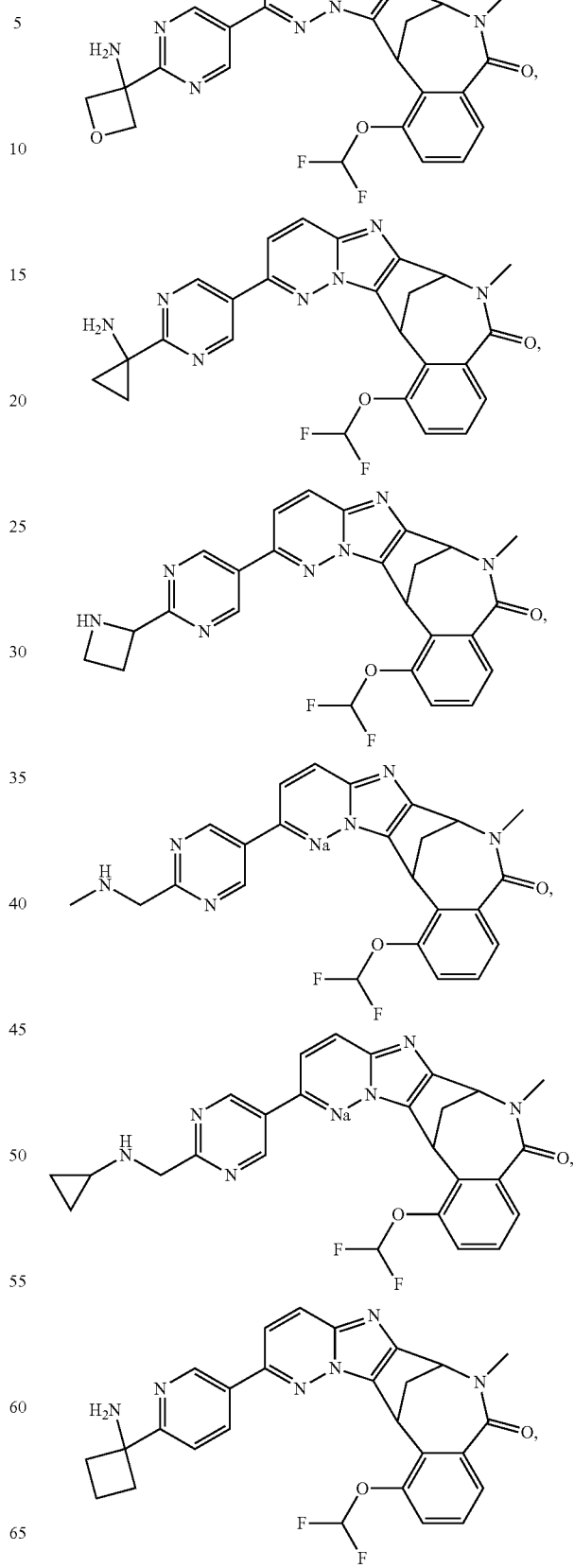

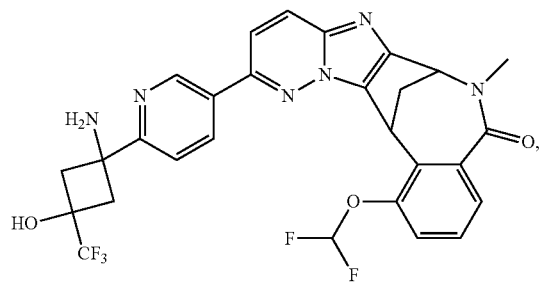
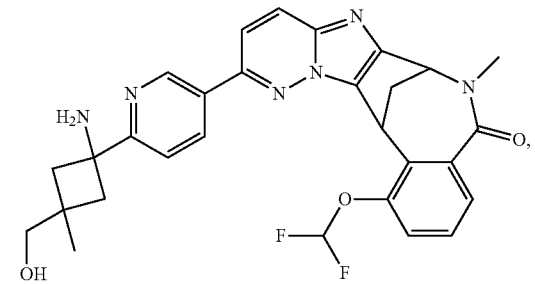
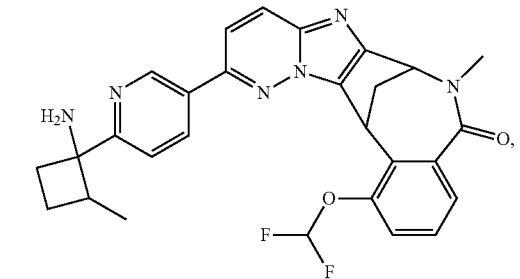
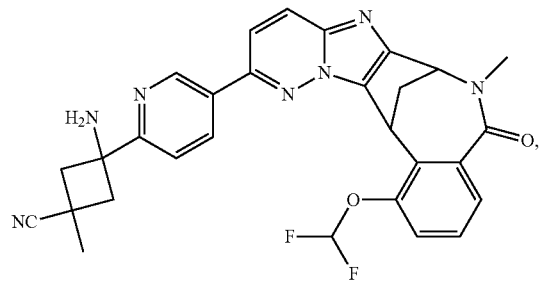
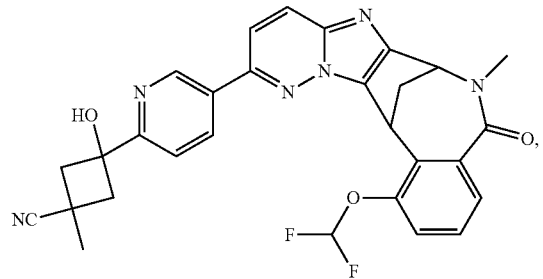
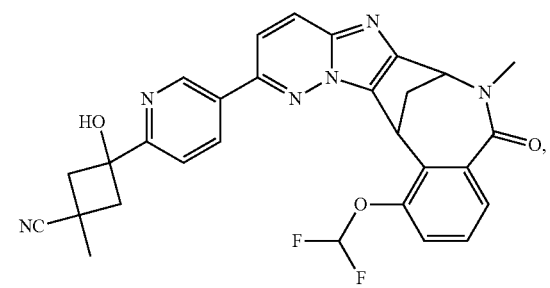
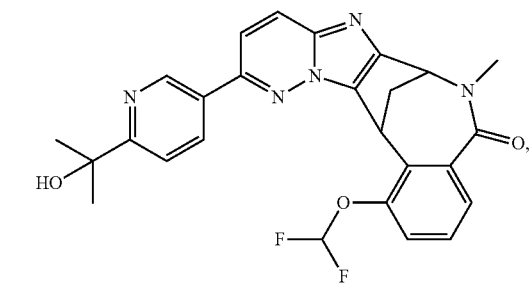
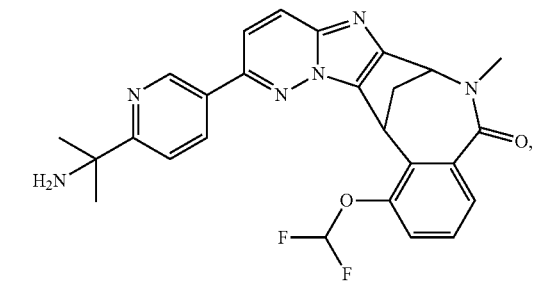
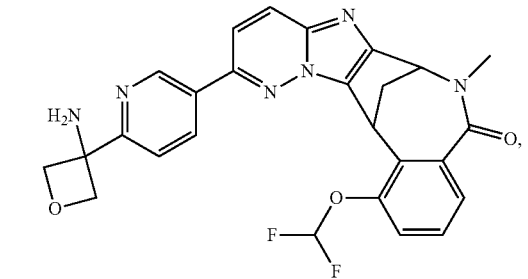
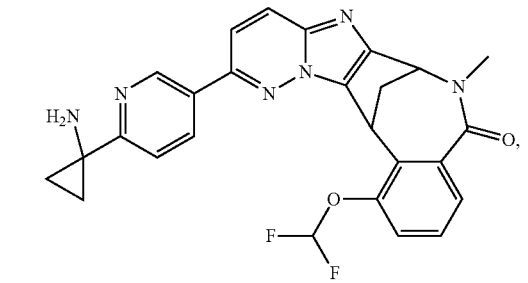
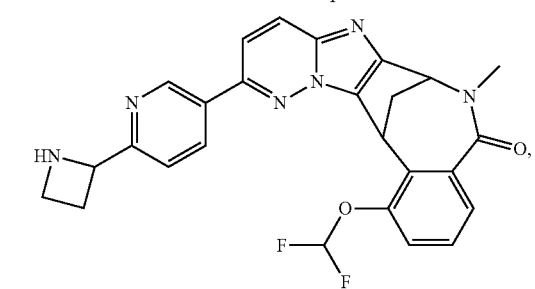

213
-continued
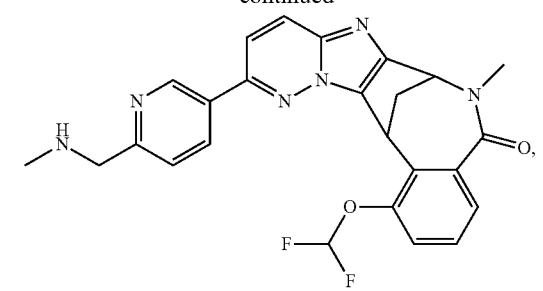
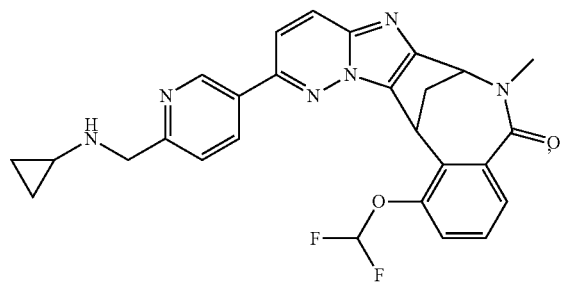
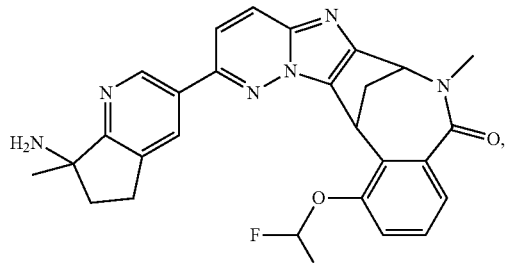
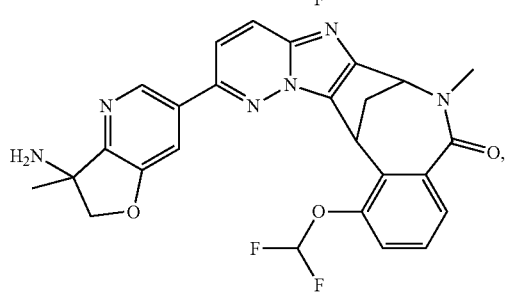
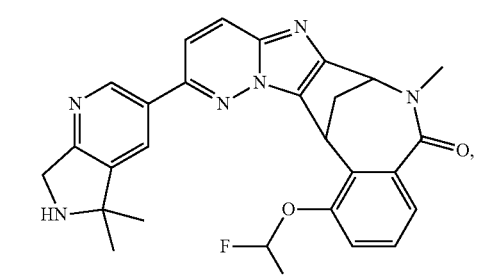
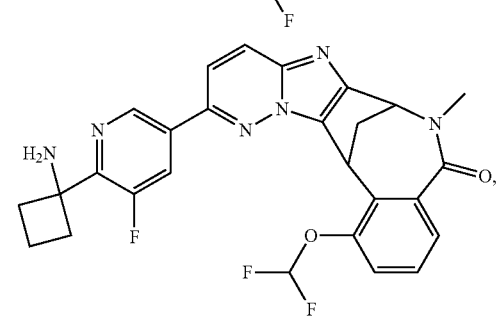
214
-continued
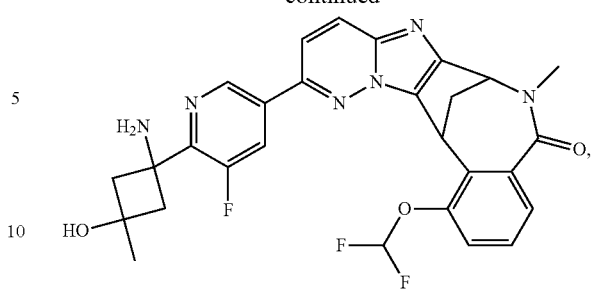
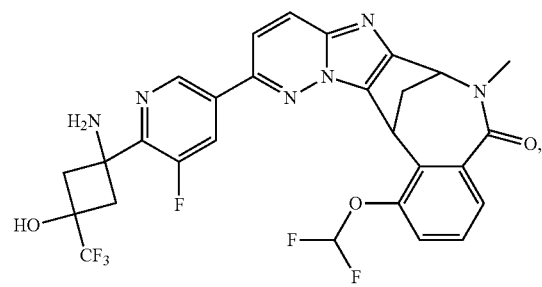
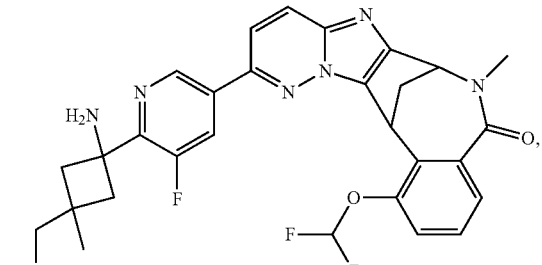
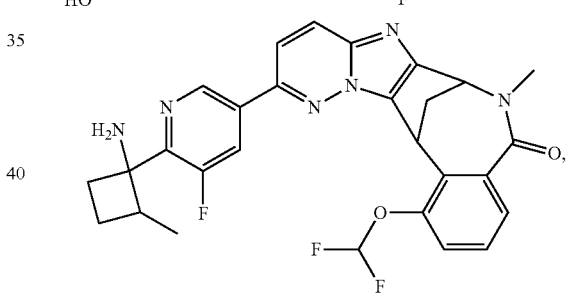
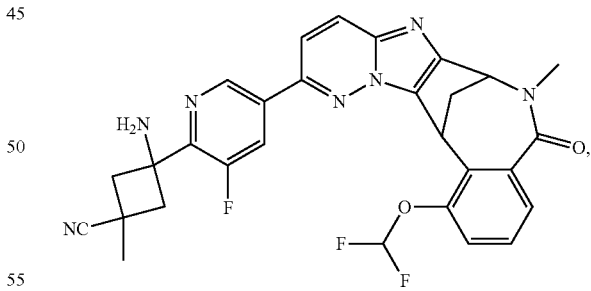
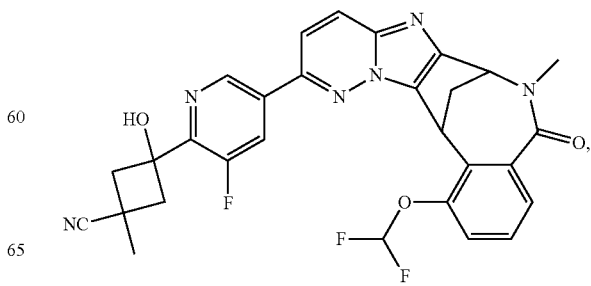

-continued
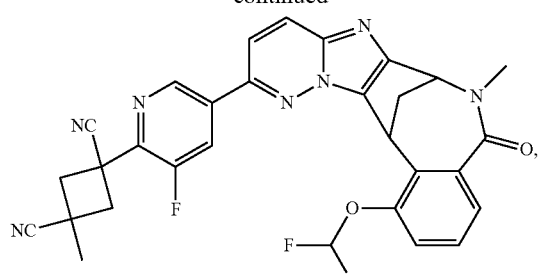
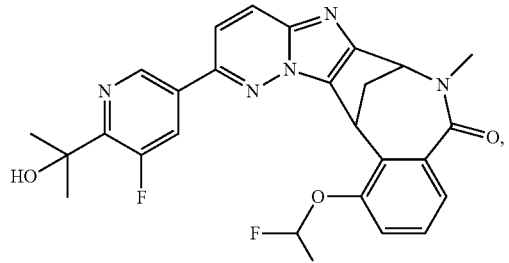
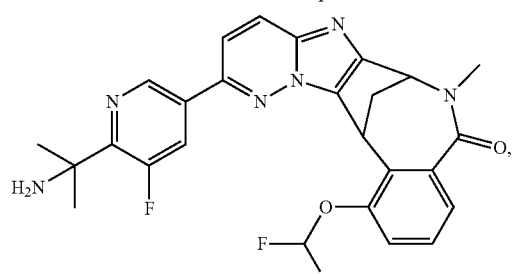
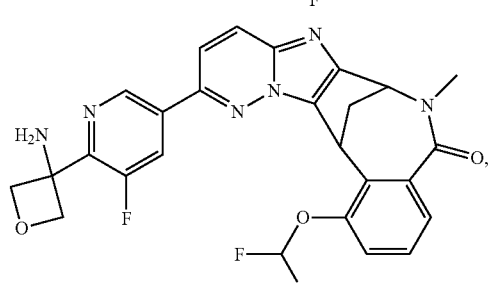
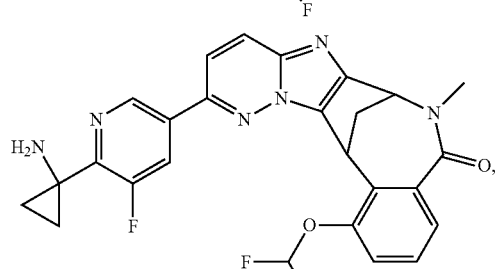
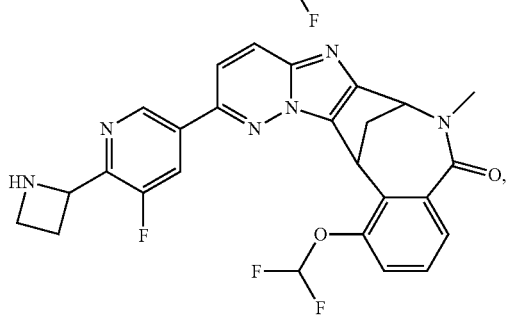
-continued
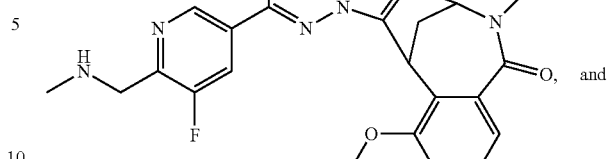
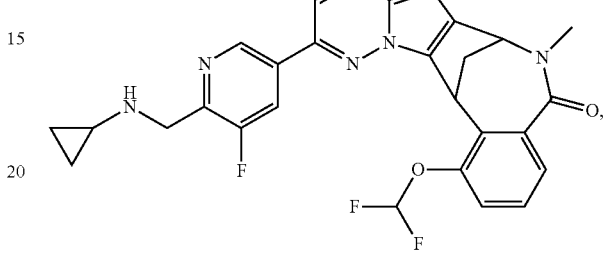
or a pharmaceutically acceptable salt, solvate, or stereoisomer thereof.
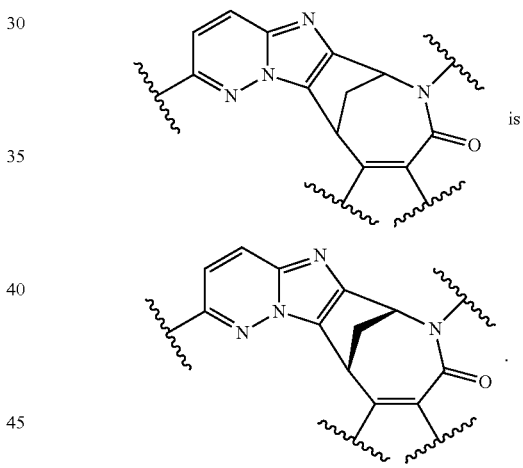
In some embodiments of the compounds disclosed above.
In some embodiments, the compound is selected from the group consisting of:
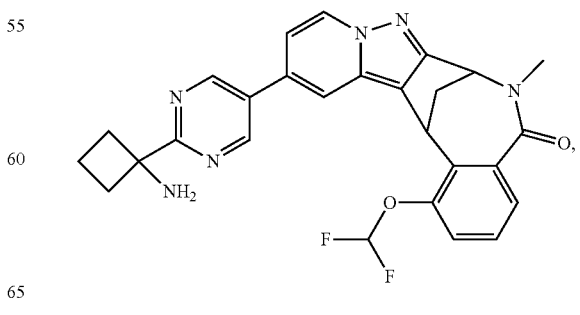

217
-continued
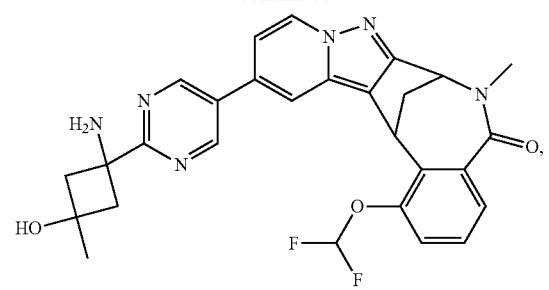
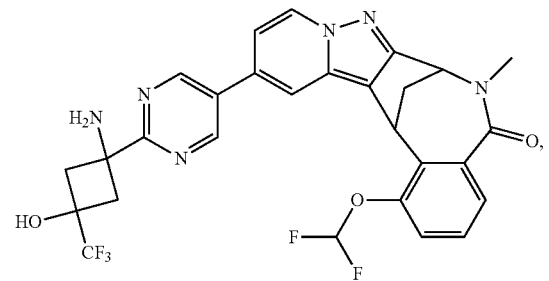
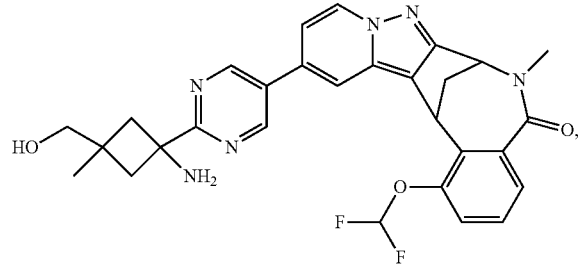
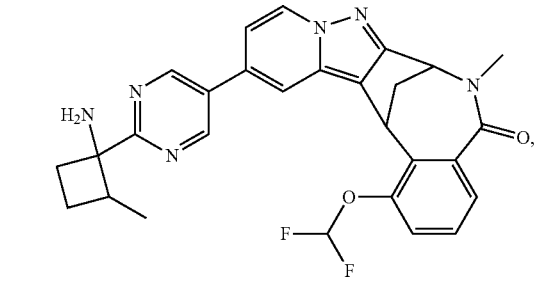
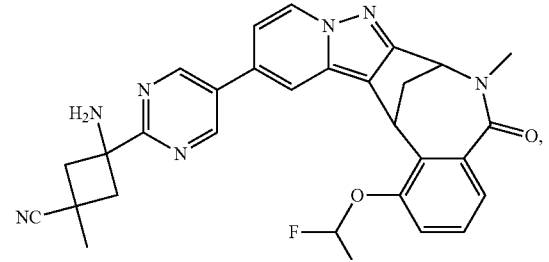
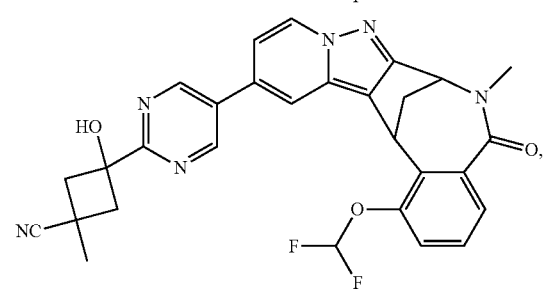
218
-continued
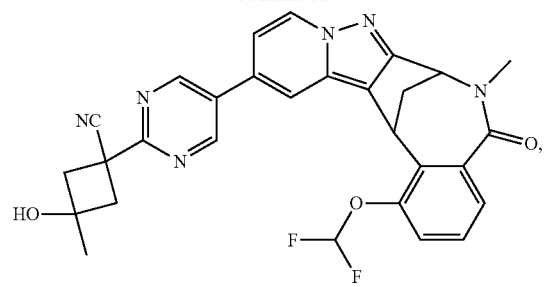
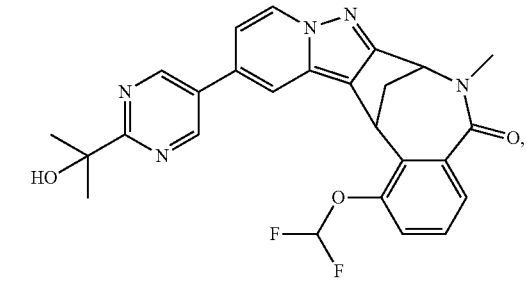
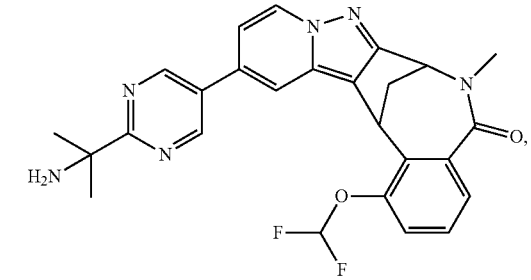
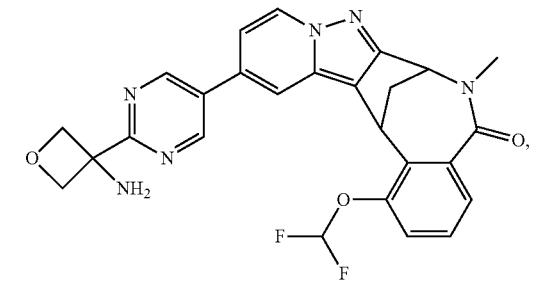
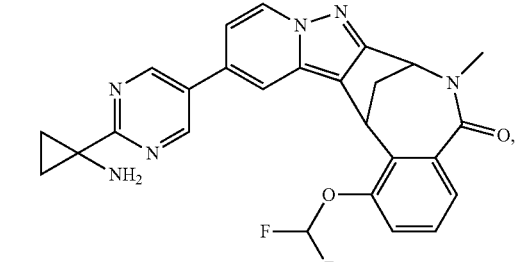
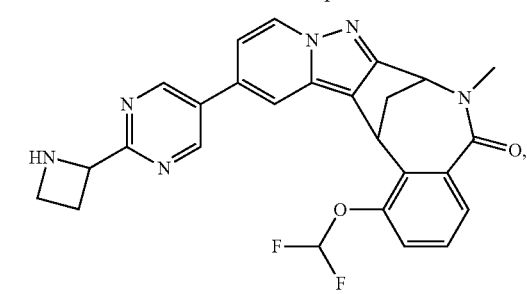

219
-continued
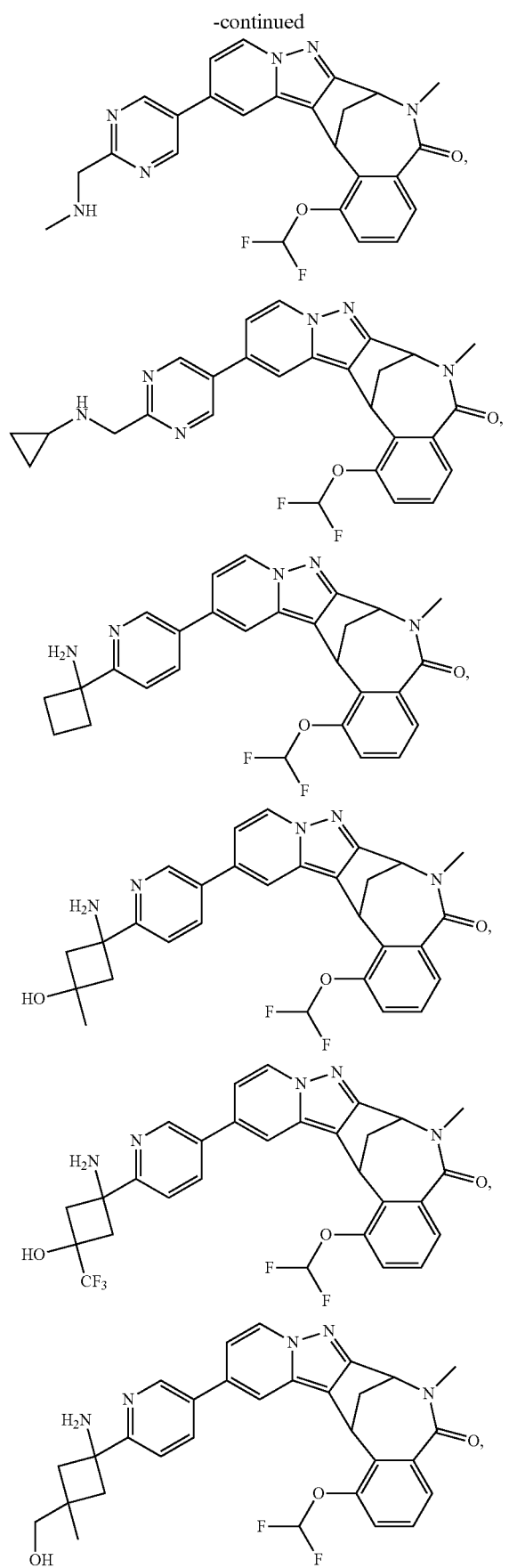
220
-continued
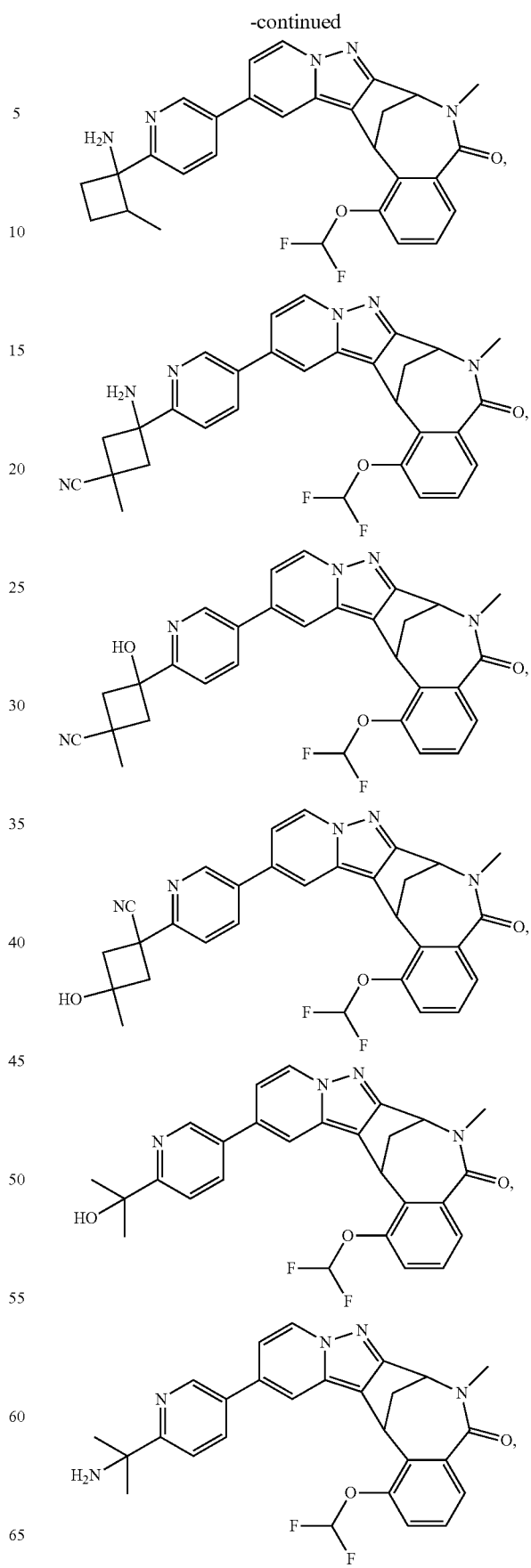

221
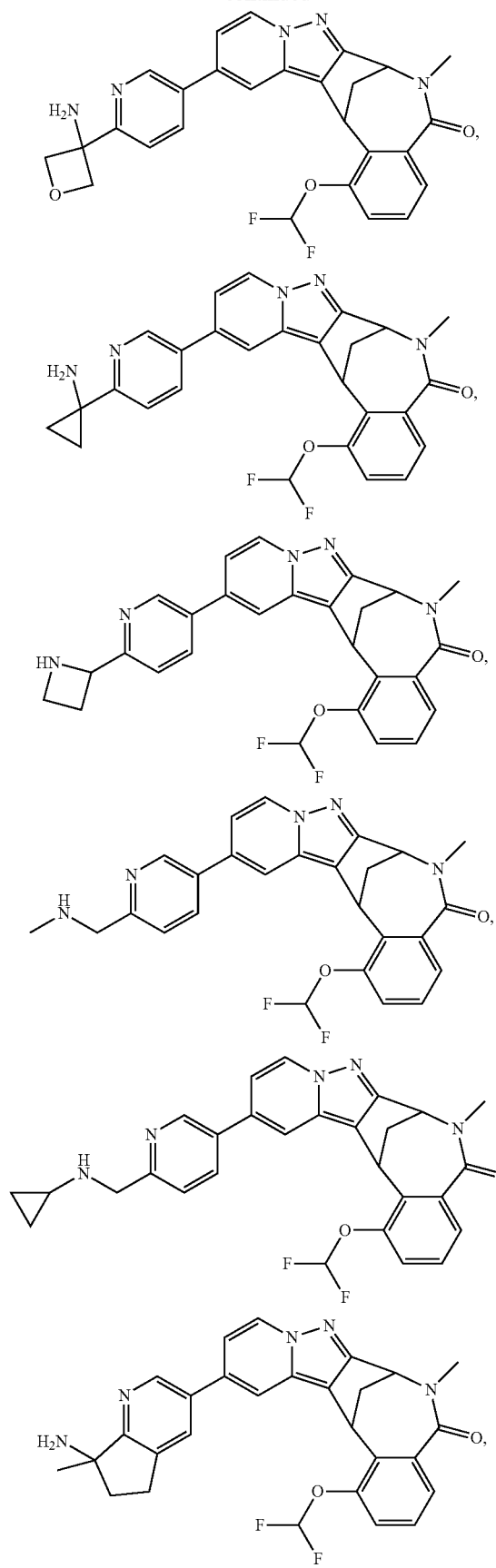
222
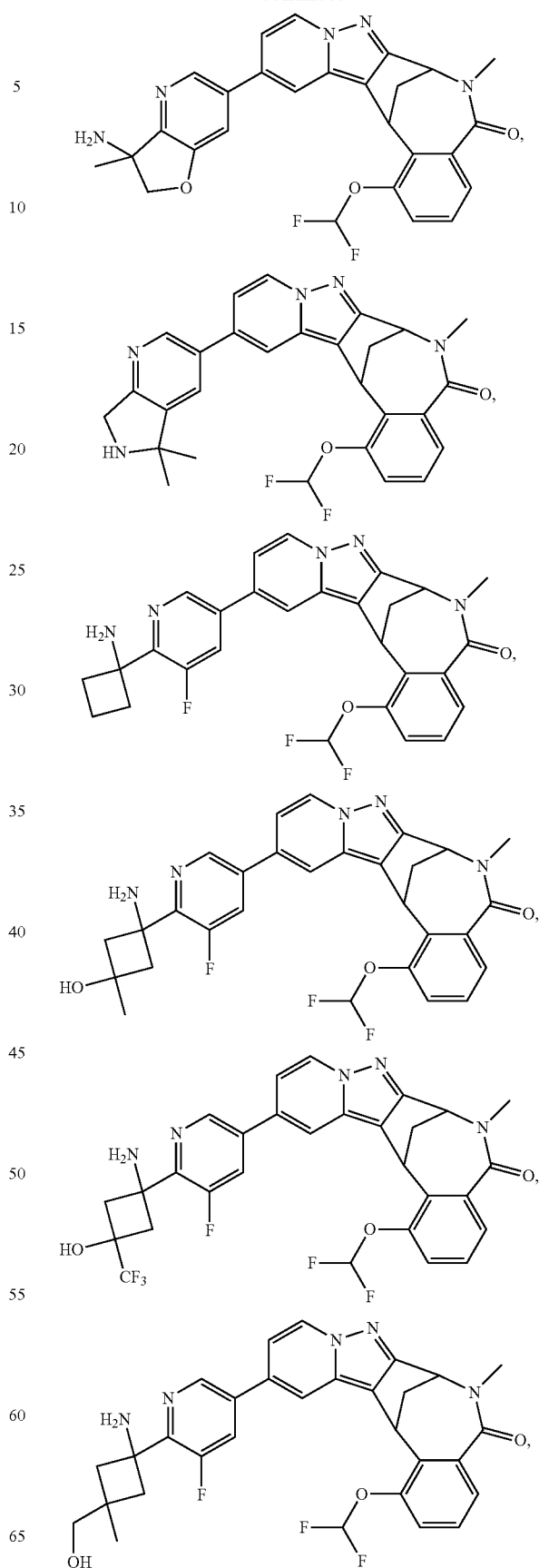

223
-continued
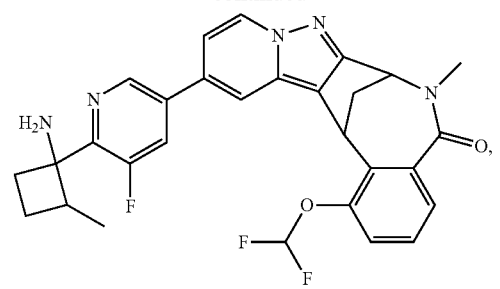
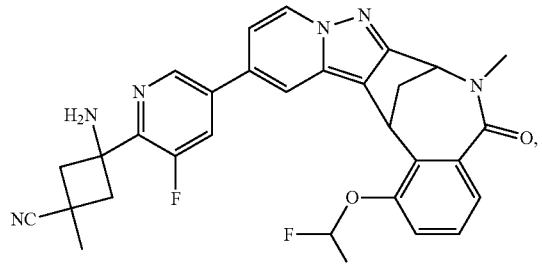
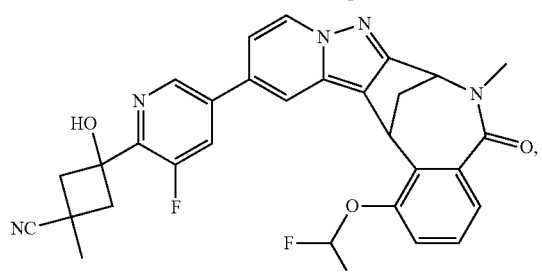
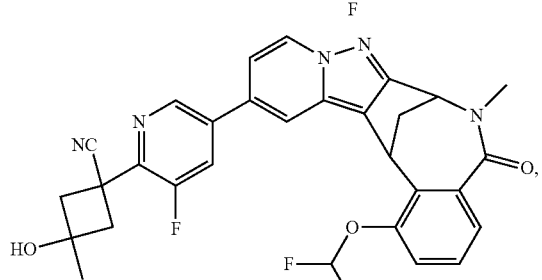
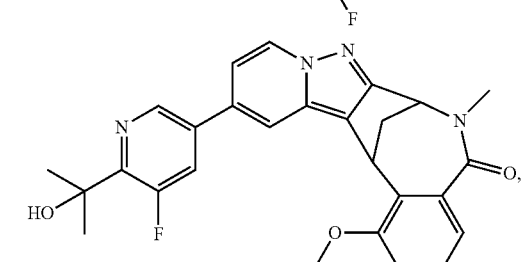
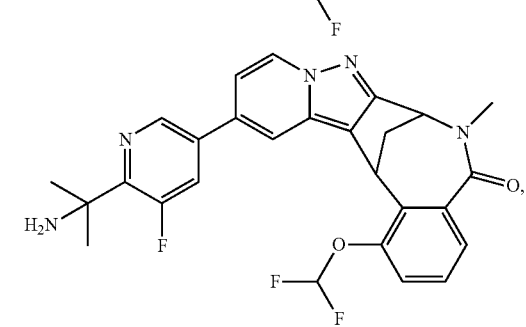
224
-continued
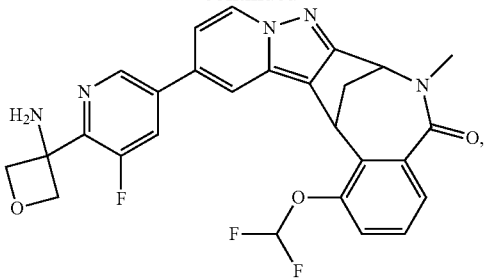
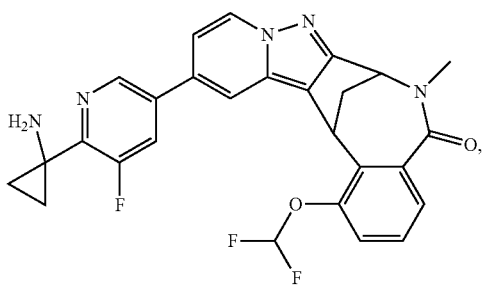
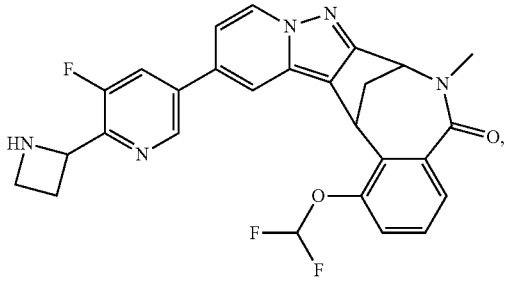
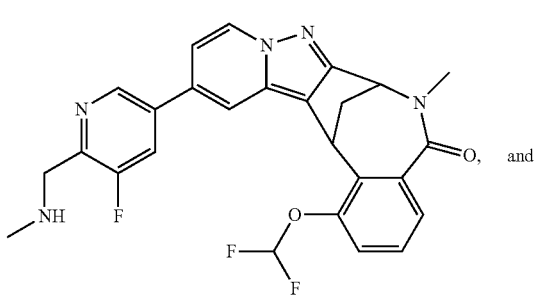
and
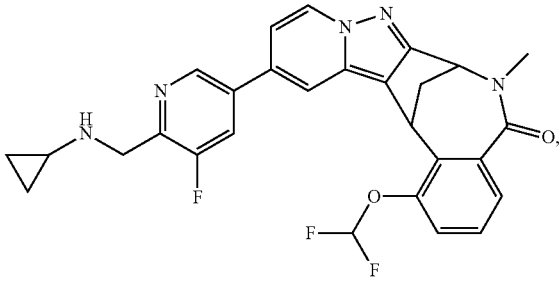
or a pharmaceutically acceptable salt, solvate, or stereoisomer thereof.

In some embodiments of the compounds disclosed above,
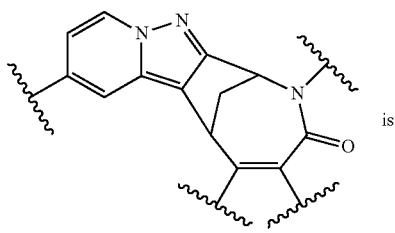
is
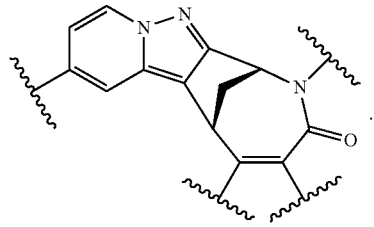
In some embodiments, the compound is selected from the group consisting of:
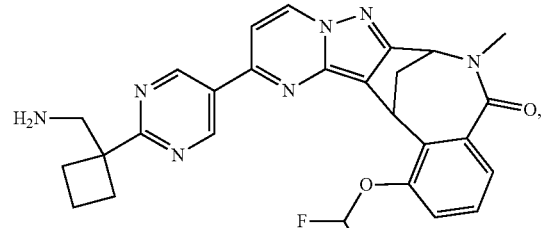
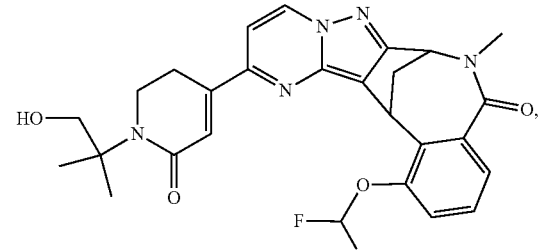
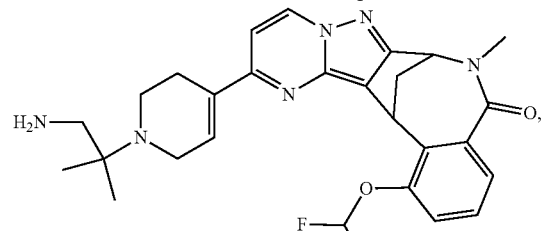
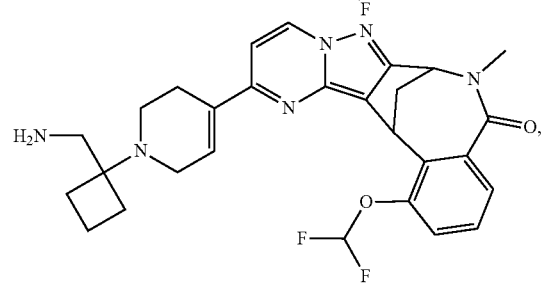
-continued
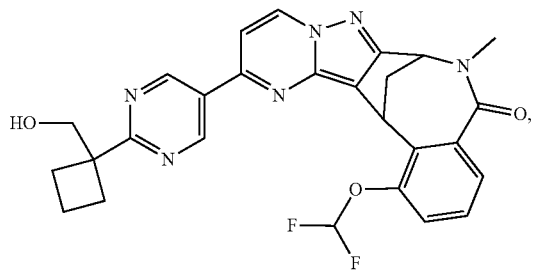
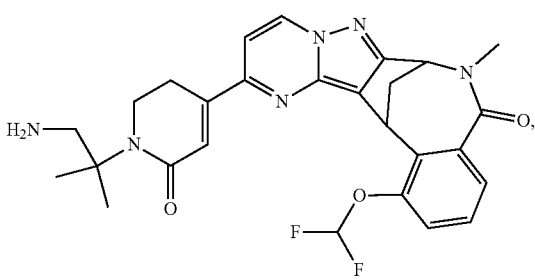
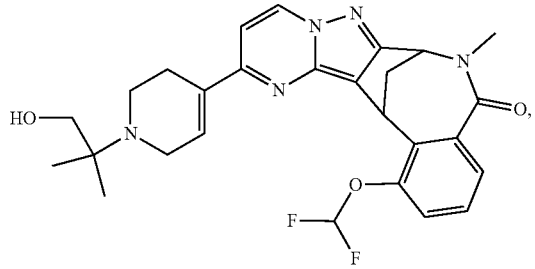
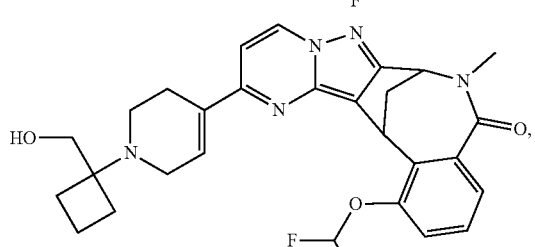
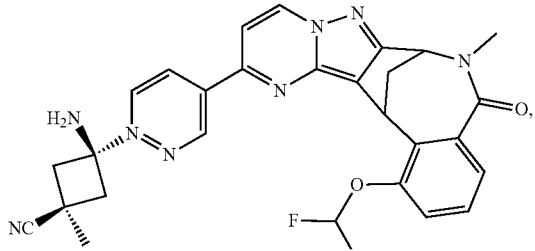
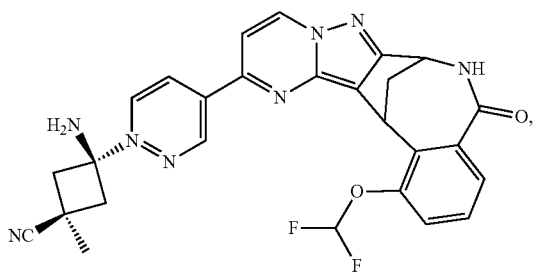

227
-continued
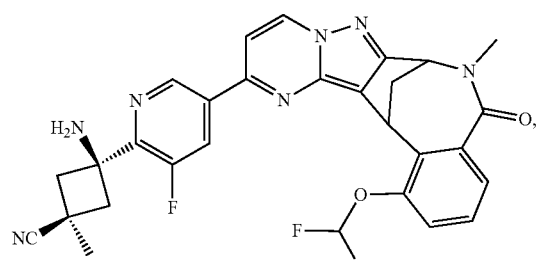
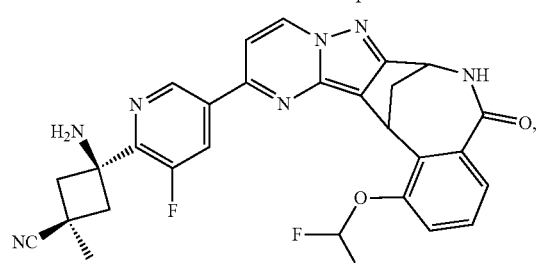
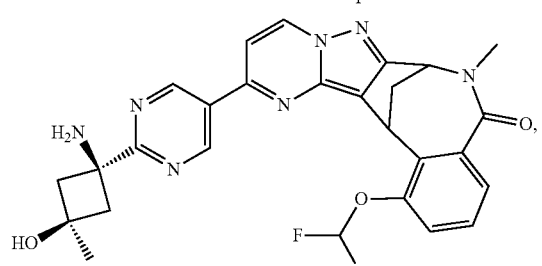
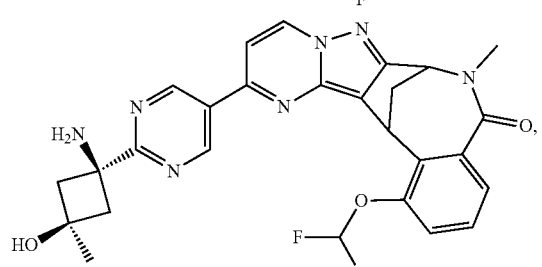
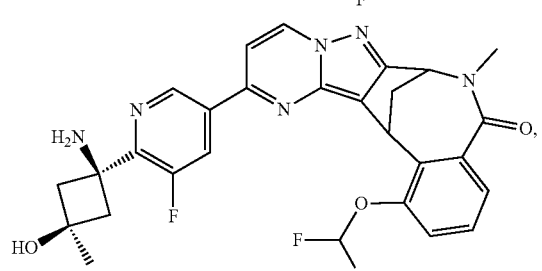
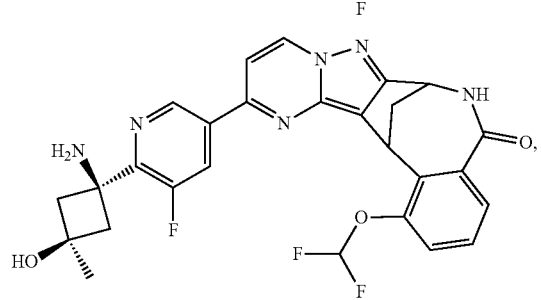
228
-continued
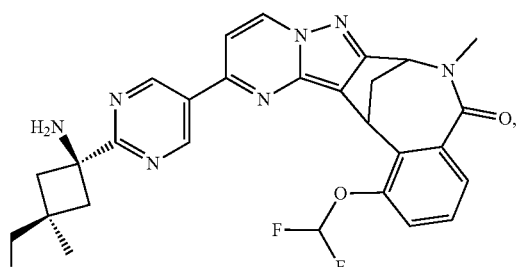
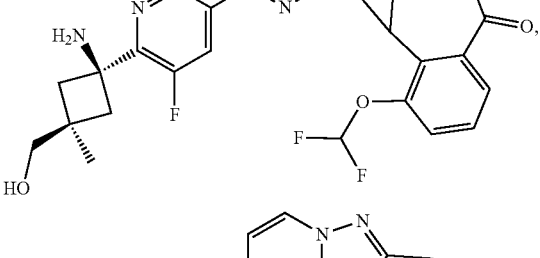
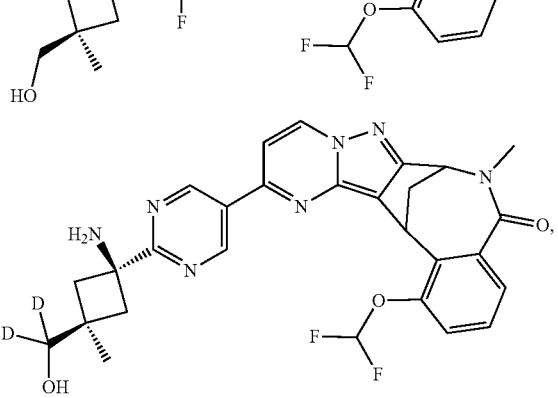
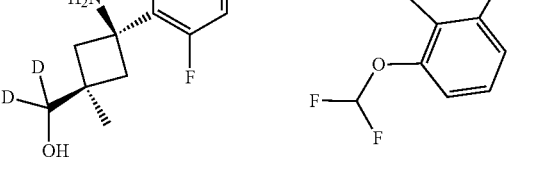
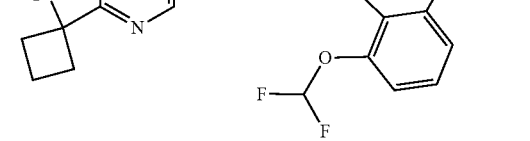

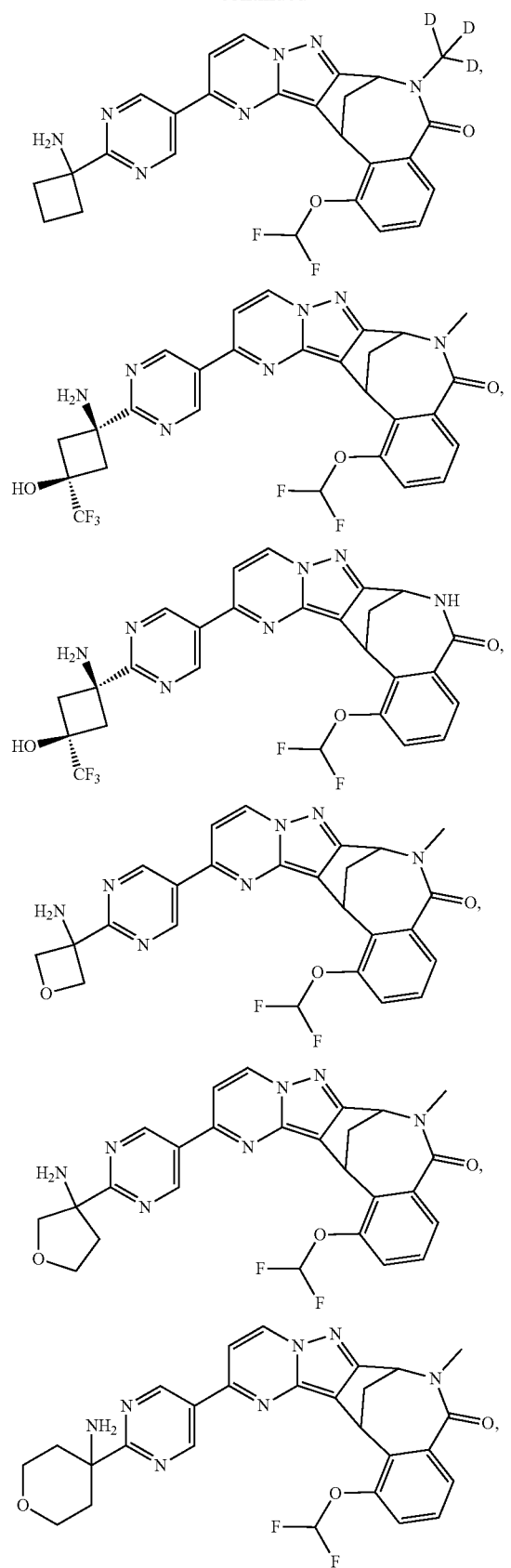
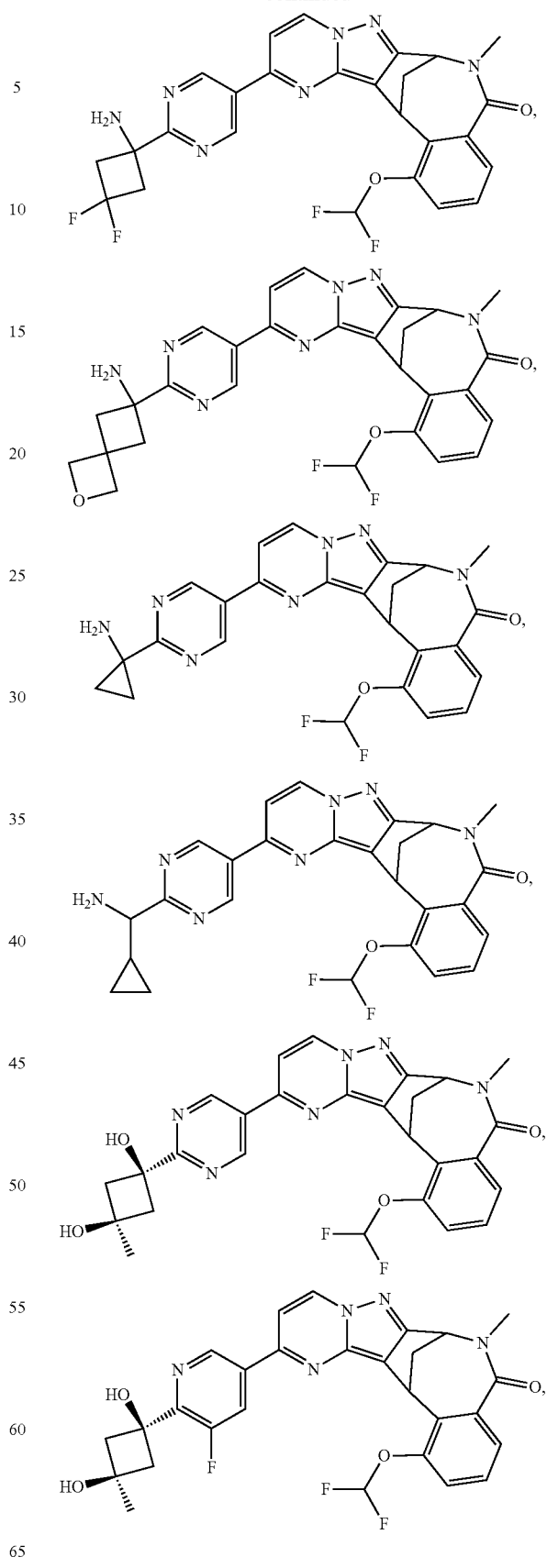

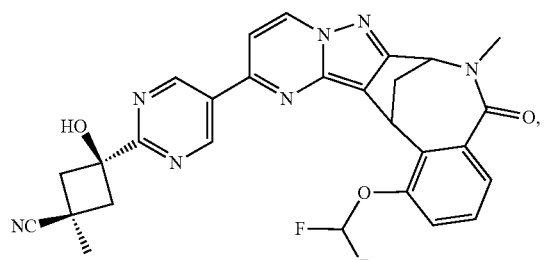
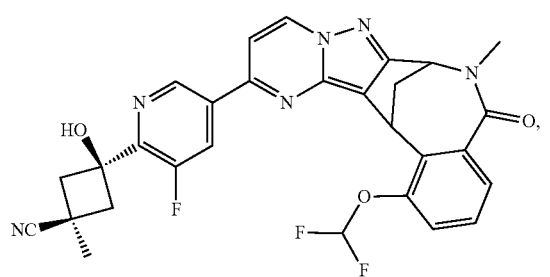
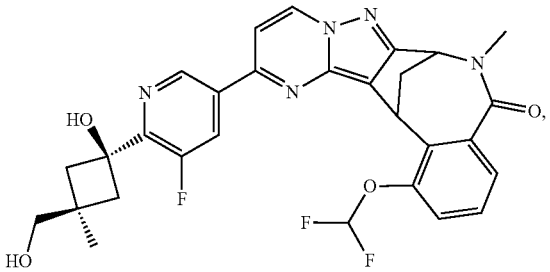
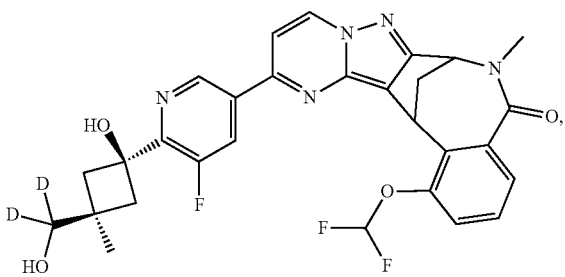
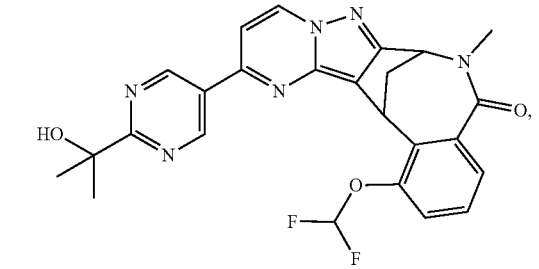
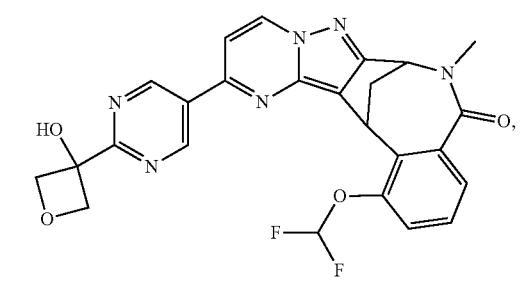
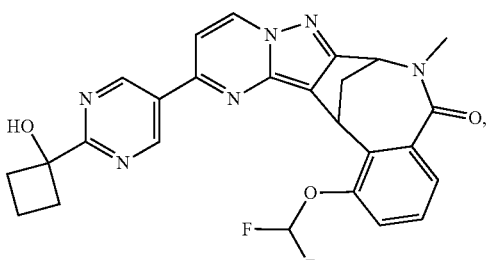
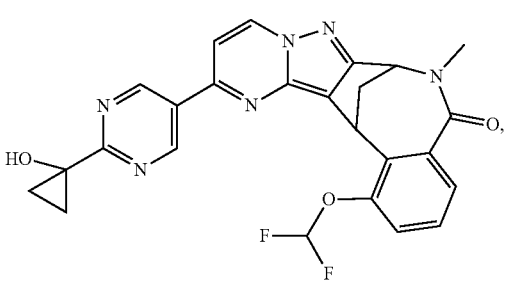
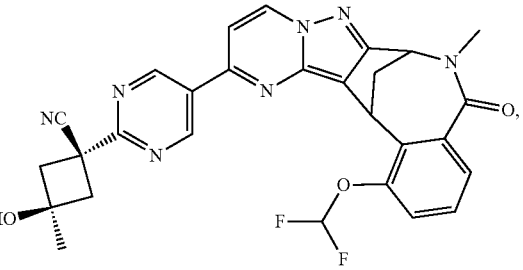
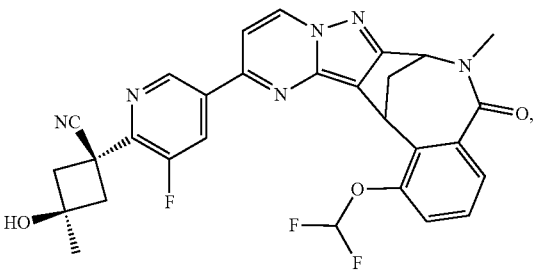
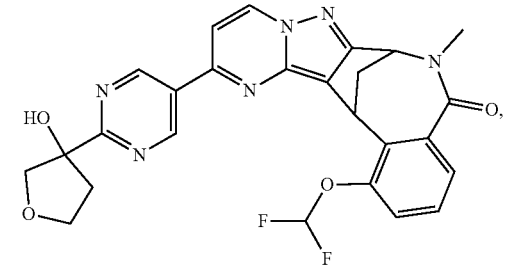
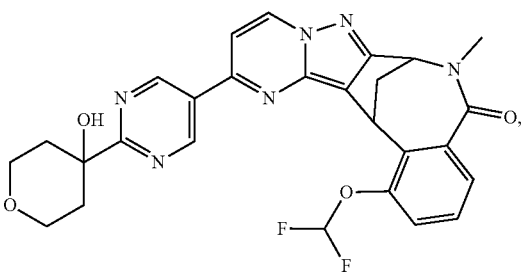

233
-continued
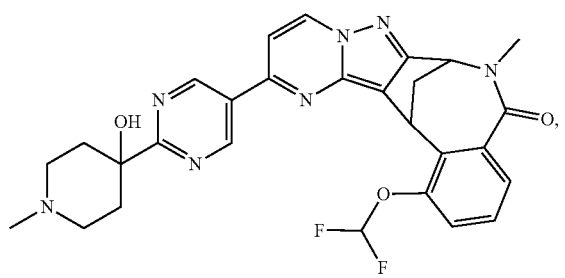
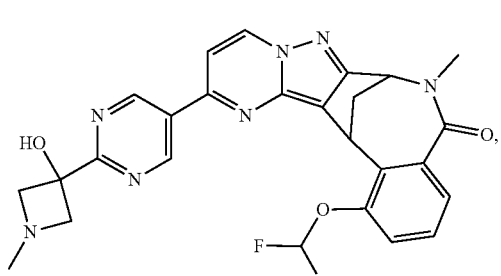
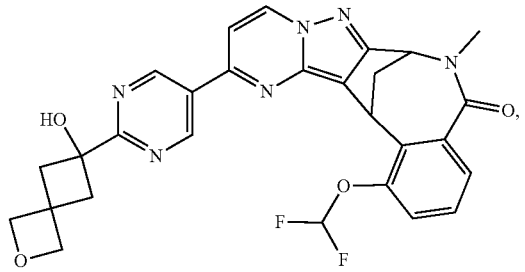
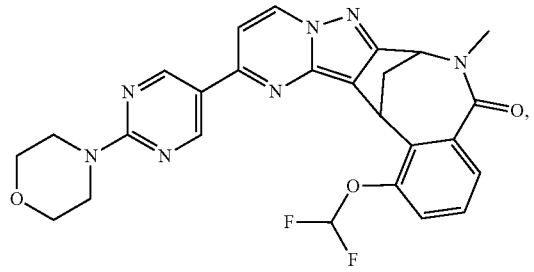
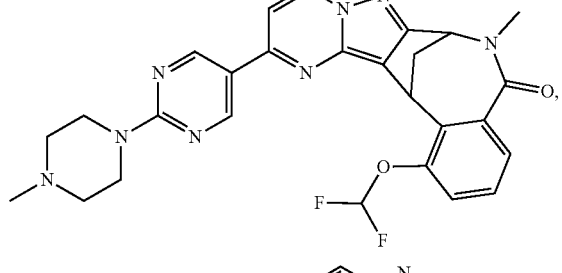
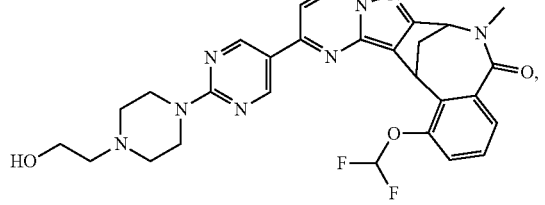
234
-continued
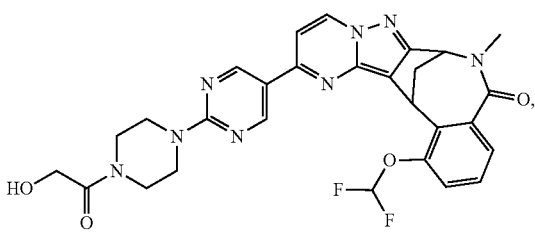
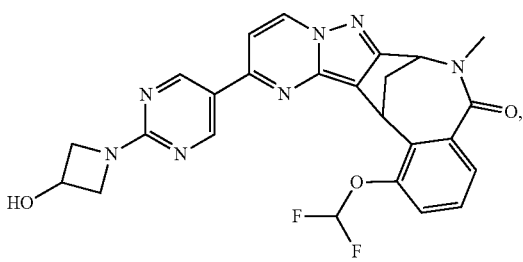
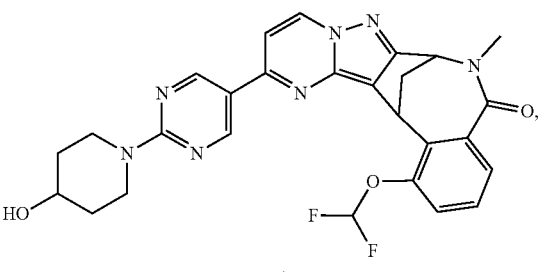
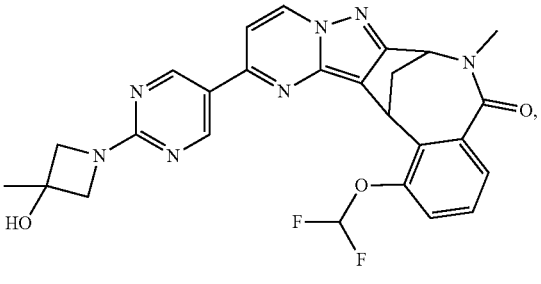
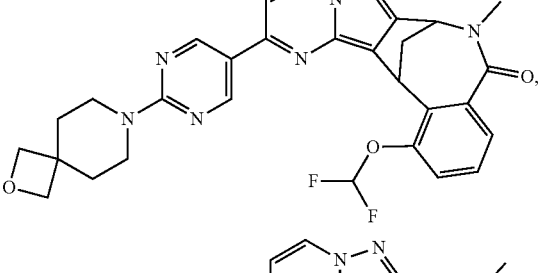
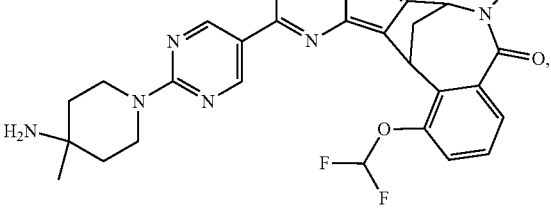

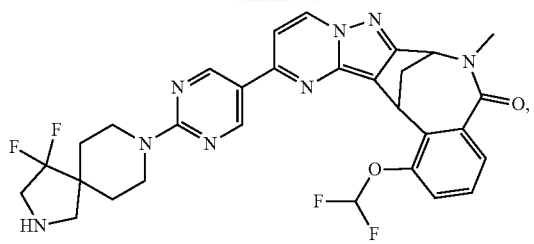
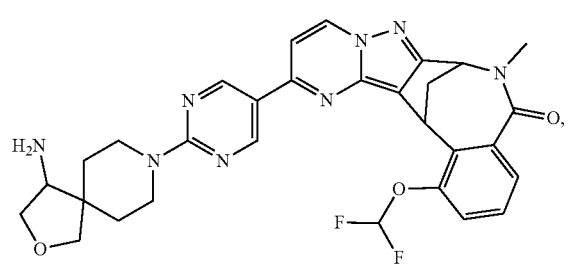
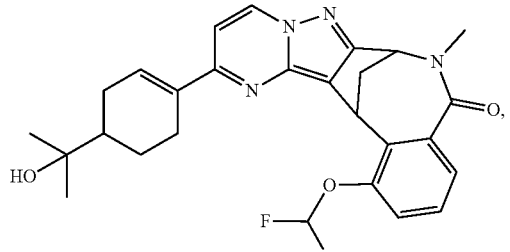
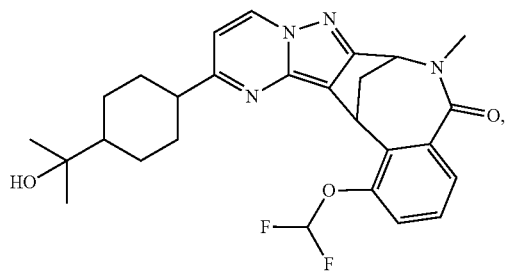
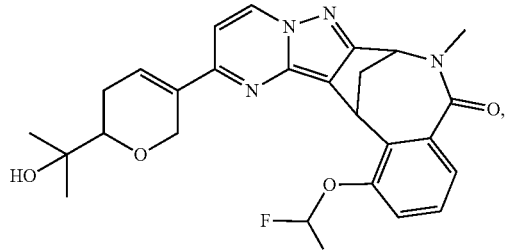
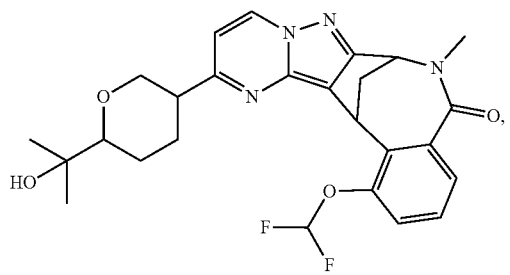
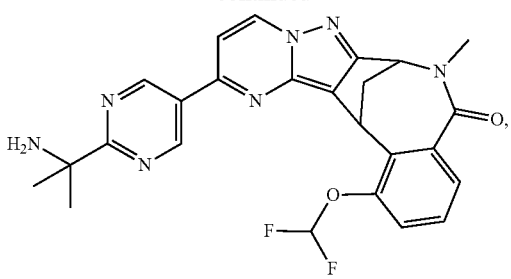
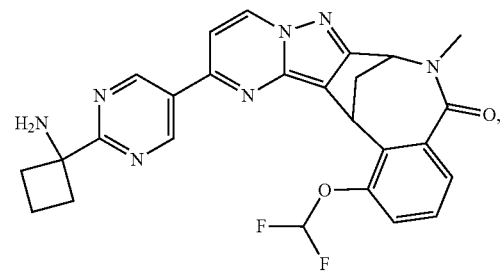
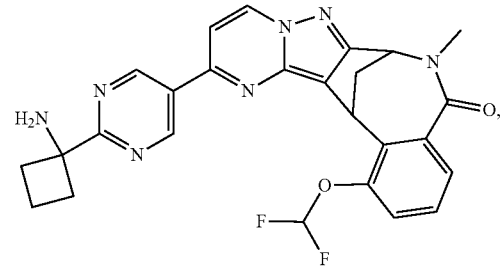
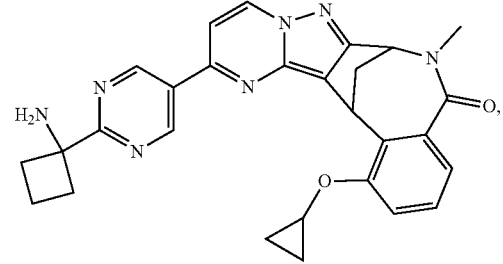
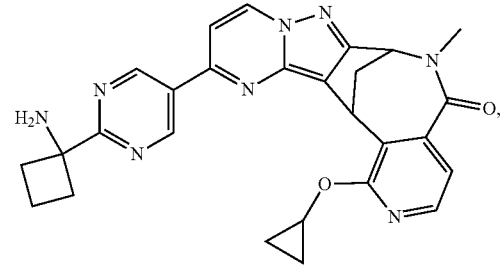
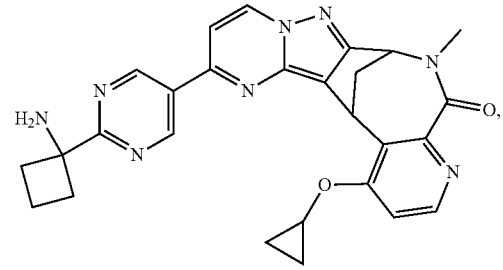

237
-continued
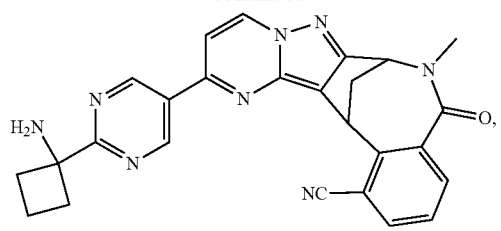
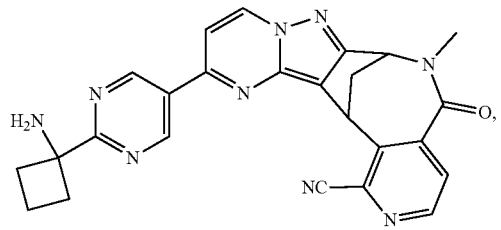
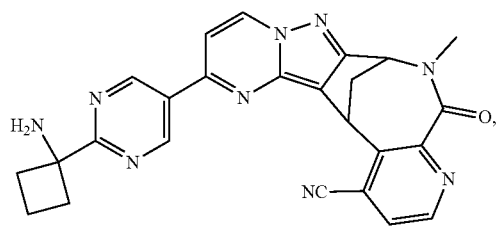
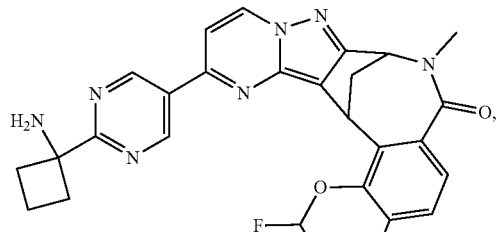
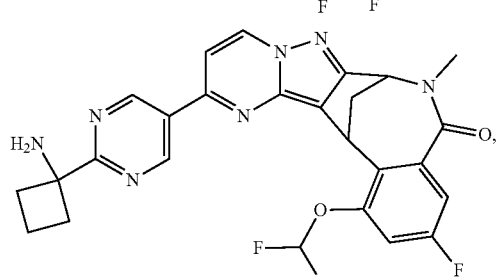
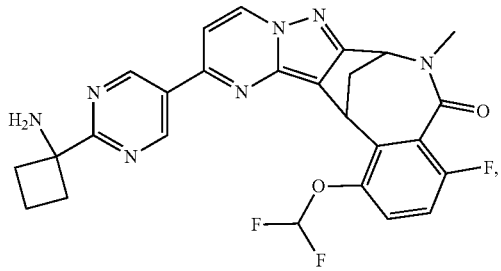
238
-continued
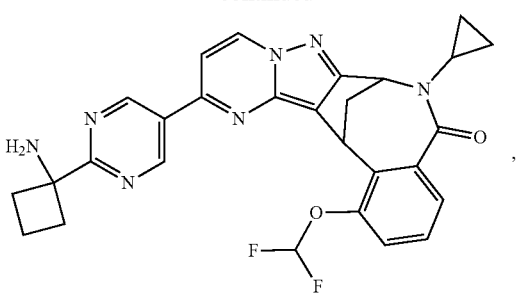
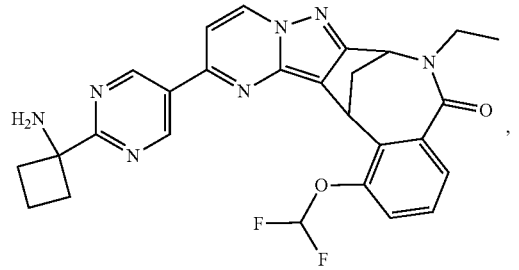
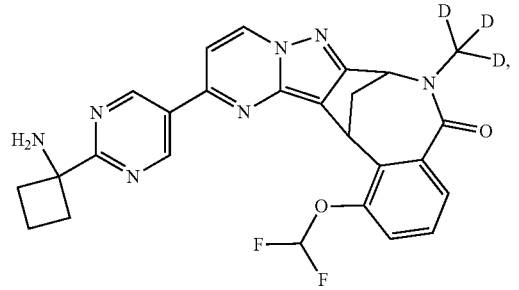
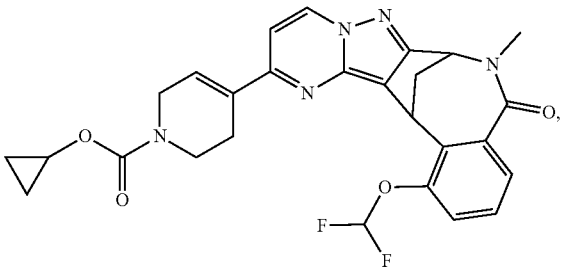
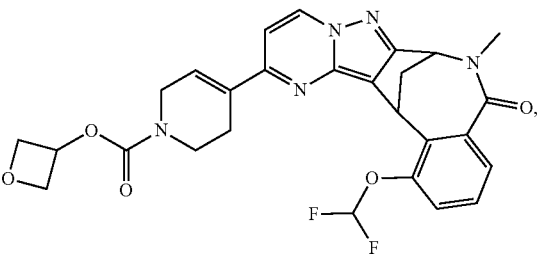
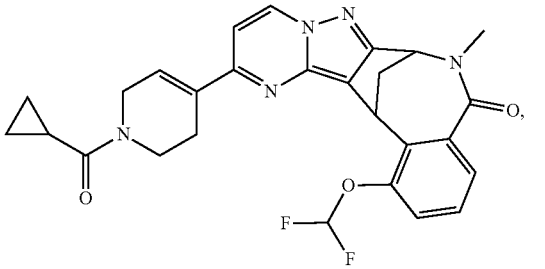

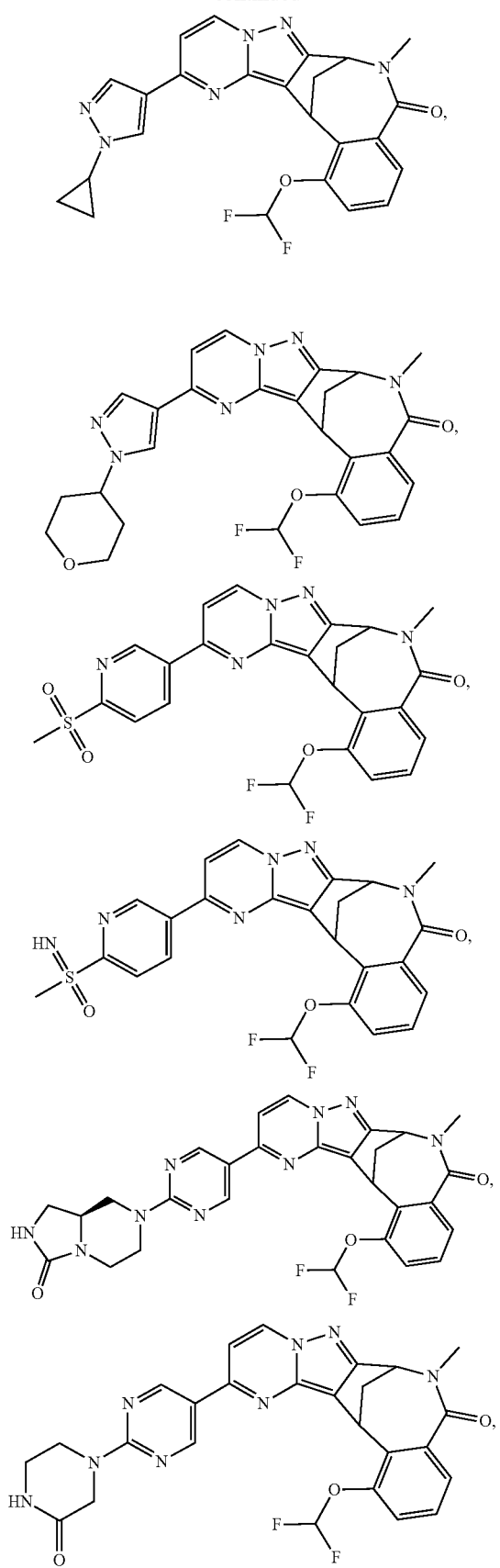
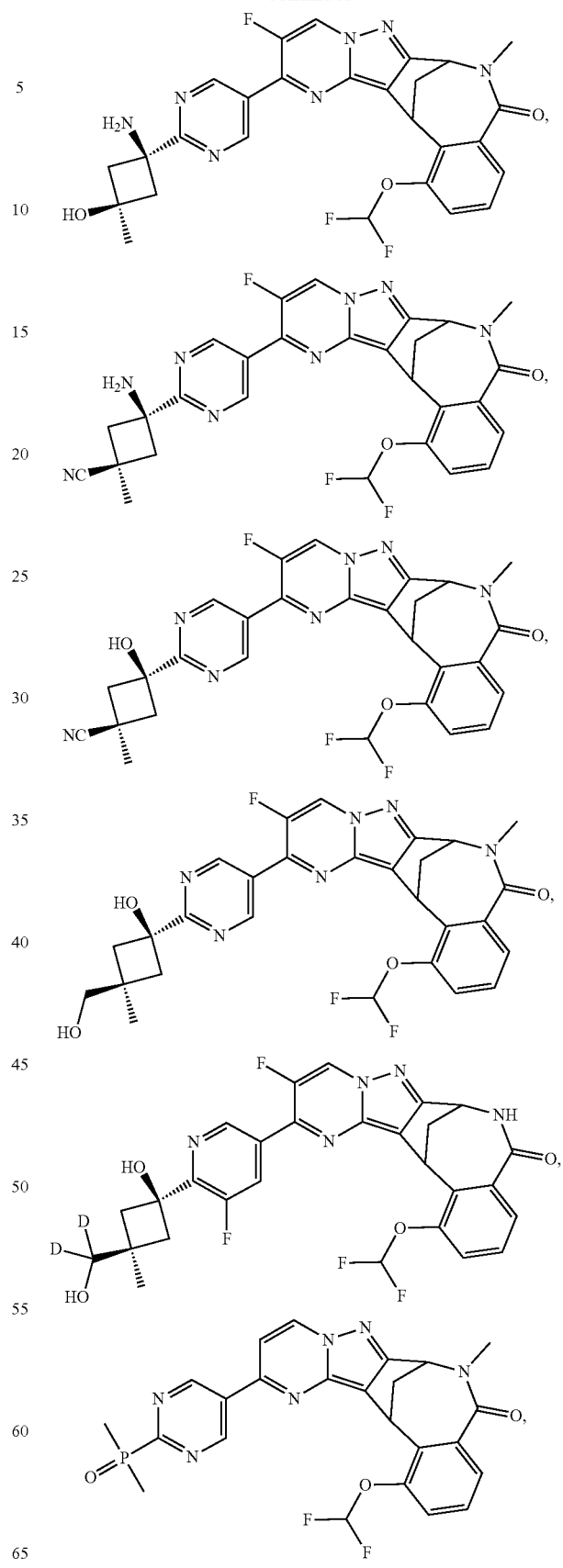

241
-continued
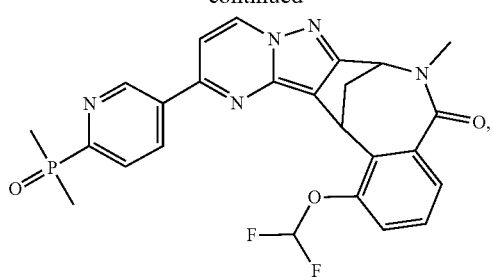
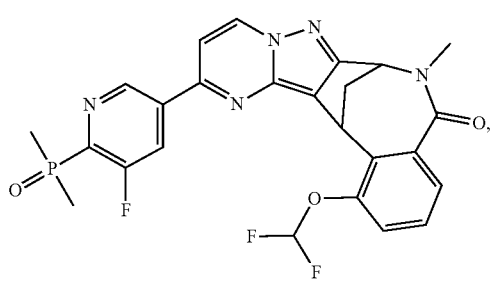
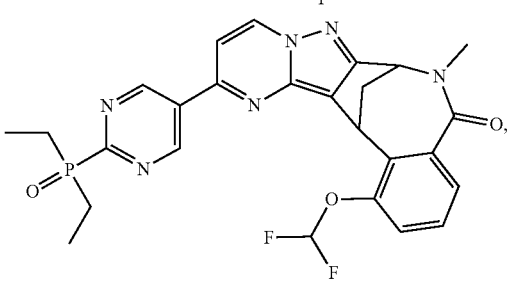
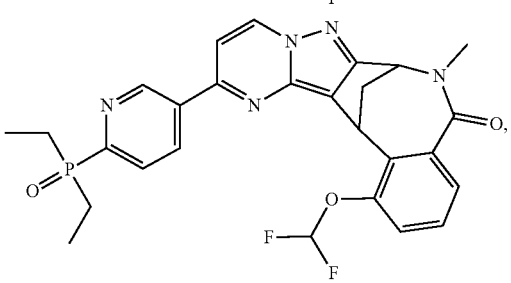
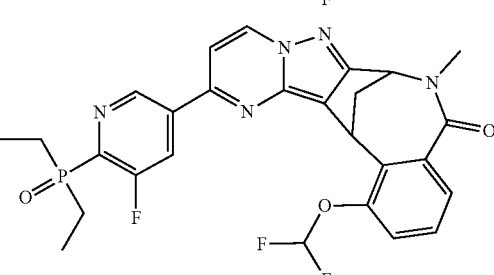
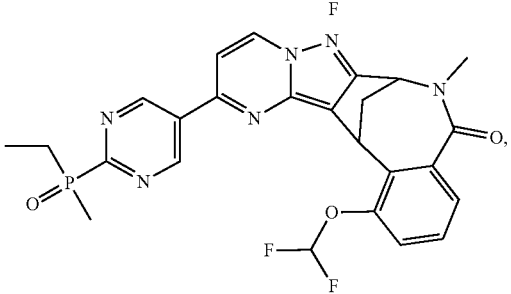
242
-continued
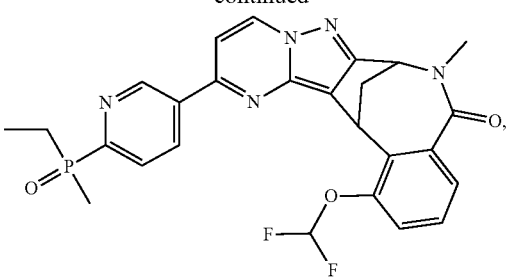
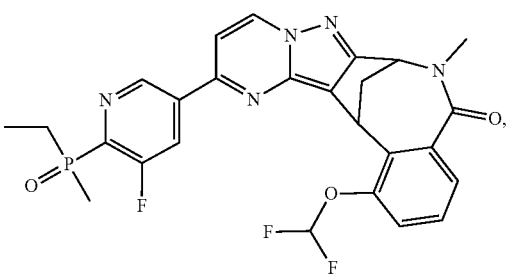
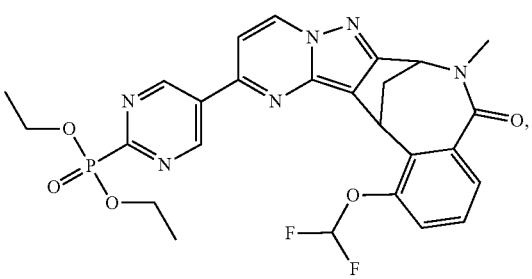
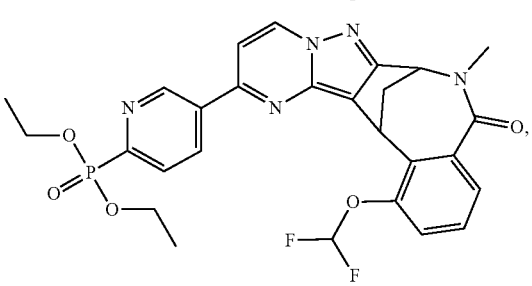
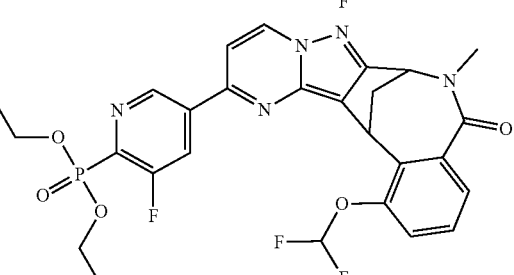
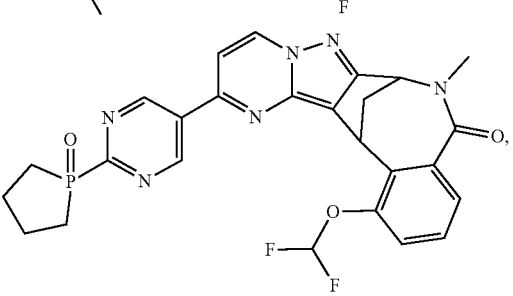

243
-continued
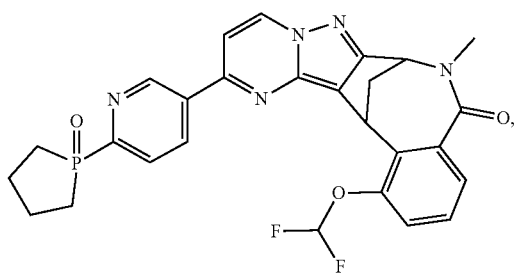
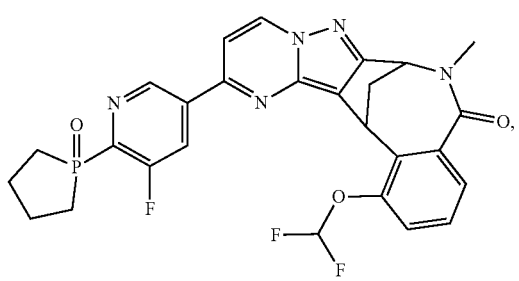
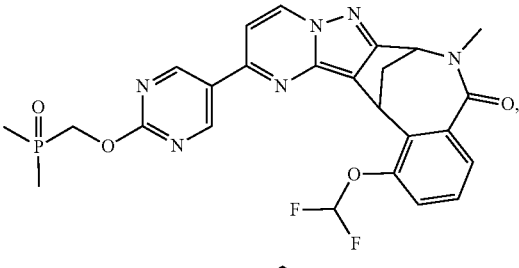
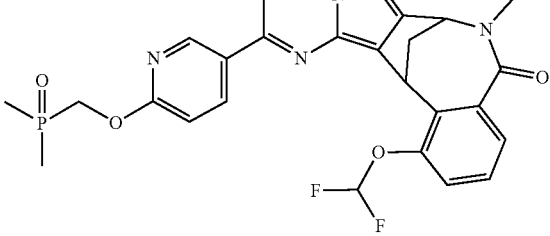
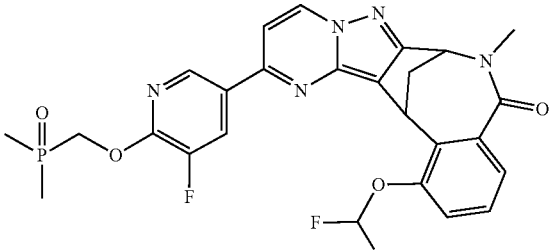
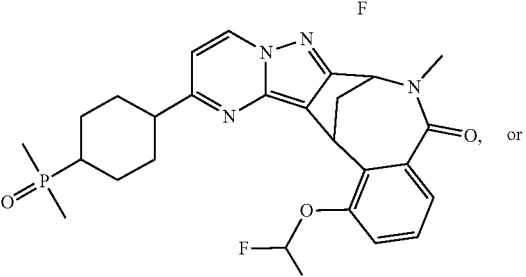
244
-continued
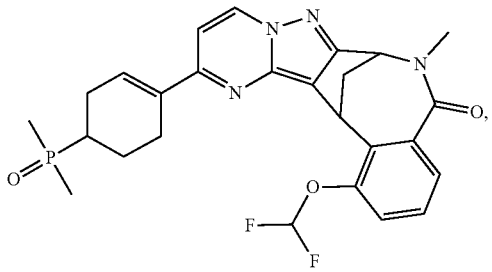
or a pharmaceutically acceptable salt, solvate, or stereoisomer thereof.
In some embodiments of the compounds disclosed above,
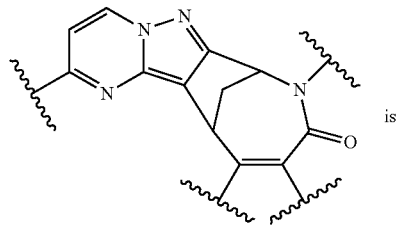 is
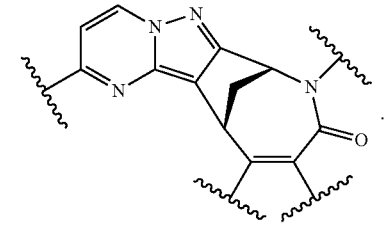.
In some embodiments, the compound is selected from the group consisting of:
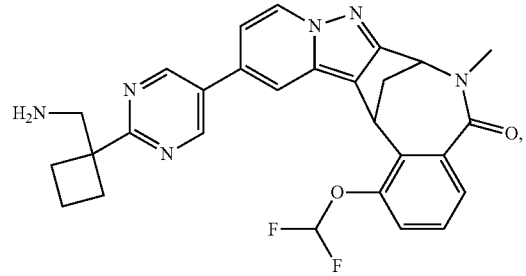
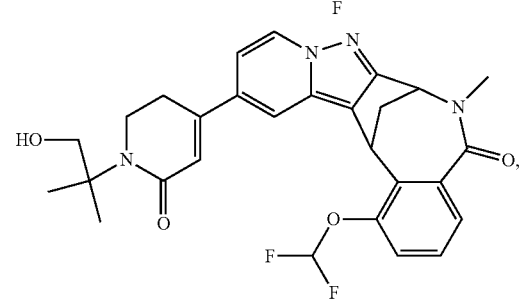

245
-continued
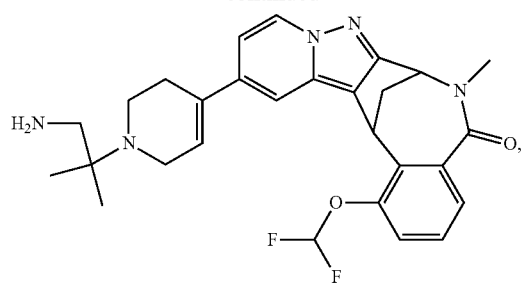
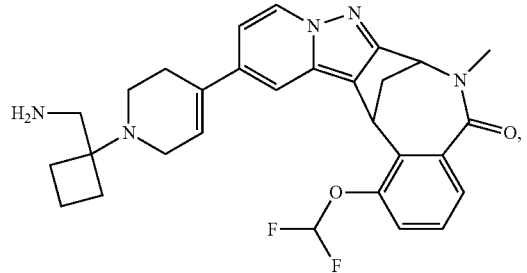
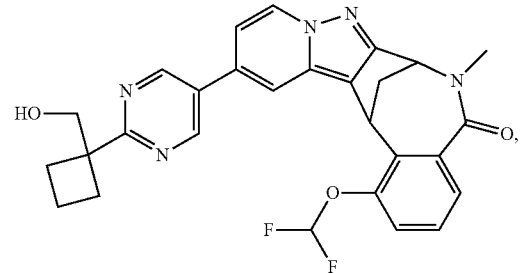
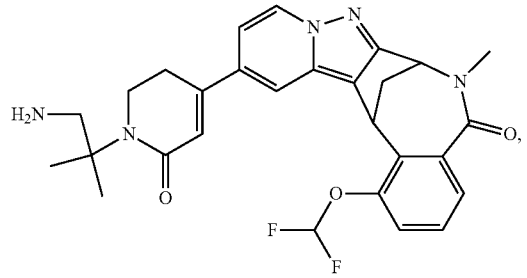
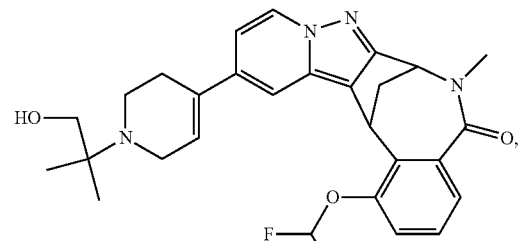
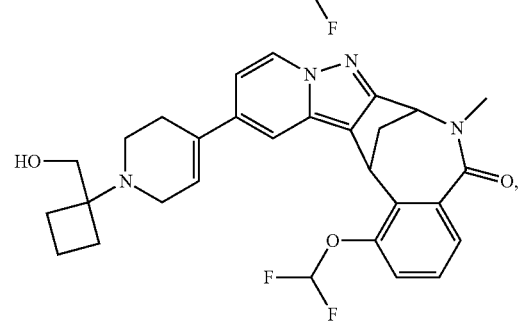
246
-continued
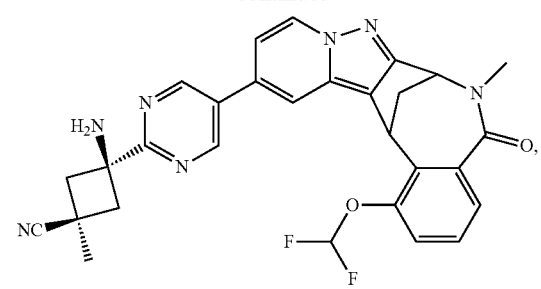
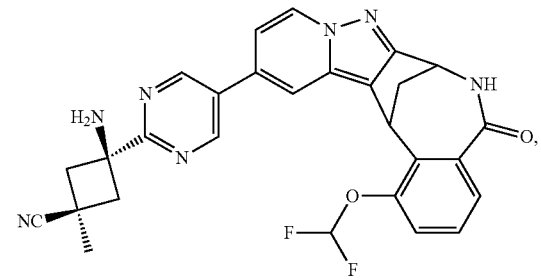
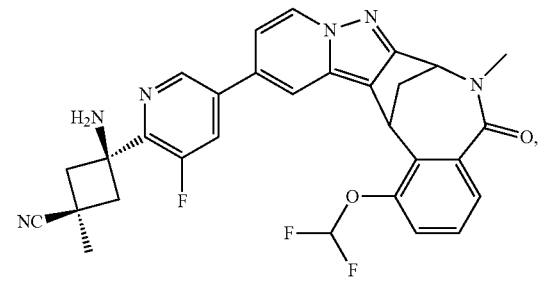
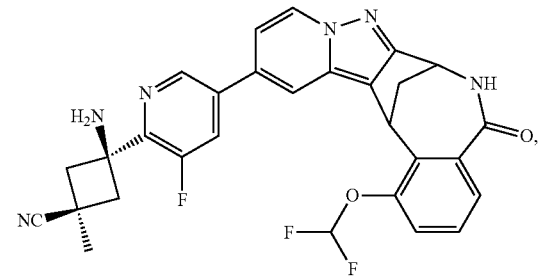
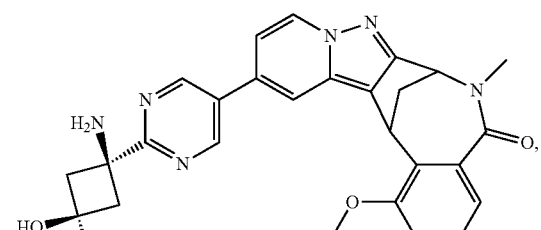
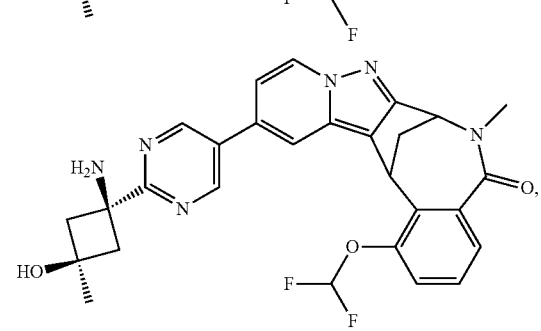

247
-continued
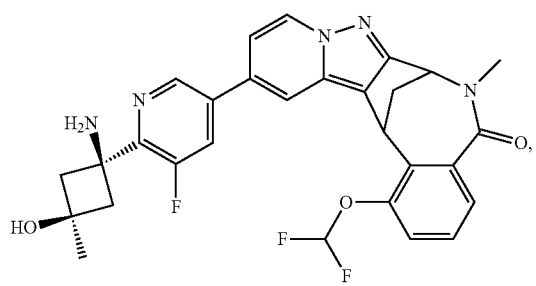
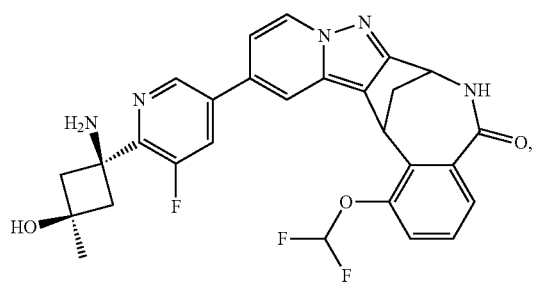
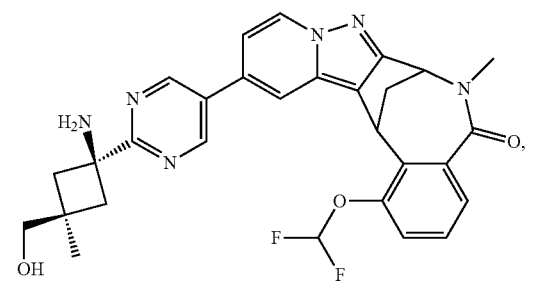
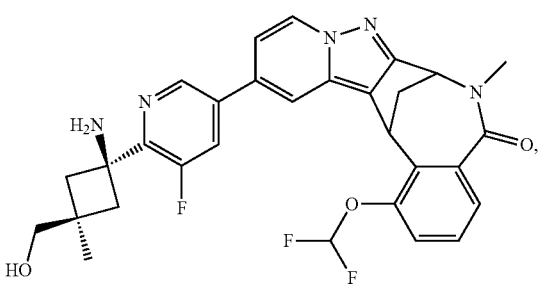
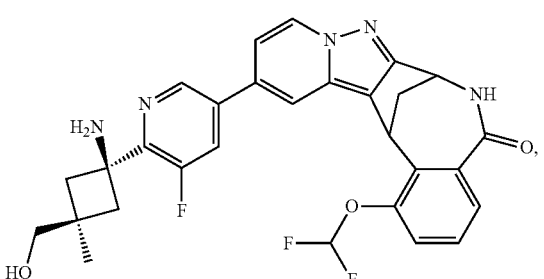
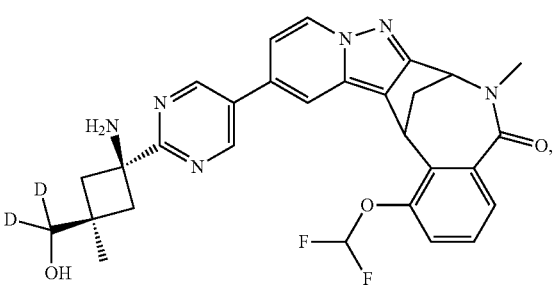
248
-continued
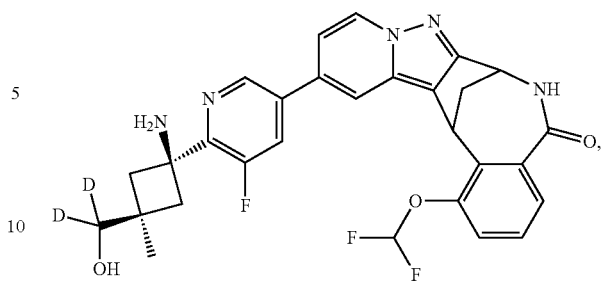
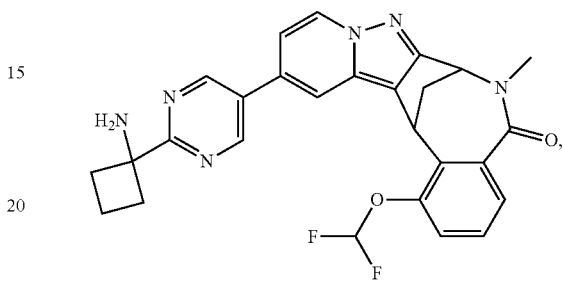
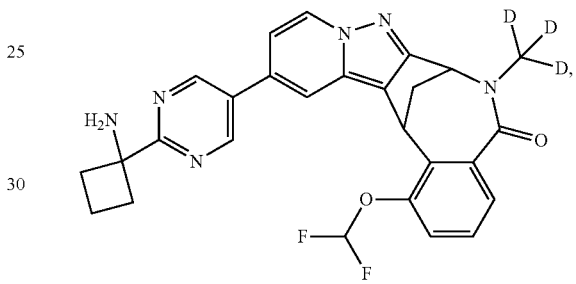
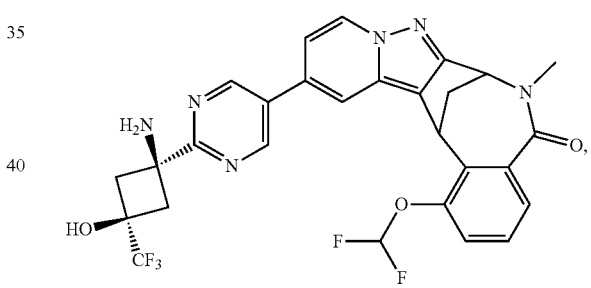
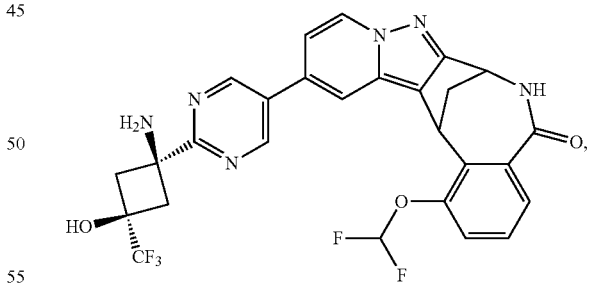
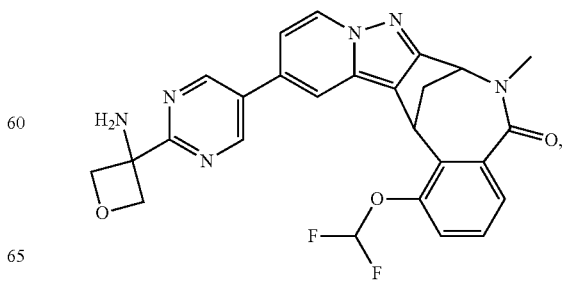

249
-continued
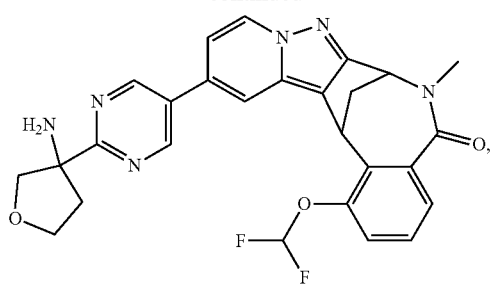
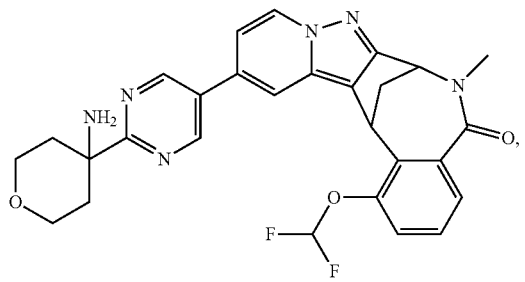
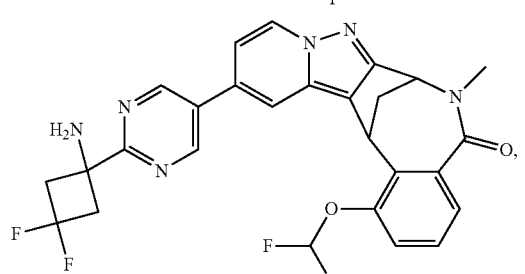
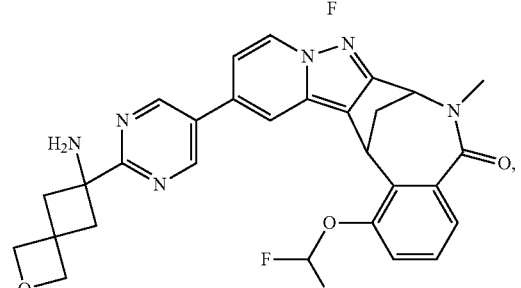
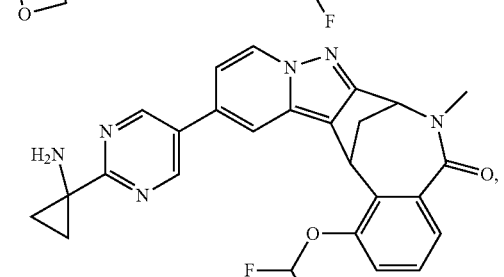
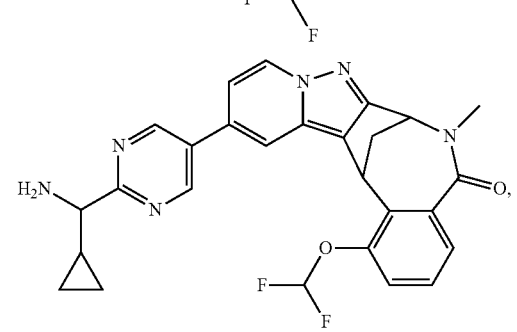
250
-continued
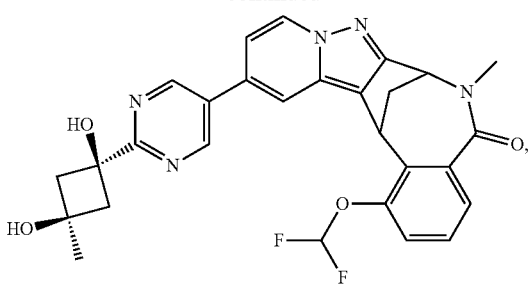
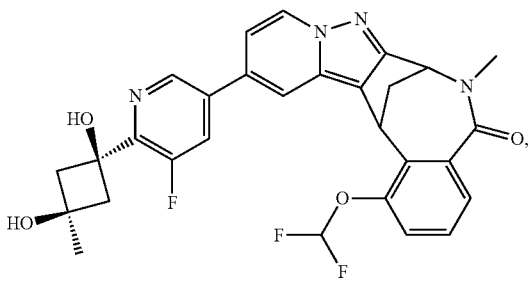
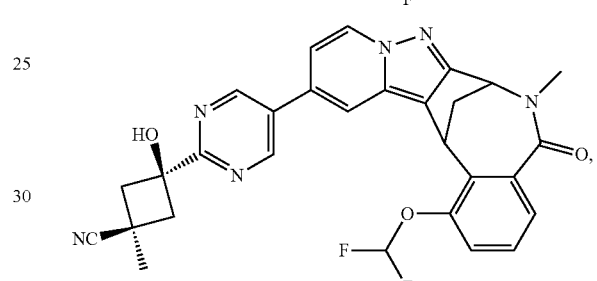
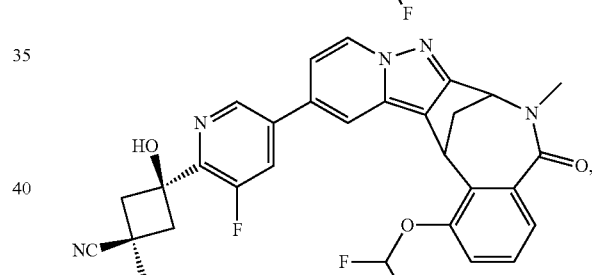
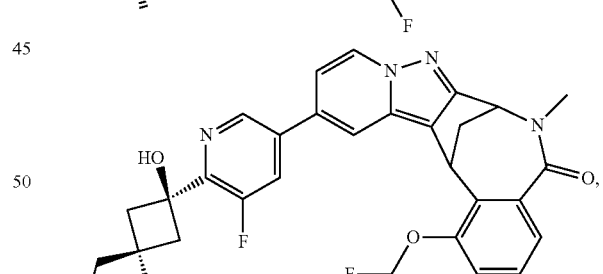
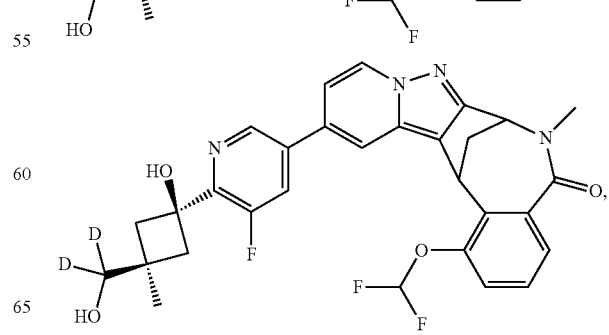

251
-continued
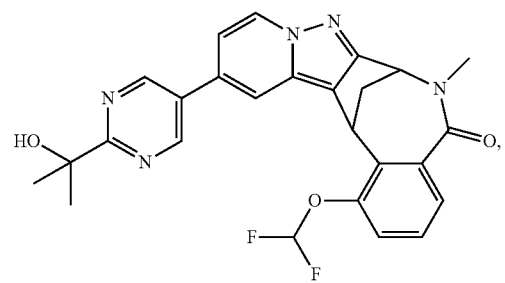
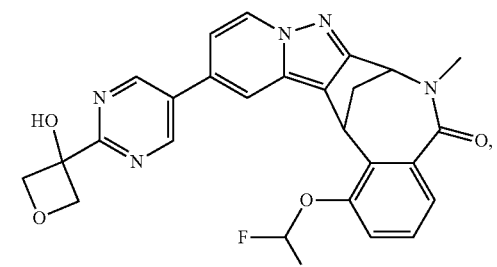
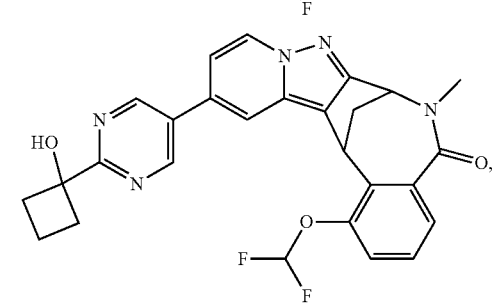
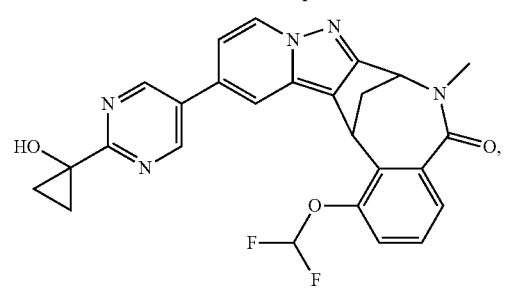
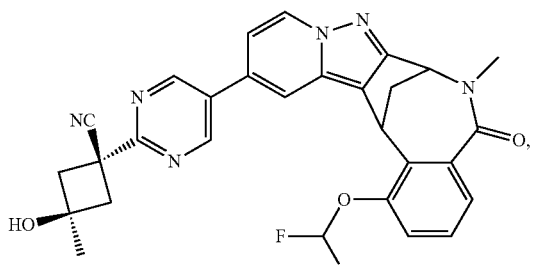
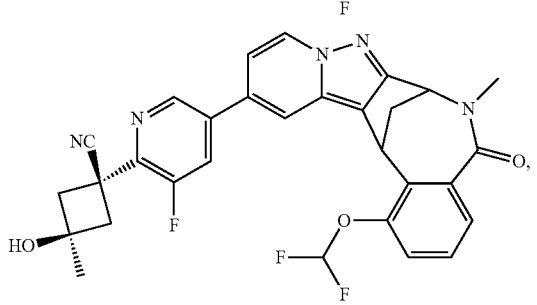
252
-continued
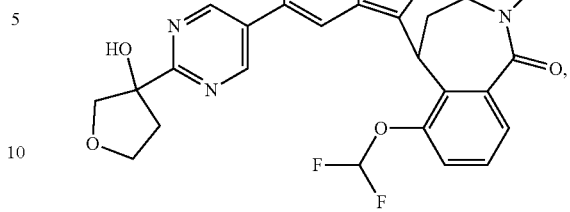
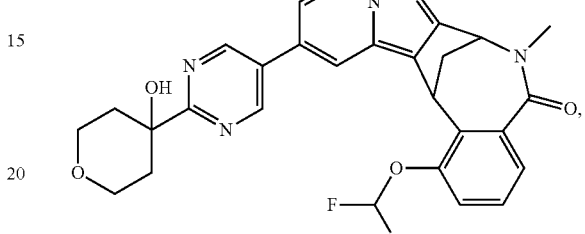
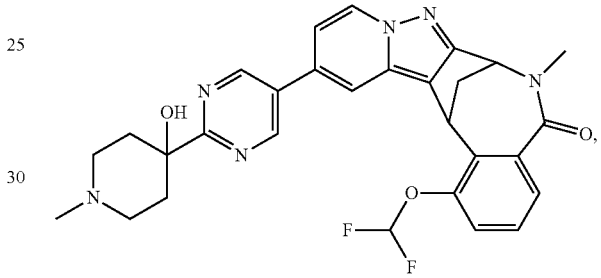
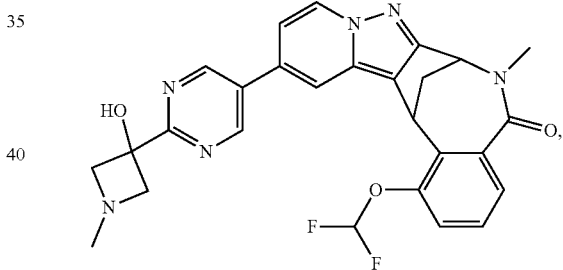
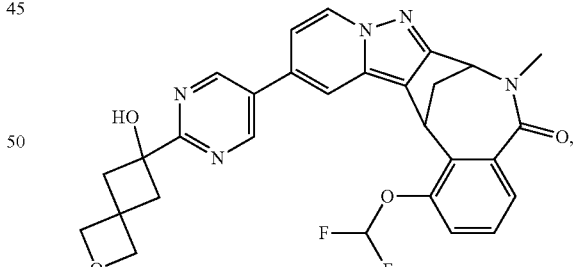
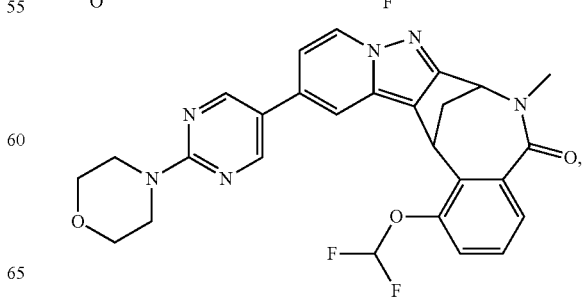

253 -continued
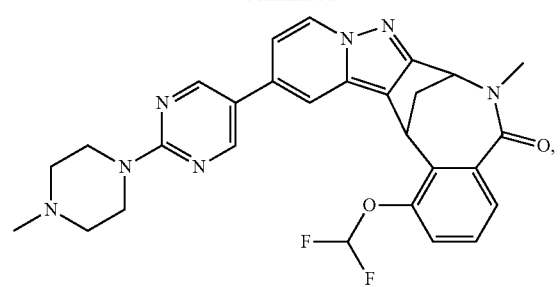
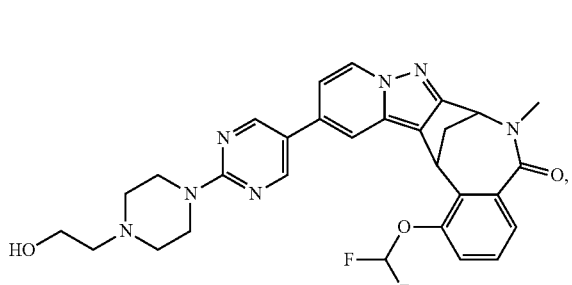
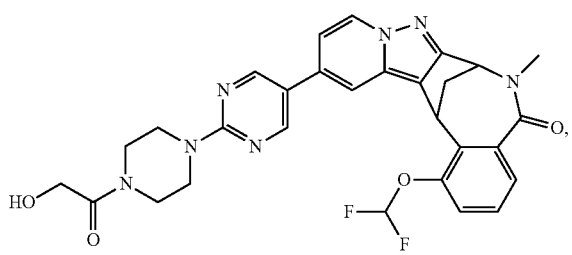
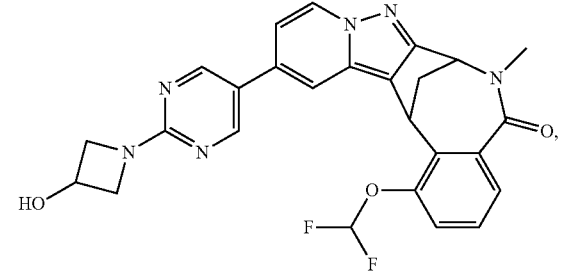
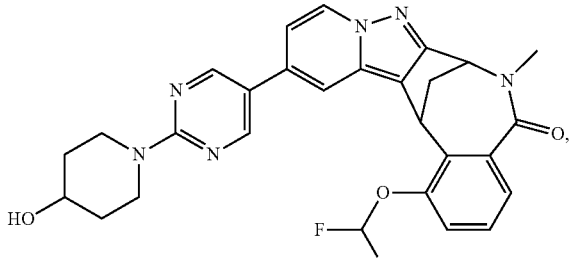
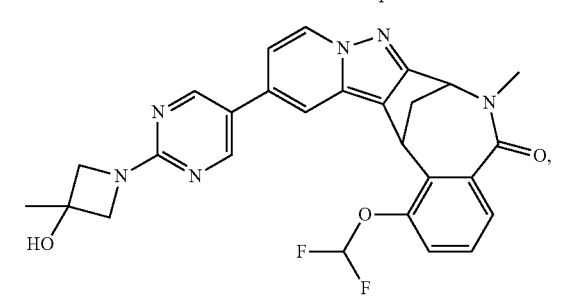
254 -continued
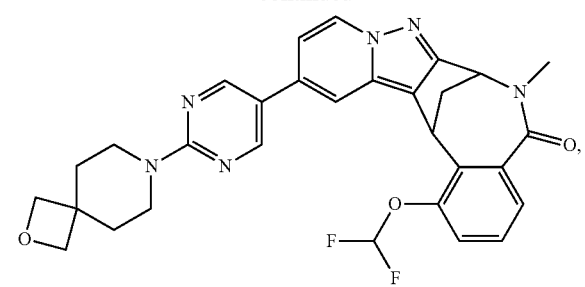
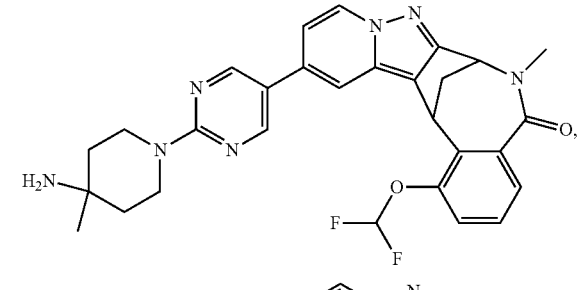
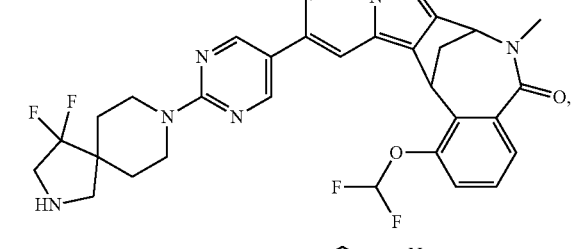
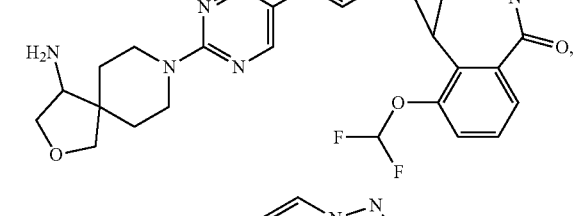
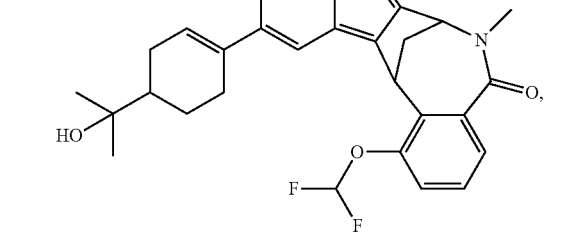
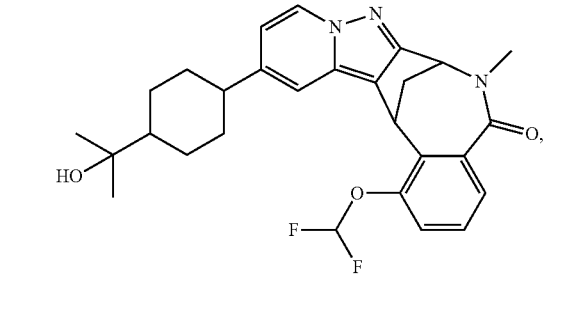

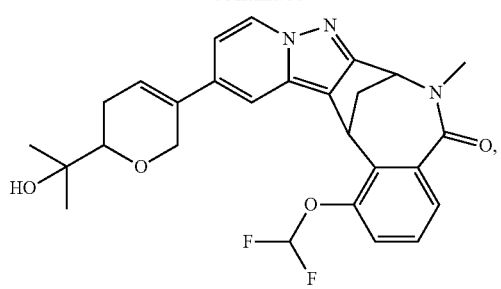
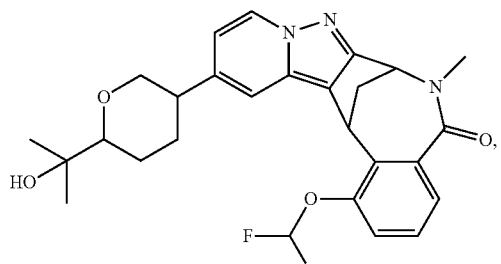
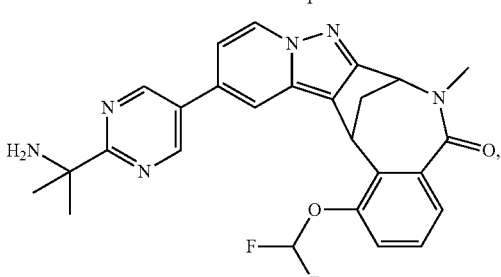
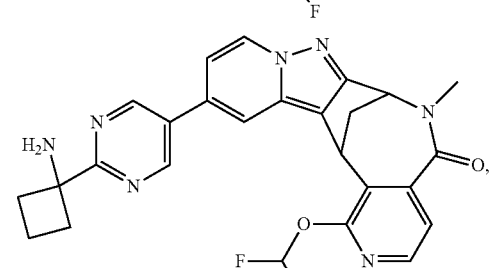
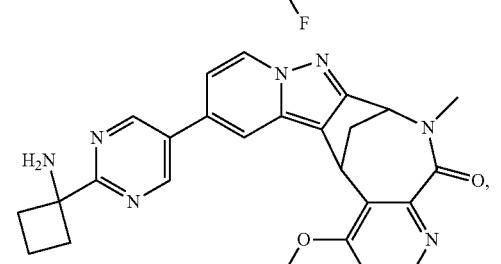
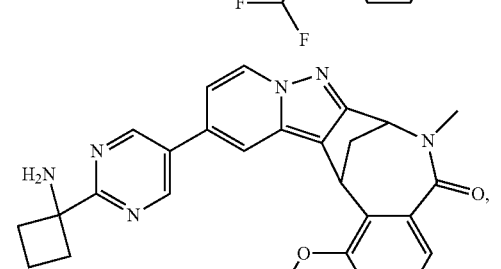
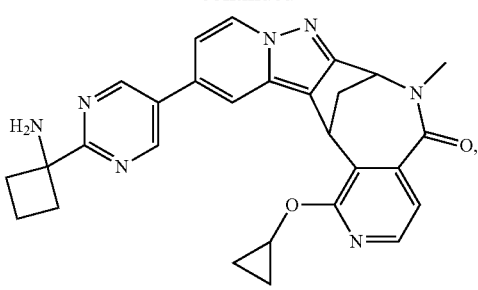
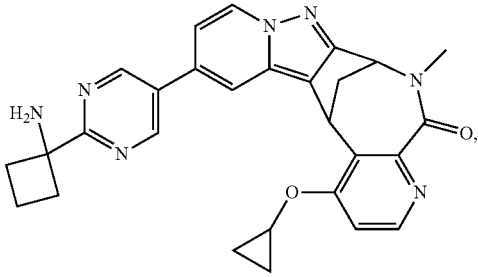
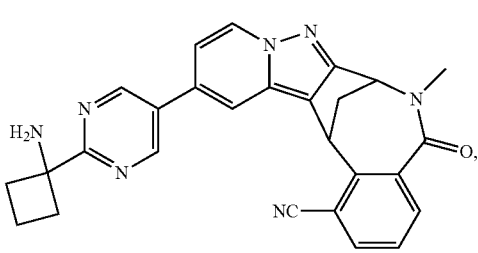
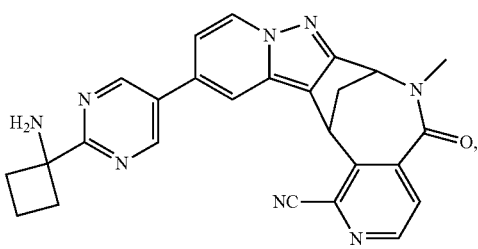
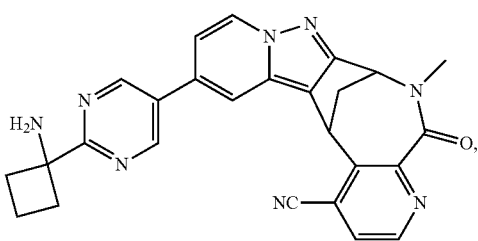
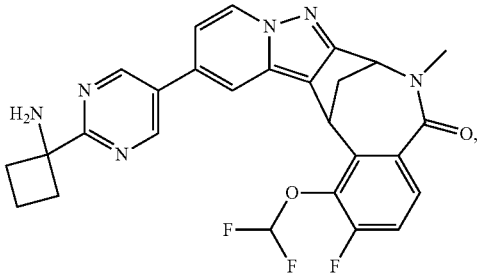

257
-continued
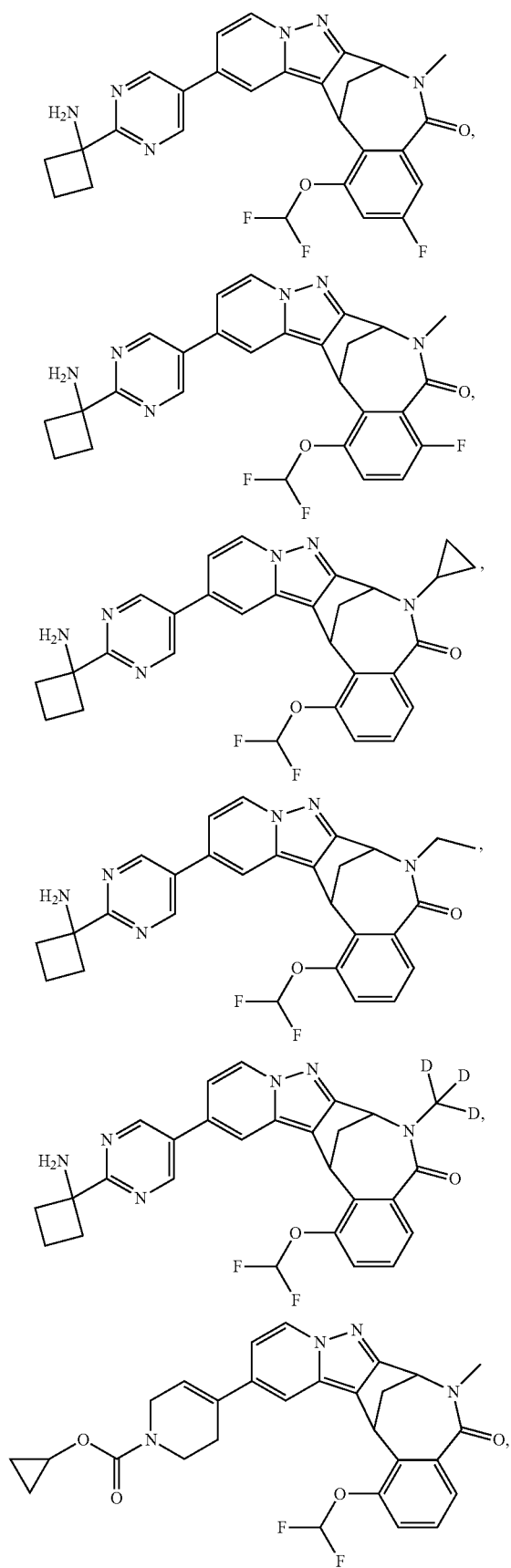
258
-continued
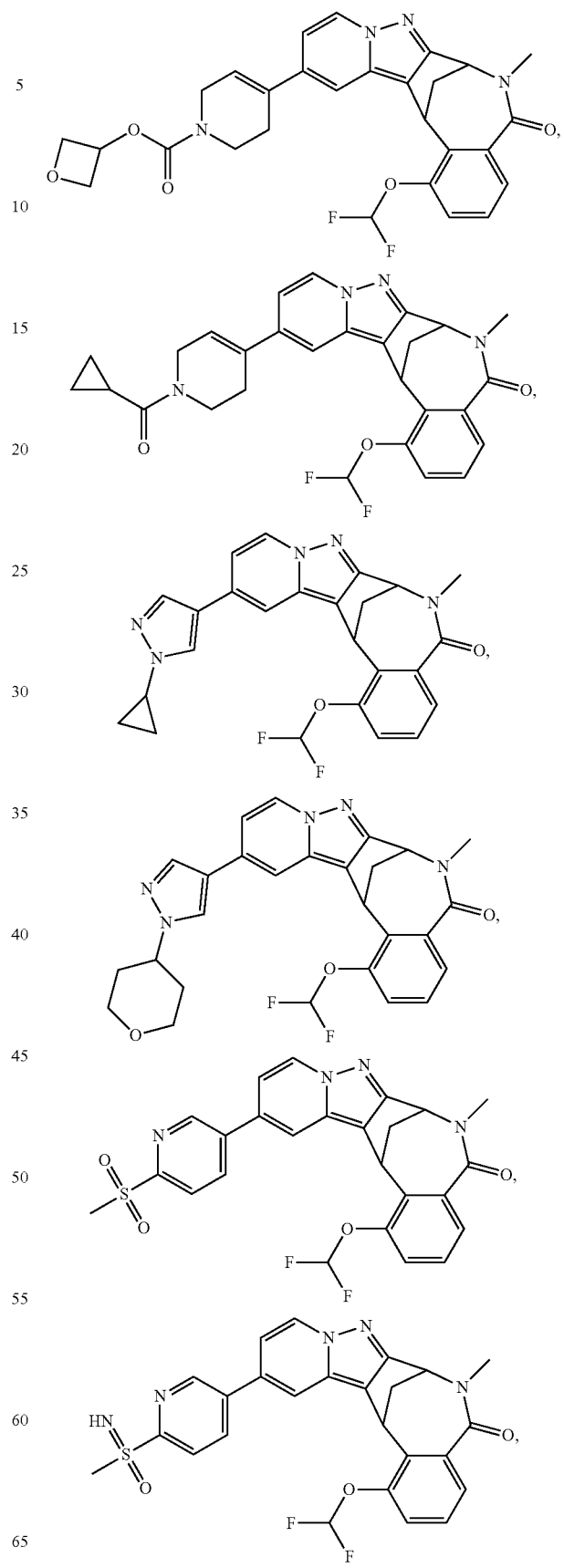

259
-continued
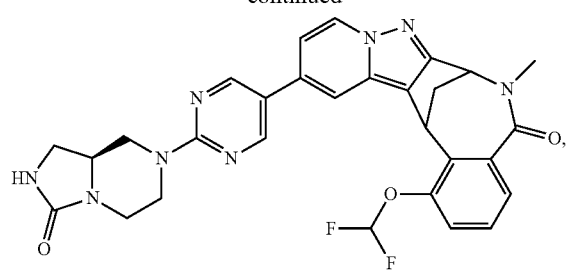
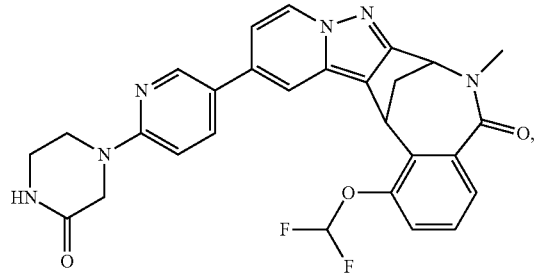
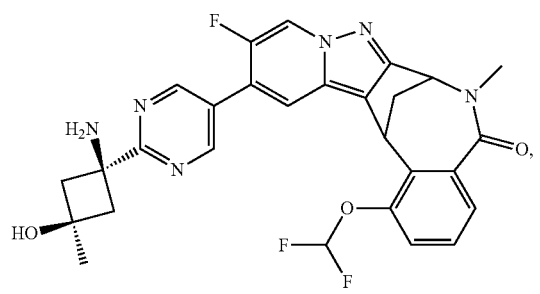
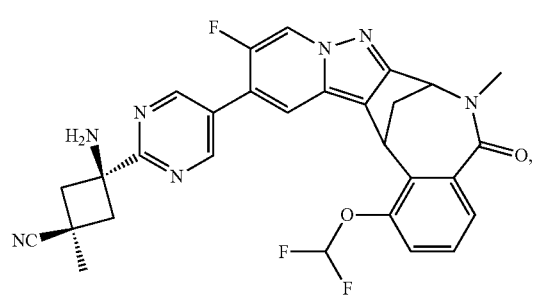
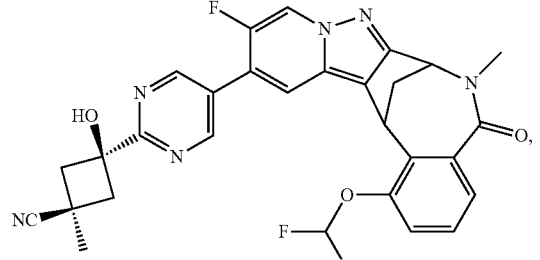
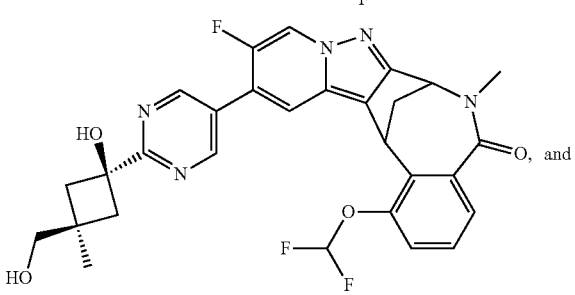
260
-continued
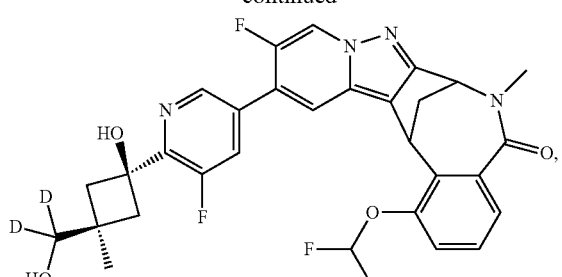
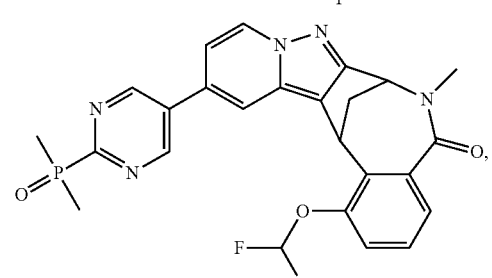
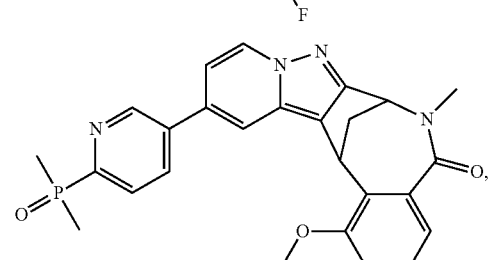
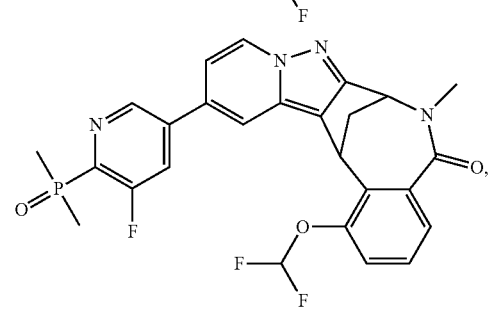
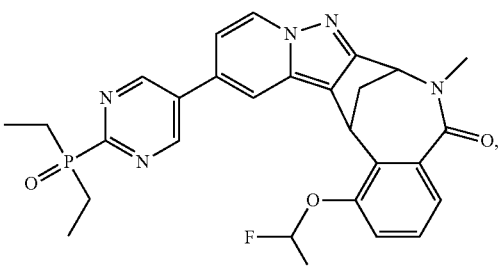
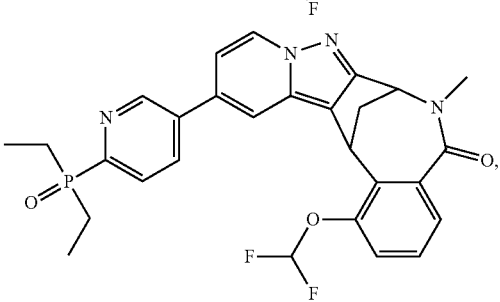

261
-continued
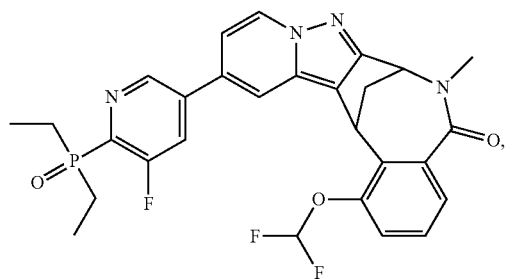
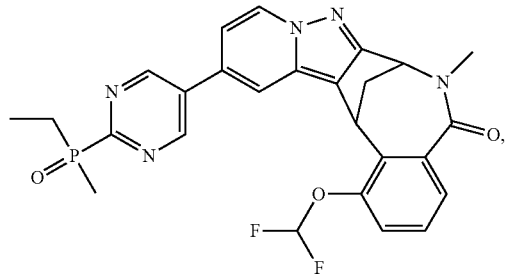
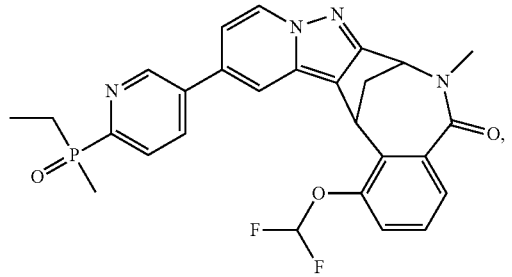
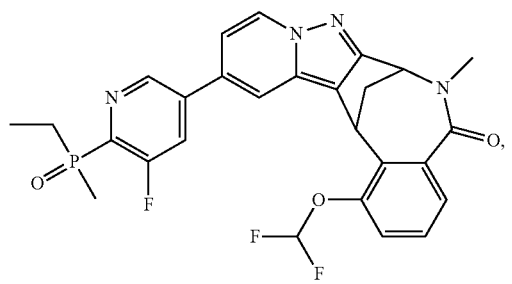
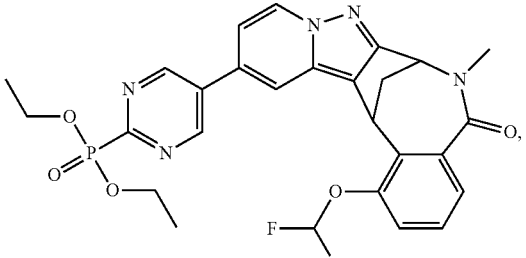
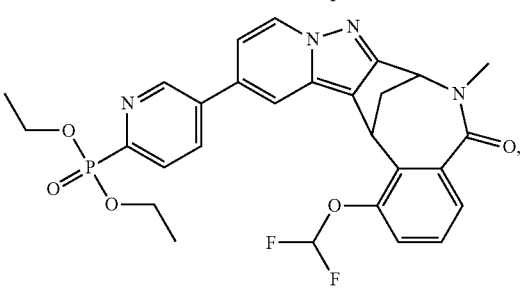
262
-continued
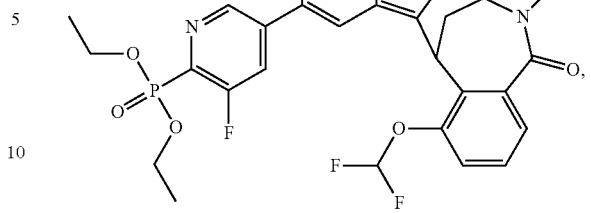
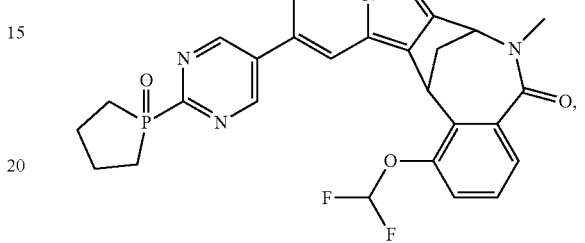
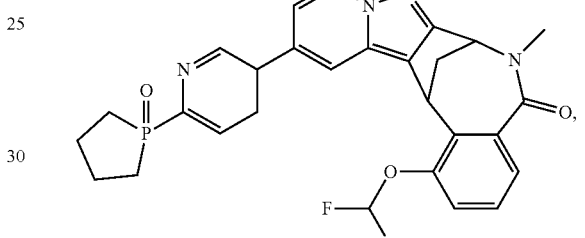
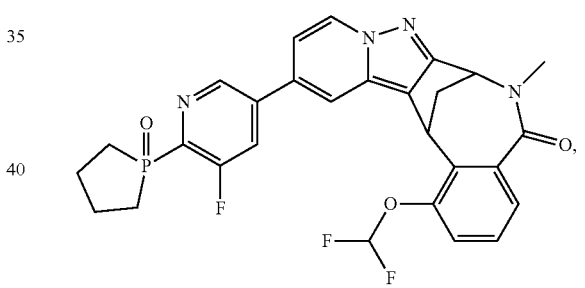
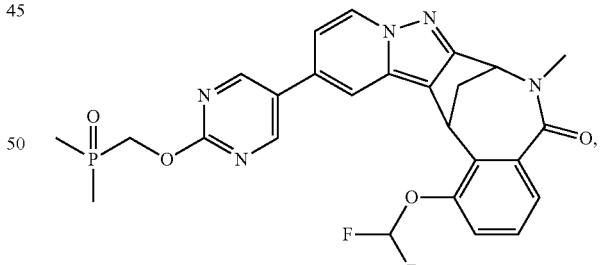
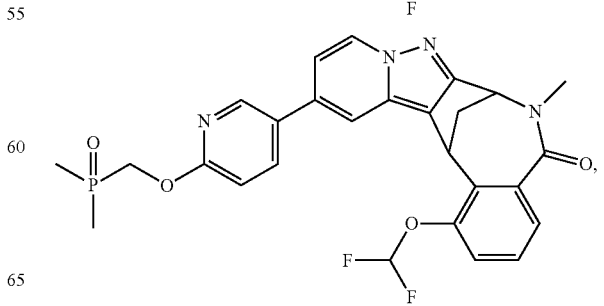

263
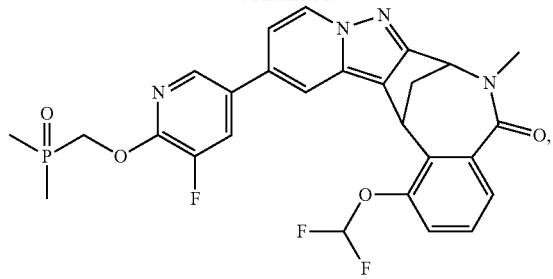
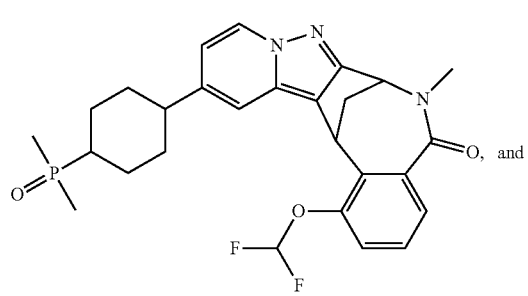
, and
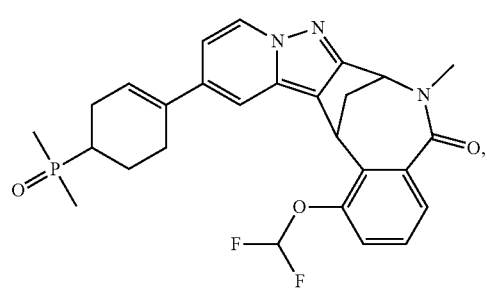
or a pharmaceutically acceptable salt, solvate, or stereoisomer thereof.
In some embodiments of the compounds disclosed above,
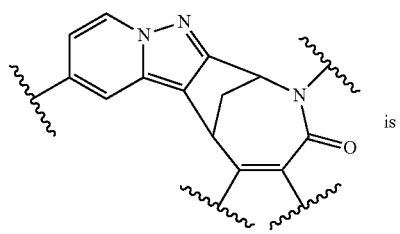 is
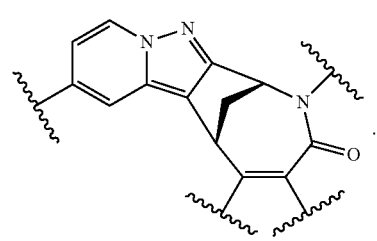.
In some embodiments, the compound is selected from the group consisting of:
264
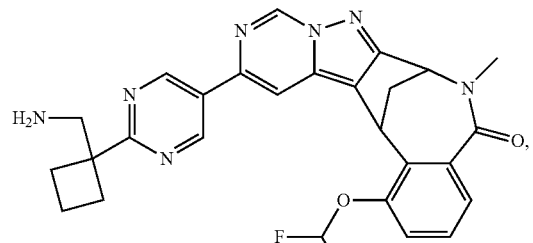
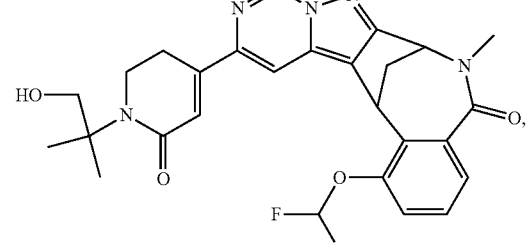
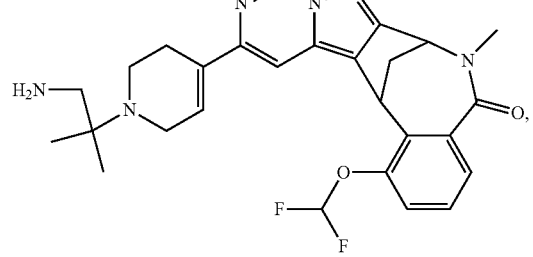
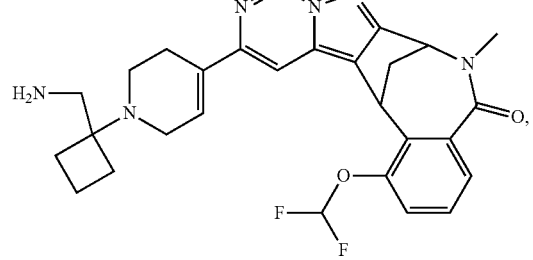
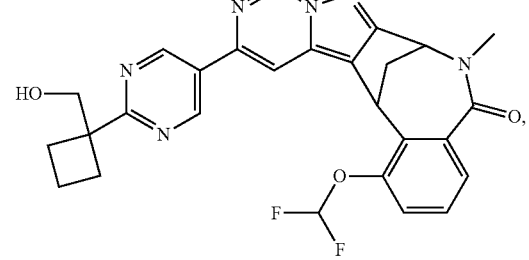
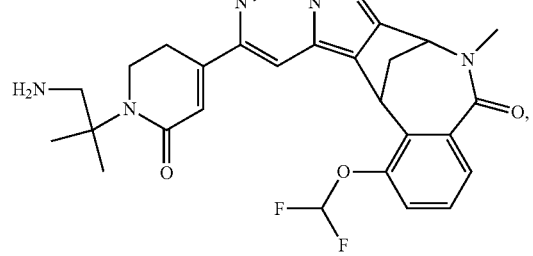

265
-continued
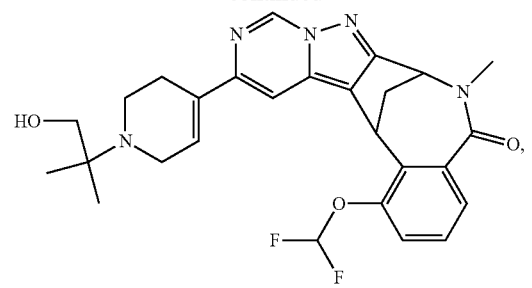
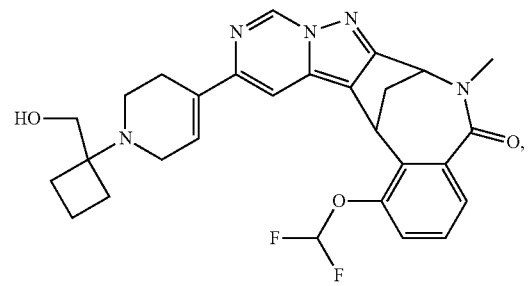
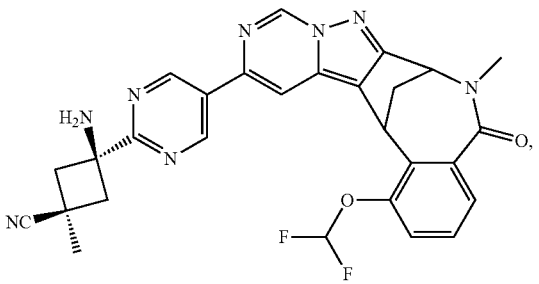
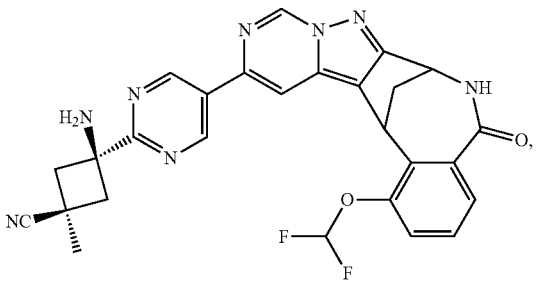
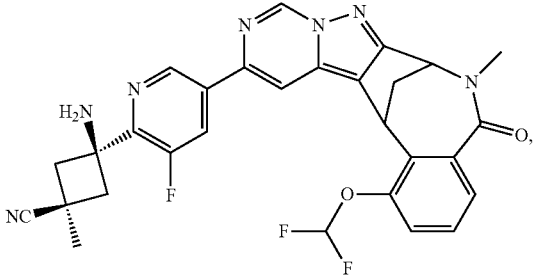
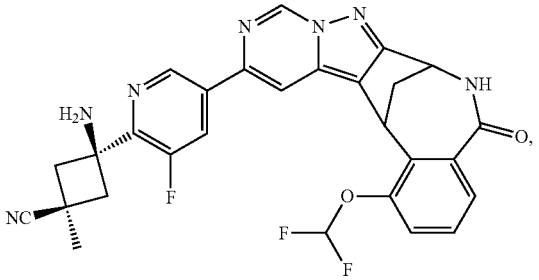
266
-continued
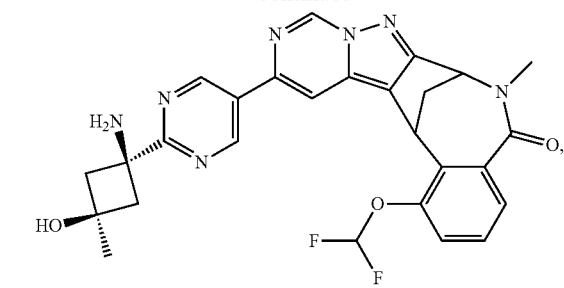
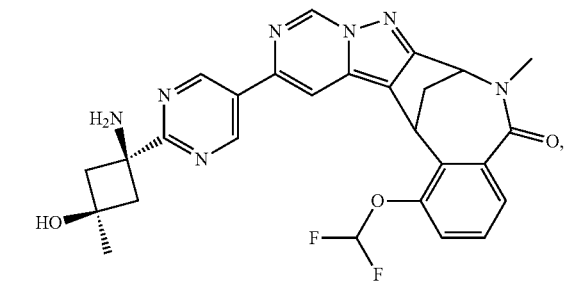
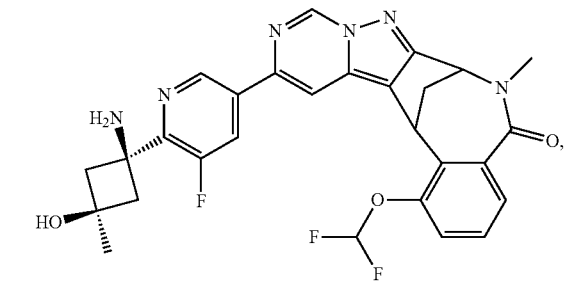
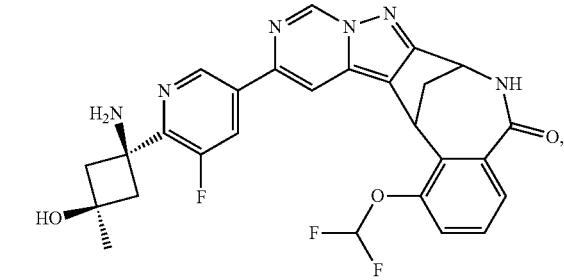
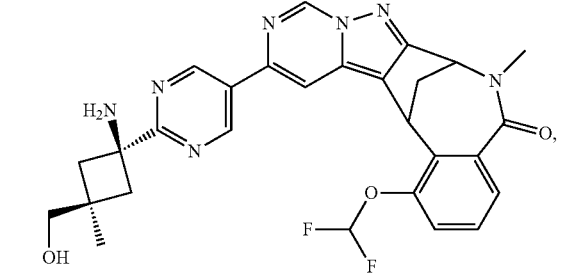
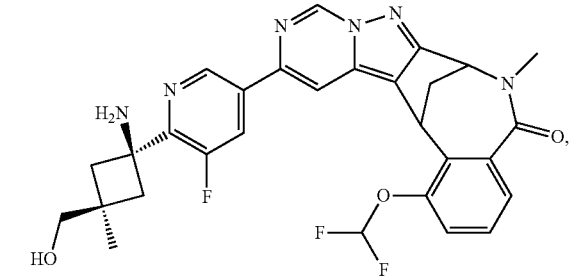

267
-continued
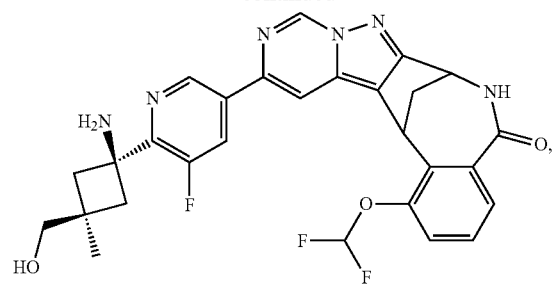
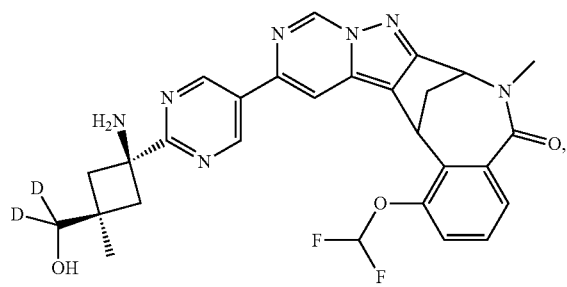
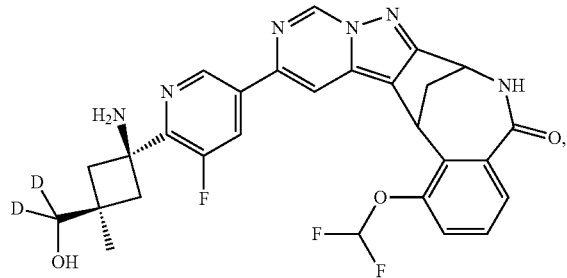
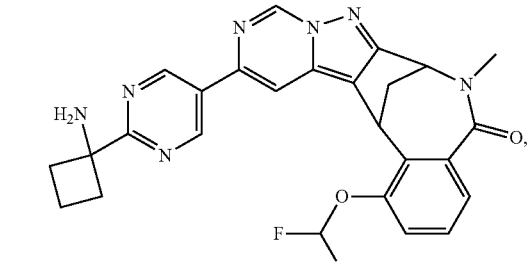
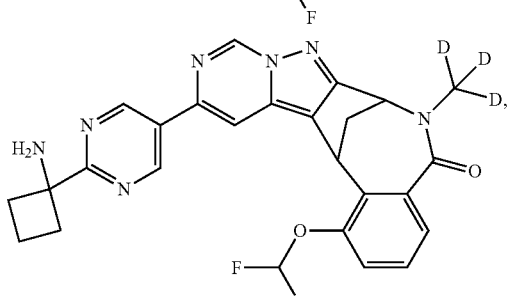
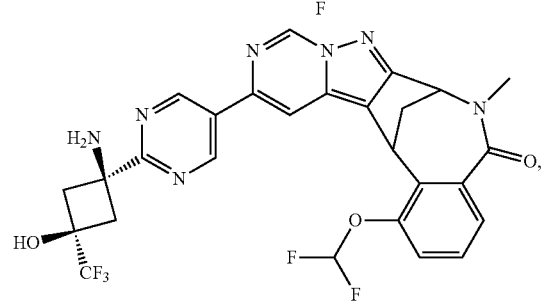
268
-continued
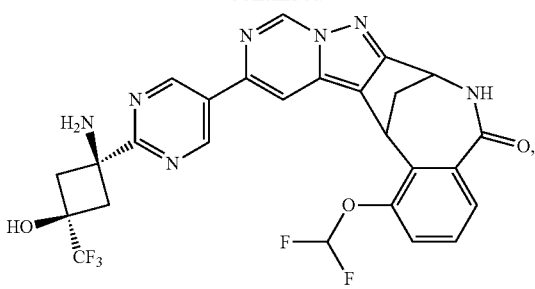
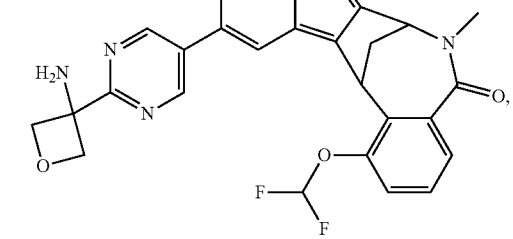
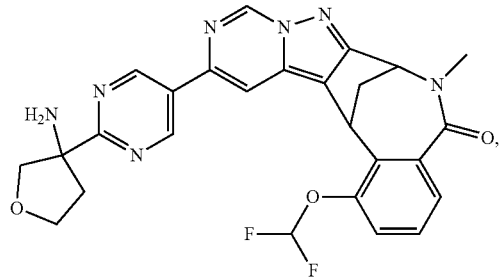
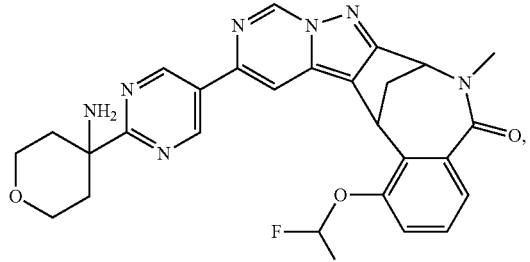
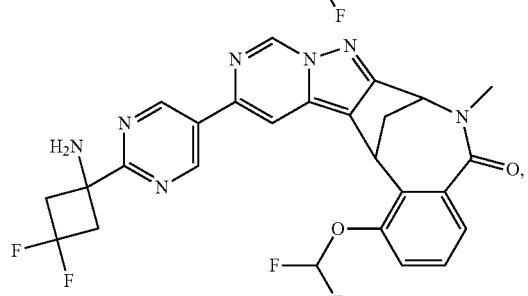
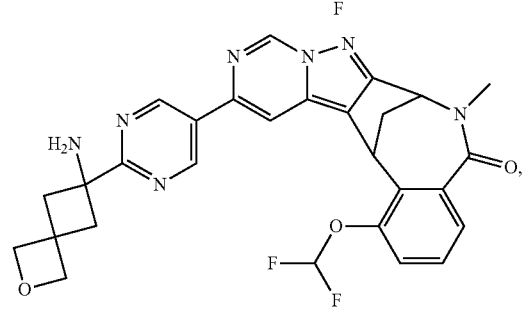

269
-continued
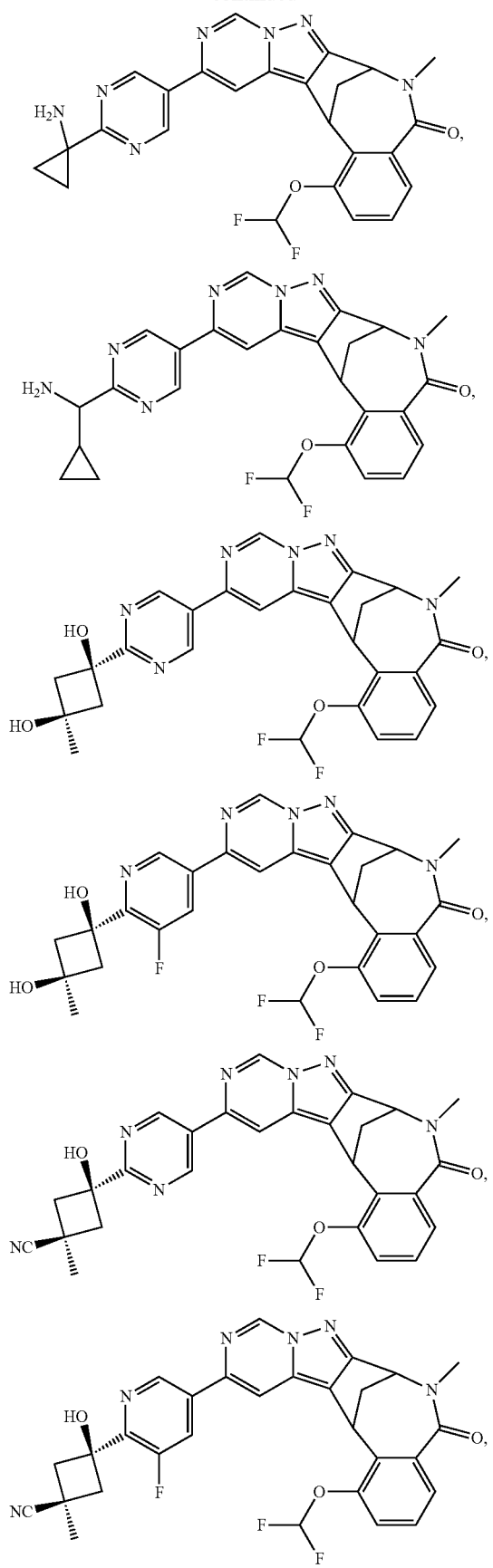
270
-continued
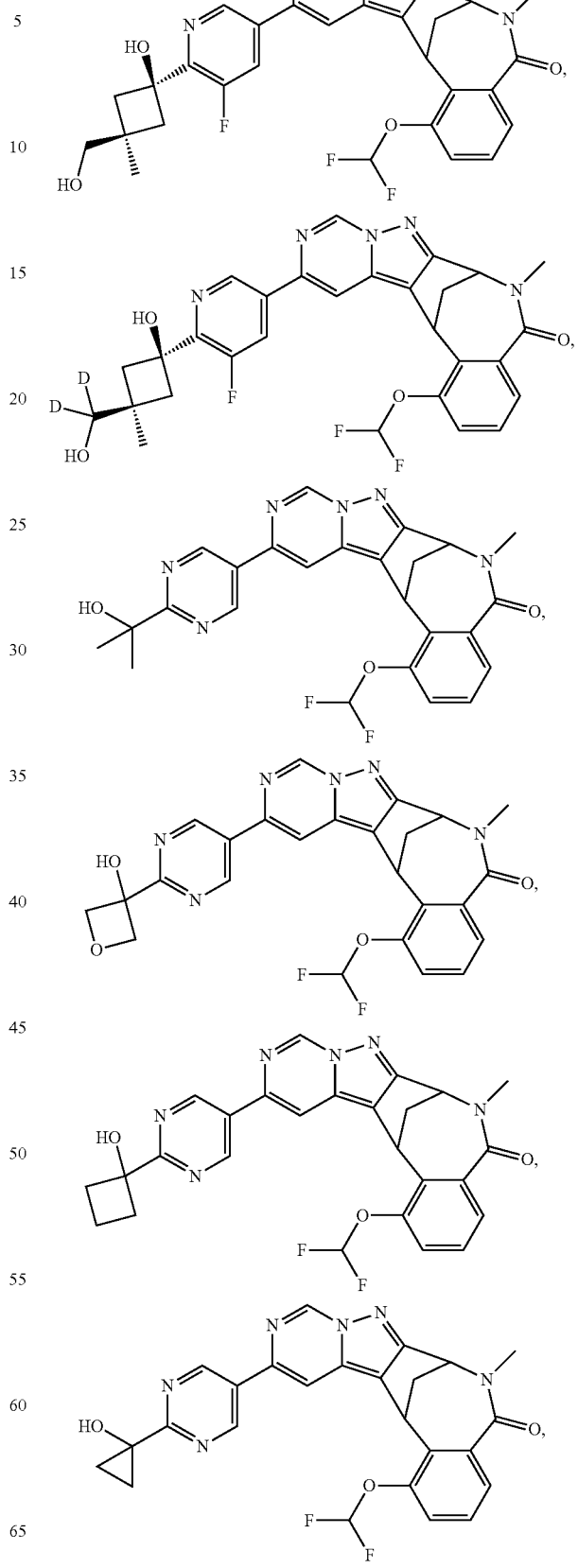

271
-continued
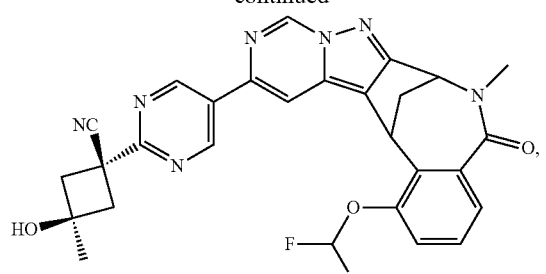
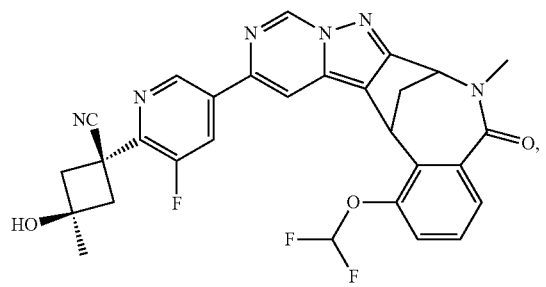
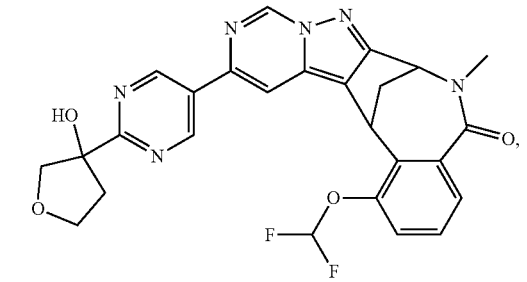
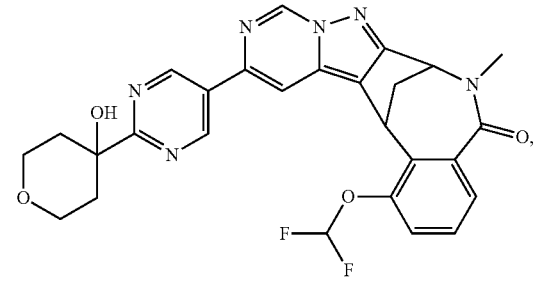
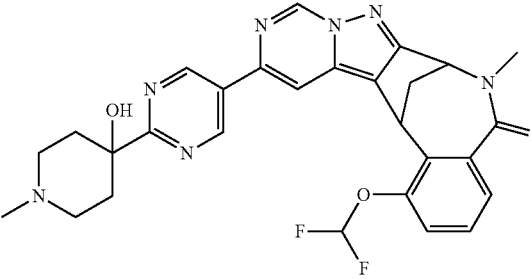
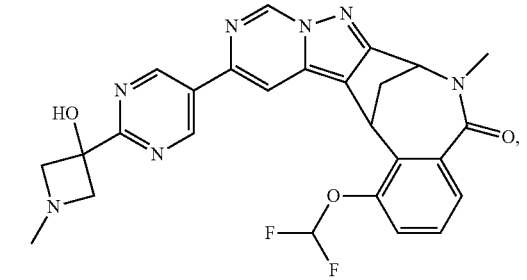
272
-continued
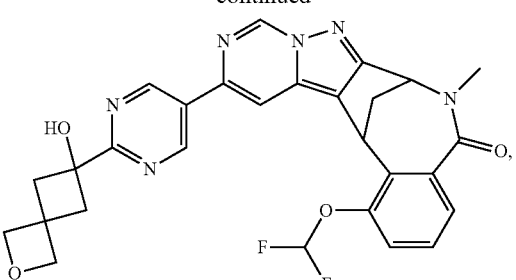
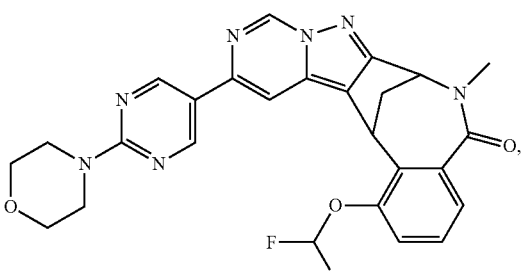
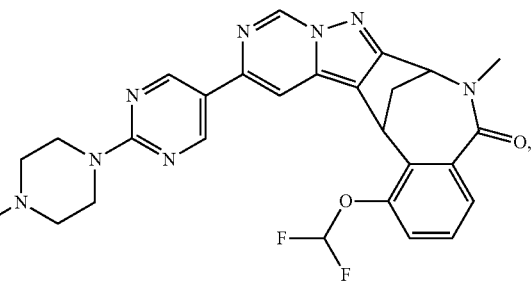
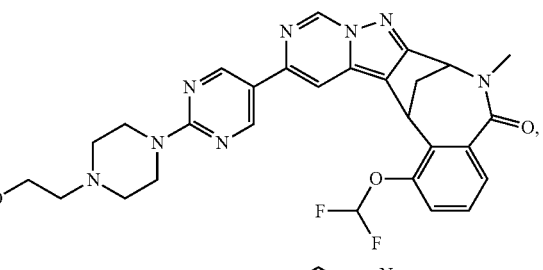
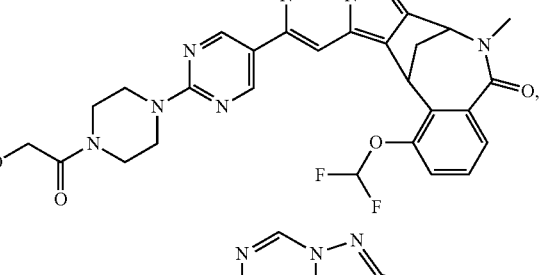
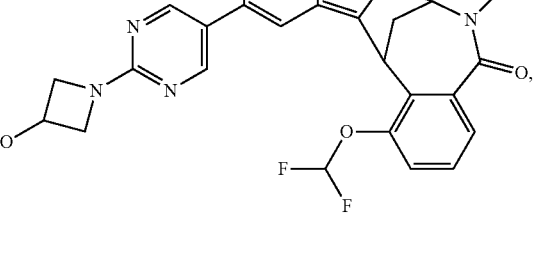

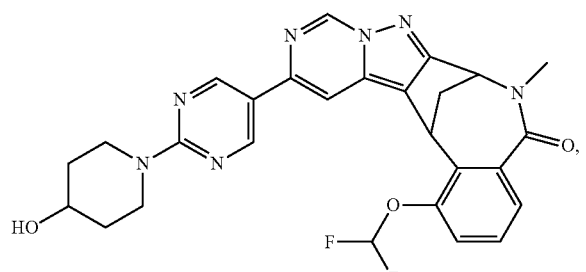
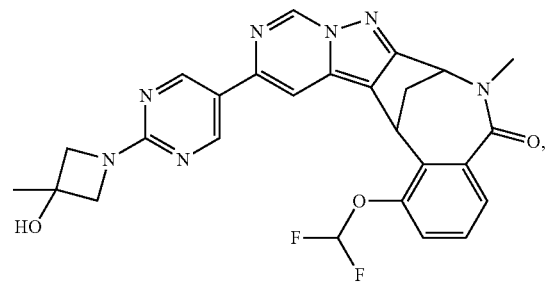
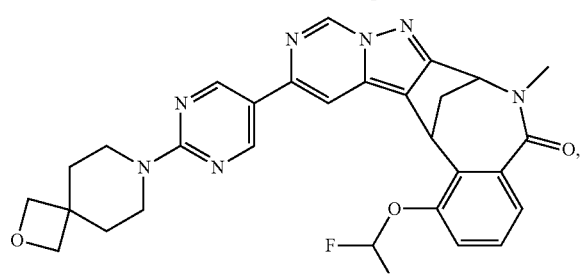
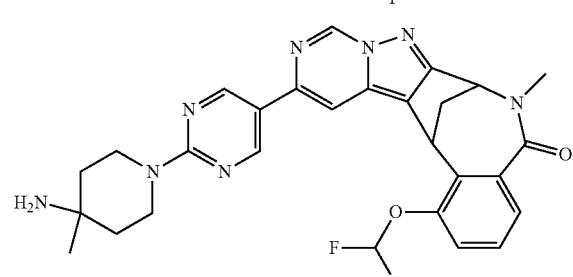
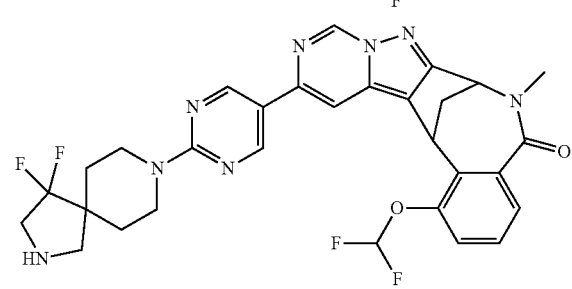
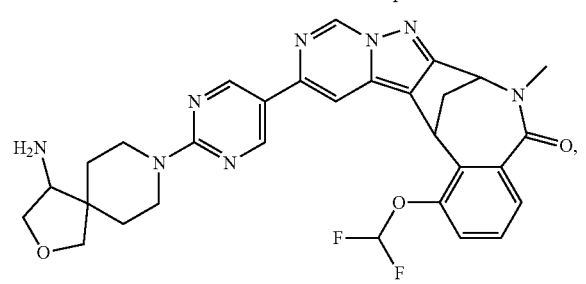
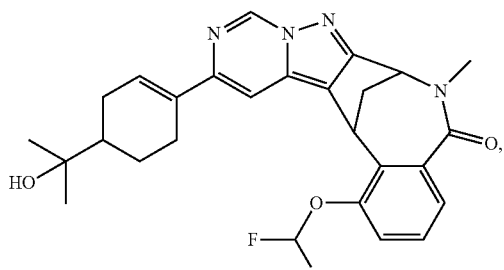
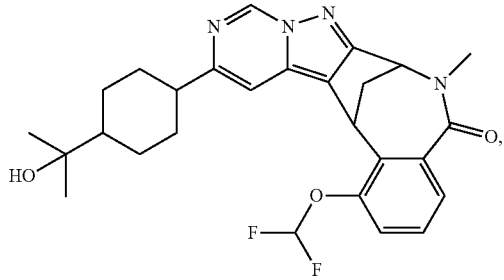
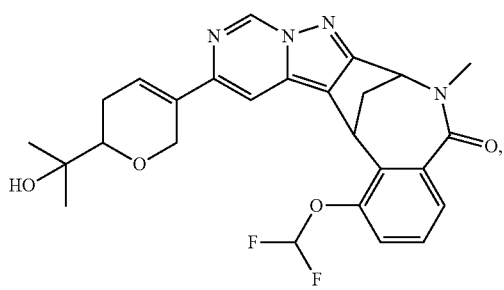
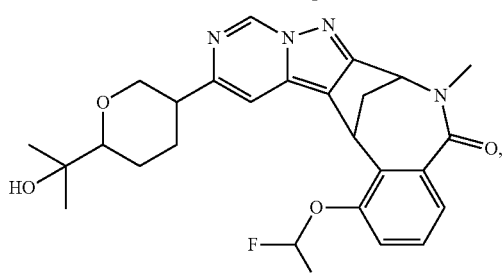
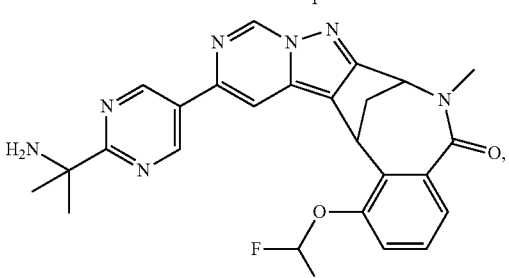
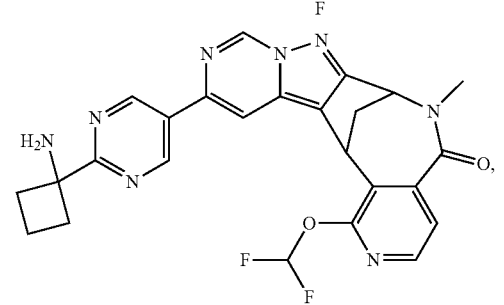

275
-continued
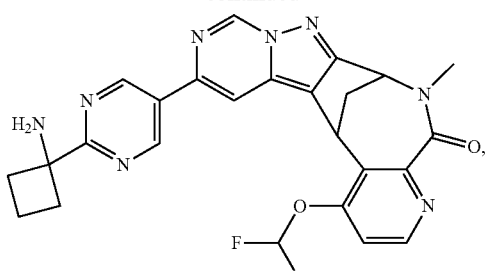
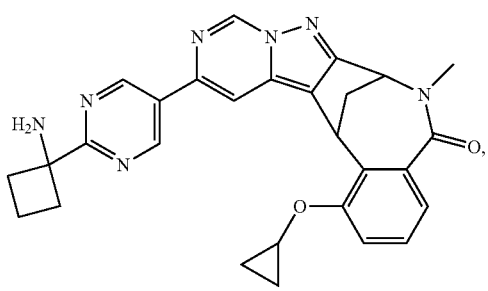
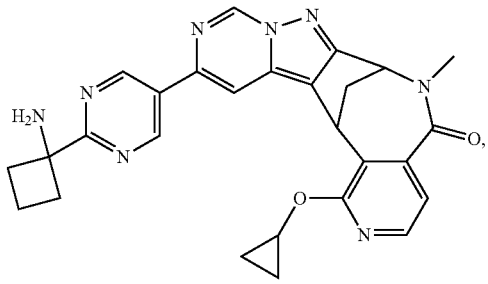
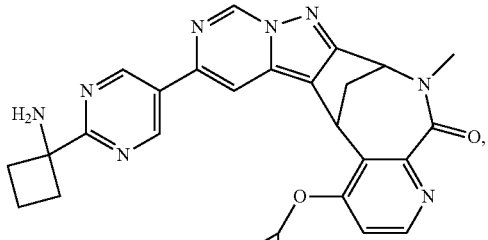
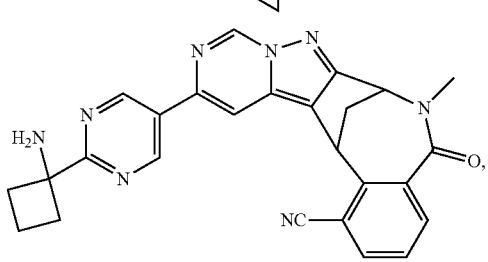
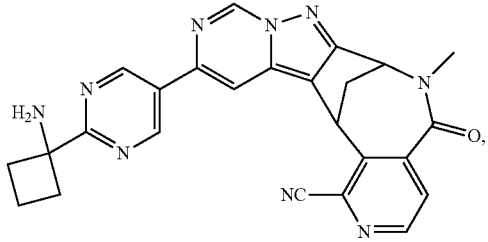
276
-continued
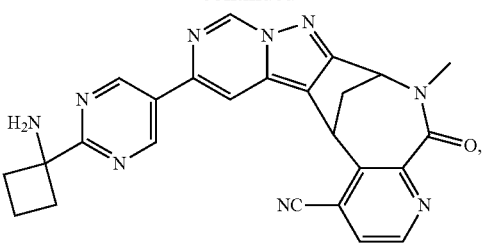
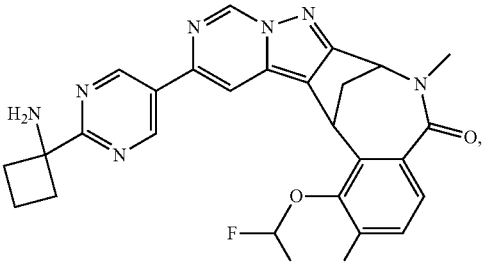
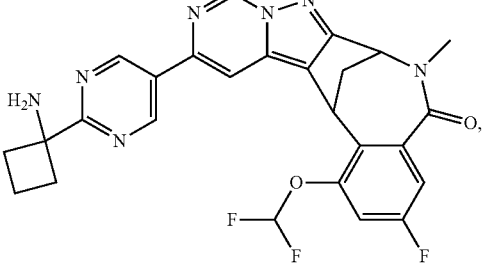
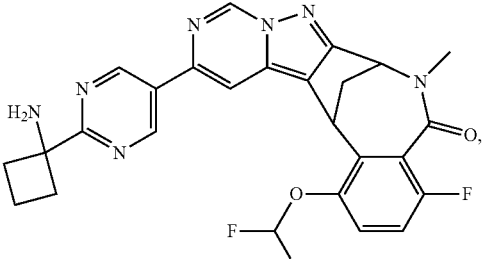
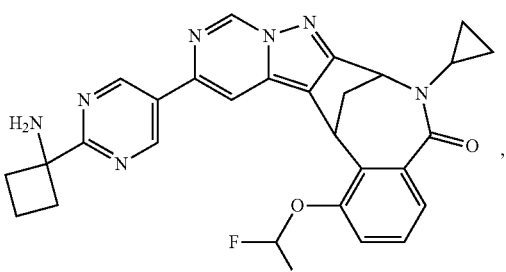
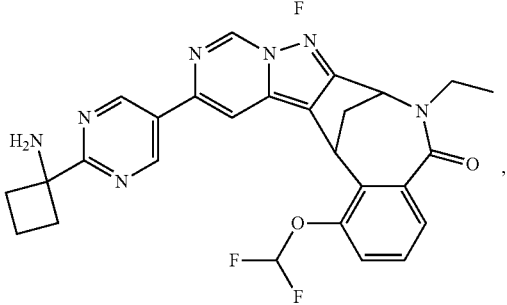

277
-continued
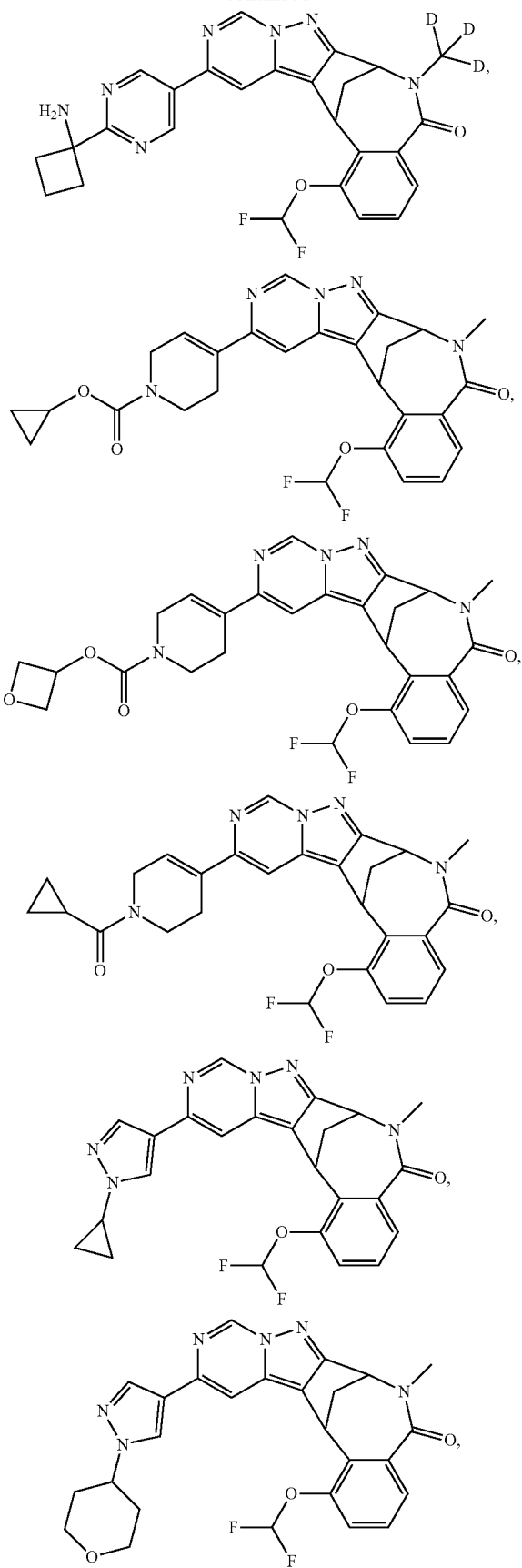
278
-continued
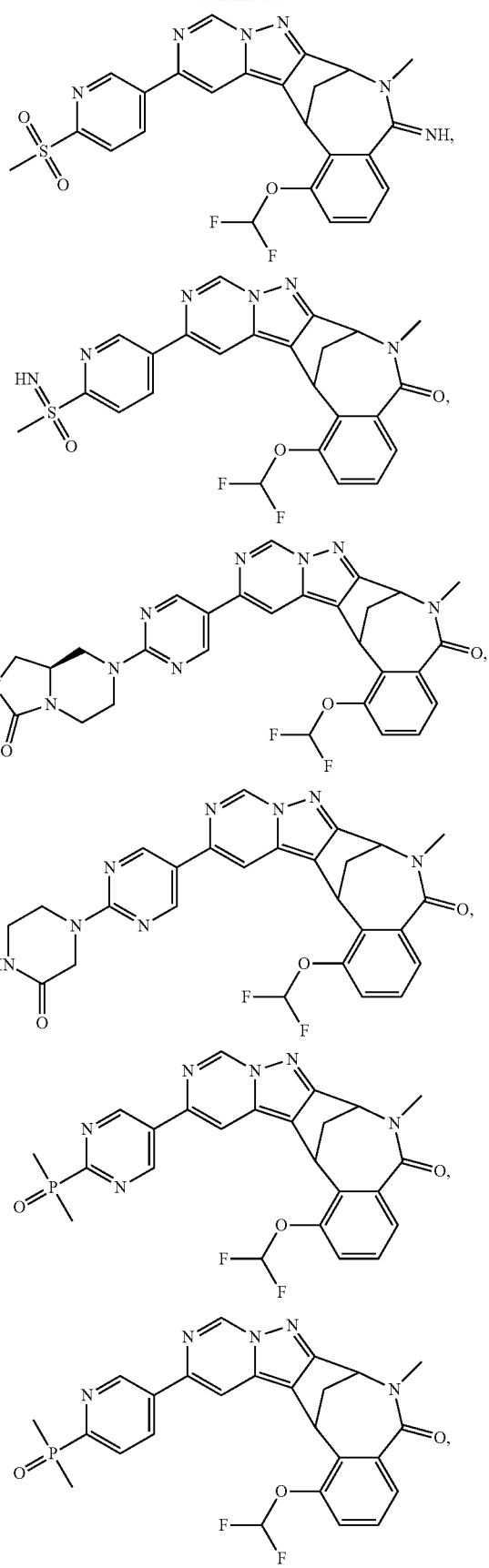

-continued
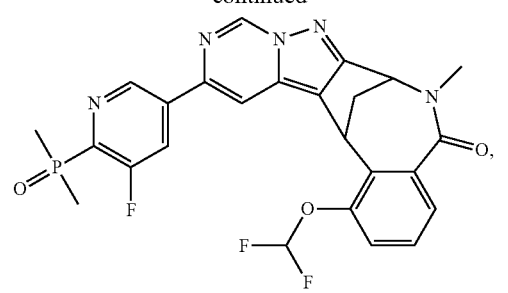
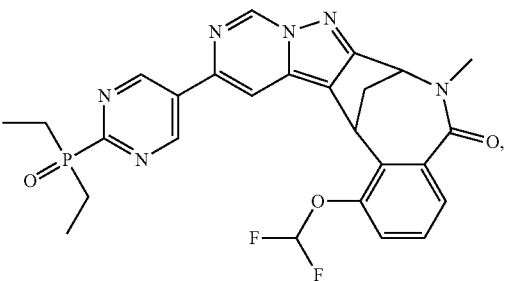
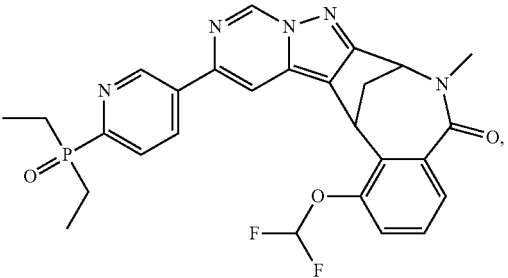
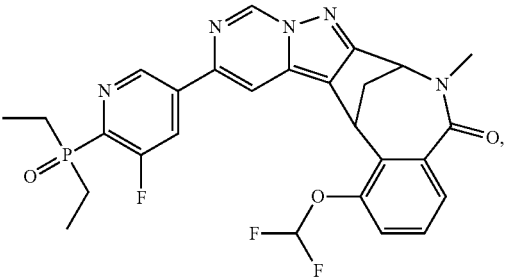
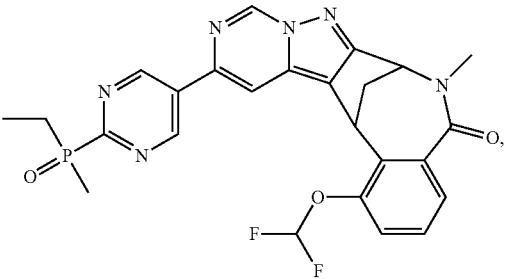
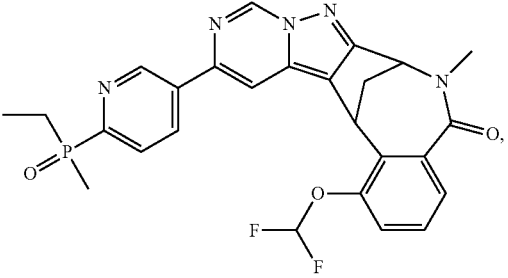
-continued
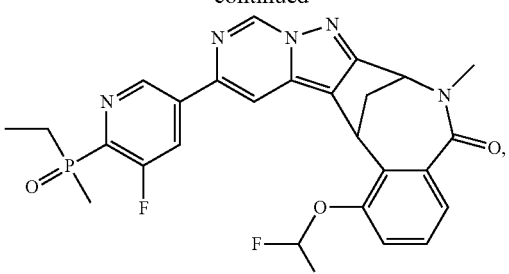
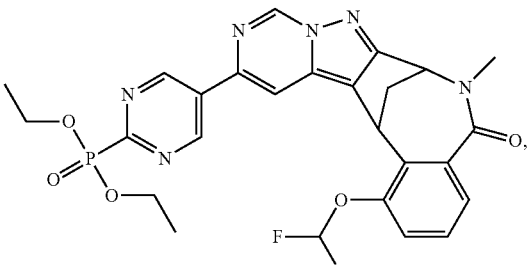
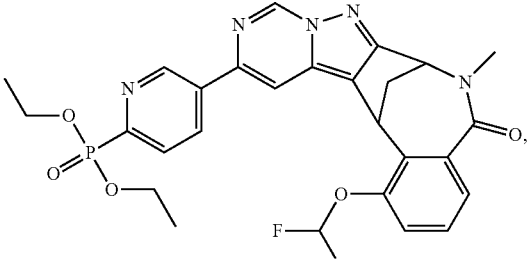
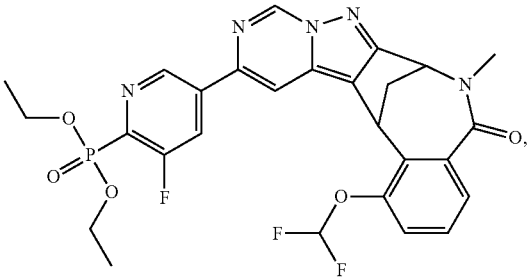
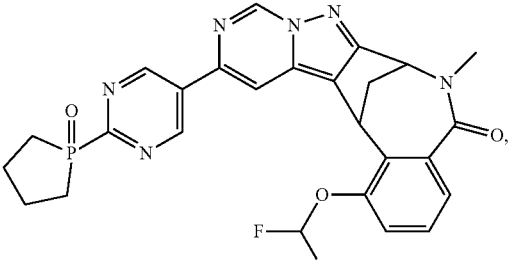
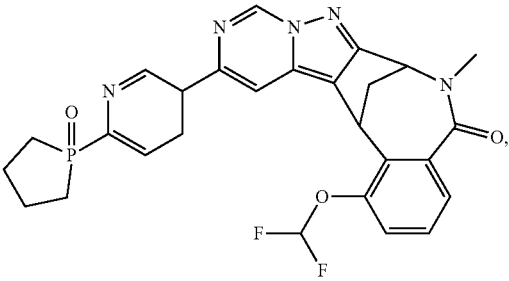

-continued
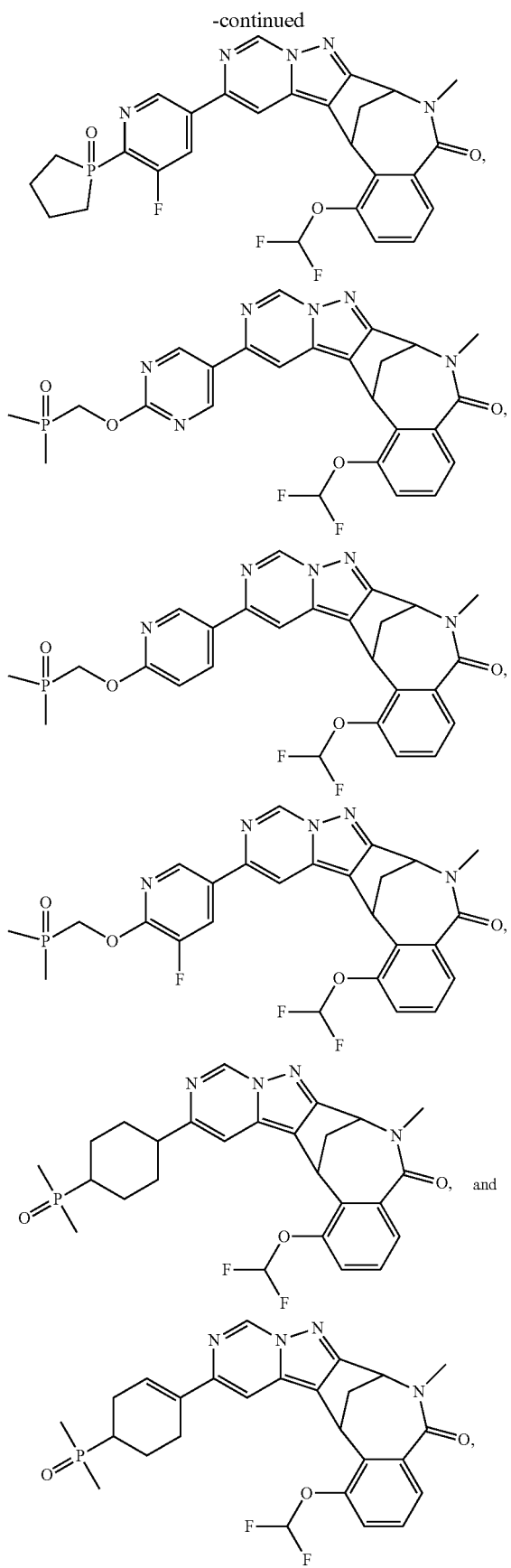
or a pharmaceutically acceptable salt, solvate, or stereoisomer thereof.
In some embodiments of the compounds disclosed above,
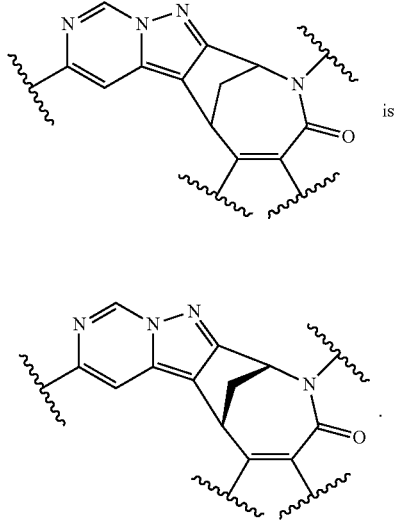
is
In some embodiments, the compound is selected from the group consisting of:
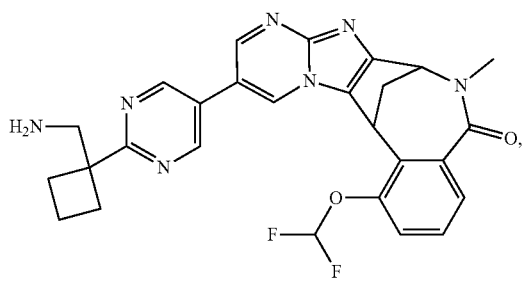
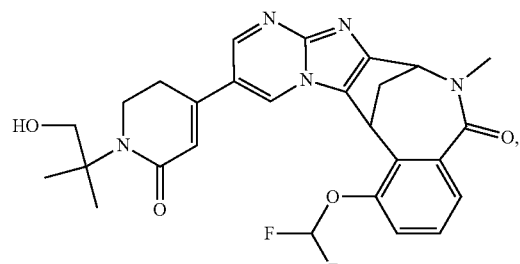
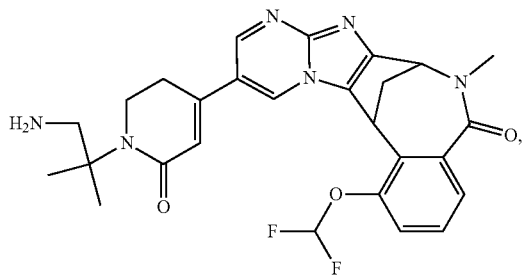

283
-continued
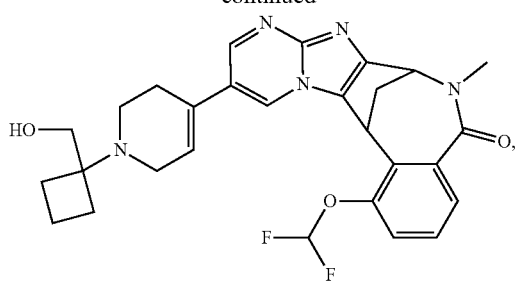
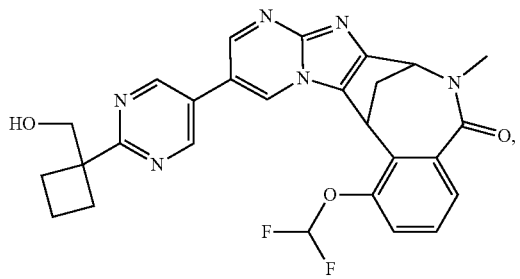
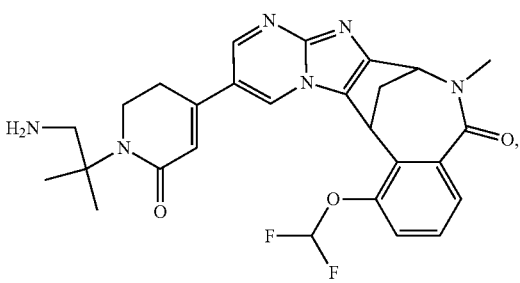
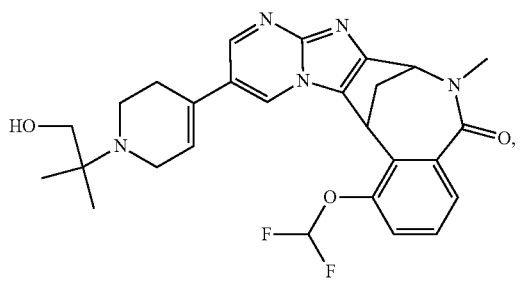
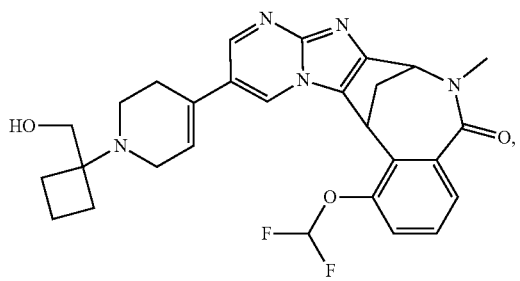
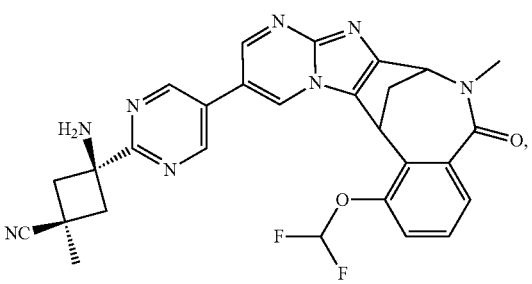
284
-continued
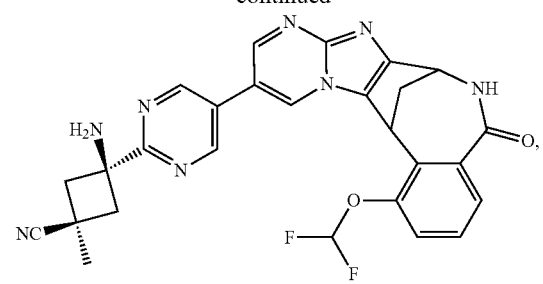
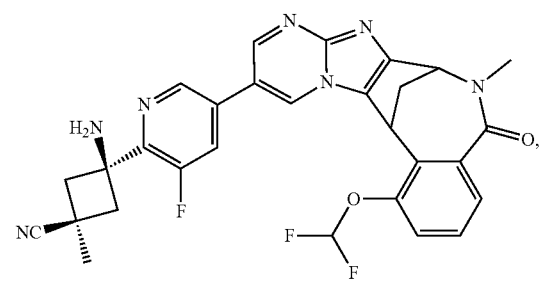
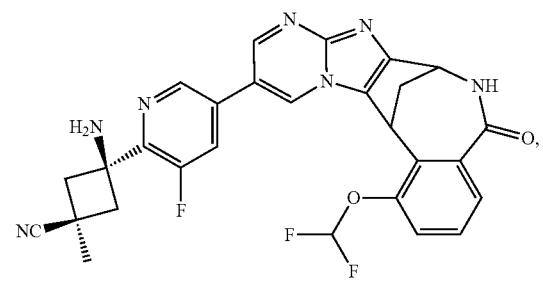
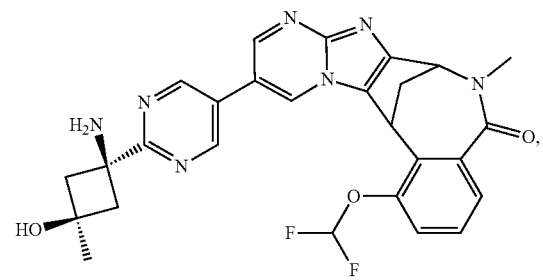
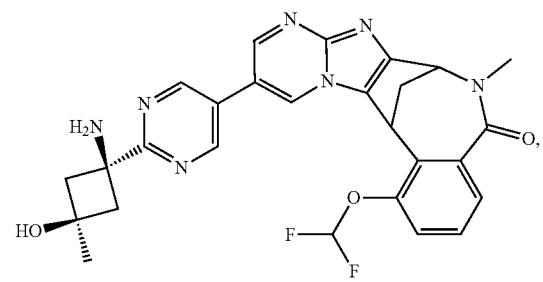
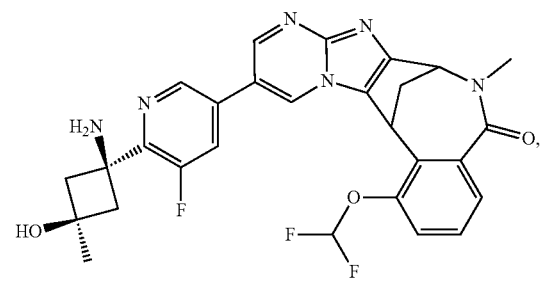

-continued
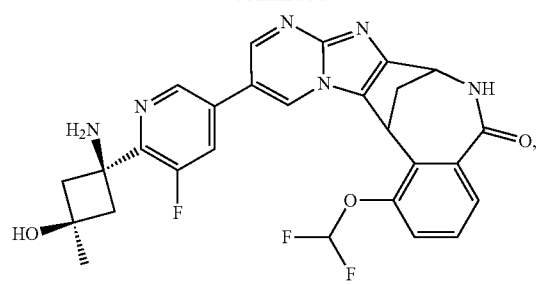
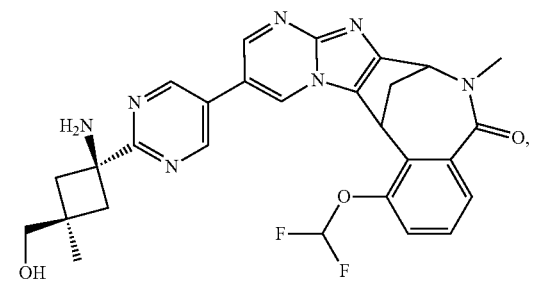
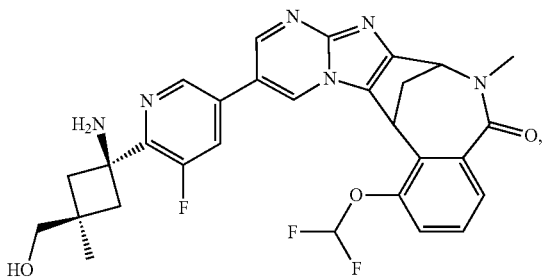
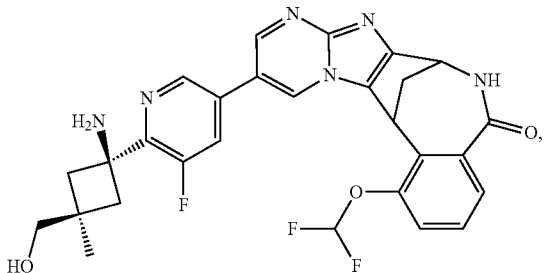
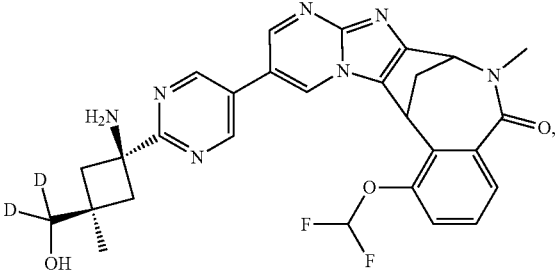
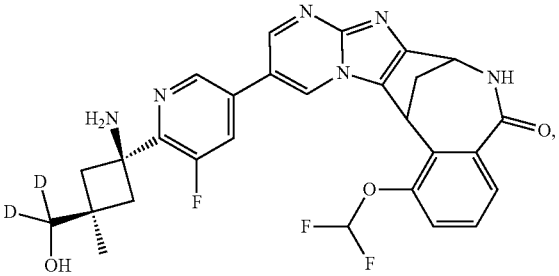
-continued
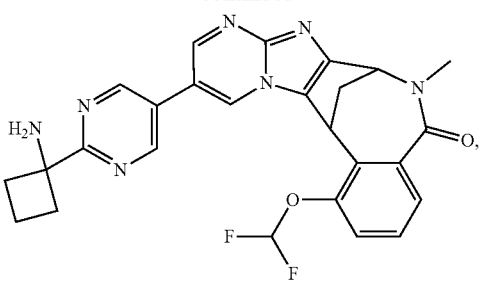
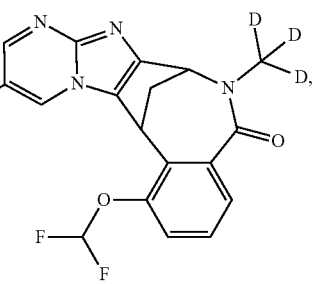
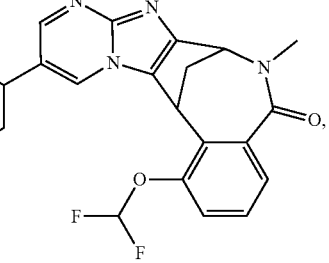
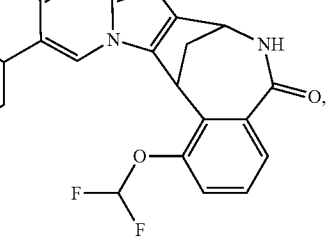
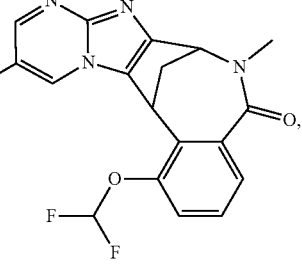
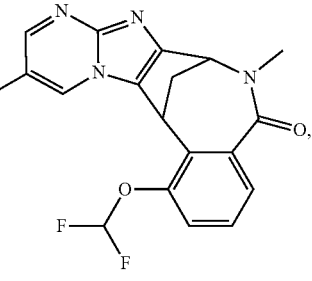

287
-continued
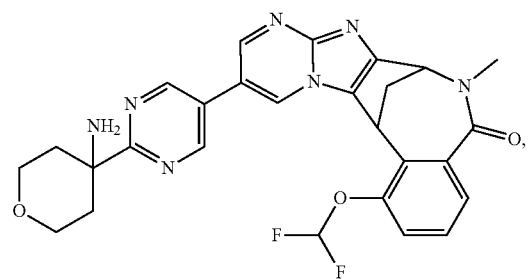
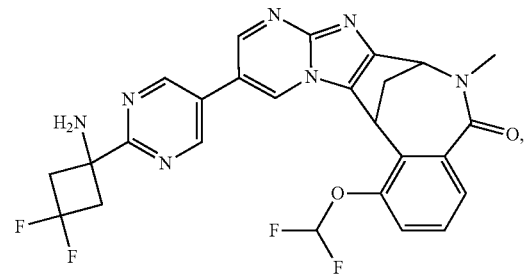
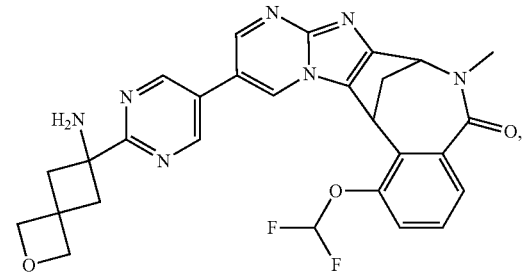
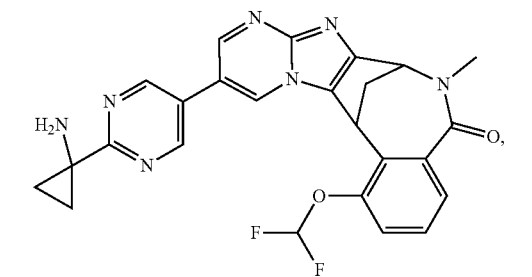
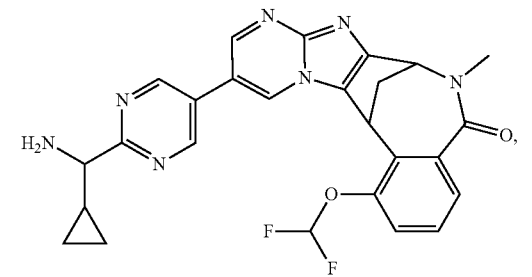
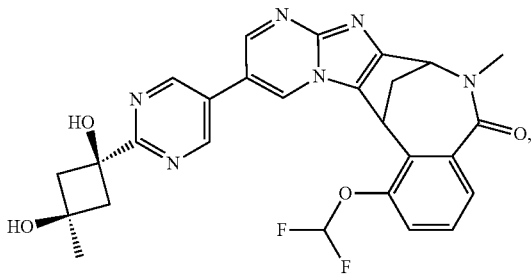
288
-continued
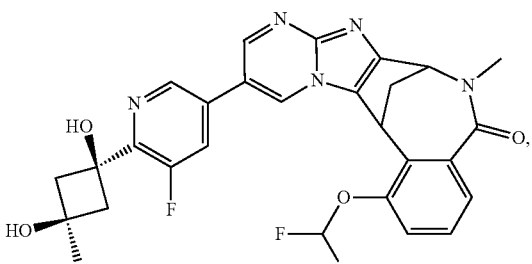
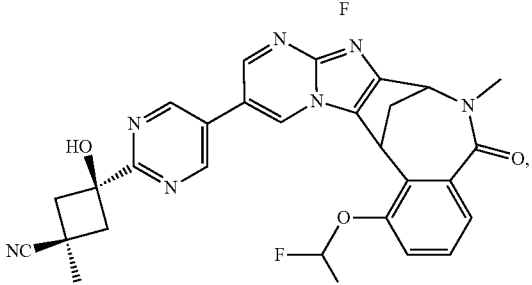
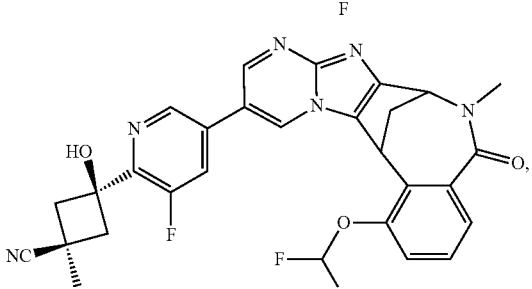
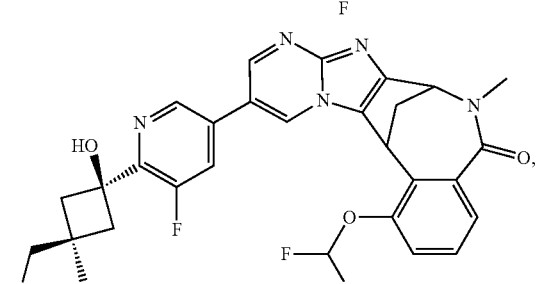
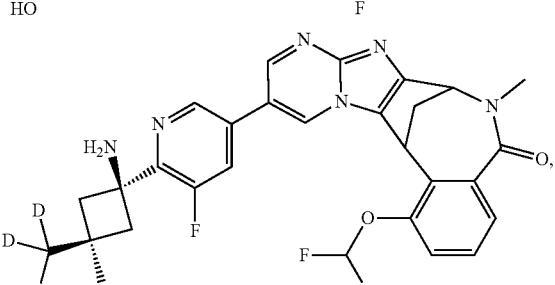
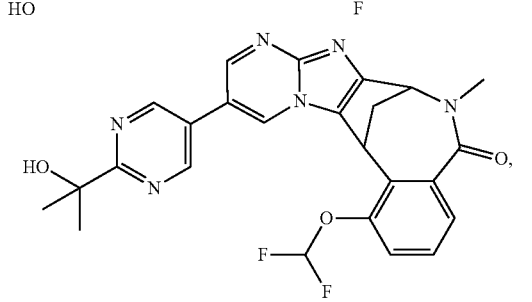

289
-continued
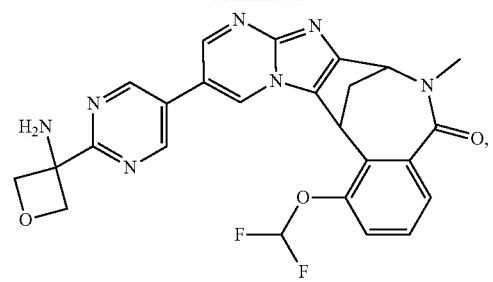
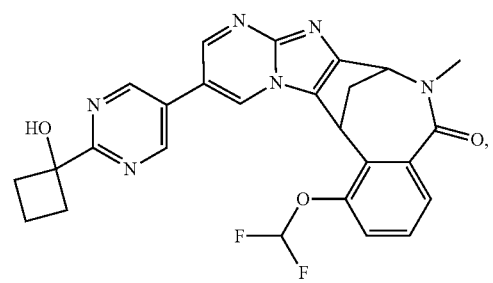
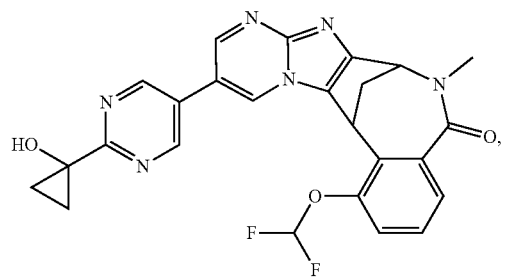
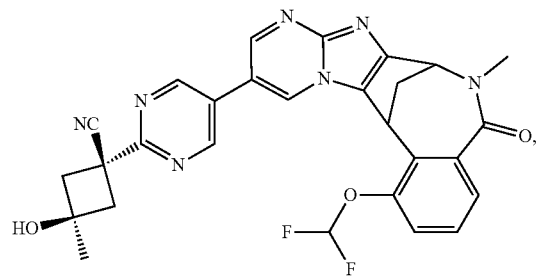
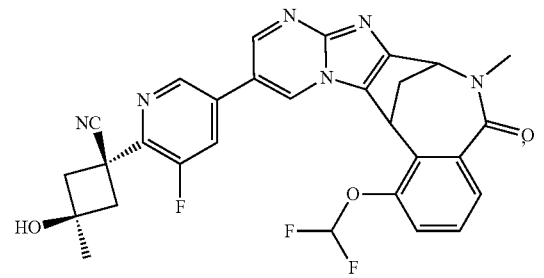
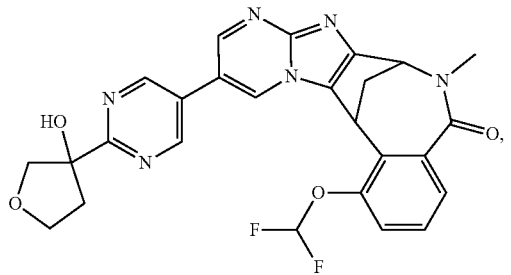
290
-continued
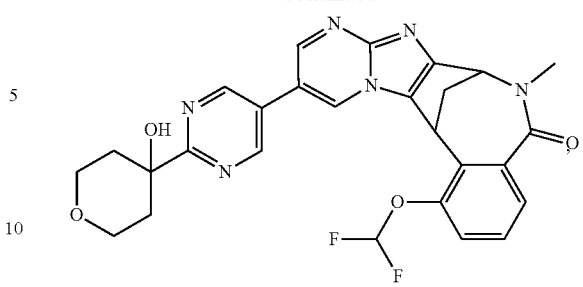
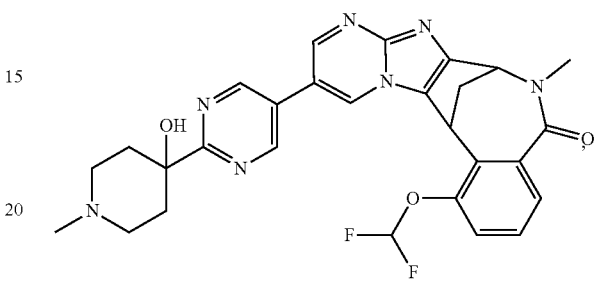
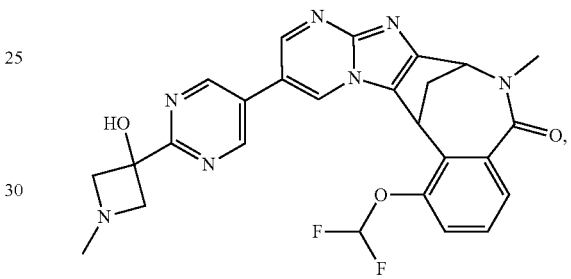
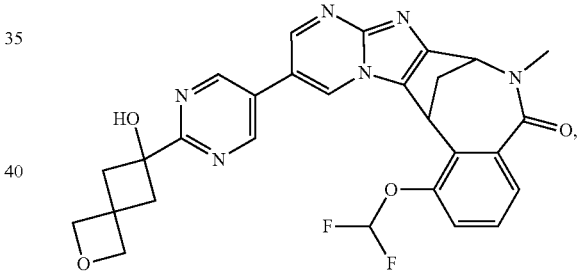
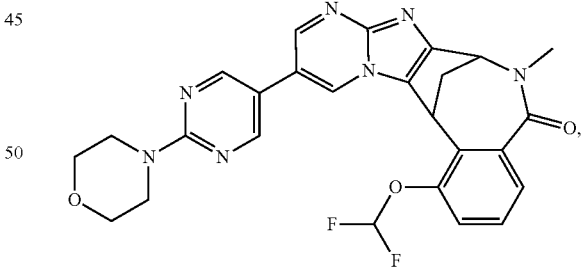
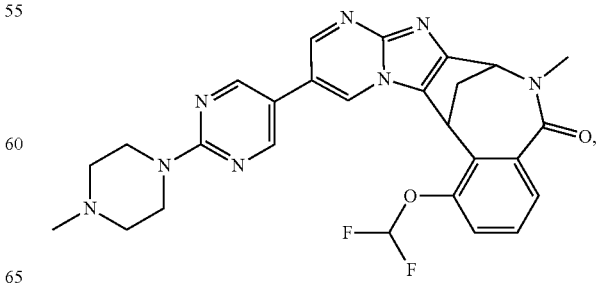

291
-continued
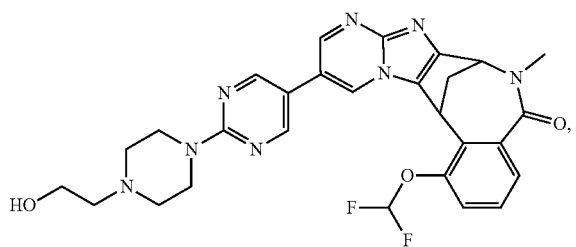
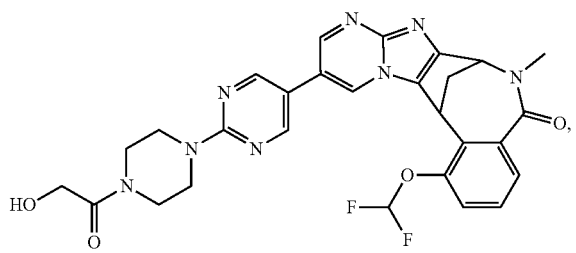
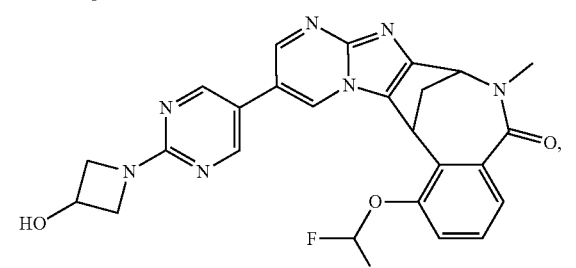
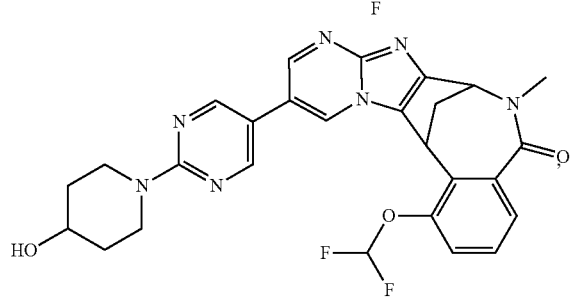
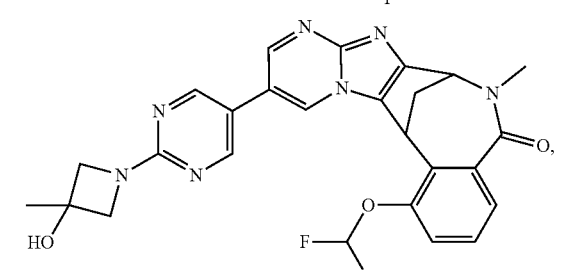
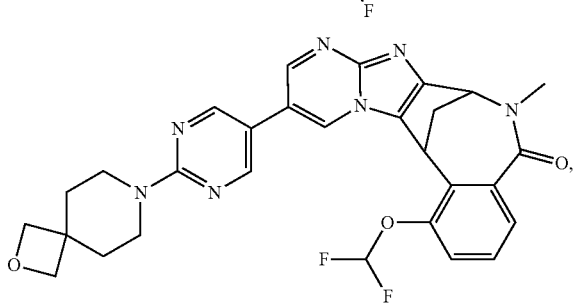
292
-continued
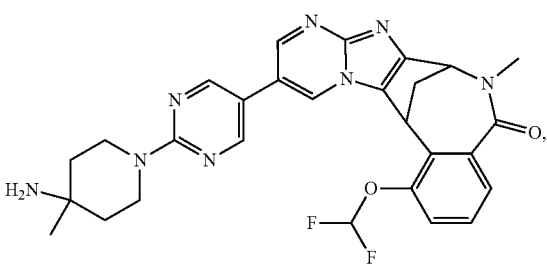
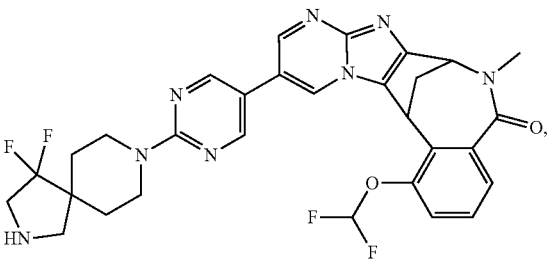
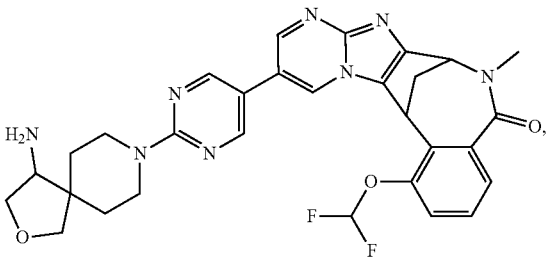
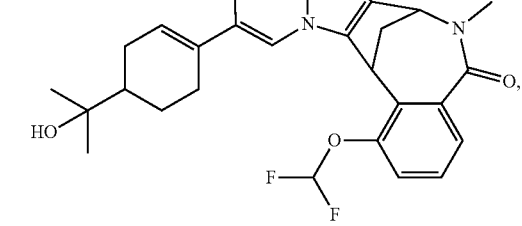
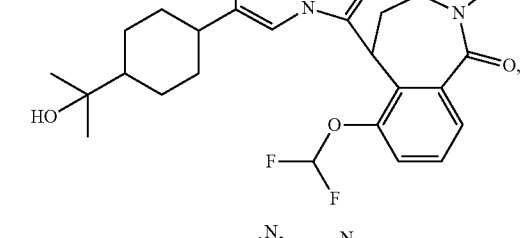
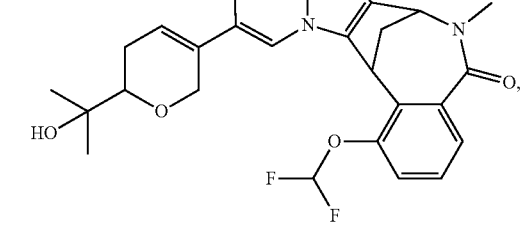

-continued
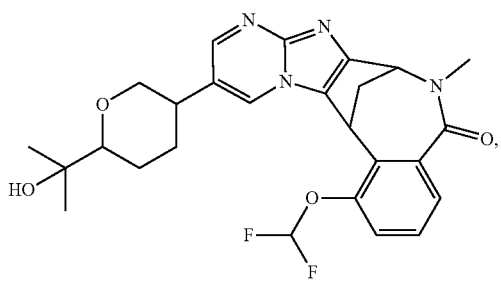
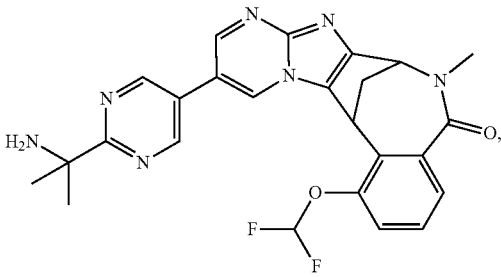
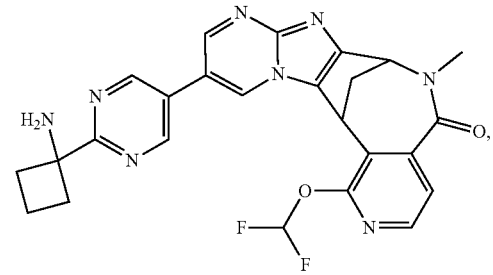
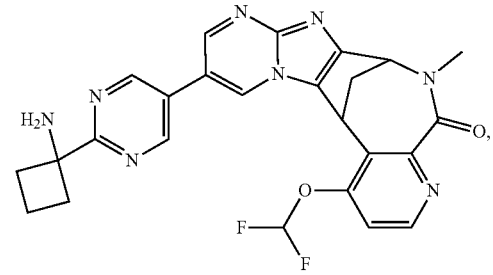
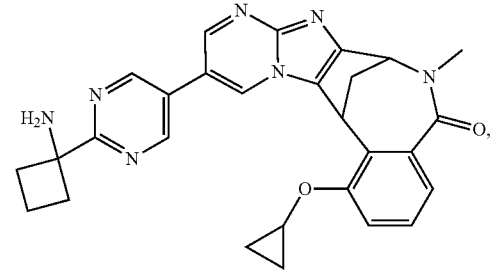
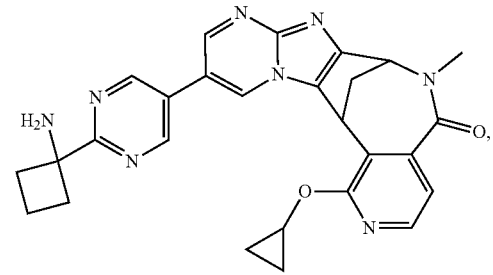
-continued
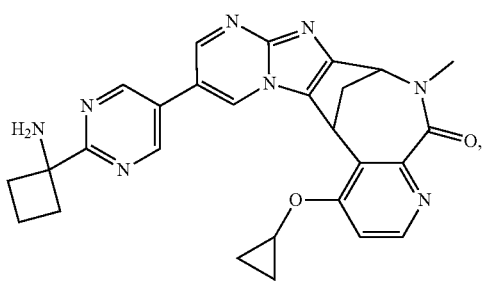
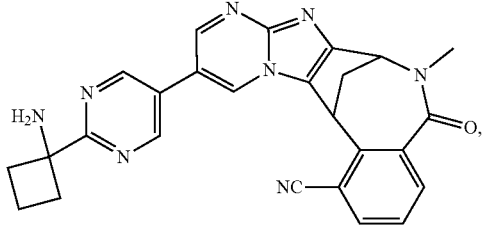
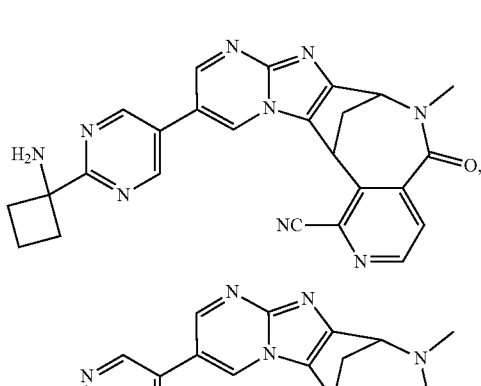
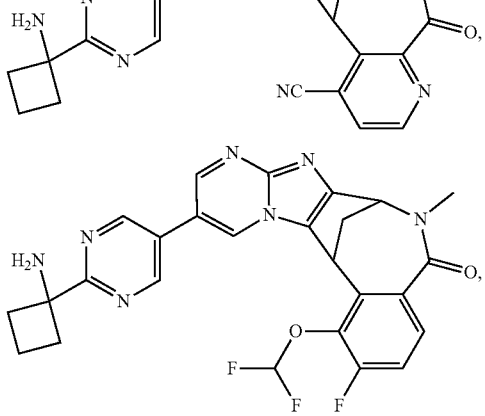
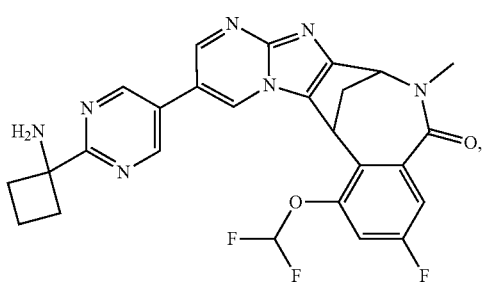

295
-continued
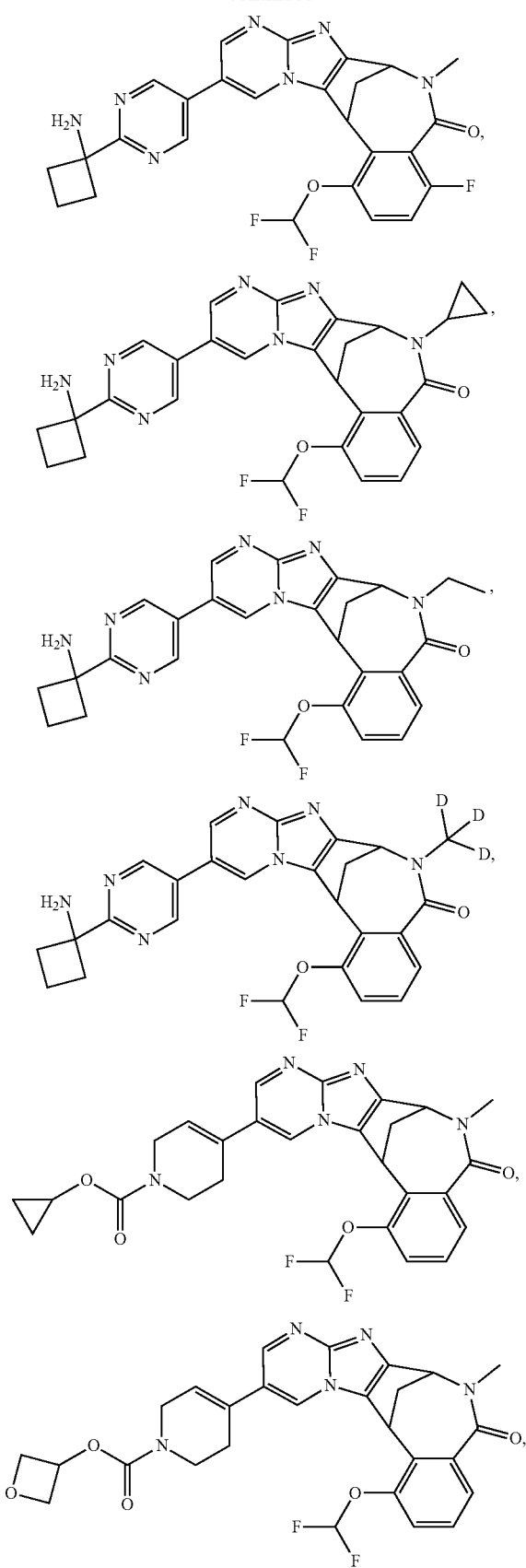
296
-continued
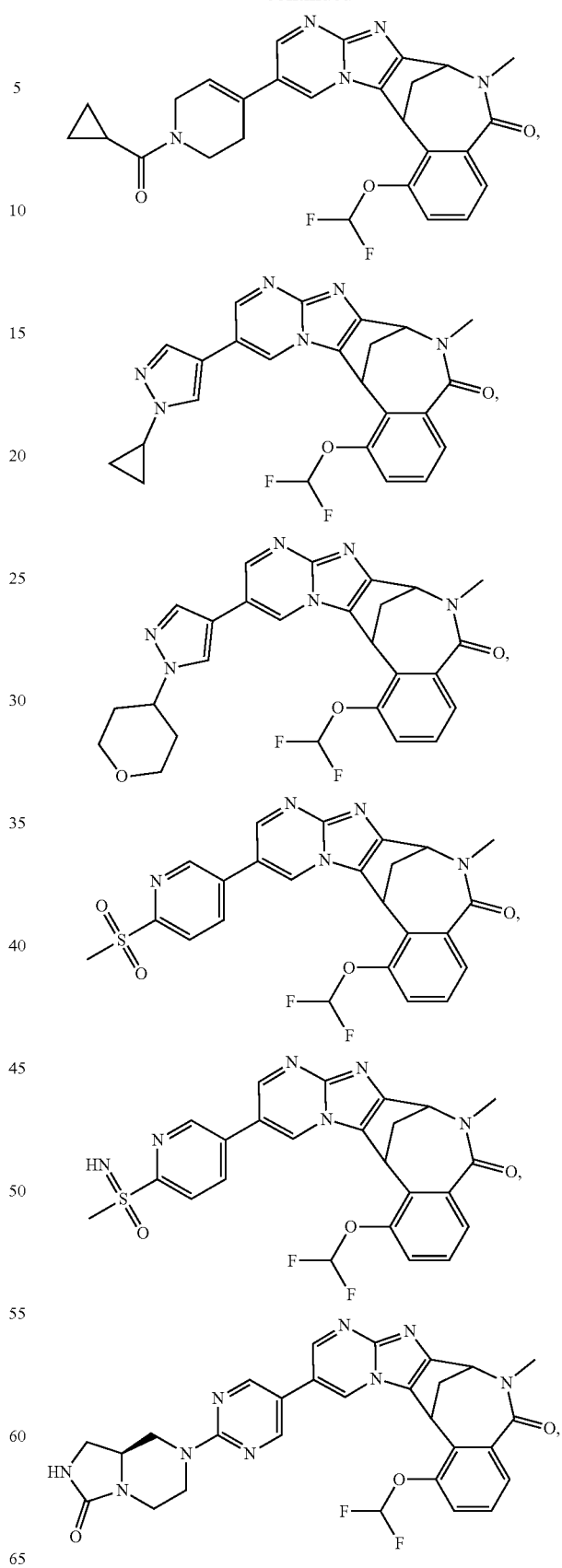

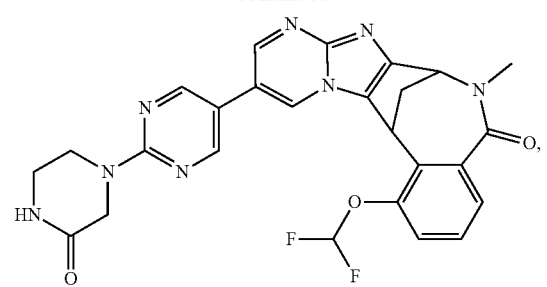
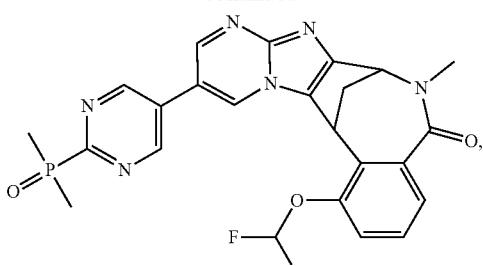
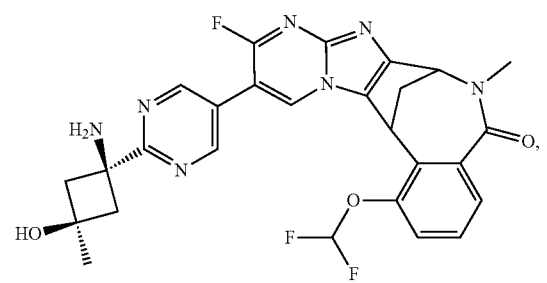
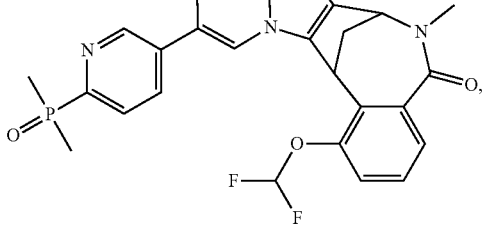
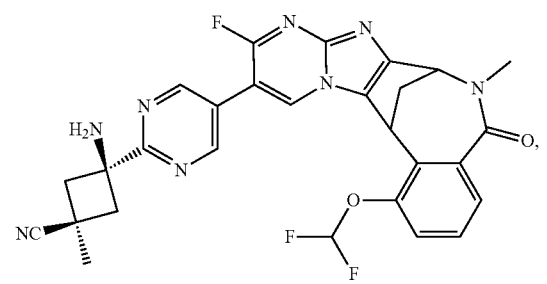
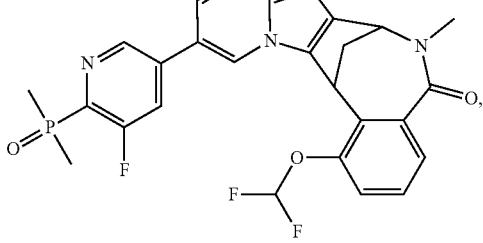
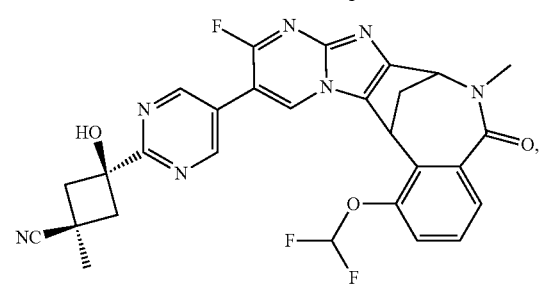
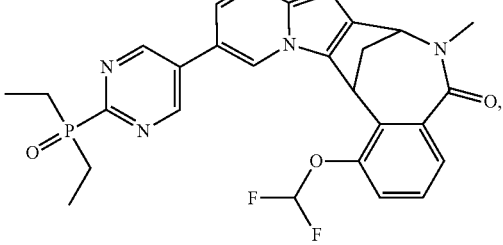
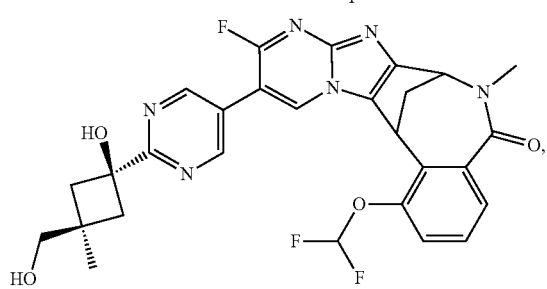
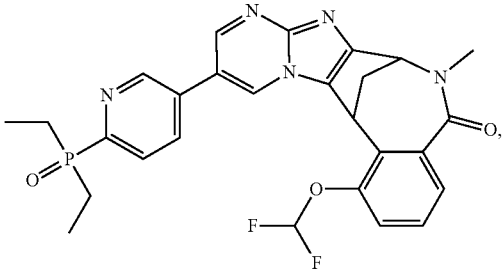
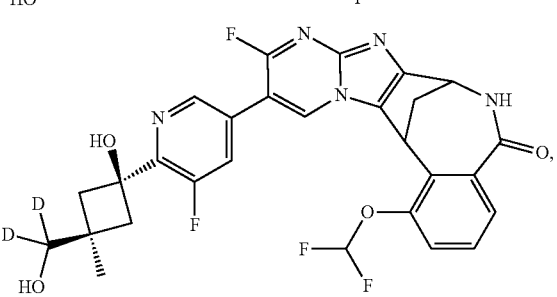
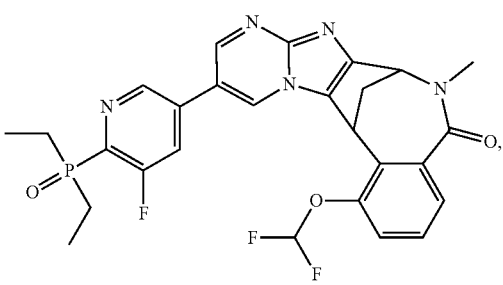

299
-continued
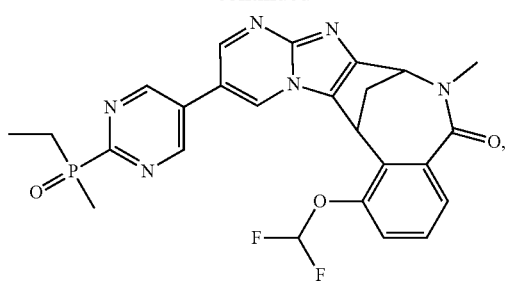
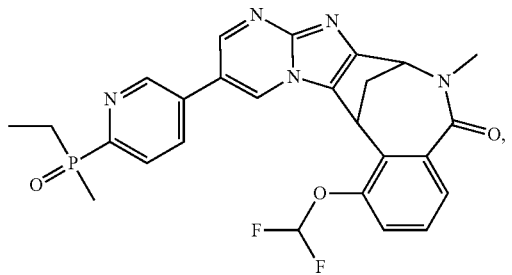
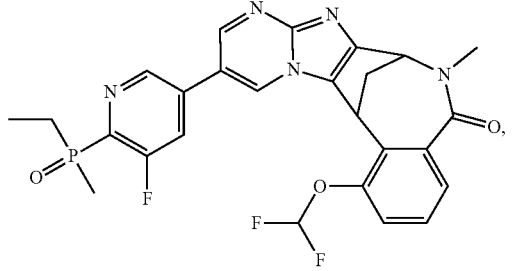
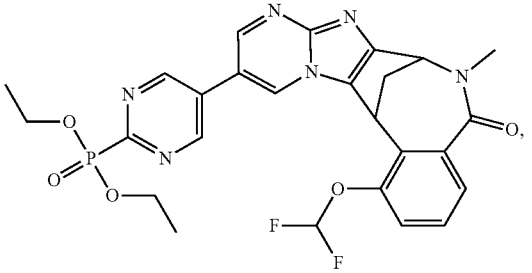
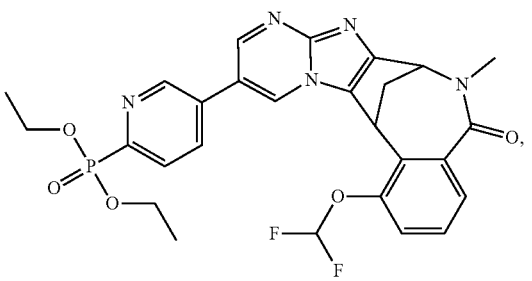
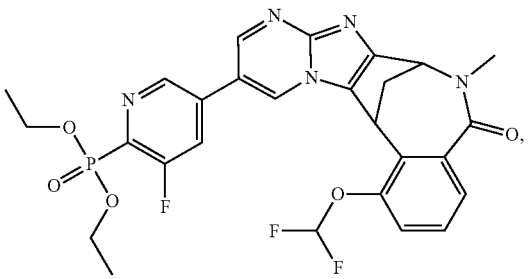
300
-continued
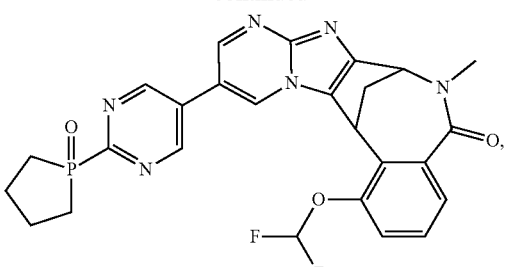
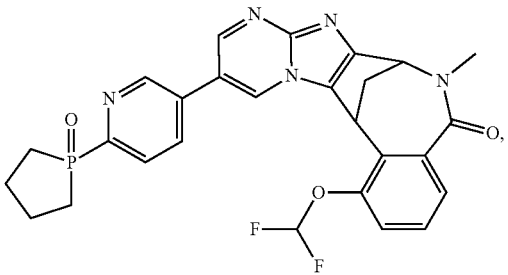
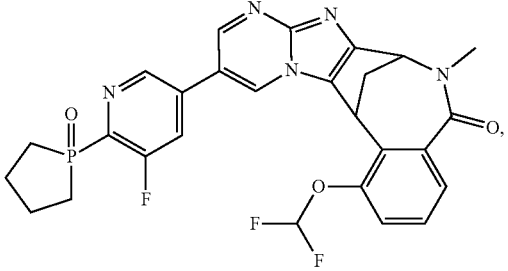
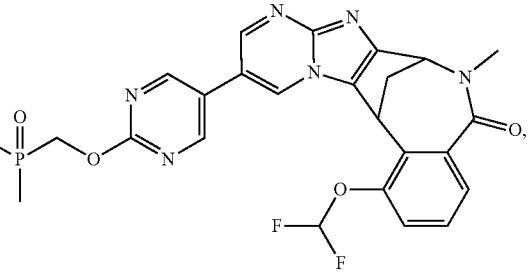
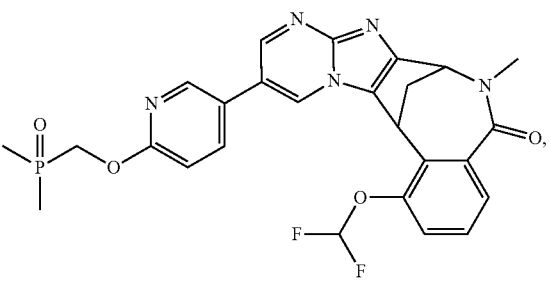
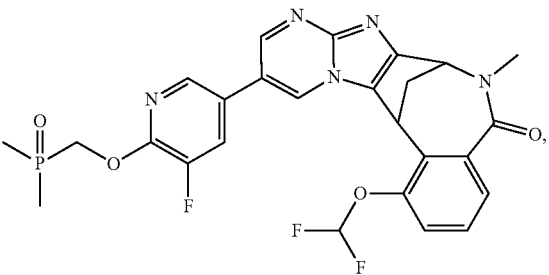

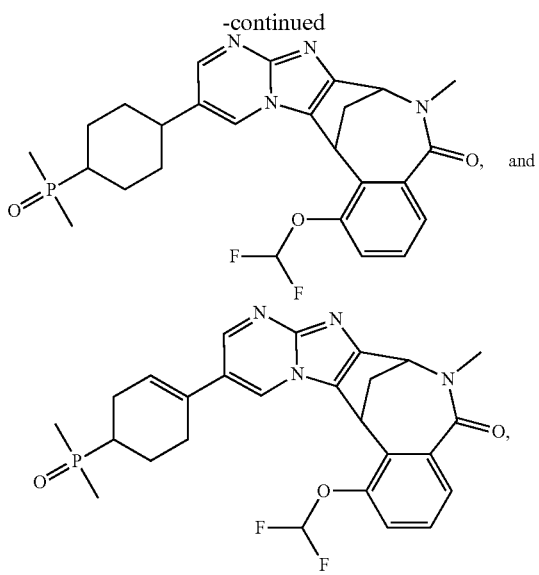

or a pharmaceutically acceptable salt, solvate, or stereoisomer thereof.

In some embodiments of the compounds disclosed above,

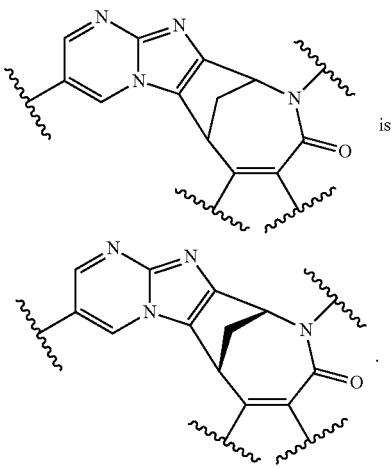

is

Further Forms of Compounds Disclosed Herein
Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center independently exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}$H and $^{14}$C are incorporated, are useful in drug and/or substrate tissue distribution assays. Tritiated, i.e., $^{3}$H and carbon-14, i.e., $^{14}$C, isotopes are particularly preferred for their ease of preparation and detectability. Further, substitution with heavy isotopes such as deuterium, i.e., $^{2}$H, produces certain therapeutic advantages resulting from greater metabolic stability, for example increased in vivo half-life or reduced dosage requirements. In some embodiments, one or more hydrogen in a compound disclosed herein has been replaced by a deuterium atom. In some embodiments, one or more alkyl substituents in a compound disclosed herein has been replaced by a deuteroalkyl substituents. In some embodiments, —CH$_3$ is -CD$_3$.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, but not limited to, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, gluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_1$-$C_4$ alkyl$)_4$ hydroxide, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Method of Treatment

Disclosed herein are methods of treating diseases or disorders in a subject in need thereof, the method comprising administering a compound disclosed herein, or a pharmaceutically acceptable salt, solvate, or stereoisomer thereof. In some embodiments, the diseases or disorders include autoimmune and Inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders, and organ-specific autoimmune disorders. Systemic autoimmune disorders include systemic lupus ery thematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anemia of chronic disease (ACD). Still's disease (juvenile and/or adult onset), Behcet's disease and Sjogren's syndrome Autoimmune endocrine disorders include thyroiditis Organ-specific autoimmune disorders include Addison's disease, hemolytic or pernicious anemia acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenia purpura inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis). Takayasu arteritis, hidradenitis suppurativa pyoderma gangrenosum, sarcoidosis, polymyalgia rheumatic and axial spondylarthrites.

Neurological and neurodegenerative disorders include Alzheimer's disease, Parkinson's disease. Huntington's disease, ischemia, stroke, amyotrophic lateral sclerosis, spinal cord injury, bead trauma, seizures, and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNF alpha function may also be of use in the treatment of myocardial infarction (see J. J. Wu et al. JAMA, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy, and retinopathy of prematurity), macular oedema (including diabetic macular oedema), age-related macular degeneration (ARMD), vascularization (including corneal vascularization and neovascularization), retinal vein occlusion, and various forms of uveitis (including iritis) and keratitis.

Oncological disorders, which may be acute or chronic, include proliferative disorders, especially cancer, and cancer-associated complications (including skeletal complications, cachexia, and anemia). Particular categories of cancer include hematological malignancy (including leukemia and lymphoma) and non-hematological malignancy (including solid tumor cancer, sarcoma meningioma, glioblastoma multiforme, neuroblastoma, melanoma, gastric carcinoma, and renal cell carcinoma). Chronic leukemia may be myeloid or lymphoid. Varieties of leukemia include lymphoblastic T cell leukemia, chronic myelogenous leukemia (CML), chronic lymphocytic/lymphoid leukemia (CLL), hairy-cell leukemia, acute lymphoblastic leukemia (ALL), acute myelogenous leukemia (AML), myelodysplastic syndrome, chronic neutrophilic leukemia, acute lymphoblastic T cell leukemia, plasmacytoma, immunoblastic large cell leukemia, mantle cell leukemia, multiple myeloma, acute megakaryoblastic leukemia, acute megakaryocytic leukemia, promyelocytic leukemia, and erythroleukemia. Varieties of lymphoma include malignant lymphoma, Hodgkin's lymphoma, non-Hodgkin's lymphoma, lymphoblastic T cell lymphoma, Burkitt's lymphoma, follicular lymphoma. MALT1 lymphoma, and marginal zone lymphoma. Varieties of non-hematological malignancy include cancer of the prostate, lung, breast, rectum, colon, lymph node, bladder, kidney, pancreas, liver, ovary, uterus, cervix, brain, skin, bone, stomach, and muscle Modulators of TNF alpha function may also be used to increase the safety of the potent anticancer effect of TNF (see F. V. Hauwermeiren et al, J Clin. Invest., 2013, 123, 2590-2603).

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long-acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended-release formulation, or in the form of an intermediate-release formulation. In some embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds disclosed herein may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Combination

Disclosed herein are methods of treating a TNF alpha-mediated disorder or disease using a compound disclosed herein, or a pharmaceutically acceptable salt, solvate, or stereoisomer thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLE

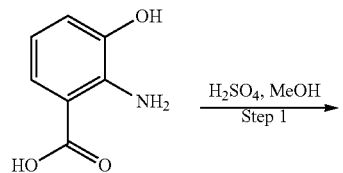

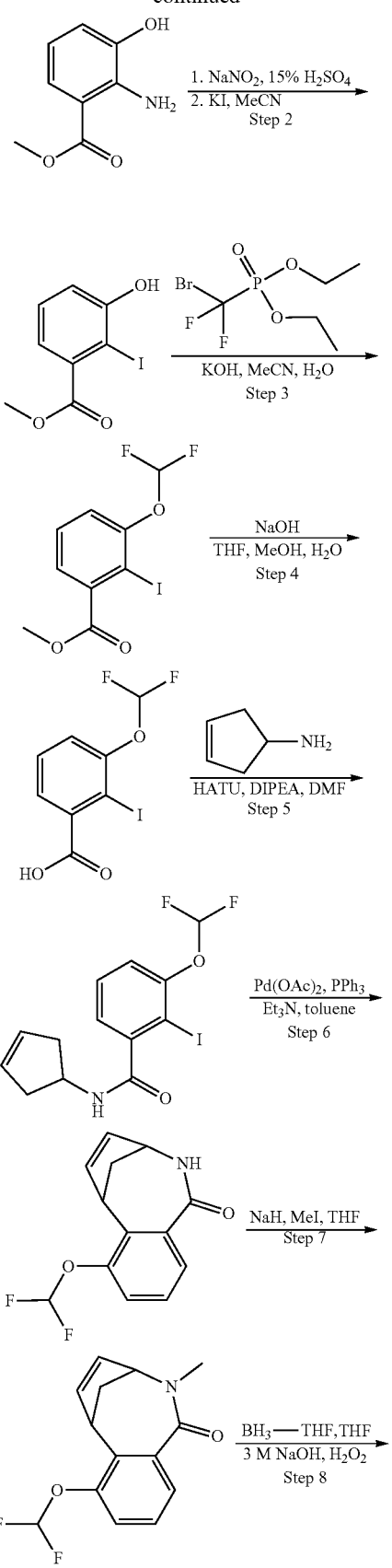

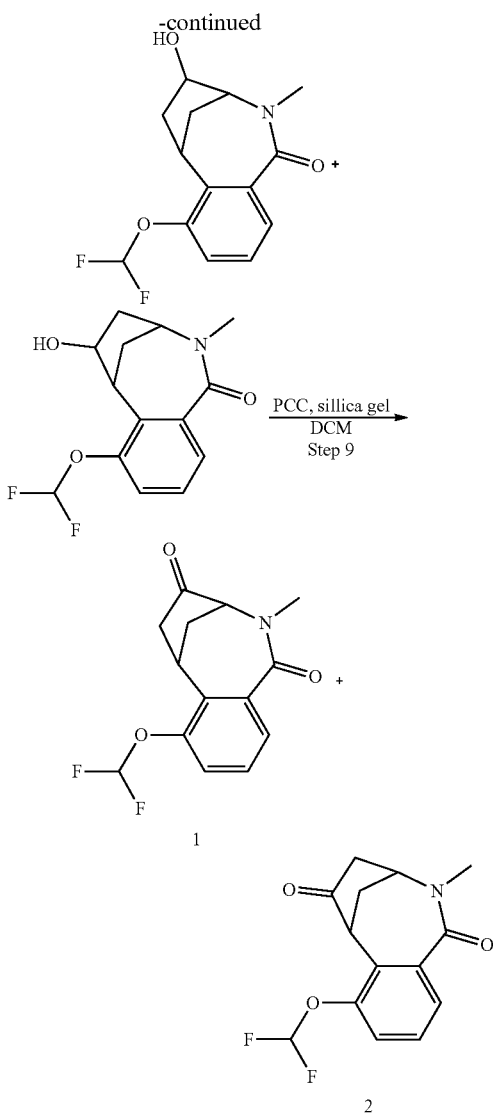

Step 1: To a stirred solution of 3-hydroxyanthranilic acid (175 g, 1.14 mol, 1.0 equiv) in MeOH (1 L) was added H$_2$SO$_4$ (150 mL) dropwise at room temperature. The resulting mixture was stirred for 24 hr at 80° C. The resulting mixture was cooled and concentrated in vacuo to remove most of the solvent. The residue was basified with NaHCO$_3$ solution until pH=8-9 and then extracted with DCM (500 mL×3). The combined organic layers were washed with brine (500 mL) and dried over anhydrous Na$_2$SO$_4$. After filtration, the filtrate was concentrated under reduced pressure. The residue was purified by silica gel column chromatography, eluted with PE:EA (3:1) to afford methyl 2-amino-3-hydroxybenzoate (150 g, 78. %) as a yellow solid. LC-MS: (M+H)$^+$ found: 168.10. $^1$H NMR (400 MHz, DMSO-d$_6$) δ 9.69 (s, 1H), 7.22 (dd, J=8.2, 1.4 Hz, 1H), 6.83 (dd, J=7.6, 1.5 Hz, 1H), 6.44-6.36 (m, 1H), 6.12 (br, 2H), 3.78 (s, 3H).

Step 2: A solution of methyl 2-amino-3-hydroxybenzoate (150 g, 0.89 mol, 1.0 equiv) in 15% H$_2$SO$_4$ (a solution of H$_2$SO$_4$ (450 mL) in H$_2$O (2.5 L)) was treated with NaNO$_2$ (68.10 g, 0.98 mol, 1.1 equiv) at 0° C. Then the mixture was stirred for 1 hr at room temperature. The resulting mixture was diluted with MeCN (1.5 L) followed by the addition of KI (1.19 kg, 7.18 mol, 8.0 equiv). The final reaction mixture was stirred overnight at 80° C. The resulting mixture was cooled and concentrated in vacuo to remove most of the solvent. The residue was basified with sat. Na$_2$CO$_3$ solution until pH=6-7 and extracted with EtOAc (2 L×3). The combined organic layers were washed with Na$_2$SO$_3$ aq. (2 L) and dried over anhydrous Na$_2$SO$_4$. After filtration, the filtrate was concentrated under reduced pressure. The residue was purified by silica gel column chromatography, eluted with DCM (100%) to afford methyl 3-hydroxy-2-iodobenzoate (180 g, 72%) as a brown solid. LC-MS: (M+H)$^+$ found: 276.90. $^1$H NMR (400 MHz, Chloroform-d) δ 7.41 (dd, J=7.6, 1.6 Hz, 1H), 7.30 (t, J=7.8 Hz, 1H), 7.19 (dd, J=8.0, 1.6 Hz, 1H), 5.99 (br, 1H), 3.96 (s, 3H).

Step 3: A solution of methyl 3-hydroxy-2-iodobenzoate (180 g, 0.65 mol, 1.0 equiv) in MeCN (1.8 L) was treated with 5 M KOH (a solution of KOH (182 g, 3.2 mol, 5.0 equiv) in H$_2$O (500 mL)) followed by the addition of diethyl bromodifluoromethylphosphonate (230 mL, 1.3 mol, 2.0 equiv) dropwise at 0° C. The final reaction mixture was stirred overnight at room temperature. The desired product was detected by TLC (PE:EA=10:1). The resulting mixture was extracted with tert-butyl methyl ether (2 L×3). The combined organic layers were washed with brine (800 mL) and dried over anhydrous Na$_2$SO$_4$. After filtration, the filtrate was concentrated under reduced pressure. The residue was purified by silica gel column chromatography, eluted with PE/EA (100:1) to afford methyl 3-(difluoromethoxy)-2-iodobenzoate (136 g, 64%) as a yellow oil. LC-MS: (M+H)$^+$ found: 328.85. $^1$H NMR (400 MHz, Chloroform-d) δ 7.55 (dd, J=7.7, 1.5 Hz, 1H), 7.42 (t, J=7.9 Hz, 1H), 7.34-7.26 (m, 1H), 6.56 (t, J=73.1 Hz, 1H), 3.98 (s, 3H).

Step 4: To a stirred solution of methyl 3-(difluoromethoxy)-2-iodobenzoate (137 g, 0.42 mol, 1.0 equiv) in THF (500 mL) were added MeOH (500 mL) and H$_2$O (500 mL) at room temperature under air atmosphere. To the above mixture was added NaOH (50 g, 1.25 mol, 3.0 equiv) at room temperature. The resulting mixture was stirred for an additional 30 min at 50° C. The resulting mixture was cooled and concentrated in vacuo to remove most of the solvent. The aqueous was acidified with 6 M HCl until pH=3-4 and extracted with EtOAc (2×1 L). The combined organic layers were washed with brine (500 mL) and dried over anhydrous Na$_2$SO$_4$. After filtration, the filtrate was concentrated under reduced pressure. This resulted in 3-(difluoromethoxy)-2-iodobenzoic acid (120 g, 92%) as a light yellow solid. LC-MS: (M−H)$^+$ found: 312.90. $^1$H NMR (400 MHz, Chloroform-d) δ 7.78 (dd, J=7.7, 1.5 Hz, 1H), 7.46 (t, J=7.9 Hz, 1H), 7.40-7.34 (m, 1H), 6.58 (t, J=73.0 Hz, 1H).

Step 5: To a stirred solution of 3-(difluoromethoxy)-2-iodobenzoic acid (120 g, 0.38 mol, 1.00 equiv) and cyclopent-3-en-1-amine hydrochloride (50.3 g, 0.42 mol, 1.1 equiv) in DMF (1 L) was added DIEA (148.2 g, 1.14 mmol, 3.0 equiv) at room temperature under air atmosphere. To the above mixture was added HATU (188.9 g, 496.8 mmol, 1.30 equiv) at room temperature. The resulting mixture was stirred for 30 min at room temperature. The reaction was poured into water (4 L) at room temperature. The resulting mixture was extracted with EtOAc (3×1 L). The combined organic layers were washed with brine (2×1 L) and dried over anhydrous Na$_2$SO$_4$. After filtration, the filtrate was concentrated under reduced pressure. The residue was purified by silica gel column chromatography, eluted with PE:EA (5:1) to afford N-(cyclopent-3-en-1-yl)-3-(difluoromethoxy)-2-iodobenzamide (126 g, 87%) as a white solid. LC-MS: (M+H)$^+$ found: 379.80. $^1$H NMR (400 MHz, Chloroform-d) δ 7.39 (t, J=7.9 Hz, 1H), 7.27-7.16 (m, 2H), 6.54 (t, J=73.1 Hz, 1H), 5.91 (br, 1H), 5.79 (s, 2H), 4.81 (qt, J=7.5, 3.3 Hz, 1H), 2.89 (dd, J=15.9, 7.4 Hz, 2H), 2.46-2.37 (m, 2H).

Step 6: A solution of N-(cyclopent-3-en-1-yl)-3-(difluoromethoxy)-2-iodobenzamide (126 g, 332.3 mmol, 1.0 equiv) in toluene (1.8 L) was added $Et_3N$ (139 mL, 997 mmol, 3.0 equiv) and $PPh_3$ (17.4 g, 66.5 mmol, 0.2 equiv) followed by $Pd(OAc)_2$ (7.5 g, 33.2 mmol, 0.1 equiv) under nitrogen atmosphere. Then the mixture was degassed with $N_2$ for 3 times and stirred overnight at 110° C. under a nitrogen atmosphere. The resulting mixture was concentrated under reduced pressure. The residue was purified by silica gel column chromatography, eluted with PE/EA (2:1) to afford 7-(difluoromethoxy)-3,6-dihydro-3,6-methanobenzo[c]azocin-1 (2H)-one (81 g, 97%) as a white solid. LC-MS: $(M+H)^+$ found: 252.05. $^1$H NMR (400 MHz, Chloroform-d) δ 8.47 (dd, J=7.8, 1.9 Hz, 1H), 7.36-7.29 (m, 2H), 6.79 (s, 1H), 6.58 (t, J=73.6 Hz, 1H), 6.05 (dd, J=5.5, 3.0 Hz, 1H), 5.92 (dd, J=5.7, 2.5 Hz, 1H), 4.58 (dd, J=7.1, 3.0 Hz, 1H), 4.22 (td, J=6.5, 2.5 Hz, 1H), 2.52 (dt, J=13.4, 6.9 Hz, 1H), 2.02 (d, J=12.8 Hz, 1H).

Step 7: A solution of 7-(difluoromethoxy)-3,6-dihydro-3,6-methanobenzo[c]azocin-1 (2H)-one (81 g, 322.41 mmol, 1.0 equiv) in THF (1 L) was treated with NaH (16.8 g, 419.13 mmol, 1.3 equiv, 60%) at 0° C. The mixture was allowed to stir at 0° C. for 0.5 hr. To the above mixture was added MeI (30 mL, 483.62 mmol, 1.5 equiv) dropwise at 0° C. under nitrogen atmosphere. The final reaction mixture was stirred for 3.5 hr at room temperature under nitrogen atmosphere. The reaction was quenched with water (500 mL) at room temperature. The resulting mixture was extracted with EtOAc (1 L×2). The combined organic layers were washed with brine (1 L) and dried over anhydrous $Na_2SO_4$. After filtration, the filtrate was concentrated under reduced pressure. The residue was purified by silica gel column chromatography, eluted with PE/EA (1:1) to afford 7-(difluoromethoxy)-2-methyl-3,6-dihydro-3,6-methanobenzo[c]azocin-1 (2H)-one (75 g, 88%) as a white solid. LC-MS: $(M+H)^+$ found: 266.00. $^1$H NMR (400 MHz, Chloroform-d) δ 8.53 (dd, J=8.2, 1.5 Hz, 1H), 7.30 (t, J=8.1 Hz, 1H), 7.22 (ddt, J=8.1, 1.6, 0.9 Hz, 1H), 6.56 (t, J=73.6 Hz, 1H), 6.05 (dd, J=5.5, 2.9 Hz, 1H), 5.99-5.93 (m, 1H), 4.47 (ddd, J=7.0, 2.9, 1.0 Hz, 1H), 4.33 (dd, J=7.3, 2.5 Hz, 1H), 3.29 (s, 3H), 2.52 (dt, J=13.0, 7.1 Hz, 1H), 2.05 (d, J=13.0 Hz, 1H).

Step 8: To a stirred solution of 7-(difluoromethoxy)-2-methyl-3,6-dihydro-3,6-methanobenzo[c]azocin-1 (2H)-one (66 g, 0.25 mol, 1.0 equiv) in THF (660 mL) was added $BH_3$-THF (498 mL, 0.5 mol, 2.0 equiv) at 0° C. under $N_2$ atmosphere. The resulting mixture was stirred for 3 hr at 0° C. under $N_2$ atmosphere. To the above mixture was added NaOH (290 mL, 0.87 mol, 3.5 equiv) and $H_2O_2$ (116 mL, 1.24 mol, 5.0 equiv, 25%) at 0° C. The resulting mixture was stirred for an additional 30 min at 0° C. TLC (PE/EA=1/1) showed the reaction was complete. The reaction was quenched with MeOH (300 mL) followed by $Na_2SO_3$ solution (500 mL) at 0° C. The resulting mixture was extracted with EtOAc (3×800 mL). The combined organic layers were washed with brine (500 mL) and dried over anhydrous $Na_2SO_4$. After filtration, the filtrate was concentrated under reduced pressure. The residue was purified by silica gel column chromatography, eluted with MeOH/DCM (0 to 5%) to afford 7-(difluoromethoxy)-4-hydroxy-2-methyl-3,4,5,6-tetrahydro-3,6-methanobenzo[c]azocin-1 (2H)-one and 7-(difluoromethoxy)-5-hydroxy-2-methyl-3,4,5,6-tetrahydro-3,6-methanobenzo[c]azocin-1 (2H)-one (43 g, 58%) as a light yellow solid. The mixture was used in the next step directly without further separation. LC-MS: $(M+H)^+$ found: 283.90.

Step 9: To a stirred solution of 7-(difluoromethoxy)-4-hydroxy-2-methyl-3,4,5,6-tetrahydro-3,6-methanobenzo[c]azocin-1 (2H)-one and 7-(difluoromethoxy)-5-hydroxy-2-methyl-3,4,5,6-tetrahydro-3,6-methanobenzo[c]azocin-1 (2H)-one (15 g, 59.25 mmol, 1.0 equiv) in DCM (300 mL) was added silica gel (6.36 g, 105.90 mmol, 2 equiv) followed by PCC (22.8 g, 105.90 mmol, 2.0 equiv) at 0° C. under $N_2$ atmosphere. The resulting mixture was stirred for 12 hrs at 25° C. under $N_2$ atmosphere. The reaction mixture was filtered through a pad of celite. The filter cake was washed with DCM (200 mL×3). The combined organic phase was washed with sat. $NaHCO_3$ solution (500 mL), brine (200 mL) and dried over $Na_2SO_4$. Filtered and the filtrate was concentrated in vacuo to give a crude product. The crude product was purified by prep-Achiral SFC (Column: Viridis BEH Prep 2-EP OBD Column 5*15 cm, 5 um; Mobile Phase A: $CO_2$, Mobile Phase B: IPA (1%-2M-$NH_3$-MeOH); Flow rate: 120 mL/min; Gradient: isocratic 30% B; Column Temperature (° C.): 35; Back Pressure(bar): 100; Wave Length: 220 nm; RT1(min): 3.9; RT2(min): 5.33; Sample Solvent: MeOH; Injection Volume: 3 mL) to give Intermediate 1: 7-(difluoromethoxy)-2-methyl-2,3,5,6-tetrahydro-3,6-methanobenzo[c]azocine-1,4-dione (3.9 g, 26%) as an off-white solid. LC-MS: $(M+H)^+$ found: 282.10. $^1$H NMR (400 MHz, DMSO-$d_6$) δ 8.26 (dd, J=7.9, 1.7 Hz, 1H), 7.46-7.04 (m, 3H), 4.16 (t, J=7.2 Hz, 1H), 4.05 (d, J=8.6 Hz, 1H), 3.20 (s, 3H), 2.98 (ddd, J=18.0, 8.1, 0.9 Hz, 1H), 2.76 (ddd, J=14.2, 8.7, 6.5 Hz, 1H), 2.25 (ddd, J=18.1, 3.1, 1.3 Hz, 1H), 2.07 (dd, J=14.2, 3.1 Hz, 1H).

Intermediate 2: 7-(difluoromethoxy)-2-methyl-3,4-dihydro-3,6-methanobenzo[c]azocine-1,5 (2H,6H)-dione (5.8 g, 39%) as an off-white solid with a total yield 65%. LC-MS: $(M+H)^+$ found: 282.10. $^1$H NMR (400 MHz, Chloroform-d) δ 8.53 (dd, J=7.1, 2.5 Hz, 1H), 7.41-7.31 (m, 2H), 6.64 (dd, J=79.6, 69.8 Hz, 1H), 4.50 (d, J=8.6 Hz, 1H), 4.29 (t, J=5.9 Hz, 1H), 3.27 (s, 3H), 2.87-2.65 (m, 3H), 2.40 (dd, J=14.2, 2.7 Hz, 1H).

Intermediate 3 and 4

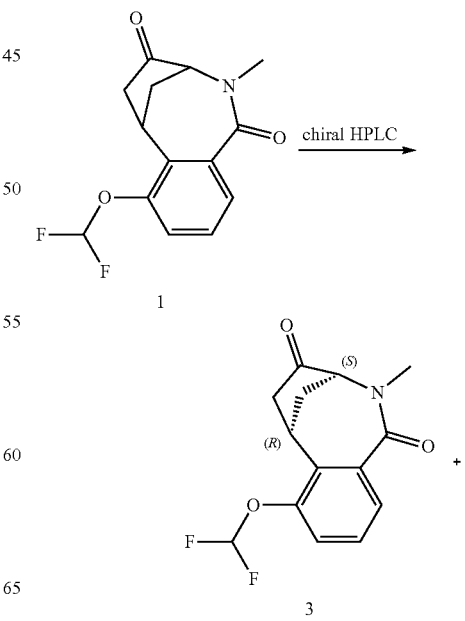

313

-continued

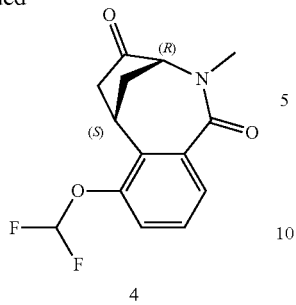

4

Intermediate 1 (250 g) was purified by chiral SFC with the following conditions (Column: DAICELCHIRALPAK®AD; 250*40 mm 10 m; Mobile Phase A: Supercritical $CO_2$, Mobile Phase B: IPA (+0.1% 7.0 mol/l Ammonia in MEOH); Flow rate: 150 mL/min; Gradient: 25% B to 25% B; Wave Length: 220/214 nm; RT1(min): 4.30; RT2(min): 5.60; Sample Solvent: IPA: DCM=1:1; Injection Volume: 3 mL; Number Of Runs: 540) to afford:

Intermediate 3: (3S,6R)-7-(difluoromethoxy)-2-methyl-2,3,5,6-tetrahydro-3,6-methanobenzo[c]azocine-1,4-dione (114.7 g, 45.9%) as a yellow oil. LCMS (ESI, m/z): 282.10 $[M+H]^+$. $^1H$ NMR (400 MHz, Chloroform-d) δ 8.46 (d, J=7.4 Hz, 1H), 7.35 (t, J=8.1 Hz, 1H), 7.25-7.23 (m, 1H), 6.56 (t, J=73.4 Hz, 1H), 4.33 (t, J=7.6 Hz, 1H), 3.81 (d, J=8.1 Hz, 1H), 3.34 (s, 3H), 2.80 (q, J=8.4 Hz, 1H), 2.68-2.61 (m, 1H), 2.49-2.43 (m, 1H), 2.25 (dd, J=14.5, 2.7 Hz, 1H).

Intermediate 4: (3R,6S)-7-(difluoromethoxy)-2-methyl-2,3,5,6-tetrahydro-3,6-methanobenzo[c]azocine-1,4-dione (115.3 mg, 46.1%) as a yellow oil. LCMS (ESI, m/z): 282.15 $[M+H]^+$. $^1H$ NMR (400 MHz, Chloroform-d) δ 8.46 (d, J=8.8 Hz, 1H), 7.35 (t, J=8.2 Hz, 1H), 7.25-7.23 (m, 1H), 6.56 (t, J=73.3 Hz, 1H), 4.33 (t, J=7.6 Hz, 1H), 3.81 (d, J=8.1 Hz, 1H), 3.34 (s, 3H), 2.80 (q, J=8.5 Hz, 1H), 2.68-2.61 (m, 1H), 2.46 (dd, J=18.9, 2.5 Hz, 1H), 2.26 (dd, J=14.4, 2.7 Hz, 1H).

Intermediate 5 and 6

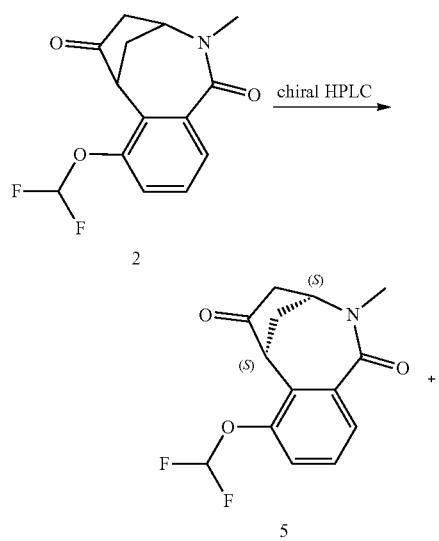

314

-continued

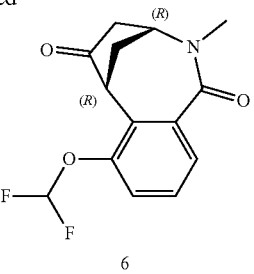

6

Intermediate 2 (240 g) was purified by chiral SFC with the following conditions (Column: DAICELCHIRALPAK®AD; 250*50 mm 10 m; Mobile Phase A: Supercritical $CO_2$, Mobile Phase B: IPA (+0.1% 7.0 mol/l Ammonia in MeOH); Flow rate: 140 mL/min; Gradient: 25% B to 25% B; Wave Length: 220/214 nm; RT1(min): 6.70; RT2(min): 8.60; Sample Solvent: IPA: DCM=1:1; Injection Volume: 8 mL; Number Of Runs: 125) to afford:

Intermediate 5: ((3S,6S)-7-(difluoromethoxy)-2-methyl-3,4-dihydro-3,6-methanobenzo[c]azocine-1,5 (2H,6H)-dione (89.5 g, 43.8%) as a white solid. LCMS (ESI, m/z): 282.1 $[M+H]^+$. $^1H$ NMR (400 MHz, Chloroform-d) δ 8.51 (dd, J=5.9, 2.6 Hz, 1H), 7.34 (t, J=4.9 Hz, 1H), 6.62 (dd, J=79.6, 69.7 Hz, 1H), 4.48 (d, J=8.7 Hz, 1H), 4.27 (t, J=5.2 Hz, 1H), 3.42 (s, 3H), 2.83-2.76 (m, 1H), 2.72-2.65 (m, 2H), 2.39 (dd, J=14.2, 2.6 Hz, 1H).

Intermediate 6: ((3R,6R)-7-(difluoromethoxy)-2-methyl-3,4-dihydro-3,6-methanobenzo[c]azocine-1,5 (2H,6H)-dione (86.4 g, 42.3%) as a white solid. LCMS (ESI, m/z): 282.1 $[M+H]^+$. $^1H$ NMR (400 MHz, Chloroform-d) δ 8.51 (d, J=5.8 Hz, 1H), 7.35-7.33 (m, 1H), 6.56 (dd, J=79.4, 69.7 Hz, 1H), 4.48 (d, J=8.5 Hz, 1H), 4.27 (s, 1H), 3.25 (s, 3H), 2.83-2.76 (m, 1H), 2.71-2.65 (m, 2H), 2.38 (d, J=14.2 Hz, 1H).

Intermediate 7

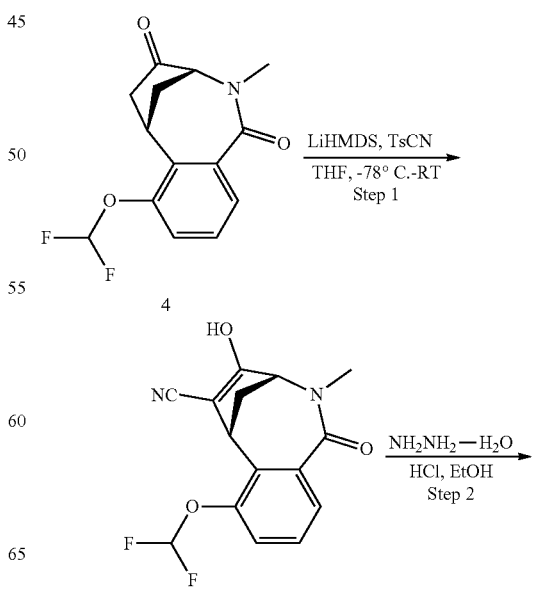

-continued

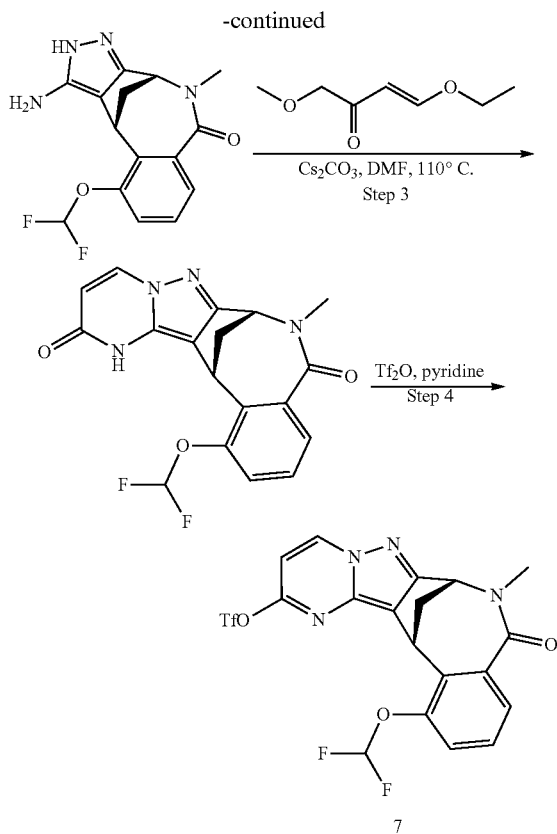

Step 1: A solution of Intermediate 4 (750 mg, 2.7 mmol, 1 equiv) in THF (20 mL) was treated with LiHMDS (3.2 mL, 3.2 mmol, 1.2 equiv) for 10 min at −78° C. under nitrogen atmosphere. The mixture was warmed to −10° C. The resulting mixture was stirred for 15 min at −10° C. under nitrogen atmosphere. The mixture was then cooled to −78° C. A solution of 4-methylbenzenesulfonyl cyanide (725 mg, 4.0 mmol, 1.5 equiv) in THF (10 mL) was added quickly (<1 min) to the cool reaction mixture. The resulting mixture was stirred for 5 min at −78° C. under nitrogen atmosphere. The resulting mixture was stirred overnight at room temperature under nitrogen atmosphere. The reaction was quenched by the addition of sat. NH$_4$Cl (aq.) (10 mL) at 0° C. The resulting mixture was extracted with EtOAc (3×20 mL). The combined organic layers were washed with brine (1×60 mL), dried over anhydrous Na$_2$SO$_4$. After filtration, the filtrate was concentrated under reduced pressure. The residue was purified by Prep-TLC (DCM/MeOH 1% NH$_3$·H$_2$O, 4:1, ref=0.2) to afford (3R,6R)-7-(difluoromethoxy)-4-hydroxy-2-methyl-1-oxo-1,2,3,6-tetrahydro-3,6-methanobenzo[c]azocine-5-carbonitrile (300 mg, 36.7%) as a yellow oil. LCMS (ESI, m/z): 306.9 [M+H]$^+$.

Step 2: A solution of (3R,6R)-7-(difluoromethoxy)-4-hydroxy-2-methyl-1-oxo-1,2,3,6-tetrahydro-3,6-methanobenzo[c]azocine-5-carbonitrile (320 mg, 1.1 mmol, 1 equiv) in EtOH (30 mL) was treated with NH$_2$NH$_2$·H$_2$O (115 mg, 2.30 mmol, 2.2 equiv) for 5 min at room temperature under nitrogen atmosphere followed by the addition of HCl(gas) in dioxane (0.1 mL, 3.1 mmol, 3 equiv) at room temperature. The resulting mixture was stirred for 3 hr at 85° C. under nitrogen atmosphere. The resulting mixture was concentrated under reduced pressure. The residue was purified by Prep-TLC (DCM/MeOH 10:1) to afford (4R,11S)-1-amino-10-(difluoromethoxy)-5-methyl-2,4,5,11-tetrahydro-6H-4,11-methanobenzo[c]pyrazolo[4,3-f]azocin-6-one (120 mg, 35.9%) as a yellow solid. LCMS (ESI, m/z): 320.90 [M+H]$^+$.

Step 3: A solution of (4R,11S)-1-amino-10-(difluoromethoxy)-5-methyl-2,4,5,11-tetrahydro-6H-4,11-methanobenzo[c]pyrazolo[4,3-f]azocin-6-one (120 mg, 0.4 mmol, 1 equiv) in DMF (2 mL) was treated with Cs$_2$CO$_3$ (195 mg, 0.6 mmol, 1.6 equiv) for 1 min at room temperature under nitrogen atmosphere followed by the addition of ethyl 3-ethoxy-2-propenoate (64.8 mg, 0.5 mmol, 1.2 equiv) at room temperature. The resulting mixture was stirred for 2 hrs at 110° C. under nitrogen atmosphere. The resulting mixture was concentrated under reduced pressure. The residue was purified by Prep-TLC (DCM/MeOH 10:1) to afford (7R,14S)-1-(difluoromethoxy)-6-methyl-6,7,13,14-tetrahydro-7,14-methanobenzo[c]pyrimido[1',2':1,5]pyrazolo[4,3-f]azocine-5,12-dione (98 mg, 70.3%) as a yellow solid. LCMS (ESI, m/z): 373.00[M+H]$^+$.

Step 4: A solution of (7R,14S)-1-(difluoromethoxy)-6-methyl-6,7,13,14-tetrahydro-7,14-methanobenzo[c]pyrimido[1',2':1,5]pyrazolo[4,3-f]azocine-5,12-dione (98 mg, 0.3 mmol, 1 equiv) in DCM (4 mL) was treated with DMAP (8. mg, 0.1 mmol, 0.25 equiv) and 2,6-lutidine (14.10 mg, 0.13 mmol, 0.5 equiv) for 1 min at 0° C. under nitrogen atmosphere followed by the addition of (trifluoromethane)sulfonyl trifluoromethanesulfonate (223 mg, 0.8 mmol, 3 equiv) at 0° C. The resulting mixture was stirred for 1 hr at room temperature under nitrogen atmosphere. The mixture was acidified to pH 8 with saturated NH$_4$Cl (aq.). The resulting mixture was extracted with DCM (3×30 mL). The combined organic layers were washed with brine (2×5 mL), dried over anhydrous Na$_2$SO$_4$. After filtration, the filtrate was concentrated under reduced pressure. The residue was purified by Prep-TLC (PE/EA 1:10) to afford Intermediate 7: (7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl trifluoromethanesulfonate (84 mg, 63.3%) as a yellow solid. LCMS (ESI, m/z): 505.05 [M+H]$^+$.

Intermediate 8

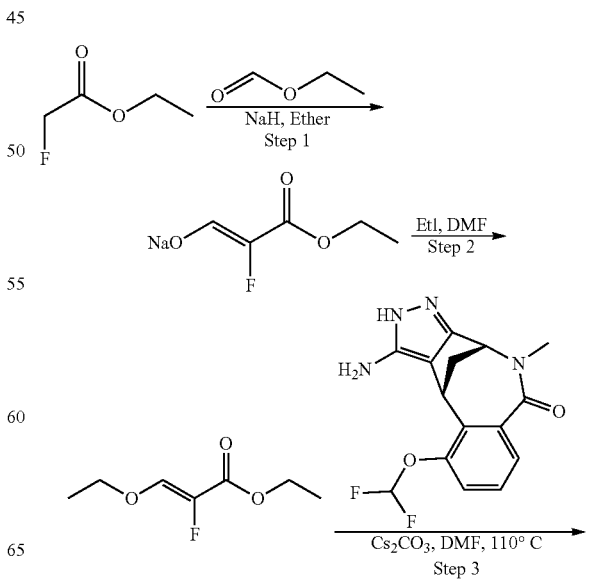

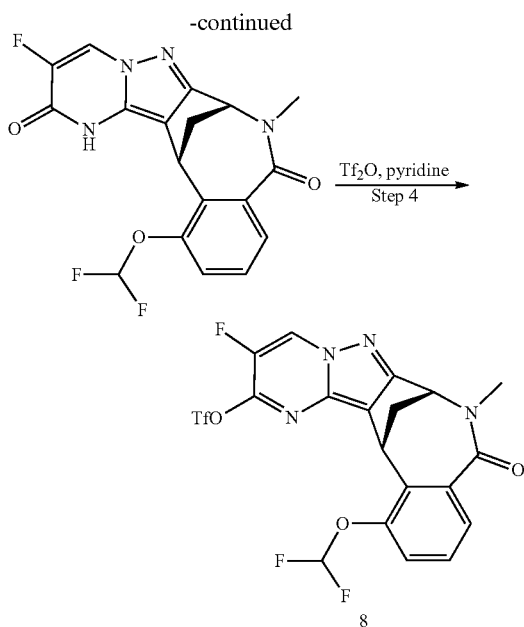

Step 1: NaH (60% suspension in mineral oil, 15.6 g, 0.39 mole) was washed with and suspended in ether (300 mL). To this suspension, ethyl formate (29.1 mL, 0.36 mole, 1.2 eq) was added and the mixture was cooled in an ice bath. Ethyl fluoroacetate (29.0 mL, 0.3 mole) was added slowly over 1 hr. After 2 hr, the ice bath was removed and the reaction was stirred for another 2 hr. The resulting mixture was concentrated under reduced pressure. The crude product was used in the next step directly without further purification.

Step 2: The residue was re-dissolved in 350 mL of dry DMF and cooled in an ice bath, and ethyl iodide (48 mL, 0.6 mole) was added dropwise. The solution was allowed to warm to room temperature and stirred overnight, then quenched with saturated aqueous solution of NH$_4$Cl (100 mL). The mixture was diluted with ether and extracted with water. The separated ether layer was washed with sodium thiosulfate, brine and dried over MgSO$_4$. After concentration under vacuum, the residue was distilled to give ethyl 3-ethoxy-2-fluoroacrylate (6 g, 73°-85° C./14 mmHg) as a colorless oil. $^1$H NMR (300 MHz, CDCl$_3$): δ 1.35 (t, 3H), 1.39 (t, 3H), 4.10 (q, 2H), 4.30 (q, 2H), 6.95 (d, 1H).

Step 3: A solution of (4R,11S)-1-amino-10-(difluoromethoxy)-5-methyl-2,4,5,11-tetrahydro-6H-4,11-methanobenzo[c]pyrazolo[4,3-f]azocin-6-one (500 mg, 1.56 mmol, 1 equiv) in DMF (1 mL) was treated with Cs$_2$CO$_3$ (1.12 g, 3.43 mmol, 2.2 equiv) at room temperature for 1 min under nitrogen atmosphere followed by the addition of ethyl (2Z)-3-ethoxy-2-fluoroprop-2-enoate (60.75 mg, 0.38 mmol, 4 equiv) at room temperature. The resulting mixture was stirred at 110° C. for 3 hr under nitrogen atmosphere. The residue was purified by reversed-phase flash chromatography with the following conditions: column, C18 silica gel; mobile phase, MeCN in Water (10 mmol/L NH$_4$HCO$_3$), 10% to 50% gradient in 10 min; detector, UV 254 nm. This resulted in (7R,14S)-1-(difluoromethoxy)-11-fluoro-6-methyl-6,7,13,14-tetrahydro-7,14-methanobenzo[c]pyrimido[1',2':1,5]pyrazolo[4,3-f]azocine-5,12-dione (140 mg, 22.97%) as a yellow solid. LCMS (ESI, m/z): 391.10 [M+H]$^+$.

Step 4: A solution of (7R,14S)-1-(difluoromethoxy)-11-fluoro-6-methyl-6,7,13,14-tetrahydro-7,14-methanobenzo[c]pyrimido[1',2':1,5]pyrazolo[4,3-f]azocine-5,12-dione (130 mg, 0.33 mmol, 1 equiv) in DCM (4 mL) was treated with DMAP (20.35 mg, 0.17 mmol, 0.5 equiv) at room temperature for 1 min under nitrogen atmosphere followed by the addition of 2,6-lutidine (53.53 mg, 0.50 mmol, 1.5 equiv) at room temperature. To the above mixture was added trifluoromethanesulfonic anhydride (281.90 mg, 1.00 mmol, 3 equiv) over 1 min at 0° C. The resulting mixture was stirred at 0° C. for 1 hr. The reaction was quenched with sat. NH$_4$Cl (aq.) at 0° C. The resulting mixture was extracted with EtOAc (3×10 mL). The combined organic layers were washed with brine (2×10 mL), dried over anhydrous Na$_2$SO$_4$. After filtration, the filtrate was concentrated under reduced pressure. The residue was purified by Prep-TLC (PE/EA 1:2) to afford Intermediate 8 (110 mg, 63.22%) as a yellow solid. LCMS (ESI, m/z): 523.15 [M+H]$^+$.

Intermediate 9

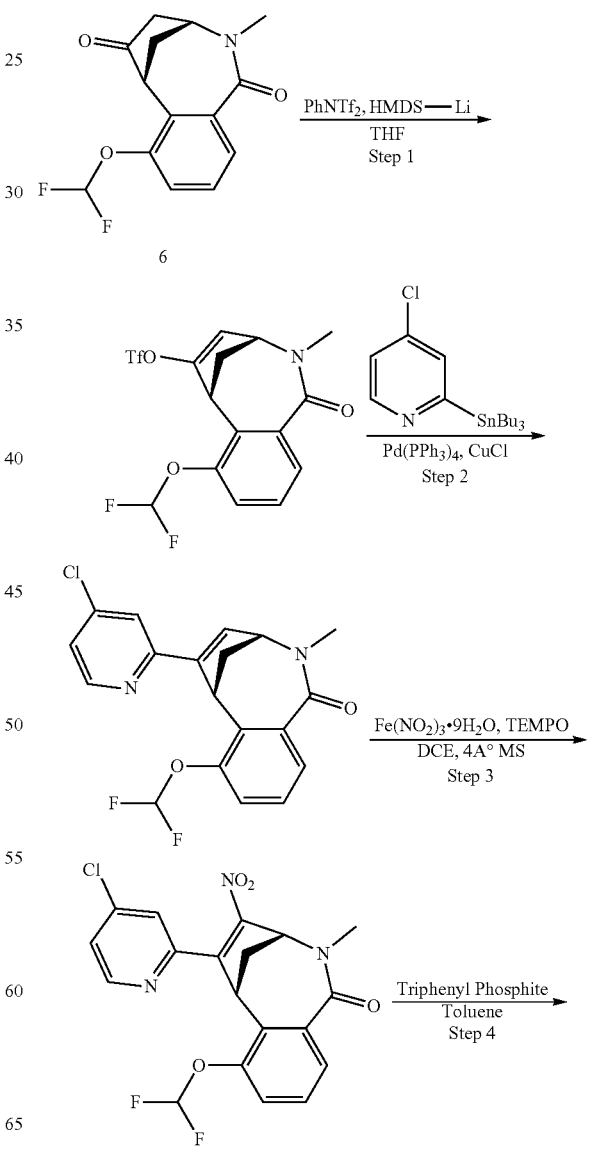

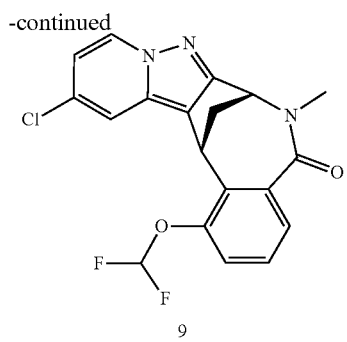

9

Step 1: To a stirred solution of Intermediate 6 (2.0 g, 7.1 mmol, 1 equiv) in THF (40 mL) was added LiHMDS (11.4 mL, 11.4 mmol, 1.6 equiv) dropwise at −78° C. under nitrogen atmosphere. The resulting mixture was stirred at −78° C. for 1 hr. To the above mixture was added 1,1,1-trifluoro-N-phenyl-N-(trifluoromethane)sulfonylmethanesulfonamide (3.8 g, 10.7 mmol, 1.5 equiv) in THF (40 mL) dropwise at −78° C. The resulting mixture was stirred at 78° C. to RT for 2 hr. The reaction was quenched by the addition of sat. NH₄Cl (aq.) (50 mL) at 0° C. The aqueous layer was extracted with EtOAc (3×30 mL). The combined organic layers were washed with brine (100 mL), dried over anhydrous Na₂SO₄. After filtration, the filtrate was concentrated under reduced pressure. The residue was purified by silica gel column chromatography, eluted with PE/EA (8:1) to afford (3R,6R)-7-(difluoromethoxy)-2-methyl-1-oxo-1,2,3,6-tetrahydro-3,6-methanobenzo[c]azocin-5-yl trifluoromethanesulfonate (1.7 g, 57.8%) as light yellow oil. LCMS (ESI, m/z): 413.90 [M+H]⁺.

Step 2: To a stirred mixture of (3R,6R)-7-(difluoromethoxy)-2-methyl-1-oxo-1,2,3,6-tetrahydro-3,6-methanobenzo[c]azocin-5-yl trifluoromethanesulfonate (1.7 g, 4.1 mmol, 1 equiv) and 4-chloro-2-(tributylstannyl)pyridine (2.5 g, 6.2 mmol, 1.5 equiv) in toluene (34 mL) was added Pd(PPh₃)₄ (475.3 mg, 0.41 mmol, 0.1 equiv) and CuCl (407.2 mg, 4.1 mmol, 1 equiv) at room temperature under nitrogen atmosphere. The resulting mixture was stirred at 100° C. for 4 hr. The resulting mixture was filtered, the filter cake was washed with DCM (3×20 mL). The filtrate was concentrated under reduced pressure. The residue was purified by Prep-TLC (PE/EA 1:1) to afford (3R,6S)-5-(4-chloropyridin-2-yl)-7-(difluoromethoxy)-2-methyl-3,6-dihydro-3,6-methanobenzo[c]azocin-1 (2H)-one (600 mg, 38.7%) as a light yellow solid. LCMS (ESI, m/z): 376.95 [M+H]⁺.

Step 3: To a stirred mixture of (3R,6S)-5-(4-chloropyridin-2-yl)-7-(difluoromethoxy)-2-methyl-3,6-dihydro-3,6-methanobenzo[c]azocin-1 (2H)-one (5.0 g, 13.3 mmol, 1 equiv) and 2,2,6,6-tetramethylpiperidin-1-olate (0.41 g, 2.7 mmol, 0.2 equiv) in DCE (100 mL) was added iron(III) nitrate nonahydrate (10.7 g, 26.5 mmol, 2.0 equiv) and 4 A-MS (15 g) at room temperature under nitrogen atmosphere. The resulting mixture was stirred at 80° C. for 2 hr. The resulting mixture was filtered, the filter cake was washed with DCE (3×50 mL). The filtrate was concentrated under reduced pressure. The residue was purified by silica gel column chromatography, eluted with PE/EA (3:1) to afford (3R,6S)-5-(4-chloropyridin-2-yl)-7-(difluoromethoxy)-2-methyl-4-nitro-3,6-dihydro-3,6-methanobenzo[c]azocin-1 (2H)-one (2.2 g, 39.3%) as a light yellow solid. LCMS (ESI, m/z): 421.90 [M+H]⁺.

Step 4: A solution of (3R,6S)-5-(4-chloropyridin-2-yl)-7-(difluoromethoxy)-2-methyl-4-nitro-3,6-dihydro-3,6-methanobenzo[c]azocin-1 (2H)-one (2.2 g, 13.5 mmol, 1 equiv) in 4oluene (44 mL) was treated with triphenyl phosphite (4.9 g, 40.5 mmol, 3 equiv) at 100° C. for 3 hr under nitrogen atmosphere. The resulting mixture was concentrated under reduced pressure. The residue was purified by silica gel column chromatography, eluted with PE/EA (1:1) to afford Intermediate 9 (1.0 g, 50%) as a yellow solid. LCMS (ESI, m/z): 390.05 [M+H]⁺.

Intermediate 10

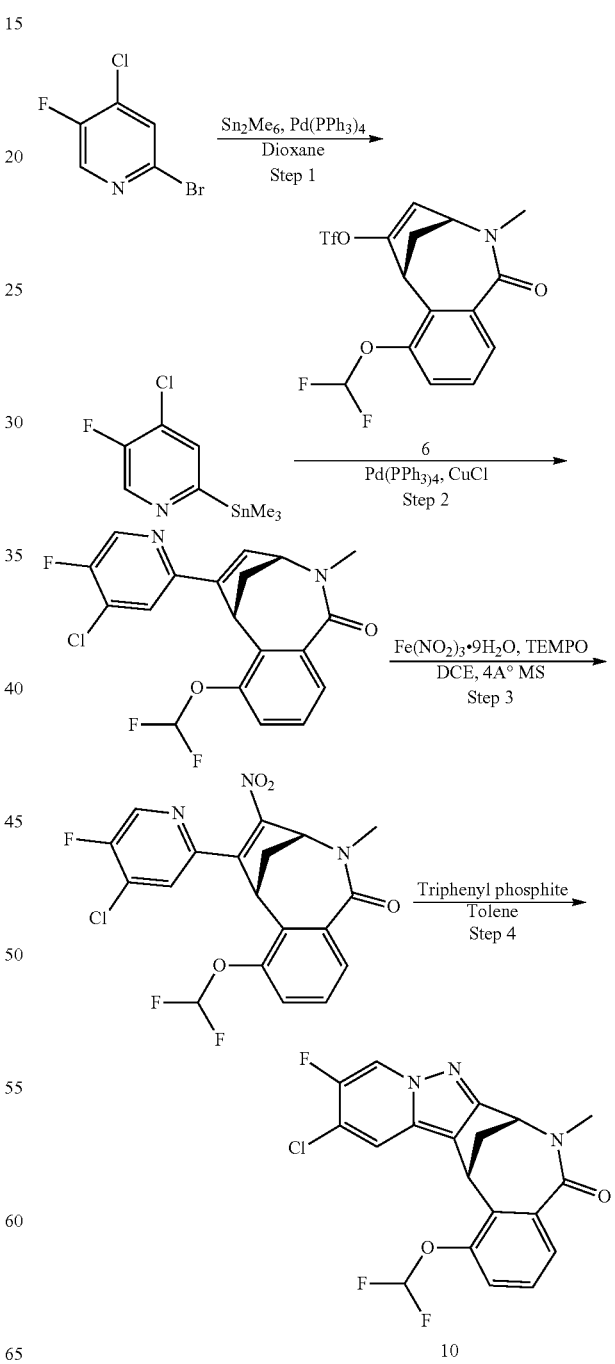

10

Step 1: A solution of 2-bromo-4-chloro-5-fluoropyridine (1 g, 4.8 mmol, 1.0 equiv), hexamethyldistannane (7.8 g, 23.8 mmol, 5.0 equiv) and Pd(PPh$_3$)$_4$ (549 mg, 0.48 mmol, 0.1 equiv) in dioxane (15 mL) was stirred at 120° C. for 1 hr under nitrogen atmosphere. The reaction was quenched with H$_2$O (30 mL) at room temperature. The resulting mixture was extracted with EtOAc (2×30 mL). The combined organic layers were washed with brine (1×30 mL), dried over anhydrous Na$_2$SO$_4$. After filtration, the filtrate was concentrated under reduced pressure. This resulted in 4-chloro-5-fluoro-2-(trimethylstannyl)pyridine (1 g, crude) as a black solid. The crude product was used in the next step directly without further purification. LCMS (ESI, m/z): 293.90 [M+H]$^+$.

Step 2: A solution of 4-chloro-5-fluoro-2-(trimethylstannyl) pyridine (925 mg, 3.2 mmol, 2.0 equiv) and Intermediate 6 (650 mg, 1.6 mmol, 1.0 equiv), CuCl (234 mg, 2.4 mmol, 1.5 equiv) and Pd(PPh$_3$)$_4$ (272.6 mg, 0.24 mmol, 0.15 equiv) in toluene (15 mL) was stirred at 100° C. for 1 hr under nitrogen atmosphere. The resulting mixture was extracted with EtOAc (2×30 mL). The combined organic layers were washed with brine (1×20 mL), dried over anhydrous Na$_2$SO$_4$. After filtration, the filtrate was concentrated under reduced pressure. The residue was purified by Prep-TLC (PE/EA 1:1) to afford (3R,6S)-5-(4-chloro-5-fluoropyridin-2-yl)-7-(difluoromethoxy)-2-methyl-3,6-dihydro-3,6-methanobenzo[c]azocin-1 (2H)-one (300 mg, 48.32%) as a white solid. LCMS (ESI, m/z): 395.10 [M+H]$^+$.

Step 3: A solution of molecular sieves 4 A (960 mg), (3R,6S)-5-(4-chloro-5-fluoropyridin-2-yl)-7-(difluoromethoxy)-2-methyl-3,6-dihydro-3,6-methanobenzo[c]azocin-1 (2H)-one (320 mg, 0.8 mmol, 1.0 equiv), iron(III) nitrate nonahydrate (660 mg, 1.6 mmol, 2.0 equiv) and TEMPO (25 mg, 0.16 mmol, 0.2 equiv) in DCE (10 mL) was stirred at 80° C. for 2 hrs under nitrogen atmosphere. The resulting mixture was filtered; the filter cake was washed with DCM (2×20 mL). The filtrate was concentrated under reduced pressure. The residue was purified by Prep-TLC (PE/EA 1:1) to afford (3R,6S)-5-(4-chloro-5-fluoropyridin-2-yl)-7-(difluoromethoxy)-2-methyl-4-nitro-3,6-dihydro-3,6-methanobenzo[c]azocin-1 (2H)-one (220 mg, 61.7%) as a yellow solid. LCMS (ESI, m/z): 440.05 [M+H]$^+$.

Step 4: To a stirred solution of (3R,6S)-5-(4-chloro-5-fluoropyridin-2-yl)-7-(difluoromethoxy)-2-methyl-4-nitro-3,6-dihydro-3,6-methanobenzo[c]azocin-1 (2H)-one (500 mg, 1.1 mmol, 1 equiv) and triphenyl phosphite (1.76 mg, 5.7 mmol, 5 equiv) in toluene (10 mL) was stirred at 100° C. for 1 hr under nitrogen atmosphere. The resulting mixture was concentrated under vacuum. The residue was purified by silica gel column chromatography, eluted with PE/EA (1:1) to afford Intermediate 10 (150 mg, 32.4%) as a yellow solid. LCMS (ESI, m/z): 408.15 [M+H]$^+$.

Intermediate 11

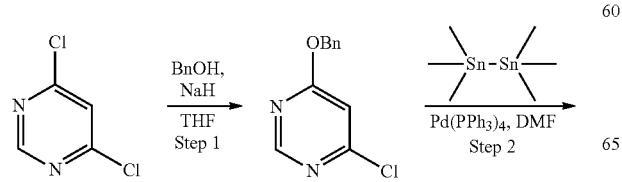

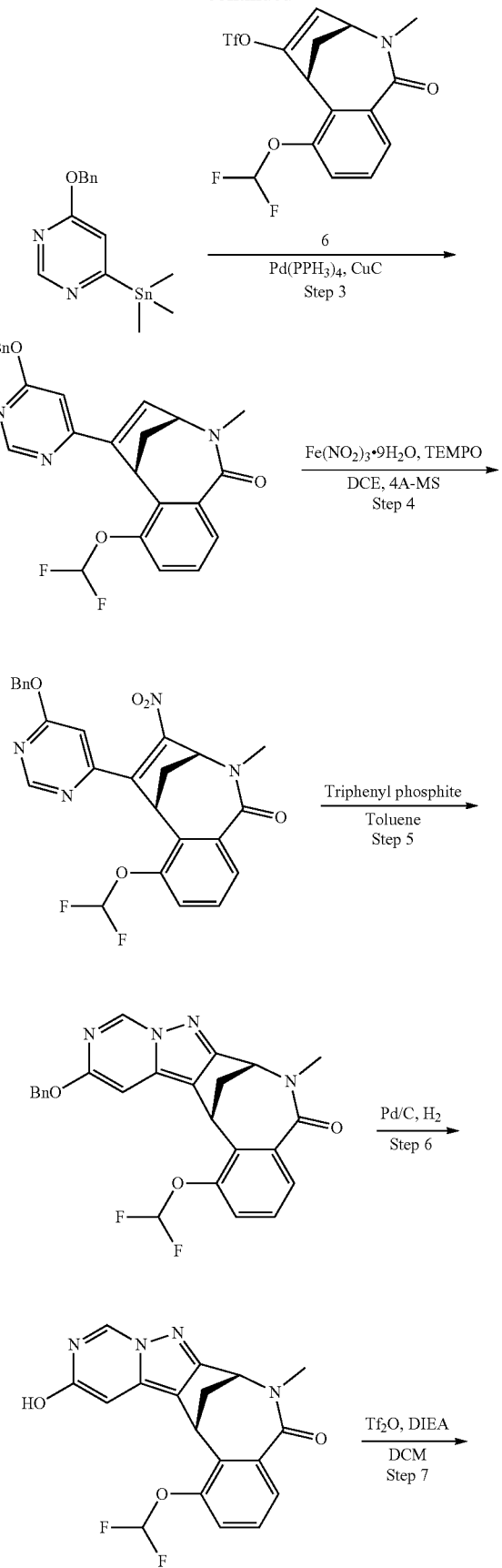

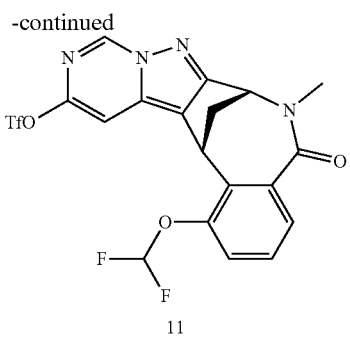

11

Step 1: A solution of benzyl alcohol (39.9 g, 369.2 mmol, 1.1 equiv) in THF (250 mL) was treated with NaH (16.1 g, 402.8 mmol, 1.2 equiv, 60%) at 0° C. for 30 min followed by the addition of 4,6-dichloropyrimidine (50 g, 335.6 mmol, 1.0 equiv) in portions at 0° C. The resulting mixture was stirred at room temperature for 2 hrs under air atmosphere. The reaction was quenched by the addition of sat. NH$_4$Cl (5 mL) at 0° C. The reaction mixture was diluted with water (100 mL), and the aqueous phase was extracted with EA (3×100 mL). The combined organic layers were washed with brine, dried over Na$_2$SO$_4$, filtered, and concentrated in vacuo. The residue was purified by reverse flash chromatography (column, C18 silica gel; mobile phase, MeCN in water (TFA, 0.1%), 50% to 90% gradient in 10 min; detector, UV 220 nm) to afford 4-(benzyloxy)-6-chloropyrimidine (30 g, 40.5%) as yellow oil. LCMS (ESI, m/z): 220.95 [M+H]$^+$.

Step 2: A solution of 4-(benzyloxy)-6-chloropyrimidine (24 g, 108.8 mmol, 1 equiv), hexamethyldistannane (35.6 g, 108.8 mmol, 1 equiv) in toluene (150 mL) was treated with Pd(PPh$_3$)$_4$ (12.6 g, 10.9 mmol, 0.1 equiv) at room temperature under nitrogen atmosphere. The resulting mixture was stirred at 120° C. for 2 hrs under nitrogen atmosphere. The reaction mixture was diluted with water (40 mL), and the aqueous phase was extracted with EA (3×60 mL). The combined organic layers were washed with brine, dried over Na$_2$SO$_4$, filtered, and concentrated in vacuo to afford 4-(benzyloxy)-6-(trimethylstannyl)pyrimidine (23 g) as a brown semi-solid. LCMS (ESI, m/z): 349.05, 351.05 [M+H]$^+$.

Step 3: A solution of Intermediate 6 (15 g, 12.1 mmol, 1 equiv), Pd(PPh$_3$)$_4$ (4.2 g, 1.2 mmol, 0.1 equiv), CuCl (3.6 g, 12.1 mmol, 1.0 equiv) and 4-(benzyloxy)-6-(trimethylstannyl)pyrimidine (25.3 g, 24.2 mmol, 2 equiv) in toluene (300 mL) was stirred at 100° C. for overnight under nitrogen atmosphere. The resulting mixture was concentrated under reduced pressure. The residue was dissolved in DCM (500 mL). The resulting mixture was filtered, the filter cake was washed with DCM (3×500 mL). The filtrate was concentrated under reduced pressure. The residue was purified by silica gel column chromatography, eluted with PE/EA (3:2) to afford (3R,6S)-5-(6-(benzyloxy)pyrimidin-4-yl)-7-(difluoromethoxy)-2-methyl-3,6-dihydro-3,6-methanobenzo[c]azocin-1 (2H)-one (11.5 g, 32.9%) as a light yellow solid. LCMS (ESI, m/z): 350.25 [M+H]$^+$.

Step 4: A solution of (3R,6S)-5-(6-(benzyloxy)pyrimidin-4-yl)-7-(difluoromethoxy)-2-methyl-3,6-dihydro-3,6-methanobenzo[c]azocin-1 (2H)-one (11.5 g, 25.6 mmol, 1 equiv) in DCE (230 mL) was treated with iron(III) nitrate nonahydrate (20.7 g, 51.2 mmol, 2 equiv) at room temperature for 1 min under nitrogen atmosphere followed by the addition of 2,2,6,6-tetramethylpiperidin-1-olate (799.6 mg, 5.1 mmol, 0.2 equiv) and 4 A-MS (34.5 g) in portions at room temperature. The resulting mixture was stirred at 80° C. for 16 hr. The resulting mixture was filtered, the filter cake was washed with DCM (3×200 mL). The filtrate was concentrated under reduced pressure. The residue was purified by silica gel column chromatography, eluted with PE/EA (13:7) to afford (3R,6S)-5-(6-(benzyloxy)pyrimidin-4-yl)-7-(difluoromethoxy)-2-methyl-4-nitro-3,6-dihydro-3,6-methanobenzo[c]azocin-1 (2H)-one (6.2 g, 49%) as a light yellow solid. LCMS (ESI, m/z): 495.25 [M+H]$^+$.

Step 5: A solution of (3R,6S)-5-(6-(benzyloxy)pyrimidin-4-yl)-7-(difluoromethoxy)-2-methyl-4-nitro-3,6-dihydro-3,6-methanobenzo[c]azocin-1 (2H)-one (6.2 g, 12.5 mmol, 1 equiv) in toluene (124 mL) was treated with triphenyl phosphite (11.7 g, 37.6 mmol, 3 equiv) at 100° C. for 1 hr under nitrogen atmosphere. The resulting mixture was concentrated under reduced pressure. The residue was purified by silica gel column chromatography, eluted with PE/EA (1:1) to afford (7R,14S)-12-(benzyloxy)-1-(difluoromethoxy)-6-methyl-6,7-dihydro-7,14-methanobenzo[c]pyrimido[1',6':1,5]pyrazolo[4,3-f]azocin-5 (14H)-one (2.0 g, 35.5%) as a light brown solid. LCMS (ESI, m/z): 463.20 [M+H]$^+$.

Step 6: A solution of (7R,14S)-12-(benzyloxy)-1-(difluoromethoxy)-6-methyl-6,7-dihydro-7,14-methanobenzo[c]pyrimido[1',6':1,5]pyrazolo[4,3-f]azocin-5 (14H)-one (2 g, 4.3 mmol, 1 equiv) and Pd/C (920.5 mg, 0.87 mmol, 0.2 equiv, 10%) in ethyl acetate (100 mL) was stirred at room temperature for 2 hrs under hydrogen atmosphere. The resulting mixture was filtered, the filter cake was washed with MeOH:DCM=1:1 (3×50 mL). The filtrate was concentrated under reduced pressure to afford (7R,14S)-1-(difluoromethoxy)-12-hydroxy-6-methyl-6,7-dihydro-7,14-methanobenzo[c]pyrimido[1',6':1,5]pyrazolo[4,3-f]azocin-5 (14H)-one (1.4 g, 86.9%) as a dark yellow solid. LCMS (ESI, m/z): 373.15 [M+H]$^+$.

Step 7: To a stirred mixture of (7R,14S)-1-(difluoromethoxy)-12-hydroxy-6-methyl-6,7-dihydro-7,14-methanobenzo[c]pyrimido[1',6':1,5]pyrazolo[4,3-f]azocin-5 (14H)-one (1.3 g, 3.5 mmol, 1 equiv) and DIEA (1.4 g, 10.5 mmol, 3 equiv) in DCM (26 mL) was added (trifluoromethane)sulfonyl trifluoromethanesulfonate (2.0 g, 7.0 mmol, 2 equiv) at 0° C. under nitrogen atmosphere. The resulting mixture was stirred at room temperature for 2 hr. The aqueous layer was extracted with EtOAc (3×200 mL). The combined organic layers were washed with brine (1×5 mL), dried over anhydrous Na$_2$SO$_4$. After filtration, the filtrate was concentrated under reduced pressure. The residue was purified by Prep-TLC (PE/EA 1:1) to afford (7R,14S)-1-(difluoromethoxy)-6-methyl-5-oxo-5,6,7,14-tetrahydro-7,14-methanobenzo[c]pyrimido[1',6':1,5]pyrazolo[4,3-f]azocin-12-yl trifluoromethanesulfonate (700 mg, 40%) as a light brown solid. LCMS (ESI, m/z): 505.15 [M+H]$^+$.

Intermediate 12-23 prepared using similar procedures.

| Intermediate | Structure |
|---|---|
| 12 | ![structure] |

| Intermediate | Structure |
|---|---|
| 13 | 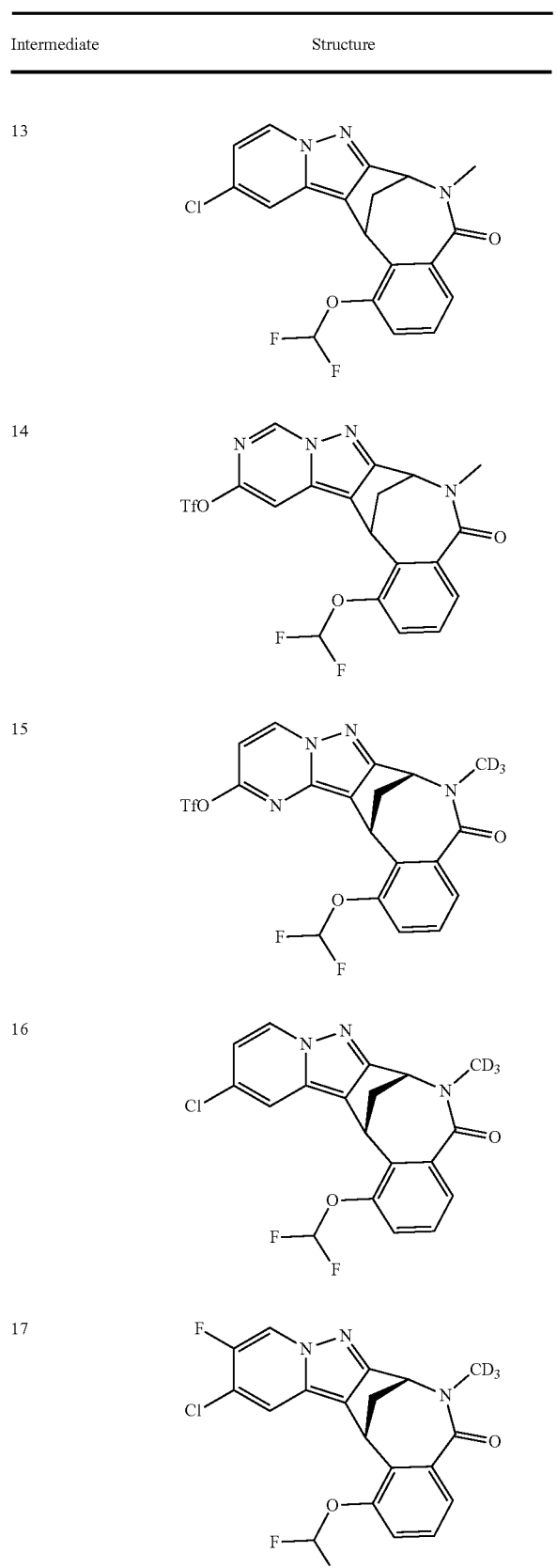 |
| 14 | |
| 15 | |
| 16 | |
| 17 | |
| Intermediate | Structure |
|---|---|
| 18 | 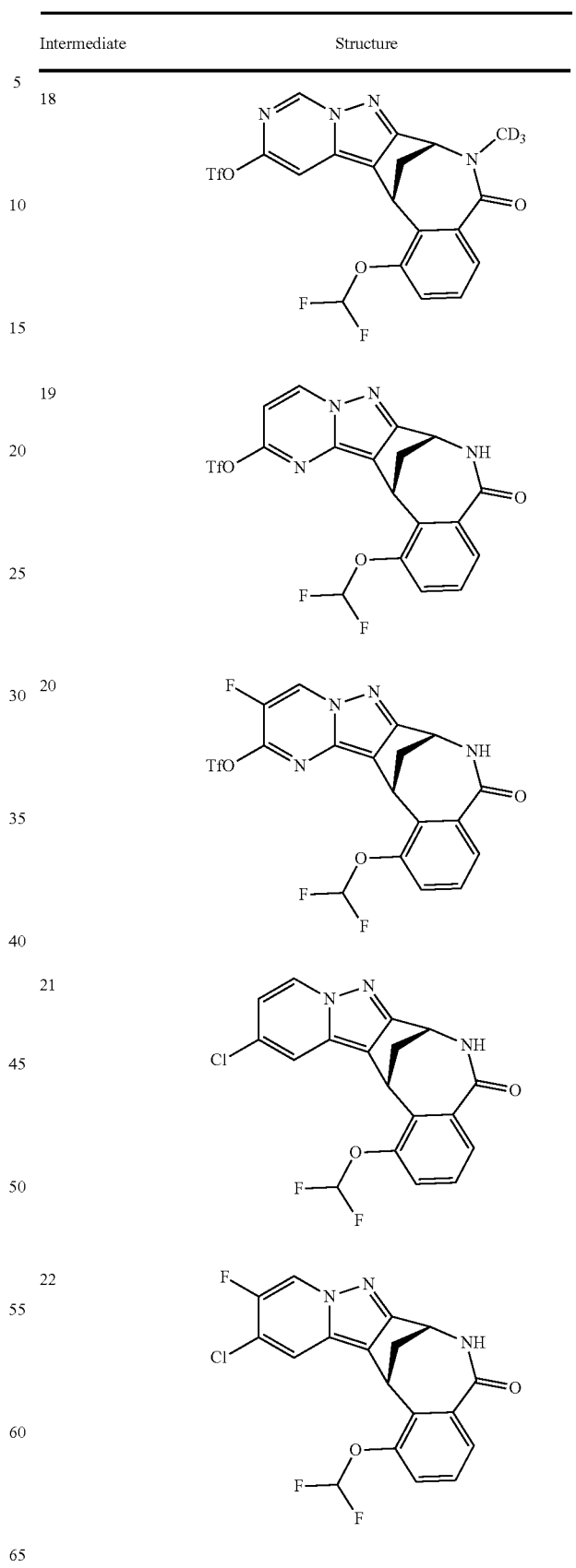 |
| 19 | |
| 20 | |
| 21 | |
| 22 | |

| Intermediate | Structure |
|---|---|
| 23 | 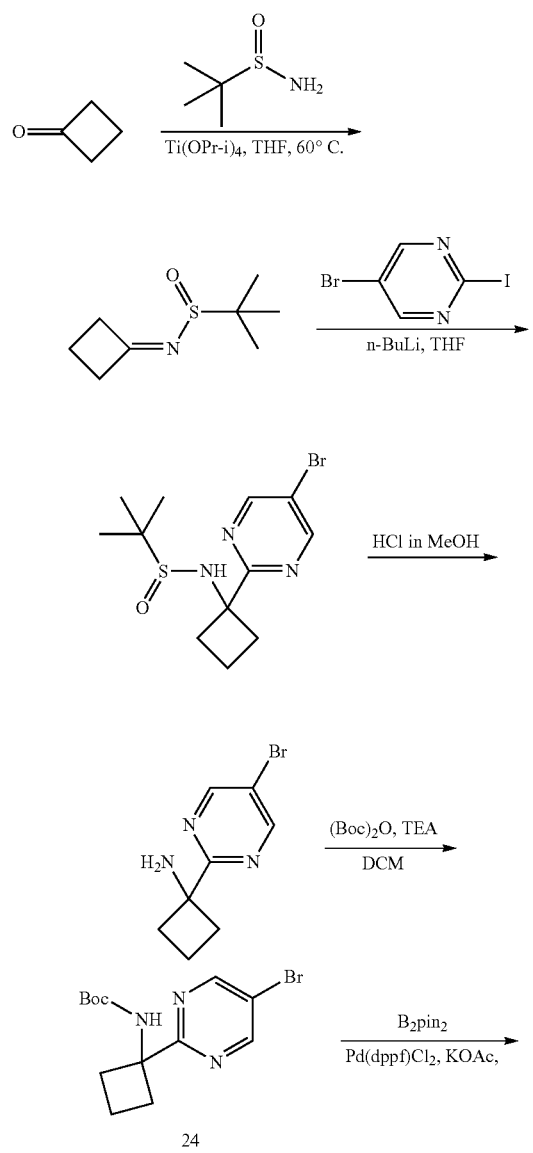 |

Intermediate 24 and 25

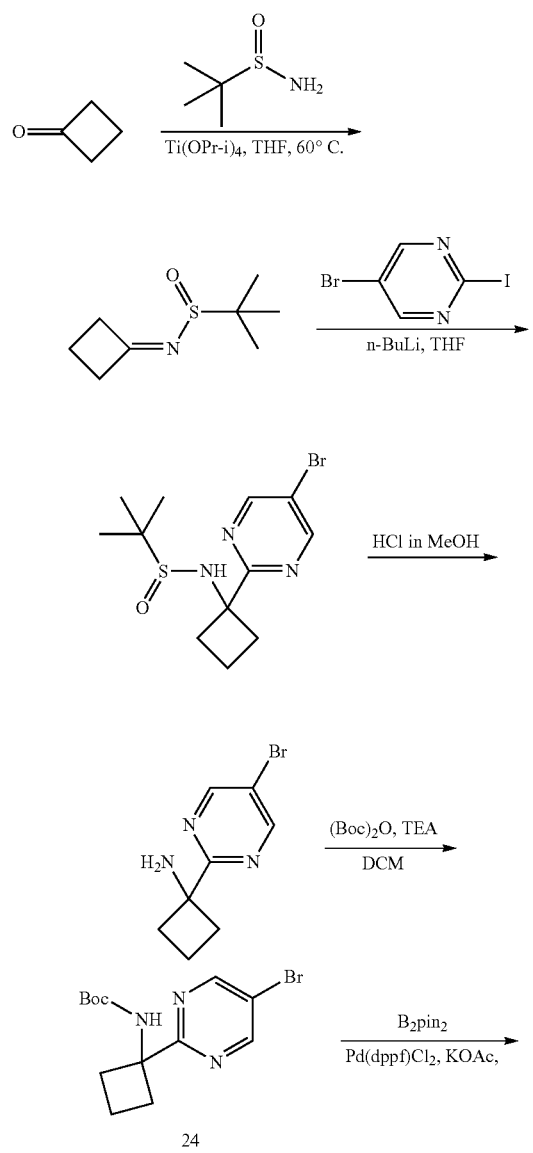

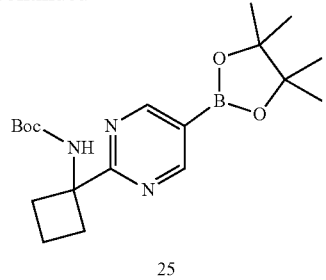

25

Step 1: A solution of cyclobutanone (20 g, 285.3 mmol, 1.0 equiv) and tert-butanesulfinamide (34.6 g, 285.3 mmol, 1.0 equiv) in THF (540 mL) was stirred with Ti(Oi-Pr)4 (128.1 mL, 428.0 mmol, 1.5 equiv) for overnight at 60° C. under nitrogen atmosphere. The resulting mixture was concentrated under vacuum. The residue was dissolved in EtOAc (100 mL). The reaction was quenched by the addition of saturated Na₂CO₃ (aq.) (50 mL) at 0° C. The resulting mixture was filtered, the filter cake was washed with EtOAc (3×400 mL). The filtrate was concentrated under reduced pressure. The resulting mixture was extracted with EtOAc (2×1000 mL). The combined organic layers were dried over anhydrous Na₂SO₄. After filtration, the filtrate was concentrated under reduced pressure. The residue was purified by silica gel column chromatography, eluted with PE/EA (10:1) to afford N-cyclobutylidene-2-methylpropane-2-sulfinamide (34.5 g, 70%) as a light yellow liquid. LCMS (ESI, m/z): 174.10 [M+H]⁺.

Step 2: A solution of 5-bromo-2-iodopyrimidine (57.3 g, 201.1 mmol, 1.01 equiv) in DCM (1225 mL) was treated with n-BuLi in hexanes (81.3 mL, 203.1 mmol, 1.02 equiv) for 10 min at −78° C. under nitrogen atmosphere followed by the addition of N-cyclobutylidene-2-methylpropane-2-sulfinamide (34.5 g, 199.1 mmol, 1 equiv) dropwise at −78° C. The resulting mixture was stirred for overnight at −20° C. under nitrogen atmosphere. The reaction was quenched with Water/Ice at 0° C. The resulting mixture was extracted with DCM (3×500 mL). The combined organic layers were washed dried over anhydrous Na₂SO₄. After filtration, the filtrate was concentrated under reduced pressure. The residue was purified by silica gel column chromatography, eluted with PE/EA (1:1) to afford N-[1-(5-bromopyrimidin-2-yl)cyclobutyl]-2-methylpropane-2-sulfinamide (23.2 g, 35.1%) as a yellow solid. LCMS (ESI, m/z): 334.00 [M+H]⁺.

Step 3: A mixture of N-[1-(5-bromopyrimidin-2-yl)cyclobutyl]-2-methylpropane-2-sulfinamide (23 g, 69.2 mmol, 1 equiv) and HCl(g) in MeOH (23 mL, 757 mmol, 10.9 equiv) in MeOH (230 mL) was stirred for 30 min at room temperature under nitrogen atmosphere. The resulting mixture was concentrated under vacuum. The crude product was used in the next step directly without further purification. This resulted in 1-(5-bromopyrimidin-2-yl)cyclobutan-1-amine (15.7 g, 99%) as a yellow oil. LCMS (ESI, m/z): 229.90 [M+H]⁺.

Step 4: A solution of 1-(5-bromopyrimidin-2-yl)cyclobutan-1-amine (15.7 g, 68.8 mmol, 1 equiv) and TEA (28.7 mL, 206.5 mmol, 3 equiv) in DCM (158 mL) was stirred with Boc₂O (22.5 g, 103.2 mmol, 1.5 equiv) for 1 hr at room temperature under air atmosphere. The resulting mixture was extracted with DCM (3×100 mL). The combined organic layers were washed with NaHCO₃.aq (3×100 mL), dried over anhydrous Na₂SO₄. After filtration, the filtrate was concentrated under reduced pressure. The residue was purified by silica gel column chromatography, eluted with PE/EA (10:1) to afford tert-butyl N-[1-(5-bromopyrimidin-2-yl)cyclobutyl]carbamate (14.7 g, 65.1%) as a light yellow solid. LCMS (ESI, m/z): 329.90 [M+H]+.

Step 5: To a stirred solution of tert-butyl N-[1-(5-bromopyrimidin-2-yl)cyclobutyl]carbamate (1 g, 3.1 mmol, 1 equiv) and bis(pinacolato)diboron (1.2 g, 4.6 mmol, 1.5 equiv) in dioxane (15 mL) were added KOAc (898 mg, 9.1 mmol, 3 equiv) and Pd(dppf)Cl$_2$·DCM (248 mg, 0.31 mmol, 0.1 equiv) in portions at room temperature under nitrogen atmosphere. The resulting mixture was stirred for an additional 2 hrs at 100° C. The resulting mixture was diluted with H$_2$O (30 mL). The resulting mixture was extracted with EtOAc (3×100 mL). The combined organic layers were washed with brine (1×30 mL), dried over anhydrous Na$_2$SO$_4$. After filtration, the filtrate was concentrated under reduced pressure. The residue was purified by Prep-TLC (DCM/MeOH 25:1) to afford tert-butyl N-{1-[5-(4,4,5,5-tetramethyl-1,3,2-dioxaborolan-2-yl)pyrimidin-2-yl]cyclobutyl}carbamate (650 mg, 57%) as a light yellow solid. LCMS (ESI, m/z): 376.10 [M+H]+.

Intermediate 26-28

−78° C. The resulting mixture was stirred for an additional 2 hrs at −78° C. Then the resulting mixture was stirred overnight at room temperature under nitrogen atmosphere. The reaction was quenched with sat. NH$_4$Cl (aq.) at 0° C. The aqueous layer was extracted with EtOAc (3×20 mL). The residue was purified by Prep-TLC (PE/EA 2:1) to afford (3r)-3-(5-bromopyrimidin-2-yl)-3-hydroxy-1-methylcyclobutane-1-carbonitrile (800 mg, 32.6%) as an off-white solid. LCMS (ESI, m/z): 269.95 [M+H]+.

Step 2: 3-(5-bromopyrimidin-2-yl)-3-hydroxy-1-methyl-cyclobutane-1-carbonitrile (1 g) was purified by prep chiral HPLC with the following conditions (Column: JW-CHIRALART Cellulose-SC, 20*250 mm, 5 um; Mobile Phase A: EtOH, Mobile Phase B: Hex (0.5% 2M NH$_3$-MeOH); Flow rate: 20 mL/min; Gradient: 70% B to 70% B in 10 min; Wave Length: 220/254 nm; RT1(min): 5.03; RT2(min): 7.78; Sample Solvent: EtOH:DCM=1:1; Injection Volume: 1.4 mL; Number Of Runs: 10) to afford:

Intermediate 26: (1r, 3r)-3-(5-bromopyrimidin-2-yl)-3-hydroxy-1-methylcyclobutane-1-carbonitrile (trans) (420 mg, 42.00%) as a yellow solid. $^1$H NMR (400 MHz, DMSO-d$_6$) δ 9.07 (s, 2H), 6.16 (s, 1H), 3.27-3.19 (m, 2H), 2.42-2.34 (m, 2H), 1.65 (s, 3H).

Intermediate 27: ((1s, 3s)-3-(5-bromopyrimidin-2-yl)-3-hydroxy-1-methylcyclobutane-1-carbonitrile (cis) (220 mg,

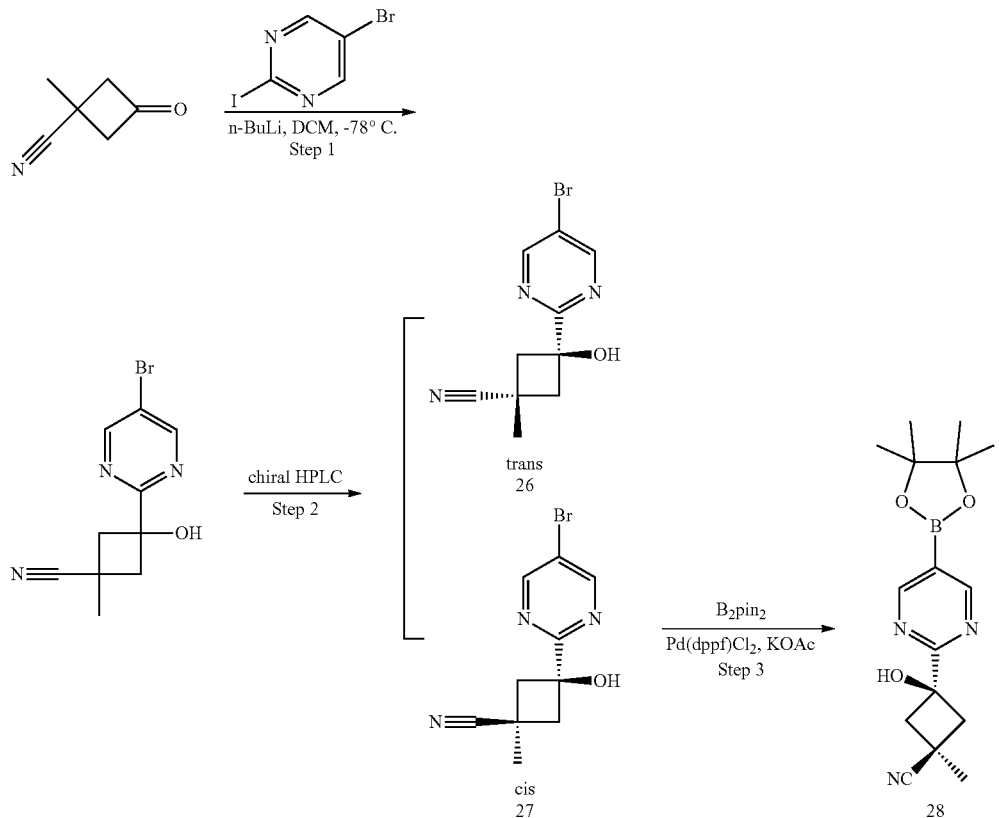

Step 1: 1-methyl-3-oxocyclobutane-1-carbonitrile (1 g, 9.2 mmol, 1 equiv) was dissolved DCM (50 mL) and cooled under nitrogen to −78° C., n-BuLi (4.40 mL, 11 mmol, 1.2 equiv) was added dropwise. The resulting mixture was stirred for 5 min at −78° C. under nitrogen atmosphere. To the above mixture was added 5-bromo-2-iodopyrimidine (3.1 g, 11 mmol, 1.2 equiv) in DCM (50 mL) dropwise at 22.0%) as a yellow solid. $^1$H NMR (400 MHz, DMSO-d$_6$) δ 9.04 (s, 2H), 6.19 (s, 1H), 2.86-2.79 (m, 2H), 2.75-2.68 (m, 2H), 1.40 (s, 3H).

Step 3: A solution of Intermediate 27 (100 mg, 0.37 mmol, 1 equiv), KOAc (109.8 mg, 1.1 mmol, 3 equiv), 4,4,5,5-tetramethyl-2-(4,4,5,5-tetramethyl-1,3,2-dioxaborolan-2-yl)-1,3,2-dioxaborolane (189.4 mg, 0.75 mmol, 2 equiv) in dioxane (3 mL) was stirred for 1 hr at 100° C. under nitrogen atmosphere. The reaction was monitored by TLC. TLC (DCM:MeOH=8:1, Rf=0.3). The resulting mixture was concentrated under reduced pressure. The resulting mixture was concentrated under vacuum. The residue was purified by reversed-phase flash chromatography with the following conditions: column, C18 silica gel; mobile phase, MeCN in Water (0.10% TFA), 10% to 50% gradient in 10 min; detector, UV 254 nm. This resulted in Intermediate 28 (50 mg, 57.5%) as a yellow solid. LCMS (ESI, m/z): 234.20 [M+H]$^+$.

Intermediate 29-31

Step 2: A mixture of 5-bromo-1,2,3-triazine (3 g, 18.8 mmol, 1.0 equiv) in can (100 mL) was added 1-(imino (morpholino)methyl)-3-methylenecyclobutane-1-carbonitrile (4.2 g, 20.6 mmol, 1.1 equiv) at 0° C. The resulting mixture was stirred at 0° C. for 10 min. To the above mixture was stirred for 6 hr at 80° C. The resulting mixture was concentrated under reduced pressure. The residue was purified by silica gel column chromatography, eluted with PE/EA (30/1) to afford 1-(5-bromopyrimidin-2-yl)-3-methylidenecyclobutane-1-carbonitrile (2.7 g, 58%) as an off-white solid. LCMS (ESI, m/z): 250.95 [M+H]$^+$.

Step 3: A mixture of 1-(5-bromopyrimidin-2-yl)-3-methylidenecyclobutane-1-carbonitrile (1.7 g, 6.8 mmol, 1 equiv) in fluoroboric acid (20 mL) at room temperature. The

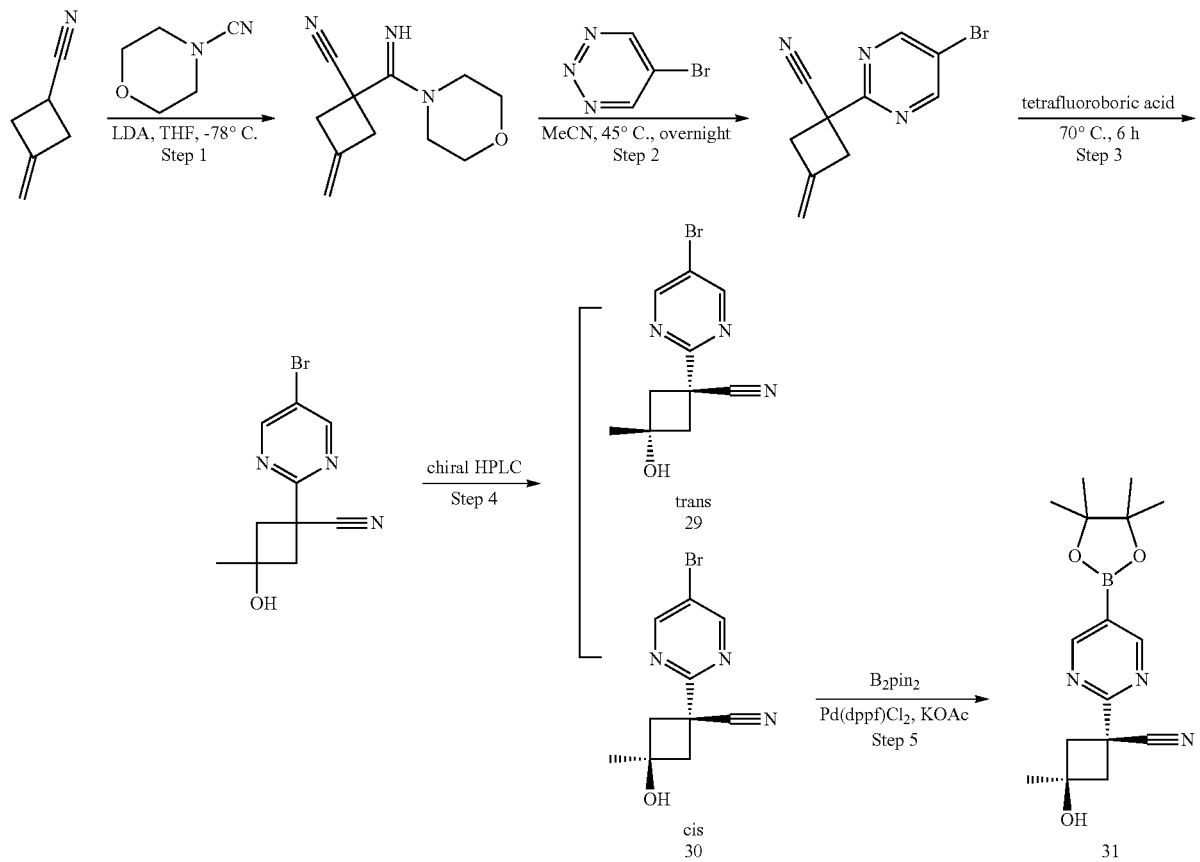

Step 1: A mixture of 3-methylidenecyclobutane-1-carbonitrile (6.5 g, 69.8 mmol, 1 equiv) in THF (100 mL) was added LDA (38.4 mL, 76.8 mmol, 1.1 equiv) at −78° C. under nitrogen atmosphere. The resulting mixture was stirred at −78° C. for 1 Hr prior addition of morpholine-4-carbonitrile (8.6 g, 76.8 mmol, 1.1 equiv). The mixture was stirred for 1 hr at −78° C. The reaction was diluted with water (300 mL) and extracted with EA (3×300 mL). The combined organic layers were washed with brine (2×400 mL), dried over anhydrous Na$_2$SO$_4$. After filtration, the filtrate was concentrated under reduced pressure. The residue was purified by silica gel column chromatography, eluted with DCM/MeOH (30/1) to afford 1-(imino(morpholino)methyl)-3-methylenecyclobutane-1-carbonitrile (5.0 g, 41%) as light-yellow oil. LCMS (ESI, m/z): 206.15 [M+H]$^+$.

resulting mixture was stirred at 70° C. for 7 hr. The reaction was quenched with saturated sodium bicarbonate solution (200 mL) and extracted with EA (3×200 mL). The combined organic layers were washed with brine (2×200 mL), dried over anhydrous Na$_2$SO$_4$. After filtration, the filtrate was concentrated under reduced pressure. The residue was purified by Prep-TLC (PE/EA=1/1) to afford 1-(5-bromopyrimidin-2-yl)-3-hydroxy-3-methylcyclobutane-1-carbonitrile (1.3 g, 71.3%) as yellow oil. LCMS (ESI, m/z): 270.00 [M+H]$^+$.

Step 4: 1-(5-bromopyrimidin-2-yl)-3-hydroxy-3-methylcyclobutane-1-carbonitrile (1 g) was separated by prep chiral HPLC (Column: JW-CHIRAL ART Cellulose-SC, 20*250 mm, 5 um; Mobile Phase A: IPA, Mobile Phase B: Hex (0.5% 2M NH$_3$-MeOH); Flow rate: 20 mL/min; Gradient: 70% B to 70% B in 15 min; Wave length: 220/254 nm;

RT1(min): 6.21; RT2(min): 12.05; Sample Solvent: EtOH; Injection Volume: 2.2 mL; Number Of Runs: 8) to afford Intermediate 29: (1s, 3s)-1-(5-bromopyrimidin-2-yl)-3-hydroxy-3-methylcyclobutane-1-carbonitrile (trans) (503 mg) as an off-white solid. $^1$H NMR (400 MHz, DMSO-$d_6$) δ 9.10 (s, 2H), 2.99-2.87 (m, 2H), 2.82-2.72 (m, 2H), 1.56 (s, 3H).

Intermediate 30: (1r, 3r)-1-(5-bromopyrimidin-2-yl)-3-hydroxy-3-methylcyclobutane-1-carbonitrile (cis) (384 mg) as an off-white solid. $^1$H NMR (400 MHz, DMSO-$d_6$) δ 9.10 (s, 2H), 2.93-2.85 (m, 2H), 2.83-2.76 (m, 2H), 1.21 (s, 3H).

Step 5: A solution of (1r, 3r)-1-(5-bromopyrimidin-2-yl)-3-hydroxy-3-methylcyclobutane-1-carbonitrile (100 mg, 0.37 mmol, 1 equiv) Pd(dppf)Cl$_2$·DCM (30 mg, 0.04 mmol, 0.1 equiv) 4,4,5,5-tetramethyl-2-(4,4,5,5-tetramethyl-1,3,2-dioxaborolan-2-yl)-1,3,2-dioxaborolane (189 mg, 0.75 mmol, 2 equiv), KOAc (110 mg, 1.2 mmol, 3 equiv) in dioxane (3 mL) was stirred for 1 hr at 100° C. under nitrogen atmosphere. The reaction was monitored by LCMS. The resulting mixture was concentrated under reduced pressure. The resulting mixture was concentrated under vacuum. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in Intermediate 31: (1r, 3r)-3-hydroxy-3-methyl-1-(5-(4,4,5,5-tetramethyl-1,3,2-dioxaborolan-2-yl)pyrimidin-2-142yclobuteneane-1-carbonitrile (30 mg, 26%) as a white solid. LCMS (ESI, m/z): 234.05 [M+H]$^+$.

Intermediate 32

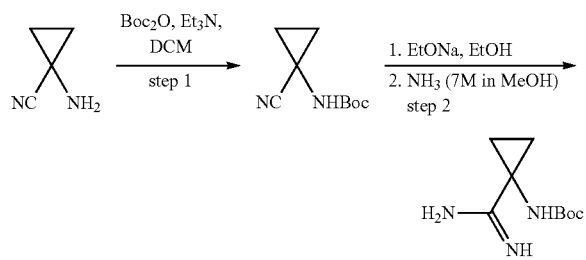

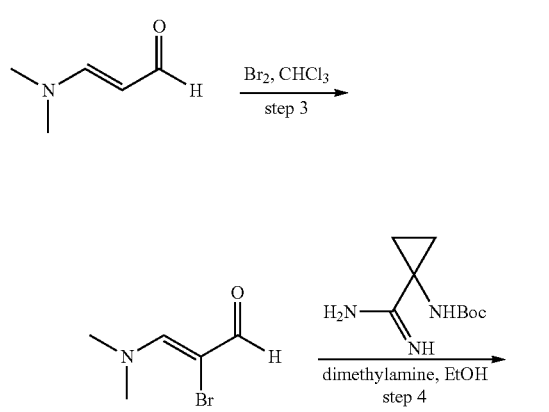

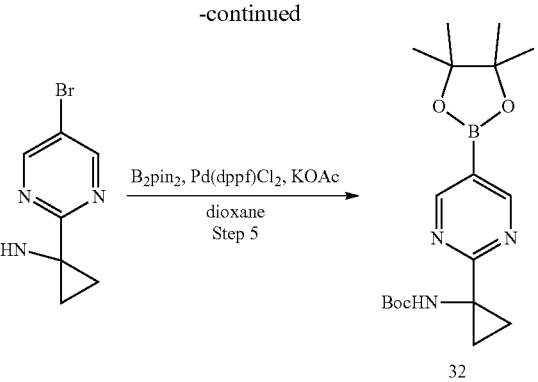

Step 1: A solution of 1-aminocyclopropane-1-carbonitrile (4.5 g, 54.8 mmol, 1 equiv) in DCM (40 mL) was treated with DIEA (21.3 g, 164.42 mmol, 3 equiv) at room temperature under nitrogen atmosphere followed by the addition of Boc$_2$O (23.9 g, 109.6 mmol, 2 equiv) in portions at room temperature. The resulting mixture was stirred for 20 hr at room temperature. The resulting mixture was quenched with 20% citric acid (100 mL) and then the organic phase was separated. The aqueous was extracted with DCM (60 mL×2). The combined organic layers were washed with brine (50 mL) and dried over anhydrous Na$_2$SO$_4$. After filtration, the filtrate was concentrated under reduced pressure. The residue was purified by Prep-TLC (DCM/MeOH=10/1) to afford tert-butyl N-(1-cyanocyclopropyl)carbamate (3.5 g, 31.5%) as an off-white solid.

Step 2: A solution of tert-butyl N-(1-cyanocyclopropyl)carbamate (2.0 g, 11.0 mmol, 1 equiv) in EtOH (35 mL) was treated with EtONa (7.1 g, 22.0 mmol, 2 equiv, 21% w.t.) for 2 hrs at room temperature under nitrogen atmosphere followed by the addition of NH$_4$Cl (2.35 g, 43.90 mmol, 4 equiv) and NH$_3$(g) in MeOH (6.3 mL, 43.9 mmol, 4 equiv) in portions at room temperature. The resulting mixture was stirred for 16 hr at room temperature. The resulting mixture was filtered, and the filter cake was washed with EtOH (35 mL×2). The filtrate was concentrated under reduced pressure. The residue was triturated with EtOAc (15 mL). The precipitated solids were collected by filtration and washed with EtOAc (10 mL) to afford tert-butyl N-(1-carbamimidoylcyclopropyl)carbamate (1.4 g, 57.6%) as an off-white solid.

Step 3: A solution of (2E)-3-(dimethylamino)prop-2-enal (5 g, 50.4 mmol, 1 equiv) in CHCl$_3$ (40 mL) was treated with Br$_2$ (16.1 g, 100.9 mmol, 2 equiv) dropwise at room temperature under nitrogen atmosphere. The resulting mixture was stirred for 30 min at room temperature. The resulting mixture was diluted with DCM (20 mL). The reaction was quenched by the addition of sat. Na$_2$S$_2$O$_3$ solution (50 mL) at room temperature. The organic phase was separated and the aqueous was extracted with DCM (2×20 mL). The combined organic layers were washed with brine (20 mL) and dried over anhydrous Na$_2$SO$_4$. After filtration, the filtrate was concentrated under reduced pressure. The residue was purified by silica gel column chromatography, eluted with PE/EA (1:2) to afford (2Z)-2-bromo-3-(dimethylamino)prop-2-enal (4 g, 40.1%) as a light brown oil.

Step 4: A solution of (2Z)-2-bromo-3-(dimethylamino)prop-2-enal (500 mg, 2.8 mmol, 1 equiv) in EtOH (3 mL) was treated with tert-butyl N-(1-carbamimidoylcyclopropyl)carbamate (839.4 mg, 4.21 mmol, 1.5 equiv), dimethylamine (2 M in THF) (1.8 mL, 3.7 mmol, 1.3 equiv) at room temperature under nitrogen atmosphere. The resulting mixture was stirred for an additional 20 hr at 70° C. The reaction mixture was concentrated in vacuo to give a residue. The residue was purified by reversed-phase flash chromatography with the following conditions: column, C18 silica gel; mobile phase, MeCN in Water (0.1% TFA), 10% to 50% gradient in 10 min; detector, UV 254 nm to afford tert-butyl (1-(5-bromopyrimidin-2-yl)cyclopropyl)carbamate (400 mg, 40.8%) as a brown oil.

Step 5: A solution of tert-butyl (1-(5-bromopyrimidin-2-yl)cyclopropyl)carbamate (100 mg, 0.31 mmol, 1 equiv) in dioxane (1 mL) was treated with KOAc (93.7 mg, 0.95 mmol, 3 equiv) at room temperature followed by the addition of 4,4,5,5-tetramethyl-2-(4,4,5,5-tetramethyl-1,3,2-dioxaborolan-2-yl)-1,3,2-dioxaborolane (161.7 mg, 0.63 mmol, 2 equiv) and Pd(dppf)Cl$_2$ (23.3 mg, 0.032 mmol, 0.1 equiv) in portions at room temperature. The resulting mixture was stirred for 1 hr at 100° C. under nitrogen atmosphere. The resulting mixture was washed with NH$_4$Cl (3×5 mL). The resulting mixture was extracted with EA (3×20 ml). The combined organic layers were washed with brine (3×10 mL), dried over anhydrous Na$_2$SO$_4$. After filtration, the filtrate was concentrated under reduced pressure to afford Intermediate 32 (266 mg, crude) as a dark yellow solid. LCMS (ESI, m/z): 362.10 [M+H]$^+$.

Intermediate 33-35 propane-2-sulfinamide (3 g, 27.5 mmol, 1 equiv) in THF (180 mL) was stirred with Ti(Oi-Pr)$_4$ (12 mL, 41.2 mmol, 1.5 equiv) overnight at 75° C. under nitrogen atmosphere. The resulting mixture was concentrated under vacuum. The reaction was quenched by the addition of water (200 mL) at room temperature. The residue was dissolved in EtOAc (250 mL). The resulting mixture was filtered, the filter cake was washed with EtOAc (5×100 mL). The filtrate was concentrated under reduced pressure. The residue was purified by silica gel column chromatography, eluted with PE/EA (2:1) to afford (R)—N-(3-cyano-3-methylcyclobutylidene)-2-methylpropane-2-sulfinamide (5 g, 85.7%) as a white solid. LCMS (ESI, m/z): 213.10 [M+H]$^+$.

Step 2: A solution of 5-bromo-2-iodopyrimidine (5 g, 19.8 mmol, 1.2 equiv) in DCM (400 mL) was treated with butyllithium (8 mL, 19.8 mmol, 1.2 equiv) for 10 min at −78° C. under nitrogen atmosphere followed by the addition of (R)—N-(3-cyano-3-methylcyclobutylidene)-2-methylpropane-2-sulfinamide (4 g, 16.5 mmol, 1 equiv) for 10 min at −78° C. The resulting mixture was stirred for 2 hrs at −78° C. The resulting mixture was stirred for 3 hr at room temperature under nitrogen atmosphere. The reaction was quenched by the addition of sat. NH$_4$Cl (aq.) (500 mL) at 0° C. The resulting mixture was extracted with DCM (3×400 mL). The combined organic layers were washed with brine (2×400 mL), dried over anhydrous Na$_2$SO$_4$. After filtration, the filtrate was concentrated under reduced pressure. The

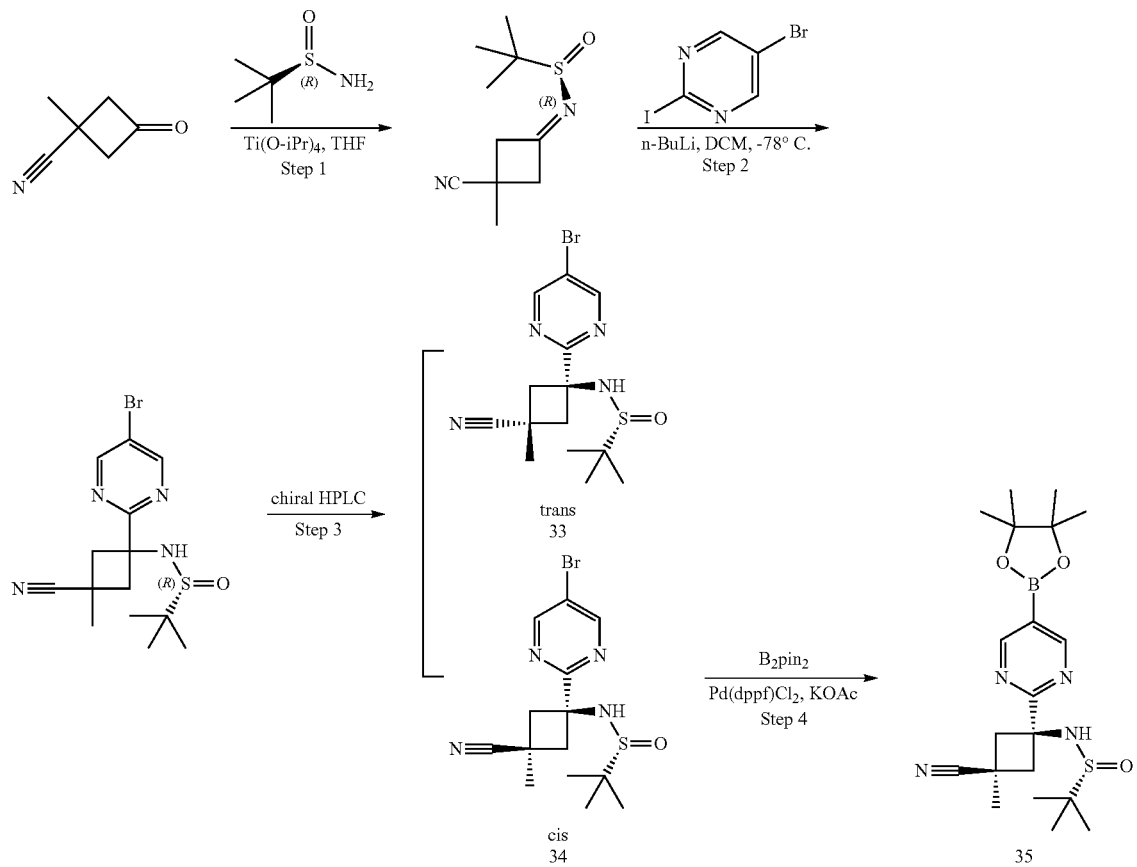

residue was purified by reversed-phase flash chromatography with the following conditions: column, C18 silica gel;

Step 1: A solution of 1-methyl-3-oxocyclobutane-1-carbonitrile (3 g, 27.5 mmol, 1 equiv) and (R)-2-methylmobile phase, MeCN in Water (0.1% NH₃·H₂O), 10% to 60% gradient in 10 min; detector, UV 254 nm. This resulted in (R)—N-[1-(5-bromopyrimidin-2-yl)-3-cyano-3-methylcyclobutyl]-2-methylpropane-2-sulfinamide) (700 mg, 8.0%) as a yellow oil. LCMS (ESI, m/z): 373.05 [M+H]⁺.

Step 3: The crude product (700 mg) was purified by Prep-HPLC with the following conditions (Column: CHIRALPAKIA3; Mobile Phase A: Hex (0.1% DEA): (IPA: MeOH=1:1)=90:10; Flow rate: 1 mL/min mL/min; Gradient: isocratic; Injection Volume: 2 ul mL) to afford Intermediate 33: (R)—N-((1r,3R)-1-(5-bromopyrimidin-2-yl)-3-cyano-3-methylcyclobutyl)-2-methylpropane-2-sulfinamide (320 mg, 45.7%) as a white solid.

Intermediate 33 (trans): ¹H NMR (400 MHz, DMSO-d₆) δ 9.08 (d, J=1.6 Hz, 2H), 6.08 (s, 1H), 3.35-3.31 (m, 2H), 2.74-2.55 (m, 2H), 1.60 (s, 3H), 1.06 (s, 9H). LCMS (ESI, m/z): 373.05 [M+H]⁺.

Intermediate 34 (cis): ((R)—N-((1s,3S)-1-(5-bromopyrimidin-2-yl)-3-cyano-3-methylcyclobutyl)-2-methylpropane-2-sulfinamide (180 mg, 25.7%). ¹H NMR (400 MHz, DMSO-d₆) δ 9.02 (s, 2H), 6.10 (s, 1H), 3.02-2.99 (m, 1H), 2.92 (d, J=1.9 Hz, 2H), 2.78 (d, J=12.6 Hz, 1H), 1.37 (s, 3H), 1.12 (s, 9H).

Step 4: To a stirred solution of Intermediate 34 (100 mg, 0.27 mmol, 1 equiv) and 4,4,5,5-tetramethyl-2-(4,4,5,5-tetramethyl-1,3,2-dioxaborolan-2-yl)-1,3,2-dioxaborolane (137 mg, 0.538 mmol, 2 equiv) in dioxane (2 mL) were added KOAc (80 mg, 0.81 mmol, 3 equiv) and Pd(dppf)Cl₂·DCM (22 mg, 0.027 mmol, 0.1 equiv) in portions at room temperature under nitrogen atmosphere. The resulting mixture was stirred for 2 hrs at 110° C. under nitrogen atmosphere. The resulting mixture was extracted with EtOAc (3×10 mL). The combined organic layers were washed with brine (1×10 mL), dried over anhydrous Na₂SO₄. After filtration, the filtrate was concentrated under reduced pressure to afford Intermediate 35 (60 mg, 54.8%) as a black solid. LCMS (ESI, m/z): 419.22 [M+H]⁺.

Intermediate 36-38

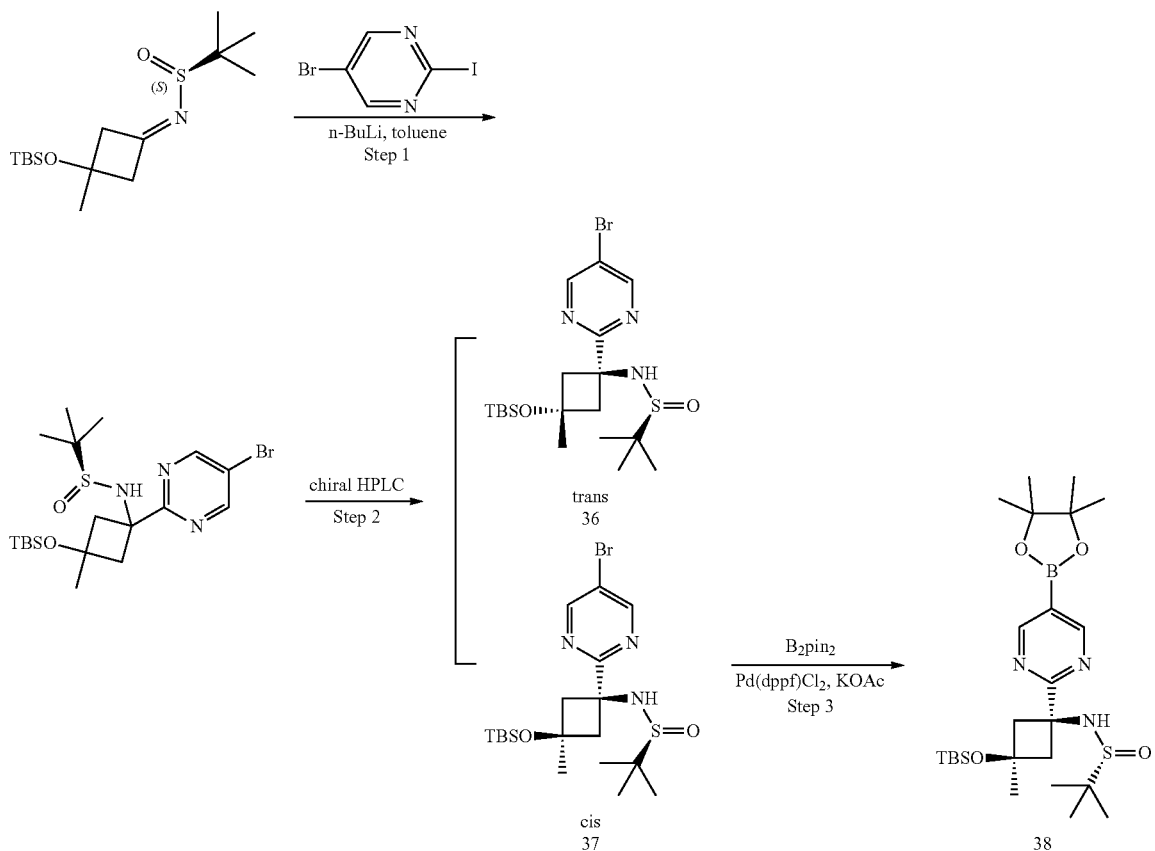

Step 1: A solution of 5-bromo-2-iodopyrimidine (1.38 g, 4.9 mmol, 1.1 equiv) in Toluene (30 mL) was treated with n-butyllithium (310. mg, 4.7 mmol, 1.1 equiv) for 20 min at −50° C. under nitrogen atmosphere. To the above mixture was added (S)—N-(3-((tert-butyldimethylsilyl)oxy)-3-methylcyclobutylidene)-2-methylpropane-2-sulfinamide (1.4 g, 4.4 mmol, 1 equiv) in toluene (30 mL) over 5 min at −50° C. The resulting mixture was stirred for an additional 2 hrs at room temperature. The reaction was quenched with sat. NH₄Cl (aq.) at 0° C. The resulting mixture was extracted with EtOAc (3×30 mL). The combined organic layers were washed with brine (2×20 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in (S)—N-(1-(5-bromopyrimidin-2-yl)-3-((tert-butyldimethylsilyl)oxy)-3-methylcyclobutyl)-2-methylpropane-2-sulfinamide (270 mg, 12.9%) as a yellow solid. LCMS (ESI, m/z): 476.10 [M+H]⁺.

Step 2: (S)—N-(1-(5-bromopyrimidin-2-yl)-3-((tert-butyldimethylsilyl)oxy)-3-methylcyclobutyl)-2-methylpropane-2-sulfinamide (270 mg) was purified by Prep-HPLC with the following conditions (Column: CHIRALPAKIG3; Mobile Phase A: Hex (0.1% DEA):IPA=95:5; Flow rate: 1 mL/min mL/min; Gradient: isocratic; Injection Volume: 2 ul mL) to afford:

Intermediate 36 (trans): ((S)—N-((1r,3S)-1-(5-bromopyrimidin-2-yl)-3-((tert-butyldimethylsilyl)oxy)-3-methylcyclobutyl)-2-methylpropane-2-sulfinamide (64 mg, 23.7%) as a white solid. $^1$H NMR (400 MHz, DMSO-$d_6$) δ 8.98 (s, 2H), 5.78 (s, 1H), 3.03 (d, J=12.7 Hz, 1H).

Intermediate 37 (cis): ((S)—N-((1s,3R)-1-(5-bromopyrimidin-2-yl)-3-((tert-butyldimethylsilyl)oxy)-3-methylcyclobutyl)-2-methylpropane-2-sulfinamide (110 mg, 40.7%) as a white solid. $^1$H NMR (400 MHz, DMSO-$d_6$) δ 9.02 (s, 2H), 5.83 (s, 1H), 3.17-3.09 (m, 1H), 2.96-2.88 (m, 1H), 2.65 (d, J=12.2 Hz, 1H), 2.60 (d, J=12.2 Hz, 1H), 1.04 (d, J=3.5 Hz, 12H), 0.87 (s, 9H), 0.08 (s, 6H).

Step 3: A solution of Intermediate 37 (60 mg, 0.13 mmol, 1 equiv) and 4,4,5,5-tetramethyl-2-(tetramethyl-1,3,2-dioxaborolan-2-yl)-1,3,2-dioxaborolane (63.94 mg, 0.25 mmol, 2 equiv) in dioxane (1 mL) was treated with KOAc (37.07 mg, 0.38 mmol, 3 equiv) for 1 hr at room temperature under nitrogen atmosphere followed by the addition of Pd(dppf)Cl$_2$·DCM (20.51 mg, 0.03 mmol, 0.2 equiv) at room temperature. The resulting mixture was stirred for 2 hrs at 110° C. under nitrogen atmosphere. The resulting mixture was filtered, the filter cake was washed with EtOAc (3×5 mL). The filtrate was concentrated under reduced pressure to afford Intermediate 38 (60 mg, 91.0%) as a black solid. LCMS (ESI, m/z): 524.30 [M+H]$^+$.

Intermediate 39-41

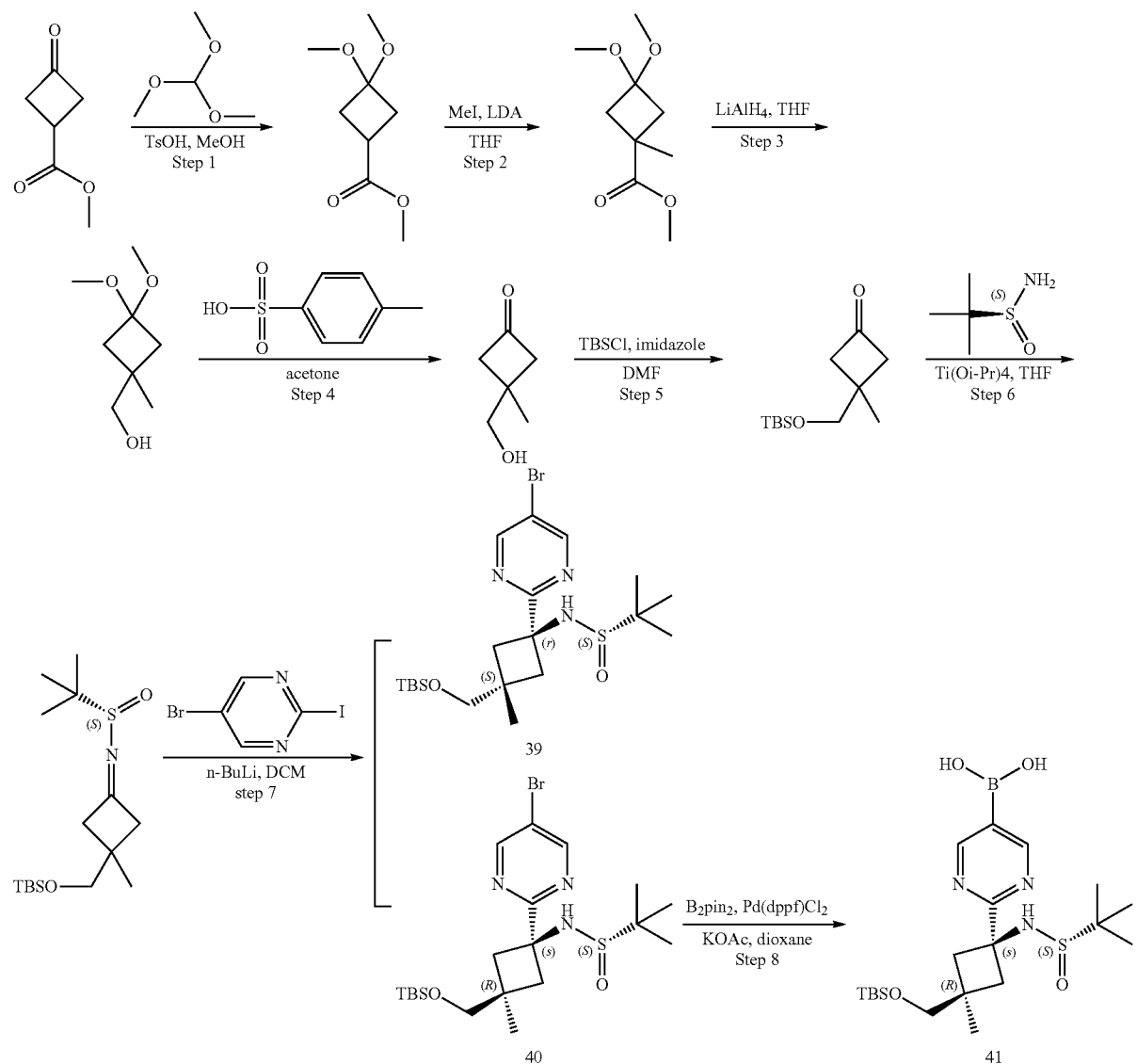

Step 1: A mixture of methyl 3-oxocyclobutane-1-carboxylate (25 g, 195.1 mmol, 1 equiv) in methanol (60 mL) was treated with trimethyl orthoformate (128.1 mL, 1170.7 mmol, 6 equiv) and 4-methylbenzene-1-sulfonic acid (3.4 g, 19.5 mmol, 0.1 equiv) dropwise at room temperature. The resulting mixture was stirred for 1 hr at 70° C. under $N_2$ atmosphere. The mixture was allowed to cool down to room temperature. The crude product was purified by distillation under vacuum and the fraction was collected at room temperature. This resulted in methyl 3,3-dimethoxycyclobutane-1-carboxylate (17 g, 51.49%) as yellow oil.

Step 2: A mixture of methyl 3,3-dimethoxycyclobutane-1-carboxylate (17.5 g, 100.5 mmol, 1 equiv) in THF (175 mL) was treated with lithiobis(propan-2-yl)amine (226 mL, 452.6 mmol, 4.5 equiv) for 30 min at −78° C. under nitrogen atmosphere followed by the addition of MeI (19.3 mL, 310 mmol, 4.5 equiv) dropwise at −78° C. The resulting mixture was stirred for 1 hr at room temperature. The reaction was quenched by the addition of saturated $NH_4Cl$ solution (250 mL). The mixture was extracted with EA (3×300 mL). The combined organic layers were washed with brine (100 ml), dried over $Na_2SO_4$ and concentrated to afford methyl 3,3-dimethoxy-1-methylcyclobutane-1-carboxylate (16 g, 82%) as yellow oil. The crude product was used in the next step directly without further purification.

Step 3: A mixture of methyl 3,3-dimethoxy-1-methylcyclobutane-1-carboxylate (16 g, 85.0 mmol, 1 equiv) in THF (250 mL) was treated with $LiAlH_4$ (3.2 g, 85.0 mmol, 1 equiv) for 1 hr at 0° C. under nitrogen atmosphere. The resulting mixture was stirred for 1 hr at room temperature. The reaction was quenched by the addition of water (3.2 mL), NaOH (10%, 6.4 mL), water (3.2 mL) at 0° C. The resulting mixture was filtered; the filter cake was washed with EA (500 mL). The filtrate was concentrated under reduced pressure. The residue was purified by silica gel column chromatography, eluted with PE:EA (8:1) to afford (3,3-dimethoxy-1-methylcyclobutyl)methanol (6.8 g, 44%) as a yellow oil.

Step 4: A mixture of (3,3-dimethoxy-1-methylcyclobutyl)methanol (6.8 g, 42.4 mmol, 1 equiv) in propan-2-one (68 mL) and $H_2O$ (21 mL) was treated with para-toluene sulfonate (7.3 g, 42.4 mmol, 1 equiv) for 1 hr at 60° C. The mixture was allowed to cool down to room temperature. The aqueous layer was extracted with EA (25 mL). The residue was purified by silica gel column chromatography, eluted with PE:EA=3:1 to afford 3-(hydroxymethyl)-3-methylcyclobutan-1-one (4.7 g, 96.6%) as yellow liquid.

Step 5: A mixture of imidazole (0.47 g, 6.8 mmol, 0.17 equiv) in DMF (47.60 mL) was treated with 3-(hydroxymethyl)-3-methylcyclobutan-1-one (4.7 g, 41.0 mmol, 1 equiv) at room temperature under nitrogen atmosphere followed by the addition of TBSCl (18.5 g, 123.0 mmol, 3 equiv) dropwise at room temperature. The resulting mixture was stirred overnight at room temperature. Diethyl ether was added, followed by brine. The organic layer was separated and washed three times with brine. The organic layer was separated and concentrated in vacuo. This resulted in 3-{[(tert-butyldimethylsilyl)oxy]methyl}-3-methylcyclobutan-1-one (7.6 g, 83.9%) as yellow oil. $^1$H NMR (400 MHz, $CDCl_3$) δ 3.53 (s, 2H), 3.00-2.94 (m, 2H), 2.58-2.52 (m, 2H), 1.23 (s, 1H), 0.85-0.80 (m, 12H).

Step 6: A mixture of 3-{[(tert-butyldimethylsilyl)oxy]methyl}-3-methylcyclobutan-1-one (7.6 g, 23.3 mmol, 1 equiv, 70%), (S)-2-methylpropane-2-sulfinamide (3.4 g, 28.0 mmol, 1.2 equiv) and $Ti(Oi-Pr)_4$ (13.2 g, 46.6 mmol, 2 equiv) in THF (80 mL) was stirred for 2 hrs at room temperature. The mixture quenched with water (60 mL). The mixture was stirred for 15 min. The resulting mixture was filtered; the filter cake was washed with EA (3×50 mL). The filtrate was extracted with EA (3×100 mL). The combined organic layers were washed with brine (50 mL), dried over $Na_2SO_4$ and concentrated under reduced pressure. The residue was purified by silica gel column chromatography, eluted with PE/EA (15:1) to afford (S)—N-(3-(((tert-butyldimethylsilyl)oxy)methyl)-3-methylcyclobutylidene)-2-methylpropane-2-sulfinamide (4.6 g, 59.6%) as yellow green oil. LCMS (ESI, m/z):332.25 [M+H]$^+$.

Step 7: A mixture of 5-bromo-2-iodopyrimidine (2.6 g, 9.0 mmol, 1.2 equiv) in DCM (30 mL) was added n-BuLi (4.0 mL, 10 mmol, 1.3 equiv) drop wise at −78° C. under nitrogen atmosphere. The mixture was stirred for 1 hr at −78° C. And then (S)—N-(3-(((tert-butyldimethylsilyl)oxy)methyl)-3-methylcyclobutylidene)-2-methylpropane-2-sulfinamide (2.5 g, 7.5 mmol, 1 equiv) was added at −78° C. The mixture was stirred for 2 hrs at −78° C., then allowed to warm to room temperature and stirred for 1 hr. The reaction was quenched with sat. $NH_4Cl$ (aq.) at 0° C. The resulting mixture was extracted with DCM (3×100 mL). The combined organic layers were washed with brine, dried over anhydrous $Na_2SO_4$. After filtration, the filtrate was concentrated under reduced pressure. The residue was purified by Prep-TLC (PE/EA=2:1) to afford:

Intermediate 39 (trans) ((S)—N-((1r,3S)-1-(5-bromopyrimidin-2-yl)-3-(((tert-butyldimethylsilyl)oxy)methyl)-3-methylcyclobutyl)-2-methylpropane-2-sulfinamide (300 mg, 8.1%) as an off-white solid.

Intermediate 40 (cis) (S)—N-((1s,3R)-1-(5-bromopyrimidin-2-yl)-3-(((tert-butyldimethylsilyl)oxy)methyl)-3-methylcyclobutyl)-2-methylpropane-2-sulfinamide (250 mg, 6.8%) as an off-white solid Step 8: To a stirred solution of 2-methyl-N-[(1r, 3s)-1-(5-bromopyrimidin-2-yl)-3-{[(tert-butyldimethylsilyl)oxy]methyl}-3-methylcyclobutyl]propane-2-sulfinamide (75 mg, 0.15 mmol, 1 equiv) and 4,4,5,5-tetramethyl-2-(4,4,5,5-tetramethyl-1,3,2-dioxaborolan-2-yl)-1,3,2-dioxaborolane (77 mg, 0.30 mmol, 2 equiv) in 1,4-dioxane (1 mL) were added KOAc (45 mg, 0.46 mmol, 3 equiv) and Pd(dppf)$Cl_2$·DCM (12 mg, 0.01 mmol, 0.1 equiv) in portions at room temperature under nitrogen atmosphere. The resulting mixture was stirred for 2 hrs at 110° C. under nitrogen atmosphere. The resulting mixture was extracted with EtOAc (3×10 mL). The combined organic layers were washed with brine (1×10 mL), dried over anhydrous $Na_2SO_4$. After filtration, the filtrate was concentrated under reduced pressure to afford Intermediate 41 (60 mg, 73.00%) as a black solid. LCMS (ESI, m/z): 456.30 [M+H]$^+$.

Intermediate 42

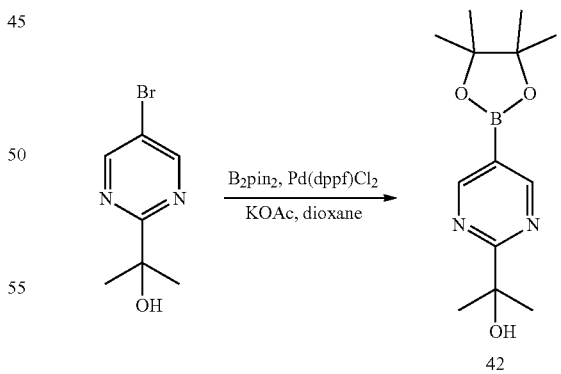

A solution of 2-(5-bromopyrimidin-2-yl)propan-2-ol (100 mg, 0.46 mmol, 1 equiv) in 1,4-dioxane (2 mL) was treated with 4,4,5,5-tetramethyl-2-(4,4,5,5-tetramethyl-1,3,2-dioxaborolan-2-yl)-1,3,2-dioxaborolane (234 mg, 0.92 mmol, 2 equiv), AcOK (135.6 mg, 1.4 mmol, 3 equiv), Pd(dppf)$Cl_2$ (33.7 mg, 0.046 mmol, 0.1 equiv) at 100° C. for 1 hr under nitrogen atmosphere. The resulting mixture was extracted with EtOAc (3×10 mL). The combined organic layers were dried over anhydrous Na$_2$SO$_4$. After filtration, the filtrate was concentrated under reduced pressure. The resulting mixture was extracted with EtOAc (3×10 mL). The combined organic layers were dried over anhydrous Na$_2$SO$_4$. After filtration, the filtrate was concentrated under reduced pressure. The residue was purified by Prep-HPLC (Column: XBridge Prep OBD RP18 Column, 30*150 mm, 5 μm; Mobile Phase A: Water (10 mmol/L NH$_4$HCO$_3$), Mobile Phase B: ACN; Flow rate: 60 mL/min mL/min; Gradient: 35% B to 55% B in 10 min; Wave Length: 254 nm/220 nm nm; RT1(min): 7.5) to afford Intermediate 42 (80 mg, 69.4%) as a white solid. LCMS (ESI, m/z): 264.9 [M+H]$^+$.

Intermediate 43

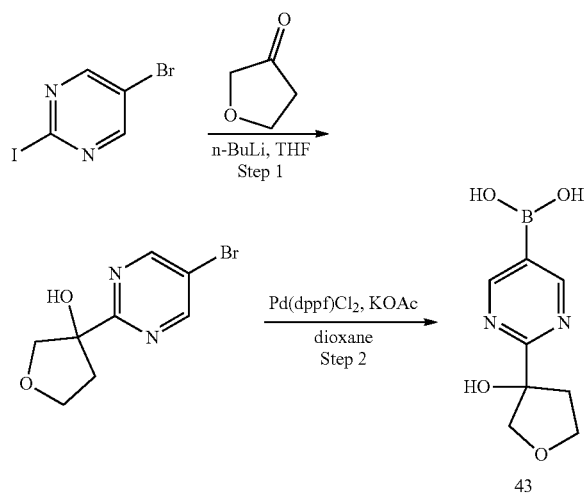

Step 1: A mixture of 5-bromo-2-iodopyrimidine (2 g, 7.0 mmol, 1.0 equiv) in Toluene (25 mL) was added n-BuLi (3.4 mL, 8.4 mmol, 1.2 equiv) drop wise at −78° C. under nitrogen atmosphere. The mixture was stirred for 1H at −78° C. And then dihydrofuran-3-one (2.4 g, 28.1 mmol, 4.0 equiv) was added at −78° C. The mixture was stirred for 1 Hr at −78° C., then allowed to warm to room temperature and stirred for 1 hr. The reaction was quenched with sat. NH$_4$Cl (aq.) at 0° C. The resulting mixture was extracted with EtOAc (3×300 mL). The combined organic layers were washed with brine, dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (0.1% TFA), 10% to 40% gradient in 10 min; detector, UV 220 nm. This resulted in 3-(5-bromopyrimidin-2-yl)oxolan-3-ol (600 mg, 35%) as a brown yellow solid. LCMS (ESI, m/z): 244.95 [M+H]$^+$.

Step 2: A solution of 3-(5-bromopyrimidin-2-yl)oxolan-3-ol (200 mg, 0.82 mmol, 1 equiv) and 4,4,5,5-tetramethyl-2-(4,4,5,5-tetramethyl-1,3,2-dioxaborolan-2-yl)-1,3,2-dioxaborolane (414.5 mg, 1.6 mmol, 2 equiv) in dioxane (2 mL) was treated with KOAc (240.3 mg, 2.5 mmol, 3 equiv) for 2 min at room temperature under nitrogen atmosphere followed by the addition of Pd(dppf)Cl$_2$ (59.7 mg, 0.08 mmol, 0.1 equiv) at room temperature. The resulting mixture was stirred for 1 hr at 100° C. under nitrogen atmosphere. Desired product could be detected by LCMS. The resulting mixture was filtered, the filter cake was washed with dioxane (3×1 mL). The filtrate was concentrated under reduced pressure. The resulting mixture was concentrated under vacuum to afford Intermediate 43 (238 mg, 99.8%) as a black oil. The crude product was used in the next step directly without further purification. LCMS (ESI, m/z): 210.08 [M+H]$^+$.

Intermediate 44-46

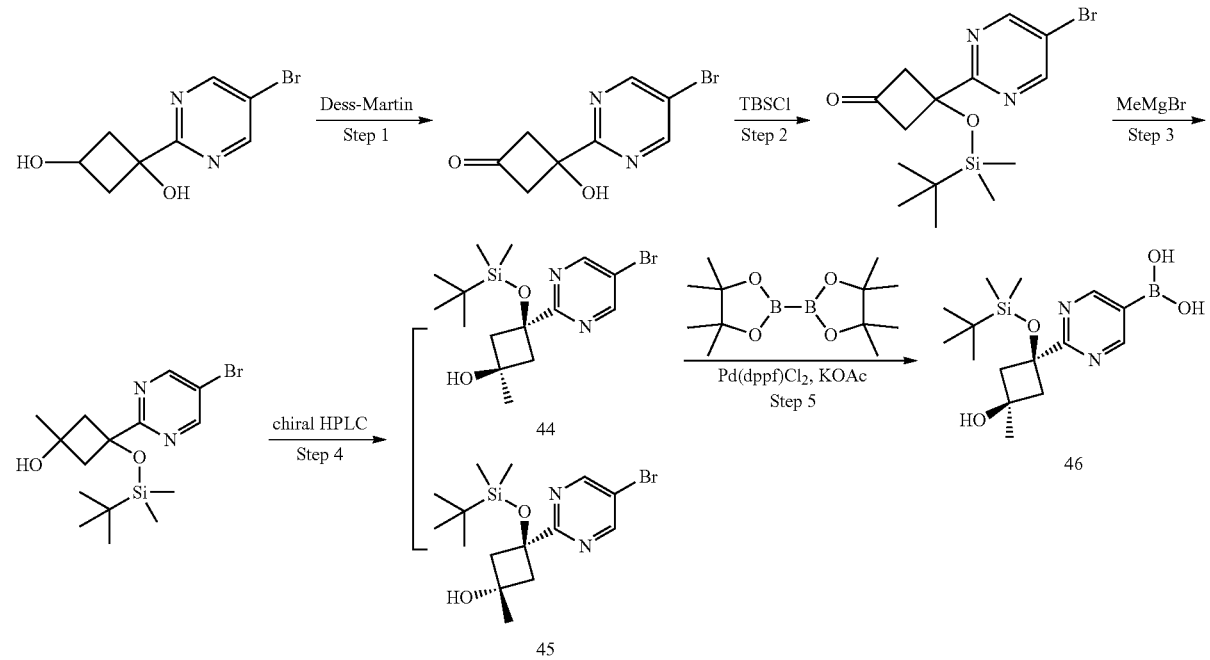

Step 1: A solution of 1-(5-bromopyrimidin-2-yl) cyclobutane-1,3-diol (200 mg, 0.82 mmol, 1 equiv) in DCM (5 mL) was treated with Dess-Martin (415.4 mg, 0.98 mmol, 1.20 equiv) for 10 min at 0° C. under nitrogen atmosphere. The resulting mixture was stirred for 2 hrs at room temperature under nitrogen atmosphere. The reaction was quenched with sat. Na$_2$SO$_3$ (aq.) at 0° C. The resulting mixture was extracted with DCM (3×10 mL). The combined organic layers dried over anhydrous Na$_2$SO$_4$. After filtration, the filtrate was concentrated under reduced pressure. The residue was purified by silica gel column chromatography, eluted with PE/EA (10:1) to afford 3-(5-bromopyrimidin-2-yl)-3-hydroxycyclobutan-1-one (150 mg, 75.6%) as a yellow solid. LCMS (ESI, m/z): 243 [M+H]$^+$.

Step 2: A solution of 3-(5-bromopyrimidin-2-yl)-3-hydroxycyclobutan-1-one (2.2 g, 9.1 mmol, 1 equiv) in DMF (30 mL) was treated with Imidazole (1.4 g, 19.9 mmol, 2.2 equiv) at 0° C. under nitrogen atmosphere followed by the addition of TBSCl (3.0 g, 19.9 mmol, 2.2 equiv) in dropwise at 0° C. The resulting mixture was stirred for 2 hrs at room temperature under nitrogen atmosphere. The reaction was quenched with sat. Na$_2$SO$_3$ (aq.) at 0° C. The resulting mixture was extracted with DCM (3×10 mL). The combined organic layers dried over anhydrous Na$_2$SO$_4$. After filtration, the filtrate was concentrated under reduced pressure. The residue was purified by silica gel column chromatography, eluted with PE/EA (10:1) to afford 3-(5-bromopyrimidin-2-yl)-3-[(tert-butyldimethylsilyl)oxy]cyclobutan-1-one (2 g, 61.8%) as a yellow oil. LCMS (ESI, m/z): 359.00 [M+H]$^+$.

Step 3: In a 250 mL round bottom flask, to a solution of 3-(5-bromopyrimidin-2-yl)-3-[(tert-butyldimethylsilyl)oxy]cyclobutan-1-one (1.8 g, 5.0 mmol, 1 equiv) in THF (40 mL) was added dropwise chloro(methyl)magnesium (0.38 g, 5.0 mmol, 1 equiv) at −78° C. under N$_2$ atmosphere. The reaction mixture was stirred at −78° C. for 3 mins. The mixture was stirred for another 4 hr. The reaction was quenched with sat. NH$_4$Cl (4 mL), and then the mixture was extracted with ether/EtOAc (2×10 mL). The combined organic extracts were washed with brine (10 mL), dried over anhydrous Na$_2$SO$_4$, and concentrated under vacuum to yield a crude product which was purified by Prep-TLC (PE/EA 10:1) to afford 3-(5-bromopyrimidin-2-yl)-3-[(tert-butyldimethylsilyl)oxy]-1-methylcyclobutan-1-ol (1.7 g, 90.4%) as a yellow oil. LCMS (ESI, m/z): 375.10 [M+H]$^+$.

Step 4: 3-(5-bromopyrimidin-2-yl)-3-[(tert-butyldimethylsilyl)oxy]-1-methylcyclobutan-1-ol (1.7 g) was purified by Prep_Chiral HPLC with the following conditions (Column: JW-CHIRAL ART Cellulose-SC, 20*250 mm, 5 um; Mobile Phase A: EtOH—HPLC, Mobile Phase B: Hex (0.5% 2M NH$_3$-MeOH)—HPLC; Flow rate: 45 mL/min; Gradient: 70% B to 70% B in 11 min; Wave Length: 220/254 nm; RT1(min): 5.21; RT2(min): 9.36; Sample Solvent: EtOH:DCM=1:1; Injection Volume: 2.0 mL; Number Of Runs: 9) to afford Intermediate 44 (1s, 3s)-3-(5-bromopyrimidin-2-yl)-3-((tert-butyldimethylsilyl)oxy)-1-methylcyclobutan-1-ol (1.4 g, 82.4%) as a yellow solid. $^1$H NMR (400 MHz, DMSO-d$_6$) δ 9.05 (s, 2H), 5.05 (s, 1H), 3.03-2.92 (m, 2H), 2.48-2.38 (m, 2H), 0.89 (s, 3H), 0.79 (s, 9H), 0.19 (s, 6H).

Step 5: A solution of Intermediate 44 (100 mg, 0.4 mmol, 1 equiv) Pd(dppf)Cl$_2$·DCM (31.4 mg, 0.4 mmol, 0.1 equiv), KOAc (113.6 mg, 1.2 mmol, 3 equiv), 4,4,5,5-tetramethyl-2-(4,4,5,5-tetramethyl-1,3,2-dioxaborolan-2-yl)-1,3,2-dioxaborolane (196.0 mg, 0.8 mmol, 2 equiv) in dioxane (2 mL) was stirred for 2 hrs at 80° C. under nitrogen atmosphere. The reaction was monitored by LCMS. TLC (DCM: MeOH=8:1, Rf=0.3). The resulting mixture was concentrated under reduced pressure. The resulting mixture was concentrated under vacuum. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in Intermediate 46 (80 mg, 92.53%) as a black solid. LCMS (ESI, m/z): 339.10 [M+H]$^+$.

Intermediate 47

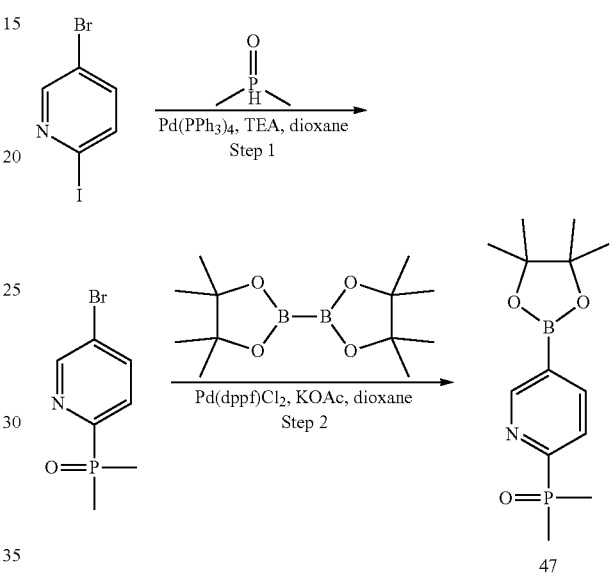

Step 1: Into a 20 mL vial were added 5-bromo-2-iodopyridine (1 g, 3.5 mmol, 1 equiv) and (methylphosphonoyl)methane (0.27 g, 3.5 mmol, 1 equiv) in dioxane (10 mL) at room temperature. To the above mixture was added (methylphosphonoyl)methane (0.27 g, 3.5 mmol, 1 equiv), TEA (1.07 g, 10.6 mmol, 3 equiv) in portions over 5 min at room temperature. The resulting mixture was stirred for 1 hr at 100° C. under nitrogen atmosphere. The resulting mixture was concentrated under reduced pressure. The residue was purified by reversed-phase flash chromatography with the following conditions: column, C18 silica gel; mobile phase, MeCN in Water (0.1% TFA), 10% to 50% gradient in 10 min; detector, UV 254 nm. The residue was purified by Prep-TLC (DCM/MeOH=5:1) to afford 5-bromo-2-(dimethylphosphoryl)pyridine (140 mg, 17%) as a white solid. LCMS (ESI-FA, m/z): 234 [M+H]$^+$.

Step 2: A solution of 5-bromo-2-(dimethylphosphoryl)pyridine (80 mg, 0.34 mmol, 1.0 equiv) in dioxane (1 mL) was treated with 4,4,5,5-tetramethyl-2-(4,4,5,5-tetramethyl-1,3,2-dioxaborolan-2-yl)-1,3,2-dioxaborolane (173.6 mg, 0.68 mmol, 2.0 equiv), KOAc (100.64 mg, 1.03 mmol, 3.0 equiv), Pd(dppf)Cl$_2$·DCM (27.9 mg, 0.034 mmol, 0.10 equiv) for 2 hrs at 100° C. under nitrogen atmosphere. The aqueous layer was extracted with EtOAc (3×10 mL). The residue was purified by silica gel column chromatography, eluted with PE/EA (5:1) to afford Intermediate 47 (80 mg, 83.3%) as a white solid. The crude product was used in the next step directly without further purification.

Intermediate 48 and 49

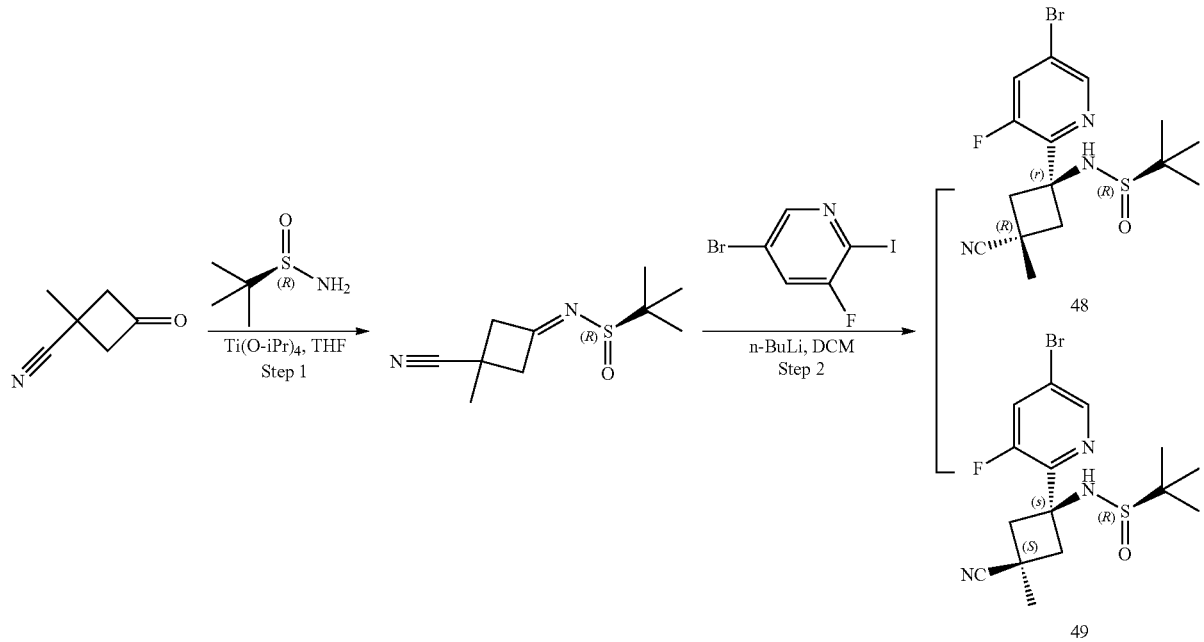

Step 1: To a stirred solution of 1-methyl-3-oxocyclobutane-1-carbonitrile (3.5 g, 32.07 mmol, 1 equiv) and (R)-2-methylpropane-2-sulfinamide (3.89 g, 32.07 mmol, 1 equiv) in THF (200 mL) was added Ti(OEt)₄ (13 mL, 32.07 mmol, 1 equiv) dropwise at room temperature under nitrogen atmosphere. The resulting mixture was stirred overnight at 75° C. under nitrogen atmosphere. The mixture was allowed to cool down to room temperature. To the above mixture was added H₂O (200 mL) dropwise at 0° C. The precipitated solids were collected by filtration and washed with ethyl acetate (3×40 mL). The resulting mixture was concentrated under reduced pressure and purified by silica gel column chromatography, eluted with PE/EA (5:1) to afford (R)—N-(3-cyano-3-methylcyclobutylidene)-2-methylpropane-2-sulfinamide (5.7 g, 83.7%) as an off-white solid. LCMS (ESI, m/z): 213.05 [M+H]⁺.

Step 2: A solution of 5-bromo-3-fluoro-2-iodopyridine (1.64 g, 5.42 mmol, 1.15 equiv) in DCM (250 mL) was treated with butyllithium (328.86 mg, 5.13 mmol, 1.09 equiv) for 5 min at −78° C. under nitrogen atmosphere. The resulting mixture was stirred for 2 min at −78° C. under nitrogen atmosphere. To the above mixture was added (R)—N-(3-cyano-3-methylcyclobutylidene)-2-methylpropane-2-sulfinamide (1 g, 4.71 mmol, 1 equiv) over 2 min at −78° C. The resulting mixture was stirred for 2 hrs at −78° C. The resulting mixture was stirred for 2 hrs at 0° C. under nitrogen atmosphere. Desired product could be detected by LCMS. The reaction was quenched by the addition of sat. NH₄Cl (aq.) (125 mL) at 0° C. The resulting mixture was extracted with DCM (3×200 mL). The combined organic layers were washed with brine (2×10 mL), dried over anhydrous Na₂SO₄. After filtration, the filtrate was concentrated under reduced pressure. The residue was purified by Prep-TLC (PE/EA 1:2) to afford Intermediate 47 (trans): (R)—N-((1r,3R)-1-(5-bromo-3-fluoropyridin-2-yl)-3-cyano-3-methylcyclobutyl)-2-methylpropane-2-sulfinamide (200 mg, 10.9%) as a white solid and Intermediate 48 (cis): (R)—N-((1s,3S)-1-(5-bromo-3-fluoropyridin-2-yl)-3-cyano-3-methylcyclobutyl)-2-methylpropane-2-sulfinamide (150 mg, 8.2%) as a white solid. LCMS (ESI, m/z):388.05 [M+H]⁺.

Intermediate 48 (trans) (trans): ¹H NMR (400 MHz, Chloroform-d) δ 8.54-8.48 (m, 1H), 7.67-7.59 (m, 1H), 3.91 (s, 1H), 3.74 (d, J=13.0 Hz, 1H), 3.35 (d, J=12.8 Hz, 1H), 2.78-2.57 (m, 2H), 1.74 (d, J=3.9 Hz, 3H), 1.20 (d, J=2.4 Hz, 9H).

Intermediate 49 (cis): ¹H NMR (400 MHz, Chloroform-d) δ 8.46 (s, 1H), 7.63-7.56 (m, 1H), 4.04 (s, 1H), 3.15 (d, J=13.1 Hz, 1H), 3.08-2.96 (m, 2H), 2.65 (d, J=12.7 Hz, 1H), 1.59-1.49 (m, 3H), 1.44-1.12 (s, 9H).

Intermediate 50 and 51

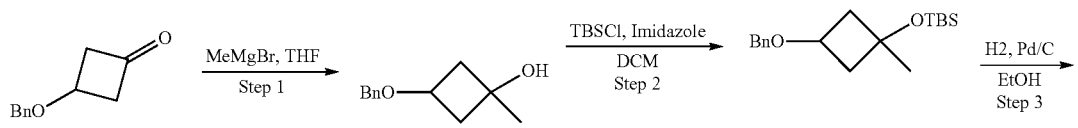

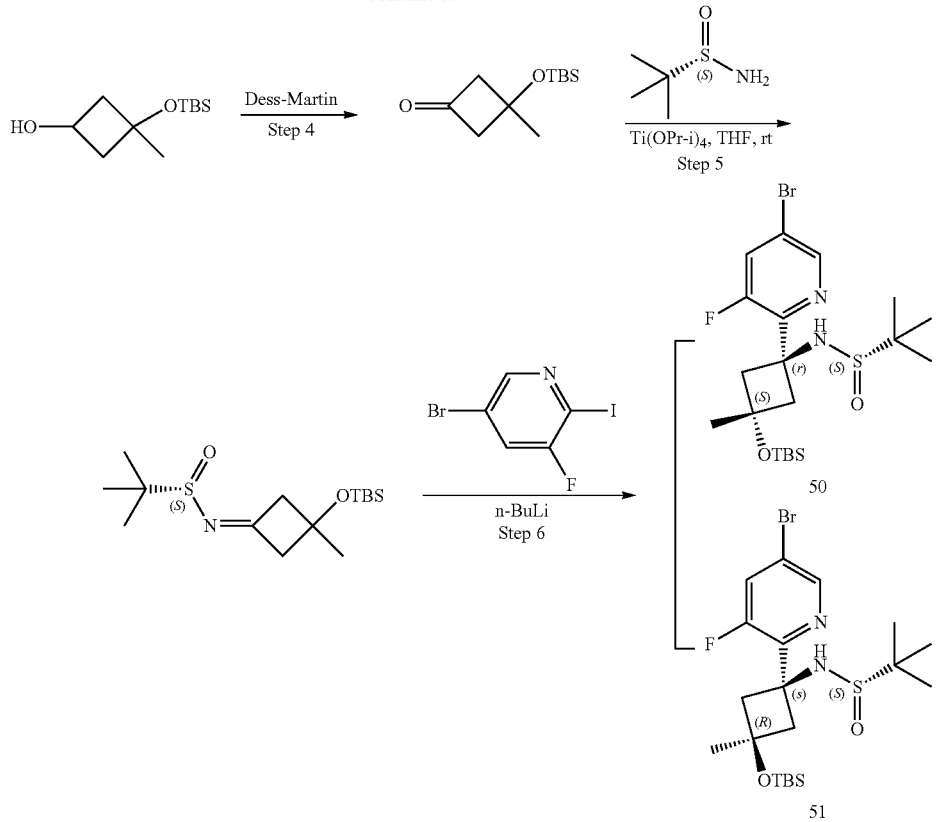

Step 1: A solution of 3-(benzyloxy)cyclobutan-1-one (10 g, 56.8 mmol, 1 equiv) in THF (100 mL) was treated with MeMgBr (20.3 g, 170.3 mmol, 3 equiv) for 15 min at −78° C. under nitrogen atmosphere. The resulting mixture was stirred for 2 hrs at room temperature under nitrogen atmosphere. The reaction was quenched with sat. NH₄Cl (aq.) at 0° C. The resulting mixture was extracted with EtOAc (3×200 mL). The combined organic layers were washed with brine (2×100 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% TFA), 50% to 100% gradient in 10 min; detector, UV 254 nm. This resulted in 3-(benzyloxy)-1-methylcyclobutan-1-ol (4 g, 36.7%) as a colorless oil. LCMS (ESI, m/z):175.10 [M+H-OH]⁺. ¹H NMR (400 MHz, Chloroform-d) δ 7.39-7.27 (m, 5H), 4.44 (s, 2H), 3.80-3.68 (m, 1H), 2.52-2.41 (m, 2H), 2.18-2.05 (m, 2H), 1.33 (t, J=1.0 Hz, 3H).

Step 2: A solution of 3-(benzyloxy)-1-methylcyclobutan-1-ol (4 g, 20.8 mmol, 1 equiv) in DCM (50 mL) was treated with Imidazole (7.1 g, 104.0 mmol, 5 equiv) for 5 min at 0° C. under nitrogen atmosphere followed by the addition of TBSCl (9.4 g, 62.4 mmol, 3 equiv) at 0° C. The resulting mixture was stirred for 5 hr at room temperature under nitrogen atmosphere. The resulting mixture was extracted with DCM (3×100 mL). The combined organic layers were washed with brine (2×100 mL), dried over anhydrous Na₂SO₄. After filtration, the filtrate was concentrated under reduced pressure. The residue was purified by silica gel column chromatography, eluted with PE/EA (40:1) to afford [3-(benzyloxy)-1-methylcyclobutoxy](tert-butyl)dimethylsilane (5 g, 78.4%) as a colorless oil. ¹H NMR (400 MHz, Chloroform-d) δ 7.42-7.28 (m, 5H), 4.44 (s, 2H), 3.75-3.64 (m, 1H), 2.41 (ddt, J=11.8, 6.9, 2.5 Hz, 2H), 2.24-2.10 (m, 2H), 1.32 (t, J=1.0 Hz, 3H), 0.91 (s, 9H), 0.10 (s, 6H).

Step 3: To a solution of [3-(benzyloxy)-1-methylcyclobutoxy](tert-butyl)dimethylsilane (5.3 g, 17.3 mmol, 1 equiv) in EtOH (60 mL) was added Pd/C (184.0 mg, 1.7 mmol, 0.1 equiv) under nitrogen atmosphere in a 250 mL round-bottom flask. The mixture was hydrogenated at room temperature for 1 day under hydrogen atmosphere using a hydrogen balloon, filtered through a Celite pad and concentrated under reduced pressure. The resulting mixture was filtered, the filter cake was washed with EtOH (60 mL) (2×10 mL). The filtrate was concentrated under reduced pressure. The residue was purified by silica gel column chromatography, eluted with PE/EA (9:1) to afford 3-[(tert-butyldimethylsilyl)oxy]-3-methylcyclobutan-1-ol (3.5 g, 94.3%) as a yellow oil. ¹H NMR (400 MHz, Chloroform-d) δ 3.99-3.88 (m, 1H), 2.53-2.41 (m, 2H), 2.13-2.01 (m, 2H), 1.86 (s, 1H), 1.30 (d, J=1.0 Hz, 3H), 0.90 (s, 9H), 0.09 (s, 6H).

Step 4: A solution of 3-[(tert-butyldimethylsilyl)oxy]-3-methylcyclobutan-1-ol (2.5 g, 11.7 mmol, 1 equiv) in DCM (26 mL) was treated with Dess-Martin (6.0 g, 14.0 mmol, 1.2 equiv) for 10 min at 0° C. under nitrogen atmosphere. The resulting mixture was stirred for 2 hrs at room temperature under nitrogen atmosphere. The reaction was quenched with sat. Na₂SO₃ (aq.) at 0° C. The resulting mixture was extracted with DCM (3×10 mL). The combined organic layers dried over anhydrous Na₂SO₄. After filtration, the filtrate was concentrated under reduced pressure. The residue was purified by silica gel column chromatography, eluted with PE/EA (10:1) to afford 3-[(tert-butyldimethylsilyl)oxy]-3-methylcyclobutan-1-one (2 g, 79.8%) as a yellow oil. $^1$H NMR (400 MHz, Chloroform-d) δ 3.28-3.16 (m, 2H), 3.05-2.95 (m, 2H), 1.66-1.56 (m, 3H), 0.91 (s, 9H), 0.14 (s, 6H).

Step 5: A solution of 3-[(tert-butyldimethylsilyl)oxy]-3-methylcyclobutan-1-one (2.2 g, 10.4 mmol, 1 equiv) and (S)-2-methylpropane-2-sulfinamide (2.0 g, 16.6 mmol, 1.6 equiv) in THF (23 mL) was treated with Ti(Oi-Pr)$_4$ (11.8 g, 41.6 mmol, 4 equiv) for 10 min at room temperature. The resulting mixture was stirred overnight at 70° C. under nitrogen atmosphere. The resulting mixture was concentrated under reduced pressure. The resulting mixture was diluted with ACN (23 mL). The reaction was quenched with water (10 mL) at 0° C. The resulting mixture was filtered, the filter cake was washed with MeCN (3×20 mL). The filtrate was concentrated under reduced pressure. The residue was purified by silica gel column chromatography, eluted with PE/EA (10:1) to afford (S)—N-{3-[(tert-butyldimethylsilyl)oxy]-3-methylcyclobutylidene}-2-methylpropane-2-sulfinamide (2.46 g, 74.47%) as a yellow oil. $^1$H NMR (400 MHz, Chloroform-d) δ 3.63-3.47 (m, 1H), 3.41-3.17 (m, 2H), 3.09-2.99 (m, 1H), 1.52 (d, J=7.4 Hz, 3H), 1.26 (d, J=1.0 Hz, 9H), 0.90 (s, 9H), 0.12 (s, 6H).

Step 6: A solution of 5-bromo-3-fluoro-2-iodopyridine (1.9 g, 6.2 mmol, 1.1 equiv) in THF (50 mL) was treated with n-BuLi in hexanes (435.7 mg, 6.8 mmol, 1.2 equiv) for 30 min at −70° C. under nitrogen atmosphere. To the above mixture was added (S)—N-{3-[(tert-butyldimethylsilyl)oxy]-3-methylcyclobutylidene}-2-methylpropane-2-sulfinamide (1.8 g, 5.7 mmol, 1 equiv) over 10 min at −66° C. The resulting mixture was stirred for 2 hrs at −70° C. The reaction was quenched with sat. NH$_4$Cl (aq.) at 0° C. The resulting mixture was extracted with EtOAc (3×100 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with PE/EA (2:1) to afford:

Intermediate 50 (trans): (S)—N-((1r,3S)-1-(5-bromo-3-fluoropyridin-2-yl)-3-((tert-butyldimethylsilyl)oxy)-3-methylcyclobutyl)-2-methylpropane-2-sulfinamide (560 mg, 20.02%) as a yellow oil. LCMS (ESI, m/z):494.85 [M+H]$^+$ $^1$H NMR (400 MHz, Chloroform-d) δ 8.47-8.40 (m, 1H), 7.58-7.50 (m, 1H), 3.86 (s, 1H), 3.19 (d, J=13.2 Hz, 1H), 2.76-2.52 (m, 3H), 1.58 (s, 3H), 1.18 (s, 9H), 0.79 (s, 9H), 0.04 (d, J=7.2 Hz, 6H).

Intermediate 51 (cis): (S)—N-((1s,3R)-1-(5-bromo-3-fluoropyridin-2-yl)-3-((tert-butyldimethylsilyl)oxy)-3-methylcyclobutyl)-2-methylpropane-2-sulfinamide (540 mg, 19.30%) as a yellow oil. $^1$H NMR (400 MHz, Chloroform-d) δ 8.48-8.44 (m, 1H), 7.62-7.52 (m, 1H), 3.99-3.89 (m, 1H), 3.38-3.32 (m, 1H), 2.97-2.91 (m, 1H), 2.74 (d, J=12.6 Hz, 1H), 2.56 (d, J=12.7 Hz, 1H), 1.16 (s, 9H), 1.12 (s, 3H), 0.91 (s, 9H), 0.11 (s, 6H).

Intermediate 52

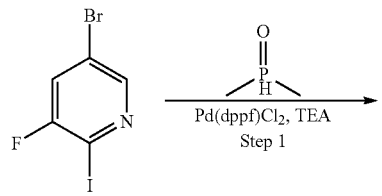

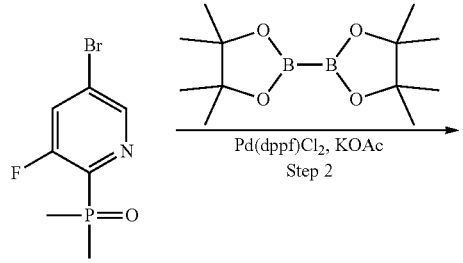

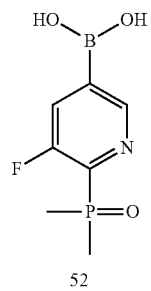

52

Step 1: Into an 8 mL vial were added 5-bromo-3-fluoro-2-iodopyridine (500 mg, 1.7 mmol, 1 equiv) and (methylphosphonoyl)methane (193.9 mg, 2.5 mmol, 1.5 equiv) in dioxane (5 mL) at room temperature. To the above mixture was added Pd(dppf)Cl$_2$·DCM (134.9 mg, 0.17 mmol, 0.1 equiv), TEA (502.8 mg, 5.0 mmol, 3 equiv) dropwise over 5 min at room temperature. The resulting mixture was stirred at 100° C. for 1 hr under nitrogen atmosphere. The resulting mixture was filtered; the filter cake was washed with EtOAc (2×50 mL). The filtrate was concentrated under reduced pressure. The resulting mixture was extracted with EtOAc (2×100 mL). The combined organic layers were washed with brine (2×50 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (10 mmol/L NH$_4$HCO$_3$), 10% to 50% gradient in 10 min; detector, UV 254 nm. This resulted in 5-bromo-2-(dimethylphosphoryl)-3-fluoropyridine (200 mg, 47.9%) as a yellow solid. LC-MS: (M+H)$^+$: 252.05.

Step 2: Into an 8 mL vial was added 5-bromo-2-(dimethylphosphoryl)-3-fluoropyridine (200 mg, 0.8 mmol, 1 equiv) and bis(pinacolato)diboron (604.6 mg, 2.4 mmol, 3 equiv) in dioxane (2 mL) at room temperature. To the above mixture was added Pd(dppf)Cl$_2$·DCM (64.6 mg, 0.08 mmol, 0.1 equiv), KOAc (233.7 mg, 2.4 mmol, 3 equiv) in portions over 5 min at room temperature. The resulting mixture was stirred at 90° C. for 1.5 hr under nitrogen atmosphere. The precipitated solids were collected by filtration and washed with MeOH (2×50 mL). The resulting mixture was concentrated under vacuum. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in Intermediate 52 (80 mg, 46.5%) as reddish-brown oil. LC-MS: (M+H)$^+$: 218.10.

Intermediate 53

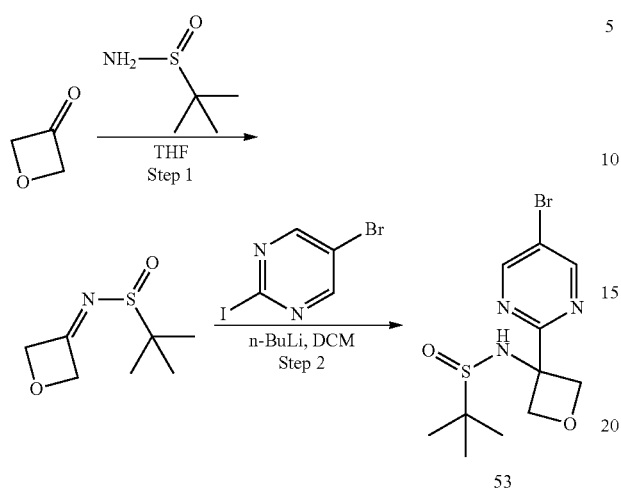

Step 1: A solution of 3-oxetanone (15 g, 208.2 mmol, 1 equiv) and tert-butanesulfinamide (25.2 g, 208.2 mmol, 1.00 equiv) in THF (150 mL) was stirred with tetrakis(propan-2-yloxy)titanium (88.7 g, 312.2 mmol, 1.5 equiv) at 0° C. for 5 min under nitrogen atmosphere. The resulting mixture was stirred at 70° C. overnight under nitrogen atmosphere. The reaction was quenched with water at 0° C. The resulting mixture was filtered, the filter cake was washed with EtOAc (5×200 mL). The filtrate was concentrated under reduced pressure. The residue was purified by silica gel column chromatography, eluted with PE/EA (2:1) to afford 2-methyl-N-(oxetan-3-ylidene)propane-2-sulfinamide (15 g, 41.1% yield) as a yellow oil. LCMS (ESI, m/z): 176.07 [M+H]$^+$.

Step 2: A solution of 5-bromo-2-iodopyrimidine (4.9 g, 17.3 mmol, 1.0 equiv) in DCM (90 mL) was treated with n-Butyllithium (2.5 M in n-hexane) (7.0 mL, 17.5 mmol, 1.0 equiv) at −78° C. for 1 hr under nitrogen atmosphere followed by the addition of 2-methyl-N-(oxetan-3-ylidene)propane-2-sulfinamide (3 g, 17.1 mmol, 1 equiv) in DCM (10 mL) dropwise at −78° C. The resulting mixture was stirred at room temperature for 2H under nitrogen atmosphere. The reaction was quenched with sat. NH$_4$Cl (aq.) at 0° C. The resulting mixture was extracted with DCM (3×100 mL). The combined organic layers were washed with DCM (2×20 mL), dried over anhydrous Na$_2$SO$_4$. After filtration, the filtrate was concentrated under reduced pressure. The residue was purified by silica gel column chromatography, eluted with PE/EA (1:1) to afford Intermediate 53 (1.5 g, 26.2%) as a yellow oil. LCMS (ESI, m/z): 334.01 [M+H]$^+$.

Intermediate 54

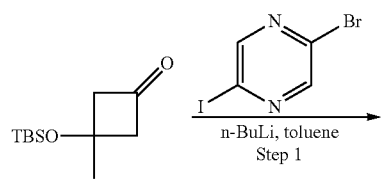

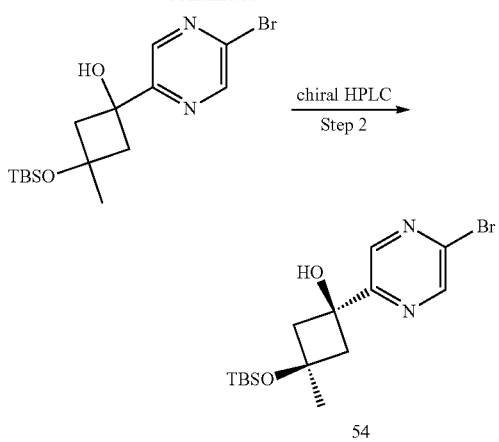

Step 1: A solution of 2-bromo-5-iodopyrazine (1 g, 3.5 mmol, 1 equiv) in toluene (100 mL) was treated with 2.5 M n-BuLi in hexanes (1.5 mL, 3.7 mmol, 1.05 equiv) at −78° C. for 30 min under nitrogen atmosphere followed by the addition of 3-[(tert-butyldimethylsilyl)oxy]-3-methylcy-clobutan-1-one (827.8 mg, 3.9 mmol, 1.1 equiv) dropwise at −78° C. The resulting mixture was stirred from −78° C. to 25° C. overnight under nitrogen atmosphere. The reaction was quenched with sat. NH$_4$Cl (aq., 50 mL) at 0° C. The resulting mixture was extracted with EtOAc (3×100 mL) and dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in 1-(5-bromopyrazin-2-yl)-3-[(tert-butyldimethylsilyl)oxy]-3-methylcyclobutan-1-ol (930 mg, 71%) as yellow oil. LCMS (ESI, m/z): 373.15 [M+H]$^+$.

Step 2: 1-(5-bromopyrazin-2-yl)-3-[(tert-butyldimethylsi-lyl)oxy]-3-methylcyclobutan-1-ol (900 mg) was separated by chiral HPLC following the condition: Column: JW-CHIRALPAK IA 3.0*25 cm, 5 um; Mobile Phase A: IPA—HPLC, Mobile Phase B: Hex (0.5% 2M NH$_3$-MeOH)—HPLC; Flow rate: 45 mL/min; Gradient: 98% B to 98% B in 16 min; Wave Length: 220/254 nm; RT1(min): 9.06; RT2(min): 12.21; Sample Solvent: IPA Hex—HPLC; Injection Volume: 2.0 mL; Number Of Runs: 6 to give Intermediate 54 (300 mg, 33%) as yellow oil. $^1$H NMR (400 MHz, DMSO-d$_6$) δ 8.81 (t, J=1.4 Hz, 1H), 8.65 (d, J=1.4 Hz, 1H), 6.06 (s, 1H), 2.88-2.80 (m, 2H), 2.52-2.44 (m, 2H), 1.24 (s, 3H), 0.89 (s, 9H), 0.10 (s, 6H).

Intermediate 55

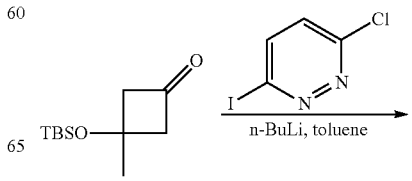

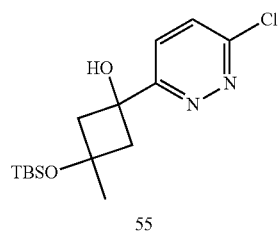

55

Step 1: A solution of 3-chloro-6-iodopyridazine (5 g, 20.8 mmol, 1 equiv) in toluene (200 mL) was treated with 2.5 M n-BuLi in hexanes (8.7 mL, 21.8 mmol, 1.05 equiv) at −78° C. for 30 min under nitrogen atmosphere followed by addition of 3-[(tert-butyldimethylsilyl)oxy]-3-methylcyclobutan-1-one (4.9 g, 22.9 mmol, 1.1 equiv) dropwise at −78° C. The resulting mixture was stirred from −78° C. to 25° C. overnight under nitrogen atmosphere. The reaction was quenched with sat. NH₄Cl (aq., 100 mL) at 0° C. The resulting mixture was extracted with EtOAc (3×200 mL) and dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% TFA), 20% to 80% gradient in 10 min; detector, UV 254 nm. This resulted in Intermediate 55 (290 mg, 4.0%) as yellow oil. LCMS (ESI, m/z): 329.15 [M+H]⁺.

Intermediate 56-81 were prepared using similar procedure.

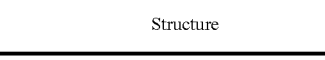

-continued

| Intermediate | Structure |
|---|---|
| 63 | 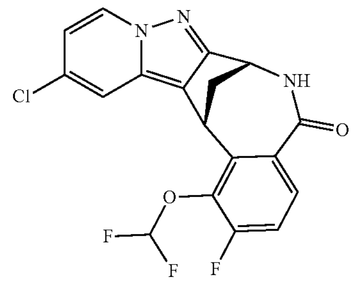 [SMILES: O=C1N[C@@H]2C[C@H](c3c1ccc(F)c3OC(F)F)c1c2nn2ccc(Cl)cc12] |
| 64 | 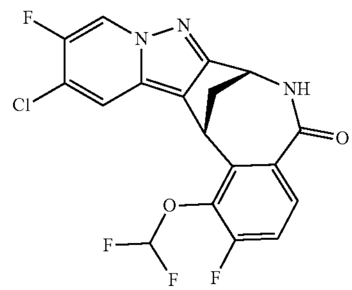 [SMILES: O=C1N[C@@H]2C[C@H](c3c1ccc(F)c3OC(F)F)c1c2nn2cc(F)c(Cl)cc12] |
| 65 | 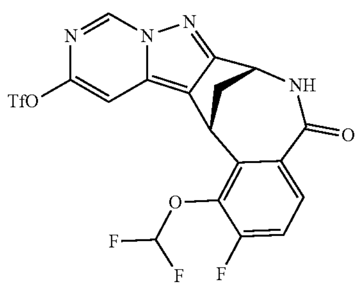 [SMILES: O=C1N[C@@H]2C[C@H](c3c1ccc(F)c3OC(F)F)c1c2nn2cnc(OS(=O)(=O)C(F)(F)F)cc12] |
| 66 | 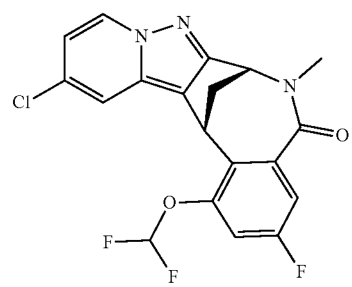 [SMILES: CN1C(=O)c2cc(F)cc(OC(F)F)c2[C@H]2C[C@@H]1c1nn3ccc(Cl)cc3c12] |
| 67 | 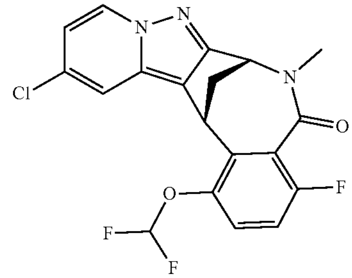 [SMILES: CN1C(=O)c2c(F)ccc(OC(F)F)c2[C@H]2C[C@@H]1c1nn3ccc(Cl)cc3c12] |

-continued

| Intermediate | Structure |
|---|---|
| 68 | |
| 69 | |
| 70 | |
| 71 | |
| 72 | |

359
-continued
| Intermediate | Structure |
|---|---|
| 73 | 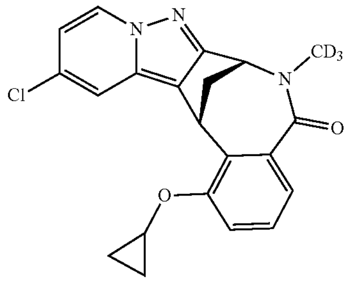 [SMILES: [2H]C([2H])([2H])N1C(=O)c2cccc(OC3CC3)c2[C@H]2C[C@@H]1c1nn3ccc(Cl)cc3c12] |
| 74 | 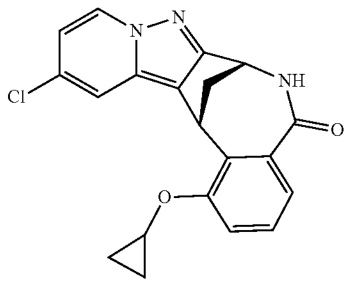 [SMILES: O=C1N[C@@H]2C[C@H](c3c(OC4CC4)cccc31)c1c2nn2ccc(Cl)cc12] |
| 75 | 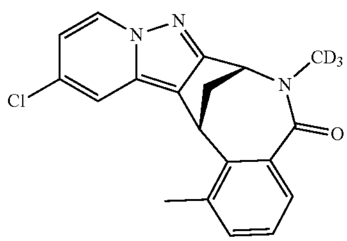 [SMILES: [2H]C([2H])([2H])N1C(=O)c2cccc(C)c2[C@H]2C[C@@H]1c1nn3ccc(Cl)cc3c12] |
| 76 | 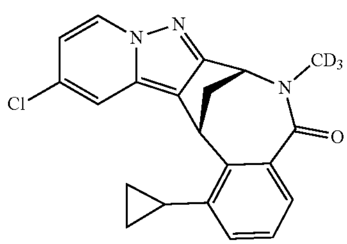 [SMILES: [2H]C([2H])([2H])N1C(=O)c2cccc(C3CC3)c2[C@H]2C[C@@H]1c1nn3ccc(Cl)cc3c12] |
| 77 | 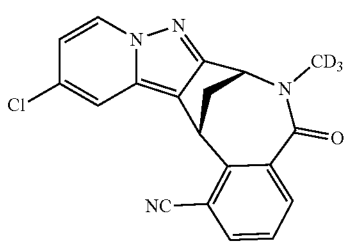 [SMILES: [2H]C([2H])([2H])N1C(=O)c2cccc(C#N)c2[C@H]2C[C@@H]1c1nn3ccc(Cl)cc3c12] |
| 78 | 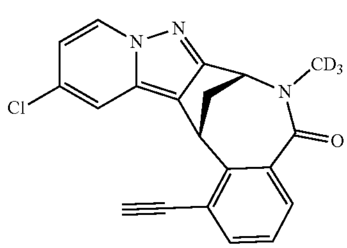 [SMILES: [2H]C([2H])([2H])N1C(=O)c2cccc(C#C)c2[C@H]2C[C@@H]1c1nn3ccc(Cl)cc3c12] |
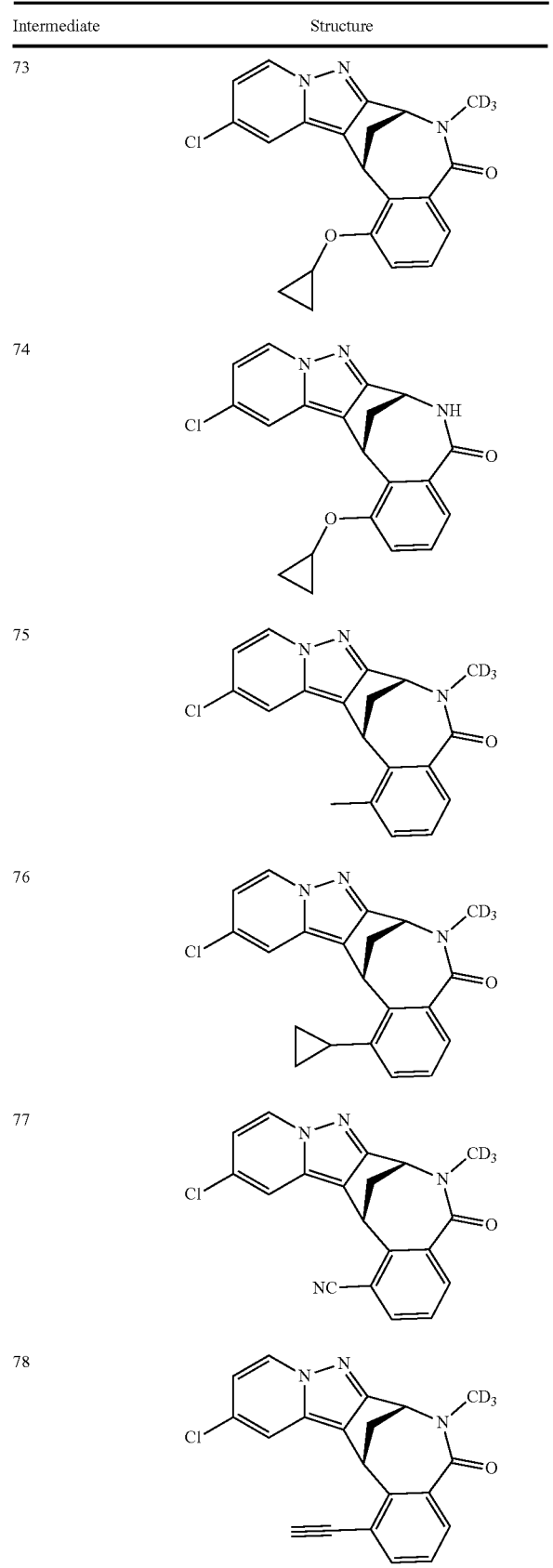
360
-continued
| Intermediate | Structure |
|---|---|
| 79 | 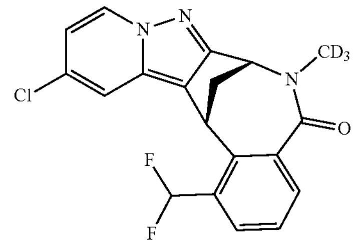 [SMILES: [2H]C([2H])([2H])N1C(=O)c2cccc(C(F)F)c2[C@H]2C[C@@H]1c1nn3ccc(Cl)cc3c12] |
| 80 | 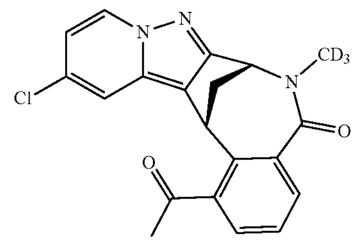 [SMILES: [2H]C([2H])([2H])N1C(=O)c2cccc(C(C)=O)c2[C@H]2C[C@@H]1c1nn3ccc(Cl)cc3c12] |
| 81 | 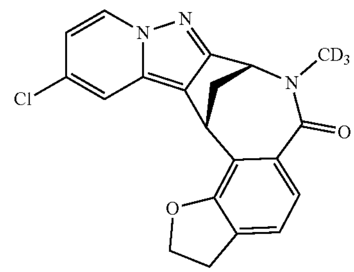 [SMILES: [2H]C([2H])([2H])N1C(=O)c2ccc3c(c2[C@H]2C[C@@H]1c1nn4ccc(Cl)cc4c12)OCC3] |
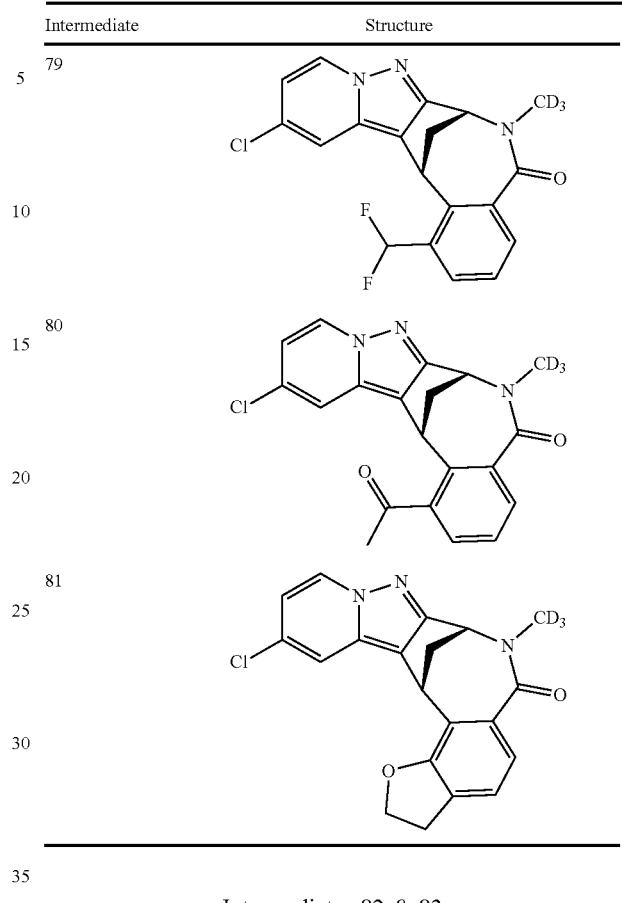
Intermediates 82 & 83
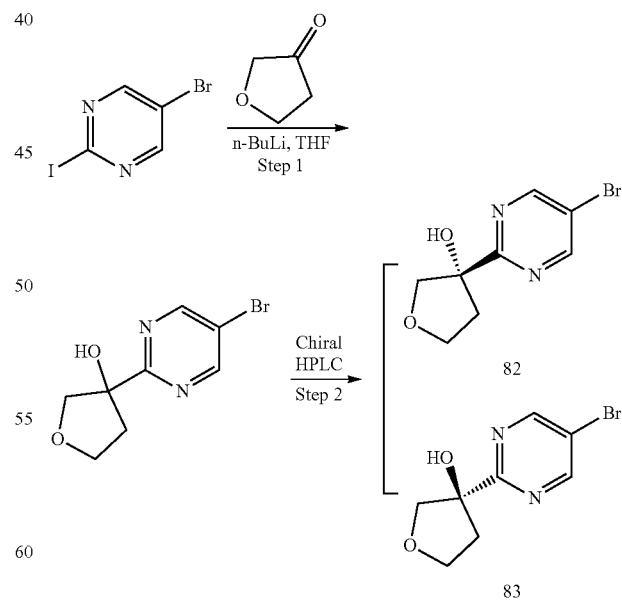
Step 1: A mixture of 5-bromo-2-iodopyrimidine (2 g, 7.0 mmol, 1.0 equiv) in Toluene (25 mL) was added n-BuLi (3.4 mL, 8.4 mmol, 1.2 equiv) drop wise at −78° C. under nitrogen atmosphere. The mixture was stirred for 1 h at −78°

C. Then dihydrofuran-3-one (2.42 g, 28.1 mmol, 4.0 equiv) was added at −78° C. The mixture was stirred for 1 h at −78° C., then allowed to warm to room temperature and stirred for 1 h. The reaction was quenched with sat. NH₄Cl (aq.) at 0° C. The resulting mixture was extracted with EtOAc (3×300 mL). The combined organic layers were washed with brine, dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% TFA), 10% to 40% gradient in 10 min; detector, UV 220 nm. This resulted in 3-(5-bromopyrimidin-2-yl)oxolan-3-ol (600 mg, 34.9%) as a brown yellow solid. LCMS (ESI, m/z): 244.95 [M+H]⁺.

Step 2: 3-(5-bromopyrimidin-2-yl)oxolan-3-ol (260 mg) was further purified by Prep-HPLC with the following conditions (Column: JW-CHIRAL ART Cellulose-SC, 20*250 mm, 5 um; Mobile Phase A: IPA-HPLC, Mobile Phase B: Hex (0.5% 2M NH₃-MeOH)-HPLC; Flow rate: 20 mL/min; Gradient: 85% B to 85% B in 18 min; Wave Length: 220/254 nm; RT1(min): 13.51; RT2(min): 17.32; Sample Solvent: EtOH—HPLC; Injection Volume: 0.2 mL; Number Of Runs: 15) to afford isomer 1 (125 mg, 48.1%) and isomer 2 (120 mg, 46.2%) as an off-white solid. LCMS (ESI, m/z): 244.95 [M+H]⁺.

Intermediate 84

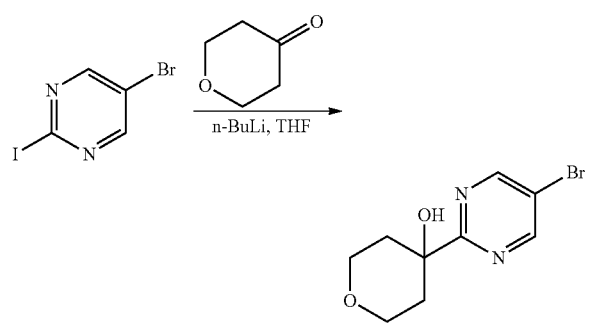

Into a 250 mL 3-necked round-bottom flask were added 5-bromo-2-iodopyrimidine (2.1 g, 7.5 mmol, 1.0 equiv) and Toluene (20 mL) at room temperature. To the above mixture was added n-BuLi (5.2 mL, 55.0 mmol, 7.3 equiv) dropwise over 3 min at −78° C. The resulting mixture was stirred for additional 1 h at −78° C. To the above mixture was added 4H-pyran-4-one, tetrahydro- (3.0 g, 30.0 mmol, 4.0 equiv) dropwise over 3 min at −78° C. The resulting mixture was stirred for 2 h at room temperature under nitrogen atmosphere. The reaction was quenched with water at room temperature. The resulting mixture was extracted with EtOAc (2×500 mL). The combined organic layers were washed with brine (2×500 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% NH₃·H₂O), 10% to 50% gradient in 10 min; detector, UV 254 nm. This resulted in 4-(5-bromopyrimidin-2-yl)oxan-4-ol (500 mg, 25.7%) as a black solid. LCMS (ESI-FA, m/z): 259 [M+H]⁺.

Intermediate 85

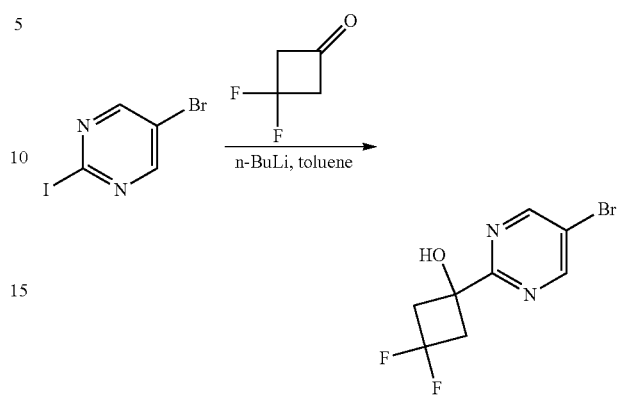

A solution of 5-bromo-2-iodopyrimidine (2.0 g, 7.0 mmol, 1.0 equiv) in Toluene (100 mL) was treated with n-BuLi in hexanes (3.0 mL, 7.4 mmol, 1.1 equiv) at −78° C. for 30 min under nitrogen atmosphere followed by the addition of 3,3-difluorocyclobutan-1-one (819.1 mg, 7.7 mmol, 1.1 equiv) dropwise at −78° C. The resulting mixture was stirred at −78 to 25° C. for 1 h under nitrogen atmosphere. The reaction was quenched with sat. NH₄Cl (aq.) at 0° C. The resulting mixture was extracted with EtOAc (3×100 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in 1-(5-bromopyrimidin-2-yl)-3,3-difluorocyclobutan-1-ol (600 mg, 32.3%) as a brown solid. LCMS:(ESI, m/z): 266.95 [M+H]⁺.

Intermediate 86

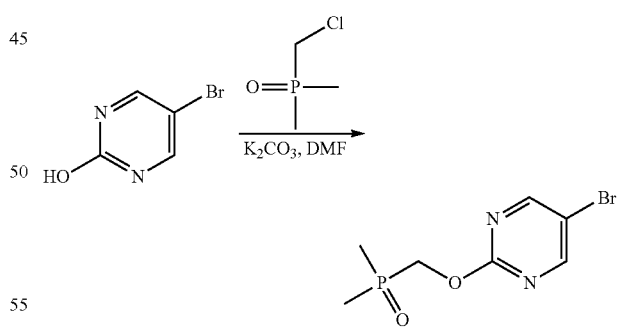

A solution of chloro(dimethylphosphoryl)methane (0.2 g, 1.6 mmol, 1.0 equiv) and 5-bromopyrimidin-2-ol (0.22 mg, 1.3 mmol, 0.8 equiv) in DMF (1 mL) was added K₂CO₃ (0.66 g, 4.8 mmol, 3.0 equiv) under nitrogen atmosphere. Then the mixture was degassed with N₂ for 3 times. The reaction mixture was stirred for 16 h at 100° C. under a nitrogen atmosphere. The reaction mixture was purified by reversed-phase flash chromatography with the following conditions: column, C18 silica gel; mobile phase, H₂O in ACN, 10% to 50% gradient in 10 min; detector, UV 254 nm.

This resulted in 5-bromo-2-[(dimethylphosphoyl)methoxy]pyrimidine (100 mg, 23.9%) as a brown oil. LCMS (ESI, m/z): 266.90 [M+H]⁺.

Intermediate 87

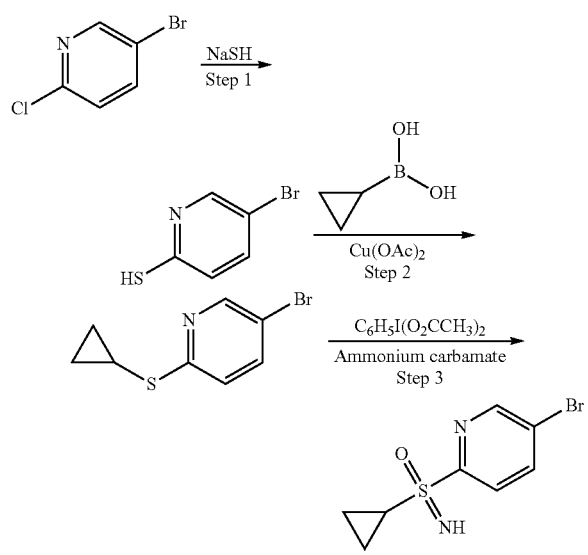

Step 1: Into a 40 mL vial were added 5-bromo-2-chloropyridine (3.0 g, 15.6 mmol, 1 equiv) and NaSH (1.3 g, 23.4 mmol, 1.5 equiv) at room temperature. The resulting mixture was stirred at 100° C. for 5 h under nitrogen atmosphere. The reaction was quenched by the addition of Water (50 mL) at room temperature. The aqueous layer was extracted with EtOAc (2×500 mL). The resulting mixture was concentrated under reduced pressure. The residue was purified by trituration with MeOH (500 mL). The resulting mixture was concentrated under vacuum. This resulted in 5-bromopyridine-2-thiol (1 g) as a yellow solid. LCMS (ESI-FA, m/z): 190 [M+H]⁺.

Step 2: Into a 40 mL vial were added 5-bromopyridine-2-thiol (1.0 g, 5.3 mmol, 1 equiv) and cyclopropylboronic acid (0.68 g, 7.9 mmol, 1.5 equiv) at room temperature. To the above mixture was added Cu(OAc)₂ (0.96 g, 5.3 mmol, 1 equiv), 2-(pyridin-2-yl)pyridine (0.82 g, 5.3 mmol, 1.0 equiv), Cs₂CO₃ (1.7 g, 5.3 mmol, 1.0 equiv) in portions over 10 min at room temperature. The resulting mixture was stirred at 70° C. for additional 5 h. The reaction was quenched with Water, NH₃·H₂O (25%) 1.5 mL at room temperature. The resulting mixture was extracted with DCM (2×50 mL). The combined organic layers were washed with brine (2×50 mL), dried over anhydrous Na₂SO₄. After filtration, the filtrate was concentrated under reduced pressure. The resulting mixture was concentrated under vacuum. The residue was purified by reversed-phase flash chromatography with the following conditions: column, C18 silica gel; mobile phase, MeCN in Water, 10% to 50% gradient in 10 min; detector, UV 254 nm. This resulted in 5-bromo-2-(cyclopropylsulfanyl)pyridine (500 mg) as a brown solid. LCMS (ESI, m/z): 230 [M+H]⁺.

Step 3: Into a 40 mL vial were added 5-bromo-2-(cyclopropylsulfanyl)pyridine (500 mg, 2.2 mmol, 1.0 equiv) and ammonium carbamate (0.25 g, 3.3 mmol, 1.5 equiv), bis(acetoxy)iodobenzene (1.8 g, 5.5 mmol, 2.5 equiv) in MeOH (25 mL) at 20° C. The resulting mixture was stirred at 20° C. for 1 h under air atmosphere. The resulting mixture was concentrated under vacuum. The residue was purified by Prep-TLC (CH₂Cl₂/MeOH 5:1) to afford (5-bromopyridin-2-yl)(cyclopropyl)imino-lambda6-sulfanylone (450 mg) as a white solid. LCMS (ESI, m/z): 261 [M+H]⁺.

Intermediate 88

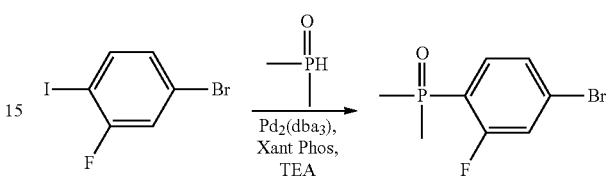

Into a 40 mL sealed tube were added 4-bromo-2-fluoro-1-iodobenzene (1.0 g, 3.3 mmol, 1.0 equiv), (methylphosphonoyl)methane (0.3 g, 3.7 mmol, 1.1 equiv), Pd₂(dba)₃ (0.15 g, 0.17 mmol, 0.05 equiv), XantPhos (0.19 g, 0.33 mmol, 0.1 equiv), Et₃N (0.67 g, 6.65 mmol, 2.0 equiv) and dioxane (15 mL) at room temperature. The resulting mixture was stirred at 100° C. for 2 h under nitrogen atmosphere. The resulting mixture was concentrated under vacuum. The residue was purified by reversed-phase flash chromatography with the following conditions: column, C18 silica gel; mobile phase, MeCN in water (0.1% TFA), 40% gradient in 10 min; detector, UV 254 nm. This resulted in 4-bromo-1-(dimethylphosphoryl)-2-fluorobenzene (600 mg, 71.9%) as a yellow solid. LCMS (ESI, m/z): 251.12 [M+H]⁺.

Intermediate 89

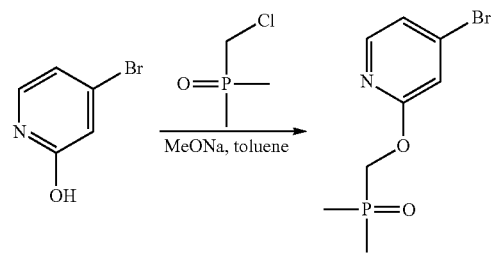

A mixture of chloro(dimethylphosphoryl)methane (200 mg, 1.581 mmol, 1.00 equiv) and 4-bromopyridin-2-ol (220.04 mg, 1.265 mmol, 0.8 equiv), K₂CO₃ (655.41 mg, 4.743 mmol, 3 equiv) in DMF (5 mL) was stirred at 100° C. for overnight under nitrogen atmosphere. The resulting mixture was extracted with EtOAc (3×10 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.10% TFA), 10% to 50% gradient in 10 min; detector, UV 254 nm. This resulted in 4-bromo-2-[(dimethylphosphoryl)methoxy]pyridine (38 mg, 9.10%) as a light yellow oil. LCMS (ESI, m/z): 263.95 [M+H]⁺.

Intermediate 90

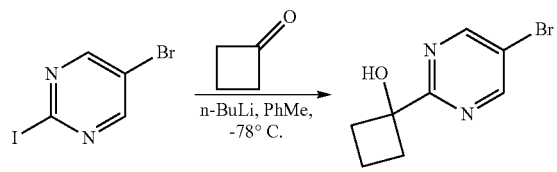

A solution of 5-bromo-2-iodopyrimidine (5.0 g, 17.6 mmol, 1.0 equiv) in Toluene (100 mL) was treated with n-BuLi in hexanes (2.3 g, 35.1 mmol, 2.0 equiv) at −78° C. for 3 min under nitrogen atmosphere for 1 h, followed by the addition of cyclobutanone (4.9 g, 70.2 mmol, 4.0 equiv) dropwise at −78° C. The resulting mixture was stirred at room temperature for 2 h under nitrogen atmosphere. The reaction was quenched by the addition of sat. $NH_4Cl$ (aq.) (300 mL) at 0° C. The aqueous layer was extracted with EtOAc (3×100 mL). The resulting mixture was concentrated under reduced pressure. The residue was purified by silica gel column chromatography, eluted with PE/EA (8:1) to afford 1-(5-bromopyrimidin-2-yl) cyclobutan-1-ol (1.1 g, 64% purity) as an off-white solid. LCMS (ESI, m/z): 229.05 $[M+H]^+$.

Intermediate 91

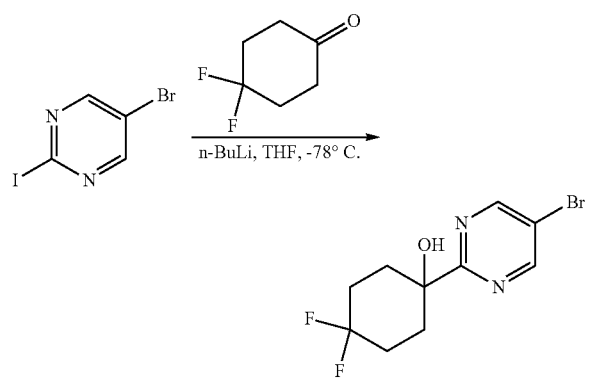

A solution of 5-bromo-2-iodopyrimidine (2.0 g, 7.0 mmol, 1.0 equiv) in Toluene (100 mL) was treated with butyllithium (3.0 mL, 7.7 mmol, 1.1 equiv) for 10 min at −78° C. under nitrogen atmosphere. To the above mixture was added 4,4-difluorocyclohexan-1-one (4.0 g, 27.7 mmol, 4.0 equiv) in Toluene (10 mL) over 5 min at −78° C. The resulting mixture was stirred for 2 h at room temperature under nitrogen atmosphere. The reaction was quenched by the addition of sat. $NH_4Cl$ (aq.) (100 mL) at 0° C. The resulting mixture was extracted with EtOAc (3×100 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EA (3:1) to afford 1-(5-bromopyrimidin-2-yl)-4,4-difluorocyclohexan-1-ol (1.8 g, 87.5%) as a yellow solid. LCMS (ESI, m/z): 295.00 $[M+H]^+$.

Intermediates 92 & 93

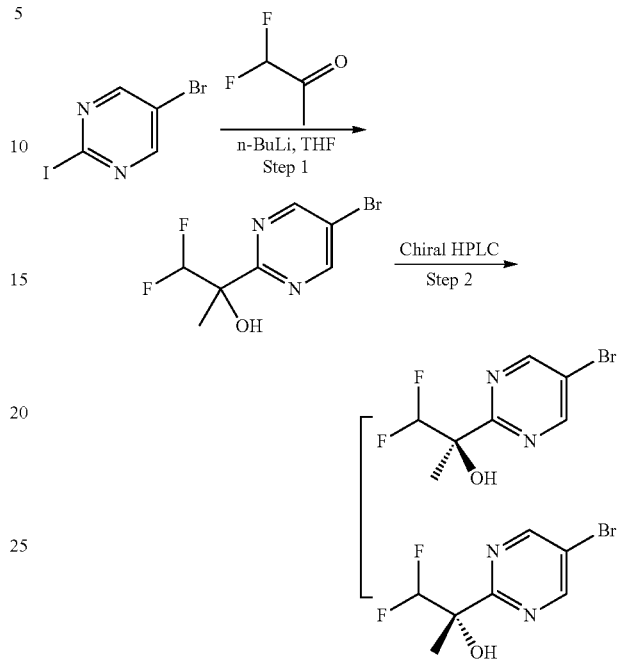

Step 1: A solution of 5-bromo-2-iodopyrimidine (11.0 g, 38.6 mmol, 1.0 equiv) in DCM (250 mL) was treated with butyllithium (30.9 mL, 77.2 mmol, 2.0 equiv) at −78° C. for 5 minute under nitrogen atmosphere followed by the addition of 1,1-difluoropropan-2-one (10.9 g, 115.8 mmol, 3.0 equiv) dropwise at −78° C. The resulting mixture was stirred at 25° C. for 1 h under nitrogen atmosphere. The reaction was quenched by the addition of water (200 mL) at 0° C. The resulting mixture was extracted with DCM (3×80 mL). The combined organic layers were dried over anhydrous $Na_2SO_4$. After filtration, the filtrate was concentrated under reduced pressure. The residue was purified by silica gel column chromatography, eluted with PE/EA (10:1) to afford 2-(5-bromopyrimidin-2-yl)-1,1-difluoropropan-2-ol (4.0 g, 40.9%) as a yellow oil. LCMS (ESI, m/z): 252.95 $[M+H]^+$.

Step 2: 2-(5-bromopyrimidin-2-yl)-1,1-difluoropropan-2-ol (4.0 g) was further purified by Prep-HPLC with the following conditions (Column: CHIRALPAKIG3; Mobile Phase A: Hex (0.1% FA): (EtOH:MeOH=1:1)=90:10; Flow rate: 1 mL/min mL/min; Gradient: isocratic; Injection Volume: 0.2 mL) to afford isomer 1 (1.4 g) and isomer 2 (1.0 g) a yellow oil.

Intermediates 94 & 95

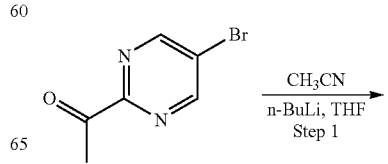

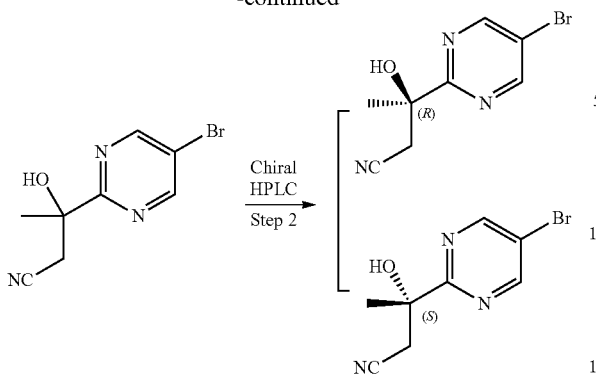

Step 1: Into a 10 mL 2-necked round-bottom flask were added ACN (204.2 mg, 5.0 mmol, 1.0 equiv), n-BuLi (318.7 mg, 5.0 mmol, 1.0 equiv) and THF (10 mL) at −78° C. The resulting mixture was stirred for 30 min at −78° C. under nitrogen atmosphere. To the above mixture was added 1-(5-bromopyrimidin-2-yl) ethanone (1.0 g, 5.0 mmol, 1.0 equiv) and THF (10 mL) dropwise at −78° C. The resulting mixture was stirred for additional 30 min at −78° C. The reaction was quenched with sat. NH$_4$Cl (aq.) at room temperature. The resulting mixture was extracted with EtOAc (3×20 mL). The combined organic layers were washed with brine (1×10 mL), dried over anhydrous Na$_2$SO$_4$. After filtration, the filtrate was concentrated under reduced pressure. The residue was purified by silica gel column chromatography, eluted with PE/EA (2:1) to afford 3-(5-bromopyrimidin-2-yl)-3-hydroxybutanenitrile (35 mg, 2.9%) as a white solid. LCMS (ESI, m/z): 201.10 [M+H]$^+$.

Step 2: The 3-(5-bromopyrimidin-2-yl)-3-hydroxybutanenitrile (200 mg) was further purified by reversed-phase flash chromatography with the following conditions: Column: JW-CHIRALPAK IG, 20*250 mm, 5 um; Mobile Phase A: EtOH—HPLC, Mobile Phase B: Hex (0.5% 2M NH$_3$-MeOH)—HPLC; Flow rate: 20 mL/min; Gradient: 70% B to 70% B in 18.5 min; Wave Length: 220/254 nm; RTT(min): 13.31; RT2(min): 15.49; Sample Solvent: EtOH: DCM=1:1—HPLC; Injection Volume: 0.3 mL; Number of Runs: 14 detector UV 254 nm. This resulted in isomer 1 (60 mg) and isomer 2 (64 mg) as a white solid.

Intermediate 96

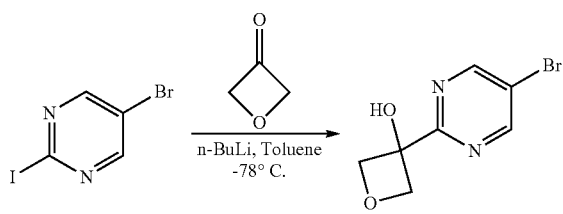 [SMILES: Brc1cnc(I)nc1 ; O=C1COC1 ; OC1(c2ncc(Br)cn2)COC1]

A solution of 5-bromo-2-iodopyrimidine (1.0 g, 3.5 mmol, 1.0 equiv) in Toluene (10 mL) was treated with n-BuLi in hexanes (3 mL, 7.5 mmol, 2.1 equiv) for 0.5 h at −78° C. under nitrogen atmosphere followed by the addition of 3-oxetanone (0.45 mL, 1.1 equiv) dropwise at −78° C. The resulting mixture was stirred for additional 30 min at −78° C. The resulting mixture was stirred for additional 1 h at room temperature. The reaction was quenched by the addition of sat. NH$_4$Cl (aq.) (5 mL) at room temperature. The resulting mixture was extracted with EtOAc (3×100 mL). The combined organic layers were washed with water (3×100 mL), dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in 3-(5-bromopyrimidin-2-yl)oxetan-3-ol (800 mg, 98.6%) as a yellow solid. LCMS (ESI, m/z): 230.90 [M+H]$^+$.

Intermediate 97

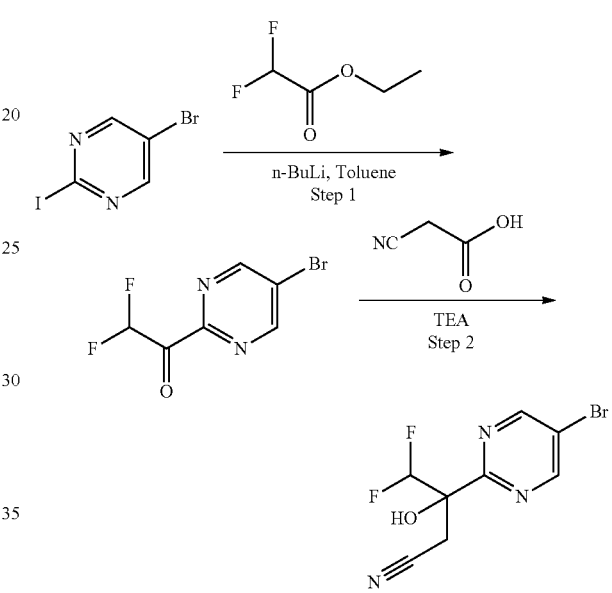

Step 1: A solution of 5-bromo-2-iodopyrimidine (10 g, 35.1 mmol, 1.0 equiv) in Toluene (6.7 mL) was treated with n-butyllithium (1M in THF, 17 mL, 42.5 mmol, 1.2 equiv) for 10 min at −78° C. under nitrogen atmosphere followed by the addition of ethyl 2,2-difluoroacetate (10.9 g, 87.8 mmol, 2.5 equiv) dropwise at −78° C. The resulting mixture was stirred for 30 min at −78° C. under nitrogen atmosphere. The reaction was quenched with sat. NH$_4$Cl (aq.) at 0° C. The resulting mixture was extracted with CH$_2$Cl$_2$ (3×20 mL). The combined organic layers were washed with brine (1×10 mL), dried over anhydrous Na$_2$SO$_4$. After filtration, the filtrate was concentrated under reduced pressure. The residue was purified by silica gel column chromatography, eluted with PE/EA (10:1) to afford 1-(5-bromopyrimidin-2-yl)-2,2-difluoroethanone (3.5 g, 41.6%) as a yellow oil. LCMS (ESI, m/z): 237 [M+H]$^+$.

Step 2: To a stirred solution of 1-(5-bromopyrimidin-2-yl)-2,2-difluoroethanone (3.6 g, 15.2 mmol, 1.0 equiv) and cyanoacetic acid (2.6 g, 30.4 mmol, 2.0 equiv) in THF (72 mL) were added TEA (0.3 g, 3.0 mmol, 0.2 equiv) in portions at room temperature under nitrogen atmosphere. The resulting mixture was stirred for 6 h at 60° C. under nitrogen atmosphere. The resulting mixture was extracted with CH$_2$Cl$_2$ (3×50 mL). The combined organic layers were washed with brine (1×20 mL), dried over anhydrous Na$_2$SO$_4$. After filtration, the filtrate was concentrated under reduced pressure. The residue was purified by silica gel column chromatography, eluted with PE/EA (3:1) to afford 3-(5-bromopyrimidin-2-yl)-4,4-difluoro-3-hydroxybutanenitrile (4 g, 94.5%) as a white solid. LCMS (ESI, m/z): 278 [M+H]$^+$.

Intermediates 98 & 99

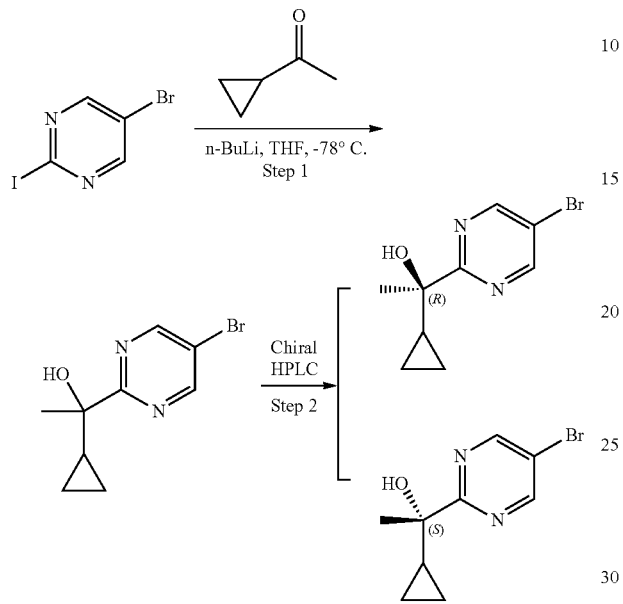

Step 1: A solution of 5-bromo-2-iodopyrimidine (48.0 mL, 120.1 mmol, 1.0 equiv) in THF (450 mL) was treated with n-BuLi in hexanes (75.8 mL, 121.3 mmol, 1.0 equiv) at −78° C. for 0.5 h under nitrogen atmosphere followed by the addition of cyclopropyl methyl ketone (10 g, 118.9 mmol, 1.0 equiv) dropwise at −78° C. The resulting mixture was stirred at room temperature for overnight under nitrogen atmosphere. The reaction was quenched by the addition of sat. NH$_4$Cl (aq.) (200 mL) at 0° C. The resulting mixture was extracted with EtOAc (3×500 mL), dried over anhydrous Na$_2$SO$_4$. After filtration, the filtrate was concentrated under reduced pressure. The residue was purified by silica gel column chromatography, eluted with PE/EA (3:1) to afford 1-(5-bromopyrimidin-2-yl)-1-cyclopropylethanol (6.5 g, 22.0%) as a yellow oil. LCMS (ESI, m/z): 243.01 [M+H]$^+$.

Step 2: 1-(5-bromopyrimidin-2-yl)-1-cyclopropylethanol (5.5 g) was further purified by Prep-Chiral-HPLC with the following conditions (Column: DAICELDC pakP4VP 4.6*50 mm, 3 μm; Mobile Phase B: ACN:MeOH=80:20 (1% 2M NH$_3$ in MeOH); Gradient: isocratic % B) to afford isomer 1 and isomer as a yellow solid. LCMS (ESI, m/z): 243.01 [M+H]$^+$.

Intermediates 100 & 101

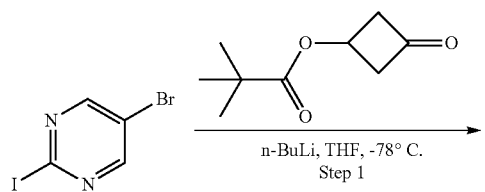

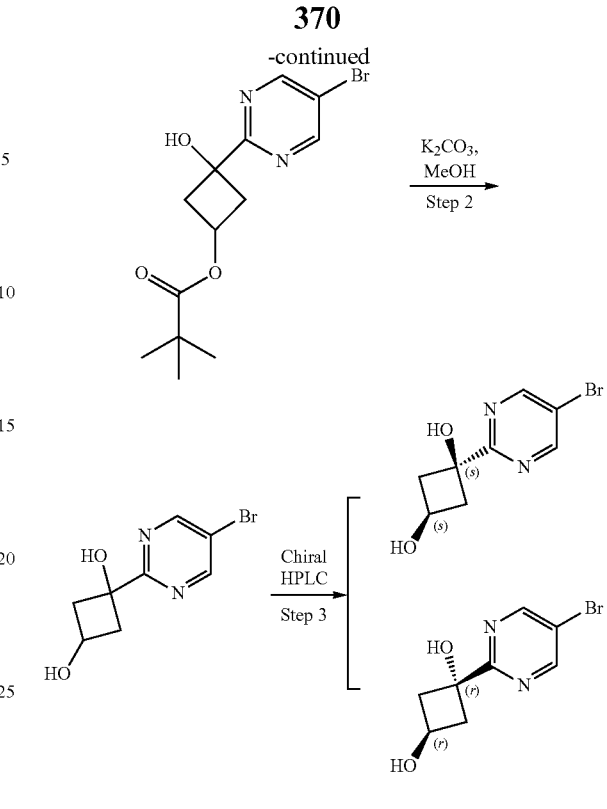

Step 1: A solution of 5-bromo-2-iodopyrimidine (8.0 g, 29.4 mmol, 1.0 equiv) in DCM (150 mL) was treated with butyllithium (12.0 mL, 29.4 mmol, 1.0 equiv) for 10 min at −78° C. under nitrogen atmosphere followed by the addition of 3-oxocyclobutyl 2,2-dimethylpropanoate (5.0 g, 29.4 mmol, 1.0 equiv) dropwise at −78° C. The resulting mixture was stirred for 30 min at −78° C. under nitrogen atmosphere. The reaction was quenched with sat. NH$_4$Cl (aq.) at 0° C. The resulting mixture was extracted with CH$_2$Cl$_2$ (3×200 mL). The combined organic layers were washed with brine (1×100 mL), dried over anhydrous Na$_2$SO$_4$. After filtration, the filtrate was concentrated under reduced pressure. The residue was purified by silica gel column chromatography, eluted with PE/EA (3:1) to afford 3-(5-bromopyrimidin-2-yl)-3-hydroxycyclobutyl 2,2-dimethylpropanoate (3.9 g, 40.3%) as a light yellow solid. LCMS (ESI, m/z): 329.00 [M+H]$^+$.

Step 2: A solution of 3-(5-bromopyrimidin-2-yl)-3-hydroxycyclobutyl 2,2-dimethylpropanoate (2.0 g, 5.5 mmol, 1.0 equiv) in MeOH (20 mL) was treated with K$_2$CO$_3$ (1.0 g, 5.5 mmol, 1.0 equiv) at room temperature under nitrogen atmosphere. The resulting mixture was stirred for 30 min at 75° C. under air atmosphere. The resulting mixture was filtered, the filter cake was washed with EtOAc (3×10 mL). The filtrate was concentrated under reduced pressure. The residue was purified by reversed-phase flash chromatography with the following conditions: column, C18 silica gel; mobile phase, ACN in Water (0.1% TFA), 10% to 30% gradient in 10 min; detector, UV 254 nm. This resulted in 1-(5-bromopyrimidin-2-yl)cyclobutane-1,3-diol (900 mg, 67.2%) as a light yellow solid. LCMS (ESI, m/z): 246.95 [M+H]$^+$.

Step 3: 1-(5-bromopyrimidin-2-yl)cyclobutane-1,3-diol (2.0 g) was further purified by Prep-HPLC with the following conditions (Column: GreenSep Basic 3*15 cm, 5 μm; Mobile Phase A: CO$_2$, Mobile Phase B: ACN:MeOH=4:1 (1%-2M-NH$_3$-MeOH); Flow rate: 75 mL/min; Gradient:

isocratic 24% B; Column Temperature (° C.): 35; Back Pressure(bar): 100; Wave Length: 220 nm; RT1(min): 2.88; RT2(min): 3.82; Sample Solvent: MeOH; Injection Volume: 2 mL) to afford (1s, 3s)-1-(5-bromopyrimidin-2-yl)cyclobutane-1,3-diol (1.2 g, 60.00%) as a white solid. LCMS (ESI, m/z): 246.95 [M+H]+. 1H NMR (400 MHz, DMSO-d6) δ 8.99 (d, J=1.3 Hz, 2H), 5.65 (d, J=1.0 Hz, 1H), 5.10 (d, J=6.3 Hz, 1H), 4.08-3.92 (m, 1H), 2.87-2.82 (m, 2H), 2.25-2.20 (m, 2H).

Intermediates 102 & 103

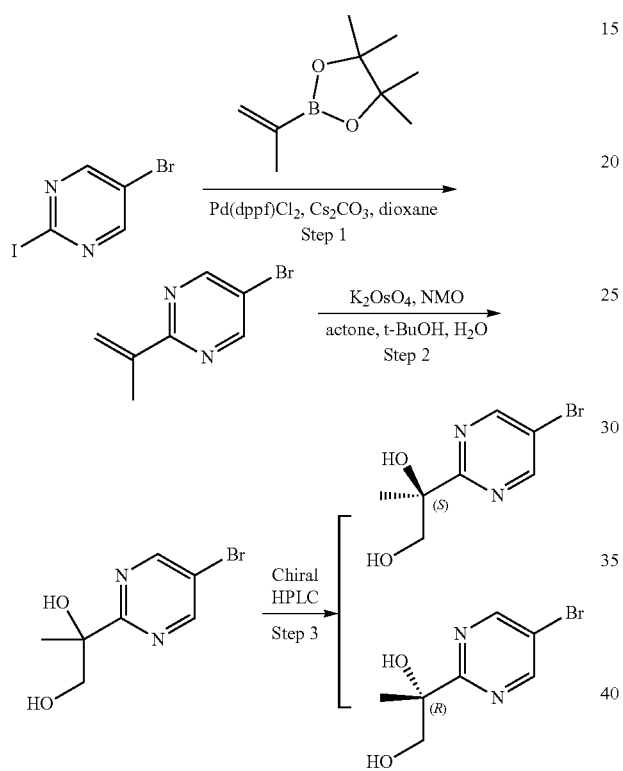

Step 1: A solution of 5-bromo-2-iodopyrimidine (5.0 g, 17.6 mmol, 1.0 equiv), 4,4,5,5-tetramethyl-2-(prop-1-en-2-yl)-1,3,2-dioxaborolane (3.2 g, 19.3 mmol, 1.1 equiv) in dioxane (15 mL), H2O (6 mL) was treated with Pd(dppf)Cl2·CH2Cl2 (1.4 g, 1.8 mmol, 0.1 equiv), Cs2CO3 (17.2 g, 52.6 mmol, 3.0 equiv). The resulting mixture was stirred for 12 h at 80° C. under nitrogen atmosphere. The resulting mixture was concentrated under reduced pressure. The residue was purified by silica gel column chromatography, eluted with PE:EA=50:1 to afford 5-bromo-2-(prop-1-en-2-yl)pyrimidine (2.0 g, 57.3%) as a white solid. LCMS (ESI, m/z): 198.95 [M+H]+.

Step 2: To a stirred mixture of 5-bromo-2-(prop-1-en-2-yl)pyrimidine (2.0 g, 10.0 mmol, 1.0 equiv) and NMO (1.3 g, 11.1 mmol, 1.1 equiv) in propan-2-one (6 mL), H2O (2.8 mL, 38.9 mmol), t-BuOH (2.8 mL, 20.1 mmol, 2.0 equiv) were added K2OsO4·2H2O (0.04 g, 0.1 mmol, 0.01 equiv) at room temperature under nitrogen atmosphere. The resulting mixture was stirred for 30 min at room temperature under nitrogen atmosphere. The resulting mixture was concentrated under reduced pressure. The resulting mixture was extracted with EtOAc (3×10 mL), dried over anhydrous Na2SO4. After filtration, the filtrate was concentrated under reduced pressure. The residue was purified by silica gel column chromatography, eluted with PE/EA (10:1) to afford 2-(5-bromopyrimidin-2-yl)propane-1,2-diol (300 mg, 12.8%) as a yellow solid. LCMS (ESI, m/z): 232.75 [M+H]+.

Step 3: 2-(5-bromopyrimidin-2-yl)propane-1,2-diol (1.3 g) was further purified by Prep_Chiral_HPLC with the following conditions (Column: CHIRALCELOD3; Mobile Phase A: Hex (0.1% FA):EtOH=92:8; Flow rate: 1 mL/min; Gradient: isocratic; Injection Volume: 2 mL) to afford isomer 1 (540 mg) and isomer 2 (500 mg) as a yellow solid.

Intermediates 104 & 105

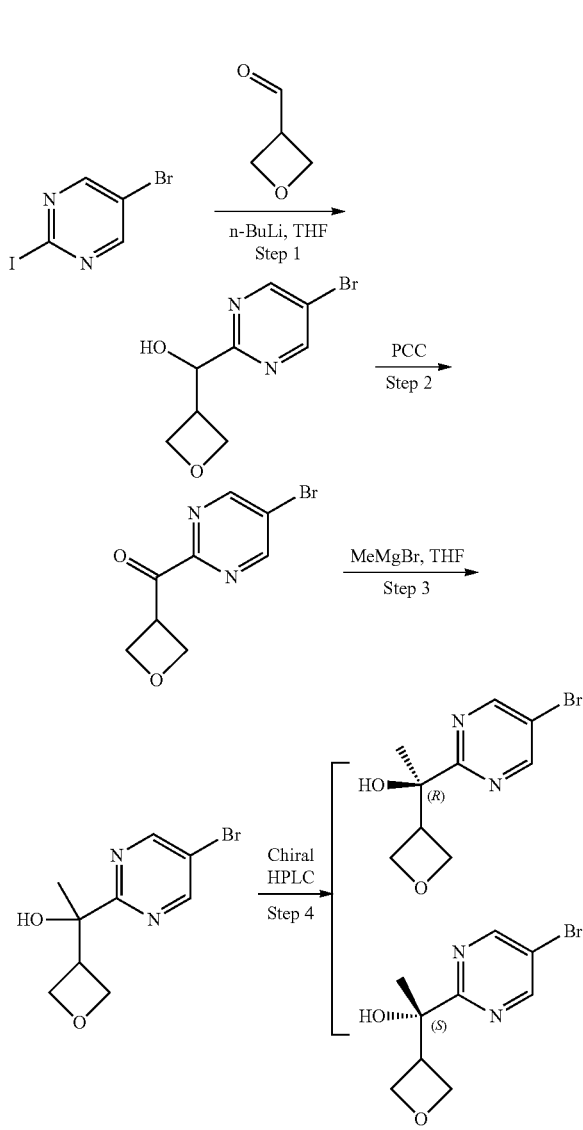

Step 1: A mixture of 5-bromo-2-iodopyrimidine (5.0 g, 17.6 mmol, 1.0 equiv) in THF (60 mL) was added n-Butyllithium (2.5 M in n-hexane) (8.5 mL, 21.1 mmol, 1.2 equiv) drop wise at −78° C. under nitrogen atmosphere. The mixture was stirred for 1 h at −78° C. And then oxetane-3-carbaldehyde (2.0 g, 22.8 mmol, 1.3 equiv) was added at −78° C. The mixture was stirred for 1 h at −78° C., then allowed to warm to room temperature and stirred for 1 h. The reaction was quenched with sat. NH4Cl (aq.) at 0° C.

The resulting mixture was extracted with EtOAc (3×300 mL). The combined organic layers were washed with brine, dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (10 mmol/L NH₄HCO₃), 20% to 40% gradient in 10 min; detector, UV 220 nm. This resulted in (5-bromopyrimidin-2-yl)(oxetan-3-yl)methanol (720 mg) as a brown yellow solid. LCMS (ESI, m/z): 244.95 [M+H]⁺.

Step 2: A mixture of (5-bromopyrimidin-2-yl)(oxetan-3-yl)methanol (720 mg, 2.9 mmol, 1.0 equiv) in DCM (15 mL) was added chlorochromiumoylol (1.3 g, 5.9 mmol, 2.0 equiv) at 0° C. The mixture was allowed to warm to room temperature and stirred for overnight. The resulting mixture was filtered, the filter cake was washed with DCM (15 mL) (3×200 mL). The filtrate was concentrated under reduced pressure. The residue was purified by Prep-TLC (CH₂Cl₂/MeOH 20:1) to afford 5-bromo-2-(oxetane-3-carbonyl)pyrimidine (352 mg) as colorless oil. LCMS (ESI, m/z): 243.05 [M+H]⁺.

Step 3: A mixture of 5-bromo-2-(oxetane-3-carbonyl)pyrimidine (300 mg, 1.2 mmol, 1.0 equiv) in THF (6 mL) was added methylmagnesium bromide (1.0M in THF) (147.2 mg, 1.2 mmol, 1.0 equiv) drop wise at −78° C. under nitrogen atmosphere. The mixture was stirred for 1 h at −78° C. The reaction was quenched with sat. NH₄Cl (aq.) at 0° C. The resulting mixture was extracted with EtOAc (3×80 mL). The combined organic layers were washed with brine, dried over anhydrous Na₂SO₄. After filtration, the filtrate was concentrated under reduced pressure. The residue was purified by Prep-TLC (CH₂Cl₂/MeOH 20:1) to afford 1-(5-bromopyrimidin-2-yl)-1-(oxetan-3-yl)ethanol (170 mg) as a colorless solid. LCMS (ESI, m/z): 258.95 [M+H]⁺.

Step 4: 1-(5-bromopyrimidin-2-yl)-1-(oxetan-3-yl)ethanol (170 mg) was further purified by Prep-HPLC with the following conditions (Column: JW-CHIRALPAK IG, 20*250 mm, 5 um; Mobile Phase A: EtOH:DCM=1:1—HPLC, Mobile Phase B: Hex (0.5% 2M NH₃-MeOH)—HPLC; Flow rate: 20 mL/min; Gradient: 40% B to 40% B in 13 min; Wave Length: 220/254 nm; RT1(min): 3.96; RT2(min): 9.79; Sample Solvent: EtOH:DCM=1:1—HPLC; Injection Volume: 1.5 mL; Number Of Runs: 4) to afford isomer 1 (55 mg) and isomer 2 (57 mg) as a colorless solid. LCMS (ESI, m/z): 259.00 [M+H]⁺.

Intermediate 106

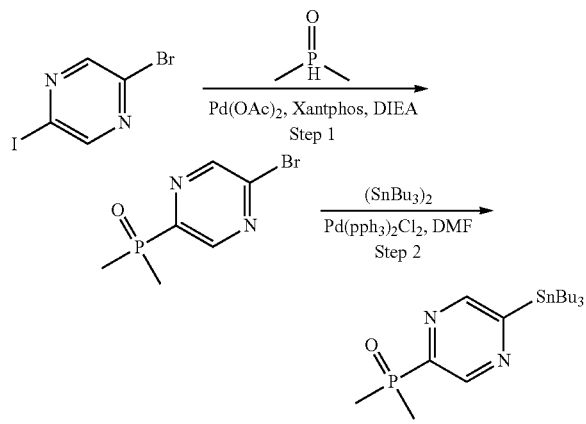

Step 1: Into a 40 mL vial were added 2-bromo-5-chloropyrazine (1.0 g, 5.2 mmol, 1.0 equiv) and (methylphosphonoyl)methane (0.48 g, 6.2 mmol, 1.2 equiv) in 1,4-dioxane (10 mL) at room temperature. To the above mixture was added Pd(OAc)₂ (0.12 g, 0.52 mmol, 0.1 equiv), XantPhos (0.6 g, 1.0 mmol, 0.2 equiv), DIEA (2.0 g, 15.5 mmol, 3.0 equiv) in portions over 10 min at room temperature. The resulting mixture was stirred at 100° C. for additional 2 h. The reaction was quenched with Water at room temperature. The resulting mixture was extracted with EtOAc (2×50 mL). The combined organic layers were washed with brine (2×50 mL), dried over anhydrous Na₂SO₄. After filtration, the filtrate was concentrated under reduced pressure. The resulting mixture was concentrated under vacuum. The residue was purified by reversed-phase flash chromatography with the following conditions: column, C18 silica gel; mobile phase, MeCN in Water (10 mmol/L NH₄HCO₃), 10% to 50% gradient in 10 min; detector, UV 254 nm. to afford 2-chloro-5-(dimethylphosphoryl)pyrazine (300 mg) as a white solid. LCMS (ESI-FA, m/z): 235 [M+H]⁺.

Step 2: Into a 8 mL vial were added 2-chloro-5-(dimethylphosphoryl)pyrazine (300 mg, 1.6 mmol, 1.0 equiv) in 1,4-dioxane (2 mL) at room temperature. To the above mixture was added Pd(PPh₃)₂Cl₂ (110.5 mg, 0.16 mmol, 0.1 equiv) in portions over 10 min at room temperature. The resulting mixture was stirred at 100° C. for additional 2 h. The precipitated solids were collected by filtration and washed with MeOH (2×50 mL). The resulting mixture was concentrated under reduced pressure. The residue was purified by Prep-TLC (CH₂Cl₂/MeOH 12:1) to afford 2-(dimethylphosphoryl)-5-(tributylstannyl)pyrazine (180 mg) as a black oil. LCMS (ESI, m/z): 447 [M+H]⁺.

Intermediate 107

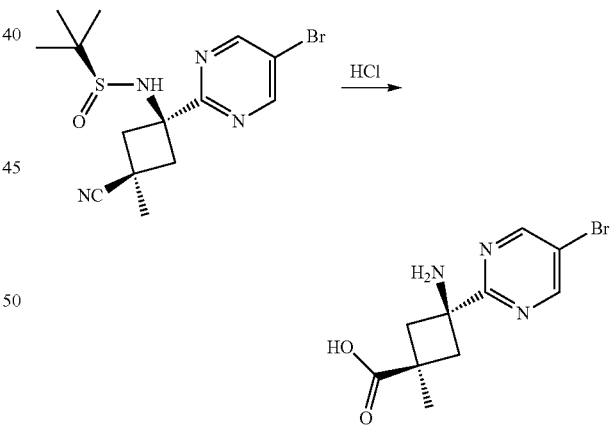

A solution of (S)-2-methyl-N-[(1r,3s)-1-(5-bromopyrimidin-2-yl)-3-cyano-3-methylcyclobutyl]propane-2-sulfinamide (100 mg, 0.26 mmol, 1.00 equiv) in HCl (6N, 1 mL) was stirred at 100° C. for overnight under nitrogen atmosphere. Desired product could be detected by LCMS. The resulting mixture was concentrated under reduced pressure. The residue was purified by reversed-phase flash chromatography with the following conditions: column, C18 silica gel; mobile phase, MeCN in Water (10 mmol/L NH₄HCO₃), 10% to 50% gradient in 10 min; detector, UV 254 nm. to afford (1s,3r)-3-amino-3-(5-bromopyrimidin-2-yl)-1-methylcyclobutane-1-carboxylic acid (20 mg, 25.95% yield, 90% purity) as a colorless oil. LCMS (ESI, m/z): 285.85 [M+H]$^+$.

Intermediates 108 & 109

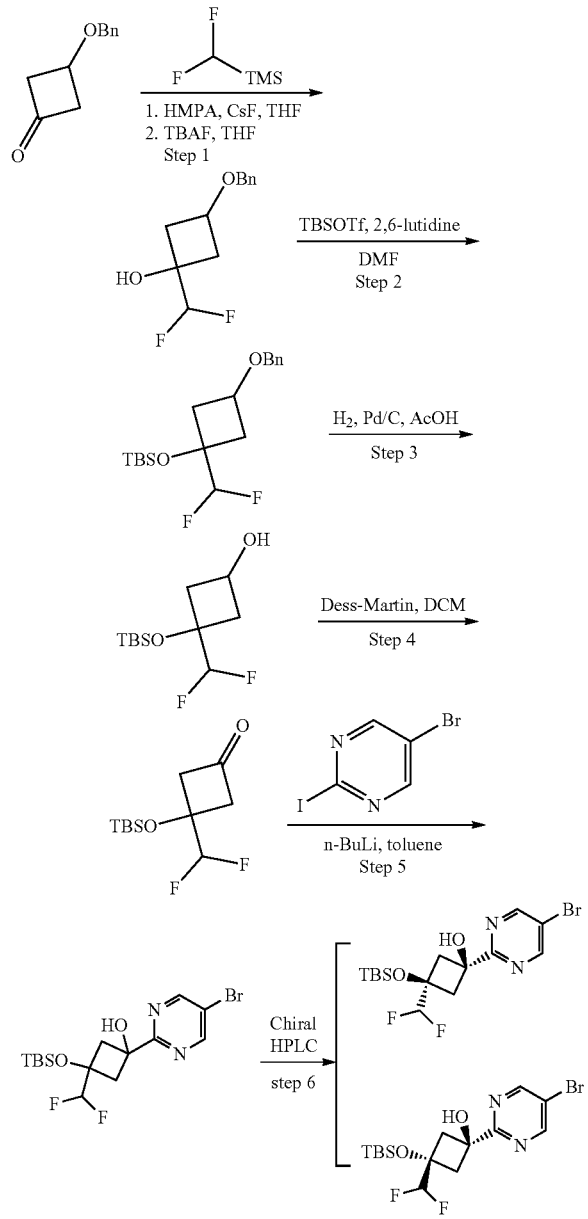

Step 1: A solution of 3-(benzyloxy)cyclobutan-1-one (20 g, 113.5 mmol, 1.0 equiv) in THF (350 mL) was treated with HMPA (101.7 g, 567.5 mmol, 5.0 equiv), CsF (5.2 g, 34.1 mmol, 0.3 equiv) at room temperature for 5 min under nitrogen atmosphere followed by the addition of (difluoromethyl)trimethylsilane (42.3 g, 340.5 mmol, 3.0 equiv) dropwise at room temperature. To the above mixture was added TBAF (200 mL) dropwise over 5 min at room temperature. The resulting mixture was stirred at room temperature for additional overnight. The mixture was acidified to pH 6 with citric acid. The resulting mixture was extracted with EtOAc (3×1 L). The combined organic layers were washed with brine (1×800 mL), dried over anhydrous Na$_2$SO$_4$. After filtration, the filtrate was concentrated under reduced pressure. The residue was purified by silica gel column chromatography, eluted with PE/EA (1:1) to afford [3-(benzyloxy)-1-(difluoromethyl)cyclobutoxy]trimethylsilane (2.2 g, 90% purity) as a light yellow oil.

Step 2: A solution of 3-(benzyloxy)-1-(difluoromethyl)cyclobutan-1-ol (2.2 g, 9.6 mmol, 1.0 equiv) in DMF (20 mL) was treated with imidazole (2.2 g, 31.8 mmol, 3.3 equiv), tert-butyl(chloro)dimethylsilane (4.8 g, 31.8 mmol, 3.3 equiv) at room temperature for 1 min under nitrogen atmosphere followed by the addition of DMAP (0.12 g, 0.96 mmol, 0.1 equiv) dropwise at room temperature. The resulting mixture was stirred at 80° C. for additional overnight. The residue was purified by reversed-phase flash chromatography with the following conditions: column, C18 silica gel; mobile phase, MeCN in Water (0.1% FA), 0% to 100% gradient in 15 min; detector, UV 254 nm to afford [3-(benzyloxy)-1-(difluoromethyl)cyclobutoxy](tert-butyl)dimethylsilane (2.1 g, 90% purity) as a light yellow oil.

Step 3: To a solution of [3-(benzyloxy)-1-(difluoromethyl)cyclobutoxy](tert-butyl)dimethylsilane (2 g, 5.8 mmol, 1.0 equiv) in AcOH (15 mL) was added Pd/C (1242.9 mg, 11.7 mmol, 2 equiv) under nitrogen atmosphere in a 50 mL vial. The mixture was hydrogenated at 50° C. for 1 h under hydrogen atmosphere using a hydrogen balloon, filtered through a Celite pad and concentrated under reduced pressure. This resulted in 3-[(tert-butyldimethylsilyl)oxy]-3-(difluoromethyl)cyclobutan-1-ol (1.3 g) as an off-white oil.

Step 4: To a stirred solution of 3-[(tert-butyldimethylsilyl)oxy]-3-(difluoromethyl)cyclobutan-1-ol (1.4 g, 5.5 mmol, 1.0 equiv) in DCM (30 mL) was added 1,1,1-tris(acetyloxy)-1,1-dihydro-1,2-benziodoxol-3-(1H)-one (3.5 g, 8.3 mmol, 1.5 equiv) in portions at 0° C. under nitrogen atmosphere. The resulting mixture was stirred at room temperature for additional 2 h. The reaction was monitored by TLC. The residue was purified by silica gel column chromatography, eluted with PE/EA (20:1) to afford 3-[(tert-butyldimethylsilyl)oxy]-3-(difluoromethyl)cyclobutan-1-one (1.2 g) as a off-white oil. LCMS (ESI, m/z): 251.1 [M+H]$^+$.

Step 5: In a 500-mL round bottom flask, to a solution of 5-bromo-2-iodopyrimidine (1.5 g, 5.3 mmol, 1.1 equiv) in toluene (35 mL) was added dropwise butyllithium (1.6 M in n-hexane) (337.8 mg, 5.3 mmol, 1.1 equiv) at −78° C. under N$_2$ atmosphere. The reaction mixture was stirred at −78° C. for 30 mins. Then a solution of 3-[(tert-butyldimethylsilyl)oxy]-3-(difluoromethyl)cyclobutan-1-one (1.2 g, 4.8 mmol, 1.0 equiv) in toluene (35 mL) was added dropwise and the mixture was stirred for another 2 h. The reaction was quenched with water/sat. NH$_4$Cl (30 mL), and then the mixture was extracted with EA (2×100 mL). The combined organic extracts were washed with brine (100 mL), dried over anhydrous Na$_2$SO$_4$, and concentrated under vacuum to yield a crude product which was directly purified by reverse phase flash with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 50% B in 7 min; Wave Length: 254 nm/220 nm nm; RT1(min): 6.56) to afford 1-(5-bromopyrimidin-2-yl)-3-[(tert-butyldimethylsilyl)oxy]-3-(difluoromethyl)cyclobutan-1-ol (1.0 g) as a off-white solid.

Step 6: 1-(5-bromopyrimidin-2-yl)-3-[(tert-butyldimethylsilyl)oxy]-3-(difluoromethyl)cyclobutan-1-ol was further purified by reverse phase flash with the following conditions (Column: X-Select Prep OBD C18 Column, 30*150 mm, 5 μm; Mobile Phase A: Water (0.1% FA), Mobile Phase B:

ACN; Flow rate: 60 mL/min mL/min; Gradient: 30% B to 50% B in 7 min; Wave Length: 254 nm/220 nm nm; RT1(min): 6.56) to afford (1s, 3s)-1-(5-bromopyrimidin-2-yl)-3-[(tert-butyldimethylsilyl)oxy]-3-(difluoromethyl)cyclobutan-1-ol (250 mg, 95% purity) as a off-white solid.

Intermediate 110

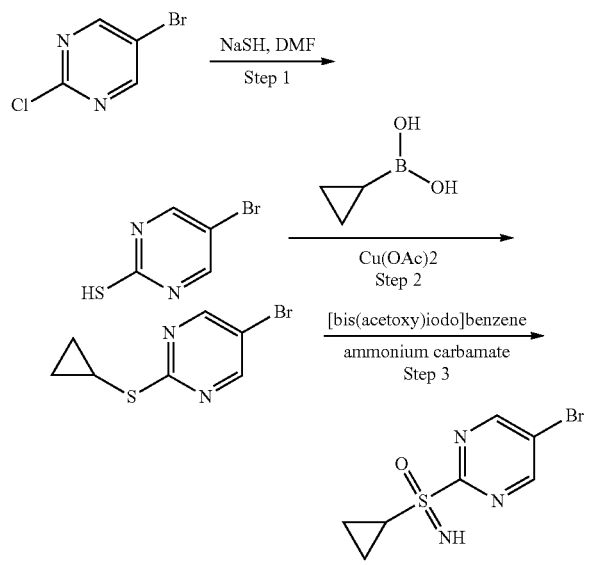

Step 1: To a stirred solution of 5-bromo-2-chloropyrimidine (10.0 g, 51.7 mmol, 1.0 equiv) in DMF (100 mL) were added NaSH (4.4 g, 77.5 mmol, 1.5 equiv) under nitrogen atmosphere. The resulting mixture was stirred for 1 h at room temperature. The reaction mixture was portioned between ethyl acetate and water, and transferred to a separatory funnel. After the layers were separated, the ethyl acetate layer was washed twice with water and 5% sodium bicarbonate (2:1). The combined aqueous layers were acidified with 1 N HCl precipitating a yellow solid. The suspension was left to stand at room temperature for 2 h, then the precipitate was collected by vacuum filtration to afford 5-bromopyrimidine-2-thiol (11.0 g) as a yellow solid. The crude product was used in the next step directly without further purification.

Step 2: To a solution of 5-bromopyrimidine-2-thiol (5.0 g, 25.9 mmol, 1.0 equiv,) in 1,2-dichloroethane (100 mL) was added cyclopropylboronic acid (3.6 g, 41.5 mmol, 1.6 equiv), Cu(OAc)$_2$ (4.7 g, 25.9 mmol, 1.0 equiv), 2-(pyridin-2-yl) pyridine (4.1 g, 25.9 mmol, 1.0 equiv). The reaction mixture was stirred at 70° C. for 12 h. The reaction was quenched with water, NH$_3$·H$_2$O (25%) (31 mL) at room temperature. The resulting mixture was extracted with CH$_2$Cl$_2$/MeOH (10:1) (4×1000 mL). The filtrate was concentrated under reduced pressure. The residue was purified by reversed-phase flash chromatography with the following conditions: column, C18 silica gel; mobile phase, Water in ACN, 50% to 80% gradient in 10 min; detector, UV 254 nm to afford 5-bromo-2-(cyclopropylsulfanyl) pyrimidine (1.6 g) as light yellow oil. LCMS (ESI, m/z): 231 [M+H]$^+$.

Step 3: A mixture of 5-bromo-2-(cyclopropylsulfanyl) pyrimidine (1.65 g, 7.1 mmol, 1.0 equiv) and (diacetoxyiodo)benzene (11.5 g, 35.7 mmol, 5.0 equiv), ammonium carbamate (1.67 g, 21.4 mmol, 3.0 equiv) in MeOH (100 mL) was stirred at room temperature for 7 h. The resulting mixture was concentrated under vacuum. The residue was purified by Prep-TLC (CH$_2$Cl$_2$/MeOH 30:1) to afford (5-bromopyrimidin-2-yl) (cyclopropyl)imino-lambda6-sulfanylone (888 mg) as a light yellow solid. LCMS (ESI, m/z): 262.00 [M+H]$^+$.

Intermediate 111

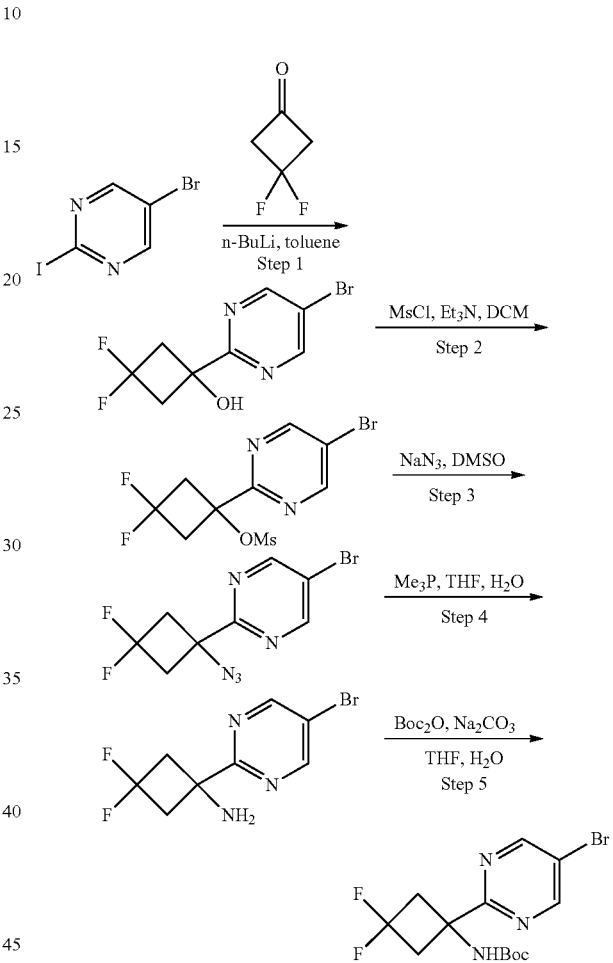

Step 1: A solution of 5-bromo-2-iodopyrimidine (12.0 g, 42.1 mmol, 1.0 equiv) in Toluene (800 mL) was treated with n-BuLi in hexanes (17.7 mL, 44.2 mmol, 1.1 equiv) at −78° C. for 30 min under nitrogen atmosphere followed by the addition of 3,3-difluorocyclobutan-1-one (4.9 g, 46.3 mmol, 1.1 equiv) dropwise at −78° C. The resulting mixture was stirred at −78 to 25° C. for 1 h under nitrogen atmosphere. The reaction was quenched with sat. NH$_4$Cl (aq.) at 0° C. The aqueous layer was extracted with EtOAc (3×800 mL), dried over anhydrous Na$_2$SO$_4$. The resulting mixture was concentrated under vacuum. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in 1-(5-bromopyrimidin-2-yl)-3,3-difluorocyclobutan-1-ol (4.6 g) as a brown solid. LCMS (ESI, m/z): 266.95 [M+H]$^+$.

Step 2: To a stirred solution of 1-(5-bromopyrimidin-2-yl)-3,3-difluorocyclobutan-1-ol (542 mg, 2.0 mmol, 1.0 equiv) in DCM (7 mL) were added Et$_3$N (0.6 mL, 4.1 mmol, 2.0 equiv) and TBDMSCl (580.7 mg, 2.7 mmol, 1.3 equiv, 69%) at 0° C. under air atmosphere. The resulting mixture was stirred at room temperature for 1 h under air atmosphere. The reaction was quenched with sat. NaHCO₃(aq.) at 0° C. The resulting mixture was extracted with EtOAc (3×20 mL). The combined organic layers were dried over anhydrous Na₂SO₄. After filtration, the filtrate was concentrated under reduced pressure. The residue was purified by Prep-TLC (PE/EA 2:1) to afford 1-(5-bromopyrimidin-2-yl)-3,3-difluorocyclobutyl methanesulfonate (500 mg, 71.3%) as alight yellow solid. LCMS (ESI, m/z): 338.30[M+H]⁺.

Step 3: To a stirred solution of 1-(5-bromopyrimidin-2-yl)-3,3-difluorocyclobutyl methanesulfonate (536 mg, 1.6 mmol, 1.0 equiv) in DMSO (7 mL) were added NaN₃ (1.1 g, 7.8 mmol, 5.0 equiv, 45%) at room temperature under air atmosphere. The resulting mixture was stirred at 70° C. for overnight under air atmosphere. The reaction was quenched with water at room temperature. The resulting mixture was extracted with EtOAc (4×10 mL). The combined organic layers were washed with brine (3×10 mL), dried over anhydrous Na₂SO₄. After filtration, the filtrate was concentrated under reduced pressure. This resulted in 2-(1-azido-3,3-difluorocyclobutyl)-5-bromopyrimidine (420 mg, 92.7% yield, 70% purity) as a light yellow oil.

Step 4: To a stirred solution of 2-(1-azido-3,3-difluorocyclobutyl)-5-bromopyrimidine (60 mg, 0.2 mmol, 1.0 equiv) in THF (2.4 mL) were added H₂O (0.6 mL) and trimethylphosphine (1.0 M in THF) (0.31 mL, 0.3 mmol, 1.5 equiv) at room temperature under nitrogen atmosphere. The resulting mixture was stirred at 60° C. for 1 h under nitrogen atmosphere. The resulting mixture was extracted with EtOAc (3×10 mL). The combined organic layers were washed with brine, dried over anhydrous Na₂SO₄. After filtration, the filtrate was concentrated under reduced pressure. The residue was purified by Prep-TLC (PE/EA 1:1) to afford 1-(5-bromopyrimidin-2-yl)-3,3-difluorocyclobutan-1-amine (16 mg, 29.3%) as off-white solid.

Step 5: A solution of 1-(5-bromopyrimidin-2-yl)-3,3-difluorocyclobutan-1-amine (50 mg, 0.18 mmol, 1.0 equiv) and di-tert-butyl dicarbonate (62 mg, 0.28 mmol, 1.5 equiv) in THF (2 mL) was stirred at 80° C. for 1 h under nitrogen atmosphere. The resulting mixture was extracted with EtOAc (3×5 mL), dried over anhydrous Na₂SO₄. After filtration, the filtrate was concentrated under reduced pressure. The residue was purified by Prep-TLC (PE/EA 1:1) to afford tert-butyl N-[1-(5-bromopyrimidin-2-yl)-3,3-difluorocyclobutyl]carbamate (50 mg) as a light yellow solid. LCMS (ESI, m/z): 366.05 [M+H]⁺.

Intermediates 112 & 113

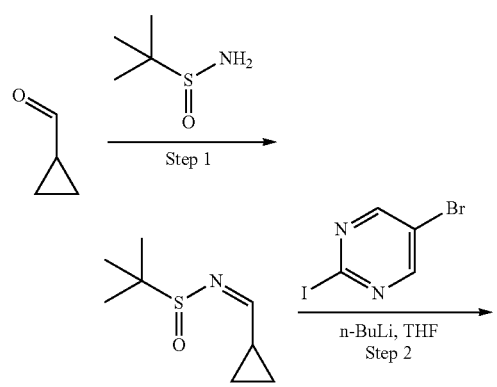

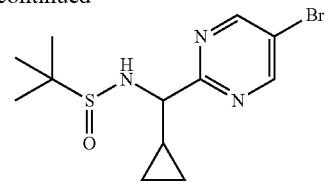

Step 1: A solution of cyclopropanecarbaldehyde (10 g, 142.7 mmol, 1.0 equiv) and tert-butanesulfinamide (17.3 g, 142.7 mmol, 0.01 equiv) in THF (200 mL) was stirred with Ti(Oi-Pr)₄ (106.7 mL, 356.7 mmol, 2.5 equiv) for overnight at 60° C. under nitrogen atmosphere. The resulting mixture was concentrated under vacuum. The residue was dissolved in EtOAc (60 mL). The reaction was quenched by the addition of Sodium bicarbonate solution (aq.) (30 mL) at 0° C. The resulting mixture was filtered, the filter cake was washed with EtOAc (3×20 mL). The filtrate was concentrated under reduced pressure. The resulting mixture was extracted with EtOAc (2×80 mL). The combined organic layers were dried over anhydrous Na₂SO₄. After filtration, the filtrate was concentrated under reduced pressure. The residue was purified by silica gel column chromatography, eluted with PE/EA (10:1) to afford N-[(1Z)-cyclopropylmethylidene]-2-methylpropane-2-sulfinamide (15 g, 60.7%) as a light yellow liquid. LCMS (ESI, m/z): 174.1 [M+H]⁺.

Step 2: A solution of 5-bromo-2-iodopyrimidine (21.4 g, 75.0 mmol, 1.3 equiv) in DCM (380 mL) was treated with butyllithium (1.6 M in n-hexane) (43.3 ml, 69.3 mmol, 1.2 equiv) at −78° C. for 30 min under nitrogen atmosphere followed by the addition of N-[(1Z)-cyclopropylmethylidene]-2-methylpropane-2-sulfinamide (10 g, 57.7 mmol, 1.0 equiv) dropwise at −78° C. The resulting mixture was stirred at 25° C. for additional 2 h. The reaction was quenched with NH₄Cl at ° C. The resulting mixture was extracted with DCM (3×200 mL). The combined organic layers were dried over anhydrous Na₂SO₄. After filtration, the filtrate was concentrated under reduced pressure. The residue was purified by silica gel column chromatography, eluted with PE/EA (1:1) to afford N-[(5-bromopyrimidin-2-yl)(cyclopropyl)methyl]-2-methylpropane-2-sulfinamide (4.5 g, 23.4%) as a yellow oil. LCMS (ESI, m/z): 332.05 [M+H]⁺.

Intermediate 114 & 115

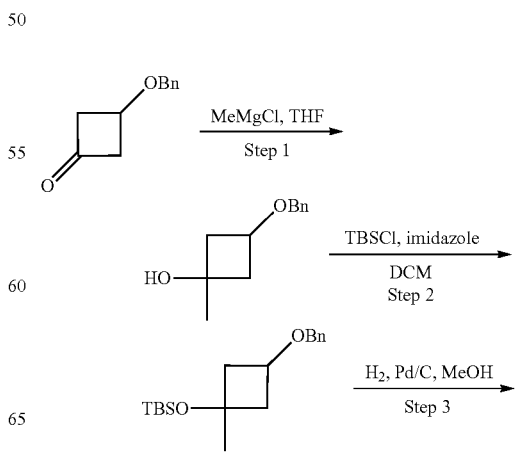

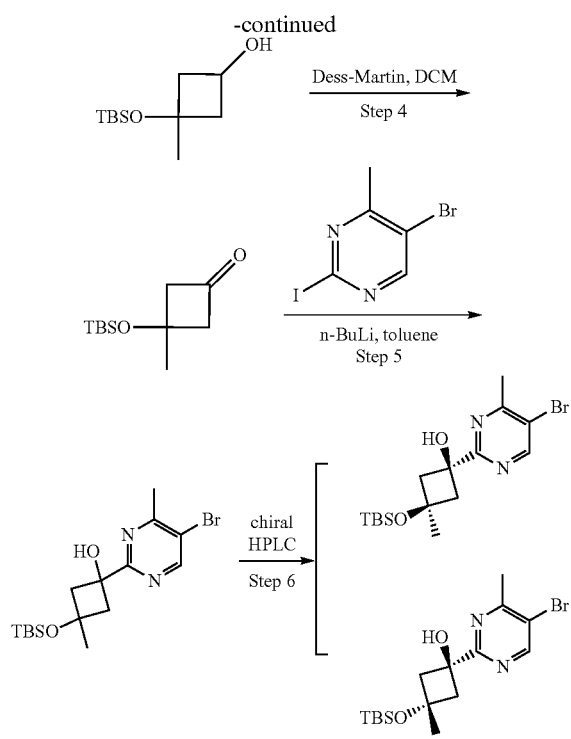

Step 1: Chloro(methyl)magnesium (170.3 mL, 510.7 mmol, 1.5 equiv) was added dropwise to a solution of 3-(benzyloxy)cyclobutan-1-one (60 g, 340.5 mmol, 1.0 equiv) in THF (600 mL) at −78° C. The mixture was stirred at −78° C. for 1 h. The reaction was then quenched by aqueous NH₄Cl solution. The aqueous layer was extracted with ethyl acetate and the combined organic layers were washed with brine, dried over Na₂SO₄ and concentrated. The residue was purified by reversed-phase flash chromatography with the following conditions: column, C18 silica gel; mobile phase, MeCN in Water (0.1% TFA), 30% to 50% gradient in 10 min; detector, UV 254 nm. This resulted in 3-(benzyloxy)-1-methylcyclobutan-1-ol (85 g) as a yellow oil. LCMS (ESI, m/z): 192.50 [M+H]⁺.

Step 2: A solution of 3-(benzyloxy)-1-methylcyclobutan-1-ol (93 g, 483.7 mmol, 1.0 equiv) in DCM (1000 mL) was treated with Imidazole (164.7 g, 2418.6 mmol, 5.0 equiv) for 5 min at 0° C. under nitrogen atmosphere followed by the addition of TBSCl (218.7 g, 1451.2 mmol, 3.0 equiv) at 40° C. The resulting mixture was stirred for 1 h at room temperature under nitrogen atmosphere. The resulting mixture was extracted with CH₂Cl₂ (3×100 mL). The combined organic layers were washed with brine (2×100 mL), dried over anhydrous Na₂SO₄. After filtration, the filtrate was concentrated under reduced pressure. The residue was purified by silica gel column chromatography, eluted with PE/EA (40:1) to afford [3-(benzyloxy)-1-methylcyclobutoxy](tert-butyl)dimethylsilane (100 g) as a yellow oil. LCMS (ESI, m/z): 307.10 [M+H]⁺.

Step 3: To a solution of [3-(benzyloxy)-1-methylcyclobutoxy](tert-butyl)dimethylsilane (56 g, 182.7 mmol, 1.0 equiv) in MeOH (1000 mL) was added Pd/C (19.5 g, 18.3 mmol, 0.1 equiv, 10%) under nitrogen atmosphere in a 2 L round-bottom flask. The mixture was hydrogenated at room temperature overnight under hydrogen atmosphere using a hydrogen balloon, filtered through a Celite pad and concentrated under reduced pressure. The resulting mixture was filtered, the filter cake was washed with MeOH (500 mL). The filtrate was concentrated under reduced pressure. The crude product was used in the next step directly without further purification. LCMS (ESI, m/z): 217.10 [M+H]⁺.

Step 4: To a stirred solution of 3-[(tert-butyldimethylsilyl)oxy]-3-methylcyclobutan-1-ol (29.6 g, 136.8 mmol, 1.0 equiv) in DCM (300 mL) was added 1,1-bis(acetyloxy)-3-oxo-3H-1l^[5],2-benziodaoxol-1-yl acetate (87.0 g, 205.2 mmol, 1.5 equiv) dropwise at 0° C. under air atmosphere. The resulting mixture was stirred at room temperature for additional 1 h. The reaction was quenched with sat. sodium hyposulfite (aq.) at 0° C. The resulting mixture was extracted with CH₂Cl₂ (3×20 mL). The combined organic layers were washed with water (3×20 mL), dried over anhydrous Na₂SO₄. After filtration, the filtrate was concentrated under reduced pressure. The residue was purified by silica gel column chromatography, eluted with PE/EA (40:1) to afford 3-[(tert-butyldimethylsilyl)oxy]-3-methylcyclobutan-1-one (25 g) as a yellow oil. LCMS (ESI, m/z): 215.10 [M+H]⁺.

Step 5: A solution of 5-bromo-2-iodo-4-methylpyrimidine (2 g, 6.7 mmol, 1.0 equiv) in toluene (200 mL) was treated with n-BuLi in hexanes (2.8 mL, 7.0 mmol, 1.05 equiv) at −78° C. for 30 min under nitrogen atmosphere followed by the addition of 3-[(tert-butyldimethylsilyl)oxy]-3-methylcyclobutan-1-one (1.6 g, 74 mmol, 1.1 equiv) dropwise at −78° C. The resulting mixture was stirred at −78 to 25° C. for overnight under nitrogen atmosphere. The reaction was quenched with sat. NH₄Cl (aq.) at 0° C. The resulting mixture was extracted with EtOAc (3×100 mL), dried over anhydrous Na₂SO₄. After filtration, the filtrate was concentrated under reduced pressure. The residue was purified by reversed-phase flash chromatography with the following conditions: column, C18 silica gel; mobile phase, MeCN in Water (0.1% TFA), 10% to 50% gradient in 10 min; detector, UV 254 nm. This resulted in 1-(5-bromo-4-methylpyrimidin-2-yl)-3-[(tert-butyldimethylsilyl)oxy]-3-methylcyclobutan-1-ol (380 mg, 14.7%) as a yellow oil.

Step 6: 1-(5-bromo-4-methylpyrimidin-2-yl)-3-[(tert-butyldimethylsilyl)oxy]-3-methylcyclobutan-1-ol (380 MG) was further purified by reverse phase flash with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 50% B in 7 min; Wave Length: 254 nm/220 nm nm; RT1(min): 6.56) to afford (1s, 3s)-1-(5-bromo-4-methylpyrimidin-2-yl)-3-((tert-butyldimethylsilyl)oxy)-3-methylcyclobutan-1-ol (150 mg) as an off-white solid.

Intermediate 116 & 117

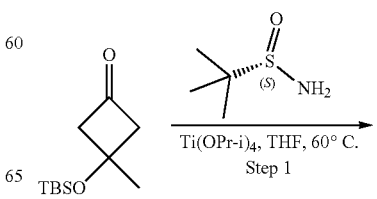

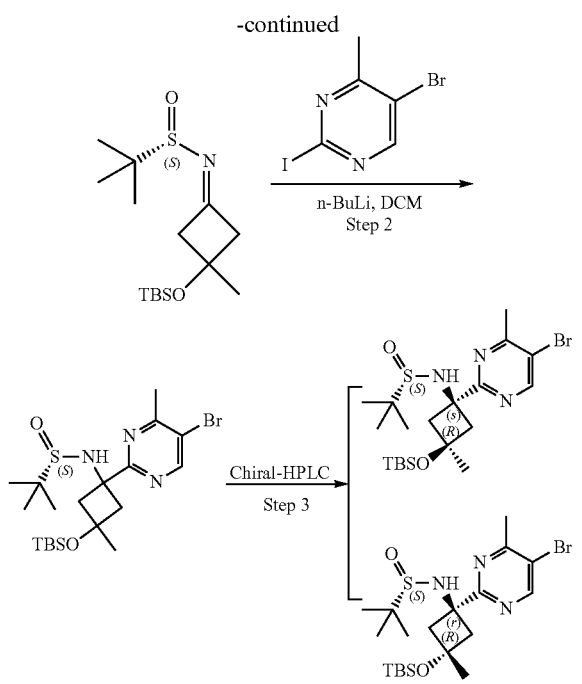

Mobile Phase A: EtOH:DCM=1:1—HPLC, Mobile Phase B: Hex (0.5% 2M NH₃-MeOH)—HPLC; Flow rate: 20 mL/min; Gradient: 98% B to 98% B in 10 min; Wave Length: 220/254 nm; RT1(min): 7.34; RT2(min): 8.68; Sample Solvent: EtOH:Hex—HPLC; Injection Volume: 0.7 mL; Number Of Runs: 12) to afford (S)—N-((1r,3S)-1-(5-bromo-4-methylpyrimidin-2-yl)-3-((tert-butyldimethylsilyl)oxy)-3-methylcyclobutyl)-2-methylpropane-2-sulfinamide (trans-isomer, peak1, Rt=7.34 min, 350 mg) as a colorless oil and (S)—N-((1s,3R)-1-(5-bromo-4-methylpyrimidin-2-yl)-3-((tert-butyldimethylsilyl)oxy)-3-methylcyclobutyl)-2-methylpropane-2-sulfinamide (cis-isomer, peak2, Rt=8.68 min, 200 mg) as a colorless oil. LCMS (ESI, m/z): 490.10 [M+H]⁺.

Peak 1: ¹H NMR (400 MHz, DMSO-d₆) δ 8.86 (s, 1H), 5.76 (d, J=1.5 Hz, 1H), 3.05 (d, J=12.7 Hz, 1H), 2.63 (d, J=2.2 Hz, 2H), 2.56 (s, 4H), 1.50 (s, 3H), 1.08 (s, 9H), 0.74 (s, 9H), 0.01 (d, J=4.0 Hz, 6H).

Peak 2: ¹H NMR (400 MHz, DMSO-d₆) δ 8.89 (s, 1H), 5.76 (d, J=1.9 Hz, 1H), 3.11 (dd, J=12.3, 4.6 Hz, 1H), 2.94 (dd, J=12.4, 4.6 Hz, 1H), 2.63 (d, J=12.0 Hz, 2H), 2.58 (s, 3H), 1.06 (s, 3H), 1.05 (s, 9H), 0.87 (s, 9H), 0.08 (s, 6H).

Intermediate 118 & 119

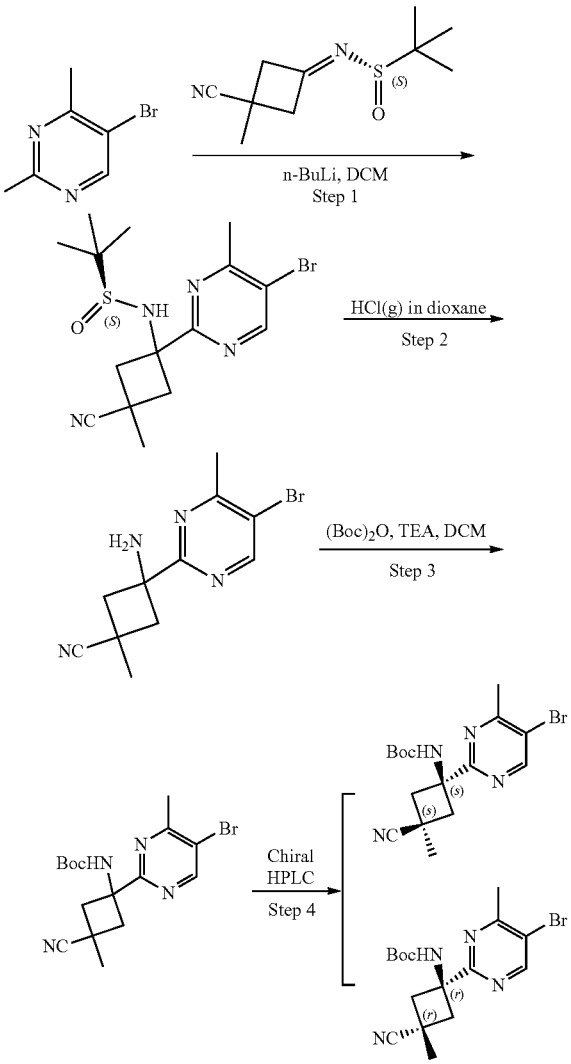

Step 1: To a stirred mixture of 3-[(tert-butyldimethylsilyl)oxy]-3-methylcyclobutan-1-one (10.0 g, 46.6 mmol, 1.0 equiv) and (S)-2-methylpropane-2-sulfinamide (5.7 g, 46.6 mmol, 1.0 equiv) in THF (100 mL) was added titanium ion tetrakis(ethanolate) (16.0 g, 70.0 mmol, 1.50 equiv) at 0° C. under nitrogen atmosphere. The resulting mixture was stirred at 60° C. overnight under nitrogen atmosphere. The reaction was quenched with water at 0° C. The resulting mixture was filtered, the filter cake was washed with EtOAc (3×500 mL). The filtrate was extracted with EtOAc (3×500 mL). The combined organic layers were washed with brine (2×500 mL), dried over anhydrous Na₂SO₄. After filtration, the filtrate was concentrated under reduced pressure. The residue was purified by silica gel column chromatography, eluted with PE/EA (1:1) to afford (S)—N-{3-[(tert-butyldimethylsilyl)oxy]-3-methylcyclobutylidene}-2-methylpropane-2-sulfinamide (12 g, 81.0%) as a colorless oil. LCMS (ESI, m/z): 318.15 [M+H]⁺.

Step 2: To a stirred solution of 5-bromo-2-iodo-4-methylpyrimidine (4.7 g, 15.7 mmol, 1.0 equiv) in DCM (150 mL) was added n-BuLi (1.01 g, 15.7 mmol, 1.0 equiv) dropwise at −78° C. under nitrogen atmosphere. The resulting mixture was stirred at −78° C. for 1 h under nitrogen atmosphere. To the above mixture was added 5-bromo-2-iodo-4-methylpyrimidine (4.7 g, 15.7 mmol, 1.0 equiv) at −78° C. The resulting mixture was stirred at −78° C. for additional 1 h. The reaction was quenched by the addition of sat. NH₄Cl (aq.) (150 mL) at 0° C. The aqueous layer was extracted with CH₂Cl₂ (3×200 mL). The organic layer was concentrated under reduced pressure. The residue was purified by silica gel column chromatography, eluted with PE/EA (1:1) to afford (S)—N-[1-(5-bromo-4-methylpyrimidin-2-yl)-3-[(tert-butyldimethylsilyl)oxy]-3-methylcyclobutyl]-2-methylpropane-2-sulfinamide (730 mg, 9.5%) as a yellow solid.

Step 3: (S)—N-(1-(5-bromo-4-methylpyrimidin-2-yl)-3-((tert-butyldimethylsilyl)oxy)-3-methylcyclobutyl)-2-methylpropane-2-sulfinamide (730 mg) was further purified by Prep-CHIRAL-HPLC with the following conditions (Column: JW-CHIRAL ART Cellulose-SC, 20*250 mm, 5 um;

Step 1: In a 50-mL round bottom flask, to a solution of 5-bromo-2-iodo-4-methylpyrimidine (3.5 g, 11.7 mmol, 1.0 equiv) in DCM (30 mL) was added dropwise n-butyllithium (2.5 Minn-hexane, 5 mL, 12.5 mmol, 1.1 equiv) at −78° C. under $N_2$ atmosphere. The resulting mixture was stirred at −78° C. for 30 min. Then a solution of (S)—N-(3-cyano-3-methylcyclobutylidene)-2-methylpropane-2-sulfinamide (2.7 g, 12.9 mmol, 1.1 equiv) in DCM (30 mL) was added dropwise and the resulting mixture was stirred for another 1 h. The reaction was quenched with saturated aqueous $NH_4Cl$ solution. The resulting solution was quenched with water (300 mL), extracted with ethyl acetate (3×300 mL). The combined organic extracts were washed with brine (2×300 mL), dried over anhydrous sodium sulfate, filtered and concentrated under reduced pressure. The residue was purified by reverse flash chromatography on C18 silica with water (0.05% TFA)/MeCN (1:2) to give (S)—N-[1-(5-chloro-4-methylpyrimidin-2-yl)-3-cyano-3-methylcyclobutyl]-2-methylpropane-2-sulfinamide (500 mg, 12.5%) as a yellow oil.

Step 2: To a solution of (S)—N-[1-(5-bromo-4-methylpyrimidin-2-yl)-3-cyano-3-methylcyclobutyl]-2-methylpropane-2-sulfinamide (500 mg, 1.3 mmol, 1.0 equiv) in methanol (6 mL) was added HCl (4.0 M in 1,4-dioxane, 0.6 mL). The resulting mixture was stirred at room temperature for 15 min under an air atmosphere. The resulting solution was concentrated under reduced pressure to give 3-amino-3-(5-bromo-4-methylpyrimidin-2-yl)-1-methylcyclobutane-1-carbonitrile (320 mg) as a yellow solid.

Step 3: To a solution of 3-amino-3-(5-bromo-4-methylpyrimidin-2-yl)-1-methylcyclobutane-1-carbonitrile (320 mg, 1.1 mmol, 1 equiv) and $Et_3N$ (345 mg, 3.1 mmol, 3.0 equiv) in DCM (5 mL) was added di-tert-butyl dicarbonate (496 mg, 2.3 mmol, 2.0 equiv). The resulting mixture was stirred overnight at 25° C. The resulting solution was quenched with water (50 mL), extracted with ethyl acetate (3×50 mL). The combined organic extracts were washed with brine (2×50 mL), dried over anhydrous sodium sulfate, filtered and concentrated under reduced pressure. The residue was purified by column chromatography on silica gel with petroleum ether/ethyl acetate (3:1) to give tert-butyl N-[1-(5-bromo-4-methylpyrimidin-2-yl)-3-cyano-3-methylcyclobutyl]carbamate (200 mg, 46.1%) as a light-yellow solid.

Step 4: The tert-butyl N-[1-(5-bromo-4-methylpyrimidin-2-yl)-3-cyano-3-methylcyclobutyl]carbamate (200 mg) was separated by chiral-HPLC with the following conditions (Column: JW-CHIRALPAK ID, 20*250 mm, 5 μm; Mobile Phase A: EtOH—HPLC, Mobile Phase B: Hex (0.5% 2M NH3-MeOH)—HPLC; Flow rate: 20 mL/min; Gradient: 85% B to 85% B in 9 min; Wave Length: 220/254 nm; RT2(min): 7.03) to afford tert-butyl ((1s, 3s)-1-(5-bromo-4-methylpyrimidin-2-yl)-3-cyano-3-methylcyclobutyl)carbamate (60 mg) as an off-white solid.

Intermediate 120

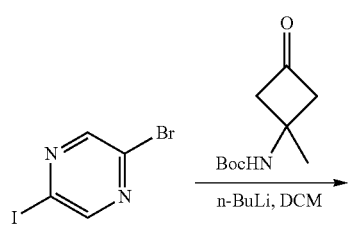

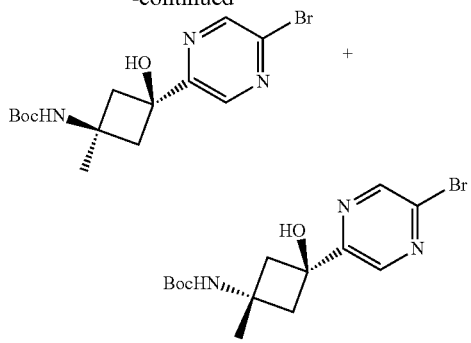

In a 50-mL round bottom flask, to a solution of 2-bromo-5-iodopyrazine (2.1 g, 7.5 mmol, 1.0 equiv) in DCM (5 mL) was added dropwise n-butyllithium (2.5 M in n-hexane) (3.0 mL, 7.5 mmol, 1.0 equiv) at −78° C. under $N_2$ atmosphere. The reaction mixture was stirred at −78° C. for 30 mins. Then a solution of tert-butyl N-(1-methyl-3-oxocyclobutyl)carbamate (1.5 g, 7.5 mmol, 1.0 equiv) was added dropwise and the mixture was stirred for another 30 mins. The reaction was quenched with sat. $NH_4Cl$ (20 mL), and then the mixture was extracted with EtOAc (2×15 mL). The combined organic extracts were washed with brine (10 mL), dried over anhydrous $Na_2SO_4$, and concentrated under vacuum to yield a crude product which was directly purified by silica gel column chromatography, elute with PE/EA (5:1) to afford tert-butyl ((1s, 3s)-3-(5-bromopyrazin-2-yl)-3-hydroxy-1-methylcyclobutyl)carbamate (cis-isomer, peak2, 200 mg, 7.4%) as a colorless oil and tert-butyl ((1r, 3r)-3-(5-bromopyrazin-2-yl)-3-hydroxy-1-methylcyclobutyl)carbamate (trans-isomer, peak1, 400 mg, 14.8%) as a brown oil. LC-MS: (M+H)$^+$ found: 360.05. cis-isomer, peak 2: 1H NMR (400 MHz, DMSO-d6) δ 8.83 (d, J=1.4 Hz, 1H), 8.62 (d, J=1.5 Hz, 1H), 7.16 (s, 1H), 6.04 (s, 1H), 2.64 (d, J=13.1 Hz, 2H), 2.55 (s, 2H), 1.41 (s, 9H), 1.30 (s, 3H).

Intermediate 121

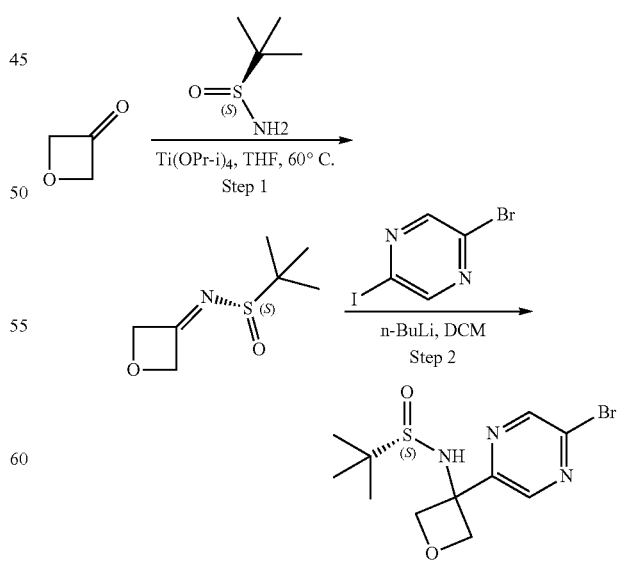

Step 1: To a stirred mixture of 3-oxetanone (5.0 g, 69.4 mmol, 1.0 equiv) and (S)-2-methylpropane-2-sulfinamide (8.4 g, 69.4 mmol, 1.0 equiv) in THF (100 mL) were added titanium ion tetrakis(ethanolate) (23.7 g, 104.1 mmol, 1.5 equiv) at 0° C. under nitrogen atmosphere. The resulting mixture was stirred at room temperature for overnight under nitrogen atmosphere. The reaction was quenched by the addition of water (100 mL) at 0° C. The aqueous layer was extracted with EtOAc (3×200 mL). The organic layers were concentrated under reduced pressure. The residue was purified by silica gel column chromatography, eluted with PE/EA (2:1) to afford (S)-2-methyl-N-(oxetan-3-ylidene) propane-2-sulfinamide (6 g, 49.3%) as a colorless oil. LCMS (ESI, m/z): 176.05 [M+H]⁺.

Step 2: To a stirred solution of 2-bromo-5-iodopyrazine (2.0 g, 6.8 mmol, 1.0 equiv) in DCM (100 mL) was added n-BuLi (2.7 mL, 6.8 mmol, 1.0 equiv) dropwise at −78° C. under nitrogen atmosphere. The resulting mixture was stirred at −78° C. for 1 h under nitrogen atmosphere. To the above mixture was added (S)-2-methyl-N-(oxetan-3-ylidene)propane-2-sulfinamide (1.2 g, 6.8 mmol, 1.0 equiv) dropwise at −78° C. The resulting mixture was stirred at −78° C. for additional 1 h. The reaction was quenched by the addition of sat. NH₄Cl (aq.) (100 mL) at 0° C. The resulting mixture was extracted with CH₂Cl₂ (3×100 mL). The combined organic layers were washed with brine (2×100 mL), dried over anhydrous Na₂SO₄. After filtration, the filtrate was concentrated under reduced pressure. The residue was purified by silica gel column chromatography, eluted with PE/EA (1:2) to afford (S)—N-[3-(5-bromopyrazin-2-yl) oxetan-3-yl]-2-methylpropane-2-sulfinamide (890 mg, 38.9%) as a brown solid. LCMS (ESI, m/z): 333.95 [M+H]⁺. ¹H NMR (400 MHz, DMSO-d₆) δ 8.93 (d, J 1.4 Hz, 1H), 8.69 (d, J=1.4 Hz, 1H), 6.61 (s, 1H), 5.05 (d, J=6.4 Hz, 1H), 4.98-4.91 (m, 2H), 4.85 (d, J=6.4 Hz, 1H), 1.17 (s, 9H).

Intermediate 122

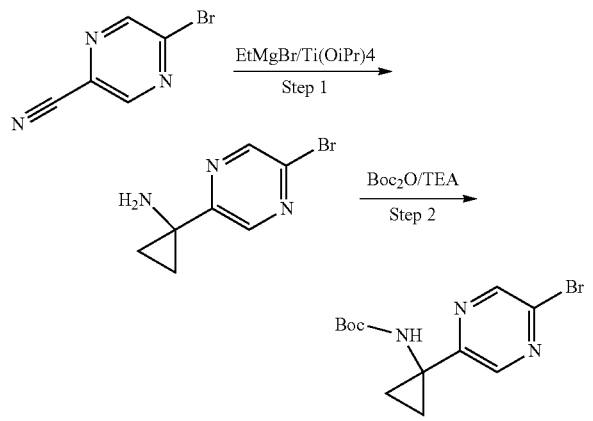

Step 1: A solution of 5-bromopyrazine-2-carbonitrile (5.0 g, 27.2 mmol, 1.0 equiv) in THF (150 mL) was treated with tetrakis(propan-2-yloxy)titanium (8.7 g, 30.7 mmol, 1.1 equiv) at 0° C. for 1 min under nitrogen atmosphere followed by the addition of ethyl magnesium bromide (1.0 M in THF) (7.4 g, 55.7 mmol, 2.05 equiv) at 0° C. The resulting mixture was stirred at room temperature overnight under nitrogen atmosphere. The resulting mixture was stirred at 50° C. for 4 h under nitrogen atmosphere. The reaction was quenched by the addition of sat. NH₄Cl (aq.) (100 mL) at 0° C. The resulting mixture was extracted with EtOAc (1×150 mL). After filtration, the water phase was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in 1-(5-bromopyrazin-2-yl)cyclopropan-1-amine (300 mg, 5.2%) as a yellow oil. LCMS (ESI, m/z): 214.05 [M+H]⁺.

Step 2: A solution of 1-(5-bromopyrazin-2-yl)cyclopropan-1-amine (300 mg, 1.4 mmol, 1.0 equiv) in THF (2 mL) and sat. Na₂CO₃ (2 mL) was treated with Boc₂O (611.7 mg, 2.8 mmol, 2.0 equiv) at room temperature for 2 min under nitrogen atmosphere. The resulting mixture was stirred at 80° C. overnight under nitrogen atmosphere. The resulting mixture was extracted with EtOAc (3×20 mL), dried over anhydrous Na₂SO₄. After filtration, the filtrate was concentrated under reduced pressure. The residue was purified by silica gel column chromatography, eluted with PE/EA (2:1) to afford tert-butyl N-[1-(5-bromopyrazin-2-yl)cyclopropyl] carbamate (100 mg, 22.7%) as a yellow oil. LCMS (ESI, m/z): 314.05 [M+H]⁺.

Intermediate 123

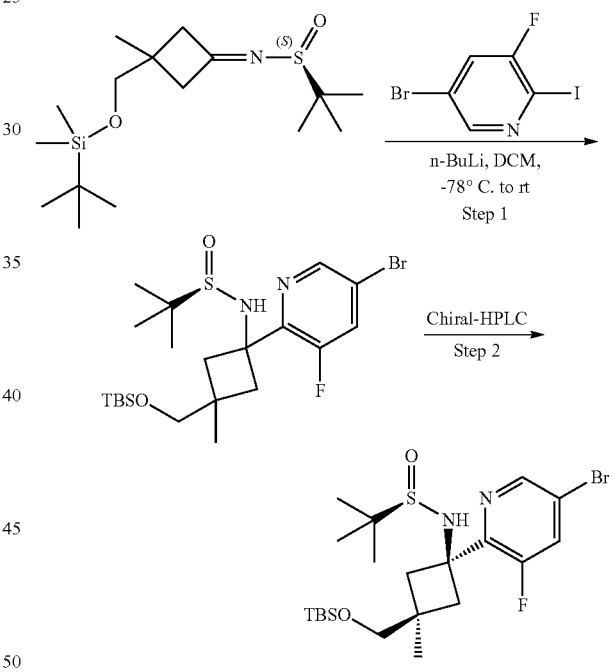

Step 1: To a stirred solution of 5-bromo-3-fluoro-2-iodopyridine (218.5 mg, 0.72 mmol, 1.2 equiv) in DCM (5 mL) was added n-BuLi (0.32 mL, 0.8 mmol, 1.3 equiv) dropwise at −78° C. under nitrogen atmosphere. Then mixture was stirred at −78° C. for 1 h. To the above mixture was added (S)—N-(3-(((tert-butyldimethylsilyl)oxy)methyl)-3-methylcyclobutylidene)-2-methylpropane-2-sulfinamide (200 mg, 0.6 mmol, 1.0 equiv) in DCM (5 mL) dropwise at −78° C. The resulting mixture was stirred at −78° C. for additional 2 h. Then the mixture was allowed to warm up to room temperature and stirred for 1 h. The reaction was quenched by the addition of sat. NH₄Cl (aq.) (5 mL) at 0° C. The resulting mixture was extracted with CH₂Cl₂ (3×5 mL). The combined organic layers were dried over anhydrous Na₂SO₄. After filtration, the filtrate was concentrated under reduced pressure. The residue was purified by Prep-TLC (PE/EA 2:1) to afford (R)—N-(1-(5-bromo-3-fluoropyridin-2-yl)-3-(((tert-butyldimethylsilyl)oxy)methyl)-3-methylcyclobutyl)-2-methylpropane-2-sulfinamide (180 mg, 58.8%) as a colorless oil.

Step 2: (R)—N-(1-(5-bromo-3-fluoropyridin-2-yl)-3-(((tert-butyldimethylsilyl)oxy)methyl)-3-methylcyclobutyl)-2-methylpropane-2-sulfinamide (180 mg) was further purified by Prep-Chiral-HPLC with the following conditions (Column: JW-CHIRALPAK IH, 20*250 mm, 5 um; Mobile Phase A: EtOH:DCM=1:1—HPLC, Mobile Phase B: Hex (0.5% 2M $NH_3$-MeOH)—HPLC; Flow rate: 20 mL/min; Gradient: 98% B to 98% B in 6.5 min; Wave Length: 220/254 nm; RT1(min): 3.65; RT2(min): 5.36; Sample Solvent: EtOH:Hex—HPLC; Injection Volume: 0.4 mL; Number Of Runs: 6) to afford (R)—N-((1s,3S)-1-(5-bromo-3-fluoropyridin-2-yl)-3-(((tert-butyldimethylsilyl)oxy)methyl)-3-methylcyclobutyl)-2-methylpropane-2-sulfinamide (85 mg) as a colorless oil. LCMS (ESI, m/z): 507.20 $[M+H]^+$.

Intermediate 124

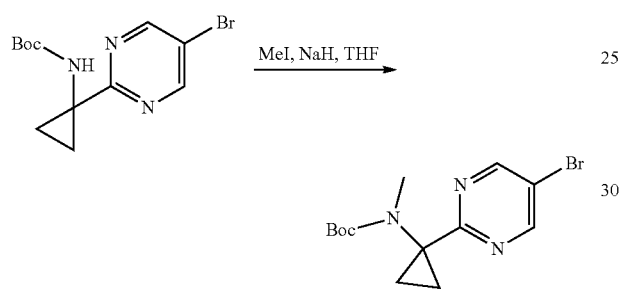

A solution of tert-butyl N-[1-(5-bromopyrimidin-2-yl)cyclopropyl]carbamate (90 mg, 0.29 mmol, 1.0 equiv) in THF (2 mL) was treated with NaH (13.8 mg, 0.34 mmol, 1.2 equiv, 60%) at 0° C. for 1 min under nitrogen atmosphere followed by the addition of $CH_3I$ (48.8 mg, 0.34 mmol, 1.2 equiv) at 0° C. The resulting mixture was stirred at 50° C. for 1 h under nitrogen atmosphere. The reaction was quenched with sat. $NH_4Cl$ (aq.) at 0° C. The resulting mixture was extracted with EtOAc (3×3 mL). The combined organic layers were washed with brine (2×2 mL), dried over anhydrous $Na_2SO_4$. After filtration, the filtrate was concentrated under reduced pressure. The residue was purified by Prep-TLC (PE/EA 8:1) to afford tert-butyl N-[1-(5-bromopyrimidin-2-yl)cyclopropyl]-N-methylcarbamate (60 mg, 63.8%) as a colorless oil. LCMS (ESI, m/z): 330.00 $[M+H]^+$.

Intermediate 125 & 126

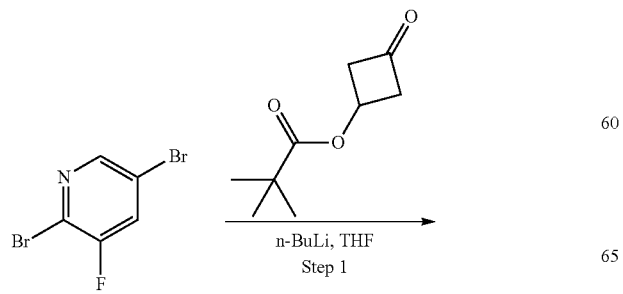

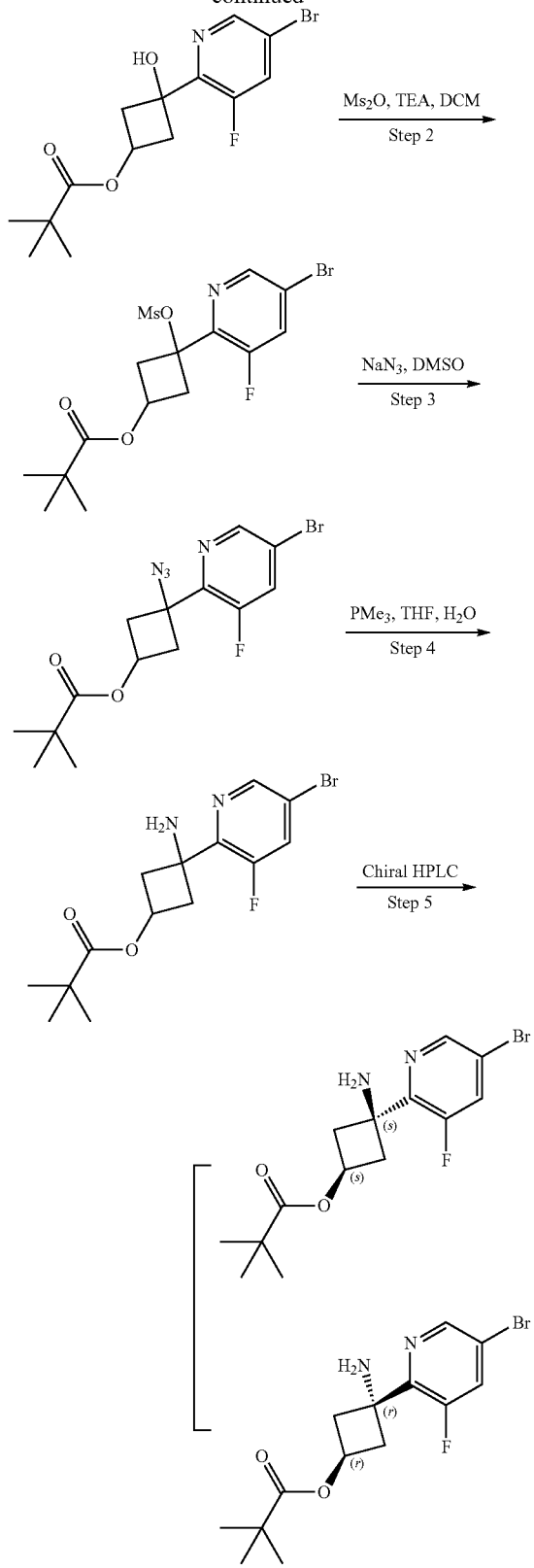

Step 1: In a 500-mL round bottom flask, to a solution of 2,5-dibromo-3-fluoropyridine (27 g, 105 mmol, 1.2 equiv) in THF (100 mL) was added dropwise n-butyllithium (2.5 M in n-hexane) (42 mL, 105 mmol, 1.2 equiv) at −78° C. under N2 atmosphere. The reaction mixture was stirred at −78° C. for 10 mins. Then a solution of 3-oxocyclobutyl 2,2-dimethylpropanoate (15 g, 88 mmol, 1.0 equiv) in 100 mL THF was added dropwise and the mixture was stirred for another 10 mins. The reaction was quenched with sat. NH$_4$Cl (100 mL), and then the mixture was extracted with EtOAc (2×150 mL). The combined organic extracts were washed with brine (100 mL), dried over anhydrous Na$_2$SO$_4$, and concentrated under vacuum to yield a crude product which was directly purified by flash chromatography (PE/EA 10:1) mixture to yield. This resulted in 3-(5-bromo-3-fluoropyridin-2-yl)-3-hydroxycyclobutyl pivalate (9 g, 29.5%) as a white solid. LCMS (ESI, m/z): 348.00 [M+H]$^+$.

Step 2: To a stirred solution of 3-(5-bromo-3-fluoropyridin-2-yl)-3-hydroxycyclobutyl pivalate (10 g, 29 mmol, 1.0 equiv) and Et$_3$N (3.5 g, 35 mmol, 1.2 equiv) in DCM (100 mL) was added methanesulfonyl methanesulfonate (6 g, 35 mmol, 1.2 equiv) in portions at 0° C. under nitrogen atmosphere. The resulting mixture was concentrated under reduced pressure. This resulted in 3-(5-bromo-3-fluoropyridin-2-yl)-3-((methylsulfonyl)oxy)cyclobutyl pivalate (10 g) as a brown oil. LCMS (ESI, m/z): 426.00 [M+H]$^+$.

Step 3: A solution of 3-(5-bromo-3-fluoropyridin-2-yl)-3-((methylsulfonyl)oxy)cyclobutyl pivalate (10 g, 24 mmol, 1.0 equiv) and NaN$_3$ (7.7 g, 118 mmol, 5.0 equiv) in DMSO (100 mL) was stirred at 70° C. for 2 h under air atmosphere. The resulting mixture was extracted with EtOAc (3×200 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EA (5:1) to afford 3-azido-3-(5-bromo-3-fluoropyridin-2-yl)cyclobutyl pivalate (8 g, 91.4%) as a yellow oil. LCMS (ESI, m/z): 373.05 [M+H]$^+$.

Step 4: A solution of 3-azido-3-(5-bromo-3-fluoropyridin-2-yl)cyclobutyl pivalate (3.5 g, 9.4 mmol, 1.0 equiv) in THF (34 mL) and H$_2$O (3.4 mL) was treated with trimethylphosphine (1.0 M in THF) (1.3 g, 16.5 mmol, 1.8 equiv) at 0° C. for 1 min under nitrogen atmosphere. The resulting mixture was stirred at room temperature for 1 h under nitrogen atmosphere. The resulting mixture was extracted with EtOAc (3×100 mL). The combined organic layers were washed with brine (2×100 mL), dried over anhydrous Na$_2$SO$_4$. After filtration, the filtrate was concentrated under reduced pressure. The residue was purified by silica gel column chromatography, eluted with PE/EA (1:2) to afford 3-amino-3-(5-bromo-3-fluoropyridin-2-yl)cyclobutyl pivalate (2 g, 61.5%) as a yellow oil. LCMS (ESI, m/z): 345.05 [M+H]$^+$.

Step 5: 3-amino-3-(5-bromo-3-fluoropyridin-2-yl)cyclobutyl pivalate (2 g) was further purified by PREP_CHIRAL_HPLC with the following conditions (Column: JW-CHIRALPAK IG 3.0*25 cm, 5 um; Mobile Phase A: IPA—HPLC, Mobile Phase B: Hex (0.5% 2M NH$_3$-MeOH)—HPLC; Flow rate: 20 mL/min; Gradient: 85% B to 85% B in 13 min; Wave Length: 220/254 nm; RT1(min): 7.21; RT2(min): 9.35; Sample Solvent: EtOH:DCM=1:1—HPLC; Injection Volume: 0.7 mL; Number Of Runs: 19) to afford (1r, 3r)-3-amino-3-(5-bromo-3-fluoropyridin-2-yl)cyclobutyl pivalate (918 mg, Rt=7.21 min, trans-isomer) as a yellow oil and (1s, 3s)-3-amino-3-(5-bromo-3-fluoropyridin-2-yl)cyclobutyl pivalate (635 mg, Rt=9.35 min, cis-isomer) as a yellow oil. trans-isomer: LCMS (ESI, m/z): 345.05 [M+H]$^+$. trans-isomer: $^1$H NMR (400 MHz, DMSO-d$_6$) δ 8.51-8.45 (m, 1H), 8.13-8.09 (m, 1.9 Hz, 1H), 5.20-5.16 (m, 1H), 2.59-2.50 (m, 2H), 2.50-2.41 (m, 2H), 2.28 (s, 2H), 1.07 (s, 9H). cis-isomer: LCMS (ESI, m/z): 345.05 [M+H]$^+$. cis-isomer: 1HNMR (400 MHz, DMSO-d6) δ 8.52 (t, J=1.5 Hz, 1H), 8.17-8.13 (m, 1H), 4.48-4.44 (m, 1H), 3.20-2.16 (m, 2H), 2.38 (s, 2H), 2.22-2.18 (m, 2H), 1.15 (s, 9H).

Intermediate 127

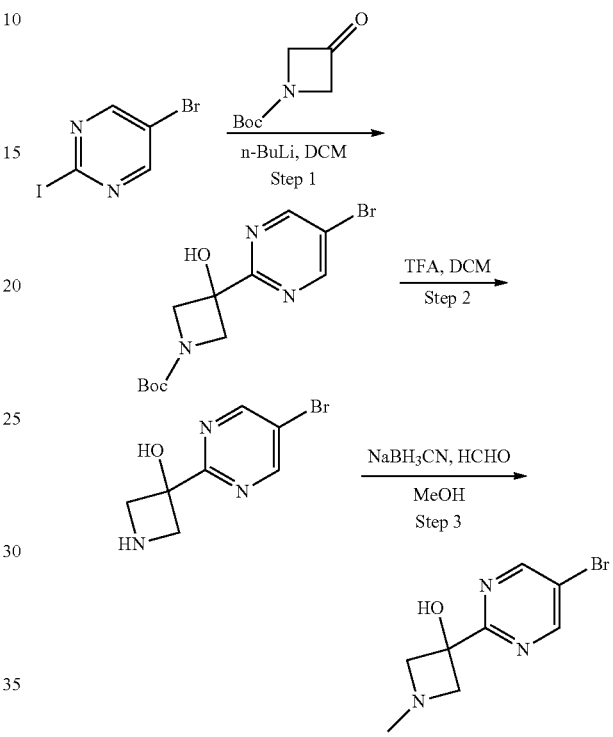

Step 1: To a stirred solution of 5-bromo-2-iodopyrimidine (5.0 g, 17.5 mmol, 1.0 equiv) in DCM (170 mL) was added n-BuLi (1.1 g, 17.5 mmol, 1.0 equiv) dropwise at 0° C. under nitrogen atmosphere. The resulting mixture was stirred at −78° C. for 1 h under nitrogen atmosphere. To the above mixture was added tert-butyl 3-oxoazetidine-1-carboxylate (3.0 g, 17.5 mmol, 1.0 equiv) dropwise at −78° C. The resulting mixture was stirred at −78° C. for additional 1 h. The reaction was quenched by the addition of sat. NH$_4$Cl (aq.) (150 mL) at 0° C. The resulting mixture was extracted with CH$_2$Cl$_2$ (3×200 mL). The combined organic layers were washed with brine (1×200 mL), dried over anhydrous Na$_2$SO$_4$. After filtration, the filtrate was concentrated under reduced pressure. The residue was purified by silica gel column chromatography, eluted with PE/EA (1:1) to afford tert-butyl 3-(5-bromopyrimidin-2-yl)-3-hydroxyazetidine-1-carboxylate (3 g, 51.9%) as a yellow solid. LCMS (ESI, m/z): 276.00 [M+H−56]$^+$.

Step 2: To a stirred solution of tert-butyl 3-(5-bromopyrimidin-2-yl)-3-hydroxyazetidine-1-carboxylate (1.0 g, 3.0 mmol, 1.0 equiv) in DCM (9 mL) was added trifluoroacetic acid (3 mL) dropwise at 0° C. under nitrogen atmosphere. The resulting mixture was stirred at room temperature for 1 h under nitrogen atmosphere. The resulting mixture was concentrated under reduced pressure. The crude product was purified by Prep-HPLC with the following conditions (Column: X-Select Prep OBD C18 Column, 30*150 mm, 5 μm; Mobile Phase A: Water (10 mmol/L NH$_4$HCO$_3$), Mobile Phase B: ACN; Flow rate: 60 mL/min mL/min; Gradient:

5% B to 10% B in 9 min; Wave Length: 254 nm/220 nm nm; RT1(min): 6.56) to afford 3-(5-bromopyrimidin-2-yl)azetidin-3-ol (620 mg, 89%) as an off-white solid. LCMS (ESI, m/z): 231.95 [M+H]$^+$.

Step 3: A mixture of 3-(5-bromopyrimidin-2-yl)azetidin-3-ol (600 mg, 2.6 mmol, 1.0 equiv) and formaldehyde solution (234.9 mg, 7.8 mmol, 3.0 equiv) in methanol (5 mL) was stirred at room temperature for 30 min under nitrogen atmosphere. To the above mixture was added NaBH$_3$CN (245.8 mg, 3.9 mmol, 1.50 equiv) at 0° C. The resulting mixture was stirred at room temperature for additional 1 h. The residue was purified by reverse phase flash with the following conditions (Column: XSelect CSH Prep C18 OBD Column, 30*150 mm, 5 μm; Mobile Phase A: Water (10 mmol/L NH$_4$HCO$_3$), Mobile Phase B: ACN; Flow rate: 60 mL/min mL/min; Gradient: 0% B to 10% B in 8 min; Wave Length: 254 nm/220 nm nm; RT1(min): 7.4) to afford 3-(5-bromopyrimidin-2-yl)-1-methylazetidin-3-ol (400 mg, 62.8%) as a white solid. LCMS (ESI, m/z): 243.95 [M+H]$^+$.

Intermediate 128

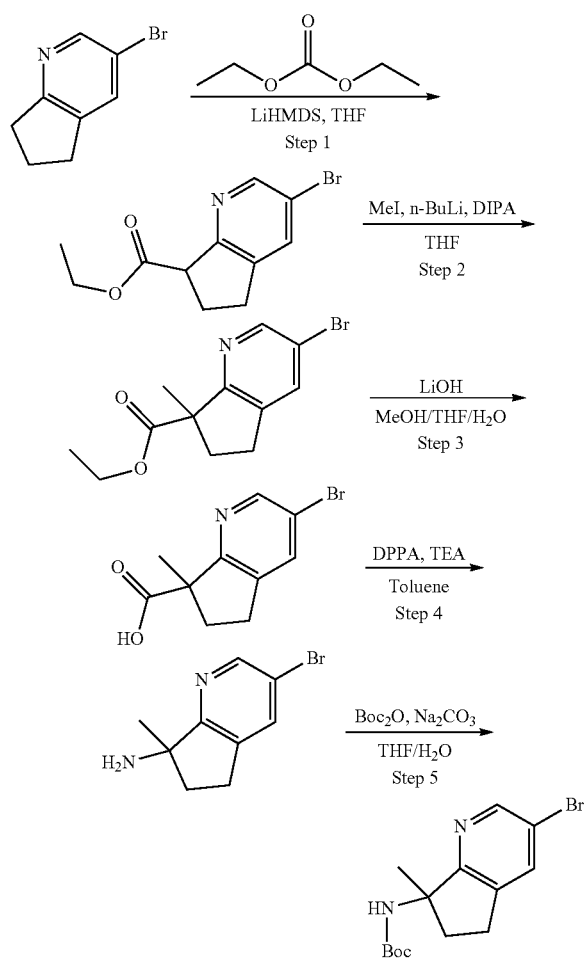

Step 1: A solution of 3-bromo-5H, 6H, 7H-cyclopenta[b]pyridine (5 g, 25.2 mmol, 1.0 equiv) in THF (85 mL) was treated with LiHMDS (1.0 M in THF) (63 mL, 63.0 mmol, 2.5 equiv) at −78° C. for 1 h under nitrogen atmosphere followed by the addition of diethyl carbonate (9 g, 75.7 mmol, 3.0 equiv) dropwise at −78° C. The resulting mixture was stirred at room temperature for 12 h under nitrogen atmosphere. The reaction was quenched with sat. NH$_4$Cl (aq.) at 0° C. The resulting mixture was extracted with EtOAc (3×30 mL), dried over anhydrous Na$_2$SO$_4$. After filtration, the filtrate was concentrated under reduced pressure. The residue was purified by silica gel column chromatography, eluted with PE/EA (10:1) to afford ethyl 3-bromo-5H, 6H, 7H-cyclopenta[b]pyridine-7-carboxylate (5 g, 73.3% yield) as a yellow oil. LC-MS (ESI, m/z): 271.95. $^1$H NMR (400 MHz, DMSO-d$_6$) δ 8.47-8.42 (m, 1H), 7.95-7.93 (m, 1H), 4.15-4.07 (m, 2H), 4.03 (dd, J=8.8, 6.7 Hz, 1H), 3.09-2.86 (m, 2H), 2.47-2.36 (m, 1H), 2.32-2.21 (m, 1H), 1.19 (t, J=7.1 Hz, 3H).

Step 2: A solution of ethyl 3-bromo-5H, 6H, 7H-cyclopenta[b]pyridine-7-carboxylate (6 g, 22.2 mmol, 1.0 equiv) in THF (80 mL) was treated with LDA (22 mL, 44.4 mmol, 2.0 equiv) at −78° C. for 1 h under nitrogen atmosphere followed by the addition of MeI (3.5 g, 24.4 mmol, 1.1 equiv) in portions at −78° C. The resulting mixture was stirred at room temperature for 1 h under nitrogen atmosphere. The reaction was quenched with sat. NH$_4$Cl (aq.) at 0° C. The resulting mixture was extracted with EtOAc (3×30 mL), dried over anhydrous Na$_2$SO$_4$. After filtration, the filtrate was concentrated under reduced pressure. The residue was purified by silica gel column chromatography, eluted with PE/EA (10:1) to afford ethyl 3-bromo-7-methyl-5H,6H-cyclopenta[b]pyridine-7-carboxylate (3.7 g, 58.6% yield) as a yellow oil. LC-MS (ESI, m/z): 285.95. $^1$H NMR (400 MHz, DMSO-d$_6$) δ 8.46 (dd, J=2.1, 1.0 Hz, 1H), 7.96-7.94 (m, 1H), 4.13-3.94 (m, 2H), 3.07-2.89 (m, 2H), 2.61-2.51 (m, 1H), 2.09-1.99 (m, 1H), 1.44 (s, 3H), 1.18 (t, J=7.1 Hz, 3H)

Step 3: A solution of ethyl 3-bromo-7-methyl-5H,6H-cyclopenta[b]pyridine-7-carboxylate (2 g, 7.0 mmol, 1.0 equiv) in methanol (25 mL), THF (25 mL) was treated with LiOH (0.51 g, 21.3 mmol, 3.0 equiv), H$_2$O (25 mL) at room temperature for 10 min under nitrogen atmosphere. The resulting mixture was stirred at room temperature for 1 h under nitrogen atmosphere. The residue was acidified to pH 4 with citric acid. The resulting mixture was extracted with EtOAc (3×10 mL). dried over anhydrous Na$_2$SO$_4$. After filtration, the filtrate was concentrated under reduced pressure. The crude product was used in the next step directly without further purification. LC-MS (ESI, m/z): 257.95.

Step 4: A solution of 3-bromo-7-methyl-5H,6H-cyclopenta[b]pyridine-7-carboxylic acid (1 g, 3.9 mmol, 1.0 equiv) in toluene (2 mL) was treated with DPPA (1.6 g, 5.9 mmol, 1.5 equiv) at room temperature for 1 h under nitrogen atmosphere. The resulting mixture was stirred at 110° C. for 2 h under nitrogen atmosphere. The resulting mixture was diluted with NaOH (1M, 20 mL), The resulting mixture was stirred at room temperature for 12 h under nitrogen atmosphere. The resulting mixture was extracted with EtOAc (3×10 mL), dried over anhydrous Na$_2$SO$_4$. After filtration, the filtrate was concentrated under reduced pressure. The crude product was used in the next step directly without further purification. LC-MS (ESI, m/z): 227.00.

Step 5: A solution of 3-bromo-7-methyl-5H,6H-cyclopenta[b]pyridin-7-amine (1 g, 4.4 mmol, 1.0 equiv) in THF (5 mL) was treated with Boc$_2$O (2.9 g, 13.2 mmol, 3.0 equiv), Na$_2$CO$_3$ (2.3 g, 22 mmol, 5.0 equiv) at room temperature for 10 min under nitrogen atmosphere. The resulting mixture was stirred at 70° C. for 1 h under nitrogen atmosphere. The resulting mixture was extracted with EtOAc (3×10 mL), dried over anhydrous Na$_2$SO$_4$. After filtration, the filtrate was concentrated under reduced pressure. The residue was purified by silica gel column chromatography, eluted with PE/EA (5:1) to afford tert-butyl N-{3-bromo-7-methyl-5H,6H-cyclopenta[b]pyridin-7-yl}carbamate (600 mg, 41.6%) as a white solid. LC-MS (ESI, m/z): 327.00.

Intermediate 129

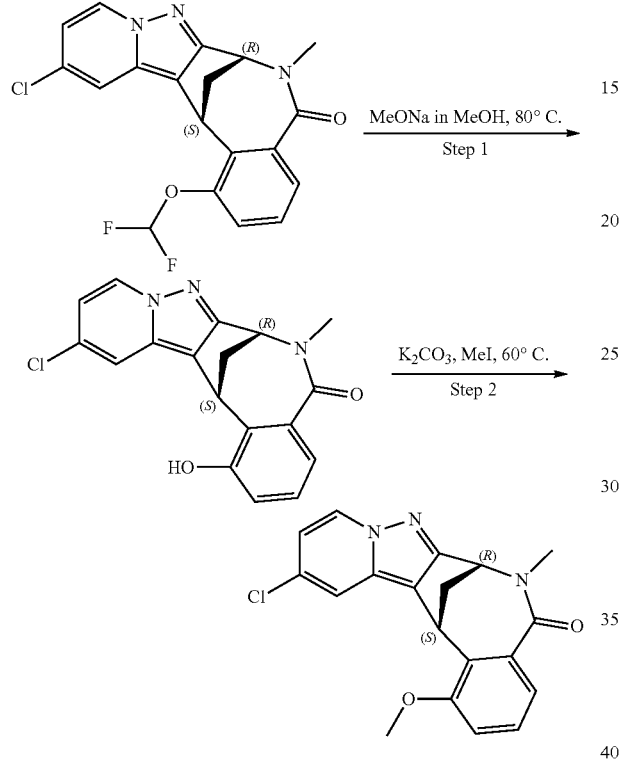

Step 1: A solution of (7R,14S)-12-chloro-1-(difluoromethoxy)-6-methyl-6,7-dihydro-7,14-methanobenzo[c]pyrido[1',2':1,5]pyrazolo[4,3-f]azocin-5 (14H)-one (100 mg, 0.26 mmol, 1.0 equiv) in sodium methoxide (30% in methanol) (3 mL) was stirred at 80° C. for 2 h under nitrogen atmosphere. The mixture was allowed to cool down to room temperature. The residue was purified by reversed-phase flash chromatography with the following conditions: column, C18 silica gel; mobile phase, MeCN in Water (0.1% FA), 50% to 70% gradient in 10 min; detector, UV 254 nm. to afford (7R,14S)-12-chloro-1-hydroxy-6-methyl-6,7-dihydro-7,14-methanobenzo[c]pyrido[1',2':1,5]pyrazolo[4,3-f]azocin-5 (14H)-one (80 mg, 91.8%) as a yellow solid. LCMS (ESI, m/z): 340.05 [M+H]⁺.

Step 2: A solution of (7R,14S)-12-chloro-1-hydroxy-6-methyl-6,7-dihydro-7,14-methanobenzo[c]pyrido[1',2':1,5]pyrazolo[4,3-f]azocin-5 (14H)-one (70 mg, 0.21 mmol, 1.0 equiv) and K₂CO₃ (142.4 mg, 0.62 mmol, 3.0 equiv, 60%), iodomethane (58.5 mg, 0.41 mmol, 2.0 equiv) in DMF (2 mL) was stirred at 60° C. for 2 h under nitrogen atmosphere. The mixture was allowed to cool down to room temperature. The residue was purified by reversed-phase flash chromatography with the following conditions: column, C18 silica gel; mobile phase, MeCN in Water (0.1% FA), 60% to 80% gradient in 10 min; detector, UV 254 nm. to afford (7R,14S)-12-chloro-1-methoxy-6-methyl-6,7-dihydro-7,14-methanobenzo[c]pyrido[1',2':1,5]pyrazolo[4,3-f]azocin-5 (14H)-one (60 mg, 82.3%) as a yellow solid. LCMS (ESI, m/z): 354.05 [M+H]⁺.

Intermediate 130

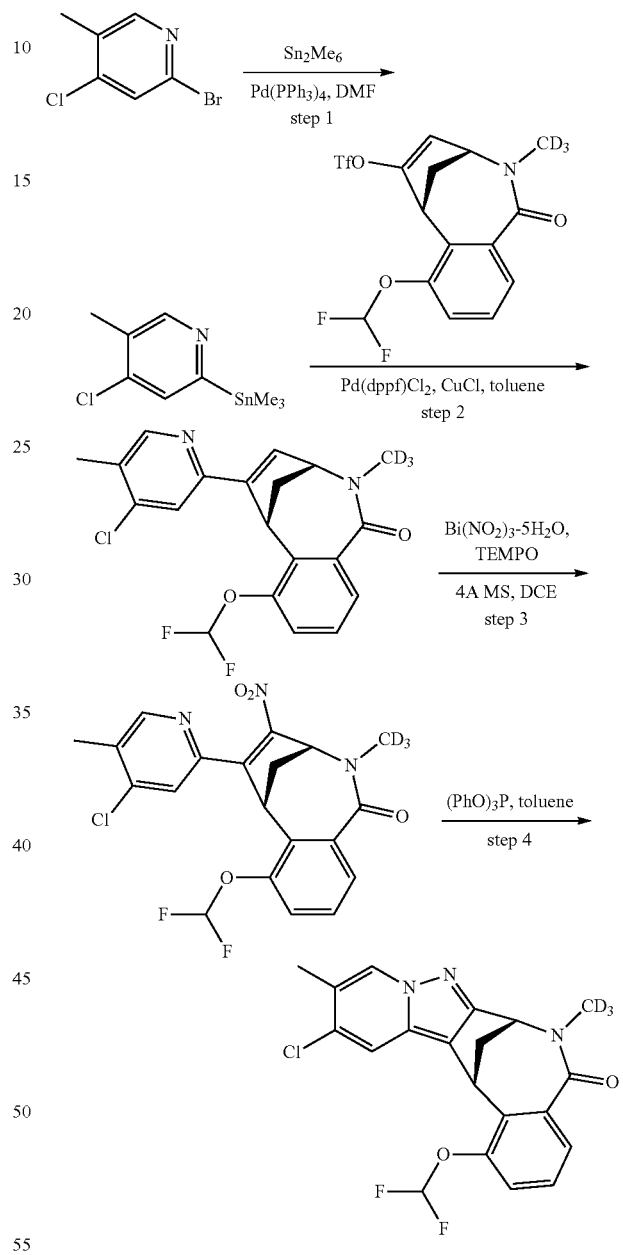

Step 1: To a stirred solution of 2-bromo-4-chloro-5-methylpyridine (1.0 g, 4.8 mmol, 1.0 equiv) in 1,4-dioxane (20 mL) were added hexamethyldistannane (2.4 g, 7.3 mmol, 1.5 equiv) and Pd(PPh₃)₄ (560 mg, 0.48 mmol, 0.1 equiv) in portions at room temperature under nitrogen atmosphere. The resulting mixture was stirred at 100° C. for 1 h under nitrogen atmosphere. The resulting mixture was diluted with brine (10 mL). The resulting mixture was extracted with EA (2×60 mL). The combined organic layers were washed with brine (1×50 mL), dried over anhydrous Na2SO4. After filtration, the filtrate was concentrated under reduced pressure. This resulted in 4-chloro-5-methyl-2-(trimethylstannyl)pyridine (2 g) as a yellow oil. LCMS (ESI, m/z): 292 [M+H]$^+$.

Step 2: To a stirred solution of 4-chloro-5-methyl-2-(trimethylstannyl)pyridine (2.1 g, 7.2 mmol, 3.0 equiv) and (3R,6R)-7-(difluoromethoxy)-2-(methyl-d3)-1-oxo-1,2,3,6-tetrahydro-3,6-methanobenzo[c]azocin-5-yl trifluoromethanesulfonate (1.0 g, 2.4 mmol, 1.0 equiv) in toluene (15 mL) were added CuCl (237.8 mg, 2.4 mmol, 1.0 equiv) and Pd(PPh$_3$)$_4$ (277.6 mg, 0.24 mmol, 0.1 equiv) in portions at room temperature under nitrogen atmosphere. The resulting mixture was stirred at 100° C. for 1 h under nitrogen atmosphere. The resulting mixture was diluted with brine (30 mL). The resulting mixture was extracted with EA (2×100 mL). The combined organic layers were washed with brine (1×100 mL), dried over anhydrous Na$_2$SO$_4$. After filtration, the filtrate was concentrated under reduced pressure. The residue was purified by Prep-TLC (CH$_2$Cl$_2$/MeOH 20:1) to afford (3R,6S)-5-(4-chloro-5-methylpyridin-2-yl)-7-(difluoromethoxy)-2-(methyl-d3)-3,6-dihydro-3,6-methanobenzo[c]azocin-1 (2H)-one (580 mg, 61.3%) as a yellow solid.

Step 3: A solution of (3R,6S)-5-(4-chloro-5-methylpyridin-2-yl)-7-(difluoromethoxy)-2-(methyl-d3)-4-nitro-3,6-dihydro-3,6-methanobenzo[c]azocin-1 (2H)-one (580 mg, 1.5 mmol, 1.0 equiv) in DCE (20 mL) was treated with 4 A-MS (1.2 g), 2,2,6,6-tetramethylpiperidin-1-olate (46.0 mg, 0.3 mmol, 0.2 equiv) and bismuth (3+) ion tris(nitrooxidane) pentahydrate (1.4 g, 3.0 mmol, 2.0 equiv) at 80° C. for overnight under nitrogen atmosphere. The resulting mixture was filtered, the filter cake was washed with CH$_2$Cl$_2$ (2×20 mL). The filtrate was concentrated under reduced pressure. The residue was purified by Prep-TLC (CH$_2$Cl$_2$/MeOH 20:1) to afford (3R,6S)-5-(4-chloro-5-methylpyridin-2-yl)-7-(difluoromethoxy)-2-(methyl-d3)-4-nitro-3,6-dihydro-3,6-methanobenzo[c]azocin-1 (2H)-onee (320 mg, 49.5%) as a light yellow solid.

Step 4: To a stirred solution of (3R,6S)-5-(4-chloro-5-methylpyridin-2-yl)-7-(difluoromethoxy)-2-(methyl-d3)-4-nitro-3,6-dihydro-3,6-methanobenzo[c]azocin-1 (2H)-one (320 mg, 0.73 mmol, 1.0 equiv) in toluene (10 mL) was added triphenyl phosphite (2.3 g, 7.3 mmol, 10.0 equiv) dropwise at room temperature under nitrogen atmosphere. The resulting mixture was stirred at 100° C. for 1 h under nitrogen atmosphere. The resulting mixture was concentrated under reduced pressure. The residue was purified by Prep-TLC (CH$_2$Cl$_2$/MeOH 20:1) to afford (7R,14S)-12-chloro-1-(difluoromethoxy)-11-methyl-6-(methyl-d3)-6,7-dihydro-7,14-methanobenzo[c]pyrido[1',2':1,5]pyrazolo[4,3-f]azocin-5 (14H)-one (160 mg, 53.9%) as a light yellow solid. LCMS (ESI, m/z): 407.10 [M+H]$^+$.

Intermediate 131

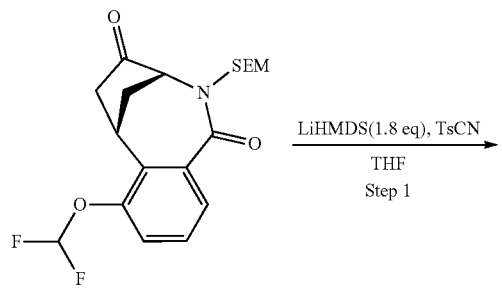

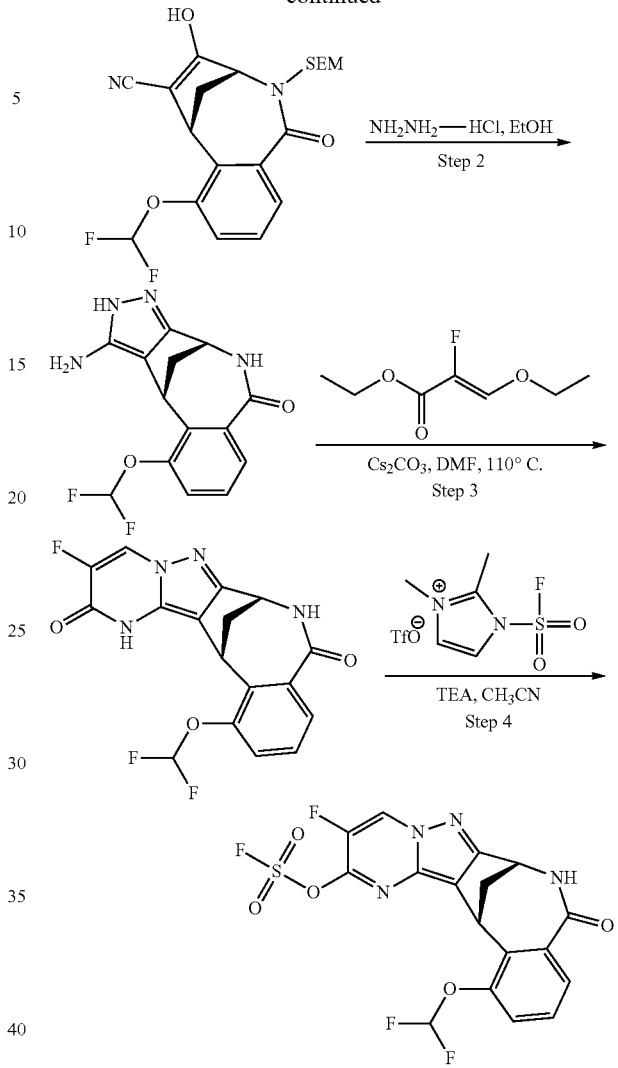

Step 1: A solution of (3R,6S)-7-(difluoromethoxy)-2-((2-(trimethylsilyl)ethoxy)methyl)-2,3,5,6-tetrahydro-3,6-methanobenzo[c]azocine-1,4-dione (1.0 g, 2.5 mmol, 1.0 equiv) in THF (3 mL) was treated at −78° C. under nitrogen atmosphere followed by the addition of LiHMDS (1.0 M in THF) (5.0 mL, 5.0 mmol, 2 equiv) dropwise at −78° C. The resulting mixture was stirred at −78° C. for 1 h under nitrogen atmosphere. To the above mixture was added 4-methylbenzenesulfonyl cyanide (820.6 mg, 4.5 mmol, 1.8 equiv) in portions at −78° C. The resulting mixture was stirred at −78° C.-RT for additional 2 h. The reaction mixture was diluted with water (300 mL), and the aqueous phase was extracted with EA (200 mL) three times. The combined organic layers were washed with brine, dried over sodium sulfate, filtered, and concentrated in vacuo. The residue was purified by silica gel column chromatography, eluted with DCM/MeOH (15:1) to afford (3R,6R)-7-(difluoromethoxy)-4-hydroxy-1-oxo-2-((2-(trimethylsilyl)ethoxy)methyl)-1,2,3,6-tetrahydro-3,6-methanobenzo[c]azocine-5-carbonitrile (350 mg, 32.9%) as light yellow oil.

Step 2: A mixture of (3R,6R)-7-(difluoromethoxy)-4-hydroxy-1-oxo-2-((2-(trimethylsilyl)ethoxy)methyl)-1,2,3,6-tetrahydro-3,6-methanobenzo[c]azocine-5-carbonitrile (2.0 g, 4.7 mmol, 1.0 equiv) and hydrazine monohydrochloride (713.4 mg, 10.4 mmol, 2.2 equiv) in EtOH (25 mL) was stirred at 85° C. for 16 h. The resulting mixture was concentrated under reduced pressure. The residue was purified by silica gel column chromatography, eluted with DCM/MeOH (10:1) to afford (4R,11S)-1-amino-10-(difluoromethoxy)-2,4,5,11-tetrahydro-6H-4,11-methanobenzo[c]pyrazolo[4,3-f]azocin-6-one (400 mg, 27.6%) as a light yellow solid. LCMS (ESI, m/z): 306.95 [M+H]⁺.

Step 3: A mixture of (4R,11S)-1-amino-10-(difluoromethoxy)-2,4,5,11-tetrahydro-6H-4,11-methanobenzo[c]pyrazolo[4,3-f]azocin-6-one (350 mg, 1.1 mmol, 1.0 equiv), ethyl (2Z)-3-ethoxy-2-fluoroprop-2-enoate (278 mg, 1.7 mmol, 1.5 equiv) and Cs₂CO₃ (820 mg, 2.5 mmol, 2.2 equiv) in DMF (5 mL) was stirred at 110° C. for 16 h. The resulting mixture was concentrated under reduced pressure. The residue was purified by silica gel column chromatography, eluted with DCM/MeOH (10:1) to afford (7R,14S)-1-(difluoromethoxy)-11-fluoro-6,7,13,14-tetrahydro-7,14-methanobenzo[c]pyrimido[1',2':1,5]pyrazolo[4,3-f]azocine-5,12-dione (110 mg, 25.6%) as a light yellow solid. LCMS (ESI, m/z): 377.20 [M+H]⁺.

Step 4: A mixture of (7R,14S)-1-(difluoromethoxy)-11-fluoro-6,7,13,14-tetrahydro-7,14-methanobenzo[c]pyrimido[1',2':1,5]pyrazolo[4,3-f]azocine-5,12-dione (100 mg, 0.27 mmol, 1.0 equiv), 3-(fluorosulfonyl)-1,2-dimethylimidazol-1-ium triflate (131 mg, 0.4 mmol, 1.5 equiv) and Et₃N (60 mg, 0.58 mmol, 2.2 equiv) in MeCN (5 mL) was stirred at room temperature for 1 h. The resulting mixture was concentrated under reduced pressure. The residue was purified by silica gel column chromatography, eluted with DCM/MeOH (10:1) to afford (7R,14S)-1-(difluoromethoxy)-11-fluoro-5-oxo-5,6,7,14-tetrahydro-7,14-methanobenzo[c]pyrimido[1',2':1,5]pyrazolo[4,3-f]azocin-12-yl sulfurofluoridate (40 mg, 32.8% yield) as a light yellow solid. LCMS (ESI, m/z): 459.10 [M+H]⁺.

Intermediate 132

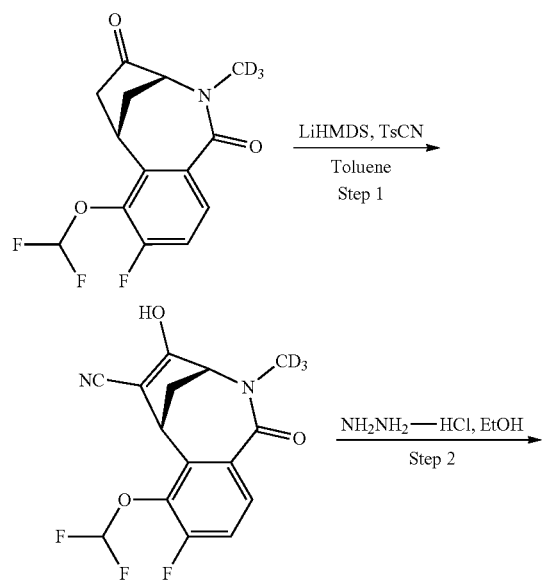

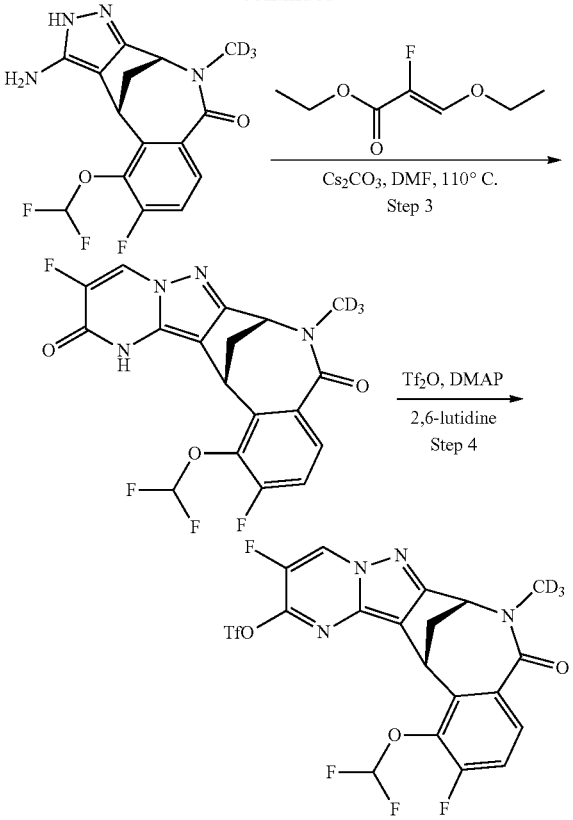

Step 1: A solution of (3R,6S)-7-(difluoromethoxy)-8-fluoro-2-(methyl-d3)-2,3,5,6-tetrahydro-3,6-methanobenzo[c]azocine-1,4-dione (1.0 g, 3.3 mmol, 1.0 equiv) in toluene (10 mL) was treated at −78° C. for 5 min under nitrogen atmosphere followed by the addition of LiHMDS (4.0 mL, 4.0 mmol, 1.2 equiv) dropwise at −78° C. The resulting mixture was stirred at −78° C. for 1 h under nitrogen atmosphere. A solution of 4-methylbenzenesulfonyl cyanide (0.72 g, 4.0 mmol, 1.2 equiv) in toluene (7 mL) was treated at −50° C. for 5 min under nitrogen atmosphere followed by the addition of the above mixture dropwise at −50° C. The resulting mixture was stirred at −50° C. for additional 1 h. The reaction was quenched by the addition of MeOH (1 mL) at −50° C. The reaction mixture was diluted with water (200 mL), and the aqueous phase was extracted with EA (200 mL) three times. The water was acidified to pH 3 with 2M HCl, and the aqueous phase was extracted with EA (200 mL) three times. The combined organic layers were washed with brine, dried over sodium sulfate, filtered, and concentrated in vacuo. The residue was purified by silica gel column chromatography, eluted with PE/EA (1:1) to afford (3R,6R)-7-(difluoromethoxy)-8-fluoro-4-hydroxy-2-(methyl-d3)-1-oxo-1,2,3,6-tetrahydro-3,6-methanobenzo[c]azocine-5-carbonitrile (500 mg, 46.2%) as a light pink solid. LCMS (ESI, m/z): 328.15 [M+H]⁺.

Step 2: A solution of (3R,6R)-7-(difluoromethoxy)-8-fluoro-4-hydroxy-2-(methyl-d3)-1-oxo-1,2,3,6-tetrahydro-3,6-methanobenzo[c]azocine-5-carbonitrile (480 mg, 1.5 mmol, 1.0 equiv) in EtOH (10 mL) was treated with hydrazine monohydrochloride (221 mg, 3.2 mmol, 2.2 equiv) at room temperature for 2 min under nitrogen atmosphere. The resulting mixture was stirred at 80° C. for 3 h under nitrogen atmosphere. The resulting mixture was concentrated under reduced pressure. The residue was purified by silica gel column chromatography, eluted with CH₂Cl₂/MeOH (20:1) to afford (4R,11S)-1-amino-10-(difluoromethoxy)-9-fluoro-5-(methyl-d3)-2,4,5,11-tetrahydro-6H-4,11-methanobenzo[c]pyrazolo[4,3-f]azocin-6-one (260 mg) as alight green solid. LCMS (ESI, m/z): 342.10 [M+H]⁺.

Step 3: A mixture of (4R,11S)-1-amino-10-(difluoromethoxy)-9-fluoro-5-(methyl-d3)-2,4,5,11-tetrahydro-6H-4,11-methanobenzo[c]pyrazolo[4,3-f]azocin-6-one (250 mg, 0.73 mmol, 1.0 equiv) and Cs₂CO₃ (501.2 mg, 1.5 mmol, 2.1 equiv) in DMF (8 mL) was treated with ethyl (2Z)-3-ethoxy-2-fluoroprop-2-enoate (237.6 mg, 1.46 mmol, 2.0 equiv) at room temperature for 2 min under nitrogen atmosphere. The resulting mixture was stirred at 110° C. for 16 h. The resulting mixture was concentrated under reduced pressure. The residue was purified by silica gel column chromatography, eluted with CH₂Cl₂/MeOH (20:1) to afford (7R,14S)-1-(difluoromethoxy)-2,11-difluoro-6-(methyl-d3)-6,7,13,14-tetrahydro-7,14-methanobenzo[c]pyrimido[1',2':1,5]pyrazolo[4,3-f]azocine-5,12-dione (150 mg, 49.8%) as a yellow solid. LCMS (ESI, m/z): 412.05 [M+H]⁺.

Step 4: A mixture of (7R,14S)-1-(difluoromethoxy)-2,11-difluoro-6-(methyl-d3)-6,7,13,14-tetrahydro-7,14-methanobenzo[c]pyrimido[1',2':1,5]pyrazolo[4,3-f]azocine-5,12-dione (140 mg, 0.34 mmol, 1.0 equiv), 2,6-lutidine (145.9 mg, 1.36 mmol, 4.0 equiv) and DMAP (166.3 mg, 1.36 mmol, 4.0 equiv) in DCM (2 mL) was treated with (trifluoromethane)sulfonyl trifluoromethanesulfonate (480.1 mg, 1.7 mmol, 5.0 equiv) at 0° C. for 2 min under nitrogen atmosphere. The resulting mixture was stirred at room temperature for 1 h. The reaction mixture was diluted with NH₄Cl (50 mL), and the aqueous phase was extracted with DCM (3×50 mL). The combined organic layers were washed with brine, dried over sodium sulfate, filtered, and concentrated in vacuo. The residue was purified by Prep-TLC (PE/EA 1:1) to afford (7R,14S)-1-(difluoromethoxy)-2,11-difluoro-6-(methyl-d3)-5-oxo-5,6,7,14-tetrahydro-7,14-methanobenzo[c]pyrimido[1',2':1,5]pyrazolo[4,3-f]azocin-12-yl trifluoromethanesulfonate (100 mg, 54.1%) as a light yellow solid. LCMS (ESI, m/z): 544.10 [M+H]⁺.

Example 1. 12-(2-(1-aminocyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one

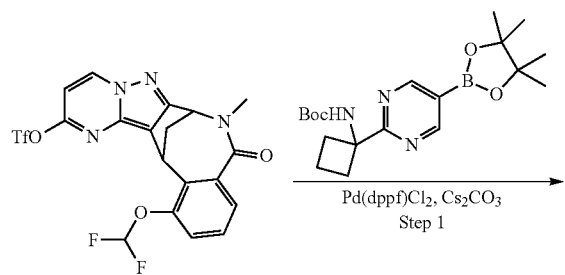

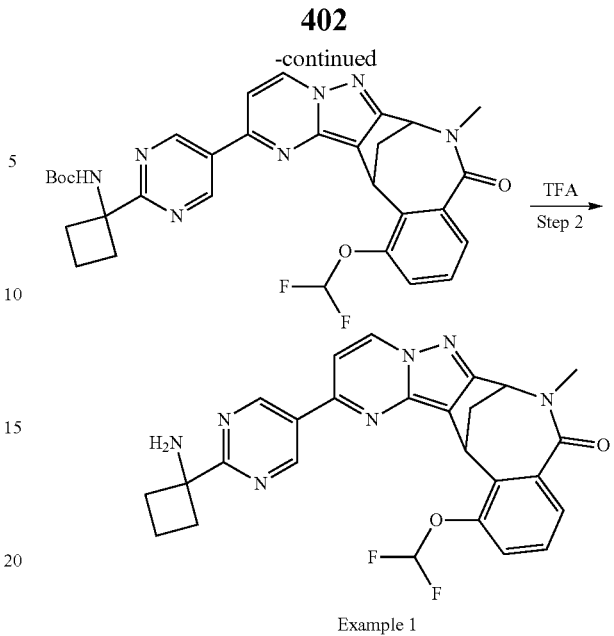

Example 1

Step 1: A solution of Intermediate 12 (30 mg, 0.06 mmol, 1 equiv) and Intermediate 25 (45 mg, 0.12 mmol, 2 equiv) in dioxane (5 mL) and H₂O (1 mL) was treated with Pd(dppf)Cl₂·DCM (4.85 mg, 0.01 mmol, 0.1 equiv) and LiOH·H₂O (7.49 mg, 0.18 mmol, 3 equiv) for 1 min at room temperature under nitrogen atmosphere. The resulting mixture was stirred for 1 hr at 50° C. under nitrogen atmosphere. Desired product could be detected by LCMS. The resulting mixture was concentrated under reduced pressure. The residue was purified by Prep-TLC (PE/EA 1:10) to afford tert-butyl (1-(5-(1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)cyclobutyl)carbamate (30 mg, 84%) as a white solid. LCMS (ESI, m/z): 604.35 [M+H]⁺.

Step 2: A solution of tert-butyl (1-(5-(1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)cyclobutyl)carbamate (40 mg, 0.07 mmol, 1 equiv) in DCM (1 mL) was treated with TFA (0.25 mL) for 1 min at 0° C. under nitrogen atmosphere. The resulting mixture was stirred for 1 hr at room temperature under nitrogen atmosphere. The mixture was basified to pH 8 with saturated Na₂CO₃ (aq.). The resulting mixture was extracted with DCM (3×5 mL). The combined organic layers were washed with brine (2×10 mL), dried over anhydrous Na₂SO₄. After filtration, the filtrate was concentrated under reduced pressure. The crude product (40 mg) was purified by Prep-HPLC with the following conditions (Column: XBridge Prep OBD C18 Column, 30*150 mm, 5 μm; Mobile Phase A: Water (10 mmol/L NH₄HCO₃), Mobile Phase B: ACN; Flow rate: 60 mL/min mL/min; Gradient: 29% B to 49% B in 10 min; Wave Length: 254 nm/220 nm nm; RT1(min): 7.3) to afford Example 1 (2.1 mg, 6.3%). LCMS (ESI, m/z): 504.15 [M+H]⁺. ¹H NMR (400 MHz, DMSO-d₆) δ 9.48 (s, 2H), 9.26 (d, J=7.4 Hz, 1H), 8.25 (d, J=7.8 Hz, 1H), 7.77-7.47 (m, 2H), 7.38-7.34 (m, 2H), 5.15-5.09 (m, 2H), 3.29 (s, 3H), 2.75-2.53 (m, 4H), 2.18-2.07 (m, 2H), 2.05-1.92 (m, 1H), 1.86-1.82 (m, 1H).

Example 2. (7S,14R)-12-(2-(1-aminocyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one Example 3. (7R,14S)-12-(2-(1-aminocyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one Example 4. (1R,3s)-3-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-hydroxy-1-methylcyclobutane-1-carbonitrile

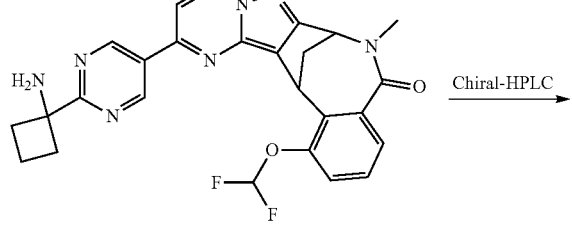

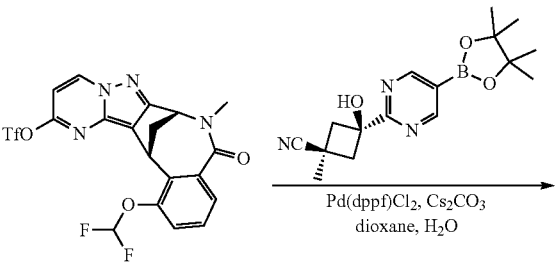

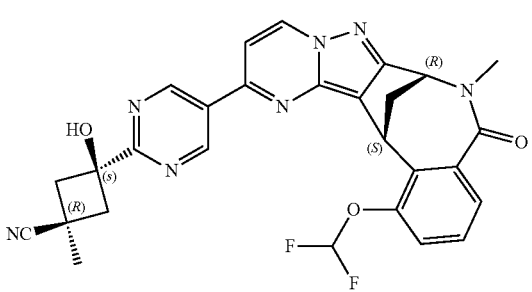

Example 4

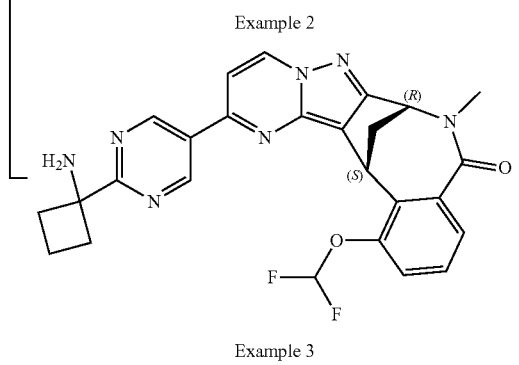

Example 2

Example 3

12-(2-(1-aminocyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one (8 mg) was separated by chiral HPLC with the following conditions (Column: CHIRAL Cellulose SB; Mobile Phase A: Hex (0.1% DEA): (EtOH:DCM=1:1)=50:50; Flow rate: 1 mL/min mL/min; Gradient: isocratic; Injection Volume: 2 uL mL) to afford Example 2 (3.0 mg, 37%). LCMS (ESI, m/z): 504.15 [M+H]⁺ and Example 3 (3.0 mg, 37%) as a white solid. LCMS (ESI, m/z): 504.15 [M+H]⁺.

A solution of Intermediate 7 (25 mg, 0.05 mmol, 1 equiv) and Intermediate 28 (19 mg, 0.06 mmol, 1.1 equiv) in dioxane (1.5 mL) and H₂O (0.3 mL) was treated with Pd(dppf)Cl₂·DCM (8.08 mg, 0.01 mmol, 0.2 equiv) and Cs₂CO₃ (49 mg, 0.15 mmol, 3 equiv) for 5 min at room temperature under nitrogen atmosphere. The resulting mixture was stirred for 2 hrs at 50° C. under nitrogen atmosphere. The resulting mixture was concentrated under reduced pressure. The crude product (25 mg) was purified by Prep-HPLC with the following conditions (Column: XBridge Prep OBD RP18 Column, 30*150 mm, 5 μm; Mobile Phase A: Water (10 mmol/L NH₄HCO₃), Mobile Phase B: ACN; Flow rate: 60 mL/min mL/min; Gradient: 36% B to 56% B in 10 min; Wave Length: 254 nm/220 nm; RT1(min): 7.97) to afford Example 4 (6 mg, 21.7%). LCMS (ESI, m/z): 544.05 [M+H]⁺. ¹H NMR (400 MHz, DMSO-d₆) δ 9.53 (s, 2H), 9.29 (d, J=7.4 Hz, 1H), 8.28-8.22 (m, 1H), 7.75 (d, J=7.5 Hz, 1H), 7.73-7.31 (m, 3H), 6.25 (s, 1H), 5.17-5.09 (m, 2H), 3.38-3.28 (m, 1H), 3.30 (s, 3H), 2.95-2.87 (m, 2H), 2.81-2.73 (m, 2H), 2.55 (s, 1H), 1.45 (s, 3H).

Example 5. (1r,3S)-1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-hydroxy-3-methylcyclobutane-1-carbonitrile

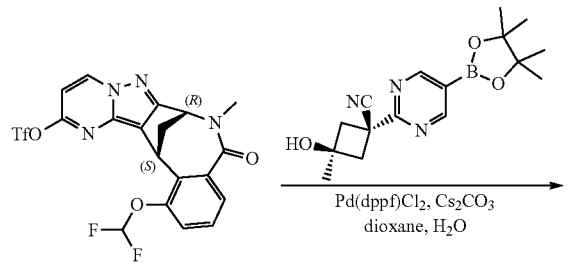

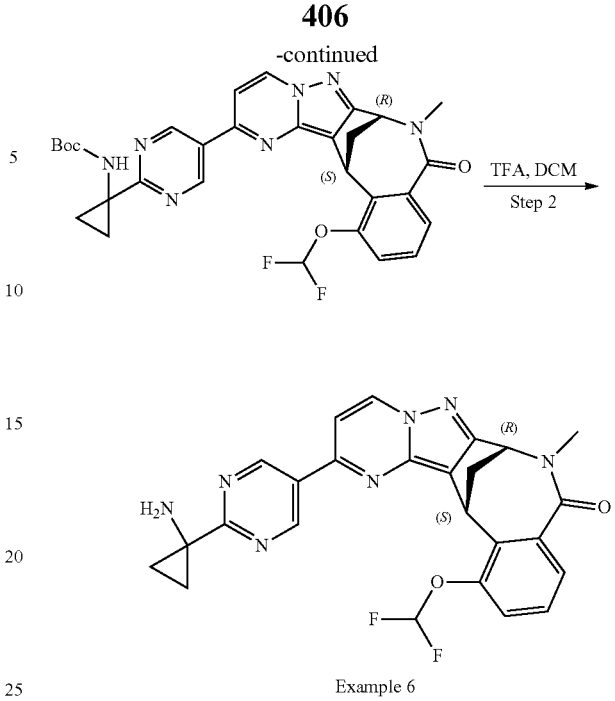

Example 6

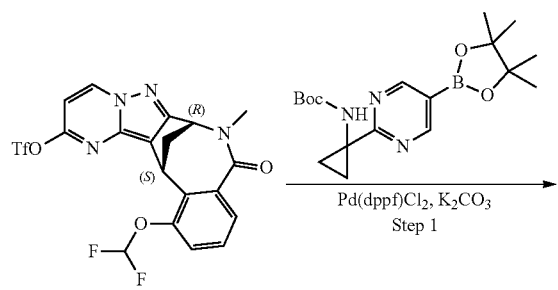

Example 5

The tile compound was prepared as described in Example 4 above by replacing Intermediate 31. LCMS (ESI, m/z): 544.20 [M+H]⁺. ¹H NMR (400 MHz, DMSO-$d_6$) δ 9.56 (s, 2H), 9.31 (d, J=7.5 Hz, 1H), 8.25 (m, 1H), 7.90-7.66 (m, 1H), 7.64-7.14 (m, 3H), 5.53 (s, 1H), 5.14 (m, 2H), 3.35 (s, 1H), 3.33-3.29 (m, 3H), 3.05-2.92 (m, 2H), 2.88-2.80 (m, 2H), 2.54-2.49 (m, 1H), 1.24 (s, 3H).

Example 6. (7R,14S)-12-(2-(1-aminocyclopropyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one Step 1: To a stirred mixture of Intermediate 7 (28 mg, 0.06 mmol, 1 equiv) and Intermediate 32 (24.1 mg, 0.067 mmol, 1.2 equiv) in dioxane (0.5 mL) and H₂O (0.1 mL) was added Pd(dppf)Cl₂·DCM (4.5 mg, 0.006 mmol, 0.1 equiv) and K₂CO₃ (23.0 mg, 0.16 mmol, 3 equiv) at room temperature under nitrogen atmosphere. The resulting mixture was stirred for 1 hr at 80° C. under nitrogen atmosphere. The resulting mixture was concentrated under reduced pressure. The resulting mixture was extracted with EtOAc (3×20 mL). The combined organic layers were washed with brine (1×20 mL), dried over anhydrous Na₂SO₄. After filtration, the filtrate was concentrated under reduced pressure. The residue was purified by Prep-TLC to afford tert-butyl (1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)cyclopropyl)carbamate (15 mg, 45.8%) as a white solid. LCMS (ESI, m/z): 590.25 [M+H]⁺.

Step 2: To a stirred solution of (1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)cyclopropyl)carbamate (15 mg, 0.025 mmol, 1 equiv) in DCM (0.6 mL) was added TFA (0.2 mL) at 0° C. under nitrogen atmosphere. The resulting mixture was stirred for 1 hr at room temperature under nitrogen atmosphere. The resulting mixture was concentrated under reduced pressure. The crude product was purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 50% B in 7 min; Wave Length: 254 nm/220 nm nm; RT1(min): 6.56) to afford Example 6 (8 mg, 61%). LCMS (ESI, m/z): 490.25 [M+H]⁺. 1H NMR (400 MHz, DMSO-$d_6$) δ 9.39 (s, 2H), 9.24 (d, J=8.0 Hz, 1H), 8.25-8.23 (m, 1H), 7.70-7.68 (m, 1H), 7.52-7.35 (m, 3H), 5.12-3.95 (m, 2H), 3.45-3.33 (m, 1H), 3.28 (s, 3H), 2.54 (s, 1H), 1.40-1.39 (m, 2H), 1.24-1.18 (m, 2H).

Example 7. (1R,3s)-3-amino-3-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-1-methylcyclobutane-1-carbonitrile eluted with DCM/MeOH (10:1) to afford (R)—N-((1s,3S)-3-cyano-1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)-2-methylpropane-2-sulfinamide (40 mg, 52.0%) as a black solid. LCMS (ESI, m/z): 647.23 [M+H]$^+$.

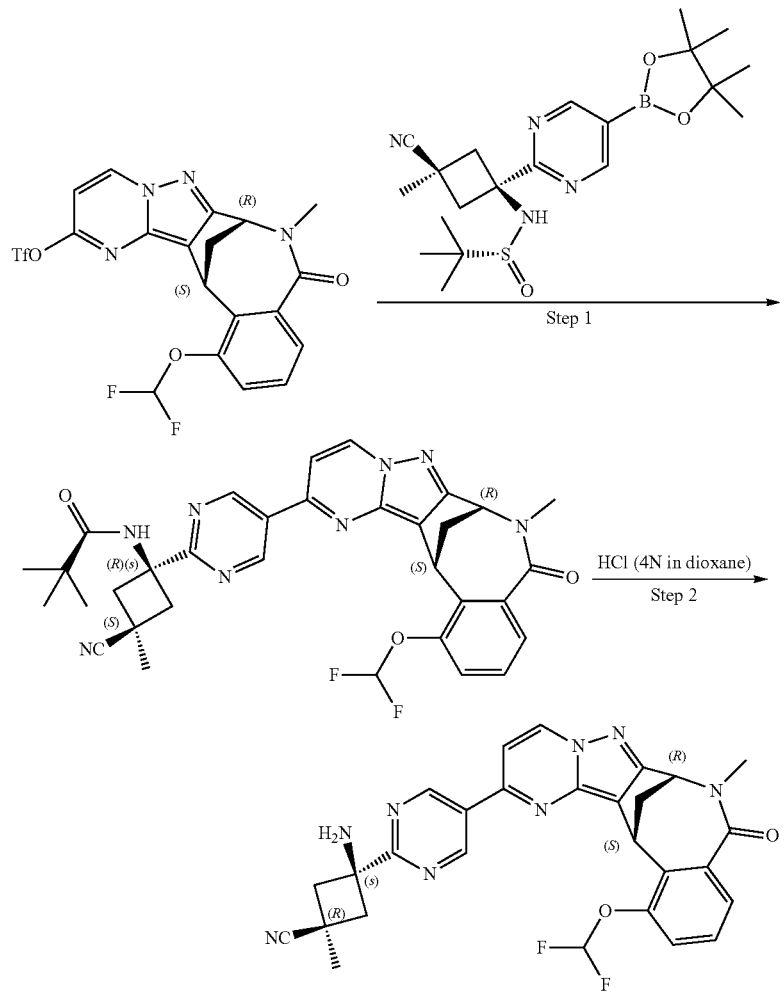

Example 7

Step 1: A solution of ((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl trifluoromethanesulfonate (60 mg, 0.12 mmol, 1 equiv) in 1,4-dioxane (1 mL) and H$_2$O (0.2 mL) was treated with (R)—N-((1s,3S)-3-cyano-3-methyl-1-(5-(4,4,5,5-tetramethyl-1,3,2-dioxaborolan-2-yl)pyrimidin-2-yl)cyclobutyl)-2-methylpropane-2-sulfinamide (50 mg, 0.12 mmol, 1 equiv) and Cs$_2$CO$_3$ (117 mg, 0.36 mmol, 3 equiv) at room temperature for 10 min under nitrogen atmosphere followed by the addition of Pd(dppf)Cl$_2$·DCM (20 mg, 0.024 mmol, 0.2 equiv) in portions at room temperature. The resulting mixture was stirred at 80° C. for 1 hr under nitrogen atmosphere. The resulting mixture was extracted with EtOAc (3×10 mL). The combined organic layers were washed with brine (2×5 mL), dried over anhydrous Na$_2$SO$_4$. After filtration, the filtrate was concentrated under reduced pressure. The residue was purified by silica gel column chromatography, Step 2: A solution of (R)—N-((1s,3S)-3-cyano-1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)-2-methylpropane-2-sulfinamide (40 mg, 0.06 mmol, 1 equiv) in DCM (1 mL) was treated with HCl(gas) in 1,4-dioxane (0.03 mL, 0.12 mmol, 2 equiv, 4M) for 2 min at 0° C. under nitrogen atmosphere. The resulting mixture was stirred for 30 min at room temperature under nitrogen atmosphere. The mixture was basified to pH 7 with saturated NaHCO$_3$ (aq.). The resulting mixture was extracted with EtOAc (3×3 mL). The combined organic layers were washed with brine (2×2 mL), dried over anhydrous Na$_2$SO$_4$. After filtration, the filtrate was concentrated under reduced pressure. The crude product (40 mg) was purified by Prep-HPLC with the following conditions (Column: XBridge Prep OBD RP18 Column, 30*150 mm, 5 μm; Mobile Phase A: Water (10 mmol/L NH$_4$HCO$_3$), Mobile Phase B: ACN; Flow rate: 60 mL/min mL/min; Gradient: 41% B to 61% B in 10 min; Wave Length: 254 nm/220 nm nm; RT1(min): 8.6) to afford (1R,3s)-3-amino-3-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-1-methylcyclobutane-1-carbonitrile (16.3 mg, 48.5%). LCMS (ESI, m/z): 543.30 [M+H]$^+$. $^1$H NMR (400 MHz, DMSO-d$_6$) δ 9.50 (s, 2H), 9.28 (d, J=7.4 Hz, 1H), 8.26-8.23 (m, 1H), 7.80-7.48 (m, 2H), 7.43-7.26 (m, 2H), 5.14-5.11 (m, 2H), 3.32 (s, 3H), 2.84-2.78 (m, 2H), 2.65-2.53 (m, 4H), 1.45 (s, 3H).

Example 8. (7R,14S)-1-(difluoromethoxy)-12-(4-(2-hydroxypropan-2-yl)cyclohex-1-en-1-yl)-6-methyl-6,7-dihydro-7,14-methanobenzo[c]pyrimido[1',2':1,5]pyrazolo[4,3-f]azocin-5 (14H)-one

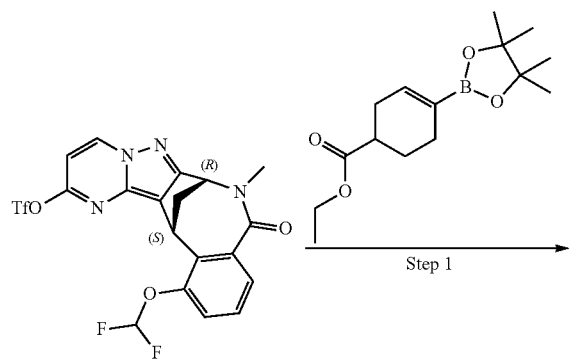

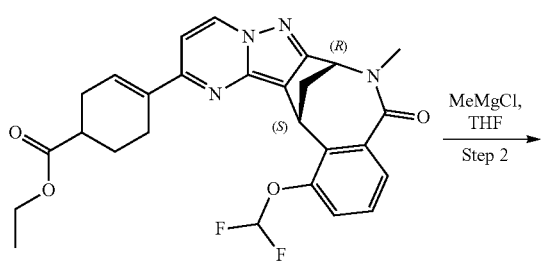

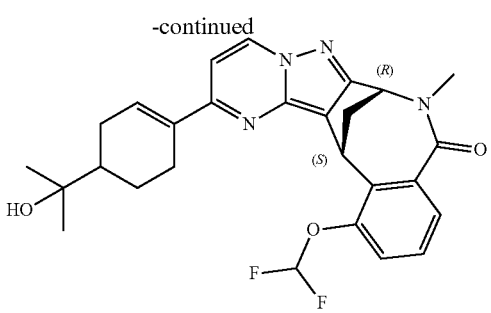

Example 8

Step 1: A solution of ((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl trifluoromethanesulfonate (60 mg, 0.12 mmol, 1 equiv) and ethyl 4-(4,4,5,5-tetramethyl-1,3,2-dioxaborolan-2-yl)cyclohex-3-ene-1-carboxylate (39.99 mg, 0.143 mmol, 1.2 equiv) in dioxane (4 mL) and H$_2$O (1 mL) was treated with Cs$_2$CO$_3$ (116.27 mg, 0.357 mmol, 3 equiv) for 1 min at room temperature under nitrogen atmosphere followed by the addition of Pd(dppf)Cl$_2$·DCM (19.38 mg, 0.024 mmol, 0.2 equiv) at room temperature. The resulting mixture was stirred for 2 hrs at 50° C. under nitrogen atmosphere. The aqueous layer was extracted with EtOAc (3×13 mL). The residue was purified by Prep-TLC (EA, RF=0.3) to afford ethyl 4-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)cyclohex-3-ene-1-carboxylate (50 mg, 82.66%) as a yellow solid.

Step 2: A solution of ethyl 4-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)cyclohex-3-ene-1-carboxylate (30 mg, 0.06 mmol, 1 equiv) in THF (2 mL) was treated with CH$_3$MgCl (0.15 mL, 0.15 mmol, 2.5 equiv) for 2 hrs at −78° C. under nitrogen atmosphere. The reaction was quenched by the addition of sat. NH$_4$Cl (aq.) (10 mL) at 0° C. The crude product (50 mg) was purified by Prep-HPLC with the following conditions (Column: XSelect CSH Prep C18 OBD Column, 19*250 mm, 5 µm; Mobile Phase A: Water (0.05% FA), Mobile Phase B: MeOH; Flow rate: 20 mL/min mL/min; Gradient: 54% B to 84% B in 8 min; Wave Length: 254 nm/220 nm nm; RT1(min): 7.6) to afford (7R,14S)-1-(difluoromethoxy)-12-(4-(2-hydroxypropan-2-yl)cyclohex-1-en-1-yl)-6-methyl-6,7-dihydro-7,14-methanobenzo[c]pyrimido[1',2':1,5]pyrazolo[4,3-f]azocin-5 (14H)-one (5.2 mg, 17.8%). LCMS (ESI, m/z): 495.20 [M+H]$^+$. $^1$H NMR (400 MHz, DMSO-d$_6$) δ 8.91 (d, J=7.6 Hz, 1H), 8.27-8.26 (m, 1H), 7.76-7.51 (m, 1H), 7.41-7.32 (m, 2H), 7.27 (dd, J=7.7, 5.5 Hz, 1H), 6.94 (d, J=2.6 Hz, 1H), 5.10-4.87 (m, 2H), 4.19 (s, 1H), 3.32-3.26 (m, 4H), 2.82-2.66 (m, 1H), 2.47 (s, 1H), 2.35-2.30 (m, 1H), 2.28-2.13 (m, 1H), 2.10-1.98 (m, 2H), 1.53-1.42 (m, 1H), 1.22-1.17 (m, 1H), 1.10 (d, J=2.9 Hz, 6H).

Example 9. (7R,14S)-12-(2-((1s,3R)-1-amino-3-hydroxy-3-methylcyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5(14H)-one ((1s,3R)-3-((tert-butyldimethylsilyl)oxy)-1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)-2-methylpropane-2-sulfinamide (60 mg, 69.6%) as a yellow solid. LCMS (ESI, m/z): 752.30 [M+H]$^+$.

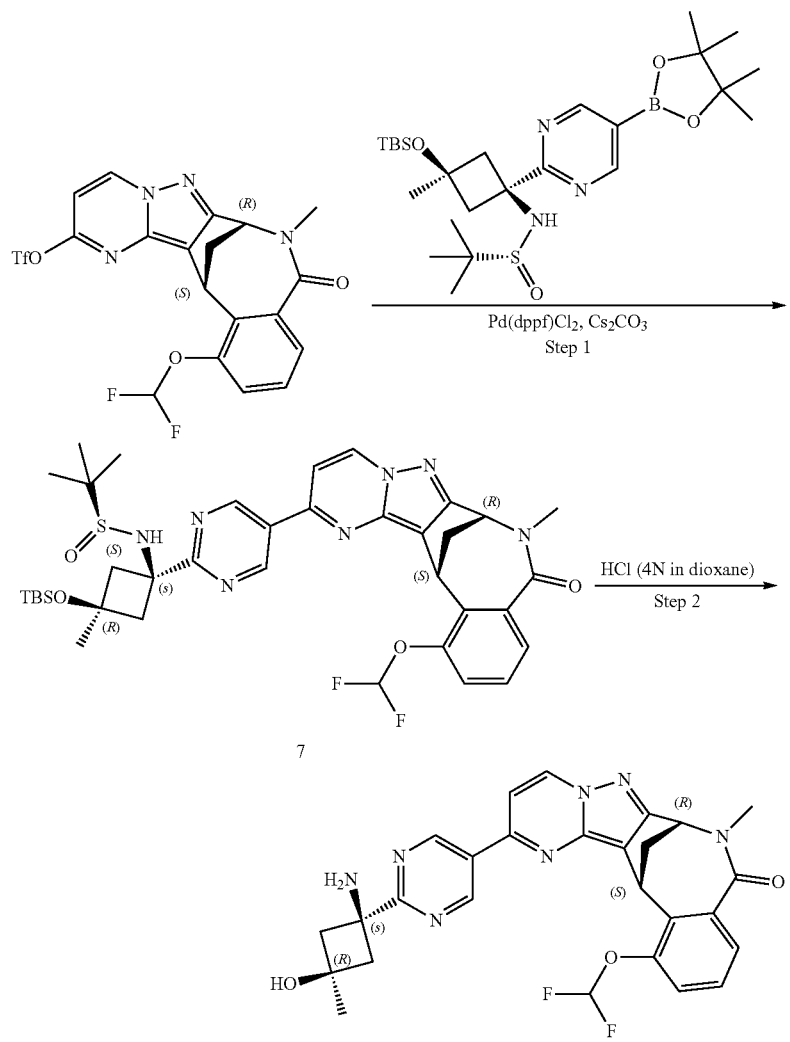

Example 9

Step 1: A solution of ((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl trifluoromethanesulfonate (60 mg, 0.12 mmol, 1 equiv) and (R)—N-((1s,3S)-3-((tert-butyldimethylsilyl)oxy)-3-methyl-1-(5-(4,4,5,5-tetramethyl-1,3,2-dioxaborolan-2-yl)pyrimidin-2-yl)cyclobutyl)-2-methylpropane-2-sulfinamide (57.8 mg, 0.12 mmol, 1 equiv) in dioxane (1 mL) and H$_2$O (0.2 mL) was treated with Cs$_2$CO$_3$ (112.0 mg, 0.35 mmol, 3 equiv) at room temperature for 1 min under nitrogen atmosphere followed by the addition of Pd(dppf)Cl$_2$·DCM (18.7 mg, 0.02 mmol, 0.2 equiv) at room temperature. The resulting mixture was stirred at 60° C. for 1 hr under nitrogen atmosphere. The resulting mixture was filtered, the filter cake was washed with EtOAc (3×5 mL). The filtrate was concentrated under reduced pressure. The residue was purified by Prep-TLC (DCM/MeOH 10:1) to afford (S)—N-

Step 2: A solution of (S)—N-((1s,3R)-3-((tert-butyldimethylsilyl)oxy)-1-(5-((7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)-2-methylpropane-2-sulfinamide (60 mg, 0.08 mmol, 1 equiv) in DCM (6 mL) was treated with HCl(gas) in dioxane (3 mL, 0.60 mmol) at 0° C. for 10 min under nitrogen atmosphere. The resulting mixture was stirred at room temperature for 2H under nitrogen atmosphere. The resulting mixture was concentrated under reduced pressure. The crude product (50 mg) was purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 50% B in 7 min; Wave Length: 254 nm/220 nm nm; RT1(min): 6.56) to afford (7R,14S)-12-(2-((1s,3R)-1-amino-3-hydroxy-3- methylcyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one (20.6 mg, 48.29%). LCMS (ESI, m/z): 534.15 [M+H]+. 1H NMR (400 MHz, DMSO-d6) δ 9.53 (s, 2H), 9.29 (d, J=7.5 Hz, 1H), 8.27-8.23 (m, 1H), 7.78-7.70 (m, 1H), 7.58-7.28 (m, 3H), 6.07 (s, 2H), 5.15-3.10 (m, 2H), 3.37-3.32 (m, 1H), 3.30 (s, 3H), 2.87 (d, J=12.5 Hz, 2H), 2.55 (s, 1H), 2.37 (d, J=12.4 Hz, 2H), 1.25 (s, 3H).

Example 10. (7R,14S)-12-(2-((1s,3R)-1-amino-3-(hydroxymethyl)-3-methylcyclobutyl)pyrimidin-5-yl)-1-(difluoromethoxy)-6-methyl-6,7-dihydro-7,14-methanobenzo[c]pyrimido[1',2':1,5]pyrazolo[4,3-f]azocin-5 (14H)-one The tile compound was prepared as described in Example 9 above by replacing Intermediate 41. LCMS (ESI, m/z): 548.30 [M+H]+. 1HNMR (400 MHz, DMSO-d6) δ 9.51 (s, 2H), 9.28 (d, J=7.5 Hz, 1H), 8.25 (dd, J=7.9, 1.6 Hz, 1H), 7.80-7.69 (m, 1H), 7.64-7.28 (m, 3H), 5.13 (dd, J=6.8, 1.6 Hz, 2H), 3.45 (s, 2H), 3.37-3.32 (m, 1H), 3.30 (s, 3H), 2.55 (s, 1H), 2.51-2.46 (m, 2H), 2.22-2.09 (m, 2H), 1.09 (s, 3H).

Example 11. (7R,14S)-1-(difluoromethoxy)-12-(2-(2-hydroxypropan-2-yl)pyrimidin-5-yl)-6-methyl-6,7-dihydro-7,14-methanobenzo[c]pyrimido[1',2':1,5]pyrazolo[4,3-f]azocin-5 (14H)-one

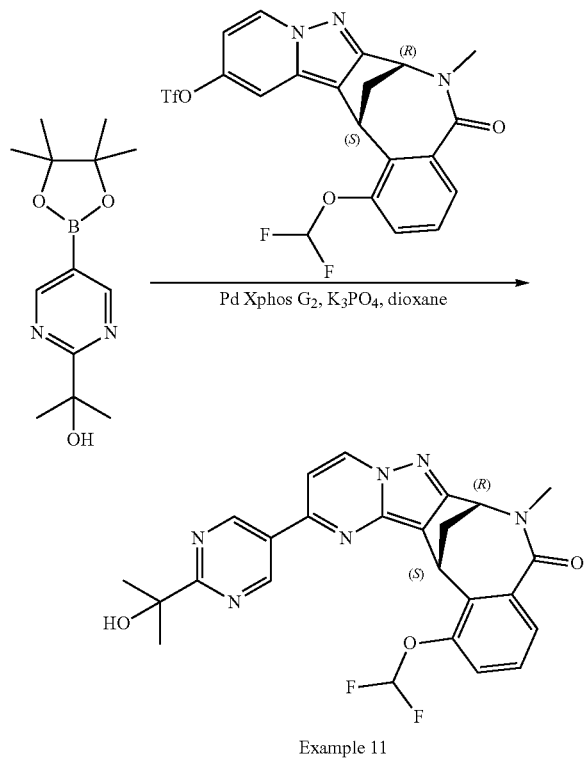

Example 11

A solution/mixture of (7R,14S)-1-(difluoromethoxy)-6-methyl-5-oxo-5,6,7,14-tetrahydro-7,14-methanobenzo[c]pyrimido[1',2':1,5]pyrazolo[4,3-f]azocin-12-yl trifluoromethanesulfonate (40 mg, 0.08 mmol, 1.00 equiv) and 2-(5-(4,4,5,5-tetramethyl-1,3,2-dioxaborolan-2-yl)pyrimidin-2-yl)propan-2-ol (21 mg, 0.08 mmol, 1 equiv), Pd(dppf)Cl2 (11.6 mg, 0.016 mmol, 0.2 equiv), Cs2CO3 (77.5 mg, 0.24 mmol, 3 equiv) in dioxane (2 mL) and H2O (0.4 mL) was stirred for 1 hr at 80° C. under nitrogen atmosphere. The resulting mixture was extracted with EtOAc (3×10 mL), then dried over anhydrous Na2SO4. After filtration, the filtrate was concentrated under reduced pressure. The crude product (40 mg) was purified by Prep-HPLC with the following conditions (Column: xBridge Prep Phenyl 5 μm OBD 19*250 mm; Mobile Phase A: Water (10 mmol/L NH4HCO3), Mobile Phase B: MeOH; Flow rate: 20 mL/min mL/min; Gradient: isocratic 35% B-65% B IN 20 MIN; Wave Length: 220/254 nm; RT1(min): 13) to afford ((7R,14S)-1-(difluoromethoxy)-12-(2-(2-hydroxypropan-2-yl)pyrimidin-5-yl)-6-methyl-6,7-dihydro-7,14-methanobenzo[c]pyrimido[1',2':1,5]pyrazolo[4,3-f]azocin-5 (14H)-one (12 mg, 30.4%) as a light green solid. LCMS (ESI, m/z): 493.25 [M+H]+. 1H NMR (400 MHz, DMSO-d6) δ 9.49 (s, 2H), 9.28-9.26 (m, 1H), 8.25-8.23 (m, 1H), 7.77-7.49 (m, 2H), 7.43-7.30 (m, 2H), 5.24 (s, 1H), 5.13 (d, J=6.7 Hz, 2H), 3.42-3.40 (m, 1H), 3.30 (s, 3H), 2.54 (s, 1H), 1.55 (s, 6H).

Example 12. (7R,14S)-1-(difluoromethoxy)-12-(2-(3-hydroxytetrahydrofuran-3-yl)pyrimidin-5-yl)-6-methyl-6,7-dihydro-7,14-methanobenzo[c]pyrimido[1',2':1,5]pyrazolo[4,3-f]azocin-5 (14H)-one The tile compound was prepared as described in Example 9 above by replacing Intermediate 43. LCMS (ESI, m/z): 521.10 [M+H]+. 1HNMR (400 MHz, DMSO-d6) δ 9.52 (s, 2H), 9.29 (d, J=7.4 Hz, 1H), 8.28-8.22 (m, 1H), 7.77-7.55 (m, 2H), 7.42-7.31 (m, 2H), 5.73 (s, 1H), 5.18-5.06 (m, 2H), 4.09 (d, J=8.9 Hz, 1H), 4.08-3.96 (m, 2H), 3.92 (d, J=8.9 Hz, 1H), 3.34-3.31 (m, 1H), 3.29 (s, 3H), 2.57-2.52 (m, 2H), 2.22-2.16 (m, 1H)

Example 13. (7R,14S)-1-(difluoromethoxy)-12-(6-(dimethylphosphoryl)pyridin-3-yl)-6-methyl-6,7-dihydro-7,14-methanobenzo[c]pyrimido[1',2':1,5]pyrazolo[4,3-f]azocin-5 (14H)-one

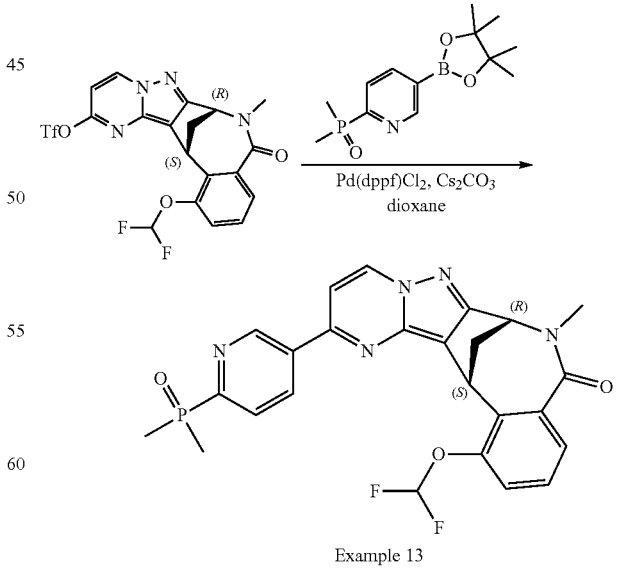

Example 13

The tile compound was prepared as described in Example 9 above by replacing Intermediate 47. LCMS (ESI, m/z):

510.05 [M+H]⁺. ¹HNMR (400 MHz, DMSO-d₆) δ 9.50 (d, J=2.2 Hz, 1H), 9.27 (d, J=7.4 Hz, 1H), 8.67-8.66 (m, 1H), 8.25 (dd, J=8.0, 1.6 Hz, 1H), 8.09 (dd, J=8.1, 5.1 Hz, 1H), 7.76-7.66 (m, 1H), 7.57-7.30 (m, 3H), 5.14 (d, J=6.8 Hz, 2H), 3.36-3.32 (m, 1H), 3.31 (s, 3H), 2.66-2.53 (m, 1H), 1.72 (d, J=13.5 Hz, 6H).

Example 14. 12-(2-(1-aminocyclobutyl)pyrimidin-5-yl)-1-(difluoromethoxy)-6-methyl-6,7-dihydro-7,14-methanobenzo[c]pyrido[1',2':1,5]pyrazolo[4,3-f]azocin-5 (14H)-one

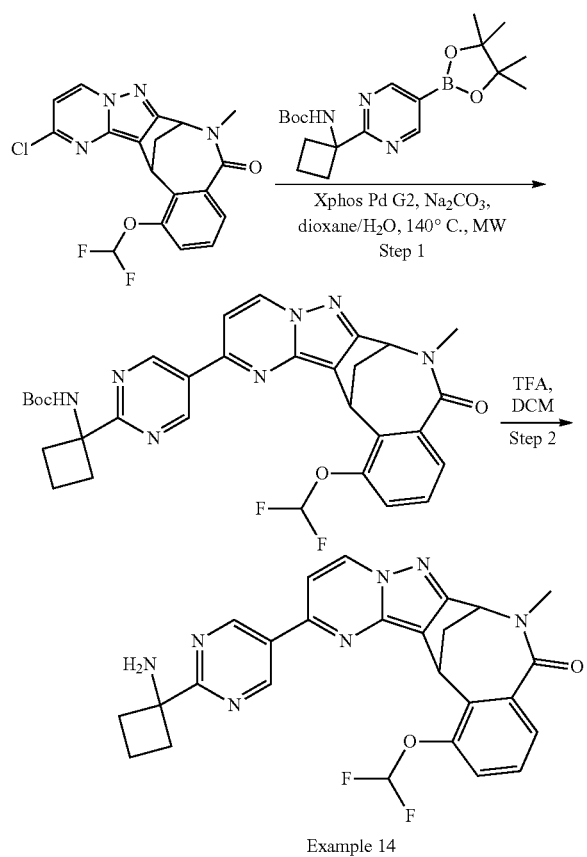

Example 14

Step 1: To a stirred solution of Intermediate 13 (18 mg, 0.046 mmol, 1 equiv) and dioxane (0.4 mL) in H₂O (0.1 mL) were added Na₂CO₃ (14.7 mg, 0.14 mmol, 3 equiv) and tert-butyl (1-(5-(4,4,5,5-tetramethyl-1,3,2-dioxaborolan-2-yl)pyrimidin-2-yl)cyclobutyl)carbamate (25.0 mg, 0.07 mmol, 1.5 equiv) at room temperature under nitrogen atmosphere. To the above mixture was added 2$^{nd}$ Generation XPhos Precatalyst/(3.6 mg, 0.005 mmol, 0.1 equiv) at room temperature. The final reac7tion mixture was irradiated with microwave radiation for 1 hr at 140° C. The resulting mixture was concentrated under vacuum. The residue was purified by Prep-TLC (DCM/MeOH=30:1) to afford tert-butyl (1-(5-(1-(difluoromethoxy)-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (20 mg, 71.9%) as an off-white solid. LCMS (ESI, m/z): 603.35 [M+H]⁺.

Step 2: A solution of tert-butyl (1-(5-(1-(difluoromethoxy)-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (15 mg, 0.025 mmol, 1 equiv) and TFA (1 mL) in DCM (5 mL) was stirred for 1 hr at room temperature. The reaction was quenched by the addition of sat. NaHCO₃ (aq.) (20 mL) at 0° C. The resulting mixture was extracted with DCM (3×20 mL). The combined organic layers were washed with brine (2×10 mL), dried over anhydrous Na₂SO₄. After filtration, the filtrate was concentrated under reduced pressure. The crude product (10 mg) was purified by Prep-HPLC to afford Example 14 (2.1 mg, 16.8%). LCMS (ESI, m/z): 503.10 [M+H]⁺. ¹H NMR (400 MHz, DMSO-d₆) δ 9.16 (s, 2H), 8.84 (d, J=7.3 Hz, 1H), 8.22 (d, J=7.9 Hz, 1H), 7.71 (s, 1H), 7.60 (s, 1H), 7.44-7.28 (m, 3H), 5.09 (d, J=6.9 Hz, 1H), 5.03 (d, J=6.5 Hz, 1H), 3.29 (s, 4H), 2.64 (s, 2H), 2.52 (d, J=14.4 Hz, 2H), 2.16 (s, 2H), 2.01 (s, 1H), 1.85 (s, 1H).

The following compounds were prepared according to similar procedures.

| Ex. | LCMS [M + H]⁺ | ¹H NMR (ppm) |
|---|---|---|
| 15 | 503.10 | ¹H NMR (400 MHz, DMSO-d₆) δ 9.16 (s, 2H), 8.84 (d, J = 7.3 Hz, 1H), 8.22 (d, J = 7.9 Hz, 1H), 7.71 (s, 1H), 7.60 (s, 1H), 7.44-7.28 (m, 3H), 5.09 (d, J = 6.9 Hz, 1H), 5.03 (d, J = 6.5 Hz, 1H), 3.29 (s, 4H), 2.64 (s, 2H), 2.52 (d, J = 14.4 Hz, 2H), 2.16 (s, 2H), 2.01 (s, 1H), 1.85 (s, 1H) |
| 16 | 535.20 | ¹H NMR (400 MHz, DMSO-d₆) δ 9.51 (s, 2H), 9.28 (d, J = 7.4 Hz, 1H), 8.28-8.21 (m, 1H), 7.76-7.71 (m, 1H), 7.56-7.32 (m, 3H), 5.74 (s, 1H), 5.17-5.09 (m, 2H), 4.98 (s, 1H), 3.31-3.36 (m, 4H), 2.96-2.86 (m, 2H), 2.55 (s, 1H), 2.46-2.39 (m, 2H), 1.08 (s, 3H) |
| 17 | 489.25 | ¹H NMR (400 MHz, DMSO-d₆) δ 9.05 (s, 2H), 8.82 (d, J = 7.4 Hz, 1H), 8.22 (dd, J = 8.0, 1.5 Hz, 1H), 7.68 (d, J = 2.0 Hz, 1H), 7.60 (d, J = 1.7 Hz, 1H), 7.44-7.25 (m, 3H), 5.09 (d, J = 6.9 Hz, 1H), 5.02 (d, J = 6.6 Hz, 1H), 3.29 (s, 3H), 2.54 (s, 1H), 1.40-1.34 (m, 2H), 1.14 (s, 2H) |
| 18 | 543.30 | ¹H NMR (400 MHz, DMSO-d₆) δ 9.20 (s, 2H), 8.85 (d, J = 7.5 Hz, 1H), 8.23 (dd, J = 8.0, 1.6 Hz, 1H), 7.78 (s, 1H), 7.73 (dd, J = 2.2, 1.0 Hz, 1H), 7.60 (d, J = 1.6 Hz, 1H), 7.41 (d, J = 5.6 Hz, 1H), 7.40-7.30 (m, 3H), 6.19 (s, 1H), 5.10 (d, J = 6.9 Hz, 1H), 5.03 (d, J = 6.6 Hz, 1H), 3.27 (s, 4H), 2.94-2.87 (m, 2H), 2.80-2.73 (m, 2H), 2.54 (s, 1H), 1.45 (s, 3H) |
| 19 | 492.20 | ¹H NMR (400 MHz, DMSO-d₆) δ 9.14 (s, 2H), 8.84 (dd, J = 7.6, 2.6 Hz, 1H), 8.22 (d, J = 8.0 Hz, 1H), 7.78 (s, 1H), 7.71 (d, J = 2.1 Hz, 1H), 7.44-7.28 (m, 3H), 5.16 (s, 1H), 5.09 (dd, J = 7.0, 2.3 Hz, 1H), 5.03 (d, J = 6.6 Hz, 1H), 3.36-3.23 (m, 4H), 1.54 (s, 6H) |
| 20 | 509.20 | ¹H NMR (400 MHz, DMSO-d₆) δ 9.10 (d, J = 2.3 Hz, 1H), 8.83 (d, J = 7.4 Hz, 1H), 8.29 (dt, J = 8.1, 2.7 Hz, 1H), 8.23 (dd, J = 8.0, 1.5 Hz, 1H), 8.06 (dd, J = 8.0, 5.0 Hz, 1H), 7.73 (d, J = 2.1 Hz, 1H), 7.60 (d, J = 1.3 Hz, 1H), 7.44-7.25 (m, 3H), 5.09 (d, J = 6.9Hz, 1H), 5.03 (d, J = 6.6 Hz, 1H), 3.29 (s, 4H), 2.54 (s, 1H), 1.71 (d, J = 13.5 Hz, 6H) |
| 21 | 527.25 | ¹H NMR (400 MHz, DMSO-d₆) δ 8.97 (q, J = 1.8 Hz, 1H), 8.85 (d, J = 7.4 Hz, 1H), 8.28-8.19 (m, 2H), 7.81-7.74 (m, |

| Ex. | LCMS [M + H]⁺ | ¹H NMR (ppm) |
|---|---|---|
|  |  | 1H), 7.60 (d, J = 1.8 Hz, 1H), 7.44-7.29 (m, 3H), 5.10 (d, J = 6.9 Hz, 1H), 5.03 (d, J = 6.6 Hz, 1H), 3.29 (s, 4H), 1.83 (dd, J = 13.8, 1.1 Hz, 6H) |
| 22 | 542.30 | ¹H NMR (400 MHz, DMSO-d₆) δ 9.17 (s, 2H), 8.85 (d, J = 7.4 Hz, 1H), 8.22 (d, J = 8.0 Hz, 1H), 7.71 (s, 1H), 7.58 (s, 1H), 7.40-7.30 (m, 3H), 5.09 (d, J = 6.9 Hz, 1H), 5.06 (s, 1H), 5.03 (d, J = 6.5 Hz, 1H), 3.32 (s, 3H), 2.81 (d, J = 11.3 Hz, 2H), 2.62 (d, J = 11.7 Hz, 2H), 2.54 (s, 1H), 1.46 (s, 3H). |
| 23 | 522.20 | ¹H NMR (400 MHz, DMSO-d₆) δ 9.73 (d, J = 6.8 Hz, 1H), 9.27 (d, J = 1.5 Hz, 2H), 8.28-8.20 (m, 1H), 7.72-7.24 (m, 3H), 5.20-5.16 (m, 2H), 3.37-3.33 (m, 1H), 3.29 (s, 3H), 2.81 (s, 2H), 2.69-2.58 (m, 2H), 2.20-2.09 (m, 2H), 2.08-1.96 (m, 1H), 1.90-1.76 (m, 1H) |
| 24 | 534.20 | ¹H NMR (400 MHz, DMSO-d₆) δ 9.17 (s, 2H), 8.84 (d, J = 7.4 Hz, 1H), 8.22 (dd, J = 7.9, 1.5 Hz, 1H), 7.73 (d, J = 2.0 Hz, 1H), 7.60 (d, J = 1.7 Hz, 1H), 7.44-7.29 (m, 3H), 5.67 (s, 1H), 5.09 (d, J = 6.8 Hz, 1H), 5.06-4.96 (m, 1H), 3.29 (s, 4H), 2.95-2.87 (m, 2H), 2.54 (s, 1H), 2.42 (d, J = 11.5 Hz, 2H), 1.09 (s, 3H) |
| 25 | 528.25 | ¹H NMR (400 MHz, DMSO-d₆) δ 9.72 (d, J = 6.9 Hz, 1H), 9.23 (d, J = 2.0 Hz, 1H), 8.48-8.42 (m, 1H), 8.24-8.23 (m, 1H), 8.14-8.12 (m, 1H), 7.63-7.24 (m, 3H), 5.14-5.11 (m, 2H), 3.34 (s, 1H), 3.29 (s, 3H), 2.54 (s, 1H), 1.75 (s, 3H), 1.71 (s, 3H) |
| 26 | 553.25 | ¹H NMR (400 MHz, DMSO-d₆) δ 9.73 (d, J = 6.8 Hz, 1H), 9.29 (d, J = 1.5 Hz, 2H), 8.26-8.23 (m, 1H), 7.69-7.05 (m, 3H), 5.77 (s, 1H), 5.16-5.11 (m, 2H), 4.99 (s, 1H), 3.35 (d, J = 7.0 Hz, 1H), 3.29 (s, 3H), 2.96-2.86 (m, 2H), 2.54 (s, 1H), 2.47-2.38 (m, 2H), 1.08 (s, 3H) |
| 27 | 552.25 | ¹H NMR (400 MHz, DMSO-d₆) δ 9.72 (d, J = 6.9 Hz, 1H), 9.26 (d, J = 1.5 Hz, 2H), 8.28-8.20 (m, 1H), 7.73-7.17 (m, 3H), 5.15-5.11 (m, 3H), 3.29 (s, 4H), 2.89-2.80 (m, 2H), 2.54 (d, J = 3.0 Hz, 1H), 2.26-2.18 (m, 2H), 1.16 (s, 3H) |
| 28 | 533.3 | ¹H NMR (400 MHz, DMSO-d₆) δ 9.16 (d, J = 0.8 Hz, 2H), 8.84 (dd, J = 7.5, 0.9 Hz, 1H), 8.22 (dd, J = 8.0, 1.6 Hz, 1H), 7.82-7.69 (m, 2H), 7.59 (d, J = 1.6 Hz, 1H), 7.49-7.23 (m, 4H), 5.09 (d, J = 6.9 Hz, 2H), 5.03 (d, J = 6.6 Hz, 1H), 3.29 (s, 4H), 2.89-2.81 (m, 2H), 2.54 (s, 1H), 2.27 (d, J = 12.2 Hz, 2H), 1.21 (d, J = 2.1 Hz, 3H) |
| 29 | 527.25 | ¹H NMR (400 MHz, DMSO-d₆) δ 9.24 (d, J = 6.2 Hz, 1H), 8.96 (s, 1H), 8.30-8.16 (m, 2H), 8.14-8.05 (m, 1H), 7.74-7.29 (m, 4H), 5.11 (d, J = 6.9 Hz, 1H), 5.02 (d, J = 6.5 Hz, 1H), 3.29 (s, 4H), 2.54 (s, 1H), 1.73 (d, J = 13.5 Hz, 6H) |
| 30 | 510.2 | ¹H NMR (400 MHz, DMSO-d₆) δ 9.65 (d, J = 1.5 Hz, 1H), 9.32 (d, J = 2.2 Hz, 1H), 8.52 (ddd, J = 8.1, 3.1, 2.2 Hz, 1H), 8.23 (dd, J = 8.1, 1.4 Hz, 1H), 8.09 (ddd, J = 8.1, 5.1, 0.9 Hz, 1H), 7.90 (d, J = 1.5 Hz, 1H), 7.79-7.42 (m, J = 73.6, 1H), 7.45-7.40 (m, 1H), 7.36 (t, J = 8.1 Hz, 1H), 5.15 (d, J = 6.9 Hz, 1H), 5.05 (d, J = 6.7 Hz, 1H), 3.30 (s, 3H), 3.25-3.30 (m, 1H), 2.56 (d, J = 13.5 Hz, 1H), 1.71 (d, J = 13.5 Hz, 6H) |
| 31 | 512.25 | ¹H NMR (400 MHz, DMSO-d₆) δ 9.10 (d, J = 2.3 Hz, 1H), 8.84 (d, J = 7.4 Hz, 1H), 8.30 (dt, J = 8.0, 2.7 Hz, 1H), 8.23 (dd, J = 7.9, 1.5 Hz, 1H), 8.06 (dd, J = 8.0, 5.1 Hz, 1H), 7.79-7.58 (m, 2H), 7.42-7.31 (m, 2H), 7.29 (dd, J = 7.4, 2.1 Hz, 1H), 5.09 (d, J = 7.0 Hz, 1H), 5.03 (d, J = 6.7Hz, 1H), 3.31-3.18 (m, 1H), 2.54 (s, 1H), 1.71 (d, J = 13.6 Hz, 6H) |
| 32 | 535.30 | ¹H NMR (400 MHz, DMSO-d₆) δ 8.57-8.51 (m, 1H), 8.21 (d, J = 8.0 Hz, 1H), 7.81-6.99 (m, 4H), 6.78-6.71 (m, 1H), 5.10-4.86 (m, 2H), 4.62-4.57 (m, 2H), 3.55 (s, 3H), 3.40 (d, J = 40.3 Hz, 1H), 2.48 (d, J = 23.6 Hz, 3H), 2.11-2.03 (m, 2H), 1.88-1.80 (m, 2H), 1.53-1.22 (m, 4H) |
| 33 | 537.35 | ¹H NMR (400 MHz, DMSO-d₆) δ 9.17 (s, 2H), 8.84 (dd, J = 7.4, 0.9 Hz, 1H), 8.22 (dd, J = 7.9, 1.5 Hz, 1H), 7.80-7.58 (m, 2H), 7.43-7.36 (m, 1H), 7.34 (ddd, J = 8.1, 5.4, 3.3 Hz, 2H), 5.66 (s, 1H), 5.09 (d, J = 6.9 Hz, 1H), 5.03 (d, J = 6.6 Hz, 1H), 4.97 (s, 1H), 3.32-3.25 (m, 1H), 2.94-2.86 (m, 2H), 2.54 (s, 1H), 2.46-2.37 (m, 2H), 1.09 (s, 3H) |
| 34 | 527.25 | ¹H NMR (400 MHz, DMSO-d₆) δ 9.11 (d, J = 2.2 Hz, 1H), 8.85 (d, J = 7.3 Hz, 1H), 8.34-8.25 (m, 2H), 8.06 (dd, J = 8.0, 5.1 Hz, 1H), 7.74-7.70 (m, 1H), 7.53 (s, 1H), 7.39-7.29 (m, 2H), 5.11 (d, J = 6.8 Hz, 1H), 5.04 (d, J = 6.7 Hz, 1H), 3.31 (d, J = 6.7 Hz, 1H), 3.27 (s, 3H), 2.54 (s, 1H), 1.71 (d, J = 13.6 Hz, 6H) |
| 35 | 527.20 | ¹H NMR (400 MHz, DMSO-d₆) δ 9.10 (d, J = 2.2 Hz, 1H), 8.83 (dd, J = 7.4, 0.9 Hz, 1H), 8.30 (dt, J = 8.0, 2.7 Hz, 1H), 8.06 (ddd, J = 8.0, 5.1, 0.9 Hz, 1H), 7.98 (dd, J = 11.7, 2.8 Hz, 1H), 7.84-7.62 (m, 2H), 7.48-7.37 (m, 1H), 7.30 (dd, J = 7.4, 2.1 Hz, 1H), 5.12 (d, J = 6.9 Hz, 1H), 4.98 (d, J = 6.6 Hz, 1H), 3.31 (s, 4H), 2.55 (s, 1H), 1.73 (s, 3H), 1.70 (s, 3H) |
| 36 | 551.35 | ¹H NMR (400 MHz, DMSO-d₆) δ 9.24 (d, J = 6.2 Hz, 1H), 9.01 (d, J = 1.7 Hz, 2H), 8.23-8.21 (m, 1H), 7.73-7.29 (m, 4H), 5.15-4.94 (m, 3H), 3.28 (s, 4H), 2.87-2.79 (m, 2H), 2.53 (s, 1H), 2.24-2.17 (m, 2H), 1.17 (s, 3H) |
| 37 | 524.35 | ¹H NMR (400 MHz, DMSO-d₆) δ 9.16 (s, 2H), 8.81 (dd, J = 7.4, 0.9 Hz, 1H), 7.97 (dd, J = 6.9, 5.6, 1.5 Hz, 1H), 7.65 (dd, J = 43.7, 2.1, 1.0 Hz, 1H), 7.48 (dd, J = 8.2, 1.3 Hz, 1H), 7.29 (dd, J = 7.4, 3.6, 2.1 Hz, 1H), 7.27-7.20 (m, 1H), 5.69 (s, 1H), 5.05 (d, J = 7.0 Hz, 1H), 5.01-4.95 (m, 2H), 4.19-4.09 (m, 1H), 3.28 (s 3H), 3.21-3.17 (m, 1H), 2.93 (d, J = 2.1 Hz, 1H), 2.91-2.86 (m, 1H), 2.47 (d, J = 13.2 Hz, 1H), 2.44-2.32 (m, 2H), 1.08 (s, 3H), 1.07-0.98 (m, 1H), 0.99-0.90 (m, 2H), 0.89-0.82 (m, 1H) |
| 38 | 520.25 | ¹H NMR (400 MHz, DMSO-d₆) δ 9.17 (s, 2H), 8.87 (d, J = 6.6 Hz, 1H), 8.80 (d, J = 7.3 Hz, 1H), 8.19 (dd, J = 8.0, 1.5 Hz, 1H), 7.95-7.57 (m, 2H), 7.50-7.08 (m, 3H), 5.66 (s, 1H), 5.08 (d, J = 6.6 Hz, 1H), 4.98 (s, 1H), 4.80 (t, J = 6.6 Hz, 1H), 3.30-3.22 (m, 1H), 2.98-2.85 (m, 2H), 2.48-2.36 (m, 3H), 1.09 (s, 3H) |
| 39 | 545.20 | ¹H NMR (400 MHz, DMSO-d₆) δ 9.27 (d, J = 6.2 Hz, 1H), 8.83 (s, 1H), 8.23 (d, J = 7.9 Hz, 1H), 8.16 (dd, J = 10.8, 4.0 Hz, 1H), 7.66-7.47 (m, 2H), 7.42-7.30 (m, 2H), 5.12 (d, J = 6.8 Hz, 1H), |

-continued

| Ex. | LCMS [M + H]⁺ | ¹H NMR (ppm) |
|---|---|---|
| 40 | 550.35 | 5.03 (d, J = 6.5 Hz, 1H), 3.29 (s, 4H), 2.61 (s, 1H), 1.85 (d, J = 13.7 Hz, 6H) ¹H NMR (400 MHz, DMSO-d₆) δ 8.81-8.79 (m, 1H), 8.71-8.70 (m, 1H), 8.24-8.21 (m, 1H), 8.04-8.00 (m, 1H), 7.82-7.58 (m, 2H), 7.44-7.31 (m, 2H), 7.29-7.26 (m, 1H), 5.16-4.95 (m, 3H), 3.27(s, 3H), 3.26-3.24(m, 1H), 2.87 (d, J = 11.4 Hz, 2H), 2.53-3.52 (m, 1H), 2.23 (d, J = 12.0 Hz, 2H), 1.00 (s, 3H) |
| 41 | 521.30 | ¹H NMR (400 MHz, DMSO-d₆) δ 9.24 (d, J = 6.2 Hz, 1H), 9.02 (d, J = 1.7 Hz, 2H), 8.22 (dd, J = 7.9, 1.6 Hz, 1H), 7.79-7.23 (m, 4H), 5.06 (dd, J = 34.5, 6.7 Hz, 2H), 3.32-3.27 (m, 4H), 2.75-2.58 (m, 2H), 2.52-2.50 (m, 1H), 2.49-2.43 (m, 1H) 2.14-2.07 (m, 2H), 2.06-1.93 (m, 1H), 1.90-1.73 (m, 1H) |
| 42 | 534.40 | ¹H NMR (400 MHz, DMSO-d₆) δ 9.17 (d, J = 1.5 Hz, 1H), 8.90 (d, J = 1.5 Hz, 1H), 8.80 (d, J = 7.4 Hz, 1H), 8.23 (dd, J = 8.1, 1.4 Hz, 1H), 8.16 (d, J = 1.7 Hz, 1H), 7.84-7.31 (m, 4H), 5.94 (s, 1H), 5.07 (dd, J = 18.2, 6.7 Hz, 2H), 4.99 (s, 1H), 3.29 (s, 4H), 2.89-2.74 (m, 2H), 2.54 (s, 1H), 1.21 (s, 3H) |
| 43 | 552.35 | ¹H NMR (400 MHz, DMSO-d₆) δ 9.22 (d, J = 6.6 Hz, 1H), 9.02-8.84 (m, 2H), 8.22 (dd, J = 8.1, 1.5 Hz, 1H), 7.99 (d, J = 7.6 Hz, 1H), 7.72-7.25 (m, 3H), 5.99 (s, 1H), 5.17-5.03 (m, 2H), 5.00 (s, 1H), 3.28 (s, 4H), 2.88-2.73 (m, 2H), 2.53 (s, 1H), 2.46-2.40 (m, 2H), 1.22 (s, 3H) |
| 44 | 532.10 | ¹H NMR (400 MHz, DMSO-d₆) δ 9.66 (d, J = 1.4 Hz, 1H), 9.23-9.16 (m, 1H), 8.35-8.31 (m, 1H), 8.28-8.16 (m, 1H), 7.95 (d, J = 1.5 Hz, 1H), 7.60 (d, J = 1.6 Hz, 1H), 7.46-7.32 (m, 2H), 5.16 (d, J = 6.9 Hz, 1H), 5.06 (d, J = 6.8 Hz, 1H), 3.30 (s, 3H), 2.57 (d, J = 13.6 Hz, 1H), 1.88-1.79 (m, J = 13.7, 1.1 Hz, 6H) |
| 45 | 544.30 | ¹H NMR (400 MHz, DMSO-d₆) δ 9.67 (s, 1H), 9.40 (s, 2H), 8.23 (d, J = 8.0 Hz, 1H), 7.92 (s, 1H), 7.60 (s, 1H), 7.46-7.36 (m, 2H), 6.16 (s, 1H), 5.16 (d, J = 6.9 Hz, 1H), 5.06 (d, J = 6.7 Hz, 1H), 3.42 (s, 4H), 2.41 (d, J = 12.5 Hz, 5H), 1.68 (s, 3H) |
| 46 | 534.35 | ¹H NMR (400 MHz, DMSO-d₆) δ 9.69-9.61 (m, 1H), 9.36-9.30 (m, 2H), 8.25-8.21 (m, 1H), 7.89-7.86 (m, 1H), 7.79-7.15(m, 1H), 7.43-7.35(m, 2H), 5.17-5.13 (m, 1H), 5.07-5.03 (m, 1H), 3.32-3.28 (m, 4H), 2.89-2.80 (m, 2H), 2.57-2.55 (m, 1H), 2.27-2.20 (m, 2H), 1.17 (s, 3H) |
| 47 | 551.35 | ¹H NMR (400 MHz, DMSO-d₆) δ 9.67-9.57 (m, 1H), 8.96-8.90 (m, 1H), 8.27-8.20 (m, 1H), 8.19-8.08 (m, 1H), 7.87-7.78 (m, 1H), 7.70-7.39 (m, 3H), 5.21-5.09 (m, 1H), 5.07-4.98 (m, 2H), 3.35-3.23 (m, 4H), 2.93-2.85 (m, 2H), 2.56-2.50 (m, 1 H), 2.28-2.14 (m, 2H), 0.99 (s, 3H) |
| 48 | 504.30 | ¹H NMR (400 MHz, DMSO-d₆) δ 9.67-9.63 (m, 1H), 9.33 (s, 2H), 8.25-8.21 (m, 1H), 7.88-7.86 (m, 1H), 7.63-7.48 (m, 1H), 7.46-7.40 (m, 1H), 7.38-7.32 (m, 1H), 5.19-5.16 (m, 1H), 5.09-5.01 (m, 1H), 3.33-3.27 (m, 4H), 2.68-2.52 (m, 2H), 2.47-2.45 (m, 1H), 2.18-2.10 (m, 2H), 2.05-1.95 (m, 1H), 1.84-1.80 (m, 1H) |
| 49 | 505.17 | ¹H NMR (400 MHz, DMSO-d₆) δ 9.22 (s, 2H), 8.86 (d, J = 7.3 Hz, 1H), 8.26-8.19 (m, 1H), 7.81-7.53 (m, 2H), 7.43-7.37 (m, 1H), 7.37-7.30 (m, 2H), 5.13-5.02 (m, 2H), 4.99 (d, J = 5.7 Hz, 2H), 4.64 (d, J = 5.7 Hz, 2H), 3.29 (s, 4H), 2.82 (s, 2H), 2.55 (s, 1H) |
| 50 | 569.20 | ¹H NMR (400 MHz, DMSO-d₆) δ 9.71 (d, J = 7.0 Hz, 1H), 8.88 (q, J = 1.7 Hz, 1H), 8.26-8.22 (m, 1H), 8.13-8.09 (m, 1H), 7.68-7.28 (m, 3H), 5.15-8.11 (m, 2H), 5.02 (s, 1H), 3.32 (d, J = 13.4 Hz, 1H), 3.29 (s, 3H), 2.90-2.86 (m, 2H), 2.54 (s, 1H), 2.25 (d, J = 12.0 Hz, 2H), 1.00 (s, 3H) |
| 51 | 561.25 | ¹H NMR (400 MHz, DMSO-d₆) δ 9.74 (d, J = 6.9 Hz, 1H), 9.29 (d, J = 1.6 Hz, 2H), 8.24 (dd, J = 7.7, 1.8 Hz, 1H), 7.59-7.24 (m, 3H), 5.13 (dd, J = 13.0, 6.8 Hz, 2H), 3.31-3.28(m, 6H), 2.82-2.80 (m, 2H), 2.65 (s, 1H), 1.48 (s, 3H), 1.24 (s, 3H) |
| 52 | 507.20 | ¹H NMR (400 MHz, DMSO-d₆) δ 9.49 (s, 2H), 9.28 (d, J = 7.4 Hz, 1H), 8.25 (dd, J = 7.9, 1.7 Hz, 1H), 7.81-7.26 (m, 4H), 5.13 (dd, J = 6.8, 1.8 Hz, 2H), 3.35 (s, 1H), 3.33 (s, 1H), 2.67-2.59 (m, 4H), 2.18-2.08 (m, 2H), 2.06-1.95 (m, 1H), 1.87-1.70 (m, 1H) |
| 53 | 554.25 | ¹H NMR (400 MHz, DMSO-d₆) δ 9.17 (d, J = 6.2 Hz, 1H), 8.87 (d, J = 6.5 Hz, 1H), 8.55 (s, 1H), 8.19 (dd, J = 8.0, 1.5 Hz, 1H), 7.92 (m, 1H), 7.80-7.23 (m, 4H), 5.06 (d, J = 6.6 Hz, 1H), 5.02 (s, 1H), 4.80 (t, J = 6.6 Hz, 1H), 3.25 (m, 1H), 2.96-2.81 (m, 2H), 2.43 (d, J = 13.0 Hz, 1H), 2.34-2.19 (m,4H), 1.01 (s, 3H) |
| 54 | 462.30 | ¹H NMR (400 MHz, DMSO-d₆) δ 9.14 (s, 2H), 8.87 (dd, J = 7.4, 1.0 Hz, 1H), 8.65 (dd, J = 8.3, 1.5 Hz, 1H), 8.02 (dd, J = 7.6, 1.5 Hz, 1H), 7.86 (dd, J = 2.1, 1.0 Hz, 1H), 7.50 (t, J = 7.9 Hz, 1H), 7.34 (dd, J = 7.4, 2.1 Hz, 1H), 5.16 (d, J = 6.9 Hz, 1H), 5.02 (d, J = 6.4 Hz, 1H), 3.39 (dd, J = 13.7, 6.9 Hz, 1H), 3.32 (s, 3H), 2.75-2.58 (m, 3H), 2.19-2.06 (m, 2H), 2.04-1.90 (m, 1H), 1.88-1.76 (m, 1H) |
| 55 | 545.25 | ¹H NMR (400 MHz, DMSO-d₆) δ 9.16 (s, 2H), 8.84 (dd, J = 7.4, 0.9 Hz, 1H), 8.22 (dd, J = 8.0, 1.5 Hz, 1H), 7.80-7.27 (m, 5H), 5.05 (dd, J = 24.1, 6.8 Hz, 2H), 3.30 (d, J = 6.8 Hz, 1H), 2.85-2.76 (m, 2H), 2.64-2.58 (m, 2H), 2.54 (s, 1H), 1.46 (s, 3H) |
| 56 | 546.25 | ¹H NMR (400 MHz, DMSO-d₆) ¹H NMR (400 MHz, DMSO-d₆) δ 9.50 (s, 2H), 9.28 (d, J = 7.4 Hz, 1H), 8.32 (s, 2H), 8.24 (dd, J = 7.9, 1.7 Hz, 1H), 7.80-7.27 (m, 5H), 5.12 (d, J = 6.7 Hz, 2H), 3.63 (s, 2H), 3.32 (dt, J = 13.7, 7.0 Hz, 1H), 2.81 (d, J = 11.8 Hz, 2H), 2.73-2.60 (m, 2H), 2.54 (s, 1H), 1.46 (s, 3H) |
| 57 | 555.20 | ¹H NMR (400 MHz, DMSO-d₆) δ 9.73 (d, J = 6.8 Hz, 1H), 9.27 (s, 2H), 8.24 (d, J = 8.1 Hz, 1H), 7.68-7.22 (m, 3H), 5.13 (dd, J = 9.4, 6.8 Hz, 2H), 3.22 (s, 1H), 2.85 (d, J = 12.2 Hz, 2H), 2.54 (s, 1H), 2.26 (d, J = 12.2 Hz, 2H), 1.18 (s, 3H) |
| 58 | 563.10 | ¹H NMR (400 MHz, DMSO-d₆) δ 9.15 (d, J = 6.2 Hz, 1H), 8.86 (d, J = 6.6 Hz, 1H), 8.65-8.48 (m, 1H), 8.19 (dd, J = 7.9, 1.5 Hz, 1H), 7.95 (m, 1H), 7.77-7.27 (m, 4H), 5.06 (d, J = 6.6 Hz, 1H), 4.80 |

| Ex. | LCMS [M + H]⁺ | ¹H NMR (ppm) |
|---|---|---|
|  |  | (t, J = 6.5 Hz, 1H), 3.30-3.06 (m, 1H), 2.82 (m, 2H), 2.63 (d, J = 12.5 Hz, 2H), 2.42 (d, J = 13.0 Hz, 1H), 1.36 (s, 3H) |
| 59 | 560.35 | ¹H NMR (400 MHz, DMSO-d₆) δ 9.63 (s, 1H), 8.96 (s, 1H), 8.29-8.14 (m, 2H), 7.89-7.57 (m, 2H), 7.50-7.28 (m, 2H), 5.15 (d, J = 6.9 Hz, 1H), 5.04 (d, J = 6.6 Hz, 1H), 3.30 (s, 3H), 2.87 (d, J = 12.2 Hz, 2H), 2.72 (d, J = 12.3 Hz, 2H), 2.56 (d, J = 15.7 Hz, 2H), 1.34 (s, 3H) |
| 60 | 529.25 | ¹H NMR (400 MHz, DMSO-d₆) δ 9.50 (s, 2H), 9.25 (d, J = 7.5 Hz, 1H), 8.91 (d, J = 6.4 Hz, 1H), 8.25-8.21 (m, 1H), 7.81-7.28 (m, 4H), 5.19 (d, J = 6.7 Hz, 1H), 4.81 (t, J = 6.5 Hz, 1H), 3.86 (brs, 2H), 3.30-3.26 (m, 1H), 2.85-2.76 (m, 2H), 2.67-2.59 (m, 2H), 2.44 (d, J = 13.0 Hz, 1H), 1.46 (s, 3H) |
| 61 | 546.15 | ¹H NMR (400 MHz, DMSO-d₆) δ 9.68-9.64 (m, 1H), 9.36-9.32 (m, 2H), 8.25-8.21 (dd, 1H), 7.89-7.87 (d, 1H), 7.80-7.45 (m, 1H), 7.44-7.40 (m, 1H), 7.38-7.34 (m, 1H), 5.17-5.13 (m, 1H), 5.07-5.03 (m, 1H), 3.34-3.24 (m, 1H), 2.85-2.77 (m, 2H), 2.65-2.57 (m, 2H), 2.57-2.55 (m, 1H), 1.45 (s, 3H) |
| 62 | 537.10 | ¹H NMR (400 MHz, DMSO-d₆) δ 9.66 (d, J = 1.5 Hz, 1H), 9.35 (s, 2H), 8.23 (dd, J = 8.1, 1.4 Hz, 1H), 7.89 (d, J = 1.6 Hz, 1H), 7.80-7.43 (m, 1H), 7.42 (s, 1H), 7.36 (t, J = 8.1 Hz, 1H), 5.15 (d, J = 6.9 Hz, 1H), 5.05 (d, J = 6.7Hz, 1H), 3.30 (dt, J = 13.7, 6.9 Hz, 1H), 2.85 (d, J = 12.2 Hz, 2H), 2.56 (d, J = 13.5 Hz, 1H), 2.29 (d, J = 13.5 Hz, 2H), 1.32-1.14 (m, 3H) |
| 63 | 520.15 | ¹H NMR (400 MHz, DMSO-d₆) δ 9.17 (s, 2H), 8.85 (d, J = 7.4 Hz, 1H), 8.23 (dd, J = 8.0, 1.5 Hz, 1H), 7.73 (d, J = 2.0 Hz, 1H), 7.60 (d, J = 1.8 Hz, 1H), 7.43-7.29 (m, 3H), 5.66 (s, 1H), 5.10 (d, J = 6.9 Hz, 1H), 5.03 (d, J = 6.6 Hz, 1H), 4.09 (d, J = 8.9 Hz, 1H), 4.01 (dtd, J = 11.7, 8.0, 2.9 Hz, 2H), 3.91 (d, J = 8.9 Hz, 1H), 3.29 (s, 4H), 2.55 (d, J = 7.0 Hz, 2H), 2.19 (ddd, J = 12.7, 6.2, 3.6 Hz, 1H) |
| 64 | 520.10 | ¹H NMR (400 MHz, DMSO-d₆) δ 9.17 (d, J = 6.1 Hz, 2H), 8.85 (t, J = 6.6 Hz, 1H), 8.26-8.18 (m, 1H), 7.80-7.69 (m, 1H), 7.62-7.56 (m, 1H), 7.43-7.35 (m, 1H), 7.38-7.28 (m, 2H), 5.67 (s, 1H), 5.10 (d, J = 6.8 Hz, 1H), 5.03 (d, J = 6.6 Hz, 1H), 4.12-3.94 (m, 3H), 3.91 (dd, J = 9.3, 4.8 Hz, 1H), 3.34-3.26 (m, 4H), 2.61-2.52 (m, 2H), 2.49 (s, 1H), 2.19 (ddd, J = 12.6, 6.4, 3.7 Hz, 1H) |
| 65 | 534.20 | ¹H NMR (400 MHz, DMSO-d₆) δ 9.10 (s, 2H), 8.28 (dd, J = 6.0, 3.4 Hz, 1H), 7.84-7.74 (m, 2H), 7.73-7.61 (m, 2H), 7.58-7.46 (m, 2H), 6.32 (d, J = 7.1 Hz, 1H), 5.26 (d, J = 7.1 Hz, 1H), 3.80 (td, J = 11.1, 2.4 Hz, 2H), 3.70 (dt, J = 11.1, 4.1 Hz, 2H), 3.53 (dt, J = 14.1, 7.3 Hz, 1H), 3.37 (s, 3H), 2.85 (d, J = 13.8 Hz, 1H), 2.22 (ddd, J = 13.1, 10.9, 4.7 Hz, 2H), 1.80-1.71 (m, 2H) |
| 66 | 540.25 | ¹H NMR (400 MHz, DMSO-d₆) δ 9.21 (s, 2H), 8.86 (d, J = 7.4 Hz, 1H), 8.22 (dd, J = 8.0, 1.6 Hz, 1H), 7.80-7.71 (m, 2H), 7.59 (d, J = 1.8 Hz, 1H), 7.39 (dd, J = 14.5, 6.7 Hz, 1H), 7.33 (td, J = 5.5, 2.9 Hz, 1H), 6.35 (s, 1H), 5.10 (d, J = 6.9 Hz, 2H), 5.03 (d, J = 6.6 Hz, 2H), 3.38 (dt, J = 15.2, 12.7 Hz, 3H), 3.29 (s, 3H), 2.95-2.81 (m, 2H), 2.54 (s, 1H) |
| 67 | 540.20 | ¹H NMR (400 MHz, DMSO-d₆) δ 9.00 (s, 2H), 8.81 (dd, J = 7.4, 0.9 Hz, 1H), 8.22 (dd, J = 8.0, 1.5 Hz, 1H), 7.78-7.30 (m, 4H), 7.24 (d, J = 1.8 Hz, 1H), 5.08 (d, J = 6.9 Hz, 1H), 5.01 (d, J = 6.6 Hz, 1H), 4.72 (d, J = 5.2 Hz, 2H), 3.29 (s, 4H), 2.53 (s, 1H), 1.56 (d, J = 13.5 Hz, 3H), 1.52 (d, J = 13.5 Hz, 3H) |
| 68 | 536.25 | ¹H NMR (400 MHz, DMSO-d₆) δ 9.07 (s, 1H), 8.85 (d, J = 7.3 Hz, 1H), 8.38 (d, J = 8.0 Hz, 1H), 8.23 (d, J = 8.0 Hz, 1H), 8.13 (d, J = 8.3 Hz, 1H), 7.76 (d, J = 12.6 Hz, 1H), 7.39 (d, J = 9.4 Hz, 1H), 7.33 (dd, J = 16.0, 7.8 Hz, 3H), 5.10 (d, J = 6.8 Hz, 1H), 5.04 (d, J = 6.8 Hz, 1H), 4.45 (s, 1H), 3.29 (s, 3H), 2.92 (s, 1H), 2.32 (s, 1H), 1.24 (s, 0H), 1.16 (s, 1H), 0.99 (d, J = 7.2 Hz, 4H) |
| 69 | 526.10 | ¹H NMR (400 MHz, DMSO-d₆) δ 8.80 (d, J = 7.4 Hz, 1H), 8.29-8.21 (m, 1H), 7.85-7.91 (m, 1H), 7.79-7.64 (m, 3H), 7.61 (s, 0H), 7.45-7.30 (m, 2H), 7.22-7.27 (m, 1H), 5.09 (d, J = 6.9 Hz, 1H), 5.02 (d, J = 6.6 Hz, 1H), 3.29 (s, 3H), 2.54 (s, 1H), 1.75 (d, J = 13.6 Hz, 5H) |
| 70 | 539.20 | ¹H NMR (400 MHz, DMSO-d₆) δ 8.79 (d, J = 7.4 Hz, 1H), 8.30 (d, J = 5.4 Hz, 1H), 8.22 (dd, J = 8.0, 1.5 Hz, 1H), 7.83-7.62 (m, 1H), 7.42-7.26 (m, 5H), 5.09 (d, J = 6.9 Hz, 2H), 5.02 (d, J = 6.6 Hz, 2H), 4.64 (d, J = 5.2 Hz, 4H), 3.29 (d, J = 13.4 Hz, 1H), 3.29 (s, 3H), 2.54 (s, 1H), 1.51 (d, J = 13.3 Hz, 6H) |
| 71 | 504.10 | ¹H NMR (400 MHz, DMSO-d₆) δ 9.17 (s, 2H), 8.82-8.87 (m, 1H), 8.20-8.17 (m, 1H), 7.70-7.67 (m, 1H), 7.60 (d, J = 1.7 Hz, 1H), 7.44-7.29 (m, 3H), 5.65 (s, 1H), 5.09 (d, J = 6.9 Hz, 1H), 5.03 (d, J = 6.6 Hz, 1H), 3.35 (s, 3H), 2.72-2.61 (m, 1H), 2.54 (s, 1H), 2.34-2.24 (m, 2H), 1.93-1.89 (m, J = 9.7, 4.9 Hz, 1H), 1.83-1.67 (m, 1H) |
| 72 | 568.30 | ¹H NMR (400 MHz, DMSO-d₆) δ 9.18 (s, 2H), 8.86-8.84 (m, 1H), 8.23-8.21 (m, 1H), 7.81-7.58 (m, 2H), 7.43-7.30 (m, 3H), 5.45 (s, 1H), 5.10-5.02 (m, 2H), 3.29 (s, 4H), 2.55 (d, J = 3.1 Hz, 1H), 2.29-2.11 (m, 4H), 2.01-1.95 (m, 4H) |
| 73 | 528.30 | ¹H NMR (400 MHz, DMSO-d₆) δ 9.22 (s, 2H), 8.87-8.86 (m, 1H), 8.24-8.21 (m, 1H), 7.79-7.57 (m, 2H), 7.43-7.31 (m, 3H), 6.66-6.08 (m, 1H), 6.08 (s, 1H), 5.10 (d, J = 6.9 Hz, 1H), 5.03 (d, J = 6.6 Hz, 1H), 3.29 (s, 4H), 2.54 (s, 1H), 1.60 (s, 3H) |
| 74 | 528.25 | ¹H NMR (400 MHz, DMSO-d₆) δ 9.22 (s, 2H), 8.86-8.85 (m, 1H), 8.22-8.21 (m, 1H), 7.80-7.58 (m, 2H), 7.43-7.30 (m, 3H), 6.41-6.27 (m, 1H), 6.06 (s, 1H), 5.10 (d, J = 6.9 Hz, 1H), 5.03 (d, J = 6.6 Hz, 1H), 3.31 (s, 4H), 2.54 (s, 1H), 1.60 (s, 3H) |
| 75 | 517.25 | ¹H NMR (400 MHz, DMSO-d₆) δ 9.21 (s, 2H), 8.89-8.83 (m, 1H), 8.24-8.20 (m, 1H), 7.80-7.56 (m, 2H), 7.43-7.29 (m, 3H), 6.00 (s, 1H), 5.12-5.10 (m, 1H), 5.03-5.01 (m, 1H), 3.35-3.25 (m, 4H), 3.19-3.15 (m, 2H), 2.55-2.48 (m, 1H), 1.66-1.62 (m, 3H) |
| 76 | 517.35 | ¹H NMR (400 MHz, DMSO-d₆) δ 9.22 (s, 2H), 8.86 (d, J = 7.3 Hz, 1H), 8.23 (dd, J = 7.9, 1.6 Hz, 1H), 7.70 (d, J = 1.8 Hz, 2H), 7.44-7.30 (m, 3H), 6.01 (s, |

| Ex. | LCMS [M + H]+ | 1H NMR (ppm) |
|---|---|---|
| | | 1H), 5.10 (d, J = 6.9 Hz, 1H), 5.03 (d, J = 6.5 Hz, 1H), 3.26 (s, 4H), 3.19 (s, 2H), 2.55 (s, 1H), 1.64 (s, 3H) |
| 77 | 506.25 | 1H NMR (400 MHz, DMSO-d6) δ 9.23 (s, 2H), 8.86 (dd, J = 7.4, 1.0 Hz, 1H), 8.22 (dd, J = 8.0, 1.5 Hz, 1H), 7.407-7.781 (m, J = 74.8, 1H), 7.74 (dd, J = 2.2, 1.0 Hz, 1H), 7.39 (d, J = 7.9 Hz, 1H), 7.36-7.31 (m, 2H), 6.43 (s, 1H), 5.09-5.11 (m, J = 6.9 Hz, 1H), 5.03-5.04 (d, J-6.9, 1H), 5.02-5.04 (d, J = 6.4, 2H), 4.72-4.74(d, J = 6.4, 2H), 3.29 (s, 3H), 3.26-3.31 (m, J = 6.4, 1H), 2.54 (d, J = 6.4, 1H) |
| 78 | 553.30 | 1H NMR (400 MHz, DMSO-d6) δ 9.31 (s, 2H), 8.92-8.82 (m, 1H), 8.27-8.18 (m, 1H), 7.78 (d, J = 1.8 Hz, 1H), 7.63-7.30 (m, 4H), 7.00 (s, 1H), 6.46 (s, 1H), 5.15-5.01 (m, 2H), 3.47 (s, 1H), 3.32-3.21 (m, 5H), 2.55 (s, 1H) |
| 79 | 553.30 | 1H NMR (400 MHz, DMSO-d6) δ 9.31 (s, 2H), 8.92-8.82 (m, 1H), 8.27-8.18 (m, 1H), 7.78 (d, J = 1.8 Hz, 1H), 7.63-7.30 (m, 4H), 7.00 (s, 1H), 6.46 (s, 1H), 5.15-5.01 (m, 2H), 3.47 (s, 1H), 3.32-3.21 (m, 5H), 2.55 (s, 1H) |
| 80 | 518.15 | 1H NMR (400 MHz, DMSO-d6) δ 9.02 (s, 2H), 8.79-8.75 (m, 1H), 8.54-8.50 (m, 1H), 8.26-8.22 (m, 1H), 7.77-7.73 (m, 1H), 7.73-7.30 (m, 3H), 5.15 (s, 1H), 5.10-5.06 (m, 2H), 3.33-2.99 (m, 4H), 2.56-2.52 (m, 1H), 1.53 (s, 3H), 1.30-1.26 (m, 1H), 0.61-0.50 (m, 1H), 0.48-0.36 (m, 2H), 0.35-0.23 (m, 1H) |
| 81 | 518.20 | 1H NMR (400 MHz, DMSO-d6) δ 9.02 (s, 2H), 8.79-8.75 (m, 1H), 8.54-8.50 (m, 1H), 8.26-8.22 (m, 1H), 7.77-7.73 (m, 1H), 7.73-7.30 (m, 3H), 5.15 (s, 1H), 5.10-5.06 (m, 2H), 3.33-2.99 (m, 4H), 2.56-2.52 (m, 1H), 1.53 (s, 3H), 1.30-1.26 (m, 1H), 0.61-0.50 (m, 1H), 0.48-0.35 (m, 2H), 0.35-0.23 (m, 1H) |
| 82 | 520.25 | 1H NMR (400 MHz, DMSO-d6) δ 9.16 (s, 2H), 8.84 (dd, J = 7.4, 0.9 Hz, 1H), 8.22 (dd, J = 8.0, 1.6 Hz, 1H), 7.72 (dd, J = 2.1, 0.9 Hz, 1H), 7.59 (d, J = 1.7 Hz, 1H), 7.45-7.32 (m, 3H), 5.65 (s, 1H), 5.10 (t, J = 6.9Hz, 2H), 5.03 (d, J = 6.7 Hz, 1H), 4.09 (h, J = 7.2 Hz, 1H), 3.29 (s, 3H), 3.29-3.22 (m, 2H), 2.89 (ddd, J = 9.6, 7.1, 2.9 Hz, 2H), 2.27 (ddd, J = 9.7, 7.4, 2.9 Hz, 3H) |
| 83 | 508.20 | 1H NMR (400 MHz, DMSO-d6) δ 9.16 (s, 2H), 8.85 (dd, J = 7.4, 0.9 Hz, 1H), 8.23 (dd, J = 8.0, 1.5 Hz, 1H), 7.82-7.68 (m, 1H), 7.63-7.20 (m, 4H), 5.10 (d, J = 6.9 Hz, 1H), 5.03 (d, J = 3.2 Hz, 2H), 4.65 (t, J = 6.1 Hz, 1H), 3.77-3.62 (m, 2H), 3.29 (s, 4H), 2.54 (s, 1H), 1.48 (s, 3H) |
| 84 | 508.25 | 1H NMR (400 MHz, DMSO-d6) δ 9.16 (s, 2H), 8.85 (dd, J = 7.4, 0.9 Hz, 1H), 8.23 (dd, J = 8.0, 1.5 Hz, 1H), 7.82-7.68 (m, 1H), 7.63-7.20 (m, 4H), 5.10 (d, J = 6.9 Hz, 1H), 5.03 (d, J = 3.2 Hz, 2H), 4.65 (t, J = 6.1 Hz, 1H), 3.77-3.62 (m, 2H), 3.29 (s, 4H), 2.54 (s, 1H), 1.48 (s, 3H) |
| 85 | 534.10 | 1H NMR (400 MHz, DMSO-d6) δ 8.98 (s, 2H), 8.76 (dd, J = 7.4, 0.9 Hz, 1H), 8.51 (dd, J = 1.9, 0.9 Hz, 1H), 8.24 (dd, J = 8.1, 1.4 Hz, 1H), 7.77-7.68 (m, 1H), 7.52 (s, 1H), 7.45-7.39 (m, 1H), 7.34 (t, J = 8.1 Hz, 1H), 5.79 (s, 1H), 5.07 (dd, J = 15.8, 6.8 Hz, 2H), 4.70 (t, J = 6.2 Hz, 1H), 4.58 (dd, J = 8.4, 5.8 Hz, 1H), 4.44 (t, J = 6.4 Hz, 1H), 4.33 (dd, J = 8.4, 5.8 Hz, 1H), 3.53 (ddd, J = 15.1, 8.4, 6.8 Hz, 1H), 3.29 (s, 4H), 2.53 (s, 1H), 1.45 (s, 3H) |
| 86 | 534.15 | 1H NMR (400 MHz, DMSO-d6) δ 8.98 (s, 2H), 8. 77 (dd, J = 7.5, 0.9 Hz, 1H), 8.51 (dd, J = 2.0, 0.9 Hz, 1H), 8.23 (dd, J = 8.2, 1.4 Hz, 1H), 7.77-7.68 (m, 1H), 7.52 (s, 1H), 7.42 (dd, J = 8.1, 1.3 Hz, 1H), 7.38-7.29 (m, 1H), 5.79 (s, 1H), 5.07 (dd, J = 15.9, 6.8 Hz, 2H), 4.70 (t, J = 6.3 Hz, 1H), 4.58 (dd, J = 8.4, 5.8 Hz, 1H), 4.44 (dd, J = 6.9, 5.8 Hz, 1H), 4.33 (dd, J = 8.4, 5.8 Hz, 1H), 3.53 (ddd, J = 15.2, 8.3, 6.8 Hz, 1H), 3.29 (s, 3H), 2.53 (s, 1H), 1.45 (s, 3H) |
| 87 | 510.30 | 1H NMR (400 MHz, DMSO-d6) δ 9.41 (t, J = 1.3 Hz, 1H), 9.14 (t, J = 1.4 Hz, 1H), 8.86 (dd, J = 7.4, 0.9 Hz, 1H), 8.27-8.20 (m, 2H), 7.66-7.56 (m, 1H), 7.44-7.38 (m,2H), 7.34 (t, J = 8.1 Hz, 1H), 5.11 (d, J = 6.9 Hz, 1H), 5.06 (d, J = 6.6 Hz, 1H), 3.29 (s, 3H), 2.55 (s, 2H), 1.78 (d, J = 13.7 Hz, 6H) |
| 88 | 561.15 | 1H NMR (400 MHz, DMSO-d6) δ 9.23 (s, 4H), 8.86 (d, J = 8.0 Hz, 1H), 8.23-8.21 (m, J = 1H), 7.81-7.41 (m, 1H), 7.39-7.32 (m, 3H), 5.09 (d, J = 8.0 Hz, 1H), 5.03 (d, J = 8.0 Hz, 1H), 3.46-3.32 (m, 4H), 2.69-2.66 (m, 2H), 2.54-2.50 (m, 2H), 2.48 (s, 2H), 1.29 (s, 3H) |
| 89 | 520.35 | 1H NMR (400 MHz, DMSO-d6) δ 9.21 (s, 2H), 8.86 (dd, J = 7.4, 0.9 Hz, 1H), 8.22 (dd, J = 7.9, 1.5 Hz, 1H), 7.79-7.56 (m, 2H), 7.44-7.30 (m, 3H), 6.00 (s, 1H), 5.06 (dd, J = 23.1, 6.8 Hz, 2H), 3.31-3.26 (m, 1H), 3.18 (s, 2H), 2.54 (s, 1H), 1.64 (s, 3H) |
| 90 | 520.30 | 1H NMR (400 MHz, DMSO-d6) δ 9.21 (s, 2H), 8.86 (dd, J = 7.3, 0.9 Hz, 1H), 8.22 (dd, J = 8.0, 1.6 Hz, 1H), 7.82-7.55 (m, 2H), 7.45-7.26 (m, 3H), 6.00 (s, 1H), 5.06 (dd, J = 23.5, 6.8 Hz, 2H), 3.30-3.26 (m, 1H), 3.18 (s, 2H), 2.54 (s, 1H), 1.64 (s, 3H) |
| 91 | 570.25 | 1H NMR (400 MHz, DMSO-d6) δ 9.16 (s, 2H), 8.87-8.81 (m, 1H), 8.22 (dd, J = 8.0, 1.5 Hz, 1H), 7.81-7.53 (m, 2H), 7.43-7.29 (m, 3H), 6.05-5.67 (m, 3H), 5.09 (d, J = 6.9 Hz, 1H), 5.03 (d, J = 6.6 Hz, 1H), 3.29 (s, 4H), 3.21-3.13 (m, 2H), 2.54 (s, 1H), 2.39 (d, J = 13.4 Hz, 2H) |
| 92 | 537.10 | 1H NMR (400 MHz, DMSO-d6) δ 9.35 (s, 2H), 8.90 (m, 1H), 8.22 (m, 1H), 7.93-7.71 (m, 1H), 7.58 (d, J = 2.2 Hz, 1H), 7.48-7.15 (m, 2H), 5.11 (d, J = 6.9 Hz, 1H), 5.04 (d, J = 6.6 Hz, 1H), 4.73 (s, 1H), 3.29 (s, 4H), 3.03 (m, 1H), 2.54 (d, J = 7.3 Hz, 1H), 1.19 (m, 1H), 1.15-1.06 (m, 2H), 1.06-0.94 (m, 1H) |
| 93 | 478.30 | 1H NMR (400 MHz, DMSO-d6) δ 9.20 (d, J = 1.9 Hz, 2H),8.84-8.83(m, 1 H), 8.31-8.24 (m, 1H), 7.92-7.69 (m, 2H), 7.52 (t, J = 4.7 Hz, 3H), 7.38 (d, J = 1.9 Hz, 3H), 5.50 (p, J = 5.5 Hz, 1H), 5.28 (d, J = 7. 1 Hz, 1H), 5.21 (d, J = 5.3 Hz, 1H), 4.43 (q, J = 5.9 Hz, 1H), 3.36 (s, 4H), 1.68(d, J = 13.9 Hz, 3H), 1.40 (t, J = 5.9 Hz, 1H) |
| 94 | 478.20 | 1H NMR (400 MHz, DMSO-d6) δ 9.20 (d, J = 1.9 Hz, 2H),8.84-8.83(m, 1H), 8.31-8.24 (m, 1H), 7.92-7.69 (m, 2H), 7.52 (t, J = 4.7 Hz, 3H), 7.38 (d, J = 1.9 Hz, 1H), 5.50 (p, J = 5.5 Hz, 1H), 5.28 (d, J = 7.1 Hz, 1H), 5.21 (d, J = 5.3 |

| Ex. | LCMS [M + H]+ | ¹H NMR (ppm) |
|---|---|---|
|  |  | Hz, 1H), 4.43 (q, J = 5.9 Hz, 1H), 3.36 (s, 4H), 2.68(d, J = 13.9 Hz, 3H), 1.40 (t, J = 5.9 Hz, 1H) |
| 95 | 528.25 | ¹H NMR (400 MHz, DMSO-$d_6$) 9.05 (s, 2H), 8.78 (dd, J = 7.5, 1.0 Hz, 1H), 8.55 (dd, J = 2.0, 0.9 Hz, 1H), 8.23 (dd, J = 8.1, 1.4 Hz, 1H), 7.78-7.69 (m, 1H), 7.53 (s, 1H), 7.42 (d, J = 7.9 Hz, 1H), 7.38-7.29 (m, 1H), 6.50 (s, 1H), 5.08 (dd, J = 15.3, 6.8 Hz, 2H), 4.81 (d, J = 10.1 Hz, 1H), 4.75 (d, J = 9.8 Hz, 1H), 4.72-4.66 (m, 1H), 4.64 (d, J = 9.5 Hz, 1H), 3.33 (ddd, J = 15.2, 8.3, 6.8 Hz, 1H), 3.29 (s, 4H), 2.54 (s, 1H) |
| 96 | 556.25 | ¹H NMR (400 MHz, DMSO-$d_6$) δ 9.32 (s, 2H), 8.89 (d, J = 7.4, 0.9Hz, 1H), 8.23 (d, J = 8.0, 1.5 Hz, 1H), 7.78 (s, 1H), 7.61 (d, J = 2.0 Hz, 1H), 7.42-7.30 (m, 3H), 7.00 (s, 1H), 6.60-6.33 (s, 1H), 5.10 (d, J = 6.9 Hz, 1H), 5.05 (d, J = 6.6 Hz, 1H), 3.44 (d, J = 16.7 Hz, 1H), 3.32-3.23 (m, 2H), 2.55 (s, 1H) |
| 97 | 556.20 | ¹H NMR (400 MHz, DMSO-$d_6$) δ 9.32 (s, 2H), 8.89 (d, J = 7.4, 0.9 Hz, 1H), 8.23 (dd, J = 8.0, 1.5 Hz, 1H), 7.79 (dd, J = 2.1, 1.0 Hz, 1H), 7.60 (d, J = 2.1 Hz, 1H), 7.44-7.38 (m, 3H), 7.00 (s, 1H), 6.60-6.33 (s, 1H), 5.11 (d, J = 6.9 Hz, 1H), 5.05 (d, J = 6.7 Hz, 1H), 3.44 (d, J = 16.7 Hz, 1H), 3.35-3.23 (m, 2H), 2.55 (s, 1H) |
| 98 | 524.20 | ¹H NMR (400 MHz, DMSO-$d_6$) δ 9.30-9.24 (m, 1H), 9.12-9.10 (m, 2H), 8.24-8.20 (m, 1H), 7.63-7.55 (m, 2H), 7.42-7.30 (m, 2H), 6.46 (s, 1H), 5.13-5.09 (m, 1H), 5.08-5.01 (m, 3H), 4.75-71 (m, 2H), 3.35-3.25 (m, 4H), 2.57-2.51 (m, 1H) |
| 99 | 539.20 | ¹H NMR (400 MHz, DMSO-$d_6$) δ 9.23 (s, 2H), 8.87 (d, J = 7.4 Hz, 1H), 8.23 (dd, J = 7.9, 1.6 Hz, 1H), 7.85-7.53 (m, 2H), 7.48-7.25 (m, 3H), 6.54 (s, 2H), 5.10 (d, J = 6.9 Hz, 1H), 5.03 (d, J = 6.5 Hz, 1H), 3.42 (s, 2H), 3.27 (d, J = 6.8 Hz, 4H), 2.90 (q, J = 12.8 Hz, 2H), 2.55 (s, 1H) |
| 100 | 510.15 | ¹H NMR (400 MHz, DMSO-$d_6$) δ 8.88 (m, 1H), 8.39 (m, 1H), 8.31-8.20 (m, 3H), 7.75-7.53 (m, 1.6 Hz, 2H), 7.42 (m, 1H), 7.34 (t, J = 8.3 Hz, 1H), 5.09 (m, 2H), 3.35 (d, J = 6.9 Hz, 1H), 3.30 (s, 3H), 2.55 (s, 1H), 1.85 (d, J = 13.8 Hz, 6H) |
| 101 | 534.20 | ¹H NMR (400 MHz, DMSO-$d_6$) δ 9.15 (s, 2H), 8.89-8.81 (m, 1H), 8.28-8.20 (m, 1H), 7.82-7.57 (m, 2H), 7.43-7.29 (m, 3H), 5.12 (s, 1H), 5.11-5.07 (m, 1H), 5.03 (d, J = 6.6 Hz, 1H), 4.70-4.58 (m, 1H), 4.49-4.36 (m, 1H), 3.29 (s, 4H), 2.54 (s, 1H), 2.43-2.31 (m, 1H), 2.24-2.08 (m, 3H), 1.88-1.79 (m, 1H), 1.70-1.59 (m, 1H) |
| 102 | 534.25 | ¹H NMR (400 MHz, DMSO-$d_6$) δ 9.15 (s, 2H), 8.88-8.79 (m, 1H), 8.27-8.19 (m, 1H), 7.80-7.59 (m, 2H), 7.42-7.29 (m, 3H), 5.13 (d, J = 1.5 Hz, 1H), 5.11-5.07 (m, 1H), 5.03 (d, J = 6.6 Hz, 1H), 4.68-4.58 (m, 1H), 4.48-4.37 (m, 1H), 3.32-3.31(m, 1H), 3.29 (s, 3H), 2.54 (s, 1H), 2.43-2.33 (m, 1H), 2.25-2.09 (m, 3H), 1.88-1.80 (m, 1H), 1.70-1.60 (m, 1H) |
| 103 | 503.19 | ¹H NMR (400 MHz, DMSO-$d_6$) δ 9.12 (s, 2H), 8.84 (d, J = 7.4 Hz, 1H), 8.26-8.19 (m, 1H), 7.86-7.40 (m, 2H), 7.38-7.32 (m, 2H), 7.32-7.29 (m, 1H), 5.09 (d, J = 6.9 Hz, 1H), 5.03 (d, J = 6.6 Hz, 1H), 3.47 (d, J = 7.4 Hz, 1H), 3.29 (s, 4H), 2.54 (s, 1H), 1.22-1.09 (m, 1H), 0.51-0.25 (m, 4H) |
| 104 | 503.30 | ¹H NMR (400 MHz, DMSO-$d_6$) δ 9.12 (s, 2H), 8.84-8.83 (m, 1H), 8.22-8.21 (m, 1H), 7.82-7.57 (m, 2H), 7.44-7.29 (m, 3H), 5.09 (d, J = 6.9 Hz, 1H), 5.03 (d, J = 6.6 Hz, 1H), 3.47 (d, J = 7.5 Hz, 1H), 3.29 (s, 4H), 2.84 (d, J = 13.7 Hz, 1H), 1.21-1.05 (m, 1H), 0.58-0.34 (m, 4H) |
| 105 | 514.10 | ¹H NMR (400 MHz, DMSO-$d_6$) δ 9.21 (s, 2H), 8.87-8.85 (m, 1H), 8.23-8.21 (m, 1H), 7.79-7.56 (m, 2H), 7.42-7.31 (m, 3H), 6.52-6.21 (m, 2H), 5.10 (d, J = 6.9 Hz, 1H), 5.03 (d, J = 6.6 Hz, 1H), 4.93-4.83 (m, 1H), 3.29 (s, 4H), 2.54 (s, 1H) |
| 106 | 514.20 | ¹H NMR (400 MHz, DMSO-$d_6$) δ 9.21 (s, 2H), 8.87-8.84 (m, 1H), 8.23-8.21 (m, 1H), 7.80-7.57 (m, 2H), 7.42-7.30 (m, 3H), 6.52-6.23 (m, 2H), 5.10-5.02 (m, 2H), 4.93-4.83 (m, 1H), 3.32 (d, J = 7.0 Hz, 1H), 3.29 (s, 3H), 2.54 (s, 1H) |
| 107 | 520.20 | ¹H NMR (400 MHz, DMSO-$d_6$) δ 8.90 (d, J = 4.0 Hz, 2H), 8.81-8.73 (m, 1H), 8.54-8.47 (m, 1H), 8.30-8.21 (m, 1H), 7.77-7.69 (m, 1H), 7.52-7.38 (m, 2H), 7.35 (dd, J = 8.4, 4.1 Hz, 1H), 5.92-5.87 (m, 1H),5.16-5.03 (m, 2H), 5.01-4.97 (m, 1H), 4.76-4.58 (m, 2H), 4.55-4.46 (m, 1H),4.43-4.40 (m, 1H), 3.39-3.34 (m, 4H), 3.31-3.27 (m, 1H), 1.27-1.22 (m, 1H) |
| 108 | 520.20 | ¹H NMR (400 MHz, DMSO-$d_6$) δ 8.98-8.91 (m, 2H), 8.81-8.73 (m, 1H), 8.54-8.47 (m, 1H), 8.30-8.21 (m, 1H), 7.77-7.69 (m, 1H), 7.66-7.45 (m, 1H), 7.41-7.30 (m, 2H), 7.27-7.18 (m, 1H), 5.92-5.87 (m, 1H),5.16-5.06 (m, 2H), 5.04-4.95 (m, 1H), 4.76-4.58 (m, 2H), 4.55-4.46 (m, 1H), 4.43-4.40 (m, 1H), 3.39-3.34 (m, 4H), 3.31-3.27 (m, 1H), 1.29-1.25 (m, 1H), 1.23-1.17(m, 1H) |
| 109 | 552.25 | ¹H NMR (400 MHz, DMSO-$d_6$) δ 9.25 (d, J = 6.2 Hz, 1H), 9.04 (d, J = 1.7 Hz, 2H), 8.22 (dd, J = 7.9, 1.6 Hz, 1H), 7.60-7.51 (m, 2H), 7.41-7.29 (m, 2H), 5.69 (s, 1H), 5.11 (d, J = 6.9 Hz, 1H), 5.05-4.96 (m, 2H), 3.28 (s, 4H), 2.94-2.86 (m, 2H), 2.54 (s, 1H), 2.46-2.38 (m, 2H), 1.09 (s, 3H) |
| 110 | 554.15 | ¹H NMR (400 MHz, DMSO-$d_6$) δ 9.25 (d, J = 6.1 Hz, 1H), 9.05 (d, J = 1.7 Hz, 2H), 8.22 (dd, J = 7.9, 1.6 Hz, 1H), 7.75-7.48 (m, 2H), 7.40-7.29 (m, 2H), 5.70 (s, 1H), 5.11 (d, J = 6.9 Hz, 1H), 5.04-4.97 (m, 2H), 3.31-3.22 (m, 1H), 2.95-2.86 (m, 2H), 2.54 (s, 1H), 2.42 (d, J = 13.0 Hz, 2H), 1.09 (s, 3H) |
| 111 | 534.25 | ¹H NMR (400 MHz, DMSO-$d_6$) δ 9.14 (s, 2H), 8.84 (dd, J = 7.4, 0.9 Hz, 1H), 8.23 (dd, J = 8.0, 1.6 Hz, 1H), 7.83-7.56 (m, 2H), 7.43-7.33 (m, 2H), 7.33-7.30 (m, 1H), 5.28 (s, 1H), 5.09 (d, J = 6.9 Hz, 1H), 5.03 (d, J = 6.6 Hz, 1H), 4.66 (d, J = 5.1 Hz, 1H), 4.36-4.22 (m, 1H), 3.28(s, 4H), 2.62-2.56 (m, 1H), 2.55 (d, J = 3.7 Hz, 1H), 2.16-2.06 (m, 1H), 2.04-1.92 (m, 2H), 1.90-1.76 (m, 2H). |
| 112 | 534.30 | ¹H NMR (400 MHz, DMSO-$d_6$) δ 9.14 (s, 2H), 8.85 (dd, J = 7.4, 0.9 Hz, 1H), 8.23 (dd, J = 8.0, 1.6 Hz, 1H), 7.87-7.57 (m, 2H), 7.42-7.30 (m, 3H), 5.28 |

| Ex. | LCMS [M + H]⁺ | ¹H NMR (ppm) |
|---|---|---|
| | | (s, 1H), 5.09 (d, J = 6.9 Hz, 1H), 5.03 (d, J = 6.6 Hz, 1H), 4.66 (s, J = 5.1 Hz, 1H), 4.34-4.23 (m, 1H), 3.29 (s, 4H), 2.62-2.56 (m, 1H), 2.55 (d, J = 3.5 Hz, 1H), 2.15-2.05 (m, 1H), 2.04-1.92 (m, 2H), 1.89-1.76 (m, 2H) |
| 113 | 530.25 | ¹H NMR (400 MHz, DMSO-d₆) δ 9.24 (d, J = 6.3 Hz, 1H), 8.96 (d, J = 2.3 Hz, 1H), 8.21 (ddd, J = 12.8, 8.0, 2.1 Hz, 2H), 8.09 (dd, J = 8.0, 5.1 Hz, 1H), 7.73-7.48 (m, 2H), 7.43-7.29 (m, 2H), 5.11 (d, J = 6.9 Hz, 1H), 5.02 (d, J = 6.6 Hz, 1H), 3.31-3.21 (m, 1H), 2.54 (s, 1H), 1.72 (d, J = 13.6 Hz, 6H) |
| 114 | 526.30 | ¹H NMR (400 MHz, DMSO-d₆) δ 9.25 (d, J = 6.2 Hz, 1H), 9.03 (d, J = 1.7 Hz, 2H), 8.29-8.17(m, 1H), 7.60-7.51 (m, 2H), 7.42-7.29 (m, 2H), 5.14-5.10 (m, 1H), 5.07-4.99 (m, 1H), 4.80-4.62 (m, 1H), 3.76-3.60 (m, 2H), 3.40-3.30 (m, 4H) 2.54 (s, 1H), 1.48 (s, 3H), 1.24 (s, 1H) |
| 115 | 526.25 | ¹H NMR (400 MHz, DMSO-d₆) δ 9.25 (d, J = 6.2 Hz, 1H), 9.03 (d, J = 1.7 Hz, 2H), 8.27-8.17 (m, 1H), 7.60-7.51 (m,2H), 7.42-7.29 (m, 2H), 5.11-5.03 (m, 1H), 5.07-4.99 (m, 1H), 4.73-4.61 (m, 1H), 3.76-3.65 (m, 2H), 3.36-3.30 (m, 4H), 1.48 (s, 3H), 1.24 (s, 1H) |
| 116 | 535.20 | ¹H NMR (400 MHz, DMSO-d₆) δ 9.30-9.24 (m, 1H), 9.10 (s, 2H), 8.24-8.20 (m, 1H), 7.72-7.50 (m, 2H), 7.42-7.28 (m, 2H), 6.03 (s, 1H), 5.19-5.01 (m, 2H), 3.32-3.28 (m, 4 H), 3.21-3.17 (m, 2H), 2.72-2.52 (m, 1H), 1.65 (s, 3H) |
| 117 | 535.30 | ¹H NMR (400 MHz, DMSO-d₆) δ 9.26 (d, J = 6.2 Hz, 1H), 9.09 (d, J = 1.7 Hz, 2H), 8.22 (dd, J = 7.9, 1.6 Hz, 1H), 7.59 (d, J = 7.7 Hz, 1H), 7.53 (d, J = 1.4 Hz, 1H), 7.35 (qd, J = 8.0, 5.3 Hz, 2H), 6.03 (s, 1H), 5.11 (d, J = 6.9 Hz, 1H), 5.02 (d, J = 6.6 Hz, 1H), 3.28 (s, 4H), 3.19 (s, 2H), 2.54 (d, J = 4.0 Hz, 1H), 1.65 (s, 3H). |
| 118 | 508.25 | ¹H NMR (400 MHz, DMSO-d₆) δ 9.15 (s, 2H), 8.85-8.83 (m, 1H), 8.22-8.21 (m, 1H), 7.81-7.58 (m, 2H), 7.46-7.27 (m, 3H), 5.09-5.07 (m, 2H), 5.03 (d, J = 6.6 Hz, 1H), 4.53 (d, J = 5.8 Hz, 1H), 4.47-4.46(m, 1H), 4.06-4.03(m, 1H), 3.29 (s, 4H), 2.84 (d, J = 13.7 Hz, 1H), 1.06 (d, J = 6.4 Hz, 3H) |
| 119 | 508.20 | ¹H NMR (400 MHz, DMSO-d₆) δ 9.15 (s, 2H), 8.85-8.83 (m, 1H), 8.22-8.21 (m, 1H), 7.81-7.58 (m, 2H), 7.46-7.27 (m, 3H), 5.09-5.07 (m, 2H), 5.03 (d, J = 6.6 Hz, 1H), 4.53 (d, J = 5.8 Hz, 1H), 4.47-4.46(m, 1H), 4.06-4.03(m, 1H), 3.29 (s, 4H), 2.84 (d, J = 13.7 Hz, 1H), 1.06 (d, J = 6.4 Hz, 3H) |
| 120 | 554.25 | ¹H NMR (400 MHz, DMSO-d₆) δ 9.25 (d, J = 6.2 Hz, 1H), 8.93 (d, J = 2.1 Hz, 1H), 8.28 (dt, J = 8.2, 2.0 Hz, 1H), 8.22 (dd, J = 7.9, 1.6 Hz, 1H), 8. 16 (dd, J = 8.2, 0.8 Hz, 1H), 7.60-7.50 (m, 2H), 7.42-7.32 (m, 2H), 5.11 (d, J = 6.9 Hz, 1H), 5.02 (d, J = 6.6 Hz, 1H), 4.50 (s, 1H), 3.29 (s, 4H), 2.93 (h, J = 6.5, 5.9 Hz, 1H), 2.54 (s, 1H), 1.20-1.10 (m, 1H), 1.06-0.94 (m, 3H) |
| 121 | 554.25 | ¹H NMR (400 MHz, DMSO-d₆) δ 9.25 (d, J = 6.2 Hz, 1H), 8.93 (d, J = 2.1 Hz, 1H), 8.28 (dt, J = 8.2, 2.0 Hz, 1H), 8.22 (dd, J = 7.9, 1.6 Hz, 1H), 8.16 (dd, J = 8.2, 0.8 Hz, 1H), 7.60-7.50 (m, 2H), 7.42-7.32 (m, 2H), 5.11 (d, J = 6.9 Hz, 1H), 5.02 (d, J = 6.6 Hz, 1H), 4.50 (s, 1H), 3.29 (s, 4H), 2.93 (h, J = 6.5, 5.9 Hz, 1H), 2.54 (s, 1H), 1.20-1.10 (m, 1H), 1.06-0.94 (m, 3H) |
| 122 | 509.10 | ¹H NMR (400 MHz, DMSO-d₆) δ 9.06-8.99 (m, 1H), 8.79 (d, J = 7.5, 0.9 Hz, 1H), 8.25-8.33 (m, 1H), 8.27-8.18 (m, 2H), 8.10 (d, J = 8.2 Hz, 1H), 7.62-7.55 (m, 2H), 7.44-7.30 (m, 2H), 5.03-5.12 (m, 2H), 2.54 (s, 1H), 1.76 (d, J = 13.5 Hz, 6H) |
| 123 | 508.20 | ¹H NMR (400 MHz, DMSO-d₆) δ 8.82-8.77 (m, 1H), 8.23 (dd, J = 8.0, 1.6 Hz, 1H), 7.95-7.76 (m, 4H), 7.68-7.50 (m, 2H), 7.44-7.29 (m, 2H), 7.23-7.17 (m, 1H), 5.08-4.93 (m, 2H), 3.37-3.29 (m, 4H), 2.53 (s, 1H), 1.80-1.77 (m, 3H), 1.75-1.65 (m, 3H) |
| 124 | 527.25 | ¹H NMR (400 MHz, DMSO-d₆) δ 9.06 (d, J = 2.3 Hz, 1H), 8.85 (dd, J = 7.4, 0.9 Hz, 1H), 8.41 (dd, J = 8.2, 2.4 Hz, 1H), 8.26-8.14 (m, 2H), 7.80-7.72 (m, 1H), 7.59 (d, J = 1.5 Hz, 1H), 7.39 (d, J = 9.7 Hz, 1H), 7.37-7.27 (m, 2H), 5.09 (d, J = 6.9 Hz, 1H), 5.04 (d, J = 6.6 Hz, 1H), 4.48 (s, 1H), 3.42-3.35 (m, 1H), 2.54 (s, 1H), 2.32 (s, 1H), 1.14 (t, J = 7.4 Hz, 3H) |
| 125 | 538.10 | ¹H NMR (400 MHz, DMSO-d₆) δ 9.26 (d, J = 6.2 Hz, 1H), 8.23 (d, J = 7.9 Hz, 1H), 7.61-7.51 (m, 1H), 7.32-7.44 (m, 2H), 5.70 (s, 1H), 5.10-5.16 (m, 2H), 5.03 (d, J = 6.5 Hz, 1H), 4.06-4.14 (m, 1H), 2.89-2.92 (m, 2H), 2.24-2.32 (m, 2H) |
| 126 | 537.25 | ¹H NMR (400 MHz, DMSO-d₆) δ 9.40 (s, 1H), 9.25 (d, J = 2.9 Hz, 1H), 8.88 (d, J = 7.4 Hz, 1H), 8.37-8.12 (m, 2H), 7.85-7.47 (m, 2H), 7.46-7.24 (m, 2H), 5.21-4.97 (m, 2H), 4.77 (s, 1H), 3.32-3.25 (m, 4H), 3.01-2.82 (m, 1H), 2.56 (s, 1H), 1.49-1.13 (m, 1H), 1.10-0.88 (m, 3H) |
| 127 | 512.20 | ¹H NMR (400 MHz, DMSO-d₆) δ 8.87 (d, J = 6.6 Hz, 1H), 8.76 (d, J = 7.4 Hz, 1H), 8.19 (m, 1H), 7.93-7.58 (m, 4H), 7.46-7.27 (m, 3H), 7.22 (m, 1H), 5.08 (d, J = 6.5 Hz, 1H), 4.79 (t, J = 6.6 Hz, 1H), 3.26 (m, 1H), 2.43-2.30 (m, 1H), 1.75 (d, J = 13.7 Hz, 6H) |
| 128 | 528.35 | ¹H NMR (400 MHz, DMSO-d₆) δ 9.28 (d, J = 6.7 Hz, 1H), 9.21 (dt, J = 6.0, 1.9 Hz, 2H), 8.23 (dd, J = 8.1, 1.5 Hz, 1H), 8.04 (d, J = 7.6 Hz, 1H), 7.50 (s, 0H), 7.40 (d, J = 8.0 Hz, 1H), 7.38-7.30 (m, 1H), 5.13 (d, J = 6.8 Hz, 1H), 5.05 (d, J = 6.6 Hz, 1H), 1.79 (d, J = 13.8 Hz, 6H) |
| 129 | 520.30 | ¹H NMR (400 MHz, DMSO-d₆) δ 8.90 (s, 2H), 8.76 (dd, J = 7.4, 0.9 Hz, 1H), 8.51 (dd, J = 2.0, 0.9 Hz, 1H), 8.23 (dd, J = 8.2, 1.4 Hz, 1H), 7.78-7.28 (m, 4H), 6.00 (d, J = 4.6 Hz, 1H), 5.07 (dd, J = 15.4, 6.8 Hz, 2H), 4.87 (t, J = 4.8 Hz, 1H), 4.79-4.72 (m, 1H), 4.53-4.34 (m, 2H), 3.33 (s, 4H), 2.54-2.52 (m, 3H) |
| 130 | 520.15 | ¹H NMR (400 MHz, DMSO-d₆) δ 8.92 (s, 2H), 8.77 (d, J = 7.4 Hz, 1H), 8.52 (t, J = 1.4 Hz, 1H), 8.23 (d, J = 8.1, 1.4 Hz, 1H), 7.77-7.26 (m, 4H), 5.91 (d, J = 5.1 Hz, 1H), 5.08 (d, J = 15.1, 6.8 Hz, 2H), 4.89-4.78 (m, 2H), 4.87-4.38 (m, 2H), 3.29 (s, 4H), 2.53 (d, J = 2.3 Hz, 3H) |

| Ex. | LCMS [M + H]+ | 1H NMR (ppm) |
| --- | --- | --- |
| 131 | 520.15 | 1H NMR (400 MHz, DMSO-d6) δ 8.92 (s, 2H), 8.77 (d, J = 7.4 Hz, 1H), 8.52 (t, J = 1.4 Hz, 1H), 8.23 (dd, J = 8.1, 1.4 Hz, 1H), 7.77-7.26 (m, 4H), 5.91 (d, J = 5.1 Hz, 1H), 5.08 (dd, J = 15.1, 6.8 Hz, 1H), 4.89-4.78 (m, 2H), 4.87-4.38 (m, 2H), 3.29 (s, 4H), 2.53 (d, J = 2.3 Hz, 3H) |
| 132 | 520.15 | 1H NMR (400 MHz, DMSO-d6) δ 8.90 (s, 2H), 8.77 (dd, J = 7.5, 1.0 Hz, 1H), 8.52 (dd, J = 2.0, 1.0 Hz, 1H), 8.23 (dd, J = 8.1, 1.4 Hz, 1H), 7.77-7.69 (m, 1H), 7.56-7.29 (m, 3H), 6.00 (d, J = 4.6 Hz, 1H), 5.07 (dd, J = 15.5, 6.8 Hz, 2H), 4.91-4.70 (m, 2H), 4.53-4.36 (m, 2H), 3.29 (s, 4H), 2.62-2.52 (m, 3H) |
| 133 | 522.15 | 1H NMR (400 MHz, DMSO-d6) δ 9.15 (s, 2H), 8.90-8.77 (m, 1H), 8.28-8.16 (m, 1H), 7.82-7.57 (m, 2H), 7.46-7.09 (m, 3H), 5.18 (d, J = 7.0 Hz, 1H), 5.12-5.05 (m, 1H), 5.03 (d, J = 6.6 Hz, 1H), 4.52 (d, J = 7.1 Hz, 1H), 4.47 (s, 1H), 3.29 (d, J = 1.5 Hz, 4H), 2.54 (s, 1H), 1.36 (s, 1H), 1.15 (d, J = 12.4 Hz, 4H), 0.60 (s, 1H) |
| 134 | 522.15 | 1H NMR (400 MHz, DMSO-d6) δ 9.15 (s, 2H), 8.85 (d, J = 7.3 Hz, 1H), 8.28-8.18 (m, 1H), 7.83-7.58 (m, 2H), 7.43-7.29 (m, 3H), 5.18 (d, J = 7.1 Hz, 1H), 5.10 (d, J = 6.9 Hz, 1H), 5.03 (d, J = 6.7 Hz, 1H), 4.53-4.41 (m, 2H), 3.26 (s, 4H), 2.54 (s, 1H), 1.15 (d, J = 13.7 Hz, 6H) |
| 135 | 508.20 | 1H NMR (400 MHz, DMSO-d6) δ 9.13 (s, 2H), 8.89-8.78 (m, 1H), 8.30-8.16 (m, 1H), 7.84-7.57 (m, 2H), 7.46-7.24 (m, 3H), 5.35 (d, J = 6.6 Hz, 1H), 5.17-4.98 (m, 2H), 4.55 (d, J = 5.8 Hz, 1H), 4.48-4.36 (m, 1H), 4.10-3.96 (m, 1H), 3.29 (s, 4H), 2.54 (s, 1H), 1.18 (d, J = 6.3 Hz, 3H) |
| 136 | 520.10 | 1H NMR (400 MHz, DMSO-d6) δ 9.17-9.03 (m, 2H), 8.76-8.60 (m, 1H), 8.43-8.27 (m, 1H), 7.87-7.79 (m, 1H), 7.47-7.06 (m, 4H), 5.25-5.19 (m, 1H),5.16-5.03 (m, 2H), 4.84-4.79 (m, 2H), 3.67-3.51 (m, 1H), 3.42-3.31 (m, 4H), 2.69-2.54 (m, 1H) |
| 137 | 520.15 | 1H NMR (400 MHz, DMSO-d6) δ 9.17-9.03 (m, 2H), 8.76-8.60 (m, 1H), 8.43-8.27 (m, 1H), 7.87-7.79 (m, 1H), 7.47-7.06 (m, 4H), 5.25-5.19 (m, 1H),5.16-5.03 (m, 2H), 4.84-4.79 (m, 2H), 3.67-3.51 (m, 1H), 3.42-3.31 (m, 4H), 2.69-2.54 (m, 1H) |
| 138 | 510.25 | 1H NMR (400 MHz, DMSO-d6) δ 9.23 (d, J = 5.7 Hz, 2H), 8.85-8.77 (m, 1H), 8.62 (d, J = 1.8 Hz, 1H), 8.24 (dd, J = 8.1, 1.4 Hz, 1H), 7.77 (dd, J = 7.4, 2.0 Hz, 1H), 7.53 (s, 1H), 7.43 (d, J = 8.0 Hz, 1H), 7.39-7.30 (m, 1H), 5.09 (dd, J = 15.9, 6.7 Hz, 2H), 2.55 (s, 4H), 1.81 (d, J = 13.9 Hz, 6H) |
| 139 | 534.30 | 1H NMR (400 MHz, DMSO-d6) δ 9.16 (s, 2H), 8.85 (d, J = 7.4, 0.9 Hz, 1H), 8.22 (dd, J = 7.9, 1.6 Hz, 1H), 7.86-7.48 (m, 2H), 7.43-7.16 (m, 3H), 5.52 (s, 1H), 5.09 (d, J = 6.9 Hz, 1H), 5.03 (d, J = 6.6 Hz, 1H), 4.91 (s, 1H), 3.30-3.23 (m, 4H), 2.82-2.62 (m, 2H), 2.54 (s, 1H), 2.31-2.10 (m, 2H), 1.51 (s, 3H) |
| 140 | 490.15 | 1H NMR (400 MHz, DMSO-d6) δ 9.18 (s, 2H), 8.88 (d, J = 6.6 Hz, 1H), 8.81 (dd, J = 7.4, 0.9 Hz, 1H), 8.20 (dd, J = 8.0, 1.5 Hz, 1H), 7.82-7.42 (m, 2H), 7.42-7.27 (m, 3H), 5.66 (s, 1H), 5.09 (d, J = 6.6 Hz, 1H), 4.80 (t, J = 6.6 Hz, 1H), 3.26 (dt, J = 13.0, 6.7 Hz, 1H), 2.73-2.62 (m, 2H), 2.44 (d, J = 13.0 Hz, 1H), 2.37-2.25 (m, 2H), 1.99-1.86 (m, 1H), 1.75 (dt, J = 10.8, 8.5 Hz, 1H) |
| 141 | 541.25 | 1H NMR (400 MHz, DMSO-d6) δ 9.67 (d, J = 1.5 Hz, 1H), 9.39 (s, 2H), 8.23 (dd, J = 8.1, 1.5 Hz, 1H), 7.91 (d, J = 1.5 Hz, 1H), 7.79-7.44 (m, 1H), 7.43-7.33 (m, 2H), 6.37 (s, 1H), 5.16 (d, J = 6.9 Hz, 1H), 5.05 (d, J = 6.8 Hz, 1H), 3.40 (td, J = 12.4, 2.8 Hz, 2H), 3.34 (s, 4H), 2.97-2.78 (m, 2H), 2.57 (d, J = 13.5 Hz, 1H) |
| 142 | 534.20 | 1H NMR (400 MHz, DMSO-d6) δ 8.99 (s, 2H), 8.78 (dd, J = 7.4, 1.0 Hz, 1H), 8.52 (dd, J = 1.9, 0.9 Hz, 1H), 8.24 (dd, J = 8.2, 1.4 Hz, 1H), 8.22 (m, 1H), 7.52 (s, 1H), 7.42 (d, J = 7.9 Hz, 1H), 7.38-7.30 (m, 3H), 5.78 (s, 1H), 5.10-5.01 (m, 3H), 3.33 (s, 4H), 2.85-2.78 (m, 2H), 2.54 (s, 1H), 2.46 (s, 2H), 1.06 (s, 3H) |
| 143 | 518.30 | 1H NMR (400 MHz, DMSO-d6) δ 8.77-8.69 (m, 3H), 8.22 (dd, J = 7.9, 1.6 Hz, 1H), 7.81-7.58 (m, 1H), 7.53 (d, J = 2.1 Hz, 1H), 7.44-7.29 (m, 2H), 7.18 (dd, J = 7.4, 2.1 Hz, 1H), 5.05 (d, J = 6.9 Hz, 1H), 4.99 (d, J = 6.6 Hz, 1H), 3.74 (t, J = 5.0 Hz, 4H), 3.28 (s, 4H), 2.83-2.70 (m, 4H), 2.48 (s, 1H) |
| 144 | 527.25 | 1H NMR (400 MHz, DMSO-d6) δ 9.62 (d, J = 1.5 Hz, 1H), 8.26-8.20 (m, 1H), 8.00 (d, J = 7.9 Hz, 1H), 7.96-7.87 (m, 1H), 7.90-7.83 (m, 2H), 7.61 (s, 1H), 7.46-7.32 (m, 2H), 5.15 (d, J = 6.9 Hz, 1H), 5.05 (d, J = 6.7 Hz, 1H), 3.30 (s, 3H), 2.56 (d, J-13.6 Hz, 1H), 1.76 (d, J = 13.7 Hz, 6H) |
| 145 | 562.35 | 1H NMR (400 MHz, DMSO-d6) δ 8.73 (s, 3H), 8.22 (dd, J = 7.9, 1.6 Hz, 1H), 7.80-7.58 (m, 1H), 7.53 (dd, J = 2.1, 1.0 Hz, 1H), 7.44-7.29 (m, 2H), 7.19 (dd, J = 7.4, 2.1 Hz, 1H), 5.06 (d, J = 6.9 Hz, 1H), 4.99 (d, J = 6.6 Hz, 1H), 4.46 (t, J = 5.4 Hz, 1H), 3.80 (t, J = 5.0Hz, 4H), 3.55 (q, J = 6.0 Hz, 2H), 3.28 (s, 5H), 2.75 (t, J = 6.2 Hz, 4H), 2.44 (t, J = 6.2 Hz, 2H) |
| 146 | 540.25 | 1H NMR (400 MHz, DMSO-d6) δ 9.66 (d, J = 1.4 Hz, 1H), 9.37 (s, 2H), 8.24 (d, J = 1.5 Hz, 1H), 7.89 (d, J = 1.5 Hz, 1H), 7.81-7.18 (m, 3H), 5.16 (d, J = 6.9 Hz, 1H), 5.05 (d, J = 6.7 Hz, 1H), 4.44 (d, J = 195.0 Hz, 2H), 3.30 (s, 6H), 2.80 (q, J = 13.4, 12.8 Hz, 2H), 2.58 (s, 1H) |
| 147 | 548.35 | 1H NMR (400 MHz, DMSO-d6) δ 8.79 (d, J = 7.3 Hz, 1H), 8.68 (s, 1H), 8.23 (dd, J = 7.7, 1.8 Hz, 1H), 7.72-7.21 (m, 4H), 7.03 (dd, J = 7.3, 2.0 Hz, 1H), 5.58 (s, 1H), 5.10 (d, J = 6.9 Hz, 1H), 5.00 (d, J = 6.6 Hz, 1H), 4.96 (s, 1H), 3.27 (d, J = 6.7 Hz, 4H), 2.97-2.82 (m, 2H), 2.49-2.36 (m, 3H), 1.14 (s, 3H) |
| 148 | 560.30 | 1H NMR (400 MHz, DMSO-d6) δ 8.79-8.69 (m, 3H), 8.29-8.20 (m, 1H), 7.60-7.50 (m, 2H), 7.44-7.29 (m, 2H), 7.23-7.17 (m, 1H), 5.06 (d, J = 6.9 Hz, 1H), 4.99 (d, J = 6.6 Hz, 1H), 3.94-3.83 (m, 2H), 3.79-3.69 (m, 2H), 3.60-3.51 (m, 4H), 3.33-3.28 (m, 4H), 2.57-2.49 (m, 1H), 2.07 (s, 3H) |
| 149 | 531.30 | 1H NMR (400 MHz, DMSO-d6) δ 8.72 (s, 3H), 8.22 (dd, J = 7.9, 1.6 Hz, 1H), 7.60-7.52 (dd, J = 2.2, 2 Hz, 1H), |

| Ex. | LCMS [M + H]+ | 1H NMR (ppm) |
|---|---|---|
| | | 7.43-7.28 (m, 2H), 7.17 (dd, J = 7.4, 2.1 Hz, 1H), 5.05 (d, J = 6.8 Hz, 1H), 4.98 (d, J = 6.6 Hz, 1H), 4.74 (s, 4H), 4.28 (s, 4H), 3.28 (s, 4H), 2.48 (s, 1H) |
| 150 | 526.15 | 1H NMR (400 MHz, DMSO-d6) δ 9.21 (s, 2H), 8.84 (dd, J = 22.4, 7.0 Hz, 2H), 8.19 (d, J = 8.0 Hz, 1H), 7.85-7.59 (m, 2H), 7.36 (dq, J = 23.8, 9.3, 7.5 Hz, 3H), 6.35 (s, 1H), 5.09 (d, J = 6.5 Hz, 1H), 4.80 (t, J = 6.6 Hz, 1H), 3.39 (d, J = 13.4 Hz, 2H), 3.26 (dt, J = 13.1, 6.4 Hz, 1H), 2.88 (td, J = 13.7, 8.8 Hz, 2H), 2.44 (d, J = 12.9 Hz, 1H) |
| 151 | 514.20 | 1H NMR (400 MHz, DMSO-d6) δ 9.22 (s, 2H), 8.87 (d, J = 6.6 Hz, 1H), 8.82 (d, J = 7.4 Hz, 1H), 8.20 (dd, J = 8.0, 1.5 Hz, 1H), 7.89-7.55 (m, 2H), 7.45-7.38 (m, 1H), 7.37-7.28 (m, 2H), 6.42 (t, J = 55.6Hz, 1H), 6.07 (s, 1H), 5.09 (d, J = 6.5 Hz, 1H), 4.81 (t, J = 6.6 Hz, 1H), 3.26 (m, 1H), 2.44 (d, J = 13.0 Hz, 1H), 1.61 (s, 3H) |
| 152 | 514.25 | 1H NMR (400 MHz, DMSO-d6) δ 9.22 (s, 2H), 8.88 (d, J = 6.6 Hz, 1H), 8.82 (d, J = 7.3 Hz, 1H), 8.20 (dd, J = 8.0, 1.5 Hz, 1H), 7.92-7.55 (m, 2H), 7.49-7.38 (m, 1H), 7.37-7.26 (m, 2H), 6.70-6.22 (m, 1H), 6.07 (s, 1H), 5.09 (d, J = 6.6 Hz, 1H), 4.81 (t, J = 6.6 Hz, 1H), 3.26 (m, 1H), 2.49-2.26 (m, 1H), 1.61 (s, 3H) |
| 153 | 509.25 | 1H NMR (400 MHz, DMSO-d6) δ 9.23 (s, 2H), 8.86 (d, J = 7.4 Hz, 1H), 8.23 (dd, J = 8.0, 1.5 Hz, 1H), 7.88-7.50 (m, 2H), 7.44-7.24 (m, 3H), 6.43 (s, 1H), 5.10 (s, 1H), 5.04-4.93 (m, 3H), 4.73 (d, J = 6.3 Hz, 2H), 3.32-3.24 (m, 1H), 2.54 (s, 1H) |
| 154 | 560.30 | 1H NMR (400 MHz, DMSO-d6) δ 9.01-8.85 (s, 2H), 8.77-8.75 (s, 1H), 8.24-8.21 (m, 1H), 7.80-7.55 (m, 4H), 7.44-7.31 (m, 3H), 7.22-7.20 (m, 1H), 5.08-5.01 (m, 2H), 3.32(s, 5H), 2.69-2.59 (m, 2H), 2.53(s, 1H), 2.52(s, 1H), 1.23 (s, 3H) |
| 155 | 532.20 | 1H NMR (400 MHz, DMSO-d6) δ 8.73 (d, J = 7.7 Hz, 3H), 8.22 (dd, J = 7.9, 1.6 Hz, 1H), 7.60 (t, J = 1.5 Hz, 1H), 7.53 (d, J = 2.2 Hz, 1H), 7.44-7.29 (m, 2H), 7.19 (dd, J = 7.4, 2.1 Hz, 1H), 5.05 (d, J = 6.9 Hz, 1H), 4.99 (d, J = 6.6 Hz, 1H), 3.81 (t, J = 5.0 Hz, 4H), 3.28 (s, 4H), 2.45-2.32 (m, 5H), 2.23 (s, 3H) |
| 156 | 533.30 | 1H NMR (400 MHz, DMSO-d6) δ 8.75-8.67 (m, 3H), 8.24-8.17 (m, 1H), 7.78-7.40 (m, 4H), 7.29-7.19 (m, 1H), 5.05-4.99 (m, 2H), 4.81-4.70 (m, 1H), 4.36-4.27 (m, 2H), 3.82-3.72 (m, 2H), 3.42-3.35 (m, 2H), 3.34-3.25 (m, 4H), 2.52-2.49 (m, 1H), 1.84-1.76 9 (m, 2H), 1.39-1.27 (m, 2H) |
| 157 | 541.30 | 1H NMR (400 MHz, DMSO-d6) δ 9.22 (s, 2H), 8.86 (d, J = 7.3 Hz, 1H), 8.17 (d, J = 5.5 Hz, 1H), 8.14-7.65 (m, 3H), 7.36 (dd, J = 7.4, 2.1 Hz, 1H), 6.37 (s, 1H), 5.17 (d, J = 7.0 Hz, 1H), 4.91 (d, J = 6.4 Hz, 1H), 4.10 (q, J = 5.3 Hz, 2H), 3.17 (d, J = 5.3 Hz, 5H), 2.88 (td, J = 14.2, 9.5 Hz, 2H), 2.63 (s, 1H), 1.29-1.13 (m, 1H) |
| 158 | 519.25 | 1H NMR (400 MHz, DMSO-d6) δ 8.74 (d, J = 16.7 Hz, 2H), 8 8.72 (d, J = 16.7 Hz, 1H), 8.22 (dd, J = 7.9, 1.6 Hz, 1H), 7.79-7.40 (d, J = 1.4 Hz, 2H), 7.35 (dd, J = 2.1, 0.9 Hz, 2H), 7.19 (dd, |
| | | J = 7.5, 2.1 Hz, 1H), 5.05-4.99 (dd, J = 6.9 Hz, 2H), 3.78 (dd, J = 5.7, 3.8 Hz, 4H), 3.68 (dd, J = 5.6, 3.9 Hz, 4H), 3.28 (s, 4H), 2.48 (s, 1H) |
| 159 | 545.25 | 1H NMR (400 MHz, DMSO-d6) δ 9.22 (d, J = 6.4 Hz, 1H), 8.18 (d, J = 5.4 Hz, 1H), 8.10-7.85 (m, 3H), 7.58 (dd, J = 30.0, 7.7 Hz, 3H), 5.17 (d, J = 6.9 Hz, 1H), 4.89 (d, J = 6.4 Hz, 1H), 3.32 (s, 3H), 3.29 (s, 3H), 2.60 (d, J = 13.6 Hz, 1H), 1.78 (d, J = 13.7 Hz, 3H), 1.74 (s, 3H) |
| 160 | 561.20 | 1H NMR (400 MHz, DMSO-d6) δ 9.14 (s, 2H), 8.84 (d, J = 7.4 Hz, 1H), 8.22 (m, 1H), 7.65 (m, 2H), 7.42-7.30 (m, 3H), 7.11 (s, 1H), 6.70 (s, 1H), 5.69 (s, 1H), 5.06 (m, 2H), 3.29 (s, 3H), 3.15-3.08 (m, 2H), 2.54 (s, 2H), 2.12-2.04 (m, 2H), 1.55 (s, 3H) |
| 161 | 569.25 | 1H NMR (400 MHz, DMSO-d6) 1H NMR (400 MHz, DMSO-d6) δ 9.24 (d, J = 6.3 Hz, 1H), 9.01 (s, 1H), 8.26-8.20 (m, 2H), 8.17 (dd, J = 7.9, 5.3 Hz, 1H), 7.72-7.50 (m, 2H), 7.43-7.29 (m, 2H), 5.11 (d, J = 6.9Hz, 1H), 5.02 (d, J = 6.6 Hz, 1H), 4.13-3.97 (m, 2H), 3.95-3.81 (m, 2H), 3.32-3.27 (m, 4H),2.54-2.52 (m, 1H), 2.48-2.42 (m, 2H), 2.13-1.97 (m, 2H) |
| 162 | 505.30 | 1H NMR (400 MHz, DMSO-d6) δ 8.85 (d, J = 6.6 Hz, 1H), 8.75 (d, J = 3.3 Hz, 2H), 8.68 (m, 1H), 8.19 (m, 1H), 7.85-7.47 (m, 2H), 7.45-7.27 (m, 2H), 7.15 (d, J = 6.1 Hz, 1H), 5.04 (d, J = 6.5 Hz, 1H), 4.76 (t, J = 6.5 Hz, 1H), 3.78 (m, 4H), 3.69 (d, J = 4.6 Hz, 4H), 3.24 (m, 1H), 2.45-2.28 (m, 1H) |
| 163 | 503.30 | 1H NMR (400 MHz, DMSO-d6) δ 9.21 (s, 2H), 8.87 (d, J = 6.6 Hz, 1H), 8.82 (m, 1H), 8.19 (dd, J = 8.0, 1.5 Hz, 1H), 7.91-7.60 (m, 2H), 7.46-7.37 (m, 1H), 7.36-7.29 (m, 2H), 6.00 (s, 1H), 5.09 (d, J = 6.6 Hz, 1H), 4.80 (t, J = 6.6 Hz, 1H), 3.30-3.22 (m, 1H), 3.19 (s, 2H), 2.44 (d, J = 13.0 Hz, 1H), 1.64 (s, 3H) |
| 164 | 503.25 | 1H NMR (400 MHz, DMSO-d6) δ 9.21 (s, 2H), 8.87 (d, J = 6.6 Hz, 1H), 8.82 (d, J = 7.5 Hz, 1H), 8.20 (dd, J = 8.0, 1.5 Hz, 1H), 7.94-7.55 (m, 2H), 7.46-7.38 (m, 1H), 7.37-7.33 (m, 1H), 7.32-7.30 (m, 1H), 6.00 (s, 1H), 5.09 (d, J = 6.6 Hz, 1H), 4.80 (t, J = 6.6 Hz, 1H), 3.25 (m, 1H), 3.18 (s, 2H), 2.44 (d, J = 13.0 Hz, 1H), 1.64 (s, 3H) |
| 165 | 560.20 | 1H NMR (400 MHz, DMSO-d6) δ 9.31-8.52 (m, 4H), 8.33-8.13 (m, 2H), 7.89 (d, J = 8.3 Hz, 1H), 7.83-7.55 (m, 2H), 7.44-7.27 (m, 3H), 5.16-4.91 (m, 2H), 3.29 (s, 3H), 2.89 (d, J = 13.4 Hz, 2H), 2.74 (d, J = 13.0 Hz, 2H), 2.61-2.52 (m, 2H), 1.27 (s, 3H) |
| 166 | 523.15 | 1H NMR (400 MHz, DMSO-d6) δ 9.15 (d, J = 7.5 Hz, 3H), 8.28-8.08 (m, 2H), 7.77-7.20 (m, 3H), 6.80 (s, 1H), 5.08 (dd, J = 26.8, 6.7 Hz, 2H), 4.92-4.74 (m, 4H), 3.29 (s, 4H), 2.54 (s, 1H) |
| 167 | 542.30 | 1H NMR (400 MHz, DMSO-d6) δ 9.20 (d, J = 1.1 Hz, 2H), 8.86-8.83 (m, 1H), 8.23-8.21 (m, 1H), 7.79-7.56 (m, 2H), 7.43-7.29 (m, 3H), 5.10-5.02 (m, 2H), 3.74 (s,2H), 3.31-3.20 (m, 6H), 2.54 (s, 1H), 2.33-2.27 (m, 2H), 1.72 (s, 3H) |
| 168 | 536.15 | 1H NMR (400 MHz, DMSO-d6) δ 8.86-8.79 (m, 1H), 8.77 (s, 1H), 8.23-8.17 (m, 1H), 8.12 (d, J = 12.4 Hz, 1H), 7.71-7.25 (m, 5H), 5.25 (s, 1H), 5.09- |

| Ex. | LCMS [M + H]+ | 1H NMR (ppm) |
|---|---|---|
| | | 4.97 (m, 2H), 3.89-3.83 (m, 1H), 3.33-3.24 (m, 4H), 3.19-3.10 (m, 2H), 2.59-2.44 (m, 3H), 2.31-2.19 (m, 2H) |
| 169 | 536.20 | 1H NMR (400 MHz, DMSO-d6) δ 8.83-8.71 (m, 1H), 8.64 (s, 1H), 8.23-8.17 (m, 1H), 8.03-7.96 (m, 1H), 7.81-7.31 (m, 4H), 7.29-7.14 (m, 1H) 5.15-4.84 (m, 3H), 4.51-4.36 (m, 1H), 3.31-3.22 (m, 4H), 2.53-2.50 (m, 1H), 2.42-2.35 (m, 4H), 2.31-2.19 (m, 2H) |
| 170 | 531.25 | 1H NMR (400 MHz, DMSO-d6) δ 9.47 (s, 1H), 9.21 (d, J = 7.4 Hz, 1H), 9.01 (s, 1H), 8.26 (dd, J = 7.9, 1.6 Hz, 1H), 7.83 (d, J = 7.4 Hz, 1H), 7.78-7.32 (m, 3H), 5.15 (dd, J = 8.0, 6.8 Hz, 2H), 3.36-3.31 (m, 1H), 2.62 (d, J = 9.3 Hz, 2H), 2.55 (s, 1H), 2.14 (p, J = 8.9 Hz, 2H), 2.10-2.00 (m, 1H), 1.88-1.75 (m, 1H) |
| 171 | 533.20 | 1H NMR (400 MHz, DMSO-d6) δ 9.13 (s, 2H), 8.84 (d, J = 7.3 Hz, 1H), 8.23 (dd, J = 7.9, 1.5 Hz, 1H), 7.72 (d, J = 2.1 Hz, 1H), 7.60 (d, J = 1.6 Hz, 1H), 7.40-7.31 (m, 3H), 5.27 (d, J = 5.9 Hz, 1H), 5.10 (d, J = 6.9 Hz, 1H), 5.03 (d, J = 6.6 Hz, 1H), 4.61 (q, J = 6.2 Hz, 1H), 3.29 (d, J = 6.6 Hz, 3H) 3.09 (p, J = 6.7 Hz, 4H), 2.93-2.87 (m, 1H), 2.75-2.66 (m, 2H), 2.54 (s, 1H), 1.90 (p, J = 7.0 Hz, 2H). |
| 172 | 533.25 | 1H NMR (400 MHz, DMSO-d6) δ 9.13 (s, 2H), 8.84 (d, J = 7.3 Hz, 1H), 8.23 (dd, J = 7.9, 1.5 Hz, 1H), 7.72 (d, J = 2.1 Hz, 1H), 7.60 (d, J = 1.6 Hz, 1H), 7.40-7.31 (m, 3H), 5.27 (d, J = 5.9 Hz, 1H), 5.10 (d, J = 6.9 Hz, 1H), 5.03 (d, J = 6.6 Hz, 1H), 4.61 (q, J = 6.2 Hz, 1H), 3.29 (d, J = 6.6 Hz, 3H) 3.09 (p, J = 6.7 Hz, 4H), 2.93-2.87 (m, 1H), 2.75-2.66 (m, 2H), 2.54 (s, 1H), 1.90 (p, J = 7.0 Hz, 2H) |
| 173 | 546.15 | 1H NMR (400 MHz, DMSO-d6) δ 9.23 (d, J = 7.5 Hz, 1H), 9.18 (t, J = 1.7 Hz, 1H), 8.91 (d, J = 6.5 Hz, 1H), 8.44-8.40 (m, 1H), 8.25-8.21 (m, 1H), 7.77-7.38 (m, 3H), 7.35 (t, J = 8.0 Hz, 1H), 5.18 (d, J = 6.6Hz, 1H), 4.81 (t, J = 6.5 Hz, 1H), 3.32-3.22 (m, 1H), 2.90 (d, J = 12.2 Hz, 2H), 2.79 (d, J = 12.4 Hz, 2H), 2.44 (d, J = 13.0 Hz, 1H), 1.34 (s, 3H) |
| 174 | 564.15 | 1H NMR (400 MHz, DMSO-d6) δ 9.68 (d, J = 7.0 Hz, 1H), 8.94-8.86 (m, 2H), 8.59-7.43 (m, 3H), 7.36 (td, J = 17.9, 9.1 Hz, 2H), 5.17 (d, J = 6.6 Hz, 1H), 4.82 (t, J = 6.5 Hz, 1H), 3.27 (dd, J = 12.9, 6.6 Hz, 1H), 2.82 (d, J = 12.1 Hz, 2H), 2.65 (d, J = 12.9 Hz, 2H), 2.43 (d, J = 13.0 Hz, 1H), 1.36 (s, 3H) |
| 175 | 563.15 | 1H NMR (400 MHz, CDCl3) δ 9.22 (d, J = 1.4 Hz, 1H), 8.93 (s, 1H), 8.46 (dd, J = 8.3, 1.3 Hz, 1H), 8.11 (d, J = 11.7 Hz, 1H), 7.82 (d, J = 1.5 Hz, 1H), 7.32 (t, J = 8.2 Hz, 1H), 7.25 (d, J = 8. 1 Hz, 1H), 7.06-6.59 (m, 1H), 5.14 (d, J = 6.7 Hz, 1H), 4.93 (d, J = 6.9 Hz, 1H), 3.30 (dt, J = 13.7, 7.0 Hz, 1H), 2.98 (q, J = 12.8 Hz, 4H), 2.71 (d, J = 13.5 Hz, 1H), 1.52 (s, 3H) |
| 176 | 532.25 | 1H NMR (400 MHz, DMSO-d6) δ 9.51 (s, 2H), 9.28 (d, J = 7.4 Hz, 1H), 8.25 (dd, J = 7.9, 1.6 Hz, 1H), 7.86-7.18 (m, 4H), 5.12 (d, J = 6.8 Hz, 2H), 3.37-3.17 (m, 2H), 2.99 (dd, J = 11.8, 8.6 Hz, 2H), 2.88 (s, 2H), 2.61-2.51 (m, 3H) |
| 177 | 509.20 | 1H NMR (400 MHz, DMSO-d6) δ 9.59-9.53 (m, 2H), 9.30 (d, J = 7.5 Hz, 1H), 8.27-8.23 (m, 1H), 7.80-7.75 (m, 1H), 7.58-7.32 (m, 3H), 5.14 (d, J = 6.8, 1.5 Hz, 2H), 5.00 (d, J = 5.7 Hz, 2H), 4.64 (d, J = 5.7 Hz, 2H), 3.32-3.28 (m, 1H), 2.57-2.53 (m, 1H) |
| 178 | 527.15 | 1H NMR (400 MHz, DMSO-d6) δ 9.77-9.73 (m, 1H), 9.33 (d, J = 1.4 Hz, 2H), 8.25 (dd, J = 7.8, 1.8 Hz, 1H), 7.70-7.25 (m, 3H), 5.14 (t, J = 7.4 Hz, 2H), 5.00 (d, J = 5.7 Hz, 2H), 4.65 (d, J = 5.7 Hz, 2H), 3.04-3.02 (m, 1H), 3.10-2.98 (m, 2H), 2.56-2.54 (m, 1H) |
| 179 | 532.25 | 1H NMR (400 MHz, DMSO-d6) δ 9.52 (s, 2H), 9.28 (d, J = 7.5 Hz, 1H), 8.25 (dd, J = 7.9, 1.7 Hz, 1H), 7.81-7.46 (m, 2H), 7.42-7.30 (m, 2H), 5.13 (dd, J = 6.9, 1.8 Hz, 2H), 3.60 (p, J = 8.8 Hz, 1H), 3.38-3.26 (m, 1H), 2.93 (td, J = 9.1, 2.7 Hz, 2H), 2.58 (d, J = 32.7 Hz, 3H), 2.45 (td, J = 9.1, 2.7 Hz, 2H) |
| 180 | 537.20 | 1H NMR (400 MHz, Methanol-d4) δ 9.54-9.50 (m, 2H), 8.99-8.94 (m, 1H), 8.49 (s, 1H), 8.32 (d, J = 8.0, 1H), 7.58-7.06 (m, 3H), 5.27 (d, J = 6.8 Hz, 1H), 5.09 (d, J = 6.8 Hz, 1H), 3.48-3.35 (m, 1H), 3.13-3.06 (m, 2H), 2.65-2.60 (m, 3H), 1.57 (s, 3H) |
| 181 | 520.25 | 1H NMR (400 MHz, DMSO-d6) δ 8.93 (s, 2H), 8.73 (s, 1H), 8.35 (s, 1H), 8.22 (d, J = 7.6, 2.0 Hz, 1H), 7.68-7.28 (m, 4H), 5.07 (d, J = 6.8 Hz, 1H), 4.97 (d, J = 6.8 Hz, 1H), 3.33-3.22 (m, 1H), 2.71-2.60 (m, 2H), 2.49-2.46 (m, 1H), 2.26-2.14 (m, 5H), 2.10-1.99 (m, 1H), 1.96-1.81 (m, 1H) |
| 182 | 506.15 | 1H NMR (400 MHz, DMSO-d6) δ 9.32 (d, J = 2.4 Hz, 1H), 9.20 (d, J = 7.6 Hz, 1H), 8.50 (dd, J = 8.4, 2.4 Hz, 1H), 8.26 (dd, J = 8.0, 1.6 Hz, 1H), 7.78 (d, J = 8.4 Hz, 1H), 7.74-7.30 (m, 4H), 5. 11 (dd, J = 6.8, 2.4 Hz, 2H), 3.37-3.24 (m, 1H), 2.64-2.55 (m, 3H), 2.20-1.99 (m, 3H), 1.89-1.77 (m, 1H) |
| 183 | 609.10 | 1H NMR (400 MHz, DMSO-d6) δ 9.73 (d, J = 6.9 Hz, 1H), 9.27 (d, J = 1.6 Hz, 2H), 8.24 (d, J = 7.8, 1.8 Hz, 1H), 7.76-7.15 (m, 3H), 6.65 (s, 1H), 5.13 (dd, J = 9.7, 6.8 Hz, 2H), 3.31-3.20 (m, 3H), 2.54 (s, 1H), 2.42-2.25 (m, 2H). |
| 184 | 489.05 | 1H NMR (400 MHz, DMSO-d6) δ 9.74 (d, J = 6.8 Hz, 1H), 9.30 (d, J = 1.5 Hz, 2H), 8.37 (s, 1H), 8.24 (dd, J = 7.6, 1.9 Hz, 1H), 7.66-7.27 (m, 3H), 5.14 (dd, J = 10.0, 6.8 Hz, 2H), 3.35-3.30 (m, 1H), 2.90 (d, J = 12.8 Hz, 2H), 2.54 (s, 1H), 2.46 (d, J = 12.2 Hz, 2H), 1.19 (s, 3H). |
| 185 | 555.15 | 1H NMR (400 MHz, DMSO-d6) δ 9.74 (d, J = 6.8 Hz, 1H), 9.30 (d, J = 1.5 Hz, 2H), 8.37 (s, 1H), 8.24 (dd, J = 7.6, 1.9 Hz, 1H), 7.66-7.27 (m, 3H), 5.14 (dd, J = 10.0, 6.8 Hz, 2H), 3.35-3.30 (m, 1H), 2.90 (d, J = 12.8 Hz, 2H), 2.54 (s, 1H), 2.46 (d, J = 12.2 Hz, 2H), 1.19 (s, 3H). |
| 186 | 489.10 | 1H NMR (400 MHz, DMSO-d6) δ 9.31 (s, 1H), 9.17 (d, J = 7.5 Hz, 1H), 8.90 (d, J = 6.4 Hz, 1H), 8.42 (d, J = 8.4, 2.2 Hz, 1H), 8.24 (dd, J = 8.0, 1.6 Hz, 1H), 7.86-7.72 (m, 1H), 7.69-7.38 (m, 3H), 7.35 (t, J = 8.0 Hz, 1H), 5.18 (d, J = 6.7 Hz, 1H), 4.80 (t, J = 6.5 Hz, 1H), 3.32-3.24 (m, 1H), 2.64-2.55 (m, 2H), 2.44 (d, J = 13.0 Hz, 1H), 2.22-2.10 (m, 2H), 2.09-2.01 (m, 1H), 1.88-1.78 (m, 1H) |
| 187 | 522.25 | 1H NMR (400 MHz, DMSO-d6) δ 9.14 (s, 2H), 8.84 (d, J = 7.3 Hz, 1H), 8.22 (dd, J = 8.0, 1.6 Hz, 1H), 7.86-7.55 |

| Ex. | LCMS [M + H]+ | 1H NMR (ppm) |
|---|---|---|
| 188 | 572.15 | (m, 2H), 7.45-7.24 (m, 3H), 5.06 (dd, J = 23.1, 6.8 Hz, 2H), 4.23-4.10 (m, 1H), 3.29 (dt, J = 13.5, 6.9Hz,1H), 2.94-2.82 (m, 2H), 2.54 (m, 1H), 2.18 (s, 2H) 1H NMR (400 MHz, DMSO-$d_6$) δ 9.71 (dd, J = 7.1, 1.0 Hz, 1H), 8.89 (q, J = 1.7 Hz, 1H), 8.24 (dd, J = 7.9, 1.7 Hz, 1H), 8.12 (dt, J = 12.1, 1.4 Hz, 1H), 7.73-7.17 (m, 3H), 5.12 (dd, J = 10.4, 6.8 Hz, 2H), 3.34-3.26 (m, 1H), 2.89 (dt, J = 10.8, 2.1 Hz, 2H), 2.54 (s, 1H), 2.27 (d, J = 12.0 Hz, 2H), 1.00 (s, 3H) |
| 189 | 554.25 | 1H NMR (400 MHz, DMSO-$d_6$) δ 9.24 (dd, J = 7.5, 1.1 Hz, 1H), 9.14 (t, J = 1.8 Hz, 1H), 8.35 (dd, J = 12.3, 1.8 Hz, 1H), 8.25 (dd, J = 8.0, 1.6 Hz, 1H), 7.84-7.24 (m, 4H), 5.12 (d, J = 6.8 Hz, 2H), 3.33-3.26 (m, 1H), 2.97-2.81 (m, 2H), 2.53 (d, J = 7.6 Hz, 1H), 2.26 (d, J = 12.3 Hz, 2H) |
| 190 | 545.20 | 1H NMR (400 MHz, DMSO-$d_6$) δ 8.87 (d, J = 6.6 Hz, 1H), 8.76 (d, J = 7.4 Hz, 1H), 8.71 (t, J = 1.8 Hz, 1H), 8.19 (dd, J = 8.0, 1.5 Hz, 1H), 8.05 (dd, J = 12.0, 1.9 Hz, 1H), 7.83-7.59 (m, 2H), 7.45-7.30 (m, 2H), 7.24 (dd, J = 7.4, 2.1 Hz, 1H), 5.07 (d, J = 6.6 Hz, 1H), 4.79 (t, J = 6.6 Hz, 1H), 3.24 (m, 1H), 2.85-2.77 (m, 2H), 2.68-2.60 (m, 2H), 2.43 (d, J = 13.0 Hz, 1H), 1.35 (s, 3H) |
| 191 | 521.10 | 1H NMR (400 MHz, DMSO-$d_6$) δ 9.23 (d, J = 6.2 Hz, 1H), 9.10 (d, J = 1.7 Hz, 2H), 8.87 (d, J = 6.5 Hz, 1H), 8.20 (dd, J = 8.0, 1.5 Hz, 1H), 7.60-7.53 (m, 3H), 7.37 (m., 1H), 6.03 (s, 1H), 5.08 (d, J = 6.6 Hz, 1H), 4.81 (t, J = 6.6 Hz, 1H), 3.28-3.23 (m, 1H), 3.19 (s, 2H), 2.44 (d, J = 12.9 Hz, 1H), 1.65 (s, 3H) |
| 192 | 521.25 | 1H NMR (400 MHz, DMSO-$d_6$) δ 9.22 (d, J = 6.2 Hz, 1H), 9.09 (d, J = 1.7 Hz, 2H), 8.87 (d, J = 6.6 Hz, 1H), 8.20 (dd, J = 8.0, 1.5 Hz, 1H), 7.79-7.32 (m, 4H), 6.03 (s, 1H), 5.07 (d, J = 6.6 Hz, 1H), 4.81 (t, J = 6.6 Hz, 1H), 3.30-3.21 (m, 1H), 3.21-3.17 (m, 2H), 2.45-2.41 (m, 1H), 1.65 (s, 3H) |
| 193 | 523.10 | 1H NMR (400 MHz, DMSO-$d_6$) δ 9.50 (s, 2H), 9.28 (d, J = 8.0 Hz, 1H), 8.25-8.17 (m, 1H), 7.74-7.33 (m, 4H), 5.11 (d, J = 4.0 Hz, 2H), 4.50 (s, 1H), 4.11-4.03 (m, 2H), 3.99-3.94 (m, 1H), 3.80 (d, J = 8.0 Hz, 1H), 3.34-3.29 (m, 1H), 2.63-2.53 (m, 2H), 2.11-2.06 (m, 1H) |
| 194 | 523.15 | 1H NMR (400 MHz, DMSO-$d_6$) δ 9.50 (s, 2H), 9.27 (d, J = 8.0 Hz, 1H), 8.25-8.23 (m, 1H), 7.74-7.71 (m, 1H), 7.53-7.32 (m, 3H), 5.11 (d, J = 4.0 Hz, 2H), 4.11-4.02 (m, 2H), 3.98-3.93 (m, 1H), 3.78 (d, J = 8.0 Hz, 1H), 3.34-3.27 (m, 1H), 2.62-2.53 (m, 2H), 2.09-2.03 (m, 1H) |
| 195 | 528.05 | 1H NMR (400 MHz, DMSO-$d_6$) δ 9.16 (s, 2H), 8.87 (d, J = 6.6 Hz, 1H), 8.80 (dd, J = 7.4, 0.9 Hz, 1H), 8.19 (dd, J = 8.0, 1.5 Hz, 1H), 7.82-7.59 (m, 2H), 7.46-7.26 (m, 3H), 5.08 (d, J = 6.6 Hz, 1H), 4.80 (t, J = 6.5 Hz, 1H), 3.26 (m, 1H), 2.86-2.77 (m, 2H), 2.67-2.58 (m, 2H), 2.44 (d, J = 13.0 Hz, 1H), 1.46 (s, 3H) |
| 196 | 507.20 | 1H NMR (400 MHz, DMSO-$d_6$) δ 9.23 (d, J = 6.2 Hz, 1H), 9.10 (d, J = 1.7 Hz, 2H), 8.88 (d, J = 6.6 Hz, 1H), 8.20 (dd, J = 7.9, 1.5 Hz, 1H), 7.79-7.23 (m, 4H), 5.77 (s, 2H), 5.08 (d, J = 6.6 Hz, 1H), 4.81 (t, J = 6.6 Hz, 1H), 3.30-3.21 (m, 1H), 2.74-2.63 (m, 2H), 2.44 (d, J = 12.9 Hz, 1H), 2.30-2.17 (m, 2H), 2.16-2.02 (m, 2H), 2.05-1.91 (m, 1H) |
| 197 | 519.40 | 1H NMR (400 MHz, DMSO-$d_6$) δ 9.15 (s, 2H), 8.87 (d, J = 6.6 Hz, 1H), 8.80 (d, J = 7.4 Hz, 1H), 8.19 (dd, J = 8.0, 1.5 Hz, 1H), 7.81-7.26 (m, 5H), 5.08 (d, J = 6.6 Hz, 1H), 4.80 (t, J = 6.6 Hz, 1H), 3.28-3.24 (m, 1H), 2.88-2.80 (m, 2H), 2.61-2.57 (m, 1H), 2.28-2.19 (m, 2H), 1.18 (s, 3H) |
| 198 | 526.15 | 1H NMR (400 MHz, DMSO-$d_6$) δ 8.87 (d, J = 6.6 Hz, 1H), 8.71 (d, J = 7.3 Hz, 1H), 8.22-8.18 (m, 1H), 7.74-7.65 (m, 1H), 7.57-7.23 (m, 5H), 6.90-6.86 (m, 1H), 5.04 (d, J = 6.6 Hz, 1H), 4.79 (t, J = 6.5 Hz, 1H), 3.27-3.24 (m, 1H), 2.43 (d, J = 12.9 Hz, 1H), 2.28 (s, 3H), 1.74 (d, J = 13.6 Hz, 6H) |
| 199 | 524.10 | 1H NMR (400 MHz, DMSO-$d_6$) δ 9.22 (dd, J = 6.8, 2.4 Hz, 1H), 9.06-9.01 (m, 1H), 8.95 (s, 2H), 8.23 (d, J = 8.0, 1.2 Hz, 1H), 7.99 (d, J = 7.8 Hz, 1H), 7.50 (t, J = 73.6 Hz, 1H), 7.40-7.31 (m, 2H), 5.11-5.02 (m, 2H), 3.30 (q, J = 6.8 Hz, 1H), 2.64-2.58 (m, 2H), 2.10-2.07 (m, 3H), 1.87-1.73 (m, 1H) |
| 200 | 563.20 | 1H NMR (400 MHz, DMSO-$d_6$) δ 9.23 (d, J = 6.8 Hz, 1H), 9.03 (d, J = 1.6 Hz, 1H), 8.96 (dd, J = 2.8, 1.6 Hz, 1H), 8.23 (dd, J = 8.0, 1.2 Hz, 1H), 8.00 (d, J = 7.6 Hz, 1H), 7.50 (t, J = 73.6 Hz, 1H), 7.39-7.31 (m, 2H), 5.10 (d, J = 6.8 Hz, 1H), 5.03 (d, J = 6.6 Hz, 1H), 3.33-3.31 (m, 1H), 2.95-2.90 (m, 2H), 2.81-2.73 (m, 2H), 2.64-2.56 (m, 1H), 1.47 (s, 3H) |
| 201 | 550.20 | 1H NMR (400 MHz, DMSO-$d_6$) δ 8.91 (s, 2H), 8.72 (s, 1H), 8.36 (s, 1H), 8.21 (d, J = 7.6, 2.0 Hz, 1H), 7.47 (t, J = 73.6 Hz, 1H), 7.37-7.26 (m, 3H), 5.06 (d, J = 6.8 Hz, 1H), 4.97 (d, J = 6.8 Hz, 1H), 3.31-3.24 (m, 1H), 2.85 (d, J = 12.0 Hz, 2H), 2.50-2.45 (m, 1H), 2.29-2.22 (m, 2H), 2.18 (s, 3H), 1.21 (s, 3H) |
| 202 | 491.15 | 1H NMR (400 MHz, DMSO-$d_6$) δ 8.87 (d, J = 6.6 Hz, 1H), 8.75 (dd, J = 7.4, 0.9 Hz, 1H), 8.26-8.22 (m, 1H), 8.19 (dd, J = 8.1, 1.4 Hz, 1H), 7.82-7.60 (m, 2H), 7.41 (d, J = 8.0Hz, 1H), 7.37-7.31 (m, 2H), 7.25 (dd, J = 7.5, 2.1 Hz, 1H), 7.23-7.19 (m, 1H), 5.61-5.60 (m, 1H), 5.08 (d, J = 6.6 Hz, 1H), 4.94-4.90(m, 2H), 4.79 (t, J = 6.6 Hz, 1H), 4.60 (dd, J = 7.5, 5.2 Hz, 2H), 3.28-3.18 (m, 1H), 2.47-2.41 (m, 1H) |
| 203 | 488.15 | 1H NMR (400 MHz, DMSO-$d_6$) δ 8.88 (dd, J = 12.4, 4.5 Hz, 2H), 8.75 (dd, J = 7.3, 0.9 Hz, 1H), 8.20 (dd, J = 8.0, 1.5 Hz, 1H), 8.11 (dd, J = 8.3, 2.4 Hz, 1H), 7.83-7.60 (m, 3H), 7.45-7.37 (m, 1H), 7.34 (t, J = 8.1 Hz, 1H), 7.22 (dd, J = 7.4, 2.1 Hz, 1H), 5.08 (d, J = 6.6 Hz, 1H), 4.79 (t, J = 6.6Hz, 1H), 3.32-3.23 (m, 1H), 2.60-2.59 (m, 2H), 2.43 (d, J = 12.9 Hz, 1H), 2.17-2.16 (m, 2H), 2.05-2.03 (m, 1H), 1.92-1.78 (m, 1H) |
| 204 | 523.10 | 1H NMR (400 MHz, DMSO-$d_6$) δ 9.49 (s, 2H), 9.28 (d, J = 7.5 Hz, 1H), 8.25 (dd, J = 7.9, 1.7 Hz, 1H), 7.78-7.29 (m, 4H), 5.12 (d, J = 6.8 Hz, 2H), 4.28-4.15 (m, 1H), 3.32 (m, 1H), 2.88 (m, 2H), 2.54 (m, 1H), 2.23 (s, 2H), 1H), 2.23 (s, 2H) |
| 205 | 541.15 | 1H NMR (400 MHz, DMSO-$d_6$) δ 9.73 (d, J = 6.9 Hz, 1H), 9.26 (d, J = 1.6 Hz, 2H), 8.24 (dd, J = 7.7, 1.8 Hz, 1H), 7.68-7.24 (m, 3H), 5.13 (dd, J = 8.8, 6.8 Hz, 2H), 4.21 (m, 1H), 3.32 (m, 1H), 2.89 |

| Ex. | LCMS [M + H]+ | 1H NMR (ppm) |
|---|---|---|
| | | (m, 2H), 2.53 (s, 1H), 2.28-2.14 (m, 2H) |
| 206 | 526.10 | 1H NMR (400 MHz, DMSO-d6) δ 9.26 (d, J = 6.0 Hz, 1H), 9.10 (s, 2H), 8.23 (dd, J = 8.0, 1.6 Hz, 1H), 7.72-7.32 (m, 4H), 5.11 (d, J = 6.8 Hz, 1H), 5.03-5.00 (m, 3H), 4.64 (d, J = 5.6 Hz, 2H), 3.34-3.26 (m, 2H) |
| 207 | 506.25 | 1H NMR (400 MHz, DMSO-d6) δ 9.17 (s, 1H), 8.98 (s, 1H), 8.81 (dd, J = 7.6, 0.8 Hz, 1H), 8.23 (d, J = 8.0, 1.2 Hz, 1H), 8.16 (dd, J = 2.0, 0.8 Hz, 1H), 7.77-7.42 (m, 2H), 7.40-7.32 (m, 2H), 5.07 (dd, J = 15.6, 6.8 Hz, 2H), 3.15-3.28 (m, 1H), 2.65-2.56 (m, 2H), 2.55-2.52 (m, 1H), 2.18-1.96 (m, 3H), 1.87-1.73 (m, 1H) |
| 208 | 536.20 | 1H NMR (400 MHz, DMSO-d6) δ 9.15 (s, 2H), 8.83 (dd, J = 7.4, 0.9 Hz, 1H), 8.22 (d, J = 7.9, 1.5 Hz, 1H), 7.79-7.40 (m, 2H), 7.38 (d, J = 7.9 Hz, 1H), 7.36-7.30 (m, 2H), 5.66 (s, 1H), 5.05 (dd, J = 22.8, 6.8 Hz, 2H), 3.33-3.23 (m, 1H), 2.87-2.79 (m, 2H), 2.53 (s, 1H), 2.20-2.13 (m, 2H), 2.07 (s, 1H), 1.07 (s, 3H) |
| 209 | 536.20 | 1H NMR (400 MHz, DMSO-d6) δ 9.15 (s, 1H), 8.94 (s, 1H), 8.79 (d, J = 7.2 Hz, 1H), 8.22 (d, J = 8.0 Hz, 1H), 8.15 (d, J = 2.0 Hz, 1H), 7.76-7.41 (m, 2H), 7.39-7.29 (m, 2H), 5.08 (d, J = 6.8 Hz, 1H), 5.04 (d, J = 6.8 Hz, 1H), 3.39-3.32 (m, 1H), 2.78 (d, J = 12.0 Hz, 2H), 2.18 (d, J = 12.0 Hz, 2H), 1.16 (s, 3H) |
| 210 | 545.25 | 1H NMR (400 MHz, DMSO-d6) δ 9.16 (s, 1H), 8.95 (s, 1H), 8.78 (d, J = 7.6 Hz, 1H), 8.22 (d, J = 8.4 Hz, 1H), 8.17 (d, J = 2.0 Hz, 1H), 7.72-7.40 (m, 2H) 7.38-7.29 (m, 2H), 5.07 (d, J = 6.8 Hz, 1H), 5.04 (d, J = 6.8 Hz, 1H),3.36-3.25 (m, 1H), 2.80-2.72 (m, 2H), 2.64-2.56 (m, 2H), 2.50-2.47 (m, 1H), 1.46 (s, 3H) |
| 211 | 506.25 | 1H NMR (400 MHz, Methanol-d4) δ 9.04-8.97 (m, 2H), 8.64-8.61 (m, 1H), 8.57 (m, 1H), 8.30-8.28 (m, 1H), 7.88-7.81 (m, 1H), 7.41-7.36 (m, 1H), 7.35-6.97 (m, 1H), 5.18-5.16 (m, 1H), 5.05-5.03 (m, 1H), 2.71-2.67 (m, 2H), 2.63-2.58 (m, 1H), 2.48-2.40 (m, 2H), 2.25-2.15 (m, 1H), 1.98-1.88 (m, 1H) |
| 212 | 527.15 | 1H NMR (400 MHz, DMSO-d6) δ 8.91-8.84 (m, 2H), 8.74 (dd, J = 7.4, 0.9 Hz, 1H), 8.19 (dd, J = 8.0, 1.5 Hz, 1H), 8.10 (dd, J = 8.3, 2.4 Hz, 1H), 7.81-7.29 (m, 5H), 7.21 (dd, J = 7.4, 2.1 Hz, 1H), 5.07 (d, J = 6.6Hz, 1H), 4.78 (t, J = 6.6 Hz, 1H), 3.26 (td, J = 12.7, 6.1 Hz, 1H), 2.79-2.71 (m, 2H), 2.60-2.53 (m, 3H), 2.43 (d, J = 13.0 Hz, 1H), 1.46 (s, 3H) |
| 213 | 564.20 | 1H NMR (400 MHz, DMSO-d6) δ 9.74 (d, J = 6.9 Hz, 1H), 9.28 (d, J = 1.5 Hz, 2H), 8.24 (dd, J = 7.8, 1.8 Hz, 1H), 7.65-7.26 (m, 3H), 5.13 (dd, J = 9.7, 6.8 Hz, 2H), 3.35 (d, J = 7.0 Hz, 1H), 3.30 (d, J = 6.8 Hz, 1H), 2.85-2.74 (m, 2H), 2.64-2.54 (m, 3H), 1.46 (s, 3H) |
| 214 | 554.20 | 1H NMR (400 MHz, DMSO-d6) δ 9.22 (dd, J = 6.8, 2.0 Hz, 1H), 9.02 (d, J = 1.6 Hz, 1H), 8.94 (t, J = 2.0 Hz, 1H), 8.23 (dd, J = 8.0, 1.6 Hz, 1H), 7.99 (d, J = 7.6 Hz, 1H), 7.59 (d, J = 73.6 Hz, 1H), 7.50-7.31 (m, 2H), 5.10 (d, J = 7.2, 2.0 Hz, 1H), 5.03 (d, J = 6.4 Hz, 1H), 3.33-3.30 (m, 1H), 2.83-2.75 (m, 2H), 2.50-2.49 (m, 1H), 2.25-2.16 (m, 2H), 1.18 (s, 3H) |
| 215 | 551.30 | 1H NMR (400 MHz, DMSO-d6) δ 9.15-9.10 (m, 2H), 8.29-8.23 (m, 2H), 7.56-7.19 (m, 3H), 5.11 (d, J = 6.8 Hz, 1H), 5.06 (d, J = 6.8 Hz, 1H), 3.32-3.27 (m, 1H), 2.87-2.84 (m, 2H), 2.51-2.49 (m, 1H), 2.36-2.30 (m, 5H), 1.24-1.22 (m, 3H) |
| 216 | 521.20 | 1H NMR (400 MHz, DMSO-d6) δ 9.15-9.10 (m, 3H), 8.29 (s, 1H), 8.24 (dd, J = 7.6, 2.4 Hz, 1H), 7.56-7.19 (m, 3H), 5.11 (d, J = 6.8 Hz, 1H), 5.07 (d, J = 6.8, Hz, 1H), 3.40-3.27 (m, 2H), 2.66-2.63 (m, 2H), 2.51-2.49 (m, 1H), 2.35 (s, 3H), 2.24-2.20 (m, 2H), 2.08-2.02 (m, 1H), 1.94-1.87 (m, 1H) |
| 217 | 528.15 | 1H NMR (400 MHz, DMSO-d6) δ 9.30 (dd, J = 2.4, 0.8 Hz, 1H), 9.16 (d, J = 7.5 Hz, 1H), 8.89 (d, J = 6.4 Hz, 1H), 8.50 (dd, J = 8.4, 2.4 Hz, 1H), 8.23 (dd, J = 7.9, 1.6 Hz, 1H), 7.79-7.70 (m, 1H), 7.64 (d, J = 7.5 Hz, 1H), 7.34 (m, 3H), 5.17 (d, J = 6.7 Hz, 1H), 4.79 (t, J = 6.5 Hz, 1H), 3.26 (q, J = 6.8 Hz, 1H), 2.80-2.70 (m, 2H), 2.58 (m, 3H), 2.42 (d, J = 13.0 Hz, 1H), 1.45 (s, 3H) |
| 218 | 537.20 | 1H NMR (400 MHz, DMSO-d6) δ 9.50 (s, 2H), 9.28 (d, J = 7.4 Hz, 1H), 8.25 (dd, J = 7.9, 1.7 Hz, 1H), 7.77-7.23 (m, 4H), 5.13 (d, J = 6.8 Hz, 1H), 3.32 (dt, J = 13.6, 6.9 Hz, 1H), 2.95-2.74 (m, 2H), 2.54 (s, 1H), 2.27 (dd, J = 12.8, 3.5 Hz, 2H), 1.19 (d, J = 1.5 Hz, 3H). |
| 219 | 520.10 | 1H NMR (400 MHz, DMSO-d6) δ 9.62 (d, J = 1.4 Hz, 1H), 9.34 (s, 2H), 8.92 (d, J = 6.7 Hz, 1H), 8.20 (dd, J = 8.1, 1.4 Hz, 1H), 7.87 (d, J = 1.5 Hz, 1H), 7.82-7.33 (m, 3H), 5.68 (s, 1H), 5.11 (d, J = 6.7 Hz, 1H), 4.98 (s, 1H), 4.85 (t, J = 6.6 Hz, 1H), 3.27 (dt, J = 13.2, 6.5 Hz, 1H), 2.94-2.87 (m, 2H), 2.48 (d, J = 13.0 Hz, 1H), 2.44-2.38 (m, 2H), 1.08 (s, 3H) |
| 220 | 519.15 | 1H NMR (400 MHz, DMSO-d6) δ 9.29 (d, J = 2.3 Hz, 1H), 9.16 (d, J = 7.5 Hz, 1H), 8.90 (d, J = 6.4 Hz, 1H), 8.48 (dd, J = 8.3, 2.3 Hz, 1H), 8.33-8.26 (m, 1H), 8.24 (d, J = 8.0, 1.5 Hz, 1H), 7.80-7.51 (m, 3H), 7.37 (dt, J = 19.9, 8.0 Hz, 2H), 5.18 (d, J = 6.7 Hz, 1H), 4.80 (s, 1H), 3.30-3.17 (m, 1H), 2.78 (d, J = 12.5 Hz, 2H), 2.43 (d, J = 13.0 Hz, 1H), 2.19 (d, J = 11.9 Hz, 2H), 2.08 (s, 1H), 1.17 (s, 3H) |
| 221 | 524.25 | 1H NMR (400 MHz, DMSO-d6) δ 9.24 (d, J = 7.5 Hz, 1H), 9.14 (t, J = 1.8 Hz, 1H), 8.34 (dd, J = 12.3, 1.8 Hz, 1H), 8.25 (dd, J = 7.9, 1.6 Hz, 1H), 7.75-7.30 (m, 4H), 5.12 (dd, J = 6.7, 1.0 Hz, 2H), 3.32 (dt, J = 13.7, 7.0 Hz, 1H), 2.67 (d, J = 6.7 Hz, 2H), 2.54 (s, 1H), 2.17-2.04 (m, 3H), 1.68 (td, J = 10.1, 9.2, 5.2 Hz, 1H) |
| 222 | 536.25 | 1H NMR (400 MHz, DMSO-d6) δ 9.17 (d, J = 1.7 Hz, 2H), 8.85 (dd, J = 7.4, 0.9 Hz, 1H), 8.22 (dd, J = 8.0, 1.6 Hz, 1H), 7.81-7.53 (m, 2H), 7.46-7.13 (m, 3H), 5.06 (dd, J = 24.0, 6.8 Hz, 2H), 3.31-3.25 (m, 1H), 2.85 (d, J = 12.4 Hz, 2H), 2.54 (s, 1H), 2.32 (d, J = 12.4 Hz, 2H), 1.22 (d, J = 4.0 Hz, 3H) |
| 223 | 538.10 | 1H NMR (400 MHz, DMSO-d6) δ 9.70 (d, J = 6.9 Hz, 1H), 9.27 (d, J = 1.5 Hz, 2H), 8.91 (d, J = 6.5 Hz, 1H), 8.29-8.19 (m, 1H), 7.47 (d, J = 4.7 Hz, 1H), 7.43-7.27 (m, 2H), 5.18 (d, J = 6.7 Hz, 1H), 4.83 (t, J = 6.5 Hz, 1H), 3.28 (q, J = 6.7 Hz, 1H), 2.89-2.81 (m, 2H), 2.44 (d, J = 13.0 Hz, 1H), 2.25 (d, J = 12.5 Hz, 2H), 1.18 (s, 3H) |

| Ex. | LCMS [M + H]+ | 1H NMR (ppm) |
|---|---|---|
| 224 | 518.10 | 1H NMR (400 MHz, DMSO-d$_6$) δ 8.92-8.83 (m, 2H), 8.74 (dd, J = 7.4, 0.9 Hz, 1H), 8.20 (dd, J = 8.0, 1.5 Hz, 1H), 8.07 (dd, J = 8.3, 2.5 Hz, 1H), 7.79-7.28 (m, 5H), 7.22 (dd, J = 7.4, 2.1 Hz, 1H), 5.07 (d, J = 6.5 Hz, 1H), 4.79 (t, J = 6.6 Hz, 1H), 3.22 (s, 1H), 2.81-2.73 (m, 2H), 2.43 (d, J = 13.0 Hz, 1H), 2.22-2.12 (m, 2H), 1.17 (s, 3H) |
| 225 | 558.15 | 1H NMR (400 MHz, DMSO-d$_6$) δ 9.71 (d, J = 7.0 Hz, 1H), 8.90-8.85 (m, 1H), 8.27-8.23 (m, 1H), 8.13-8.09 (m, 1H), 7.68-7.28 (m, 3H), 5.15-5.11 (m, 2H), 5.05 (d, J = 5.8 Hz, 1H), 3.73-3.67 (m, 1H), 3.14-3.10 (m, 2H), 2.54 (s, 1H), 2.13-2.04 (m, 2H) |
| 226 | 467.20 | 1H NMR (400 MHz, DMSO-d$_6$) δ 9.21 (s, 2H), 8.81 (d, J = 7.4 Hz, 1H), 7.94 (dd, J = 7.7, 1.7 Hz, 1H), 7.73 (dd, J = 2.2, 1.0 Hz, 1H), 7.28 (dd, J = 7.4, 2.1 Hz, 1H), 7.24-7.14 (m, 2H), 5.07 (dd, J = 16.9, 6.8 Hz, 2H), 4.08 (s, 3H), 3.28 (s, 3H), 3.26-3.18 (m, 1H), 2.63 (d, J = 13.7 Hz, 2H), 2.46 (s, 0H), 2.19 (q, J = 9.2 Hz, 2H), 2.04 (dp, J = 14.7, 4.9 Hz, 1H), 1.89 (p, J = 8.3 Hz, 1H) |
| 227 | 550.20 | 1H NMR (400 MHz, DMSO-d$_6$) δ 9.80 (d, J = 6.8 Hz, 1H), 9.37 (d, J = 1.5 Hz, 2H), 8.79 (s, 3H), 8.25 (dd, J = 7.8, 1.8 Hz, 1H), 7.66-7.21 (m, 3H), 5.16 (d, J = 6.9 Hz, 1H), 5.12 (d, J = 6.8 Hz, 1H), 3.68 (p, J = 9.2 Hz, 1H), 3.36 (d, J = 7.1 Hz, 0.5H), 3.30 (s, 0.5H), 3.04 (d, J = 9.4 Hz, 4H), 2.55 (s, 1H). |
| 228 | 561.20 | 1H NMR (400 MHz, DMSO-d$_6$) δ 9.74 (d, J = 6.9 Hz, 1H), 9.30 (d, J = 1.5 Hz, 2H), 8.24 (dd, J = 7.8, 1.8 Hz, 1H), 7.74-7.16 (m, 3H), 5.13 (t, J = 7.3 Hz, 2H), 3.37-3.33 (m, 1H), 3.32-3.25 (m, 1H), 2.85-2.61 (m, 4H), 2.54 (s, 1H) |
| 229 | 537.30 | HNMR: 1H NMR (400 MHz, Methanol-d$_4$) δ 9.16 (s, 2H), 8.66 (dt, J = 7.5, 1.6 Hz, 1H), 8.42-8.36 (m, 1H), 7.82-7.77 (m, 1H), 7.40-7.00 (m, 3H), 5.29 (d, J = 6.7 Hz, 1H), 4.92 (m, 1H), 4.60 (s, 1H), 3.42-3.35 (m, 1H), 3.05 (d, J = 13.1 Hz, 2H), 2.60 (d, J = 13.1 Hz, 1H), 2.48 (d, J = 13.1 Hz, 3H), 1.51 (s, 3H) |
| 230 | 560.20 | 1H NMR (400 MHz, DMSO-d$_6$) δ 9.23 (d, J = 7.3 Hz, 1H), 8.92 (s, 1H), 8.24 (dd, J = 7.2, 2.4 Hz, 1H), 7.61-7.18 (m, 4H), 5.11 (dd, J = 17.3, 6.8 Hz, 2H), 3.30 (d, J = 6.8 Hz, 1H), 2.98-2.76 (m, 2H), 2.66 (s, 3H), 2.64-2.58 (m, 2H), 2.54 (s, 1H), 1.46 (s, 3H) |
| 231 | 558.24 | 1H NMR (400 MHz, DMSO-d$_6$) δ 8.79 (d, J = 7.2 Hz, 1H), 8.69 (s, 1H), 8.23 (dd, J = 8.0, 1.6 Hz, 1H), 7.48 (t, J = 73.6 Hz, 1H), 7.40-7.31 (m, 3H), 7.00 (dd, J = 7.2, 2.0 Hz, 1H), 5.09 (d, J = 6.8 Hz, 1H), 4.99 (d, J = 6.8 Hz, 1H), 3.30-3.27 (m, 1H), 2.84-2.76 (m, 2H), 2.64-2.56 (m, 2H), 2.55-2.52 (m, 1H), 2.49 (s, 3H), 1.47 (s, 3H) |
| 232 | 546.30 | 1H NMR (400 MHz, DMSO-d$_6$) δ 9.57 (s, 2H), 9.31 (d, J = 7.5 Hz, 1H), 8.25 (dd, J = 7.9, 1.7 Hz, 1H), 7.78-7.71 (m, 1H), 7.55-7.32 (m, 3H), 5.14 (d, J = 6.8 Hz, 2H), 3.32-3.30 (m, 1H), 2.98-2.88 (m, 2H), 2.81-2.73 (m, 2H), 2.55 (s, 1H), 1.14 (s, 3H) |
| 233 | 479.20 | 1H NMR (400 MHz, DMSO-d$_6$) δ 9.32 (s, 2H), 8.92-8.77 (m, 3H), 8.74 (d, J = 6.7 Hz, 1H), 7.94 (dd, J = 8.2, 1.2 Hz, 1H), 7.61 (dd, J = 2.2, 1.0 Hz, 1H), 7.51 (dd, J = 8.1, 1.3 Hz, 1H), 7.30 (dd, J = 7.5, 2.1 Hz, 1H), 7.25 (t, J = 8.1 Hz, 1H), 5.06 (d, J = 6.5 Hz, 1H), 4.78 (t, J = 6.7 Hz, 1H), 4.09 (tt, J = 5.9, 2.9 Hz, 1H), 3.18 (dt, J = 13.0, 6.7 Hz, 1H), 2.80-2.70 (m, 2H), 2.57 (s, 2H), 2.39 (d, J = 12.8 Hz, 1H), 2.29-2.08 (m, 2H), 1.07 (dt, J = 10.1, 4.6 Hz, 1H), 1.01-0.84 (m, 3H) |
| 234 | 503.20 | 1H NMR (400 MHz, DMSO-d$_6$) δ 9.74 (d, J = 6.9 Hz, 1H), 9.28 (d, J = 1.5 Hz, 2H), 8.24 (dd, J = 7.7, 1.8 Hz, 1H), 7.70-7.20 (m, 3H), 5.13 (dd, J = 9.3, 6.8 Hz, 2H), 3.34 (d, J = 11.6 Hz, 1H), 3.31-3.21 (m, 2H), 3.05-2.94 (m, 3H), 2.61-2.53 (m, 3H) |
| 235 | 547.05 | 1H NMR (400 MHz, DMSO-d$_6$) δ 9.71 (d, J = 6.9 Hz, 1H), 9.28 (d, J = 1.6 Hz, 2H), 8.91 (d, J = 6.4 Hz, 1H), 8.23 (dd, J = 7.9, 1.6 Hz, 1H), 7.73-7.13 (m, 3H), 5.18 (d, J = 6.7 Hz, 1H), 4.83 (t, J = 6.5 Hz, 1H), 3.29-3.23 (m, 1H), 2.85-2.77 (m, 2H), 2.66-2.60 (m, 2H), 2.44 (d, J = 13.0 Hz, 1H), 1.47 (s, 3H) |
| 236 | 546.25 | 1H NMR (400 MHz, DMSO-d$_6$) δ 9.55 (s, 2H), 9.31 (d, J = 7.4 Hz, 1H), 8.25 (dd, J = 7.9, 1.7 Hz, 1H), 7.82-7.68 (m, 1H), 7.56-7.28 (m, 3H), 5.14 (dd, J = 6.8, 1.3 Hz, 2H), 3.33-3.29(m, 1H), 2.89-2.73 (m, 4H), 2.55 (s, 1H), 2.21 (s, 2H), 1.51 (s, 3H) |
| 237 | 560.20 | 1H NMR (400 MHz, DMSO-d$_6$) δ 9.15 (d, J = 1.2 Hz, 1H), 9.09 (s, 2H), 8.23 (dd, J = 7.3, 2.2 Hz, 1H), 7.56-7.18 (m, 3H), 5.10 (d, J = 6.9 Hz, 1H), 5.06 (d, J = 6.7 Hz, 1H), 3.32-3.24 (m, 1H), 2.84-2.76 (m, 2H), 2.65-2.57 (m, 2H), 2.55-2.53 (m, 1H), 2.33 (d, J = 1.0 Hz, 3H), 1.46 (s, 3H) |
| 238 | 493.30 | 1H NMR (400 MHz, DMSO-d$_6$) δ 9.39 (s, 2H), 9.24 (d, J = 7.5 Hz, 1H), 8.25 (dd, J = 7.8, 1.7 Hz, 1H), 7.73-7.31 (m, 4H), 5.11 (d, J = 6.7 Hz, 2H), 3.33-3.25 (m, 1H), 2.75 (s, 2H), 2.53 (s, 1H), 1.39 (q, J = 3.4 Hz, 2H), 1.15 (q, J = 3.5 Hz, 2H) |
| 239 | 511.25 | 1H NMR (400 MHz, DMSO-d$_6$) δ 9.70 (d, J = 6.9 Hz, 1H), 9.17 (d, J = 1.6 Hz, 2H), 8.24 (dd, J = 7.7, 2.0 Hz, 1H), 7.69-7.23 (m, 3H), 5.12 (dd, J = 9.1, 6.8 Hz, 2H), 3.29 (d, J = 6.9 Hz, 2H), 3.04 (s, 2H), 2.53 (s, 1H), 1.41 (q, J = 3.5 Hz, 2H), 1.18 (q, J = 3.6 Hz, 2H) |
| 240 | 563.25 | 1H NMR (400 MHz, DMSO-d$_6$) δ 9.25 (d, J = 6.2 Hz, 1H), 9.04 (d, J = 1.7 Hz, 2H), 8.22 (dd, J = 7.9, 1.6 Hz, 1H), 7.76-7.23 (m, 4H), 5.10 (d, J = 6.9 Hz, 1H), 5.01 (d, J = 6.6 Hz, 1H), 3.30-3.23 (m, 1H), 2.84-2.76 (m, 2H), 2.65-2.57 (m, 2H), 2.53 (s, 1H), 1.46 (s, 3H) |
| 241 | 520.25 | 1H NMR (400 MHz, DMSO-d$_6$) δ 8.79 (dd, J = 7.3, 0.9 Hz, 1H), 8.68 (s, 1H), 8.29 (s, 1H), 8.23 (dd, J = 7.7, 1.8 Hz, 1H), 7.68-7.27 (m, 4H), 7.02 (dd, J = 7.3, 2.0 Hz, 1H), 5.09 (d, J = 6.9 Hz, 1H), 5.00 (d, J = 6.6 Hz, 1H), 3.29 (dt, J = 13.5, 6.9 Hz, 2H), 2.64 (ddt, J = 14.7, 8.7, 3.6Hz, 2H), 2.53 (s, 3H), 2.15 (d, J = 8.9 Hz, 1H), 2.08-1.79 (m, |
| 242 | 521.15 | 1H NMR (400 MHz, DMSO-d$_6$) δ 9.22 (d, J = 7.4 Hz, 1H), 8.89 (s, 1H), 8.24 (dd, J = 7.2, 2.4 Hz, 1H), 7.60-7.21 (m, 4H), 5.11 (dd, J = 14.9, 6.8 Hz, 2H), 3.29-3.27 (m, 1H), 2.67-2.65(m, 3 H), |

| Ex. | LCMS [M + H]+ | 1H NMR (ppm) |
|---|---|---|
| | | 2.63-56 (m, 2H), 2.53 (s, 1H), 2.15-2.04 (m, 2H), 2.04-1.90 (m, 1H), 1.78-1.82 (m, 1H) |
| 243 | 507.15 | 1H NMR (400 MHz, DMSO-d6) δ 9.40 (s, 2H), 9.25 (d, J = 7.4 Hz, 1H), 8.27-8.23 (m, 1H), 7.75-7.28 (m, 4H), 5.11 (d, J = 6.8 Hz, 2H), 3.33-3.25 (m, 1H), 3.01 (s, 1H), 2.53 (s, 1H), 2.38 (s, 3H), 1.40-1.33 (m, 2H), 1.19-1.12 (m, 2H) |
| 244 | 563.20 | 1H NMR δ 9.25 (d, J = 6.2 Hz, 1H), 9.07 (d, J = 1.7 Hz, 2H), 8.22 (dd, J = 8.0, 1.6 Hz, 1H), 7.85-7.12 (m, 4H), 5.10 (d, J = 6.9 Hz, 1H), 5.02 (d, J = 6.6 Hz, 1H), 3.32-3.22 (m, 3H), 2.53-2.50 (m, 1H), 2.34-2.26 (m, 2H), 1.73 (s, 3H). |
| 245 | 493.15 | 1H NMR (400 MHz, DMSO-d6) δ 9.63 (d, J = 1.4 Hz, 1H), 9.23 (s, 2H), 8.23 (dd, J = 8.0, 1.5 Hz, 1H), 7.83 (d, J = 1.5 Hz, 1H), 7.80-7.42 (m, 1H), 7.42-7.33 (m, 2H), 5.14 (d, J = 6.9 Hz, 1H), 5.04 (d, J = 6.7 Hz, 1H), 3.30-3.17 (m, 1H), 2.56 (d, J = 13.6 Hz, 1H), 1.37 (d, J = 3.3 Hz, 2H), 1.14 (q, J = 3.5 Hz, 2H) |
| 246 | 553.15 | 1H NMR (400 MHz, Methanol-d4) δ 8.72 (d, J = 1.6 Hz, 1H), 8.61 (m, 2H), 8.32 (dd, J = 8.2, 1.4 Hz, 1H), 7.94 (dd, J = 11.6, 1.9 Hz, 1H), 7.81 (d, J = 2.1 Hz, 1H), 7.54-7.00 (m, 4H), 5.18 (d, J = 6.6 Hz, 1H), 5.07 (d, J = 6.9 Hz, 1H), 3.42-3.36 (m, 1H), 3.14 (d, J = 13.2 Hz, 2H), 2.74-2.51 (m, 3H), 1.31 (s, 3H) |
| 247 | 508.20 | 1H NMR (400 MHz, DMSO-d6) δ 9.23 (d, J = 2.0 Hz, 1H), 9.00 (s, 1H), 8.80 (d, J = 8.0 Hz, 1H), 8.23-8.21 (m, 1H), 8.17 (s, 1H), 7.76-7.31 (m, 4H), 5.09-5.03 (m, 2H), 4.94 (d, J = 8.0 Hz, 2H), 4.62 (d, J = 8.0 Hz, 2H), 3.32-3.26 (m, 1H), 2.86 (s, 2H), 2.53 (s, 1H) |
| 248 | 506.10 | 1H NMR (400 MHz, DMSO-d6) δ 9.19 (s, 2H), 8.85 (dd, J = 7.4, 0.8 Hz, 1H), 8.23 (dd, J = 8.0, 1.5 Hz, 1H), 7.80-7.41 (m, 2H), 7.41-7.30 (m, 3H), 5.06 (dd, J = 22.4, 6.8 Hz, 2H), 3.29 (dt, J = 13.6, 6.9 Hz, 1H), 2.65 (ddd, J = 11.8, 9.1, 5.5 Hz, 2H), 2.54 (s, 1H), 2.25 (ddd, J = 11.7, 9.2, 6.7 Hz, 2H), 2.13-1.99 (m, 1H), 1.92 (dtt, J = 10.8, 9.2, 6.9 Hz, 1H). |
| 249 | 564.30 | 1H NMR (400 MHz, DMSO-d6) δ 9.25 (d, J = 7.5 Hz, 1H), 9.17 (t, J = 1.6 Hz, 1H), 8.39 (dd, J = 11.8, 1.8 Hz, 1H), 8.25 (dd, J = 7.9, 1.6 Hz, 1H), 7.73-7.28 (m, 4H), 6.29 (s, 1H), 5.12 (d, J = 6.8 Hz, 2H), 3.35 (s, 0.2H), 3.32-3.27 (m, 0.8H), 2.97 (d, J = 12.8 Hz, 2H), 2.86-2.77 (m, 2H), 2.54 (s, 1H), 1.33 (s, 3H) |
| 250 | 523.10 | 1H NMR (400 MHz, DMSO-d6) δ 8.79 (dd, J = 7.4, 0.9 Hz, 1H), 8.69 (t, J = 1.8 Hz, 1H), 8.22 (dd, J = 8.0, 1.5 Hz, 1H), 8.00 (dd, J = 12.3, 1.9 Hz, 1H), 7.82-7.23 (m, 5H), 5.05 (dd, J = 21.9, 6.8 Hz, 2H), 3.31-3.24 (m, 1H), 2.72-2.61 (m, 2H), 2.60-2.51 (m, 1H), 2.20 (s, 2H), 2.07 (tt, J = 7.4, 3.5 Hz, 3H), 1.71-1.58 (m, 1H) |
| 251 | 470.15 | 1H NMR (400 MHz, DMSO-d6) δ 9.21 (s, 2H), 8.80 (d, J = 7.4 Hz, 1H), 8.26 (s, 1H), 7.94 (dd, J = 7.7, 1.7 Hz, 1H), 7.72 (dd, J = 2.1, 0.9 Hz, 1H), 7.28 (dd, J = 7.4, 2.1 Hz, 1H), 7.21 (t, J = 7.9 Hz, 1H), 7.17 (dd, J = 8.2, 1.8 Hz, 1H), 5.07 (dd, J = 19.8, 6.8 Hz, 2H), 4.08 (s, 3H), 3.23 (dt, J = 13.5, 6.9 Hz, 1H), |
| | | 2.65 (q, J = 8.6 Hz, 2H), 2.48 (d, J = 13.1 Hz, 1H), 2.22 (s, 2H), 2.04 (d, J = 10.0 Hz, 1H), 1.90 (d, J = 9.4 Hz, 1H) |
| 252 | 510.25 | 1H NMR (400 MHz, DMSO-d6) δ 9.23 (d, J = 6.2 Hz, 1H), 8.92 (s, 2H), 8.22 (dd, J = 7.8, 1.8 Hz, 1H), 7.88-7.21 (m, 4H), 5.09 (d, J = 6.9 Hz, 1H), 5.01 (d, J = 6.6 Hz, 1H), 3.31-3.20 (m, 1H), 2.52 (s, 5H), 1.26 (dd, J = 89.1, 3.5 Hz, 4H) |
| 253 | 536.15 | 1H NMR (400 MHz, Methanol-d4) δ 9.09 (d, J = 1.5 Hz, 1H), 8.92 (d, J = 1.5 Hz, 1H), 8.60-8.50 (m, 2H), 8.30 (dd, J = 8.2, 1.3 Hz, 1H), 8.21 (dd, J = 2.1, 1.0 Hz, 1H), 7.51 (dd, J = 7.5, 2.0 Hz, 1H), 7.44-7.01 (m, 3H), 5.17 (d, J = 6.6 Hz, 1H), 5.06 (d, J = 6.9 Hz, 1H), 3.37 (dd, J = 13.6, 6.8 Hz, 1H), 3.05-2.96 (m, 2H), 2.65-2.55 (m, 3H), 1.55 (s, 3H) |
| 254 | 494.25 | 1H NMR (400 MHz, DMSO-d6) δ 9.18 (s, 2H), 8.85 (d, J = 7.4 Hz, 1H), 8.34 (s, 1H), 8.23 (dd, J = 8.0, 1.6 Hz, 1H), 7.80-7.57 (m, 2H), 7.44-7.30 (m, 3H), 5.09 (d, J = 6.9 Hz, 1H), 5.03 (d, J = 6.6 Hz, 1H), 3.29 (m, 1H), 2.54 (d, J = 4.4 Hz, 1H), 1.56 (s, 6H) |
| 255 | 492.10 | 1H NMR (400 MHz, DMSO-d6) δ 9.06 (s, 2H), 8.82 (d, J = 7.4 Hz, 1H), 8.22 (dd, J = 7.9, 1.6 Hz, 1H), 7.84-7.27 (m, 5H), 5.05 (dd, J = 24.2, 6.8 Hz, 2H), 3.30-3.19 (m, 1H), 2.53 (s, 1H), 1.26 (dq, J = 87.9, 3.8 Hz, 4H) |
| 256 | 571.15 | 1H NMR (400 MHz, DMSO-d6) δ 9.22 (d, J = 6.1 Hz, 1H), 8.56 (d, J = 1.7 Hz, 1H), 8.22 (d, J = 7.9, 1.6 Hz, 1H), 7.93 (d, J = 11.7 Hz, 1H), 7.80-7.25 (m, 4H), 5.75 (s, 1H), 5.09 (d, J = 6.9 Hz, 1H), 5.01 (d, J = 6.6 Hz, 1H), 3.33 (m, 2H), 3.33-3.23 (m, 1H), 2.90 (d, J = 12.0 Hz, 2H), 2.73-2.62 (m, 1H), 2.24 (d, J = 12.6 Hz, 2H), 0.96 (s, 3H) |
| 257 | 506.15 | 1H NMR (400 MHz, DMSO-d6) δ 9.12 (s, 2H), 8.84 (dd, J = 7.4, 0.9 Hz, 1H), 8.23 (dd, J = 8.0, 1.5 Hz, 1H), 7.80-7.41 (m, 2H), 7.41-7.35 (m, 1H), 7.35-7.32 (m, 1H), 7.32-7.30 (m, 1H), 5.06 (dd, J = 23.1, 6.7 Hz, 2H), 3.48 (d, J = 7.5 Hz, 1H), 3.31-3.24 (m, 1H), 2.61 (m, 2H), 1.27-1.01 (m, 1H), 0.56-0.33 (m, 4H) |
| 258 | 506.10 | 1H NMR (400 MHz, DMSO-d6) δ 9.12 (s, 2H), 8.84 (dd, J = 7.4, 0.9 Hz, 1H), 8.23 (dd, J = 7.9, 1.5 Hz, 1H), 7.80-7.41 (m, 2H), 7.38 (dd, J = 8.8, 7.4 Hz, 1H), 7.34-7.32 (m, 1H), 7.32-7.30 (m, 1H), 5.09 (d, J = 6.9 Hz, 1H), 5.03 (d, J = 6.7 Hz, 1H), 3.47 (d, J = 7.5 Hz, 1H), 3.31-3.24 (m, 1H), 2.54 (d, J = 2.6 Hz, 1H), 2.44 (s, 1H), 1.34-1.04 (m, 1H), 0.56-0.30 (m, 4H) |
| 259 | 559.40 | 1H NMR (400 MHz, DMSO-d6) δ 8.92 (s, 2H), 8.72 (t, J = 1.2 Hz, 1H), 8.21 (dd, J = 7.7, 1.8 Hz, 1H), 7.70-7.25 (m, 4H), 5.06 (d, J = 6.9 Hz, 1H), 4.96 (d, J = 6.6 Hz, 1H), 3.27 (dt, J = 13.5, 6.9 Hz, 1H), 2.85-2.77 (m, 2H), 2.65-2.57 (m, 2H), 2.47 (s, 1H), 2.17 (d, J = 1.1 Hz, 3H), 1.48 (s, 3H) |
| 260 | 554.15 | 1H NMR (400 MHz, DMSO-d6) δ 9.23 (d, J = 6.7 Hz, 1H), 9.05-8.91 (m, 2H), 8.23 (dd, J = 8.0, 1.5 Hz, 1H), 7.99 (d, J = 7.6 Hz, 1H), 7.75-7.27 (m, 3H), 6.09 (s, 1H), 5.10 (d, J = 6.9 Hz, 1H), 5.03 (d, J = 6.6 Hz, 1H), 3.27 (s, 1H), 2.77-2.70 (m, 2H), 2.53-2.50 (m, |

| Ex. | LCMS [M + H]+ | 1H NMR (ppm) |
|---|---|---|
| | | 1H), 2.17 (d, J = 9.9 Hz, 2H), 1.20 (s, 3H) |
| 261 | 537.25 | 1H NMR (400 MHz, DMSO-d6) δ 9.65 (d, J = 1.4 Hz, 1H), 9.34 (s, 2H), 8.23 (dd, J = 8.1, 1.4 Hz, 1H), 7.88 (d, J = 1.5 Hz, 1H), 7.79-7.42 (m, 1H), 7.41 (d, J = 1.3 Hz, 1H), 7.36 (t, J = 8. 1 Hz, 1H), 5.68 (s, 1H), 5.15 (d, J = 7.0 Hz, 1H), 5.04 (d, J = 6.7 Hz, 1H), 3.32-3.24 (m, 1H), 2.88-2.78 (m, 2H), 2.56 (d, J = 13.5 Hz, 1H), 2.20-2.13 (m, 2H), 1.06 (s, 3H) |
| 262 | 507.15 | 1H NMR (400 MHz, DMSO-d6) δ 9.65 (d, J = 1.4 Hz, 1H), 9.33 (s, 2H), 8.23 (dd, J = 8.0, 1.4 Hz, 1H), 7.87 (d, J = 1.5 Hz, 1H), 7.81-7.30 (m, 3H), 5.15 (d, J = 7.0 Hz, 1H), 5.05 (d, J = 6.7 Hz, 1H), 3.31-3.26 (m, 1H), 2.70-2.52 (m, 5H), 2.18-2.06 (m, 2H), 2.05-1.93 (m, 1H), 1.89-1.75 (m, 1H) |
| 263 | 551.20 | 1H NMR (400 MHz, DMSO-d6) δ 9.62 (d, J = 2.0 Hz, 1H), 8.81 (s, 1H), 8.24-8.22 (m, 1H), 7.69-7.32 (m, 4H), 5.15 (d, J = 8.0 Hz, 1H), 5.02 (d, J = 8.0 Hz, 2H), 3.32-3.26 (m, 1H), 2.85-2.80 (m, 2H), 2.58 (s, 4H), 2.45 (s, 1H), 2.33-2.19 (m, 2H), 1.17 (s, 3H) |
| 264 | 519.30 | 1H NMR (400 MHz, DMSO-d6) δ 9.19 (s, 2H), 8.85 (dd, J = 7.4, 0.9 Hz, 1H), 8.22 (dd, J = 8.0, 1.6 Hz, 1H), 7.80-7.31 (m, 5H), 5.06 (dd, J = 23.3, 6.8 Hz, 2H), 3.30-3.26 (m, 1H), 3.08 (d, J = 1.3 Hz, 2H), 3.04 (s, 1H), 2.53 (d, J = 3.0 Hz, 1H), 1.56 (s, 3H) |
| 265 | 519.30 | 1H NMR (400 MHz, DMSO-d6) δ 9.19 (s, 2H), 8.88-8.83 (m, 1H), 8.23 (dd, J = 8.0, 1.5 Hz, 1H), 7.81-7.58 (m, 3H), 7.44-7.38 (m, 1H), 7.34 (ddd, J = 8.1, 5.4, 3.3 Hz, 2H), 5.09 (d, J = 6.9 Hz, 1H), 5.03 (d, J = 6.6 Hz, 1H), 3.31-3.25 (m, 1H), 3.09 (d, J = 1.3 Hz, 2H), 2.54 (s, 1H), 2.43 (s, 2H), 1.56 (s, 3H) |
| 266 | 492.20 | 1H NMR (400 MHz, DMSO-d6) δ 9.11 (d, J = 1.5 Hz, 1H), 9.03 (d, J = 1.5 Hz, 1H), 8.80-8.76 (m, 1H), 8.25-8.21 (m, 1H), 8.15-8.11 (m, 1H), 7.78-7.29 (m, 4H), 5.08-5.04 (m, 2H), 3.32-3.24 (m, 1H), 2.92-2.60 (m, 2H), 2.53 (s, 1H), 1.31-1.27 (m, 2H), 1.11-1.07 (m, 2H) |
| 267 | 554.25 | 1H NMR (400 MHz, DMSO-d6) δ 9.23 (d, J = 6.2 Hz, 1H), 9.00 (d, J = 1.7 Hz, 2H), 8.21 (dd, J = 7.9, 1.6 Hz, 1H), 7.80-7.26 (m, 4H), 5.22-4.86 (m, 3H), 3.30-3.25 (m, 1H), 2.91-2.73 (m, 2H), 2.52 (s, 1H), 2.19 (d, J = 12.6 Hz, 2H), 1.16 (s, 3H) |
| 268 | 586.05 | 1H NMR (400 MHz, DMSO-d6) δ 9.70 (d, J = 7.0 Hz, 1H), 8.88 (q, J = 1.8 Hz, 1H), 8.24 (dd, J = 7.9, 1.7 Hz, 1H), 8.10 (dt, J = 12.0, 1.5 Hz, 1H), 7.75-7.12 (m, 3H), 5.12 (dd, J = 9.4, 6.8 Hz, 2H), 3.43 (s, 2H), 3.29 (d, J = 10.2 Hz, 1H), 2.53 (s, 1H), 2.48 (d, J = 11.0Hz, 2H), 2.16 (d, J = 13.0 Hz, 2H), 0.93 (s, 3H) |
| 269 | 550.30 | 1H NMR (400 MHz, DMSO-d6) δ 9.15 (s, 2H), 8.84 (dd, J = 7.4, 0.9 Hz, 1H), 8.22 (dd, J = 8.0, 1.5 Hz, 1H), 7.80-30 (m, 5H), 5.12-5.02 (m, 2H), 3.50-3.42 (m, 2H), 3.33-3.23 (m, 1H), 2.56-2.52 (m, 1H), 2.50-2.42 (m, 2H), 2.13-2.06 (m, 2H), 1.07 (s, 3H) |
| 270 | 568.20 | 1H NMR (400 MHz, DMSO-d6) δ 9.24 (d, J = 6.2 Hz, 1H), 9.02 (d, J = 1.6 Hz, 2H), 8.22 (dd, J = 7.9, 1.6 Hz, 1H), 7.83-7.15 (m, 4H), 5.06 (dd, J = 32.4, 6.7 Hz, 2H), 3.45 (s, 2H), 3.31-3.24 (m, 1H), 2.52 (s, 1H), 2.46 (d, J = 12.2 Hz, 2H), 2.14-2.06 (m, 2H), 1.07 (s, 3H) |
| 271 | 547.25 | 1H NMR (400 MHz, DMSO-d6) δ 9.53 (s, 2H), 9.28 (d, J = 7.5 Hz, 1H), 8.24 (dd, J = 7.9, 1.7 Hz, 1H), 7.78-7.69 (m, 1H), 7.55-7.30 (m, 3H), 6.25 (s, 1H), 5.12 (d, J = 6.8 Hz, 2H), 3.32-3.28 (m, 1H), 2.94-2.86 (m, 2H), 2.80-2.72 (m, 2H), 2.56-2.52 (m, 1H), 1.44 (s, 3H) |
| 272 | 547.25 | 1H NMR (400 MHz, DMSO-d6) δ 9.56 (s, 2H), 9.29 (d, J = 7.5 Hz, 1H), 8.25 (dd, J = 7.9, 1.6 Hz, 1H), 7.77 (d, J = 7.5 Hz, 1H), 7.73-7.32 (m, 3H), 6.22 (s, 1H), 5.13 (d, J = 6.8, 2.9 Hz, 2H), 3.35-3.34 (m,0.5H), 3.32-3.29 (m, 1.5H), 2.53 (d, J = 11.4 Hz, 2H), 2.47-2.40 (m, 2H), 1.69 (s, 3H) |
| 273 | 547.25 | 1H NMR (400 MHz, DMSO-d6) δ 9.67 (d, J = 1.4 Hz, 1H), 9.40 (s, 2H), 8.23 (dd, J = 8.1, 1.4 Hz, 1H), 7.92 (d, J = 1.5 Hz, 1H), 7.81-7.33 (m, 3H), 6.16 (s, 1H), 5.15 (d, J = 6.9 Hz, 1H), 5.05 (d, J = 6.7 Hz, 1H), 3. 36-3.32 (m, 0.3H), 3.31-3.27 (m, 1.7H), 2.56 (d, J = 13.6 Hz, 2H), 2.45-2.38 (m, 2H), 1.68 (s, 3H) |
| 274 | 569.20 | 1H NMR (400 MHz, DMSO-d6) δ 9.72 (d, J = 6.8 Hz, 1H), 9.27 (d, J = 1.5 Hz, 2H), 8.24 (dd, J = 7.7, 1.8 Hz, 1H), 7.86-7.05 (m, 3H), 5.13 (t, J = 7.4 Hz, 2H), 3.45 (s, 2H), 3.30 (m, 1H), 2.53 (d, J = 3.7 Hz, 1H), 2.49-2.42 (m, 2H), 2.15-2.07 (m, 2H), 1.06 (s, 3H) |
| 275 | 504.20 | 1H NMR (400 MHz, DMSO-d6) δ 9.18 (d, J = 7.4 Hz, 1H), 8.94-8.88 (m, 2H), 8.23 (dd, J = 7.6, 1.9 Hz, 1H), 7.68-7.03 (m, 4H), 5.16 (d, J = 6.7 Hz, 1H), 4.82 (t, J = 6.5 Hz, 1H), 3.26 (d, J = 6.7 Hz, 1H), 2.68-2.57 (m, 5H), 2.43 (d, J = 13.1 Hz, 1H), 2.11 (td, J = 9.8, 6.7 Hz, 2H), 2.05-1.92 (m, 1H), 1.82 (dtd, J = 16.3, 9.1, 6.5 Hz, 1H) |
| 276 | 507.20 | 1H NMR (400 MHz, DMSO-d6) δ 9.47 (s, 2H), 9.27 (d, J = 7.5 Hz, 1H), 8.25 (dd, J = 7.9, 1.7 Hz, 1H), 7.75-7.69 (m, 1H), 7.56-7.32 (m, 3H), 5.12 (d, J = 6.8 Hz, 2H), 3.51 (d, J = 7.5 Hz, 1H), 3.35 (s, 1H), 3.28 (s, 1H), 2.54 (s, 1H), 1.25-1.13 (m, 1H), 0.52-0.32 (m, 4H) |
| 277 | 507.25 | 1H NMR (400 MHz, DMSO-d6) δ 9.46 (s, 2H), 9.27 (d, J = 7.5 Hz, 1H), 8.25 (dd, J = 7.9, 1.7 Hz, 1H), 7.77-7.70 (m, 1H), 7.57-7.31 (m, 3H), 5.12 (d, J = 6.8 Hz, 2H), 3.50 (d, J = 7.4 Hz, 1H), 3.29 (d, J = 6.9 Hz, 1H), 2.88 (s, 1H), 2.54 (s, 1H), 1.29-1.06 (m, 1H), 0.58-0.29 (m, 4H) |
| 278 | 522.25 | 1H NMR (400 MHz, DMSO-d6) δ 9.17 (s, 2H), 8.85 (d, J = 8.0, 1.2 Hz, 1H), 8.23-8.21 (m, 1H), 7.78-7.59 (m, 2H), 7.41-7.31 (m, 2H), 7.36-7.30 (m, 2H), 6.03 (s, 1H), 5.08 (d, J = 4.0 Hz, 1H), 5.03 (d, J = 8.0 Hz, 1H), 3.930-3.88 (m, 2H), 3.32-3.26 (m, 1H), 3.23-3.21 (m, 2H), 2.54 (s, 1H), 2.30 (s, 3H) |
| 279 | 545.25 | 1H NMR (400 MHz, DMSO-d6) δ 9.23 (s, 2H), 8.86 (dd, J = 7.4, 0.9 Hz, 1H), 8.22 (dd, J = 8.0, 1.5 Hz, 1H), 7.87-7.20 (m, 5H), 5.06 (dd, J = 23.2, 6.8 Hz, 2H), 3.33 (s, 1H), 2.86-2.73 (m, 4H), 2.53 (s, 1H), 2.20 (d, J = 7.7 Hz, 2H), 1.50 (s, 3H) |
| 280 | 545.35 | 1H NMR (400 MHz, DMSO-d6) δ 9.24 (s, 2H), 8.86 (dd, J = 7.4, 0.9 Hz, 1H), 8.22 (dd, J = 8.1, 1.5 Hz, 1H), 7.86-7.23 (m, 5H), 5.06 (dd, J = 23.0, 6.8 Hz, |

| Ex. | LCMS [M + H]+ | ¹H NMR (ppm) |
|---|---|---|
| | | 2H), 3.32 (s, 1H), 2.96-2.88 (m, 2H), 2.75-2.67 (m, 2H), 2.54 (s, 1H), 1.14 (s, 3H) |
| 281 | 550.15 | ¹H NMR (400 MHz, DMSO-d₆) δ 8.78 (dd, J = 7.4, 0.9 Hz, 1H), 8.65 (s, 1H), 8.23 (dd, J = 7.7, 1.8 Hz, 1H), 7.73-7.26 (m, 4H), 7.01 (dd, J = 7.3, 2.0 Hz, 1H), 5.09 (d, J = 6.9 Hz, 1H), 5.05-4.96 (m, 2H), 3.31 (m, 1H), 2.88-2.78 (m, 2H), 2.54-2.53 (m, 1H), 2.48 (s, 3H), 2.22-2.14 (m, 2H), 1.19 (s, 3H) |
| 282 | 525.25 | ¹H NMR (400 MHz, DMSO-d₆) δ 9.52 (s, 2H), 9.33 (d, J = 7.4 Hz, 1H), 8.45-8.06 (m, 1H), 7.82-7.41 (m, 2H), 7.36 (t, J = 9.2 Hz, 1H), 6.97-5.72 (s, 1H), 5.13 (dd, J = 19.0, 6.8 Hz, 2H), 3.35 (m, 1H), 2.69-2.61 (m, 2H), 2.55 (d, J = 13.5 Hz, 1H), 2.27 (m, 2H), 2.08 (m, 1H), 2.00-1.87 (m, 1H) |
| 283 | 537.20 | ¹H NMR (400 MHz, MeOD) δ 8.38 (d, J = 7.4 Hz, 1H), 8.28 (d, J = 8.3 Hz, 1H), 7.48-7.23 (m, 4H), 7.08-6.98 (m, 1H), 6.34 (s, 1H), 5.19 (d, J = 6.6 Hz, 1H), 4.79 (s, 2H), 4.61-4.53 (m, 1H), 4.18 (s, 2H), 3.99-3.91 (m, 1H), 3.71 (s, 2H), 3.23-3.18 (m, 1H), 2.80 (d, J = 11.1 Hz, 2H), 2.55 (d, J = 10.6 Hz, 3H), 2.03 (s, 2H) |
| 284 | 554.15 | ¹H NMR (400 MHz, MeOD) δ 9.07 (d, J = 1.6 Hz, 2H), 8.84 (d, J = 6.0 Hz, 1H), 8.56 (s, 1H), 8.32 (dd, J = 8.1, 1.5 Hz, 1H), 7.70 (d, J = 7.6 Hz, 1H), 7.43-6.96 (m, 3H), 5.18 (d, J = 6.7 Hz, 1H), 5.09 (d, J = 6.9 Hz, 1H), 3.38 (dd, J = 13.6, 6.8 Hz, 1H), 3.13-3.04 (m, 2H), 2.67-2.58 (m, 3H), 1.58 (s, 3H) |
| 285 | 551.20 | ¹H NMR (400 MHz, DMSO-d₆) δ 9.22 (d, J = 7.4 Hz, 1H), 8.89 (s, 1H), 8.24 (dd, J = 7.1, 2.4 Hz, 1H), 7.67-7.13 (m, 4H), 5.13 (d, J = 6.9 Hz, 1H), 5.09 (d, J = 6.8 Hz, 1H), 5.04 (s, 1H), 3.30 (d, J = 8.4 Hz, 1H), 2.88-2.79 (m, 2H), 2.65 (s, 3H), 2.54 (s, 1H), 2.20 (d, J = 12.5 Hz, 1H), 1.18 (s, 3H) |
| 286 | 495.25 | ¹H NMR (400 MHz, MeOD) δ 9.52 (s, 2H), 9.00 (d, J = 7.5 Hz, 1H), 8.35 (dd, J = 8.2, 1.4 Hz, 1H), 7.59 (d, J = 7.5 Hz, 1H), 7.43-7.24 (m, 3H), 5.30 (d, J = 6.8 Hz, 1H), 5.11 (d, J = 6.9 Hz, 1H), 3.39 (dt, J = 13.7, 6.9 Hz, 1H), 2.64 (d, J = 13.5 Hz, 1H), 1.70 (s, 6H) |
| 287 | 513.25 | ¹H NMR (400 MHz, DMSO-d₆) δ 9.74 (d, J = 6.8 Hz, 1H), 9.27 (d, J = 1.5 Hz, 2H), 8.24 (dd, J = 7.7, 1.7 Hz, 1H), 7.72-7.15 (m, 3H), 5.18-5.09 (m, 2H), 3.33 (dt, J = 13.6, 7.0 Hz, 1H), 2.53 (d, J = 8.8 Hz, 1H), 1.58-1.52 (m, 6H) |
| 288 | 555.30 | ¹H NMR (400 MHz, DMSO-d₆) δ 9.48 (s, 2H), 9.31 (d, J = 7.4 Hz, 1H), 8.33 (dd, J = 9.3, 5.7 Hz, 1H), 7.85-7.41 (m, 2H), 7.35 (t, J = 9.2 Hz, 1H), 5.14 (d, J = 6.8 Hz, 1H), 5.09 (d, J = 6.8 Hz, 1H), 3.34 (m, 1H), 2.84 (m, 2H), 2.54 (d, J = 14.0 Hz, 1H), 2.30 (d, J = 12.1 Hz, 2H), 1.20 (s, 3H) |
| 289 | 572.25 | ¹H NMR (400 MHz, DMSO-d₆) δ 9.28 (d, J = 7.5 Hz, 1H), 9.13 (s, 1H), 8.38-8.28 (m, 2H), 8.22 (s, 1H), 7.83-7.44 (m, 2H), 7.35 (t, J = 9.2 Hz, 1H), 5.11 (dd, J = 18.5, 6.8 Hz, 2H), 3.37-3.32 (m, 1H), 2.87 (s, 2H), 2.55 (m, 2H), 2.28 (d, J = 13.0 Hz, 2H), 1.00 (s, 3H) |
| 290 | 549.20 | ¹H NMR (400 MHz, DMSO-d₆) δ 9.26 (d, J = 6.2 Hz, 1H), 9.06 (d, J = 1.7 Hz, 2H), 8.23 (dd, J = 7.9, 1.6 Hz, 1H), 7.78-7.51 (m, 2H), 7.44-7.24 (m, 2H), 5.11 (d, J = 7.0 Hz, 1H), 5.02 (d, J = 6.6 Hz, 1H), 3.61 (p, J = 8.7 Hz, 1H), 3.33 (s, 1H), 2.94 (td, J = 9.0, 2.6 Hz, 2H), 2.54 (s, 1H), 2.44 (td, J = 9.1, 2.6 Hz, 2H). |
| 291 | 521.25 | ¹H NMR (400 MHz, DMSO-d₆) δ 8.70 (d, J = 4.8 Hz, 3H), 8.22 (dd, J = 7.9, 1.7 Hz, 1H), 7.79-7.50 (m, 2H), 7.42-7.28 (m, 2H), 7.16 (dd, J = 7.5, 2.1 Hz, 1H), 5.01 (dd, J = 24.1, 6.7 Hz, 2H), 3.92-3.80 (m, 4H), 3.29-3.19 (m, 1H), 2.25 (s, 1H), 1.38 (s, 3H) |
| 292 | 562.30 | ¹H NMR (400 MHz, DMSO-d₆) δ 8.84 (dd, J = 6.8, 1.3 Hz, 2H), 8.28-8.19 (m, 2H), 7.85-7.52 (m, 2H), 7.44-7.33 (m, 2H), 7.31 (dd, J = 7.3, 2.0 Hz, 1H), 5.09 (d, J = 6.9 Hz, 1H), 5.03 (d, J = 6.7 Hz, 1H), 3.30-3.24 (m, 1H), 2.96 (d, J = 12.0 Hz, 2H), 2.74 (d, J = 12.1 Hz, 2H), 2.54 (d, J = 4.6 Hz, 1H), 1.01 (s, 3H) |
| 293 | 562.30 | ¹H NMR (400 MHz, DMSO-d₆) δ 8.87-8.80 (m, 2H), 8.26-8.18 (m, 2H), 7.80-7.42 (m, 2H), 7.41-7.32 (m, 2H), 7.29 (dd, J = 7.4, 2.1 Hz, 1H), 5.09 (d, J = 6.9 Hz, 1H), 5.03 (d, J = 6.6 Hz, 1H), 3.29-3.14 (m, 1H), 2.87-2.74 (m, 4H), 2.54 (s, 1H), 1.51 (s, 3H) |
| 294 | 512.30 | ¹H NMR (400 MHz, DMSO-d₆) δ 9.24 (d, J = 6.1 Hz, 1H), 9.00 (d, J = 1.7 Hz, 2H), 8.22 (dd, J = 7.9, 1.6 Hz, 1H), 7.75-7.31 (m, 4H), 5.10-5.02 (m, 2H), 3.33-3.23 (m, 1H), 2.55-2.51 (m, 1H), 2.33-2.29 (m, 1H), 1.51-1.42 (m, 6H) |
| 295 | 492.10 | ¹H NMR (400 MHz, DMSO-d₆) δ 9.46 (s, 2H), 9.27 (d, J = 7.4 Hz, 1H), 8.25 (dd, J = 7.8, 1.7 Hz, 1H), 7.80-7.27 (m, 4H), 5.13 (d, J = 6.7 Hz, 2H), 3.32 (s, 1H), 3.30 (s, 3H), 2.54 (s, 1H), 2.22 (s, 6H), 1.47 (s, 6H) |
| 296 | 509.03 | ¹H NMR (400 MHz, DMSO-d₆) δ 9.18-9.01 (m, 3H), 8.24 (dd, J = 7.4, 2.1 Hz, 1H), 7.55-7.12 (m, 3H), 5.08 (dd, J = 16.1, 6.8 Hz, 2H), 3.33-3.25 (m, 1H), 2.49-2.47 (m, 1H), 2.40-2.25 (m, 3H), 2.20-2.12 (m, 2H), 2.50-2.30 (m, 6H) |
| 297 | 513.25 | ¹H NMR (400 MHz, DMSO-d₆) δ 9.50 (s, 2H), 9.33 (d, J = 7.5 Hz, 1H), 8.33 (dd, J = 9.3, 5.7 Hz, 1H), 7.81-7.42 (m, 2H), 7.36 (t, J = 9.2 Hz, 1H), 5.15 (d, J = 6.8 Hz, 1H), 5.10 (d, J = 6.7 Hz, 1H), 3.38-3.31 (m, 1H), 2.56 (s, 1H), 1.69-1.43 (m, 6H) |
| 298 | 495.10 | ¹H NMR (400 MHz, DMSO-d₆) δ 9.65 (d, J = 1.4 Hz, 1H), 9.30 (s, 2H), 8.23 (d, J = 8.0, 1.4 Hz, 1H), 7.86 (d, J = 1.6 Hz, 1H), 7.80-7.33 (m, 3H), 5.15 (d, J = 6.9 Hz, 1H), 5.05 (d, J = 6.7 Hz, 1H), 3.34-3.24 (m, 1H), 2.52 (d, J = 2.0 Hz, 1H), 2.42-2.21 (m, 2H), 1.47 (s, 6H) |
| 299 | 487.25 | ¹H NMR (400 MHz, DMSO-d₆) δ 9.12 (s, 2H), 8.85 (d, J = 7.4 Hz, 1H), 8.48 (d, J = 8.2 Hz, 1H), 7.82-7.72 (m, 3H), 7.43 (t, J = 7.9 Hz, 1H), 7.31 (dd, J = 7.4, 2.0 Hz, 1H), 5.09 (d, J = 6.8 Hz, 1H), 4.97 (d, J = 6.7 Hz, 1H), 3.27 (s, 1H), 3.24 (s, 3H), 2.62 (s, 3H), 2.13 (s, 2H), 1.99 (s, 1H), 1.83 (d, J = 8.6 Hz, 1H) |
| 300 | 508.25 | ¹H NMR (400 MHz, DMSO-d₆) δ 8.93 (s, 2H), 8.76-8.71 (m, 1H), 8.22 (dd, J = 7.6, 1.8 Hz, 1H), 7.47-7.26 (m, 4H), 5.06 (d, J = 6.9 Hz, 1H), 4.97 (d, J = 6.6 Hz, 1H), 3.27 (dt, J = 13.5, 6.9 Hz, 1H), 2.48 (s, 1H), 2.18 (d, J = 1.1 Hz, 3H), 1.55 (s, 6H) |

447 -continued

| Ex. | LCMS [M + H]+ | 1H NMR (ppm) |
|---|---|---|
| 323 | 573.25 | 1H NMR (400 MHz, DMSO-d6) δ 9.76 (d, J = 6.8 Hz, 1H), 9.25 (d, J = 1.6 Hz, 2H), 8.32 (dd, J = 9.3, 5.7 Hz, 1H), 7.72-7.31 (m, 2H), 5.16 (d, J = 6.8 Hz, 1H), 5.09 (d, J = 6.8 Hz, 1H), 5.06 (s, 1H), 3.42-3.34 (m, 1H), 2.91-2.76 (m, 2H), 2.55 (s, 1H), 2.22 (d, J = 12.4 Hz, 2H), 1.16 (s, 3H) |
| 324 | 491.20 | 1H NMR (400 MHz, DMSO-d6) δ 9.12 (s, 2H), 8.84 (d, J = 7.4 Hz, 1H), 8.22 (dd, J = 7.9, 1.5 Hz, 1H), 7.80-7.52 (m, 2H), 7.42-7.25 (m, 3H), 5.09-5.02 (m, 2H), 3.30-3.27 (m, 4H), 2.56-2.52 (m, 1H), 2.30-2.26 (m, 1H), 1.50-1.43 (m, 6H) |
| 325 | 511.25 | 1H NMR (400 MHz, DMSO) δ 8.82 (dd, J = 7.4, 0.9 Hz, 1H), 8.78 (t, J = 1.8 Hz, 1H), 8.28 (s, 1H), 8.23 (dd, J = 7.9, 1.5 Hz, 1H), 8.12 (dd, J = 13.1, 1.8 Hz, 1H), 7.82-7.42 (m, 2H), 7.41-7.32 (m, 2H), 7.29 (dd, J = 7.4, 2.1 Hz, 1H), 5.08 (d, J = 6.9 Hz, 1H), 5.02 (d, J = 6.6 Hz, 1H), 3.29 (m, 1H), 2.53 (d, J = 2.9 Hz, 1H), 1.57 (s, 6H) |
| 326 | 512.25 | 1H NMR (400 MHz, DMSO) δ 9.26 (d, J = 7.5 Hz, 1H), 9.18 (s, 1H), 8.39 (dd, J = 13.2, 1.6 Hz, 1H), 8.25 (dd, J = 7.9, 1.7 Hz, 1H), 7.84-7.26 (m, 4H), 5.12 (d, J = 6.8 Hz, 2H), 3.32 (m, 1H), 2.53 (d, J = 4.8 Hz, 1H), 1.54 (s, 6H) |
| 327 | 505.25 | 1H NMR (400 MHz, DMSO) δ 8.77 (d, J = 7.4 Hz, 1H), 8.68 (d, J = 1.7 Hz, 1H), 8.23 (dd, J = 7.9, 1.5 Hz, 1H), 7.90 (s, 1H), 7.83-7.59 (m, 2H), 7.45-7.30 (m, 2H), 7.19 (dd, J = 7.4, 2.0 Hz, 1H), 5.04 (dd, J = 24.4, 6.8 Hz, 2H), 3.31-3.23 (m, 1H), 3.04-2.90 (m, 1H), 2.84 (dt, J = 16.1, 7.7 Hz, 1H), 2.57 (m, 1H), 2.17-1.94 (m, 3H), 1.34 (s, 3H) |
| 328 | 505.25 | 1H NMR (400 MHz, DMSO) δ 8.77 (d, J = 7.4 Hz, 1H), 8.68 (d, J = 2.1 Hz, 1H), 8.23 (dd, J = 8.0, 1.6 Hz, 1H), 7.90 (d, J = 2.1 Hz, 1H), 7.82-7.58 (m, 2H), 7.36 (dt, J = 16.1, 7.9 Hz, 2H), 7.19 (dd, J = 7.4, 2.1 Hz, 1H), 5.04 (dd, J = 24.1, 6.8 Hz, 2H), 3.28 (q, J = 6.8 Hz, 1H), 3.01-2.90 (m, 1H), 2.84 (dt, J = 16.0, 7.5 Hz, 1H), 2.57 (m, 1H), 2.26-1.89 (m, 4H), 1.34 (s, 3H) |
| 329 | 559.25 | 1H NMR (400 MHz, DMSO) δ 9.16 (s, 2H), 8.84 (dd, J = 7.4, 0.9 Hz, 1H), 8.07 (dd, J = 7.9, 1.6 Hz, 1H), 7.82-7.43 (m, 2H), 7.38-7.09 (m, 3H), 5.15 (d, J = 7.2 Hz, 1H), 4.97 (d, J = 6.4 Hz, 1H), 3.29-3.27 (m, 1H), 3.12-3.06 (m, 1H), 2.95-2.76 (m, 2H), 2.55 (s, 1H), 2.26 (d, J = 12.4 Hz, 2H), 1.30 (dd, J = 10.3, 4.5 Hz, 1H), 1.20 (s, 1H), 1.01-0.77 (m, 2H), 0.50-0.43 (m, 1H) |

Example 301

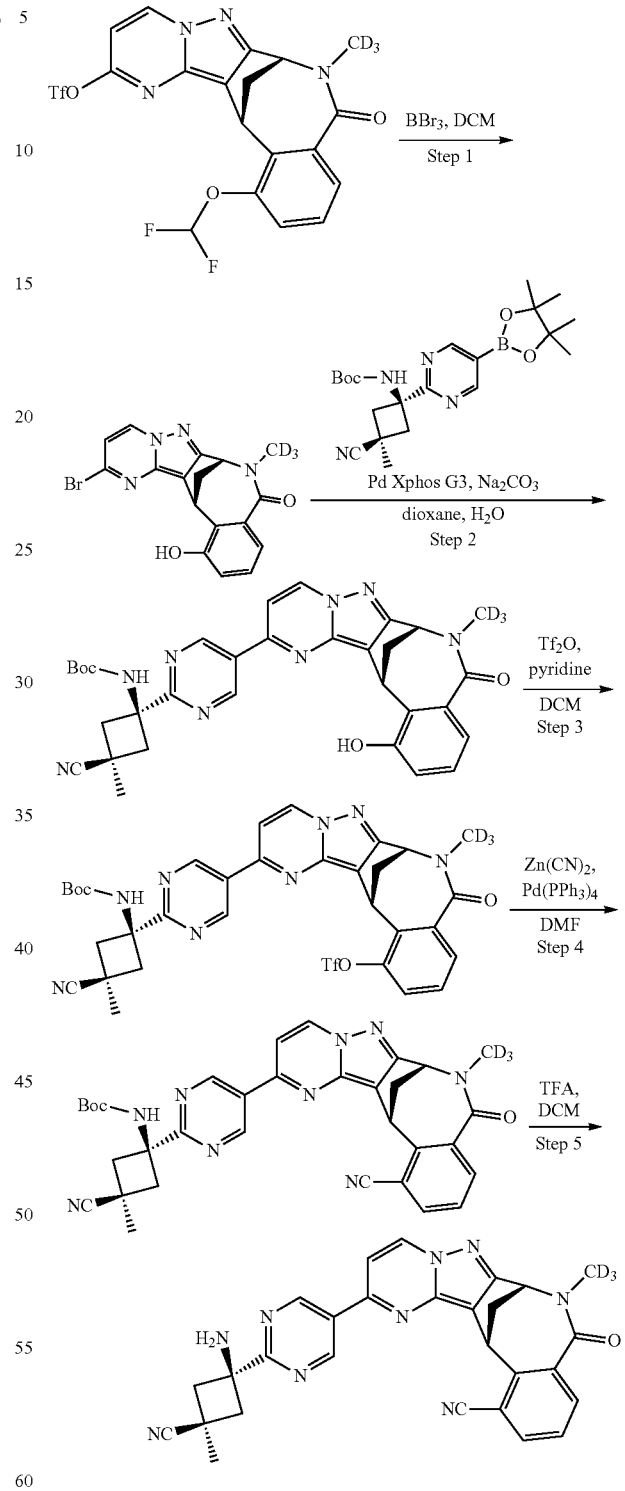

Step 1: A solution of (7R,14S)-1-(difluoromethoxy)-6-(methyl-d3)-5-oxo-5,6,7,14-tetrahydro-7,14-methanobenzo[c]pyrimido[1',2':1,5]pyrazolo[4,3-f]azocin-12-yl trifluoromethanesulfonate (500 mg, 1.0 mmol, 1.0 equiv) in DCM (100 mL) under nitrogen atmosphere followed by the addition of BBr3 (6 mL, 6.0 mmol, 6 equiv) dropwise at 0° C.

The resulting mixture was stirred at room temperature for 1 h under nitrogen atmosphere. The reaction mixture was diluted with water (100 mL), and the aqueous phase was extracted with DCM (3×100 mL) three times. The combined organic layers were washed with brine, dried over sodium sulfate, filtered, and concentrated in vacuo. The residue was purified by Prep-TLC (PE/EA 1:2) to afford (7R,14S)-12-bromo-1-hydroxy-6-(methyl-d3)-6,7-dihydro-7,14-methanobenzo[c]pyrimido[1',2':1,5]pyrazolo[4,3-f]azocin-5 (14H)-one (300 mg, 78.4%) as a yellow oil. LCMS (ESI, m/z): 388.14 [M+H]$^+$.

Step 2: A solution of tert-butyl ((1s, 3s)-3-cyano-3-methyl-1-(5-(4,4,5,5-tetramethyl-1,3,2-dioxaborolan-2-yl)pyrimidin-2-yl)cyclobutyl)carbamate (320 mg, 0.8 mmol, 1.0 equiv), (7R,14S)-12-bromo-1-hydroxy-6-(methyl-d3)-6,7-dihydro-7,14-methanobenzo[c]pyrimido[1',2':1,5]pyrazolo[4,3-f]azocin-5 (14H)-one (300 mg, 0.8 mmol, 1.0 equiv), Na$_2$CO$_3$ (246 mg, 2.4 mmol, 3.0 equiv), Pd(dppf)Cl$_2$'CH$_2$Cl$_2$ (63 mg, 0.08 mmol, 0.1 equiv) in 1,4-dioxane (15 mL), H$_2$O (3 mL) was stirred at 80° C. for 2 h under nitrogen atmosphere. The reaction mixture was diluted with water (100 mL), and the aqueous phase was extracted with EA (3×100 mL). The combined organic layers were washed with brine, dried over sodium sulfate, filtered, and concentrated in vacuo. The residue was purified by Prep-TLC (EA) to afford tert-butyl ((1s,3R)-3-cyano-1-(5-((7R,14S)-1-hydroxy-6-(methyl-d3)-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)carbamate (300 mg, 65.2%) as a yellow oil. LCMS (ESI, m/z): 596.30 [M+H]$^+$.

Step 3: A solution of tert-butyl ((1s,3R)-3-cyano-1-(5-((7R,14S)-1-hydroxy-6-(methyl-d3)-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)carbamate (250 mg, 0.42 mmol, 1.0 equiv) in DCM (10 mL) was treated with pyridine (83 mg, 1.1 mmol, 2.5 equiv) at 0° C. for 5 min under nitrogen atmosphere followed by the addition of (trifluoromethane)sulfonyl trifluoromethanesulfonate (178 mg, 0.63 mmol, 1.5 equiv) dropwise at 0° C. The resulting mixture was stirred at room temperature for 1 h under nitrogen atmosphere. The reaction mixture was diluted with water (100 mL), and the aqueous phase was extracted with EA (3×100 mL). The combined organic layers were washed with brine, dried over sodium sulfate, filtered, and concentrated in vacuo. The residue was purified by Prep-TLC (CH$_2$Cl$_2$/MeOH 30:1) to afford (7R,14S)-12-(2-((1s,3R)-1-((tert-butoxycarbonyl)amino)-3-cyano-3-methylcyclobutyl)pyrimidin-5-yl)-6-(methyl-d3)-5-oxo-5,6,7,14-tetrahydro-7,14-methanobenzo[c]pyrimido[1',2':1,5]pyrazolo[4,3-f]azocin-1-yl trifluoromethanesulfonate (250 mg, 81.9%) as a yellow solid. LCMS (ESI, m/z): 728.35 [M+H]$^+$.

Step 4: A solution of (7R,14S)-12-(2-((1s,3R)-1-((tert-butoxycarbonyl)amino)-3-cyano-3-methylcyclobutyl)pyrimidin-5-yl)-6-(methyl-d3)-5-oxo-5,6,7,14-tetrahydro-7,14-methanobenzo[c]pyrimido[1',2':1,5]pyrazolo[4,3-f]azocin-1-yl trifluoromethanesulfonate (250 mg, 0.34 mmol, 1.0 equiv) Zn(CN)$_2$ (81 mg, 0.68 mmol, 2.0 equiv), Pd(PPh$_3$)$_4$ (79 mg, 0.068 mmol, 0.2 equiv) in DMF (5 mL) was stirred at 100° C. for 1 h under nitrogen atmosphere. The reaction mixture was diluted with water (50 mL), and the aqueous phase was extracted with EA (3×50 mL). The combined organic layers were washed with brine, dried over sodium sulfate, filtered, and concentrated in vacuo. The residue was purified by Prep-TLC (CH$_2$Cl$_2$/MeOH 30:1) to afford tert-butyl ((1s,3S)-3-cyano-1-(5-((7R,14R)-1-cyano-6-(methyl-d3)-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)carbamate (180 mg, 86.7%) as a yellow solid. LCMS (ESI, m/z): 605.40 [M+H]$^+$.

Step 5: A solution of tert-butyl ((1s,3S)-3-cyano-1-(5-((7R,14R)-1-cyano-6-(methyl-d3)-5-oxo-5,6,7,14-tetrahydro-7,14-methanobenzo[c]pyrimido[1',2':1,5]pyrazolo[4,3-f]azocin-12-yl)pyrimidin-2-yl)-3-methylcyclobutyl)carbamate (150 mg, 0.25 mmol, 1.0 equiv) in DCM (1 mL), trifluoroacetic acid (4 mL) was stirred at room temperature for 1 h under nitrogen atmosphere. The mixture/residue was basified to pH 8 with saturated NaHCO$_3$ (aq.). The reaction mixture was diluted with water (10 mL), and the aqueous phase was extracted with EA (3×10 mL). The combined organic layers were washed with brine, dried over sodium sulfate, filtered, and concentrated in vacuo. The crude product was purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 70% B in 9 min; Wave Length: 254 nm/220 nm nm; RT1(min): 6.56) to afford (7R,14R)-12-(2-((1s,3S)-1-amino-3-cyano-3-methylcyclobutyl)pyrimidin-5-yl)-6-(methyl-d3)-5-oxo-5,6,7,14-tetrahydro-7,14-methanobenzo[c]pyrimido[1',2':1,5]pyrazolo[4,3-f]azocine-1-carbonitrile (65 mg, 51.8%). LCMS (ESI, m/z): 505.10 [M+H]$^+$. $^1$H NMR (400 MHz, DMSO-d$_6$) δ 9.59 (s, 2H), 9.28 (d, J=7.4 Hz, 1H), 8.64 (dd, J=8.3, 1.5 Hz, 1H), 8.03 (dd, J=7.6, 1.5 Hz, 1H), 7.78 (d, J=7.5 Hz, 1H), 7.49 (t, J=7.9 Hz, 1H), 5.13 (dd, J=42.2, 6.7 Hz, 2H), 3.41 (dt, J 13.6, 6.8 Hz, 1H), 2.86-2.77 (m, 2H), 2.69-2.58 (m, 3H), 1.46 (s, 3H).

Example 302

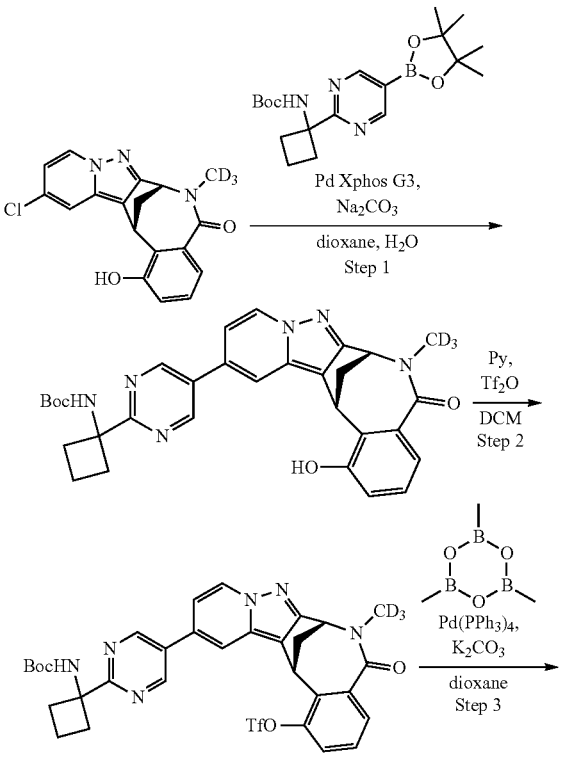

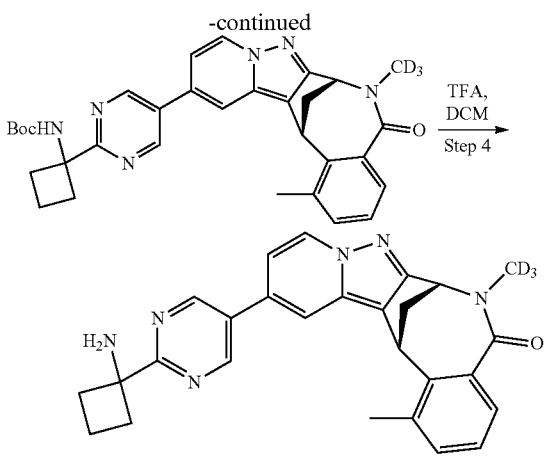

Step 1: To a stirred solution of (7R,14S)-12-chloro-1-hydroxy-6-(methyl-d3)-6,7-dihydro-7,14-methanobenzo[c]pyrido[1',2':1,5]pyrazolo[4,3-f]azocin-5 (14H)-one (320 mg, 0.9 mmol, 1.0 equiv) and tert-butyl (1-(5-(4,4,5,5-tetramethyl-1,3,2-dioxaborolan-2-yl)pyrimidin-2-yl)cyclobutyl)carbamate (1.05 g, 2.80 mmol, 3.0 equiv) in 1,4-dioxane (5 mL), H₂O (1 mL) were added Na₂CO₃ (296.8 mg, 2.8 mmol, 3.0 equiv) and XPhos Pd G2 (74 mg, 0.09 mmol, 0.1 equiv) in portions at room temperature under nitrogen atmosphere. The resulting mixture was stirred at 140° C. for 1 h under nitrogen atmosphere. The resulting mixture was filtered, the filter cake was washed with EA (2×10 mL). The filtrate was concentrated under reduced pressure. The residue was purified by Prep-TLC (CH₂Cl₂/MeOH 15:1) to afford tert-butyl (1-(5-((7R,14S)-1-hydroxy-6-(methyl-d3)-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (400 mg, 77.1%) as a light brown solid. LCMS (ESI, m/z): 556.35 [M+H]⁺.

Step 2: A solution of tert-butyl (1-(5-((7R,14S)-1-hydroxy-6-(methyl-d3)-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (400 mg, 0.72 mmol, 1.0 equiv) in DCM (20 mL) was treated with pyridine (284.7 mg, 3.6 mmol, 5.0 equiv) at 0° C. for 1 min under nitrogen atmosphere followed by the addition of (trifluoromethane)sulfonyl trifluoromethanesulfonate (610 mg, 2.2 mmol, 3 equiv) dropwise at 0° C. The resulting mixture was stirred at room temperature for 1 h under nitrogen atmosphere. The reaction was quenched by the addition of sat. NH₄Cl (aq.) (20 mL) at room temperature. The resulting mixture was extracted with EA (2×100 mL). The combined organic layers were washed with brine (1×50 mL), dried over anhydrous Na₂SO. After filtration, the filtrate was concentrated under reduced pressure. The residue was purified by Prep-TLC (PE/EA 1:1) to afford (7R,14S)-12-(2-(1-((tert-butoxycarbonyl)amino)cyclobutyl)pyrimidin-5-yl)-6-(methyl-d3)-5-oxo-5,6,7,14-tetrahydro-7,14-methanobenzo[c]pyrido[1',2':1,5]pyrazolo[4,3-f]azocin-1-yl trifluoromethanesulfonate (300 mg, 60.6% yield, 90% purity) as a light brown solid. LCMS (ESI, m/z): 688.30 [M+H]⁺.

Step 3: To a stirred solution of (7R,14S)-12-(2-(1-((tert-butoxycarbonyl)amino)cyclobutyl)pyrimidin-5-yl)-6-(methyl-d3)-5-oxo-5,6,7,14-tetrahydro-7,14-methanobenzo[c]pyrido[1',2':1,5]pyrazolo[4,3-f]azocin-1-yl trifluoromethanesulfonate (100 mg, 0.15 mmol, 1.0 equiv) and trimethyl-1,3,5,2,4,6-trioxatriborinane (37 mg, 0.29 mmol, 2.0 equiv) in 1,4-dioxane (10 mL) were added K₂CO₃ (60 mg, 0.44 mmol, 3.0 equiv) and Pd(PPh₃)₄ (17 mg, 0.02 mmol, 0.1 equiv) in portions at room temperature under nitrogen atmosphere. The resulting mixture was stirred at 100° C. for 16 h under nitrogen atmosphere. The resulting mixture was filtered, the filter cake was washed with EA (2×50 mL). The filtrate was concentrated under reduced pressure. The residue was purified by Prep-TLC (CH₂Cl₂/MeOH 15:1) to afford tert-butyl (1-(5-((7R,14R)-1-methyl-6-(methyl-d3)-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (50 mg, 62.1%) as a light brown solid. LCMS (ESI, m/z): 554.20 [M+H]⁺.

Step 4: To a stirred solution of tert-butyl (1-(5-((7R,14R)-1-methyl-6-(methyl-d3)-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (50 mg, 0.09 mmol, 1.0 equiv) in DCM (1 mL) was added trifluoroacetic acid (0.5 mL) dropwise at room temperature under nitrogen atmosphere. The resulting mixture was stirred at room temperature for 1 h under nitrogen atmosphere. The mixture was neutralized to pH 8 with saturated NaHCO₃ (aq.). The resulting mixture was extracted with CH₂Cl₂ (2×40 mL). The combined organic layers were dried over anhydrous Na₂SO₄. After filtration, the filtrate was concentrated under reduced pressure. The crude product was purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 70% B in 9 min; Wave Length: 254 nm/220 nm nm; RT1(min): 6.56) to afford (7R,14R)-12-(2-(1-aminocyclobutyl)pyrimidin-5-yl)-1-methyl-6-(methyl-d3)-6,7-dihydro-7,14-methanobenzo[c]pyrido[1',2':1,5]pyrazolo[4,3-f]azocin-5 (14H)-one (13 mg, 32.2% yield). LCMS (ESI, m/z): 454.20 [M+H]⁺. ¹H NMR (400 MHz, DMSO-d₆) δ 9.22 (s, 2H), 8.83 (dd, J=7.4, 0.9 Hz, 1H), 8.17 (dd, J=8.3, 1.5 Hz, 1H), 7.84 (dd, J=2.1, 1.0 Hz, 1H), 7.35 (dd, J=7.6, 1.5 Hz, 1H), 7.28 (dd, J=7.4, 2.1 Hz, 1H), 7.14 (t, J=7.8 Hz, 1H), 5.03 (d, J=6.9 Hz, 1H), 4.86 (d, J=6.9 Hz, 1H), 3.25 (dt, J=13.6, 7.0 Hz, 1H), 2.79 (s, 3H), 2.62 (t, J=8.4 Hz, 2H), 2.46 (s, 1H), 2.20 (d, J=10.0 Hz, 2H), 2.02 (s, 1H), 1.94-1.85 (m, 1H).

The following compounds were prepared by modifications of the methods exemplified herein.

| Ex. | LCMS [M + H]⁺ | ¹H NMR (ppm) |
|---|---|---|
| 303 | 468.25 | ¹H NMR (400 MHz, DMSO-d₆) δ 9.10 (d, J = 2.2 Hz, 1H), 8.87 (d, J = 7.3 Hz, 1H), 8.66 (dd, J = 8.3, 1.4 Hz, 1H), 8.29-8.26 (m, 1H), 8.08 (dd, J = 8.0, 5.0 Hz, 1H), 8.03 (dd, J = 7.6, 1.4 Hz, 1H), 7.91-7.86 (m, 1H), 7.51 (t, J = 7.9 Hz, 1H), 7.32 (dd, J = 7.4, 2.1 Hz, 1H), 5.17 (d, J = 6.9 Hz, 1H), 5.03 (d, J = 6.4 Hz, 1H), 3.40-3.38 (m 1H), 3.33 (s, 3H), 2.65 (d, J = 13.6 Hz, 1H), 1.72 (d, J = 13.6 Hz, 6H) |

| Ex. | LCMS [M + H]+ | 1H NMR (ppm) |
|---|---|---|
| 304 | 483.10 | 1H NMR (400 MHz, DMSO-d6) δ 9.14 (d, J = 2.2 Hz, 1H), 8.82 (d, J = 7.4 Hz, 1H), 8.40-8.28 (m, 1H), 8.16 (dd, J = 8.0, 1.7 Hz, 1H), 8.08-8.00 (m, 1H), 7.87 (dd, J = 2.1, 0.9 Hz, 1H), 7.26 (dd, J = 7.4, 2.1 Hz, 1H), 7.21 (dd, J = 7.6, 1.7 Hz, 1H), 7.16 (t, J = 7.8 Hz, 1H), 5.39 (d, J = 6.9 Hz, 1H), 5.05 (d, J = 6.8 Hz, 1H), 3.31-3.20 (m, 4H), 2.73-2.58 (m, 1H), 2.48 (s, 1H), 1.70 (d, J = 13.6 Hz, 6H), 1.31-1.16 (m, 2H), 1.08-0.94 (m, 1H), 0.72-0.59 (m, 1H) |
| 305 | 492.25 | 1H NMR (400 MHz, DMSO-d6) δ 9.16 (s, 2H), 8.84 (dd, J = 7.4, 0.9 Hz, 1H), 8.40 (dd, J = 8.2, 1.5 Hz, 1H), 7.92 (dd, J = 2.2, 0.9 Hz, 1H), 7.67 (dd, J = 7.6, 1.5 Hz, 1H), 7.39-7.24 (m, 2H), 5.63 (s, 1H), 5.24 (d, J = 6..6 Hz, 1H), 5.11 (d, J = 6.9 Hz, 1H), 4.99 (d, J = 11.4 Hz, 2H), 3.30 (s, 4H), 2.99-2.86 (m, 2H), 2.57 (d, J = 13.4 Hz, 1H), 2.45-2.39 (m, 2H), 1.09 (s, 3H) |
| 306 | 465.15 | 1H NMR (400 MHz, DMSO-d6) δ 9.15 (s, 2H), 8.86 (dd, J = 7.3, 0.8 Hz, 1H), 8.64 (dd, J = 8.3, 1.4 Hz, 1H), 8.00 (dd, J = 7.6, 1.5 Hz, 1H), 7.86 (, J = 2.3 Hz, 1H), 7.49 (t, J = 7.9 Hz, 1H), 7.33 (dd, J = 7.4, 2.1 Hz, 1H), 5.14 (d, J = 6.9 Hz, 1H), 5.01 (d, J = 6.4 Hz, 1H), 3.42-3.35 (m, 1H), 2.68-2.61 (m, 3H), 2.23-2.16 (m, 2H), 2.07-1.96 (m, 1H), 1.93-1.82 (m, 1H) |
| 307 | 483.15 | 1H NMR (400 MHz, DMSO-d6) δ 9.28 (d, J = 6.0 Hz, 1H), 9.07 (s, 2H), 8.64 (d, J = 8.0 Hz, 1H), 8.00 (d, J = 7.6 Hz, 1H), 7.71 (d, J = 7.6 Hz, 1H), 7.50 (t, J = 8.0 Hz, 1H), 5.17 (d, J = 6.8 Hz, 1H), 5.01 (d, J = 6.4 Hz, 1H), 3.52-3.35 (m, 1H), 2.66-2.62 (m, 1H), 2.26-2.24 (m, 2H), 2.07-2.04 (m, 1H), 1.95-1.92 (m, 1H) |
| 308 | 504.20 | 1H NMR (400 MHz, DMSO-d6) δ 9.16 (s, 2H), 8.87 (dd, J = 7.4, 0.9 Hz, 1H), 8.65 (dd, J = 8.3, 1.5 Hz, 1H), 8.01 (dd, J = 7.6, 1.5 Hz, 1H), 7.86 (dd, J = 2.1, 0.9 Hz, 1H), 7.50 (t, J = 7.9 Hz, 1H), 7.33 (dd, J = 7.4, 2.1 Hz, 1H), 5.15 (d, J = 7.0 Hz, 1H), 5.01 (d, J = 6.4 Hz, 1H), 3.38 (dt, J = 13.6, 6.8 Hz, 1H), 2.88 (s, 2H), 2.86-2.77 (m, 2H), 2.68-2.58 (m, 3H), 1.47 (s, 3H) |
| 309 | 512.15 | 1H NMR (400 MHz, DMSO-d6) δ 8.84 (dd, J = 7.4, 0.9 Hz, 1H), 8.71 (d, J = 1.9 Hz, 1H), 8.65 (dd, J = 8.2, 1.5 Hz, 1H), 8.08-7.99 (m, 2H), 7.85 (dd, J = 2.2, 0.9 Hz, 1H), 7.55-7.46 (m, 1H), 7.30 (dd, J = 7.4, 2.1 Hz, 1H), 5.15 (d, J = 7.0 Hz, 1H), 5.01 (d, J = 6.4 Hz, 1H), 4.75-4.49 (m, 2H), 3.38 (dt, J = 13.5, 6.8 Hz, 1H), 2.93-2.86 (m, 2H), 2.64 (d, J = 13.6 Hz, 1H), 2.27 (d, J = 12.1 Hz, 2H), 1.01 (s, 3H) |
| 310 | 466.15 | 1H NMR (400 MHz, DMSO-d6) δ 9.57 (s, 2H), 9.26 (d, J = 7.5 Hz, 1H), 8.63 (dd, J = 8.3, 1.5 Hz, 1H), 8.02 (dd, J = 7.6, 1.5 Hz, 1H), 7.76 (d, J = 7.5 Hz, 1H), 7.56-7.40 (m, 1H), 5.17 (d, J = 6.9 Hz, 1H), 5.08 (d, J = 6.5 Hz, 1H), 3.44-3.39 (m, 1H), 2.67-2.58 (m, 3H), 2.16-2.09 (m, 2H), 2.04-1.94 (m, 1H), 1.88-1.78 (m, 1H) |
| 311 | 523.20 | 1H NMR (400 MHz, DMSO-d6) δ 9.73 (dd, J = 7.0, 1.2 Hz, 1H), 9.34 (d, J = 1.3 Hz, 2H), 8.63 (dd, J = 8.3, 1.5 Hz, 1H), 8.02 (dd, J = 7.6, 1.4 Hz, 1H), 7.53-7.44 (m, 1H), 5.23-5.17 (m, 1H), 5.07 (d, J = 6.5 Hz, 1H), 3.41 (dt, J = 13.7, 6.9 Hz, 1H), 2.97 (s, 2H), 2.85-2.77 (m, 2H), 2.69-2.57 (m, 3H), 1.46 (s, 3H) |
| 312 | 522.20 | 1H NMR (400 MHz, DMSO-d6) δ 9.28 (d, J = 5.9 Hz, 1H), 9.05 (d, J = 1.6 Hz, 2H), 8.64 (dd, J = 8.3, 1.6 Hz, 1H), 8.01 (dd, J = 7.6, 1.5 Hz, 1H), 7.69 (d, J = 7.6 Hz, 1H), 7.50 (td, J = 8.3, 3.5 Hz, 1H), 5.16 (dd, J = 7.3, 3.1 Hz, 1H), 5.00 (dd, J = 6.5, 2.6 Hz, 1H), 3.44-3.34 (m, 1H), 3.12 (s, 1H), 2.86-2.77 (m, 3H), 2.63 (dd, J = 13.1, 10.3 Hz, 3H), 1.47 (s, 3H). |
| 313 | 480.30 | 1H NMR (400 MHz, DMSO-d6) δ 9.19 (s, 2H), 8.83 (dd, J = 7.1, 2.2 Hz, 1H), 8.16 (dd, J = 8.0, 1.6 Hz, 1H), 7.88 (s, 1H), 7.28 (dd, J = 7.2, 2.7 Hz, 1H), 7.22 (dd, J = 7.7, 1.6 Hz, 1H), 7.16 (t, J = 7.8 Hz, 1H), 5.39 (d, J = 6.9 Hz, 1H), 5.04 (d, J = 6.8 Hz, 1H), 3.29 (m, 3H), 2.63 (m, 3H), 2.47 (s, 1H), 2.14 (d, J = 9.0 Hz, 2H), 1.99 (m, 1H), 1.91-1.75 (m, 1H), |

| Ex. | LCMS [M + H]+ | 1H NMR (ppm) |
|---|---|---|
| | | 1.22 (m, 2H), 1.03 (d,, J = 9.8, 4.4 Hz, 1H), 0.65 (m, 1H) |

Example 314

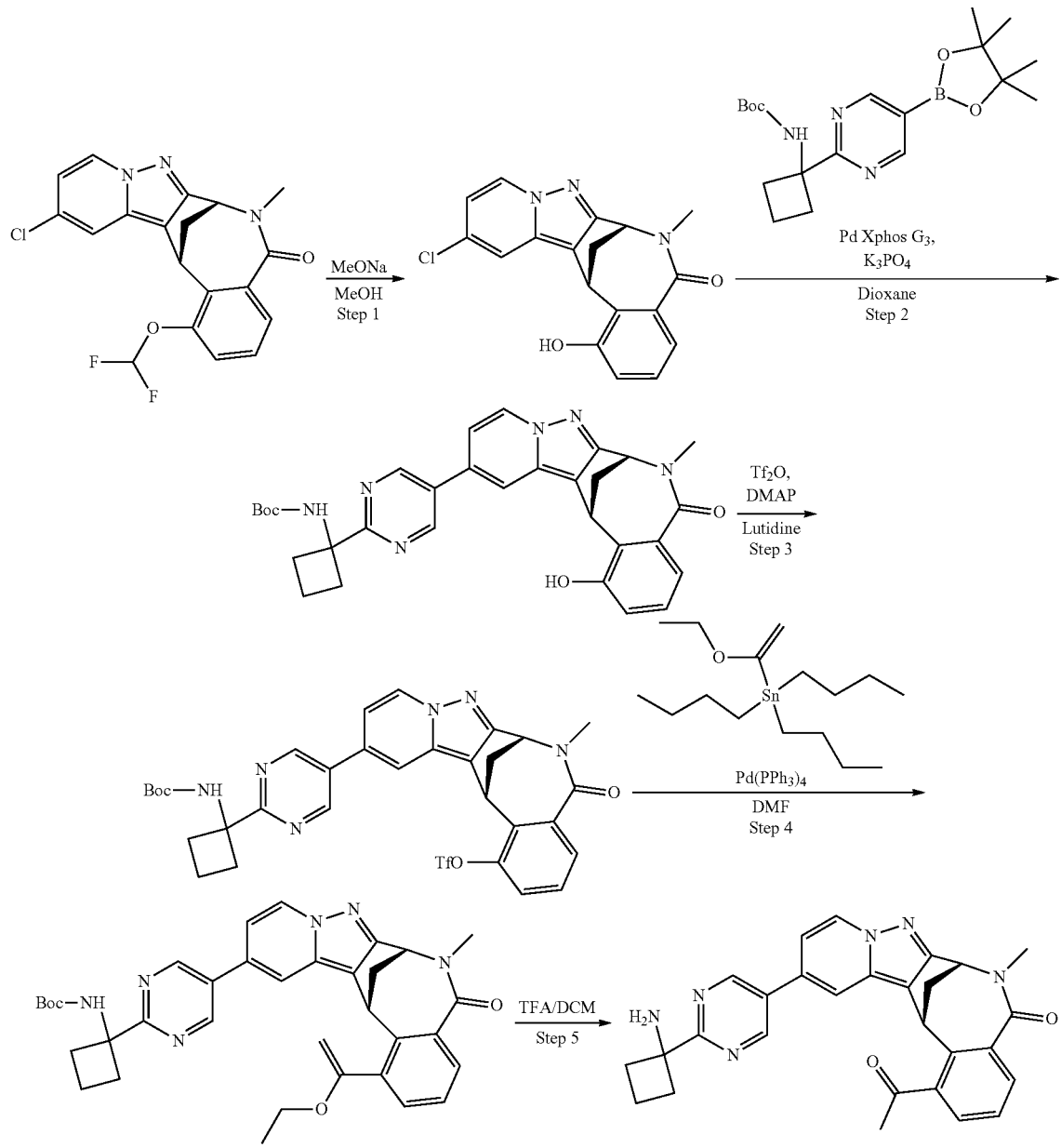

Step 1: A mixture of (7R,14S)-12-chloro-1-(difluoromethoxy)-6-methyl-6,7-dihydro-7,14-methanobenzo[c]pyrido[1',2':1,5]pyrazolo[4,3-f]azocin-5 (14H)-one (500 mg, 1.3 mmol, 1.0 equiv) in sodium methoxide (30% in methanol) (8 mL, 4.0 mmol, 3.0 equiv) was stirred at 80° C. for 1 h under air atmosphere. The resulting mixture was extracted with EtOAc (3×100 mL). The combined organic layers were washed with water (2×100 mL), dried over anhydrous Na₂SO₄. After filtration, the filtrate was concentrated under reduced pressure. The residue was purified by silica gel column chromatography, eluted with PE/EA (1:1) to afford (7R,14S)-12-chloro-1-hydroxy-6-methyl-6,7-dihydro-7,14-methanobenzo[c]pyrido[1',2':1,5]pyrazolo[4,3- f]azocin-5 (14H)-one (400 mg, 92%) as a yellow solid. LCMS (ESI, m/z): 340.05 [M+H]⁺.

Step 2: A solution of (7R,14S)-12-chloro-1-hydroxy-6-methyl-6,7-dihydro-7,14-methanobenzo[c]pyrido[1',2':1,5]pyrazolo[4,3-f]azocin-5 (14H)-one (390 mg, 1.15 mmol, 1.0 equiv) and tert-butyl (1-(5-(4,4,5,5-tetramethyl-1,3,2-dioxaborolan-2-yl)pyrimidin-2-yl)cyclobutyl)carbamate (517 mg, 1.4 mmol, 1.2 equiv), XPhos Pd G2 (90 mg, 0.12 mmol, 0.1 equiv), Na$_2$CO$_3$ (365 mg, 3.4 mmol, 3.0 equiv) in 1,4-dioxane (5 mL) and H$_2$O (1 mL) was stirred at 140° C. for 1 h under nitrogen atmosphere. The resulting mixture was extracted with EtOAc (3×60 mL). The combined organic layers were washed with water (3×40 mL), dried over anhydrous Na$_2$SO$_4$. After filtration, the filtrate was concentrated under reduced pressure. The residue was purified by Prep-TLC (CH$_2$Cl$_2$/MeOH=20:1) to afford tert-butyl (1-(5-((7R,14S)-1-hydroxy-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (510 mg, 80.4%) as a yellow solid. LCMS (ESI, m/z): 553.25 [M+H]⁺.

Step 3: A solution of tert-butyl (1-(5-((7R,14S)-1-hydroxy-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (20 mg, 0.04 mmol, 1.0 equiv) in DCM (1 mL) was treated with pyridine (15 mg, 0.18 mmol, 5.0 equiv) at room temperature for 2 min under nitrogen atmosphere followed by the addition of trifluoromethanesulfonic anhydride (31 mg, 0.11 mmol, 3.0 equiv) dropwise at 0° C. The resulting mixture was stirred at room temperature for 1 h under nitrogen atmosphere. The resulting mixture was extracted with EtOAc (3×50 mL). The combined organic layers were washed with water (2×100 mL), and dried over anhydrous Na$_2$SO$_4$. After filtration, the filtrate was concentrated under reduced pressure. The residue was purified by silica gel column chromatography, eluted with DCM/MeOH (20:1) to afford (7R,14S)-12-(2-(1-((tert-butoxycarbonyl)amino)cyclobutyl)pyrimidin-5-yl)-6-methyl-5-oxo-5,6,7,14-tetrahydro-7,14-methanobenzo[c]pyrido[1',2':1,5]pyrazolo[4,3-f]azocin-1-yl trifluoromethanesulfonate (380 mg, 61.3%) as a yellow solid. LCMS (ESI, m/z): 685.30 [M+H]⁺.

Step 4: A solution of (7R,14S)-12-(2-(1-((tert-butoxycarbonyl)amino)cyclobutyl)pyrimidin-5-yl)-6-methyl-5-oxo-5,6,7,14-tetrahydro-7,14-methanobenzo[c]pyrido[1',2':1,5]pyrazolo[4,3-f]azocin-1-yl trifluoromethanesulfonate (100 mg, 0.15 mmol, 1.0 equiv), tributyl(1-ethoxyethenyl)stannane (74 mg, 0.2 mmol, 1.4 equiv) and LiCl (19 mg, 0.44 mmol, 3.0 equiv) in 1,4-dioxane (1 mL) was treated with Pd(PPh$_3$)$_4$ (20 mg, 0.015 mmol, 0.1 equiv) and stirred at 95° C. for 1 h under nitrogen atmosphere. The resulting mixture was extracted with EtOAc (3×50 mL). The combined organic layers were washed with brine, dried over anhydrous Na$_2$SO$_4$. After filtration, the filtrate was concentrated under reduced pressure. The residue was purified by Prep-TLC (DCM/MeOH 15:1) to afford tert-butyl (1-(5-((7R,14R)-1-(1-ethoxyvinyl)-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (80 mg, 90.3%) as a yellow solid. LCMS (ESI, m/z): 607.25 [M+H]⁺.

Step 5: A mixture of tert-butyl (1-(5-((7R,14R)-1-(1-ethoxyvinyl)-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (75 mg, 0.12 mmol, 1.0 equiv) in DCM (2 mL) was added trifluoroacetic acid (1 mL) at room temperature and stirred for 1 h under nitrogen atmosphere. The mixture was neutralized to pH 7 with saturated NaHCO$_3$(aq.). The resulting mixture was extracted with EtOAc (3×20 mL). The combined organic layers were washed with brine, dried over anhydrous Na$_2$SO$_4$. After filtration, the filtrate was concentrated under reduced pressure. The crude product was purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 70% B in 9 min; Wave Length: 254 nm/220 nm nm; RT1(min): 6.56) to (7R,14R)-1-acetyl-12-(2-(1-aminocyclobutyl)pyrimidin-5-yl)-6-methyl-6,7-dihydro-7,14-methanobenzo[c]pyrido[1',2':1,5]pyrazolo[4,3-f]azocin-5 (14H)-one (31.5 mg, 53.3%). LCMS (ESI, m/z): 479.20 [M+H]⁺. ¹H NMR (400 MHz, DMSO-d$_6$) δ 9.16 (s, 2H), 8.84 (d, J=7.3 Hz, 1H), 8.48-8.41 (m, 2H), 7.91 (dd, J=7.6, 1.5 Hz, 1H), 7.41 (t, J=7.9 Hz, 1H), 7.32 (dd, J=7.4, 2.1 Hz, 1H), 5.44 (s, 2H), 5.04 (d, J=6.8 Hz, 1H), 4.75 (d, J=6.8 Hz, 1H), 3.26 (s, 3H), 3.25-3.16 (m, 1H), 2.79 (s, 3H), 2.71-2.61 (m, 2H), 2.43 (d, J=13.5 Hz, 1H), 2.26 (d, J=10.3 Hz, 2H), 2.05 (d, J=10.4 Hz, 1H), 2.01-1.90 (m, 1H).

Example 315

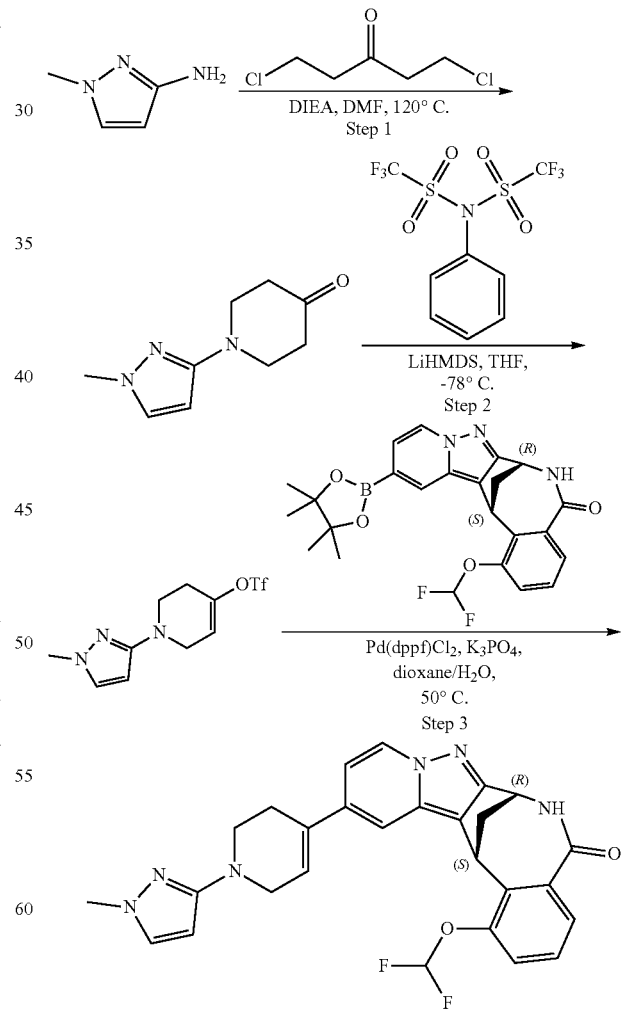

Step 1: To a stirred solution of 1-methylpyrazol-3-amine (1.2 g, 11.8 mmol, 1.0 equiv) and DIEA (3.8 g, 29.6 mmol, 2.5 equiv) in DMF (12 mL) was added 1,5-dichloropentan-3-one (2.0 g, 13.0 mmol, 1.1 equiv) dropwise at room temperature under nitrogen atmosphere. Then the mixture was stirred at 120° C. overnight. The reaction was quenched by the addition of water (12 mL) at room temperature. The resulting mixture was extracted with EtOAc (3×24 mL). The combined organic layers were washed with water (2×24 mL) and brine (2×24 mL), dried over anhydrous $Na_2SO_4$. After filtration, the filtrate was concentrated under reduced pressure. The residue was purified by Prep-TLC (EA) to afford 1-(1-methylpyrazol-3-yl)piperidin-4-one (513 mg, 24.2%) as a yellow oil. LCMS (ESI, m/z): 180.20 $[M+H]^+$.

Step 2: To a stirred solution of 1-(1-methylpyrazol-3-yl)piperidin-4-one (510 mg, 2.8 mmol, 1.0 equiv) in THF (4 mL) was added LiHMDS (1.0 M in THF) (3.1 mL, 3.1 mmol, 1.1 equiv) dropwise at −78° C. under nitrogen atmosphere. The resulting mixture was stirred at −78° C. for 1 h under nitrogen atmosphere. To the above mixture was added 1,1,1-trifluoro-N-phenyl-N-(trifluoromethane)sulfonylmethanesulfonamide (1.2 g, 3.4 mmol, 1.2 equiv) in THF (4 mL) dropwise at 0° C. The resulting mixture was stirred at room temperature for additional 1 h. The reaction was quenched by the addition of sat. $NH_4Cl$ (aq.) (10 mL) at 0° C. The resulting mixture was extracted with EtOAc (3×20 mL). The combined organic layers were dried over anhydrous $Na_2SO_4$. After filtration, the filtrate was concentrated under reduced pressure. The residue was purified by Prep-TLC (PE/EA 1:1) to afford 1 1-(1-methyl-1H-pyrazol-3-yl)-1,2,3,6-tetrahydropyridin-4-yl trifluoromethanesulfonate (227 mg, 25.6%) as a light yellow oil. LCMS (ESI, m/z): 312.05 $[M+H]^+$.

Step 3: To a stirred solution of 1-(1-methyl-1H-pyrazol-3-yl)-1,2,3,6-tetrahydropyridin-4-yl trifluoromethanesulfonate (20 mg, 0.06 mmol, 1.0 equiv) and (7R,14S)-1-(difluoromethoxy)-12-(4,4,5,5-tetramethyl-1,3,2-dioxaborolan-2-yl)-6,7-dihydro-7,14-methanobenzo[c]pyrido[1′,2′:1,5]pyrazolo[4,3-f]azocin-5 (14H)-one (30 mg, 0.06 mmol, 1.0 equiv) in 1,4-dioxane (1 mL) and $H_2O$ (0.2 mL) were added Pd(dppf)$Cl_2 \cdot CH_2Cl_2$ (5.2 mg, 0.006 mmol, 0.1 equiv) and $K_3PO_4$ (41 mg, 0.18 mmol, 3.0 equiv) in portions at room temperature under nitrogen atmosphere. Then the mixture was stirred at 50° C. for 0.5 h. The mixture was allowed to cool down to room temperature. The reaction was quenched by the addition of water (1 mL) at room temperature. The resulting mixture was extracted with EtOAc (3×1 mL). The combined organic layers were dried over anhydrous $Na_2SO_4$. After filtration, the filtrate was concentrated under reduced pressure. The crude product was purified by Prep-HPLC with the following conditions (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min mL/min; Gradient: 41% B to 61% B in 10 min; Wave Length: 254 nm/220 nm nm; RT1(min): 9.18) to afford (7R,14S)-1-(difluoromethoxy)-12-(1-(1-methyl-1H-pyrazol-3-yl)-1,2,3,6-tetrahydropyridin-4-yl)-6,7-dihydro-7,14-methanobenzo[c]pyrido[1′,2′:1,5]pyrazolo[4,3-f]azocin-5 (14H)-one (2 mg, 6.8%). LCMS (ESI, m/z): 503.20 $[M+H]^+$. $^1$H NMR (400 MHz, DMSO-$d_6$) δ 8.83 (d, J=6.6 Hz, 1H), 8.53 (dd, J=7.5, 0.8 Hz, 1H), 8.18 (dd, J=8.0, 1.5 Hz, 1H), 7.82-7.43 (m, 2H), 7.43-7.36 (m, 1H), 7.34 (d, J=8.0 Hz, 1H), 7.31 (s, 1H), 7.06 (dd, J=7.7, 2.1 Hz, 1H), 6.50 (s, 1H), 5.77 (d, J=2.3 Hz, 1H), 5.02 (d, J=6.5 Hz, 1H), 4.74 (t, J=6.6 Hz, 1H), 3.80 (d, J=3.5 Hz, 2H), 3.67 (s, 3H), 3.38 (t, J=5.7 Hz, 3H), 3.23 (dt, J=12.9, 6.9 Hz, 2H), 2.40 (d, J=13.0 Hz, 1H)

Examples 316 & 317

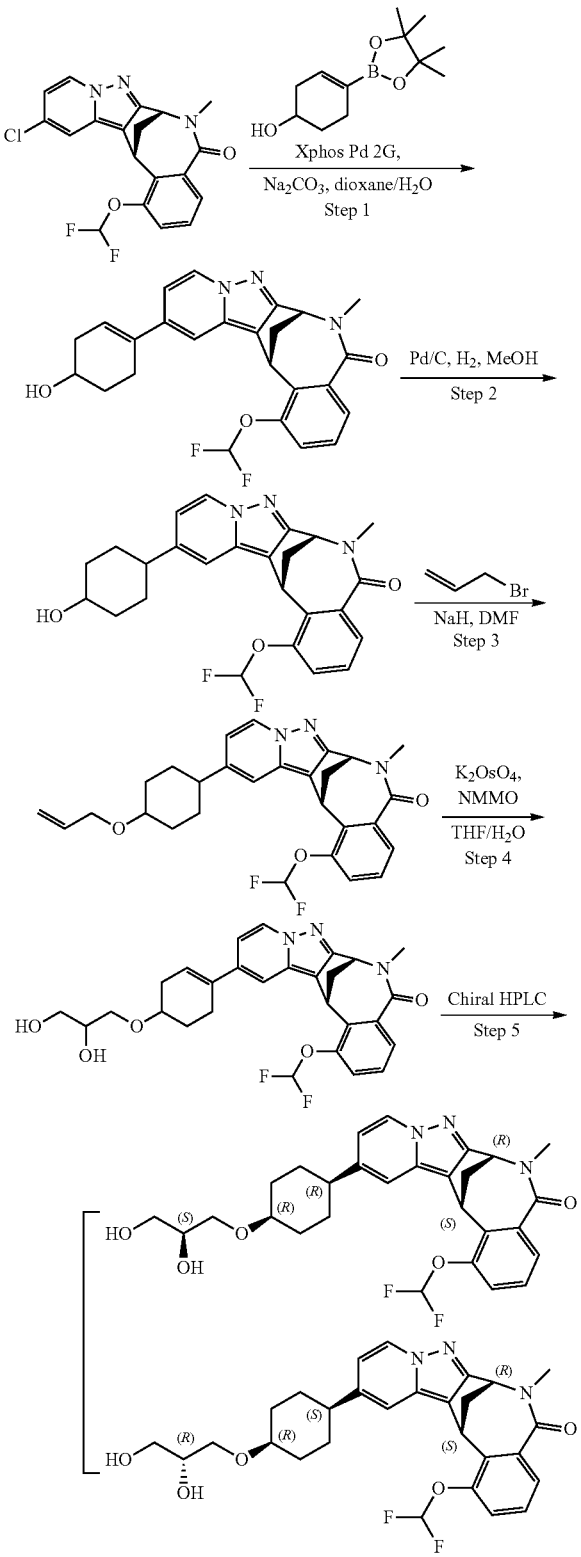

Step 1: To a stirred solution of (7R,14S)-12-chloro-1-(difluoromethoxy)-6-methyl-6,7-dihydro-7,14-methanobenzo[c]pyrido[1′,2′:1,5]pyrazolo[4,3-f]azocin-5 (14H)-one (200 mg, 0.5 mmol, 1.0 equiv) and dioxane (10 mL) in H₂O (2 mL) were added 4-(4,4,5,5-tetramethyl-1,3,2-dioxaborolan-2-yl) cyclohex-3-en-1-ol (230 mg, 1.0 mmol, 2.0 equiv) and Na₂CO₃ (163 mg, 1.5 mmol, 3.0 equiv) at room temperature. To the above mixture was added XPhos Pd G2 (40 mg, 0.05 mmol, 0.1 equiv) at room temperature. The final reaction mixture was irradiated with microwave radiation at 140° C. for 1 h. The resulting mixture was concentrated under vacuum. The residue was purified by Prep-TLC (CH₂Cl₂/MeOH 15:1) to afford (7R,14S)-1-(difluoromethoxy)-12-(4-hydroxycyclohex-1-en-1-yl)-6-methyl-6,7-dihydro-7,14-methanobenzo[c]pyrido[1',2':1,5]pyrazolo[4,3-f]azocin-5 (14H)-one (220 mg, 95%) as an off-white solid. LCMS (ESI, m/z): 452.20 [M+H]⁺.

Step 2: To a solution of (7R,14S)-1-(difluoromethoxy)-12-(4-hydroxycyclohex-1-en-1-yl)-6-methyl-6,7-dihydro-7,14-methanobenzo[c]pyrido[1',2':1,5]pyrazolo[4,3-f]azocin-5 (14H)-one (214 mg, 0.47 mmol, 1.0 equiv) in MeOH (30 mL) was added Pd/C (10%, 1 mg) under nitrogen atmosphere. The mixture was hydrogenated at room temperature for 2 h using a hydrogen balloon, filtered through a Celite pad and concentrated under reduced pressure. The resulting mixture was concentrated under reduced pressure. The residue was purified by Prep-TLC (PE/EA 1:1) to afford (7R,14S)-1-(difluoromethoxy)-12-(4-hydroxycyclohexyl)-6-methyl-6,7-dihydro-7,14-methanobenzo[c]pyrido[1',2':1,5]pyrazolo[4,3-f]azocin-5 (14H)-one (150 mg, 70%) as a white solid. LCMS (ESI, m/z): 454.15 [M+H]⁺.

Step 3: To a solution of (7R,14S)-1-(difluoromethoxy)-12-(4-hydroxycyclohexyl)-6-methyl-6,7-dihydro-7,14-methanobenzo[c]pyrido[1',2':1,5]pyrazolo[4,3-f]azocin-5 (14H)-one (140 mg, 0.31 mmol, 1.0 equiv) in DMF (3 mL) was added sodium hydride (60% in oil, 9 mg) at 0° C. The mixture was stirred for 30 min. allyl bromide (56 mg, 0.46 mmol, 1.5 equiv) was added and the mixture was allowed to warm to RT and stirred for 2 h. The reaction mixture was quenched by water and extracted with DCM (3×25 mL). The residue was purified by Prep-TLC (CH₂Cl₂/MeOH 20:1) to afford (7R,14S)-12-(4-(allyloxy)cyclohexyl)-1-(difluoromethoxy)-6-methyl-6,7-dihydro-7,14-methanobenzo[c]pyrido[1',2':1,5]pyrazolo[4,3-f]azocin-5 (14H)-one (100 mg, 65.6%) as a white solid. LCMS (ESI, m/z): 494.35 [M+H]⁺.

Step 4: To a stirred solution of (7R,14S)-12-(4-(allyloxy)cyclohexyl)-1-(difluoromethoxy)-6-methyl-6,7-dihydro-7,14-methanobenzo[c]pyrido[1',2':1,5]pyrazolo[4,3-f]azocin-5 (14H)-one (130 mg, 0.26 mmol, 1.0 equiv) and H₂O (0.3 mL) in THF (3 mL) were added 4-methylmorpholin-4-ium-4-olate (93 mg, 0.8 mmol, 3.0 equiv) and potassium osmate(VI) dihydrate (10 mg, 0.026 mmol, 0.1 equiv) at room temperature. The resulting mixture was stirred at room temperature for 2 h. The reaction was quenched by the addition of sat. sodium sulfite (aq.) (10 mL) at room temperature. The aqueous layer was extracted with EtOAc (3×10 mL). The residue was purified by Prep-TLC (CH₂Cl₂/MeOH 10:1) to afford (7R,14S)-1-(difluoromethoxy)-12-(4-(2,3-dihydroxypropoxy)cyclohexyl)-6-methyl-6,7-dihydro-7,14-methanobenzo[c]pyrido[1',2':1,5]pyrazolo[4,3-f]azocin-5 (14H)-one (60 mg, 43.2%) as an off-white solid. LCMS (ESI, m/z): 528.35 [M+H]⁺.

Step 5: ((7R,14S)-1-(difluoromethoxy)-12-(4-(2,3-dihydroxypropoxy)cyclohexyl)-6-methyl-6,7-dihydro-7,14-methanobenzo[c]pyrido[1',2':1,5]pyrazolo[4,3-f]azocin-5 (14H)-one (40 mg) was further purified by Prep-HPLC with the following conditions (Column: X-Select Prep OBD C18 Column, 30*150 mm, 5 μm; Mobile Phase A: Water (0.1% FA), Mobile Phase B: ACN; Flow rate: 60 mL/min mL/min; Gradient: 30% B to 50% B in 7 min; Wave Length: 254 nm/220 nm; RT1 (min): 6.56 to afford: (7R,14S)-1-(difluoromethoxy)-12-((1R,4R)-4-((S)-2,3-dihydroxypropoxy)cyclohexyl)-6-methyl-6,7-dihydro-7,14-methanobenzo[c]pyrido[1',2':1,5]pyrazolo[4,3-f]azocin-5 (14H)-one (9 mg). LCMS (ESI, m/z): 528.25 [M+H]⁺. ¹H NMR (400 MHz, DMSO-d₆) δ 8.57-8.51 (m, 1H), 8.21 (d, J=8.0 Hz, 1H), 7.81-6.99 (m, 4H), 6.78-6.71 (m, 1H), 5.10-4.86 (m, 2H), 4.62-4.57 (m, 2H), 3.55 (s, 3H), 3.40 (d, J=40.3 Hz, 4H), 2.48 (d, J=23.6 Hz, 3H), 2.11-2.03 (m, 2H), 1.88-1.80 (m, 2H), 1.53-1.22 (m, 4H). (7R,14S)-1-(difluoromethoxy)-12-((1S,4R)-4-((R)-2,3-dihydroxypropoxy)cyclohexyl)-6-methyl-6,7-dihydro-7,14-methanobenzo[c]pyrido[1',2':1,5]pyrazolo[4,3-f]azocin-5 (14H)-one (4 mg) as a white solid. LCMS (ESI, m/z): 528.25 [M+H]⁺. 1HNMR (400 MHz, DMSO-d6) δ 8.57-8.51 (m, 1H), 8.21 (d, J=8.0 Hz, 1H), 7.81-6.99 (m, 4H), 6.78-6.71 (m, 1H), 5.10-4.86 (m, 2H), 4.62-4.57 (m, 2H), 3.55 (s, 3H), 3.40 (d, J=40.3 Hz, 4H), 2.48 (d, J=23.6 Hz, 3H), 2.11-2.03 (m, 2H), 1.88-1.80 (m, 2H), 1.53-1.22 (m, 4H).

Examples 318 & 319

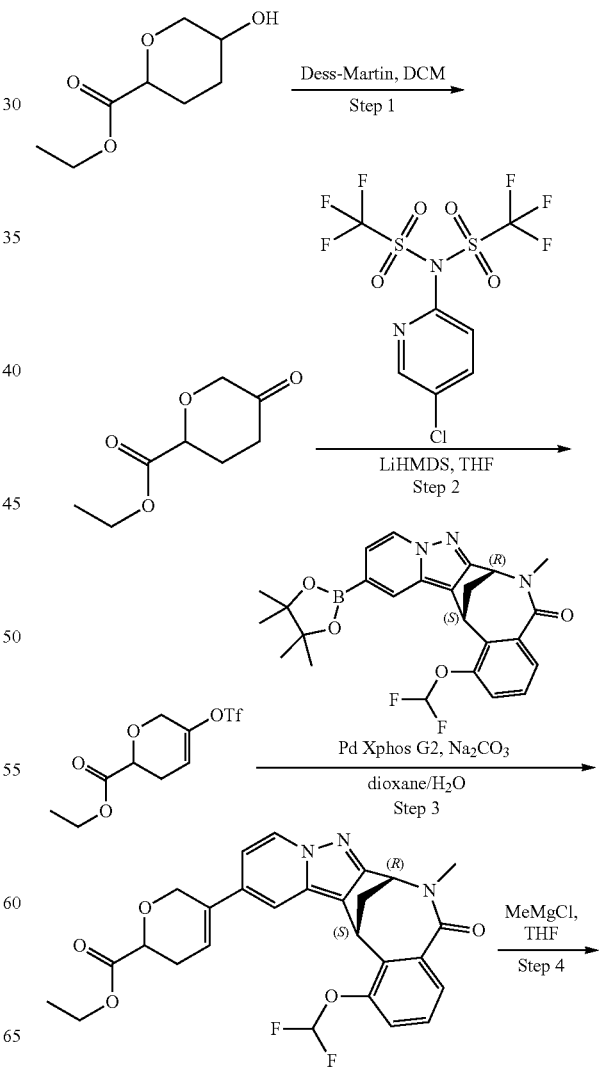

463

-continued

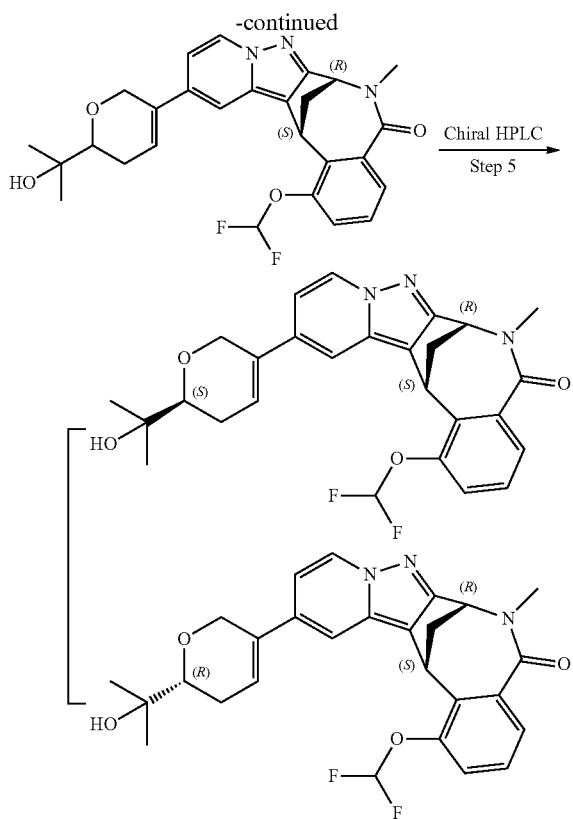

Chiral HPLC
Step 5

Step 1: To a stirred solution of ethyl 5-hydroxyoxane-2-carboxylate (4 g, 23 mmol, 1.0 equiv) in DCM (100 mL) were added Dess-Martin (14.6 g, 34.4 mmol, 1.5 equiv) at 0° C. under air atmosphere. The resulting mixture was stirred at room temperature for overnight under air atmosphere. The reaction was quenched with sat. $Na_2S_2O_3$ (aq.) and sat. $NaHCO_3$(aq.) at 0° C. The resulting mixture was extracted with $CH_2Cl_2$ (3×25 mL). The combined organic layers were washed with brine, dried over anhydrous $Na_2SO_4$. After filtration, the filtrate was concentrated under reduced pressure. The residue was purified by silica gel column chromatography, eluted with PE/EA (1:1) to afford ethyl 5-oxooxane-2-carboxylate (3 g, 75.9%) as a yellow oil.

Step 2: To a mixture of ethyl 5-oxooxane-2-carboxylate (600 mg, 3.5 mmol, 1.0 equiv) in THF (3 mL) was added LiHMDS (1.0 Min THF) (17.4 mL, 17.4 mmol, 5.0 equiv) dropwise at −78° C. under nitrogen atmosphere. The mixture was stirred for 1 h at −78° C. prior addition of Comins' reagent (2.1 g, 5.2 mmol, 1.50 equiv). The mixture was stirred for 1 h at −78° C. The mixture was acidified to pH 6 with saturated $NH_4Cl$ (aq.) at −60° C. The reaction mixture was diluted with water (20 mL), and the aqueous phase was extracted with EA (3×30 mL). The combined organic layers were washed with brine, dried over sodium sulfate, filtered, and concentrated in vacuo. The residue was purified by TLC (PE/EA 3:1) to afford ethyl 5-(trifluoromethanesulfonyloxy)-3,6-dihydro-2H-pyran-2-carboxylate (200 mg, 18.9%) as a yellow oil.

Step 3: A solution of ethyl 5-(trifluoromethanesulfonyloxy)-3,6-dihydro-2H-pyran-2-carboxylate (450 mg, 1.5 mmol, 1.0 equiv), (7R,14S)-1-(difluoromethoxy)-6-methyl-12-(4,4,5,5-tetramethyl-1,3,2-dioxaborolan-2-yl)-6,7-dihydro-7,14-methanobenzo[c]pyrido[1',2':1,5]pyrazolo[4,3-f]azocin-5 (14H)-one (722 mg, 1.5 mmol, 1.0 equiv) in

464

1,4-dioxane (5 mL) and $H_2O$ (1 mL) was treated with $Na_2CO_3$ (470 mg, 4.4 mmol, 3.0 equiv) followed by the addition of XPhos Pd G2 (120 mg, 0.15 mmol, 0.1 equiv). The reaction mixture was diluted with water (30 mL), and the aqueous phase was extracted with EA (3×30 mL). The combined organic layers were washed with brine, dried over sodium sulfate, filtered, and concentrated in vacuo. The residue was purified by reverse flash chromatography with the following conditions: column, C18 silica gel; mobile phase, MeCN in water, 0% to 100% gradient in 10 min; detector, UV 220 nm. Concentration in vacuo resulted in ethyl 5-((7R,14S)-1-(difluoromethoxy)-6-methyl-5-oxo-5,6,7,14-tetrahydro-7,14-methanobenzo[c]pyrido[1',2':1,5]pyrazolo[4,3-f]azocin-12-yl)-3,6-dihydro-2H-pyran-2-carboxylate (120 mg, 15.9%) as a yellow oil. LCMS (ESI, m/z): 510.25 [M+H]⁺.

Step 4: To a mixture of chloro(methyl)magnesium (0.76 mL, 2.3 mmol, 20.0 equiv) in THF (3 mL) was added ethyl 5-((7R,14S)-1-(difluoromethoxy)-6-methyl-5-oxo-5,6,7,14-tetrahydro-7,14-methanobenzo[c]pyrido[1',2':1,5]pyrazolo[4,3-f]azocin-12-yl)-3,6-dihydro-2H-pyran-2-carboxylate (58 mg, 0.11 mmol, 1.0 equiv) dropwise at −65° C. under nitrogen atmosphere. The mixture was stirred for 1 h at −45° C. The reaction was quenched with sat. $NH_4Cl$ (aq.) at −60° C. The reaction mixture was diluted with water (20 mL), and the aqueous phase was extracted with EA (3×20 mL). The combined organic layers were washed with brine, dried over sodium sulfate, filtered, and concentrated in vacuo. The residue was purified by TLC (PE/EA; ratio: 0/1) to afford (7R,14S)-1-(difluoromethoxy)-12-(6-(2-hydroxypropan-2-yl)-5,6-dihydro-2H-pyran-3-yl)-6-methyl-6,7-dihydro-7,14-methanobenzo[c]pyrido[1',2':1,5]pyrazolo[4,3-f]azocin-5 (14H)-one (25 mg, 44.3%) as a yellow solid. LCMS (ESI, m/z): 496.35 [M+H]⁺.

Step 5: (7R,14S)-1-(difluoromethoxy)-12-(6-(2-hydroxypropan-2-yl)-5,6-dihydro-2H-pyran-3-yl)-6-methyl-6,7-dihydro-7,14-methanobenzo[c]pyrido[1',2':1,5]pyrazolo[4,3-f]azocin-5 (14H)-one (25 mg) was further purified by Prep-HPLC with the following conditions (Column: CHIRALPAKIF3; Mobile Phase A: Hex (0.1% DEA): (EtOH:MeOH=1:1)=70:30; Flow rate: 1 mL/min mL/min; Gradient: isocratic; Injection Volume: 2 ul mL) to afford: (7R,14S)-1-(difluoromethoxy)-12-((R)-6-(2-hydroxypropan-2-yl)-5,6-dihydro-2H-pyran-3-yl)-6-methyl-6,7-dihydro-7,14-methanobenzo[c]pyrido[1',2':1,5]pyrazolo[4,3-f]azocin-5 (14H)-one (4 mg) as an off-white solid. LCMS (ESI, m/z): 496.35 [M+H]⁺. 1H NMR (400 MHz, DMSO-d6) δ 8.58 (d, J=7.5 Hz, 1H), 8.21 (dd, J=7.8, 1.7 Hz, 1H), 7.59 (t, J=73.8 Hz, 1H), 7.38-7.30 (m, 2H), 7.12 (d, J=2.1 Hz, 1H), 7.02 (dd, J=7.6, 2.0 Hz, 1H), 6.56 (s, 1H), 5.02 (d, J=6.9 Hz, 1H), 4.94 (d, J=6.6 Hz, 1H), 4.59 (d, J=15.3 Hz, 1H), 4.45 (s, 1H), 4.41 (s, 1H), 3.26 (s, 6H), 2.46 (s, 1H), 2.26-2.14 (m, 2H), 1.24 (s, 1H), 1.12 (d, J=15.9 Hz, 6H). (7R,14S)-1-(difluoromethoxy)-12-((S)-6-(2-hydroxypropan-2-yl)-5,6-dihydro-2H-pyran-3-yl)-6-methyl-6,7-dihydro-7,14-methanobenzo[c]pyrido[1',2':1,5]pyrazolo[4,3-f]azocin-5 (14H)-one (6 mg) as an off-white solid. LCMS (ESI, m/z): 496.25 [M+H]⁺. 1H NMR (400 MHz, DMSO-d6) δ 8.57 (d, J=7.6 Hz, 1H), 8.21 (dd, J=7.9, 1.6 Hz, 1H), 7.59 (t, J=73.8 Hz, 1H), 7.39-7.29 (m, 2H), 7.12 (d, J=2.0 Hz, 1H), 7.02 (dd, J=7.6, 2.1 Hz, 1H), 6.56 (d, J=4.4 Hz, 1H), 5.03 (d, J=6.9 Hz, 1H), 4.94 (d, J=6.6 Hz, 1H), 4.59 (d, J=15.7 Hz, 1H), 4.44 (s, 1H), 4.41 (s, 1H), 3.29-3.19 (m, 5H), 2.46 (s, 1H), 2.31-2.17 (m, 2H), 1.12 (d, J=15.2 Hz, 6H).

Example 320
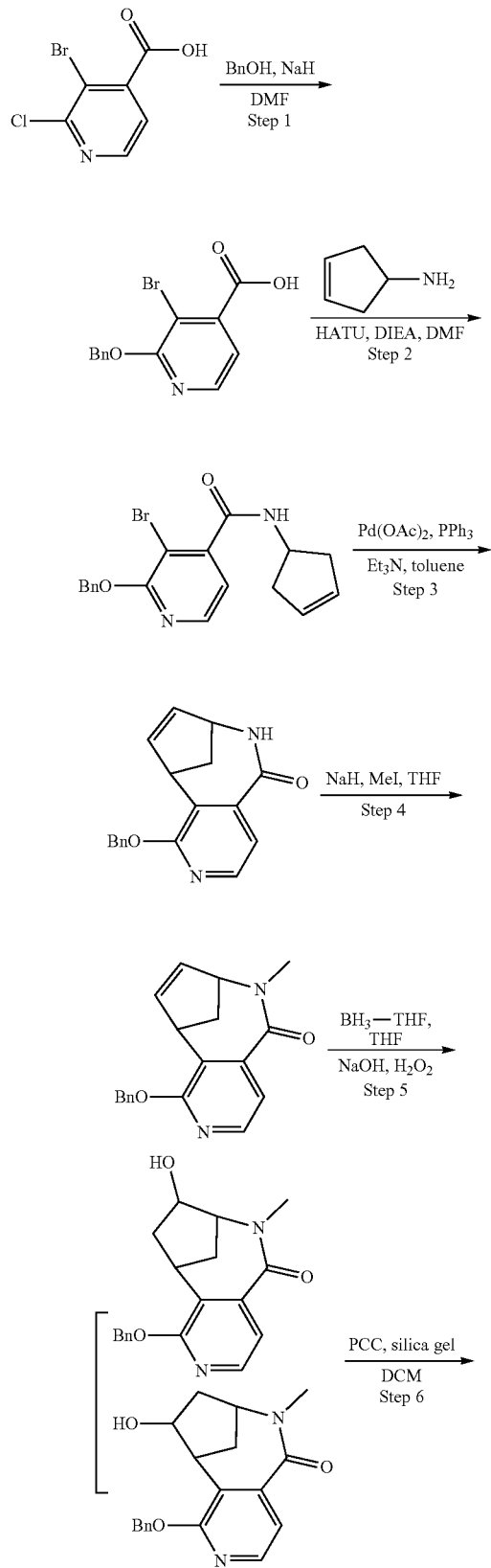
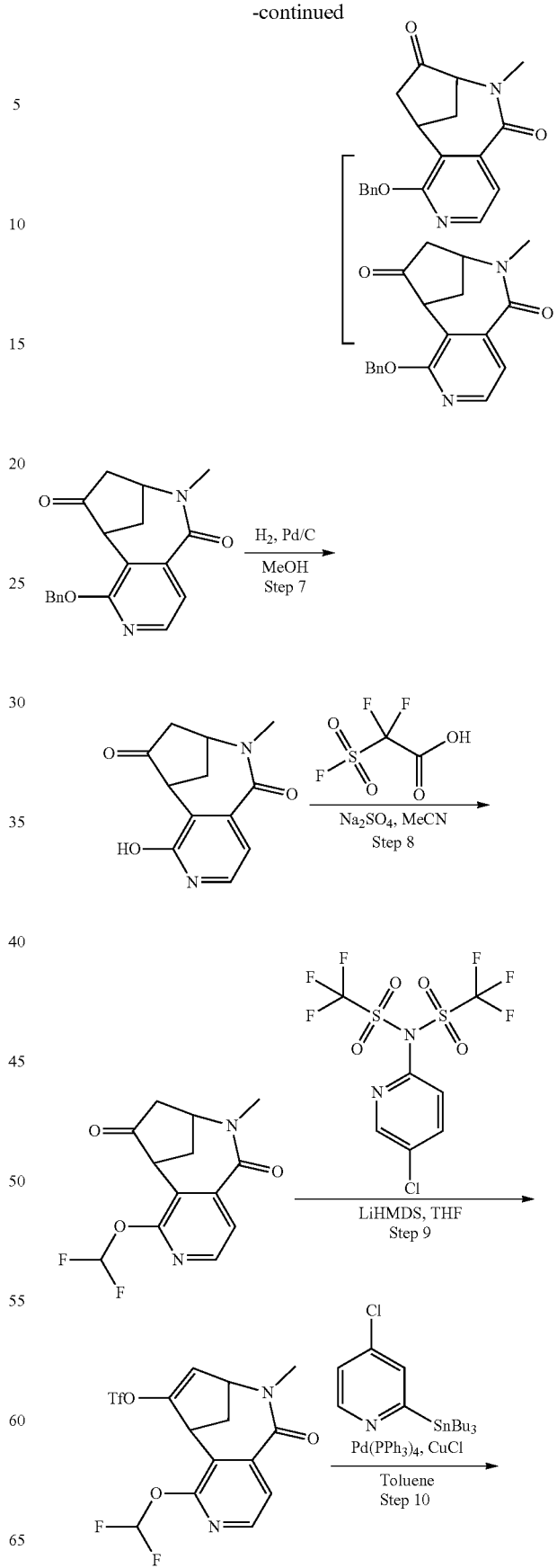

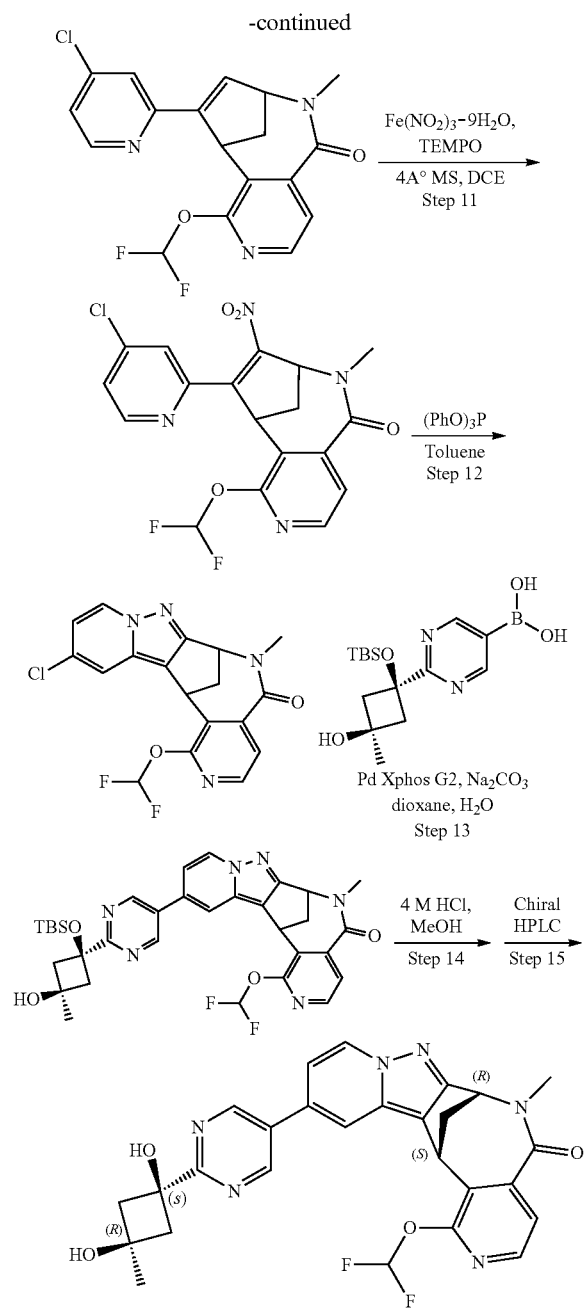

Step 1: To a stirred solution of benzyl alcohol (686.0 g, 6.3 mol, 5.0 equiv) in DMF (3 L) were added NaH (152.2 g, 3.8 mol, 3.0 equiv, 60%) at 0° C. under air atmosphere. To the above mixture was added 3-bromo-2-chloropyridine-4-carboxylic acid (300 g, 1.3 mol, 1.0 equiv) at room temperature. The resulting mixture was stirred for additional 1 h at 85° C. The mixture was acidified to pH 5 with HCl. The resulting mixture was extracted with EA (3×10 L). The combined organic layers were washed with H$_2$O (3×5 L), dried over anhydrous Na$_2$SO$_4$. After filtration, the filtrate was concentrated under reduced pressure. The residue was purified by reversed-phase flash chromatography with the following conditions: column, C18 silica gel; mobile phase, H$_2$O (0.5% TFA) in ACN, 10% to 50% gradient in 10 min; detector, UV 254 nm to afford 2-(benzyloxy)-3-bromopyridine-4-carboxylic acid (240 g, 60.2%) as a white solid. LCMS (ESI, m/z): 310.00 [M+H]$^+$.

Step 2: To a stirred solution of 2-(benzyloxy)-3-bromopyridine-4-carboxylic acid (240.0 g, 778.9 mmol, 1.0 equiv) and cyclopent-3-en-1-amine hydrochloride (111.8 g, 934.7 mmol, 1.2 equiv) in DMF (1.2 L) was added NaHCO$_3$ (327.2 g, 3.9 mol, 5.0 equiv) and HATU (444.2 g, 1.2 mol, 1.5 equiv) at 0° C. under air atmosphere. The resulting mixture was stirred for additional 1 h at 25° C. The resulting mixture was extracted with EA (3×10 L). The combined organic layers were washed with H$_2$O (3×5 L), dried over anhydrous Na$_2$SO$_4$. After filtration, the filtrate was concentrated under reduced pressure. The residue was purified by trituration with PE:EA=8:1 (5 L). This resulted in 2-(benzyloxy)-3-bromo-N-(cyclopent-3-en-1-yl)pyridine-4-carboxamide (280.0 g, 91.5%) as a white solid. LCMS (ESI, m/z): 373.05 [M+H]$^+$.

Step 3: To a stirred solution of 3-(benzyloxy)-N-(cyclopent-3-en-1-yl)-6-fluoro-2-iodobenzamide (280.0 g, 640.4 mmol, 1.0 equiv) and Pd(OAc)$_2$ (14.4 g, 64.0 mmol, 0.1 equiv) in toluene (3 L) was added PPh$_3$ (33.6 g, 128.1 mmol, 0.2 equiv) and Et3N (194.40 g, 1921.09 mmol, 3.0 equiv) at 25° C. under a nitrogen atmosphere. The resulting mixture was stirred for additional 1 h at 25° C. The resulting mixture was extracted with EA (3×10 L). The combined organic layers were washed with H$_2$O (3×5 L), dried over anhydrous Na$_2$SO$_4$. After filtration, the filtrate was concentrated under reduced pressure. The residue was purified by silica gel column chromatography, eluted with PE:EA (5:1) to afford 1-(benzyloxy)-7,10-dihydro-7,10-methanopyrido[4,3-c]azocin-5 (6H)-one (160.0 g, 76.7%) as a white solid. LCMS (ESI, m/z): 293.15 [M+H]$^+$.

Step 4: To a stirred solution of 1-(benzyloxy)-7,10-dihydro-7,10-methanopyrido[4,3-c]azocin-5 (6H)-one (160.0 g, 547.3 mmol, 1.0 equiv) in THF (2 L) were added NaH (32.8 g, 821 mmol, 1.5 equiv, 60%) and methyl iodide (116.5 g, 821 mmol, 1.5 equiv) at 0° C. under air atmosphere. The resulting mixture was stirred for additional 1 h at 25° C. The resulting mixture was extracted with EA (3×10 L). The combined organic layers were washed with H$_2$O (3×5 L), dried over anhydrous Na$_2$SO$_4$. After filtration, the filtrate was concentrated under reduced pressure. The residue was purified by silica gel column chromatography, eluted with PE:EA (5:1) to afford 1-(benzyloxy)-6-methyl-7,10-dihydro-7,10-methanopyrido[4,3-c]azocin-5 (6H)-one (165.0 g, 93.5%) as a white solid. LCMS (ESI, m/z): 307.15 [M+H]$^+$.

Step 5: A solution of 1-(benzyloxy)-6-methyl-7,10-dihydro-7,10-methanopyrido[4,3-c]azocin-5 (6H)-one (165.0 g, 538.6 mmol, 1.0 equiv) in THF (2 L) was treated with BH$_3$-THF (92.6 g, 1.1 mol, 2.0 equiv) at 0° C. for 3 h under nitrogen atmosphere followed by the addition of NaOH (538.6 mL, 1.6 mol, 3.0 equiv) and H$_2$O$_2$ (146.6 mL, 1.7 mol, 3.0 equiv, 40%) dropwise at 0° C. The resulting mixture was stirred at 0° C. for additional 30 min. The resulting mixture was extracted with DCM:MeOH=10:1 (3×5 L). The combined organic layers were washed with Na$_2$SO$_3$(aq.) (3×3 L), dried over anhydrous Na$_2$SO$_4$. After filtration, the filtrate was concentrated under reduced pressure. This resulted in 1-(benzyloxy)-8-hydroxy-6-methyl-7,8,9,10-tetrahydro-7,10-methanopyrido[4,3-c]azocin-5 (6H)-one and 1-(benzyloxy)-9-hydroxy-6-methyl-7,8,9,10-tetrahydro-7,10-methanopyrido[4,3-c]azocin-5 (6H)-one (160 g, crude) as a white solid. LCMS (ESI, m/z): 325.15 [M+H]$^+$.

Step 6: A solution of 1-(benzyloxy)-8-hydroxy-6-methyl-7,8,9,10-tetrahydro-7,10-methanopyrido[4,3-c]azocin-5 (6H)-one and 1-(benzyloxy)-9-hydroxy-6-methyl-7,8,9,10- tetrahydro-7,10-methanopyrido[4,3-c]azocin-5 (6H)-one (160.0 g, 493.2 mmol, 1.0 equiv) molecular sieves (4 A) (430 g) in DCM (2 L) was treated with chlorochromiumoylol; pyridine (212.6 g, 986.5 mmol, 2.0 equiv) at 0° C. for 16 h under air atmosphere. The resulting mixture was filtered, the filter cake was washed with DCM (3×3 L). The filtrate was concentrated under reduced pressure. The residue was extracted with DCM (3×3 L). The combined organic layers were washed with H$_2$O (3×3 L), dried over anhydrous Na$_2$SO$_4$. After filtration, the filtrate was concentrated under reduced pressure. The residue was purified by silica gel column chromatography, eluted with PE:EA (3:1) to afford 1-(benzyloxy)-6-methyl-6,7,9,10-tetrahydro-7,10-methanopyrido[4,3-c]azocine-5,8-dione (100 g) and 1-(benzyloxy)-6-methyl-7,8-dihydro-7,10-methanopyrido[4,3-c]azocine-5,9 (6H, 10H)-dione (30 g) as a white solid. LCMS (ESI, m/z): 323.20 [M+H]$^+$.

Step 7: A solution of 1-(benzyloxy)-6-methyl-7,8-dihydro-7,10-methanopyrido[4,3-c]azocine-5,9 (6H, 10H)-dione (30.0 g, 93.1 mmol, 1.0 equiv) in MeOH (300 mL) was added Pd/C (1.0 g, 9.3 mmol, 0.1 equiv) under H$_2$ atmosphere. Then the mixture was degassed with H$_2$ for 3 times. The reaction mixture was stirred for 16 h at 25° C. under H$_2$ atmosphere. The resulting mixture was filtered, the filter cake was washed with EtOAc (3×1 L). The filtrate was concentrated under reduced pressure. This resulted in 1-hydroxy-6-methyl-7,8-dihydro-7,10-methanopyrido[4,3-c]azocine-5,9 (6H, 10H)-dione (20 g, 90.7%) as a white solid. LCMS (ESI, m/z): 233.12 [M+H]$^+$.

Step 8: To a stirred solution of 1-hydroxy-6-methyl-7,8-dihydro-7,10-methanopyrido[4,3-c]azocine-5,9 (6H, 10H)-dione (20.0 g, 86.1 mmol, 1.0 equiv) and Na$_2$SO$_4$ (36.7 g, 258.4 mmol, 3.0 equiv) in anhydrous ACN (200 mL) was added difluoro(sulfo)acetic acid (23.0 g, 129.2 mmol, 1.5 equiv) at 25° C. The reaction mixture was stirred at 25° C. for a period of 1 h. The resulting mixture was extracted with DCM (3×600 mL). The combined organic layers were washed with H$_2$O (3×200 mL), dried over anhydrous Na$_2$SO$_4$. After filtration, the filtrate was concentrated under reduced pressure. The residue was purified by silica gel column chromatography, eluted with PE:EA (5:1) to afford 1-(difluoromethoxy)-6-methyl-7,8-dihydro-7,10-methanopyrido[4,3-c]azocine-5,9 (6H, 10H)-dione (20 g, 78.2%) as a white solid. LCMS (ESI, m/z): 283.25 [M+H]$^+$.

Step 9: A solution of 1-(difluoromethoxy)-6-methyl-7,8-dihydro-7,10-methanopyrido[4,3-c]azocine-5,9 (6H, 10H)-dione (6.0 g, 21.3 mmol, 1.0 equiv) in tetrahydrofuran (50 mL) was treated with LiHMDS (85.0 mL, 85.0 mmol, 4.0 equiv) at −65° C. for 1 h under nitrogen atmosphere followed by the addition of N-(5-chloropyridin-2-yl)-1,1,1-trifluoro-N-(trifluoromethane)sulfonylmethanesulfonamide (18.4 g, 46.8 mmol, 2.2 equiv) dropwise at −65° C. The resulting mixture was stirred at −65° C. for additional 1 h. The resulting mixture was extracted with DCM:MeOH=10:1 (3×100 mL). The combined organic layers were washed with H$_2$O (3×100 mL), dried over anhydrous Na$_2$SO$_4$. After filtration, the filtrate was concentrated under reduced pressure. The residue was purified by Prep-TLC (PE:EA 1:1) to afford 1-(difluoromethoxy)-6-methyl-5-oxo-5,6,7,10-tetrahydro-7,10-methanopyrido[4,3-c]azocin-9-yl trifluoromethanesulfonate (7.7 g, 84%) as an off-white solid. LCMS (ESI, m/z): 415.15 [M+H]$^+$.

Step 10: A solution of 1-(difluoromethoxy)-6-methyl-5-oxo-5,6,7,10-tetrahydro-7,10-methanopyrido[4,3-c]azocin-9-yl trifluoromethanesulfonate (5.0 g, 12.1 mmol, 1.0 equiv) in toluene (50 mL) were treated with 4-chloro-2-(tributylstannyl)pyridine (7.3 g, 18.1 mmol, 1.5 equiv), Pd(PPh$_3$)$_4$ (1.4 g, 1.2 mmol, 0.1 equiv) and CuCl (1.2 g, 12.0 mmol, 1.0 equiv) at 100° C. for 1 h under nitrogen atmosphere. The resulting mixture was concentrated under reduced pressure. The residue was purified by silica gel column chromatography, eluted with PE/EA (1:1) to afford 9-(4-chloropyridin-2-yl)-1-(difluoromethoxy)-6-methyl-7,10-dihydro-7,10-methanopyrido[4,3-c]azocin-5 (6H)-one (2.5 g, 52.1%) as a yellow solid. LCMS (ESI, m/z): 378.10 [M+H]$^+$.

Step 11: A solution of 9-(4-chloropyridin-2-yl)-1-(difluoromethoxy)-6-methyl-7,10-dihydro-7,10-methanopyrido[4,3-c]azocin-5 (6H)-one (2.5 g, 6.6 mmol, 1.0 equiv) and molecular sieves (4 A) (1.2 g) in 1,2-dichloroethane (40 mL) was treated with iron(III) nitrate nonahydrate (3.2 g, 8.0 mmol, 1.2 equiv) and TEMPO (103.4 mg, 0.7 mmol, 0.1 equiv) at 80° C. for 12 h under nitrogen atmosphere. The resulting mixture was filtered, the filter cake was washed with DCM (3×200 mL). The filtrate was concentrated under reduced pressure. The residue was purified by Prep-TLC (PE:EA 1:1) to afford 9-(4-chloropyridin-2-yl)-1-(difluoromethoxy)-6-methyl-8-nitro-7,10-dihydro-7,10-methanopyrido[4,3-c]azocin-5 (6H)-one (1.3 g, 45.5%) as a yellow solid. LCMS (ESI, m/z): 423.05 [M+H]$^+$.

Step 12: A solution of 9-(4-chloropyridin-2-yl)-1-(difluoromethoxy)-6-methyl-8-nitro-7,10-dihydro-7,10-methanopyrido[4,3-c]azocin-5 (6H)-one (300.0 mg, 0.7 mmol, 1.0 equiv) in toluene (10 mL) was treated with triphenyl phosphite (2.2 g, 7.1 mmol, 10.0 equiv) at room temperature. The resulting mixture was stirred at 100° C. for 2 h. The resulting mixture was concentrated under reduced pressure. The residue was purified by TLC (PE/EA 1:1) to afford 12-chloro-1-(difluoromethoxy)-6-methyl-6,7-dihydro-7,14-methanopyrido[4,3-c]pyrido[1',2':1,5]pyrazolo[4,3-f]azocin-5 (14H)-one (230 mg, 82.9%) as a yellow solid. LCMS (ESI, m/z): 510.51 [M+H]$^+$.

Step 13: A solution of 12-chloro-1-(difluoromethoxy)-6-methyl-6,7-dihydro-7,14-methanopyrido[4,3-c]pyrido[1',2':1,5]pyrazolo[4,3-f]azocin-5 (14H)-one (200.0 mg, 0.5 mmol, 1.0 equiv) and 2-[(1s, 3r)-3-[(tert-butyldimethylsilyl)oxy]-1-hydroxy-3-methylcyclobutyl]pyrimidin-5-ylboronic acid (519.4 mg, 1.5 mmol, 3.0 equiv) in dioxane (3 mL) and H$_2$O (1 mL) was treated with Na$_2$CO$_3$ (162.7 mg, 1.5 mmol, 3.0 equiv) at room temperature followed by the addition of Xphos Pd G2 (40.3 mg, 0.05 mmol, 0.1 equiv) in portions at room temperature. The final reaction mixture was irradiated with microwave radiation at 140° C. for 1 h. The reaction mixture was diluted with water (20 mL), and the aqueous phase was extracted with EA (3×50 mL). The combined organic layers were washed with brine, dried over sodium sulfate, filtered, and concentrated in vacuo. The residue was purified by TLC (CH$_2$Cl$_2$/MeOH 15:1) to afford 12-(2-((1s, 3s)-1-((tert-butyldimethylsilyl)oxy)-3-hydroxy-3-methylcyclobutyl)pyrimidin-5-yl)-1-(difluoromethoxy)-6-methyl-6,7-dihydro-7,14-methanopyrido[4,3-c]pyrido[1',2':1,5]pyrazolo[4,3-f]azocin-5 (14H)-one (50 mg, 15.1%) as an off-white solid. LCMS (ESI, m/z): 649.10 [M+H]$^+$.

Step 14: A solution of 12-(2-((1s, 3s)-1-((tert-butyldimethylsilyl)oxy)-3-hydroxy-3-methylcyclobutyl)pyrimidin-5-yl)-1-(difluoromethoxy)-6-methyl-6,7-dihydro-7,14-methanopyrido[4,3-c]pyrido[1',2':1,5]pyrazolo[4,3-f]azocin-5 (14H)-one (50.0 mg, 0.08 mmol, 1.0 equiv) in MeOH (1 mL) was treated with HCl (0.3 mL) at room temperature. The resulting mixture was stirred at 25° C. for 0.5 h. The resulting mixture was concentrated under reduced pressure. The residue was purified by TLC (PE/EA 1:1) to afford 1-(difluoromethoxy)-12-(2-((1s, 3s)-1,3-dihydroxy-3-methylcyclobutyl)pyrimidin-5-yl)-6-methyl-6,7-dihydro-7,14- methanopyrido[4,3-c]pyrido[1',2':1,5]pyrazolo[4,3-f]azocin-5 (14H)-one (50 mg) as a yellow solid. LCMS (ESI, m/z): 534.53 [M+H]+.

Step 15: 1-(difluoromethoxy)-12-(2-((1s, 3s)-1,3-dihydroxy-3-methylcyclobutyl)pyrimidin-5-yl)-6-methyl-6,7-dihydro-7,14-methanopyrido[4,3-c]pyrido[1',2':1,5]pyrazolo[4,3-f]azocin-5 (14H)-one (50 mg) was further purified by Prep-HPLC with the following conditions (Column: CHIRALPAKIG3; Mobile Phase A: Hex (0.1% FA): (EtOH: DCM=1:1)=70:30; Flow rate: 1 mL/min mL/min; Gradient: isocratic; Injection Volume: 2 mL) to afford (7R,14S)-1-(difluoromethoxy)-12-(2-((1s,3R)-1,3-dihydroxy-3-methylcyclobutyl)pyrimidin-5-yl)-6-methyl-6,7-dihydro-7,14-methanopyrido[4,3-c]pyrido[1',2':1,5]pyrazolo[4,3-f]azocin-5 (14H)-one (13 mg). LCMS (ESI, m/z): 534.53 [M+H]+. 1H NMR (400 MHz, DMSO-d6) δ 9.18 (s, 2H), 8.85 (dd, J=7.3, 0.9 Hz, 1H), 8.18 (d, J=5.4 Hz, 1H), 8.13-7.91 (m, 2H), 7.78-7.73 (m, 1H), 7.36 (dd, J=7.4, 2.1 Hz, 1H), 5.68 (s, 1H), 5.17 (d, J=7.0 Hz, 1H), 4.98 (s, 1H), 4.91 (d, J=6.4 Hz, 1H), 3.31-3.28 (m, 4H), 2.94-2.87 (m, 2H), 2.61 (d, J=13.5 Hz, 1H), 2.46-2.38 (m, 2H), 1.08 (s, 3H).

Example 321

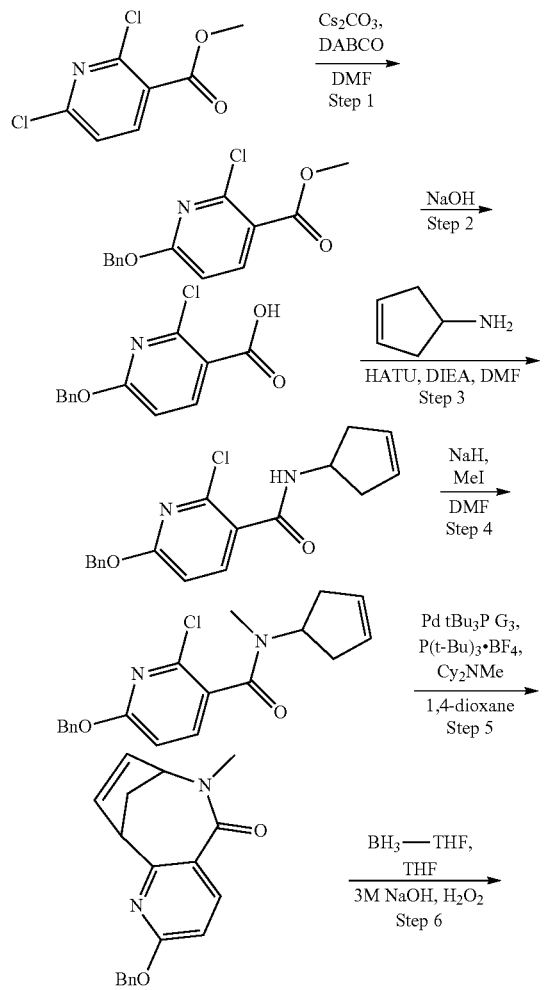

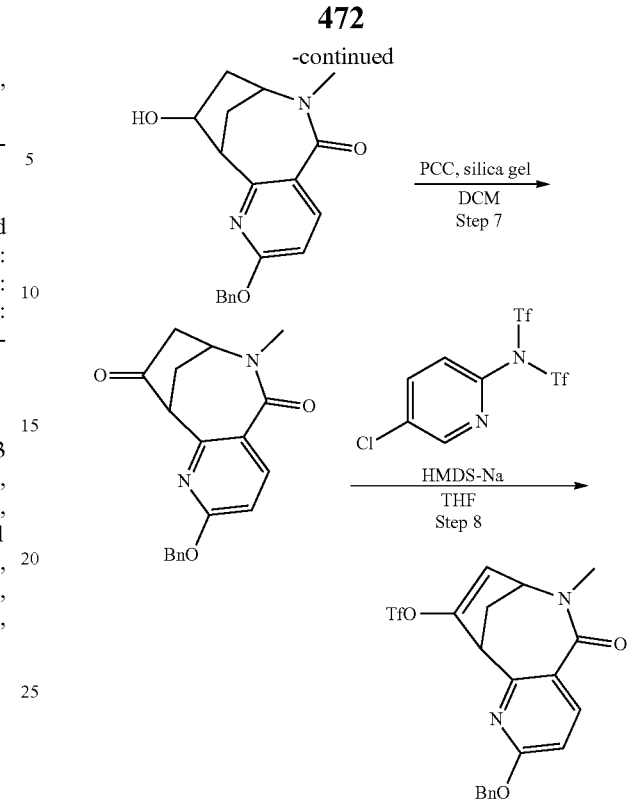

Step 1: To a stirred solution of methyl 2,6-dichloropyridine-3-carboxylate (5.0 g, 24.3 mmol, 1.0 equiv), benzyl alcohol (2.6 mL, 25.5 mmol, 1.05 equiv), DABCO (816.7 mg, 7.31 mmol, 0.3 equiv) in DMF (20 mL) was added Cs2CO3 (9.5 g, 29.1 mmol, 1.2 equiv) at room temperature under nitrogen atmosphere. The resulting mixture was stirred at room temperature for 12 h under nitrogen atmosphere. The resulting mixture was diluted with EA (100 mL). The resulting mixture was washed with water (4×100 mL) and then brine (50 mL). The organic layer was dried over anhydrous Na2SO4. After filtration, the filtrate was concentrated under reduced pressure to afford methyl 6-(benzyloxy)-2-chloropyridine-3-carboxylate (6.8 g, 86%) as a yellowish solid. LCMS (ESI, m/z): 278.05 [M+H]+.

Step 2: A mixture of methyl 6-(benzyloxy)-2-chloropyridine-3-carboxylate (6.8 g, 24.5 mmol, 1.0 equiv) and caustic soda (3.9 g, 97.9 mmol, 4.0 equiv) in THF (40 mL), MeOH (40 mL) and H2O (8 mL) was stirred at room temperature for 2 h under air atmosphere. The resulting mixture was concentrated under reduced pressure then diluted with water (50 mL). The mixture was acidified to pH 3-4 with HCl (aq.). The resulting mixture was extracted with EtOAc (3×80 mL). The combined organic layers were washed with brine, dried over anhydrous Na2SO4. After filtration, the filtrate was concentrated under reduced pressure to afford 6-(benzyloxy)-2-chloropyridine-3-carboxylic acid (5.8 g, 79% yield) as an off-white solid. LCMS (ESI, m/z): 264.00 [M+H]+.

Step 3: To a stirred solution of 6-(benzyloxy)-2-chloropyridine-3-carboxylic acid (5.8 g, 22.0 mmol, 1.0 equiv) and Cyclopent-3-en-1-amine hydrochloride (2.6 g, 22.0 mmol, 1.0 equiv) in DCM (100 mL) was added DIEA (11.5 mL, 66.0 mmol, 3.0 equiv) and then HATU (12.6 g, 33.0 mmol, 1.5 equiv) at room temperature. The resulting mixture was stirred at room temperature for 3 h. The resulting mixture was washed with water (3×100 mL), dried over anhydrous Na2SO4. After filtration, the filtrate was concentrated under reduced pressure. The residue was purified by silica gel column chromatography, eluted with DCM-DCM/EA (40:1) to afford 6-(benzyloxy)-2-chloro-N-(cyclopent-3-en-1-yl) pyridine-3-carboxamide (6.4 g, 80%) as a white solid. LCMS (ESI, m/z): 329.10 [M+H]$^+$.

Step 4: To a stirred solution of 6-(benzyloxy)-2-chloro-N-(cyclopent-3-en-1-yl) pyridine-3-carboxamide (4.7 g, 14.3 mmol, 1.0 equiv) in DMF (20 mL) was added sodium hydride (0.69 g, 17.2 mmol, 1.2 equiv, 60%) at room temperature under nitrogen atmosphere. The resulting mixture was stirred at room temperature for 40 min under nitrogen atmosphere. To the above mixture was added methyl iodide (1.2 mL, 18.6 mmol, 1.3 equiv) dropwise at 0° C. The resulting mixture was stirred at room temperature for additional 40 min. The resulting mixture was diluted with aq. NH$_4$Cl (120 mL). The resulting mixture was extracted with EA (2×120 mL). The combined organic layers were washed with water (3×150 mL) and then brine, dried over anhydrous Na$_2$SO$_4$. After filtration, the filtrate was concentrated under reduced pressure to afford 6-(benzyloxy)-2-chloro-N-(cyclopent-3-en-1-yl)-N-methylpyridine-3-carboxamide (4.8 g, 88%) as a yellow wax. LCMS (ESI, m/z): 343.20 [M+H]$^+$.

Step 5: A solution of 6-(benzyloxy)-2-chloro-N-(cyclopent-3-en-1-yl)-N-methylpyridine-3-carboxamide (4.8 g, 13.9 mmol, 1.0 equiv), [(tri-tert-butylphosphine)-2-(2-aminobiphenyl)]palladium(II)methanesulfonate (793 mg, 1.4 mmol, 0.1 equiv), tBu3P·HBF$_4$ (402 mg, 1.4 mmol, 0.1 equiv), Cy2NMe (4 mL, 18.0 mmol, 1.3 equiv) in 1,4-dioxane (50 mL) was stirred at 100° C. for 16 h under nitrogen atmosphere. The resulting mixture was concentrated under reduced pressure. The residue was purified by silica gel column chromatography, eluted with PE/DCM/EA (6:2:1-3:1:1) to afford 2-(benzyloxy)-6-methyl-7,10-dihydro-7,10-methanopyrido[3,2-c]azocin-5 (6H)-one (3.1 g, 67%) as a colorless wax. LCMS (ESI, m/z): 307.15 [M+H]$^+$.

Step 6: To a stirred solution of 2-(benzyloxy)-6-methyl-7,10-dihydro-7,10-methanopyrido[3,2-c]azocin-5 (6H)-one (3.1 g, 10.0 mmol, 1.0 equiv) in THF (40 mL) was added Borane-tetrahydrofuran complex (1.0 Min THF) (20 mL, 20.0 mmol, 2.0 equiv) dropwise at 0° C. under nitrogen atmosphere. The resulting mixture was stirred at 0° C. for 3 h under nitrogen atmosphere. To the above mixture was added NaOH (11.7 mL, 35.1 mmol, 3.5 equiv) dropwise at first until gas bubbling receded, then the rest of NaOH (3M) and hydrogen peroxide (30%) (10 mL, 60.0 mmol, 6.0 equiv) was added all at once at 0° C. The resulting mixture was stirred at 0° C. for additional 1 h. The reaction was quenched by the addition of sat. aq. Na$_2$SO$_3$ (20 mL) at 0° C. The resulting mixture was stirred at 0° C. for 30 min. Then, 2M HCl was added until precipitates dissolved, at which point the pH was 3-4. The resulting mixture was extracted with EA (2×80 mL). The combined organic layers were washed with brine (100 mL), dried over anhydrous Na$_2$SO$_4$. After filtration, the filtrate was concentrated under reduced pressure. The resulting mixture (2.8 g) was used in the next step directly without further purification. LCMS (ESI, m/z): 325.15 [M+H]$^+$.

Step 7: 2-(benzyloxy)-9-hydroxy-6-methyl-7,8,9,10-tetrahydro-7,10-methanopyrido[3,2-c]azocin-5 (6H)-one (2.8 g, 8.6 mmol, 1.0 equiv) and silica gel (1.5 g) in DCM (30 mL) was added chlorochromiumoyol; pyridine (5.6 g, 25.9 mmol, 3.0 equiv) in one portion at room temperature in open air. The resulting mixture was stirred at room temperature for 16 h. The organic liquid was decanted into a flask, the gummy solid at the bottom of the reaction flask was washed with 50 mL of DCM, then 50 mL of EA. The combined organic phase was concentrated under reduced pressure. The residue was purified by Prep-TLC (PE/DCM/EA=3:1:6) to afford 2-(benzyloxy)-6-methyl-7,8-dihydro-7,10-methanopyrido[3,2-c]azocine-5,9 (6H, 10H)-dione (594 mg, 20%) as a yellow wax. LCMS (ESI, m/z): 323.20 [M+H]$^+$.

Step 8: To a mixture of 2-(benzyloxy)-6-methyl-7,8-dihydro-7,10-methanopyrido[3,2-c]azocine-5,9 (6H, 10H)-dione (594 mg, 1.8 mmol, 1.0 equiv) in THF (10 mL) was added NaHMDS (2.0 M in THF) (3 mL, 5.6 mmol, 3.0 equiv) in portions at −60° C. under nitrogen atmosphere. The mixture was stirred for 30 min at −60° C. prior addition of Comins' reagent (1.5 g, 3.7 mmol, 2.0 equiv). The mixture was stirred for 1 h at −60° C. The mixture was quenched with sat. aq. NH$_4$Cl. The resulting mixture was extracted with EA (2×20 mL). The combined organic layers were washed with brine (30 mL), dried over anhydrous Na$_2$SO$_4$. After filtration, the filtrate was concentrated under reduced pressure. The residue was purified by Prep-TLC (DCM/EA=10:1) to afford 2-(benzyloxy)-6-methyl-5-oxo-5,6,7,10-tetrahydro-7,10-methanopyrido[3,2-c]azocin-9-yl trifluoromethanesulfonate (560 mg, 64%) as a yellow wax. LCMS (ESI, m/z): 455.15 [M+H]$^+$.

Step 9: A mixture of 2-(benzyloxy)-6-methyl-5-oxo-5,6,7,10-tetrahydro-7,10-methanopyrido[3,2-c]azocin-9-yl trifluoromethanesulfonate (560 mg, 1.2 mmol, 1.0 equiv), 4-chloro-2-(tributylstannyl) pyridine (0.6 mL, 1.9 mmol, 1.5 equiv), Pd(PPh$_3$)$_4$ (142 mg, 0.12 mmol, 0.1 equiv) and CuCl (122 mg, 1.23 mmol, 1 equiv) in toluene (6 mL) was stirred at 100° C. for 3 h under nitrogen atmosphere. The resulting mixture was filtered, the filter cake was washed with DCM (2×20 mL). The filtrate was concentrated under reduced pressure. The residue was purified by Prep-TLC (DCM/MeOH=20:1) to afford 2-(benzyloxy)-9-(4-chloropyridin-2-yl)-6-methyl-7,10-dihydro-7,10-methanopyrido[3,2-c]azocin-5 (6H)-one (403 mg, 63%) as a yellow wax. LCMS (ESI, m/z): 418.20 [M+H]$^+$.

Step 10: Into a 40 mL vial were added 2-(benzyloxy)-9-(4-chloropyridin-2-yl)-6-methyl-7,10-dihydro-7,10-methanopyrido[3,2-c]azocin-5 (6H)-one (403 mg, 1 mmol, 1.0 equiv), iron(III) nitrate nonahydrate (780 mg, 2 mmol, 2 equiv), 2,2,6,6-tetramethylpiperidin-1-olate (15.1 mg, 0.1 mmol, 0.1 equiv) and molecular sieve (800 mg), DCE (6 mL) at room temperature. The resulting mixture was stirred at 80° C. for 16 h under nitrogen atmosphere. The resulting mixture was filtered, the filter cake was washed with DCM (2×20 mL). The filtrate was concentrated under reduced pressure. The residue was purified by Prep-TLC (DCM/MeOH=20:1) to afford 2-(benzyloxy)-9-(4-chloropyridin-2-yl)-6-methyl-8-nitro-7,10-dihydro-7,10-methanopyrido[3,2-c]azocin-5 (6H)-one (174 mg, 40%) as a white solid. LCMS (ESI, m/z): 463.15 [M+H]$^+$.

Step 11: A resealable reaction vial was charged with 2-(benzyloxy)-9-(4-chloropyridin-2-yl)-6-methyl-8-nitro-7,10-dihydro-7,10-methanopyrido[3,2-c]azocin-5 (6H)-one (174 mg, 0.4 mmol, 1.0 equiv), triphenyl phosphate (1.2 mL, 4.0 mmol, 10 equiv), toluene (3 mL) and a stir bar before being evacuated and purged with nitrogen three times, and the mixture was stirred for 1 h at 100° C. The reaction concentrated in vacuo. The residue was purified by Prep-TLC (DCM/MeOH=15:1) to afford 2-(benzyloxy)-12-chloro-6-methyl-6,7-dihydro-7,14-methanopyrido[3,2-c]pyrido[1',2':1,5]pyrazolo[4,3-f]azocin-5 (14H)-one (95 mg, 59%) as a white solid.

Step 12: A solution of 2-(benzyloxy)-12-chloro-6-methyl-6,7-dihydro-7,14-methanopyrido[3,2-c]pyrido[1',2':1,5]pyrazolo[4,3-f]azocin-5 (14H)-one (95 mg, 0.22 mmol, 1.0 equiv) in TFA (3 mL) was stirred at room temperature for 16 h under nitrogen atmosphere. The resulting mixture was concentrated under reduced pressure. The resulting mixture (130 mg) was used in the next step directly without further purification. LCMS (ESI, m/z): 341 [M+H]$^+$.

Step 13: A mixture of 12-chloro-6-methyl-6,7-dihydro-7,14-methanopyrido[3,2-c]pyrido[1',2':1,5]pyrazolo[4,3-f]azocine-2,5 (1H, 14H)-dione (56 mg, 0.16 mmol, 1.0 equiv), (bromodifluoromethyl) trimethylsilane (0.2 mL, 1.31 mmol, 8 equiv) and Na$_2$CO$_3$ (122 mg, 1.2 mmol, 7.0 equiv) in DMF (2 mL) was stirred at 60° C. for 16 h under nitrogen atmosphere. The resulting mixture was diluted with DCM (20 mL). The resulting mixture was washed with water (4×20 mL), dried over Na$_2$SO$_4$. The resulting mixture was concentrated under reduced pressure. The residue was purified by Prep-TLC (DCM/MeOH 15:1) to afford 12-chloro-2-(difluoromethoxy)-6-methyl-6,7-dihydro-7,14-methanopyrido[3,2-c]pyrido[1',2':1,5]pyrazolo[4,3-f]azocin-5 (14H)-one (12 mg, 17%) as a beige solid.

Step 14: A mixture of (1s, 3s)-3-((tert-butyldimethylsilyl)oxy)-1-methyl-3-(5-(4,4,5,5-tetramethyl-1,3,2-dioxaborolan-2-yl)pyrimidin-2-yl)cyclobutan-1-ol (32 mg, 0.08 mmol, 2.5 equiv), 12-chloro-2-(difluoromethoxy)-6-methyl-6,7-dihydro-7,14-methanopyrido[3,2-c]pyrido[1',2':1,5]pyrazolo[4,3-f]azocin-5 (14H)-one (12 mg, 0.03 mmol, 1.0 equiv), Na$_2$CO$_3$ (9.76 mg, 0.10 mmol, 3 equiv), XPhos Pd G2 (2.4 mg, 0.01 mmol, 0.1 equiv) in 1,4-dioxane (1 mL) and H$_2$O (0.1 mL) was stirred at 140° C. for 2.5 h under nitrogen atmosphere. The resulting mixture was concentrated under reduced pressure. The residue was purified by Prep-TLC (DCM/MeOH=15:1) to afford 12-(2-((1s, 3s)-1-((tert-butyldimethylsilyl)oxy)-3-hydroxy-3-methylcyclobutyl)pyrimidin-5-yl)-2-(difluoromethoxy)-6-methyl-6,7-dihydro-7,14-methanopyrido[3,2-c]pyrido[1',2':1,5]pyrazolo[4,3-f]azocin-5 (14H)-one (16 mg, 61.03%) as light yellow oil. LCMS (ESI, m/z): 649.25 [M+H]$^+$.

Step 15: A mixture of 12-(2-((1s, 3s)-1-((tert-butyldimethylsilyl)oxy)-3-hydroxy-3-methylcyclobutyl)pyrimidin-5-yl)-2-(difluoromethoxy)-6-methyl-6,7-dihydro-7,14-methanopyrido[3,2-c]pyrido[1',2':1,5]pyrazolo[4,3-f]azocin-5 (14H)-one (16 mg, 0.02 mmol, 1.0 equiv) in HCl (1 mL) and methanol (1 mL) was stirred at room temperature for 30 min. The mixture neutralized to pH 7 with NaHCO$_3$. The resulting mixture was concentrated under reduced pressure to afford 2-(difluoromethoxy)-12-(2-((1s, 3s)-1,3-dihydroxy-3-methylcyclobutyl)pyrimidin-5-yl)-6-methyl-6,7-dihydro-7,14-methanopyrido[3,2-c]pyrido[1',2':1,5]pyrazolo[4,3-f]azocin-5 (14H)-one (13 mg, 90.73%). LCMS (ESI, m/z): 535.35 [M+H]$^+$.

2-(difluoromethoxy)-12-(2-((1s, 3s)-1,3-dihydroxy-3-methylcyclobutyl)pyrimidin-5-yl)-6-methyl-6,7-dihydro-7,14-methanopyrido[3,2-c]pyrido[1',2':1,5]pyrazolo[4,3-f]azocin-5 (14H)-one (13 mg) was separated by Prep chiral HPLC (Column: JW-CHIRAL ART Cellulose-IG 20*250 mm, 5 um; Mobile Phase A: (EtOH:DCM=1:1)(0.5% NH$_3$-MeOH+0.1% FA)—HPLC, Mobile Phase B: Hex—HPLC; Flow rate: 20 mL/min; Gradient: 65% B to 65% B in 25 min; Wave Length: 220/254 nm; RT1(min): 19.02; RT2(min): 22.47; Sample Solvent: EtOH:DCM=1:1—HPLC; Injection Volume: 0.3 mL; Number Of Runs: 5) to afford (7R,14S)-2-(difluoromethoxy)-12-(2-((1s,3R)-1,3-dihydroxy-3-methylcyclobutyl)pyrimidin-5-yl)-6-methyl-6,7-dihydro-7,14-methanopyrido[3,2-c]pyrido[1',2':1,5]pyrazolo[4,3-f]azocin-5 (14H)-one (2.5 mg). LCMS (ESI, m/z): 535.15 [M+H]$^+$. $^1$H NMR (400 MHz, DMSO-d$_6$) δ 9.24 (s, 2H), 8.83 (d, J=7.4 Hz, 1H), 8.67 (d, J=8.8 Hz, 1H), 8.42-7.83 (m, 2H), 7.36 (m, 1H), 6.99 (d, J=8.8 Hz, 1H), 5.67 (s, 1H), 5.17 (d, J=7.0 Hz, 1H), 4.99 (s, 1H), 4.59 (d, J=6.3 Hz, 1H), 3.32 (s, 3H), 3.26 (q, J=6.7 Hz, 1H), 2.99-2.83 (m, 2H), 2.69 (d, J=13.4 Hz, 1H), 2.46-2.27 (m, 2H), 1.08 (s, 3H).

Example 322

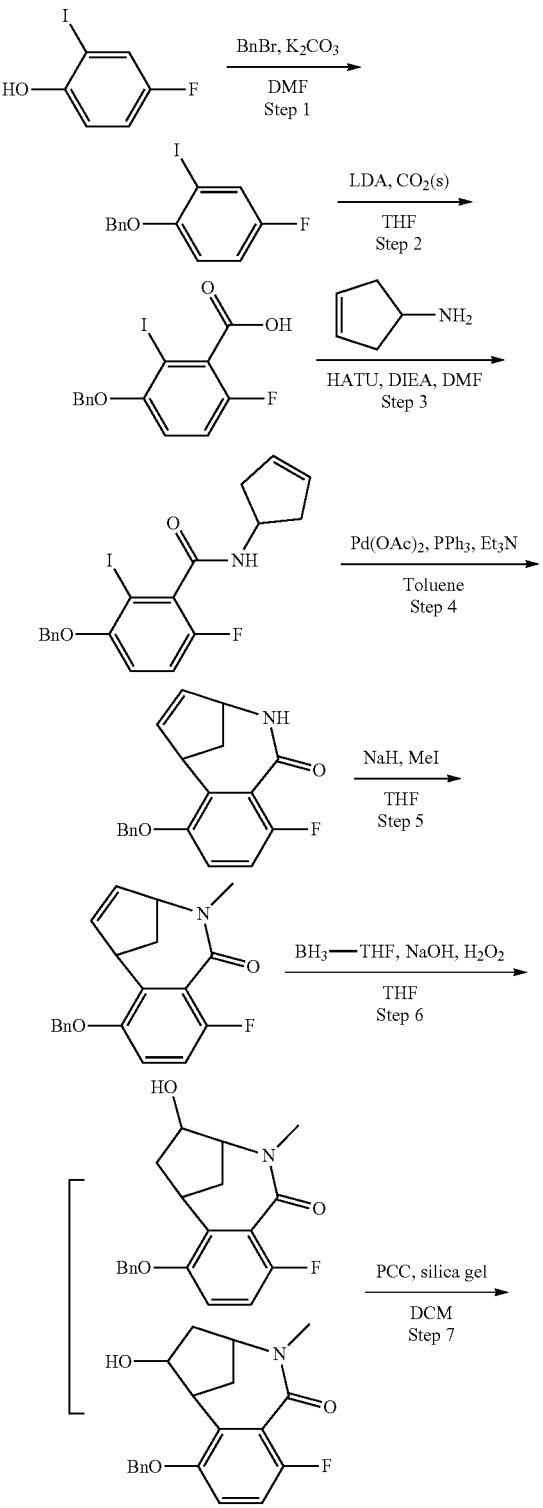

477
-continued

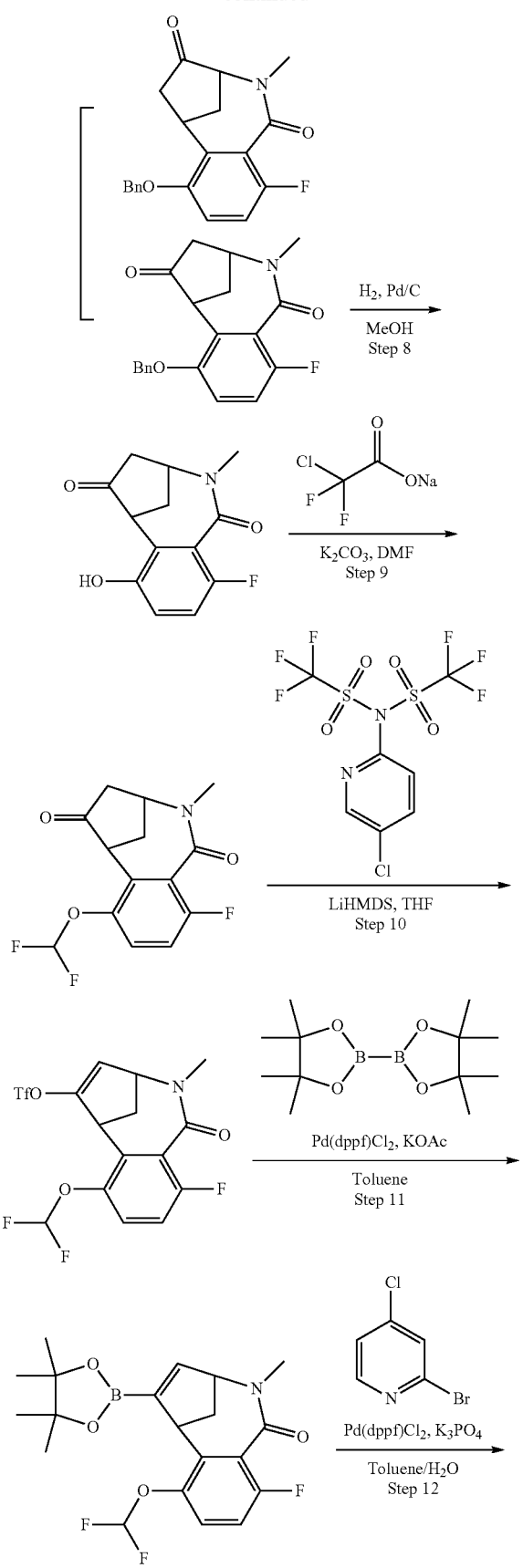

478
-continued

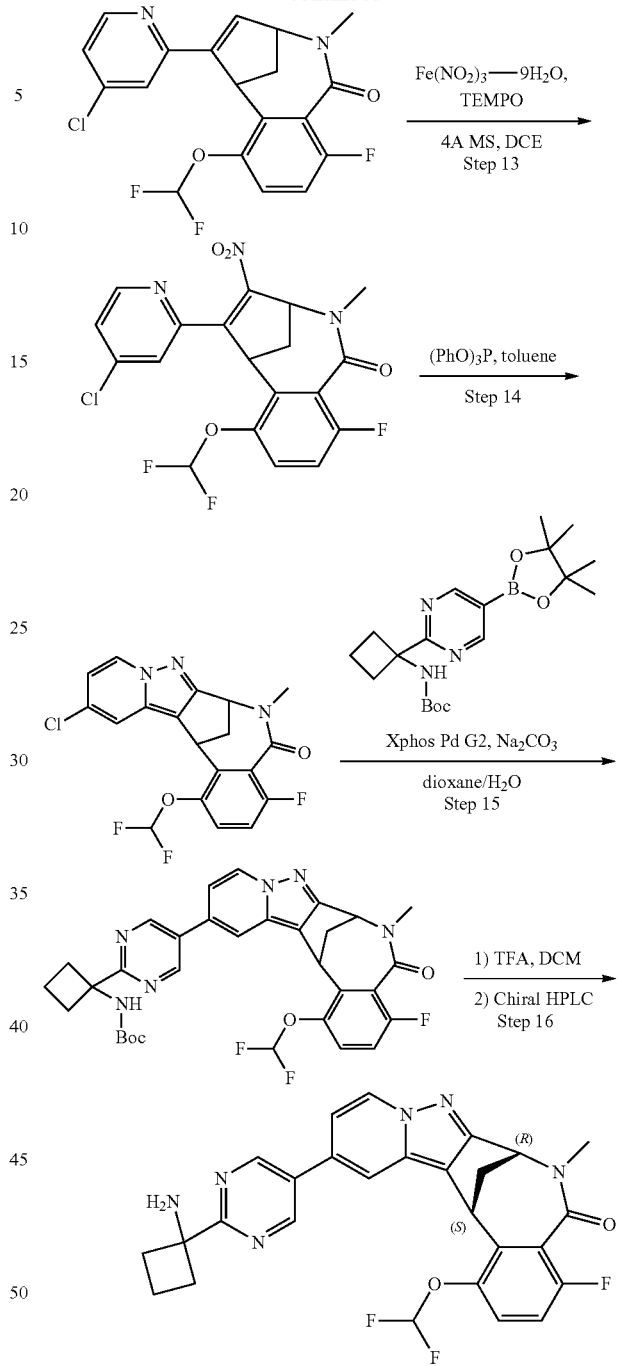

Step 1: A solution of 4-fluoro-2-iodophenol (100 g, 420.2 mmol, 1.0 equiv), benzyl bromide (86.2 g, 504.2 mmol, 1.2 equiv), $K_2CO_3$ (87.1 g, 630.3 mmol, 1.5 equiv) in DMF (500 mL) was stirred at 50° C. for overnight under air atmosphere. The resulting mixture was concentrated under reduced pressure. This resulted in 1-(benzyloxy)-4-fluoro-2-iodobenzene (130 g, 94%) as a white solid. LCMS (ESI, m/z): 329.12 $[M+H]^+$.

Step 2: Into a 2 L 3-necked round-bottom flask were added 1-(benzyloxy)-4-fluoro-2-iodobenzene (130 g, 396.2 mmol, 1.0 equiv) in THF (1.3 L) was added LDA (2.0 M in THF) (297 mL, 594.3 mmol, 1.5 equiv) dropwise at −78° C. under nitrogen atmosphere. The resulting mixture was stirred for additional 1 h at −78° C. To the above mixture was added solid dry ice (34.9 g, 792.4 mmol, 2.0 equiv) in portions over 1 min at −60° C. The resulting mixture was stirred for additional overnight at −60-20° C. The mixture was acidified to pH 6 with HCl (1M) (aq.). The resulting mixture was extracted with EtOAc (2×4 L). The combined organic layers were washed with brine (1×5 L), dried over anhydrous $Na_2SO_4$. After filtration, the filtrate was concentrated under reduced pressure to afford 3-(benzyloxy)-6-fluoro-2-iodobenzoic acid (130 g, 88.2%) as a light brown oil. LCMS (ESI, m/z): 373.05 [M+H]$^+$.

Step 3: A solution of 3-(benzyloxy)-6-fluoro-2-iodobenzoic acid (130 g, 349.3 mmol, 1.0 equiv) and cyclopent-3-en-1-amine hydrochloride (50.1 g, 419.2 mmol, 1.2 equiv) in DMF (1 L) was treated with DIEA (135.5 g, 1.0 mol, 3.0 equiv) followed by the addition of HATU (199.2 g, 0.52 mol, 1.5 equiv) in portions at 0° C. The resulting mixture was extracted with EtOAc (3×3 L). The combined organic layers were washed with brine (3×1 L), dried over anhydrous $Na_2SO_4$. After filtration, the filtrate was concentrated under reduced pressure. The residue was purified by trituration with MTBE (1 L). This resulted in 3-(benzyloxy)-N-(cyclopent-3-en-1-yl)-6-fluoro-2-iodobenzamide (130 g, 85.1%) as an off-white solid. LCMS (ESI, m/z): 438.25 [M+H]$^+$.

Step 4: To a stirred solution of 3-(benzyloxy)-N-(cyclopent-3-en-1-yl)-6-fluoro-2-iodobenzamide (116 g, 265.3 mmol, 1.0 equiv) in toluene (1 L) was added $Et_3N$ (80.5 g, 796.0 mmol, 3.0 equiv), Pd(OAc)$_2$ (6.0 g, 26.5 mmol, 0.1 equiv), PPh$_3$ (13.9 g, 53.0 mmol, 0.2 equiv) in portions at room temperature under nitrogen atmosphere. The resulting mixture was stirred at 100° C. for 12 h under nitrogen atmosphere. The resulting mixture was filtered, the filter cake was washed with $CH_2Cl_2$ (3×1 L). The filtrate was concentrated under reduced pressure. The residue was purified by silica gel column chromatography, eluted with PE/EA (2:1) to afford 7-(benzyloxy)-10-fluoro-3,6-dihydro-3,6-methanobenzo[c]azocin-1 (2H)-one (50 g, 60.9%) as a yellow solid. LCMS (ESI, m/z): 310.34 [M+H]$^+$.

Step 5: To a solution of 7-(benzyloxy)-10-fluoro-3,6-dihydro-3,6-methanobenzo[c]azocin-1 (2H)-one (50.0 g, 161.6 mmol, 1.0 equiv) in THF (500 mL) was added NaH (60%, 9.7 g, 242.5 mmol, 1.5 equiv) at 0° C. The mixture was stirred for 15 min. methyl iodide (27.5 g, 194.0 mmol, 1.2 equiv) was added and the mixture was allowed to warm to room temperature and stirred for 2 h. The reaction mixture was quenched by water and extracted with EA (3×100 mL), washed with $H_2O$ (3×500 mL), dried over anhydrous $Na_2SO_4$. After filtration, the filtrate was concentrated under reduced pressure. The residue was purified by silica gel column chromatography, eluted with PE:EA (3:1) to afford 7-(benzyloxy)-10-fluoro-2-methyl-3,6-dihydro-3,6-methanobenzo[c]azocin-1 (2H)-one (50 g, 95.7%) as a white solid. LCMS (ESI, m/z): 324.37 [M+H]$^+$.

Step 6: A solution of 7-(benzyloxy)-10-fluoro-2-methyl-3,6-dihydro-3,6-methanobenzo[c]azocin-1 (2H)-one (27.0 g, 83.5 mmol, 1.0 equiv) in THF (30 mL) was treated with BH3-THF (167 mL, 167.0 mmol, 2.0 equiv) at 0° C. for 3 h under nitrogen atmosphere followed by the addition of NaOH (83.5 mL, 250.5 mmol, 3.0 equiv) and $H_2O_2$ (26%, 60 mL, 667.9 mmol, 8.0 equiv) in portions at 0° C. The resulting mixture was stirred at 0° C. for additional 1 h. The resulting mixture was extracted with DCM:MeOH=10:1 (3×500 mL). The combined organic layers were washed with $Na_2SO_3$(aq.) (3×500 mL), dried over anhydrous $Na_2SO_4$. After filtration, the filtrate was concentrated under reduced pressure. This resulted in 7-(benzyloxy)-10-fluoro-4-hydroxy-2-methyl-3,4,5,6-tetrahydro-3,6-methanobenzo[c]azocin-1 (2H)-one and 7-(benzyloxy)-10-fluoro-5-hydroxy-2-methyl-3,4,5,6-tetrahydro-3,6-methanobenzo[c]azocin-1 (2H)-one (26 g, crude) as a white solid. LCMS (ESI, m/z): 342.38 [M+H]$^+$.

Step 7: A solution of 7-(benzyloxy)-10-fluoro-4-hydroxy-2-methyl-3,4,5,6-tetrahydro-3,6-methanobenzo[c]azocin-1 (2H)-one and 7-(benzyloxy)-10-fluoro-5-hydroxy-2-methyl-3,4,5,6-tetrahydro-3,6-methanobenzo[c]azocin-1 (2H)-one (26.0 g, 76.2 mmol, 1.0 equiv) in DCM (500 mL) were treated with pyridinium chlorochromate (757.7 mg, 3.5 mmol, 2.0 equiv) and molecular sieves (4 A) (50 g) at 0° C. for 16 h under air atmosphere. The resulting mixture was filtered, the filter cake was washed with DCM (3×500 mL). The filtrate was concentrated under reduced pressure. The residue was purified by Prep-TLC (PE:EA 1:1) to afford 7-(benzyloxy)-10-fluoro-2-methyl-2,3,5,6-tetrahydro-3,6-methanobenzo[c]azocine-1,4-dione (15 g, 58.0%) and 7-(benzyloxy)-10-fluoro-2-methyl-3,4-dihydro-3,6-methanobenzo[c]azocine-1,5 (2H,6H)-dione (3.5 g, 13.5%) as a white solid. LCMS (ESI, m/z): 340.38 [M+H]$^+$.

Step 8: A solution of 7-(benzyloxy)-10-fluoro-2-methyl-3,4-dihydro-3,6-methanobenzo[c]azocine-1,5 (2H,6H)-dione (3.5 g, 10.3 mmol, 1.0 equiv) in MeOH (50 mL) was treated with Pd/C (0.11 g, 1.03 mmol, 0.1 equiv) at 25° C. for 16 h under $H_2$. The resulting mixture was filtered, the filter cake was washed with DCM (3×500 mL). The filtrate was concentrated under reduced pressure. This resulted in 6 10-fluoro-7-hydroxy-2-methyl-3,4-dihydro-3,6-methanobenzo[c]azocine-1,5 (2H,6H)-dione (2.5 g, 97.3%) as a white solid. LCMS (ESI, m/z): 250.24 [M+H]$^+$.

Step 9: A solution of 10-fluoro-7-hydroxy-2-methyl-3,4-dihydro-3,6-methanobenzo[c]azocine-1,5 (2H,6H)-dione (2.5 g, 10.0 mmol, 1.0 equiv) in DMF (30 mL) was treated with $K_2CO_3$ (4.2 g, 30.1 mmol, 3.0 equiv) and sodium 2-chloro-2,2-difluoroacetate (7.7 g, 50.2 mmol, 5.0 equiv) at 80° C. for 16 h. The resulting mixture was extracted with EA (3×100 mL). The combined organic layers were washed with NaCl(aq.) (3×100 mL), dried over anhydrous $Na_2SO_4$. After filtration, the filtrate was concentrated under reduced pressure. The residue was purified by Prep-TLC (PE:EA 2:1) to afford 7-(difluoromethoxy)-10-fluoro-2-methyl-3,4-dihydro-3,6-methanobenzo[c]azocine-1,5 (2H,6H)-dione (1.5 g, 50%) as a yellow solid. LCMS (ESI, m/z): 300.25 [M+H]$^+$.

Step 10: A solution of 7-(difluoromethoxy)-10-fluoro-2-methyl-3,4-dihydro-3,6-methanobenzo[c]azocine-1,5 (2H,6H)-dione (1.5 g, 5.0 mmol, 1.0 equiv) in THF (30 mL) was treated with NaHMDS (2.0 M in THF) (5 mL, 10.0 mmol, 2.0 equiv) at −65° C. for 1 h under nitrogen atmosphere followed by the addition of Comins' reagent (3.9 g, 10.0 mmol, 2.0 equiv) dropwise at −65° C. The resulting mixture was stirred at −65° C. for additional 1 h. The reaction was quenched by the addition of NH4Cl(aq.) (20 mL) at −65° C. The resulting mixture was extracted with EA (3×300 mL). The combined organic layers were washed with $H_2O$ (3×100 mL), dried over anhydrous $Na_2SO_4$. After filtration, the filtrate was concentrated under reduced pressure. The residue was purified by silica gel column chromatography, eluted with PE:EA (3:1) to afford 7-(difluoromethoxy)-10-fluoro-2-methyl-1-oxo-1,2,3,6-tetrahydro-3,6-methanobenzo[c]azocin-5-yl trifluoromethanesulfonate (1.5 g, 69.4%) as a yellow solid. LCMS (ESI, m/z): 432.31 [M+H]$^+$.

Step 11: A solution of 7-(difluoromethoxy)-10-fluoro-2-methyl-1-oxo-1,2,3,6-tetrahydro-3,6-methanobenzo[c]azocin-5-yl trifluoromethanesulfonate (1.5 g, 3.5 mmol, 1.0 equiv) in toluene (20 mL) were treated with bis(pinacolato)

diboron (0.97 g, 3.8 mmol, 1.1 equiv), Pd(dppf)Cl$_2$ (0.25 g, 0.35 mmol, 0.1 equiv) and AcOK (0.68 g, 6.9 mmol, 2.0 equiv) at 100° C. for 2 h under nitrogen atmosphere. The resulting mixture was used in the next step directly without further purification. LCMS (ESI, m/z): 410.21 [M+H]$^+$.

Step 12: A solution of 7-(difluoromethoxy)-10-fluoro-2-methyl-5-(4,4,5,5-tetramethyl-1,3,2-dioxaborolan-2-yl)-3,6-dihydro-3,6-methanobenzo[c]azocin-1 (2H)-one (1.4 g, 3.5 mmol, 1.0 equiv), 2-bromo-4-chloropyridine (0.85 g, 4.49 mmol, 1.2 equiv) was treated with Pd(dppf)Cl$_2$ (0.27 g, 0.37 mmol, 0.1 equiv), K$_3$PO$_4$ (2.33 g, 10.0 mmol, 3.0 equiv), H$_2$O (0.5 mL) and toluene (2 mL) at 100° C. for 2 h under nitrogen atmosphere. The resulting mixture was extracted with EA (3×100 mL). The combined organic layers were washed with H$_2$O (3×100 mL), dried over anhydrous Na$_2$SO$_4$. After filtration, the filtrate was concentrated under reduced pressure. The residue was purified by Prep-TLC (PE:EA 1:1) to afford 5-(4-chloropyridin-2-yl)-7-(difluoromethoxy)-10-fluoro-2-methyl-3,6-dihydro-3,6-methanobenzo[c]azocin-1 (2H)-one (1 g, 69.1%) as a yellow solid. LCMS (ESI, m/z): 395.78 [M+H]$^+$.

Step 13: A solution of 5-(4-chloropyridin-2-yl)-7-(difluoromethoxy)-10-fluoro-2-methyl-3,6-dihydro-3,6-methanobenzo[c]azocin-1 (2H)-one (1 g, 2.5 mmol, 1.0 equiv) and molecular sieves (4 A) (2.0 g) in DCE (20 mL) was treated with iron(III) nitrate nonahydrate (1.5 g, 3.8 mmol, 1.5 equiv) and 2,2,6,6-tetramethylpiperidin-1-olate (0.04 g, 0.25 mmol, 0.1 equiv) at 80° C. for 1 h under nitrogen atmosphere. The resulting mixture was extracted with EA (3×100 mL). The combined organic layers were washed with H$_2$O (3×100 mL), dried over anhydrous Na$_2$SO$_4$. After filtration, the filtrate was concentrated under reduced pressure. The residue was purified by Prep-TLC (PE:EA 1:1) to afford 5-(4-chloropyridin-2-yl)-7-(difluoromethoxy)-10-fluoro-2-methyl-4-nitro-3,6-dihydro-3,6-methanobenzo[c]azocin-1 (2H)-one (600 mg, 53.9%) as a yellow solid. LCMS (ESI, m/z): 440.78 [M+H]$^+$.

Step 14: A solution of 5-(4-chloropyridin-2-yl)-7-(difluoromethoxy)-10-fluoro-2-methyl-4-nitro-3,6-dihydro-3,6-methanobenzo[c]azocin-1 (2H)-one (600 mg, 1.4 mmol, 1.0 equiv) in toluene (20 mL) was treated with triphenyl phosphite (4.2 g, 13.6 mmol, 10.0 equiv) at 80° C. for 1 h under nitrogen atmosphere. The resulting mixture was extracted with EA (3×100 mL). The combined organic layers were washed with H$_2$O (3×100 mL), dried over anhydrous Na$_2$SO$_4$. After filtration, the filtrate was concentrated under reduced pressure. The residue was purified by Prep-TLC (PE:EA 1:1) to afford 12-chloro-1-(difluoromethoxy)-4-fluoro-6-methyl-6,7-dihydro-7,14-methanobenzo[c]pyrido[1',2':1,5]pyrazolo[4,3-f]azocin-5 (14H)-one (300 mg, 53.9%) as a yellow solid. LCMS (ESI, m/z): 408.78 [M+H]$^+$.

Step 15: A solution of 12-chloro-1-(difluoromethoxy)-4-fluoro-6-methyl-6,7-dihydro-7,14-methanobenzo[c]pyrido[1',2':1,5]pyrazolo[4,3-f]azocin-5 (14H)-one (100 mg, 0.25 mmol, 1.0 equiv) and tert-butyl (1-(5-(4,4,5,5-tetramethyl-1,3,2-dioxaborolan-2-yl)pyrimidin-2-yl)cyclobutyl)carbamate (110 mg, 0.29 mmol, 1.2 equiv) in dioxane (5 mL) and H$_2$O (1 mL) was treated with Xphos Pd G2 (19.3 mg, 0.03 mmol, 0.1 equiv) and Na$_2$CO$_3$ (78 mg, 0.74 mmol, 3.0 equiv) at 140° C. for 1 h under nitrogen atmosphere. The resulting mixture was filtered, the filter cake was washed with DCM (3×50 mL). The residue was purified by Prep-TLC (PE:EA 1:1) to afford tert-butyl (1-(5-(1-(difluoromethoxy)-4-fluoro-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (50 mg, 29.2%) as a yellow solid. LCMS (ESI, m/z): 698.72 [M+H]$^+$.

Step 16: A solution of tert-butyl (1-(5-(1-(difluoromethoxy)-4-fluoro-6-methyl-5-oxo-5,6,7,14-tetrahydro-7,14-methanobenzo[c]pyrido[1',2':1,5]pyrazolo[4,3-f]azocin-12-yl)pyrimidin-2-yl)cyclobutyl)carbamate (50 mg, 0.07 mmol, 1.0 equiv) in DCM (2 mL) was added TFA (0.5 mL) at 25° C. for 10 min. The mixture was basified to pH 8 with NaHCO$_3$(aq.). The resulting mixture was extracted with EA (3×20 mL). The combined organic layers were washed with H$_2$O (3×10 mL), dried over anhydrous Na$_2$SO$_4$. After filtration, the filtrate was concentrated under reduced pressure. The residue was purified by Prep-TLC (DCM:MeOH 10:1) to afford 12-(2-(1-aminocyclobutyl)pyrimidin-5-yl)-1-(difluoromethoxy)-4-fluoro-6-methyl-6,7-dihydro-7,14-methanobenzo[c]pyrido[1',2':1,5]pyrazolo[4,3-f]azocin-5 (14H)-one (30 mg, 70.1%) as a white solid. LCMS (ESI, m/z): 521.25 [M+H]$^+$. The above compound (10 mg) was separated by chiral HPLC to afford (7R,14S)-12-(2-(1-aminocyclobutyl)pyrimidin-5-yl)-1-(difluoromethoxy)-4-fluoro-6-methyl-6,7-dihydro-7,14-methanobenzo[c]pyrido[1',2':1,5]pyrazolo[4,3-f]azocin-5 (14H)-one (2.2 mg) as a yellow oil. 1H NMR (400 MHz, Methanol-d4) δ 9.30-8.41 (m, 3H), 7.82 (t, J=2.5 Hz, 1H), 7.54-7.36 (m, 1H), 7.35-7.24 (m, 1H), 7.22-7.11 (m, 1H), 7.11-6.92 (m, 1H), 5.14 (dd, J=6.9, 2.7 Hz, 1H), 4.98-4.92 (m, 1H), 3.32 (d, J=1.5 Hz, 1H), 3.19 (d, J=2.8 Hz, 3H), 3.14-2.43 (m, 5H), 2.40-2.12 (m, 2H).

Additional compounds of the invention were prepared by modifications of the methods exemplified herein. When chiral starting reactants were available, compounds were prepared and isolated as single stereoisomers having a known absolute configuration, as indicated by (R) and (S) labels on their structures. When racemic starting reactants were used, compounds were carried through synthesis as a mixture of diastereomers and then separated into single stereoisomers by an appropriate chiral preparative HPLC or SFC method before characterization and testing.

Example A: HEK-Blue™ hTNFα Reporter Assay

Stimulation of HEK293 cells by TNFα leads to activation of the NF-κB pathway. The potency of compounds was examined in HEK-Blue™ hTNFα reporter cells (Invivogen, Cat #hkb-tnfdmyd). HEK-Blue™ TNFα cells were generated by stable transfection of HEK293 cell line with a SEAP reporter gene under the control of the IFN-0 minimal promoter fused to NF-κB binding sites. Stimulation of HEK-Blue™ TNFα cells with TNFα triggers the activation of the NF-κB-inducible promoter and the production of SEAP. Levels of SEAP in the supernatant can be easily determined using QUANTI-Blue™ Solution (Invivogen, cat #rep-qbs) by reading the OD at 620-655 nm. The compound inhibits TNF-α and prevents the production of SEAP in the cells.

HEK-Blue™ TNFα cells were cultured in DMEM supplemented with 10% FBS, 100p/mL penicillin, 100 µg/mL streptomycin, 100 µg/mL normocin, 1 µg/mL puromycin, and 100 µg/mL zeocin. The culture was maintained in culture incubator with 5% CO$_2$ at 37° C. When used for assay, the cells were gently rinsed twice with pre-warmed phosphate buffered saline (PBS) and detached in presence of PBS by tapping the flask or by using a cell scraper. The cells were spun to remove PBS and resuspended in fresh, pre-warmed test medium (DMEM supplemented with 10% FBS, 100p/mL penicillin, and 100 µg/mL streptomycin). A serial dilution of work solution of tested compound was made in DMSO with 1000× of final concentration, and 40 nL of compound DMSO solution was transferred into 384-well plates (Corning 3764) by Echo, and incubated with 10 μL of recombinant hTNFα (R&D biosystem, Cat #210-TA-020/CF) for 1 h at 37° C. The compound/hTNFα mixture well received 30 μL HEK-Blue™ TNFα cell suspension at 10000 cells/well, and then incubated at 37° C. with 5% $CO_2$ for 24 h. The final concentration of hTNFα is 120 μg/mL. After incubation, 5 μL of induced cell supernatant was transferred to a new 384-well plate well (Coring 3764) to mix with 45 μL of QUANTI-Blue Solution. After 1 h incubation at 37° C., the plate was read using a spectrophotometer at 620 nm.

The percentage of inhibition was calculated by the following formula:

% inhibition=(positive control−Sample)/(positive control−negative control)*100

Positive control: OD620 reading of cells with hTNFα stimulation.
Negative control: OD620 reading of cells without hTNFα stimulation.
Sample: OD620 reading of cells with compound at specific concentration and hTNFα stimulation The % inhibition was plotted against compound concentration in logarithmic scale and the $IC_{50}$ was rendered using 4-parameter nonlinear regression (GraphPad Prism).

The data is shown in Table 3.

TABLE 3

| Ex. | Range |
|---|---|
| 1 | B |
| 2 | C |
| 3 | A |
| 4 | A |
| 5 | A |
| 6 | A |
| 7 | A |
| 8 | B |
| 9 | A |
| 10 | A |
| 11 | B |
| 12 | B |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | B |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |

TABLE 3-continued

| Ex. | Range |
| --- | --- |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | B |
| 172 | C |
| 173 | A |
| 174 | A |
| 175 | A |
| 176 | A |
| 177 | B |
| 178 | A |
| 179 | A |
| 180 | C |
| 181 | A |
| 182 | A |
| 183 | A |
| 184 | A |
| 185 | B |
| 186 | B |
| 187 | A |
| 188 | A |
| 189 | A |
| 190 | A |
| 191 | A |
| 192 | A |
| 193 | A |
| 194 | B |
| 195 | A |
| 196 | A |
| 197 | A |
| 198 | A |
| 199 | A |
| 200 | A |
| 201 | A |

TABLE 3-continued

| Ex. | Range |
| --- | --- |
| 202 | A |
| 203 | A |
| 204 | B |
| 205 | B |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | B |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | C |
| 233 | B |
| 234 | A |
| 235 | A |
| 236 | C |
| 237 | A |
| 238 | A |
| 239 | A |
| 240 | A |
| 241 | A |
| 242 | A |
| 243 | B |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | B |
| 261 | B |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | B |
| 277 | A |
| 278 | A |
| 279 | A |

TABLE 3-continued

| Ex. | Range |
|---|---|
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | B |
| 303 | A |
| 304 | A |
| 305 | A |
| 306 | A |
| 307 | B |
| 308 | A |
| 309 | A |
| 310 | B |
| 311 | B |
| 312 | A |
| 313 | A |
| 314 | A |
| 315 | B |
| 316 | A |
| 317 | A |
| 318 | A |
| 319 | A |
| 320 | A |
| 321 | B |
| 322 | B |
| 323 | A |
| 324 | A |
| 325 | A |
| 326 | A |
| 327 | A |
| 328 | A |
| 329 | A |

$IC_{50}$ data are designated Within the following ranges:

| $IC_{50}$ |
|---|
| A: $0 < IC_{50} \leq 25$ nM |
| B: $25$ nM $< IC_{50} \leq 100$ nM |
| C: $100$ nM $< IC_{50} \leq 1000$ nM |

Comparative data is shown in table 4.

TABLE 4

| Ex. | Structure | TNFα reporter, $IC_{50}$ (nM)/ Emax (%) |
|---|---|---|
| Comp. Ex #1 | 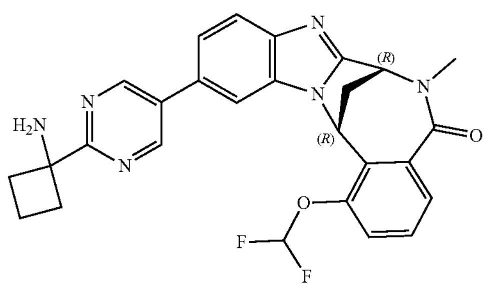 | 4.8/96 |
| 15 | 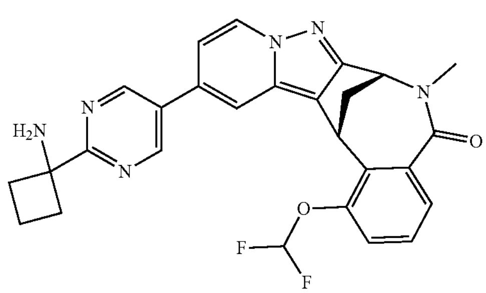 [SMILES: CN1C(=O)c2cccc(OC(F)F)c2[C@H]2C[C@@H]1c1nn3ccc(-c4cnc(C5(N)CCC5)nc4)cc3c12] | 4.1/95 |

TABLE 4-continued

| Ex. | Structure | TNFα reporter, IC$_{50}$ (nM)/ Emax (%) |
|---|---|---|
| Comp. Ex #2 | 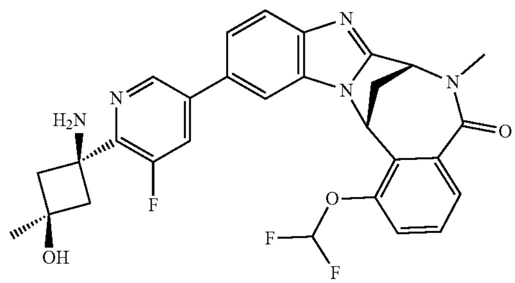 [SMILES: CN1C(=O)c2cccc(OC(F)F)c2[C@H]2C[C@@H]1c1nc3ccc(-c4cnc([C@]5(N)C[C@@](C)(O)C5)c(F)c4)cc3n12] | 4.7/85 |
| 47 | 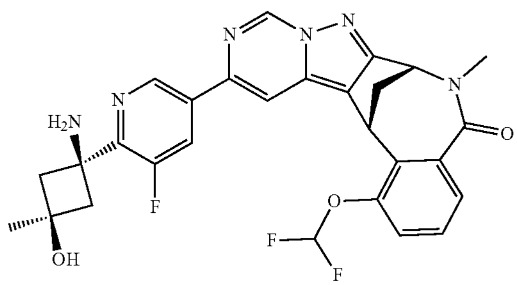 [SMILES: CN1C(=O)c2cccc(OC(F)F)c2[C@H]2C[C@@H]1c1nn3cnc(-c4cnc([C@]5(N)C[C@@](C)(O)C5)c(F)c4)cc3c12] | 3.6/94 |
| Comp. Ex #3 | 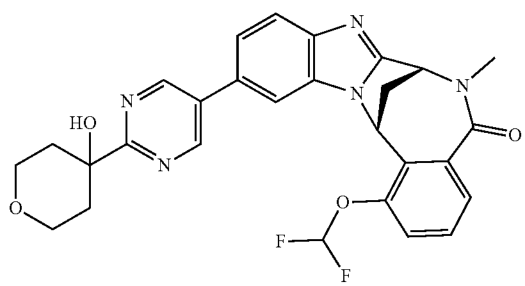 [SMILES: CN1C(=O)c2cccc(OC(F)F)c2[C@H]2C[C@@H]1c1nc3ccc(-c4cnc(C5(O)CCOCC5)nc4)cc3n12] | 8.2/70 |
| 65 | 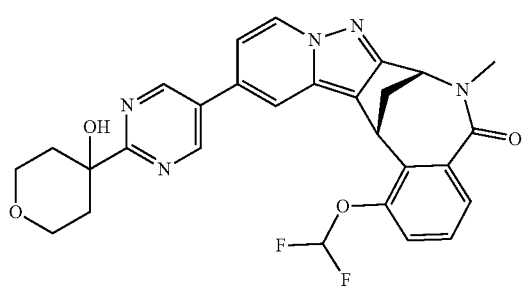 [SMILES: CN1C(=O)c2cccc(OC(F)F)c2[C@H]2C[C@@H]1c1nn3ccc(-c4cnc(C5(O)CCOCC5)nc4)cc3c12] | 3.1/90 |
| Comp. Ex #4 | 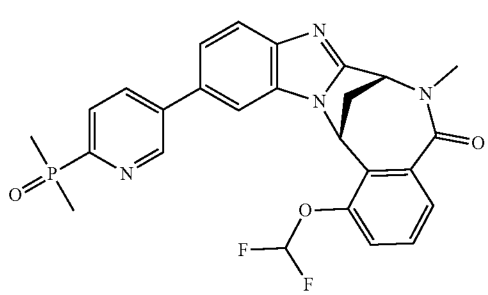 [SMILES: CN1C(=O)c2cccc(OC(F)F)c2[C@H]2C[C@@H]1c1nc3ccc(-c4ccc(P(C)(C)=O)nc4)cc3n12] | 7.9/82 |

TABLE 4-continued

| Ex. | Structure | TNFα reporter, IC$_{50}$ (nM)/ Emax (%) |
|---|---|---|
| 20 | 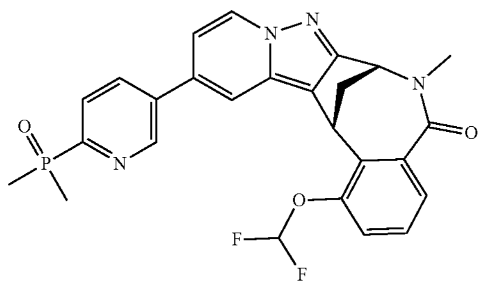 [SMILES: CN1C(=O)c2cccc(OC(F)F)c2[C@H]2C[C@@H]1c1nn3ccc(-c4ccc(P(C)(C)=O)nc4)cc3c12] | 3.8/89 |
| Comp. Ex #5 | 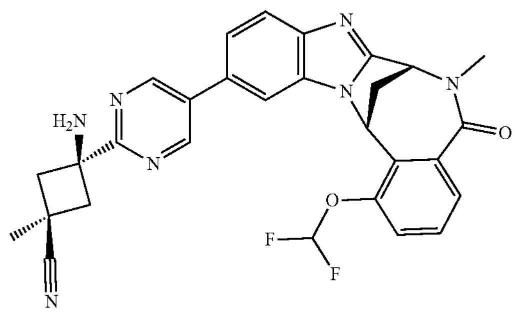 [SMILES: CN1C(=O)c2cccc(OC(F)F)c2[C@H]2C[C@@H]1c1nc3ccc(-c4cnc([C@]5(N)C[C@@](C)(C#N)C5)nc4)cc3n12] | 16.1/83 |
| 22 | 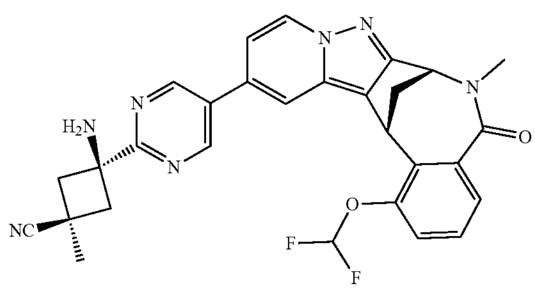 [SMILES: CN1C(=O)c2cccc(OC(F)F)c2[C@H]2C[C@@H]1c1nn3ccc(-c4cnc([C@]5(N)C[C@@](C)(C#N)C5)nc4)cc3c12] | 4.6/93 |
| Comp. Ex #6 | 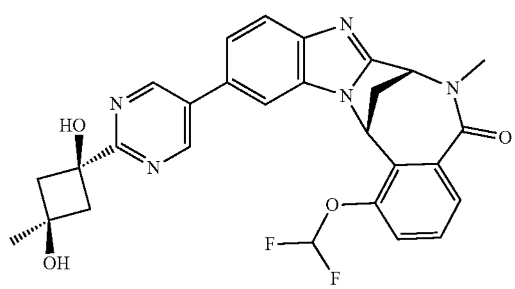 [SMILES: CN1C(=O)c2cccc(OC(F)F)c2[C@H]2C[C@@H]1c1nc3ccc(-c4cnc([C@]5(O)C[C@@](C)(O)C5)nc4)cc3n12] | 5.2/82 |
| 24 | 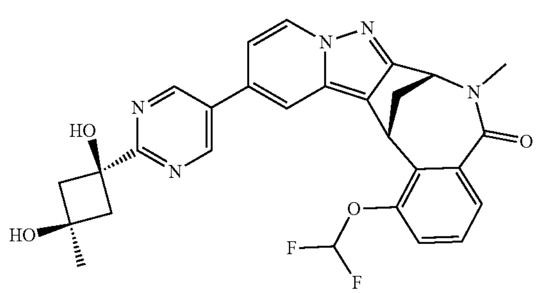 | 2.3/91 |

TABLE 4-continued

| Ex. | Structure | TNFα reporter, IC$_{50}$ (nM)/ Emax (%) |
|---|---|---|
| Comp. Ex #7 | 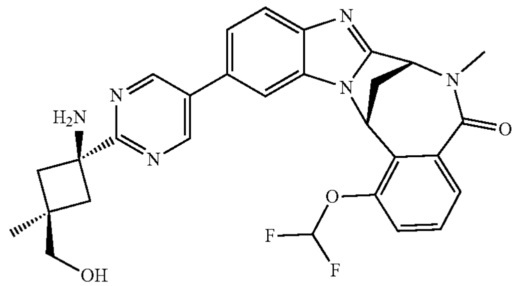 [SMILES: CN1C(=O)c2cccc(OC(F)F)c2[C@H]2C[C@@H]1c1nc3ccc(-c4cnc([C@]5(N)C[C@@](C)(CO)C5)nc4)cc3n12] | 4.2/92 |
| 10 | 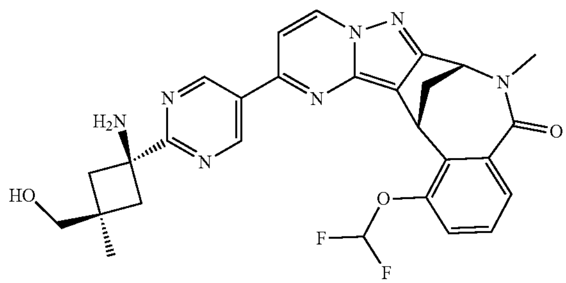 [SMILES: CN1C(=O)c2cccc(OC(F)F)c2[C@H]2C[C@@H]1c1nn3ccc(-c4cnc([C@]5(N)C[C@@](C)(CO)C5)nc4)nc3c12] | 12.7/93 |
| Comp. Ex #8 | 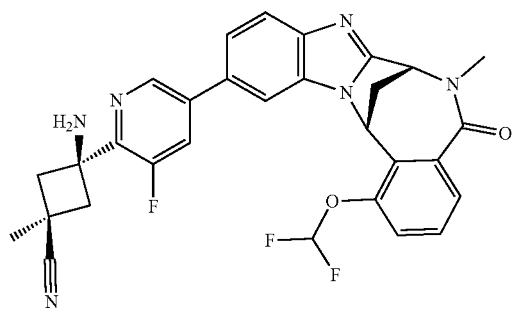 [SMILES: CN1C(=O)c2cccc(OC(F)F)c2[C@H]2C[C@@H]1c1nc3ccc(-c4cnc([C@]5(N)C[C@@](C)(C#N)C5)c(F)c4)cc3n12] | 5.3/80 |
| 59 | 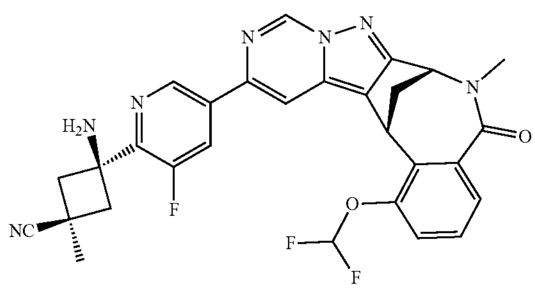 [SMILES: CN1C(=O)c2cccc(OC(F)F)c2[C@H]2C[C@@H]1c1nn3cnc(-c4cnc([C@]5(N)C[C@@](C)(C#N)C5)c(F)c4)cc3c12] | 4.1/98 |

Example B: Coco-2 Assay

1. Preparation of Caco-2 Cells 1) 50 L and 25 mL of cell culture medium were added to each well of the Transwell insert and reservoir, respectively. And then the HTS Transwell plates were incubated at 37° C., 5% CO2 for 1 hour before cell seeding.

2) Caco-2 cell cells were diluted to 6.86×10$^5$ cells/mL with culture medium and 50 μL of cell suspension were dispensed into the filter well of the 96-well HTS Transwell plate. Cells were cultivated for 14-18 days in a cell culture incubator at 37° C., 5% CO2, 95% relative humidity. Cell culture medium was replaced every other day, beginning no later than 24 hours after initial plating.

2. Preparation of Stock Solutions 10 mM stock solutions of test compounds were prepared in DMSO. The stock solutions of positive controls were prepared in DMSO at the concentration of 10 mM. Digoxin, prazosin and metoprolol were used as control compounds in this assay.

3. Assessment of Cell Monolayer Integrity

1) Medium was removed from the reservoir and each Transwell insert and replaced with prewarmed fresh culture medium.

2) Transepithelial electrical resistance (TEER) across the monolayer was measured using Millicell Epithelial Volt-Ohm measuring system (Millipore, USA).

3) The Plate was returned to the incubator once the measurement was done. The TEER value was calculated according to the following equation:

TEER measurement (ohms)×Area of membrane $(cm^2)$=TEER value (ohm·$cm^2$)

TEER value should be greater than 230 ohm·$cm^2$, which indicates the well-qualified Caco-2 monolayer.

4. Assay Procedures

1) The Caco-2 plate was removed from the incubator and washed twice with pre-warmed HBSS (10 mM HEPES, pH 7.4), and then incubated at 37° C. for 30 minutes.

2) The stock solutions of controls compounds were diluted in DMSO to get 1 mM solutions and then diluted with HBSS (10 mM HEPES, pH 7.4) to get 5 µM working solutions. The stock solutions of the test compounds were diluted in DMSO to get 1 mM solutions and then diluted with HBSS (10 mM HEPES, pH 7.4) to get 5 µM working solutions. The final concentration of DMSO in the incubation system was 0.5%.

3) To determine the rate of drug transport in the apical to basolateral direction. 75 µL of 5 µM working solutions of test compounds was added to the Transwell insert (apical compartment) and the wells in the receiver plate (basolateral compartment) were filled with 235 µL of HBSS (10 mM HEPES, pH 7.4).

4) To determine the rate of drug transport in the basolateral to apical direction. 235 µL of 5 µM working solutions of test compounds were to the receiver plate wells (basolateral compartment) and then the Transwell inserts (apical compartment) were filled with 75 µL of HBSS (10 mM HEPES, pH 7.4). Time 0 samples were prepared by transferring 50 µL of 5 µM working solution to wells of the 96-deepwell plate, followed by the addition of 200 µL cold methanol containing appropriate internal standards (IS).

5) The plates were incubated at 37° C. for 2 hours.

6) At the end of the incubation, 50 µL samples from donor sides (apical compartment for Ap→Bl flux, and basolateral compartment for Bl→Ap) and receiver sides (basolateral compartment for Ap→Bl flux, and apical compartment for Bl→Ap) were transferred to wells of a new 96-well plate, followed by the addition of 4 volume of cold methanol containing appropriate internal standards (IS). Samples were vortexed for 5 minutes and then centrifuged at 3,220 g for 40 minutes. An aliquot of 100 µL of the supernatant was mixed with an appropriate volume of ultra-pure water before LC-MS/MS analysis.

7) To determine the Lucifer Yellow leakage after 2 hour transport period, stock solution of Lucifer yellow was prepared in ultra-pure water and diluted with HBSS (10 mM HEPES, pH 7.4) to reach the final concentration of 100 µM. 100 µL of the Lucifer yellow solution was added to each Transwell insert (apical compartment), followed by filling the wells in the receiver plate (basolateral compartment) with 300 µL of HBSS (10 mM HEPES, pH 7.4). The plates were incubated at 37° C. for 30 minutes. 80 µL samples were removed directly from the apical and basolateral wells (using the basolateral access holes) and transferred to wells of new 96 wells plates. The Lucifer Yellow fluorescence (to monitor monolayer integrity) signal was measured in a fluorescence plate reader at 485 nM excitation and 530 nM emission.

5. Data Analysis

The apparent permeability coefficient (Papp), in units of centimeter per second, can be calculated for Caco-2 drug transport assays using the following equation:

$$P_{app} = (V_A \times [drug]_{acceptor})/(Area \times Time \times [drug]_{initial,donor})$$

Where VA is the volume (in mL) in the acceptor well, Area is the surface area of the membrane (0.143 $cm^2$ for Transwell-96 Well Permeable Supports), and time is the total transport time in seconds.

The efflux ratio will be determined using the following equation:

$$\text{Efflux Ratio} = P_{app(B-A)}/P_{app(A-B)}$$

Where Papp (B-A) indicates the apparent permeability coefficient in basolateral to apical direction, and Papp (A-B) indicates the apparent permeability coefficient in apical to basolateral direction.

Comparative data is shown in table 5.

TABLE 5

| Ex. | Caco-2, $P_{app}$ (A-B) ($10^{-6}$ cm/s)/ER |
|---|---|
| Comp. Ex #1 | 2.1/17.2 |
| 15 | 1.9/4.4 |
| Comp. Ex #2 | 1.7/22.6 |
| 47 | 3.2/3.2 |
| Comp. Ex #3 | 4.6/4.9 |
| 65 | 5.7/1.3 |
| Comp. Ex #4 | 0.6/47.5 |
| 20 | 1.7/22.8 |
| Comp. Ex #5 | 1.7/9.0 |
| 22 | 1.3/5.5 |
| Comp. Ex #6 | 1.6/20.3 |
| 24 | 4.7/5.4 |
| Comp. Ex #7 | 0.09/291.3 |
| 10 | 0.3/58.0 |
| Comp. Ex #8 | 1.8/6.7 |
| 59 | 2.5/1.2 |

Example C: Cardiomyocytes Inhibitory Assay with Multielectrode Arrays (MEA)

Figure 2:
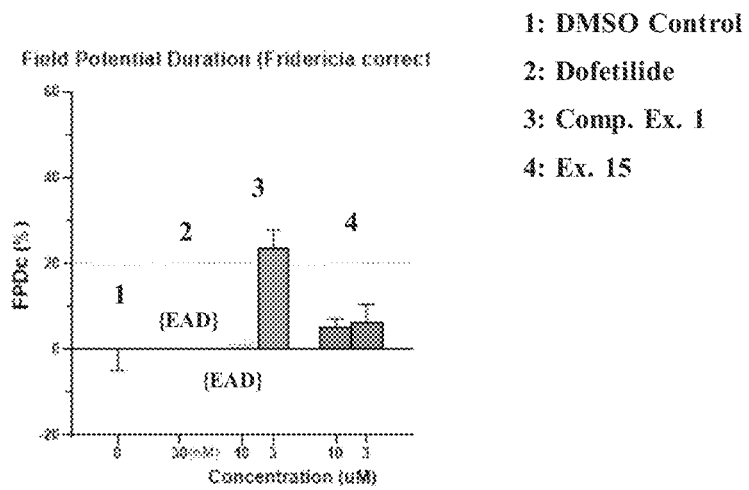
FIG. 2 depicts the Field Potential Duration (Fridericia corrected) for Comp. Ex. 1 and Ex. 15.
Figure 3:
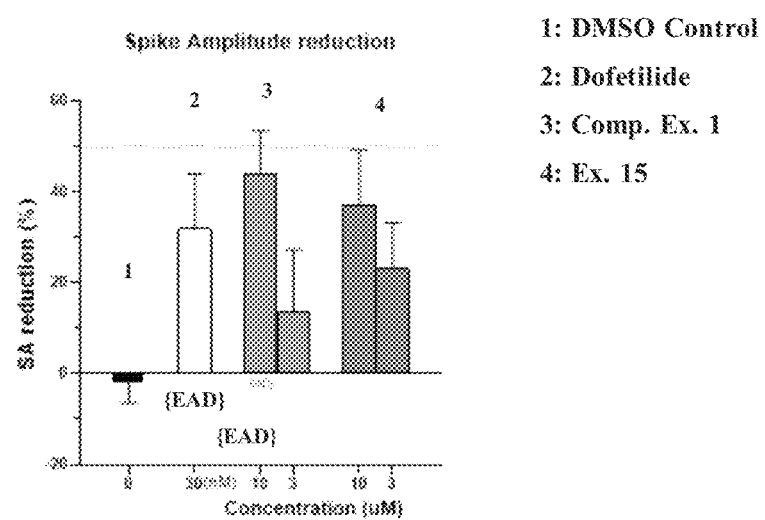
FIG. 3 depicts the Spike Amplitude reduction for Comp. Ex. 1 and Ex. 15.

The MEA study was designed to assess the in vitro inhibitory effect of compounds on extracellular field potential (EFP) of human induced pluripotent stem cell-derived cardiomyocytes (hiPSC-CMs) using the Maestro Pro multielectrode arrays system. The concentration response relationship was determined for each compound at 10 µM and 3 µM in duplicate to calculate the % change in EFP parameters.

hiPSC-CMs (Help Stem Cell Innovations Co.) were seeded in fibronectin-coated CytoView MEA 96-White plate at 20000 cells/well. The next day 2/3 of the plating medium volume was removed and replaced by maintenance media. Half of the maintenance medium was removed and replaced every 2 days. On day 6, compounds were made 2× final concentration (20 µM and 6 µM) in maintenance media. Half of the medium was removed from the wells and an equal volume of the appropriate treatment mix was added, and the EFP signal was recorded. The following criteria was used to determine data acceptability: 1) stable initial spike amplitude should be >300 VX; and 2) the hiPSC-CMs should beat regularly within the initial sampling interval of 20s. Data that meet the above criteria for EFP recording quality were further analyzed as described in the following steps:

Three parameters upward are performed to describe the effects of drugs on cardiomyocyte field potential in different dimension:

SA: Spike Amplitude (see FIG. 3).
BP: Beat Period (see FIG. 1).
FPD: Field Potential Durations (see FIG. 2).

$$FPD_C = FPD \div \sqrt[3]{BP}$$

Axis Navigator 2.0.4. software was used to extract the peak current from the original data. The percentage of amplitude change from baseline was calculated using the following equation.

$$\% \text{ change of } EFP \text{ Parameter} = \frac{(\text{Baseline} - \text{Compound}) \times 100}{\text{Basline}}$$

% Normalization with Vehicle =

$$100\% \times \frac{\% \text{ change of Compound} - \% \text{ change of Blank Vehicle}}{1 - \% \text{ change of Blank Vehicle}}$$

Two important readouts in MEA assay are used to evaluate risk of QT prolongation.

EAD (early afterdepolarization), which is known to cause cardiac arrhythmias, including torsades de pointes and tachycardia. EADs can be triggered by drugs that prolong the QT interval. In the MEA assay, Comp. Ex #1 has EAD at 10 µM while Ex. 15 doesn't at both concentrations.

Field Potential Duration, which is another commonly used parameters in cardiac toxicity assays on MEAs. 20% FPDc is the threshold for QT prolongation. Comp. Ex #1 at 3 µM showed 24% FDPc while Ex. 15 is ~6%.

These results support that Ex. 15 is clearly differentiated from Comp. Ex #1 in CV effect.

Comparative data is shown in table 6.

TABLE 6

| Ex. | Cardiomyocytes FPDc prolong. (%) @10 uM |
|---|---|
| Comp. Ex #1 | >20% EAD |
| 15 | −1.9 |

REFERENCE

1: Corina T. Bot, Krisztina Juhasz, Fabian Haeusermann, Liudmila Polonchuk, Martin Traebert, Sonja Stoelzle-Feix, Cross-site comparison of excitation-contraction coupling using impedance and field potential recordings in hiPSC cardiomyocytes, Journal of Pharmacological and Toxicological Methods, Volume 93, 2018, Pages 46-58.
2: William J. Crumb, Jose Vicente, Lars Johannesen, David G. Strauss, An evaluation of 30 clinical drugs against the comprehensive in vitro proarrhythmia assay (CiPA) proposed ion channel panel, Journal of Pharmacological and Toxicological Methods, Volume 81, 2016, Pages 251-262.
3: SOP-ADMET-MAN-007: The Standard Operating Procedure for Compound Management Example D: TNFα human whole blood screening assay The compounds according to the Examples were assessed in a human whole blood assay driven by endogenously expressed TNFα by measuring the expression of CD11b on granulocytes in human whole blood challenged with zymosan. A serial diluted compound was pre-incubated with human whole blood for 1 h at 37° C./5% $CO_2$. Zymosan (Invivogen, Tlrl-zyn) was added (final assay concentration 1 g/ml in a total volume of 100 µl) with thorough mixing and incubated for 3 h at 37° C./5% $CO_2$. The samples were then incubated with 10 µl antibody cocktail containing APC-conjugated anti-human CD45 antibody (Biolegend, cat #304012) and PE-conjugated anti-human CD11b antibody (Biolegend, cat #101208) for 30 min at 4° C. The blood was fixed/lysed for 10-15 min at 37° C. using FACS/lysing solution (BD sciences, cat #558049) and analyzed with CytoFlex S (Beckman Coulter). The number of single cells (SSC-A, SSC—W) positive for CD45 and expressing CD11b was determined using FlowJo software (BD Biosciences). Inhibition of CD11b activation was calculated against DMSO control. The % inhibition was plotted against compound concentration in logarithmic scale and the $IC_{50}$ was rendered using 4-parameter nonlinear regression (GraphPad Prism).

A calculated $IC_{50}$ for the free compound (free $IC_{50}$) that considers the extent of fraction unbound in blood was determined by multiplying the $IC_{50}$ generated from the human whole blood screening assay by the unbound fraction, generated from the plasma protein binding assay.

Comparative data is shown in table 7.

TABLE 7

| Ex. | CD11b in hWB, free $IC_{50}$ (nM) |
|---|---|
| Comp. Ex #1 | 9.3 |
| 15 | 2.1 |

Example E: Human Dermal Fibroblast Cell Potency Assay

The potency of compounds was examined in Human dermal fibroblast cells (HDF). HDF was cultured in human dermal fibroblast complete culture medium (Procell, CM-H103) as suggested by manufacturer. When used for assay, 40 µL of HDF suspension (2000 cell/well) was seeded into each well of 384-well plates (Corning 3764). After overnight culture, replenish fresh culture medium with 5% fetal bovine serum. A serial dilution of work solution of tested compound was made in DMSO with 1000× of final concentration, and 50 nL of compound DMSO solution was transferred into another set of 384-well plates by Echo, and incubated with 10 µL of recombinant hTNFα (R&D biosystem, Cat #210-TA-020/CF) for 1 h at 37° C. The compound/hTNFα mixture was then transferred to the 384-plate containing HDF, and then incubated at 37° C. with 5% $CO_2$ for 24 h. The final concentration of hTNFα is 10 ng/mL.

After incubation, 16 µL of induced cell supernatant was transferred to a new 384-well Optiplate well to mix with 4 µL of IL-8 antibody cocktail (Revvity #62HIL08PEH). After overnight incubation, the plate was read using EnSight™ Multimode Microplate Reader (Perkin Elmer) for HTRF signal.

The percentage of inhibition was calculated by the following formula:

% inhibition=(positive control−Sample)/(positive control−negative control)*100

Positive control: HTRF reading of cells with hTNFα stimulation.

Negative control: HTRF reading of cells without hTNFα stimulation.

Sample: HTRF reading of cells with compound at specific concentration and hTNFα stimulation The % inhibition was plotted against compound concentration in logarithmic scale and the $IC_{50}$ was rendered using 4-parameter nonlinear regression (GraphPad Prism).

Comparative data is shown in table 8.

TABLE 8

| Ex. | HDF_IL-8, $IC_{50}$ (nM)/Emax (%) |
|---|---|
| Comp. Ex #1 | 6.7/93 |
| 15 | 2.8/97 |

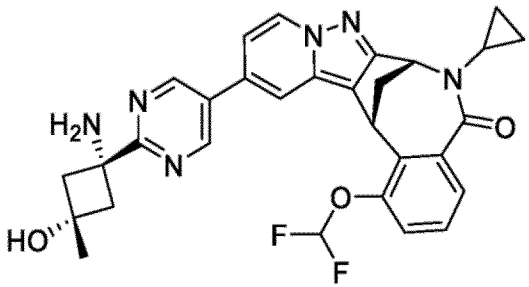

What is claimed is:

1. A compound of Formula (I*), or a pharmaceutically acceptable salt, solvate, or stereoisomer thereof:

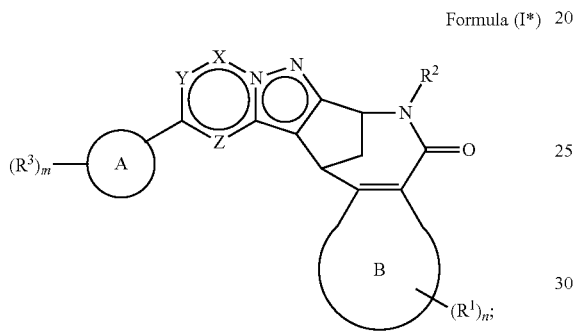

Formula (I*)

wherein:

Ring B is phenyl;

each $R^1$ is independently halogen, —CN, —OH, —$OR^a$, —$NR^cR^d$, $C_1$-$C_6$alkyl, or $C_1$-$C_6$haloalkyl;

n is 0, 1, or 2;

$R^2$ is hydrogen, $C_1$-$C_6$alkyl, $C_1$-$C_6$deuteroalkyl, or cycloalkyl;

X is $CR^X$;

$R^X$ is hydrogen;

Y is $CR^Y$;

$R^Y$ is hydrogen, halogen, or $C_1$-$C_6$alkyl;

Z is $CR^Z$;

$R^Z$ is hydrogen;

Ring A is heteroaryl;

each $R^3$ is independently halogen, -L-CN, -L-$NO_2$, -L-OH, -L-$OR^a$, -L-OC(=O)$R^a$, -L-OC(=O)$OR^b$, -L-OC(=O)$NR^cR^d$, -L-SH, -L-$SR^a$, -L-S(=O)$R^a$, -L-S(=O)$_2R^a$, -L-S(=O)(=NH)$R^a$, -L-S(=O)$_2OR^b$, -L-S(=O)$_2NR^cR^d$, -L-$NR^cR^d$, -L-$NR^bC$(=O)$NR^cR^d$, -L-$NR^bC$(=O)$R^a$, -L-$NR^bC$(=O)$OR^b$, -L-$NR^bS$(=O)$_2R^a$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

or two $R^3$ on adjacent atoms are taken together to form a cycloalkyl, heterocycloalkyl, aryl, or heteroaryl; each independently optionally substituted with one or more R;

m is 0, 1, or 2;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, heteroalkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl independently optionally substituted with one or more R; and L is absent or $C_1$-$C_3$alkylene optionally substituted with one or more R;

each R is independently halogen, —CN, —OH, —$OC_1$-$C_3$alkyl, —S(=O) $C_1$-$C_3$alkyl, —S(=O)$_2C_1$-$C_3$alkyl, —S(=O)$_2NH_2$, —S(=O)$_2NHC_1$-$C_3$alkyl, —S(=O)$_2N(C_1$-$C_3$alkyl)$_2$, —$NH_2$, —$NHC_1$-$C_3$alkyl, —$N(C_1$-$C_3$alkyl)$_2$, —NHC(=O)$OC_1$-$C_3$alkyl, —C(=O)$C_1$-$C_3$alkyl, —C(=O)OH, —C(=O)$OC_1$-$C_3$alkyl, —C(=O)$NH_2$, —C(=O)$N(C_1$-$C_3$alkyl)$_2$, —C(=O)$NHC_1$-$C_3$alkyl, —P(=O)$(C_1$-$C_3$alkyl)$_2$, —P(=O)$(OC_1$-$C_3$alkyl)$_2$, $C_1$-$C_3$alkyl, $C_1$-$C_3$haloalkyl, $C_1$-$C_3$hydroxyalkyl, $C_1$-$C_3$aminoalkyl, $C_1$-$C_3$heteroalkyl, $C_1$-$C_6$cycloalkyl, or 3- to 6-membered heterocycloalkyl;

or two R on the same atom are taken together to form an oxo.

2. The compound of claim 1, or a pharmaceutically acceptable salt, solvate, or stereoisomer thereof; wherein the compound is of Formula (Ia-1):

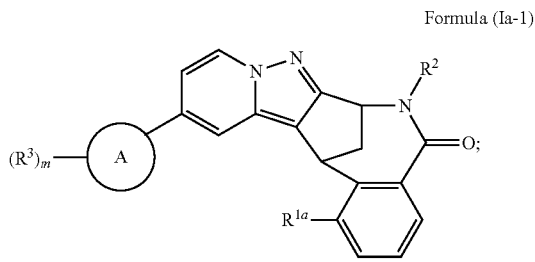

Formula (Ia-1)

wherein $R^{1a}$ is hydrogen or $R^1$.

3. The compound of claim 1, or a pharmaceutically acceptable salt, solvate, or stereoisomer thereof; wherein $R^2$ is —$CH_3$ or —$CD_3$.

4. The compound of claim 2, or a pharmaceutically acceptable salt, solvate, or stereoisomer thereof; wherein $R^{1a}$ is —$OCHF_2$.

5. The compound of claim 1, or a pharmaceutically acceptable salt, solvate, or stereoisomer thereof; wherein Ring A is pyrimidinyl.

6. The compound of claim 1, or a pharmaceutically acceptable salt, solvate, or stereoisomer thereof; wherein each $R^3$ is independently halogen, -L-$OR^a$, -L-$NR^cR^d$, -L-C(=O)$R^a$, -L-C(=O)$OR^b$, -L-C(=O)$NR^cR^d$, -L-P(=O)$R^cR^d$, -L-P(=O)$OR^cOR^d$, $C_1$-$C_6$alkyl, -L-cycloalkyl, or -L-heterocycloalkyl; wherein each alkyl, cycloalkyl, and heterocycloalkyl is independently optionally substituted with one or more R.

7. The compound of claim 6, or a pharmaceutically acceptable salt, solvate, or stereoisomer thereof; wherein each $R^3$ is independently halogen or cycloalkyl independently optionally substituted with one or more R.

8. The compound of claim 6, or a pharmaceutically acceptable salt, solvate, or stereoisomer thereof; wherein each $R^3$ is independently cycloalkyl independently optionally substituted with one or more R.

9. The compound of claim 6, or a pharmaceutically acceptable salt, solvate, or stereoisomer thereof; wherein each $R^3$ is independently halogen or -L-$NR^cR^d$.

10. The compound of claim 6, or a pharmaceutically acceptable salt, solvate, or stereoisomer thereof; wherein each $R^3$ is independently -L-$NR^cR^d$.

11. The compound of claim 1, or a pharmaceutically acceptable salt, solvate, or stereoisomer thereof; wherein each R is independently halogen, —CN, —OH, —$NH_2$, $C_1$-$C_3$alkyl, or $C_1$-$C_3$haloalkyl.

12. The compound of claim 1, or a pharmaceutically acceptable salt, solvate, or stereoisomer thereof; wherein each $R^3$ is independently

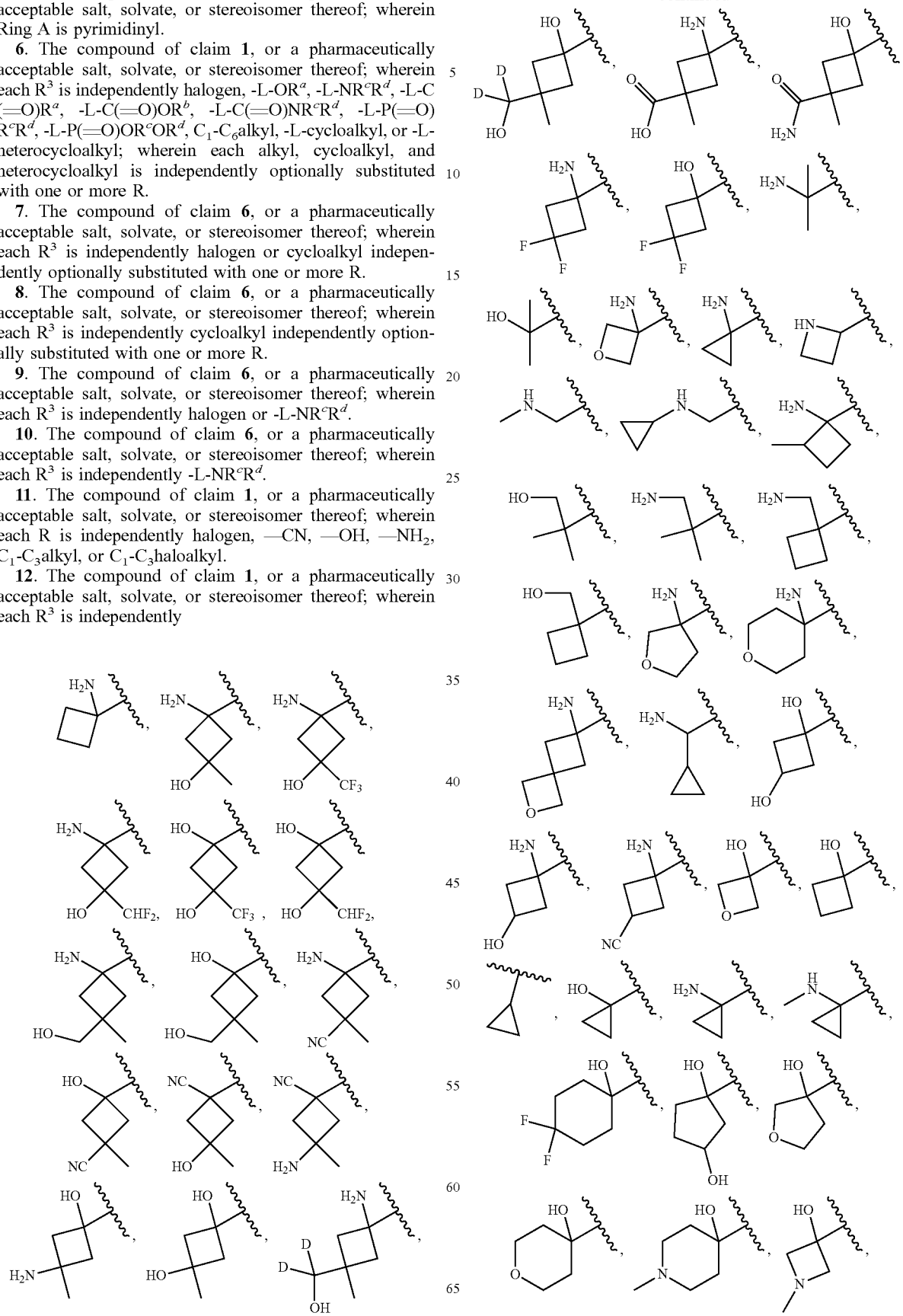

503
-continued
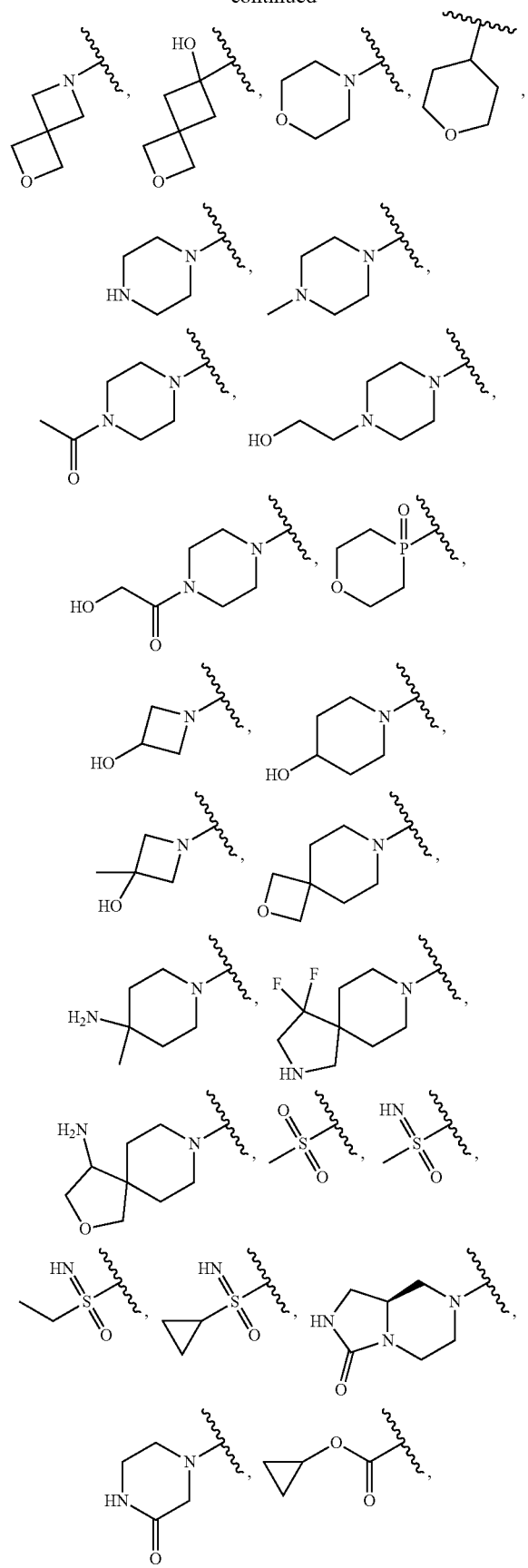
504
-continued
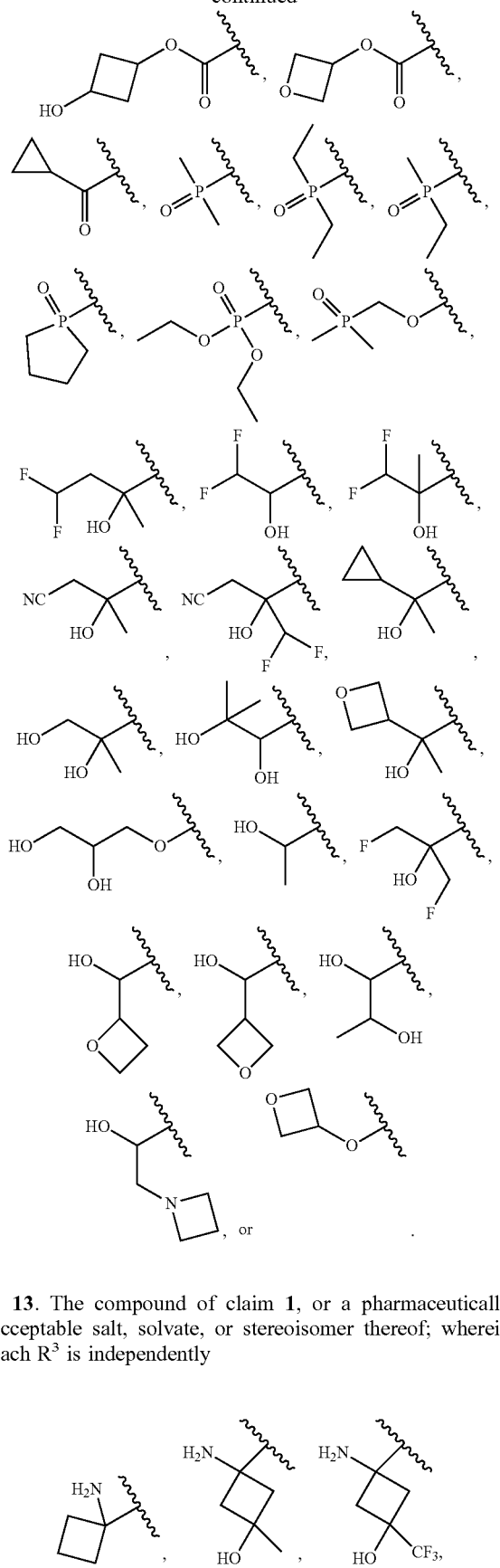
13. The compound of claim 1, or a pharmaceutically acceptable salt, solvate, or stereoisomer thereof; wherein each $R^3$ is independently
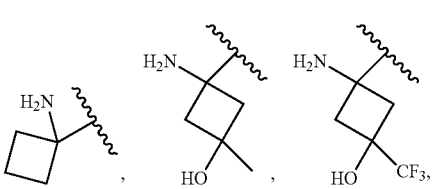

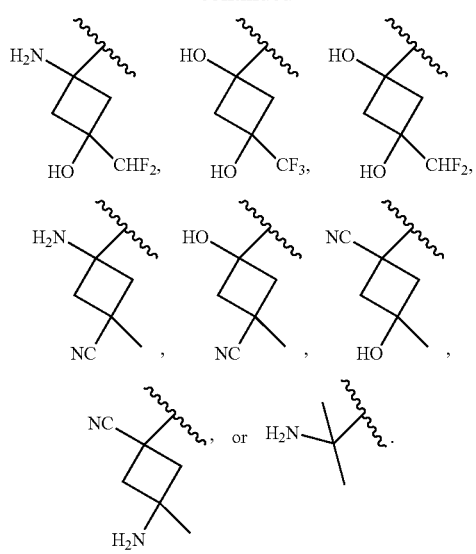
14. The compound of claim 1 selected from the group consisting of:
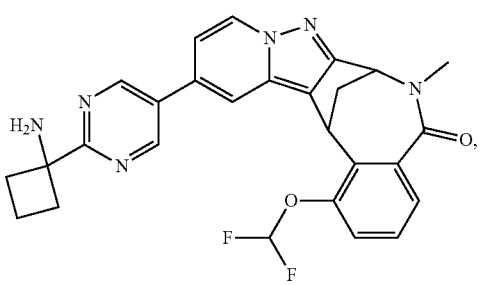
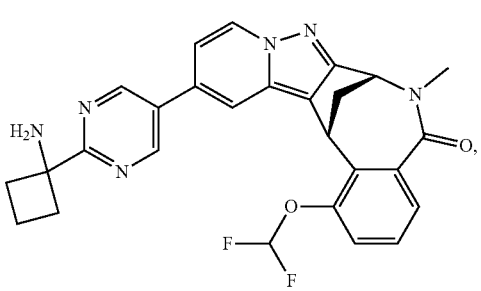
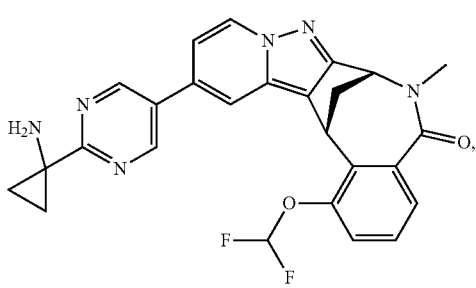
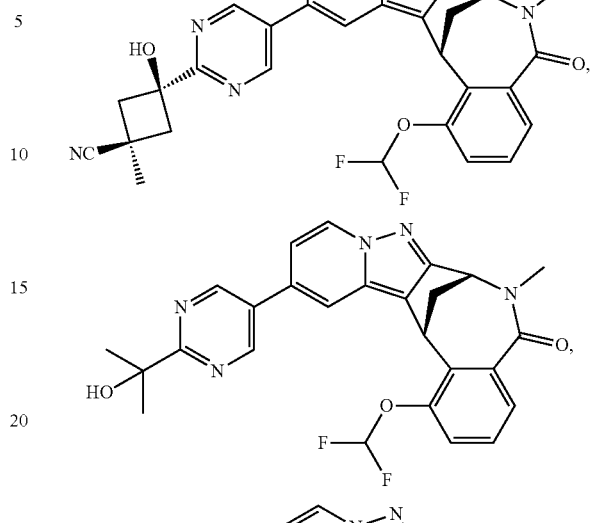
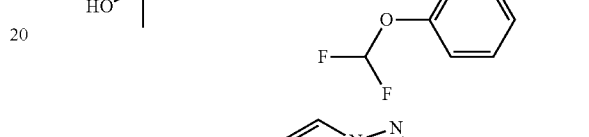
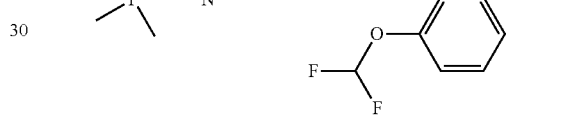
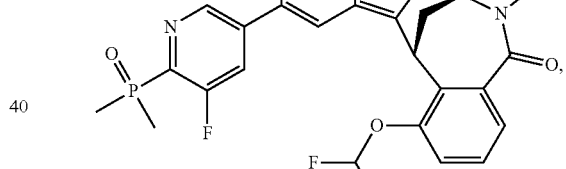
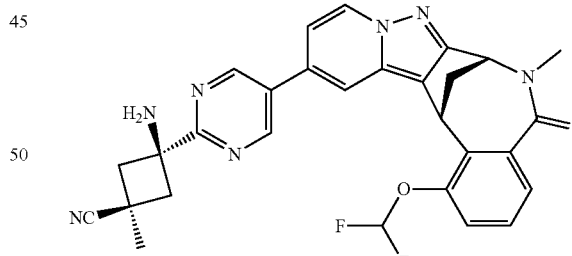
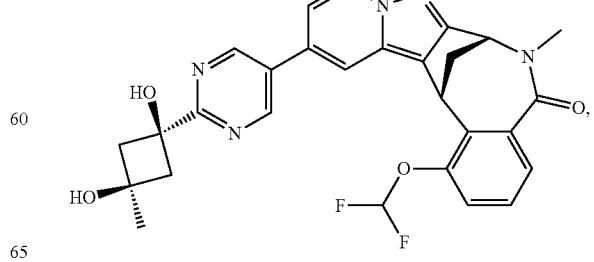

507
-continued
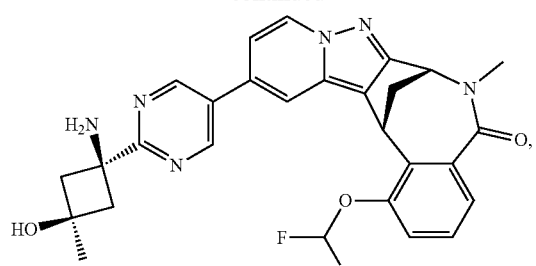
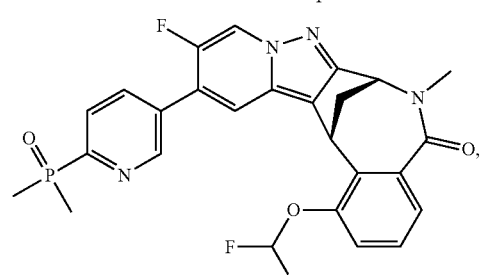
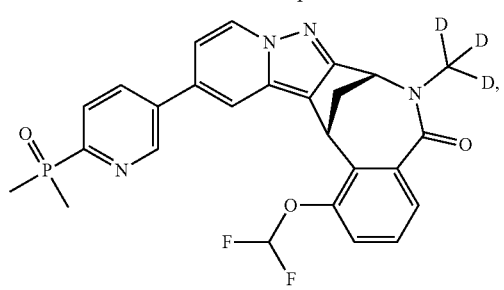
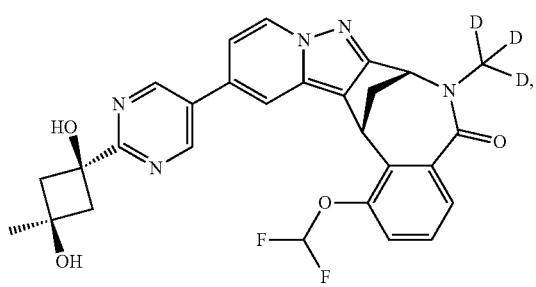
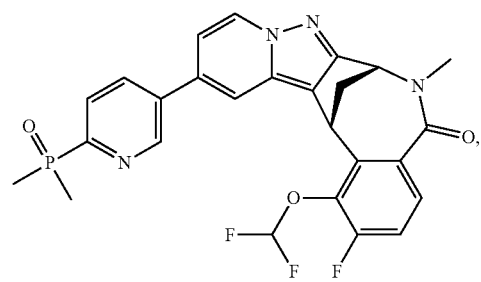
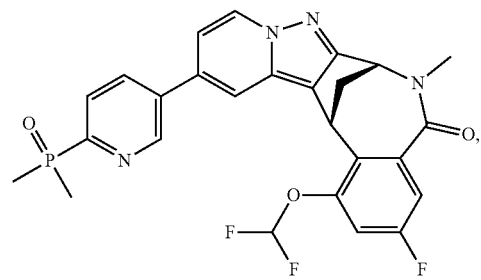
508
-continued
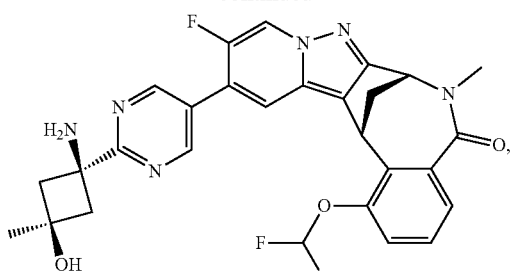
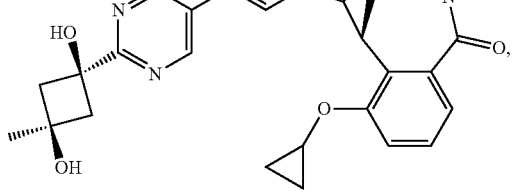
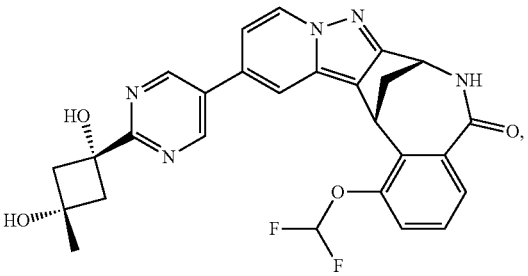
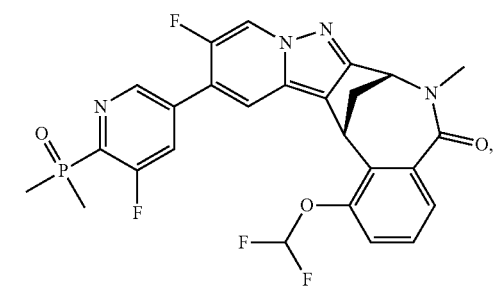
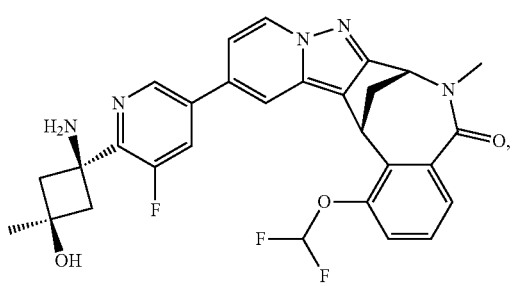
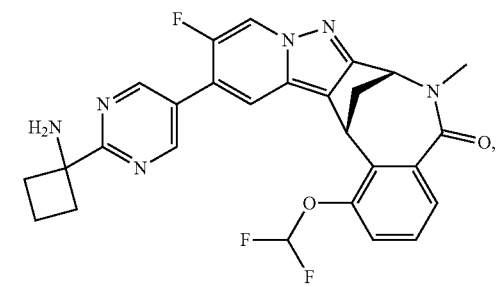

509
-continued
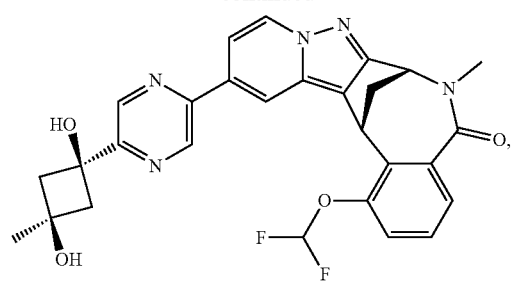
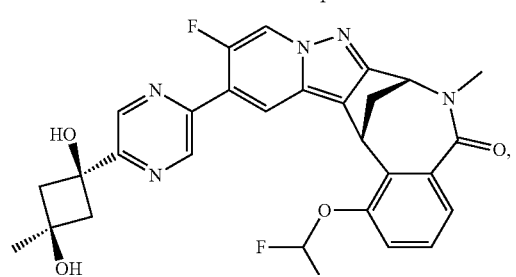
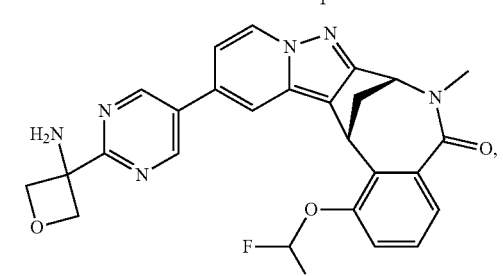
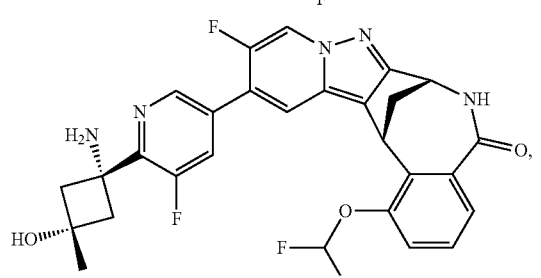
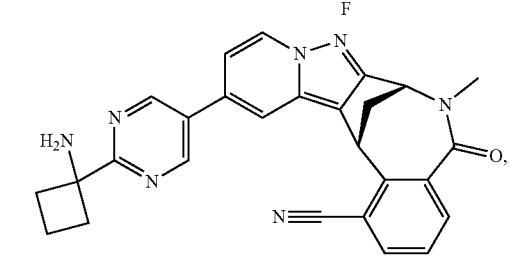
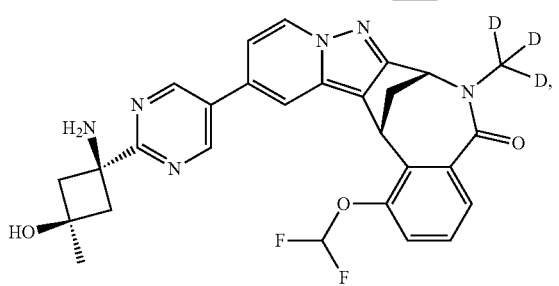
510
-continued
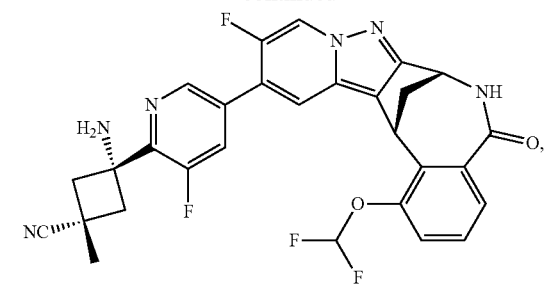
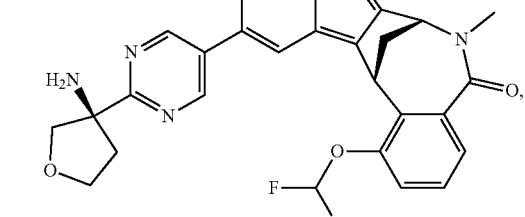
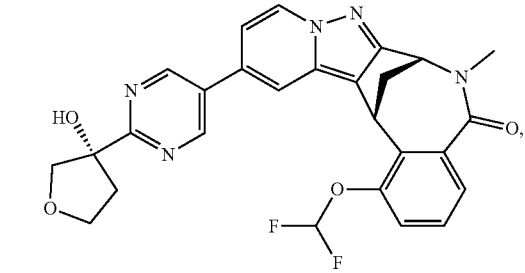
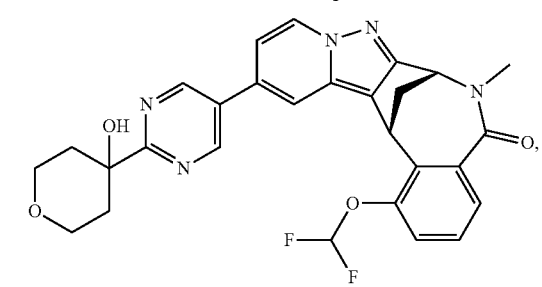
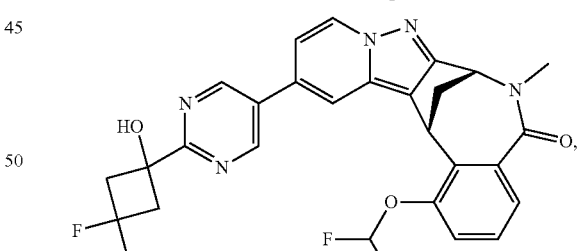
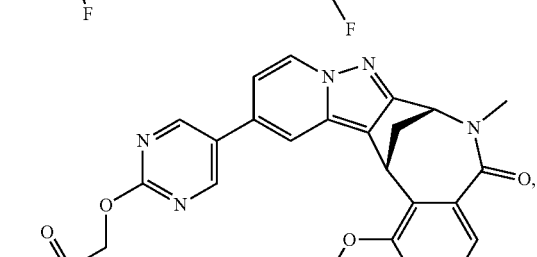

511
-continued
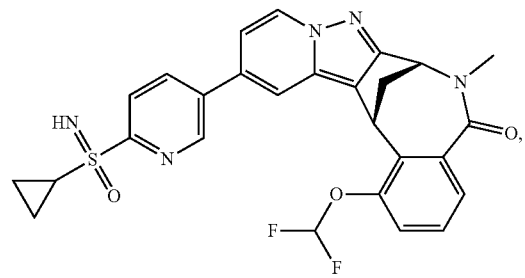
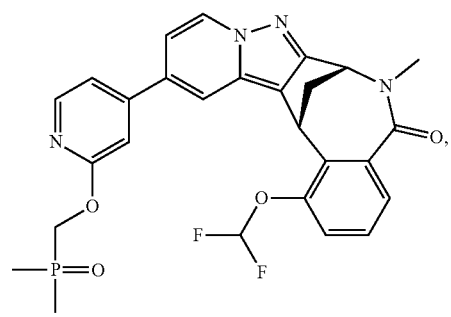
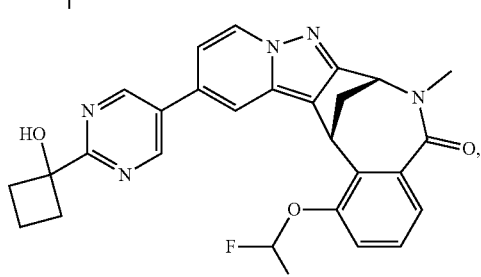
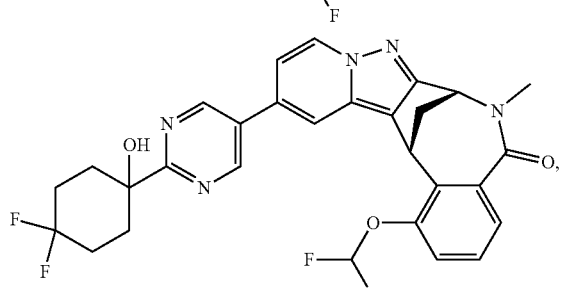
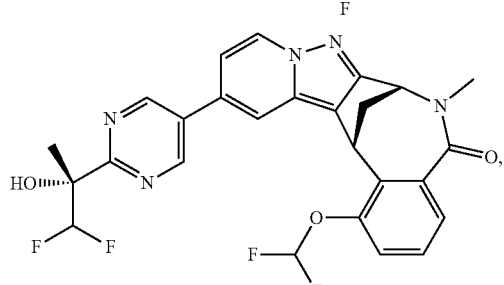
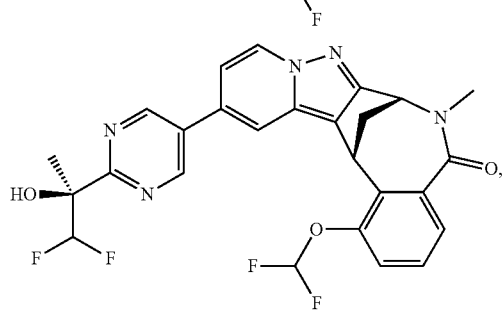
512
-continued
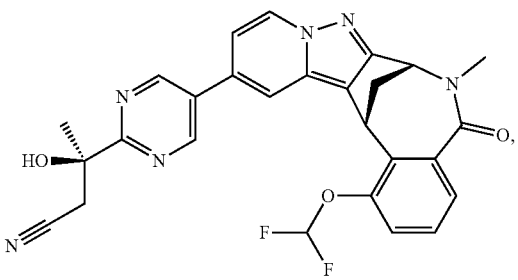
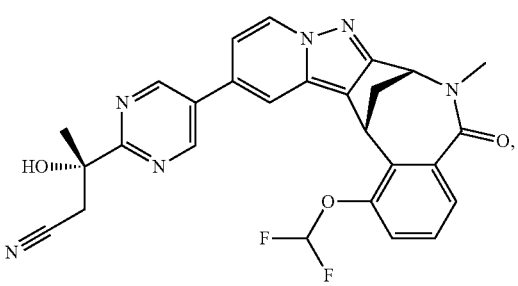
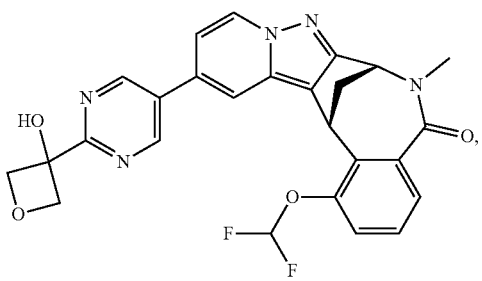
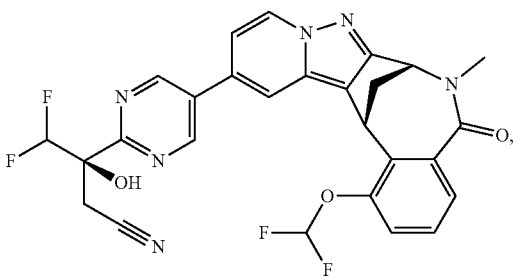
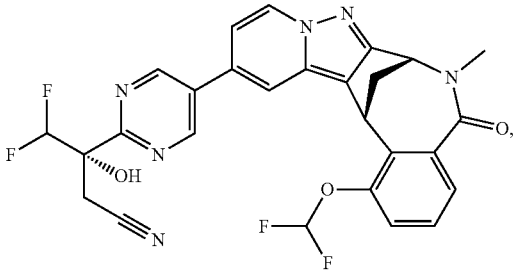
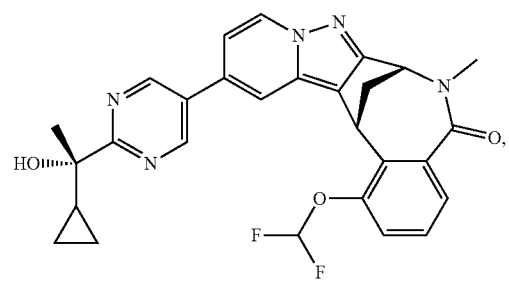

513
-continued
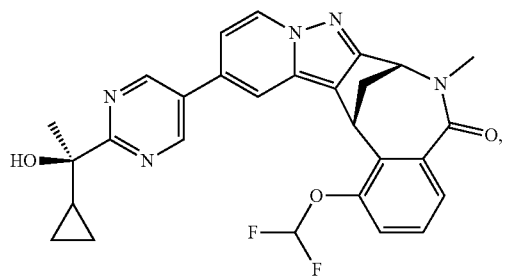
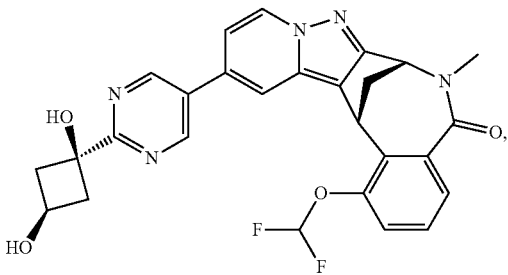
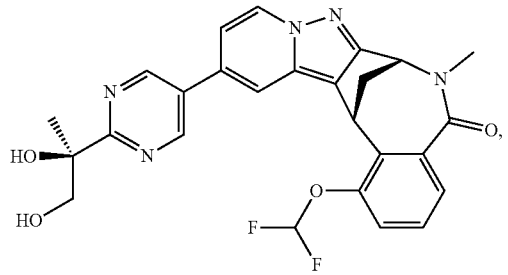
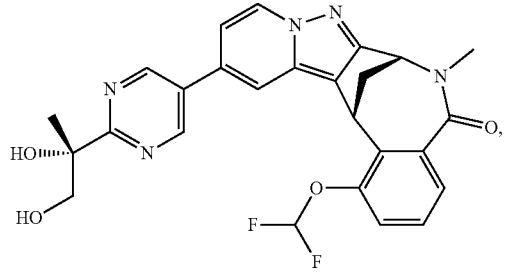
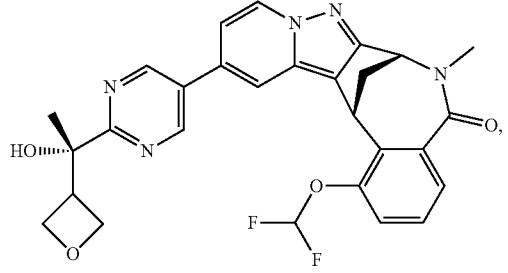
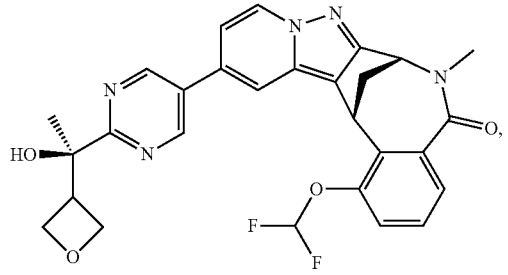
514
-continued
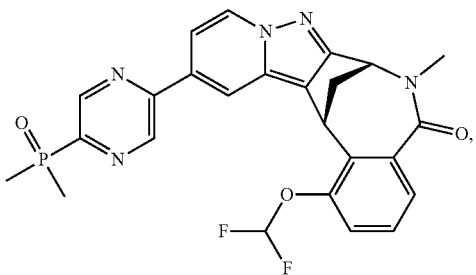
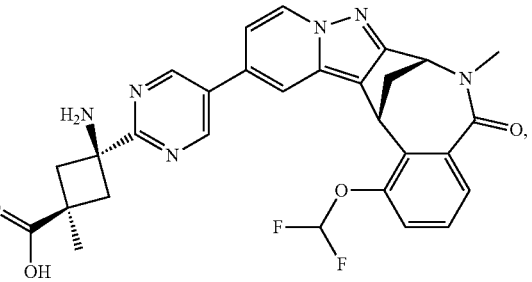
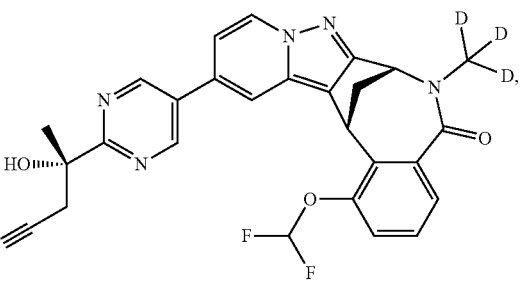
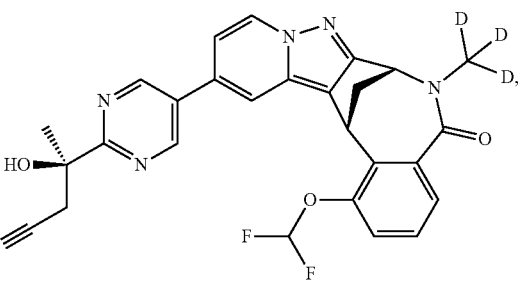
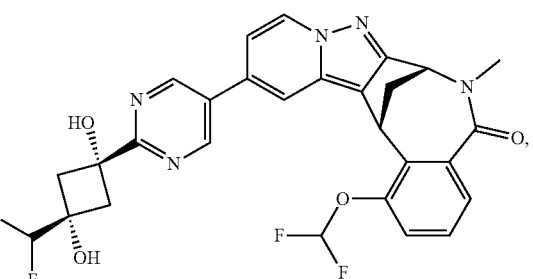
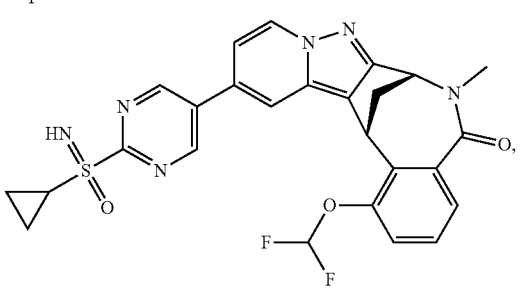

515
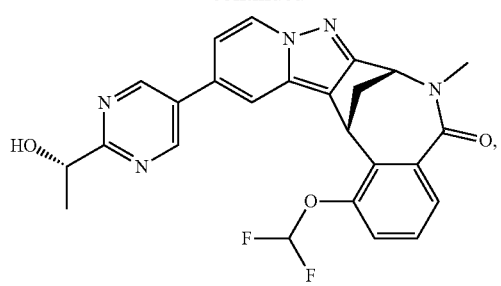
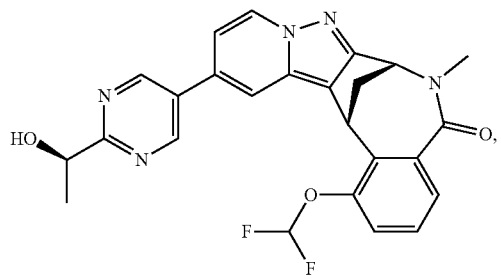
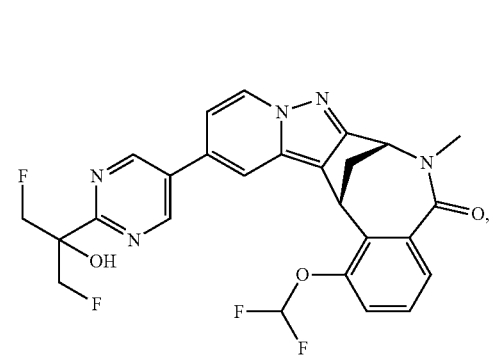
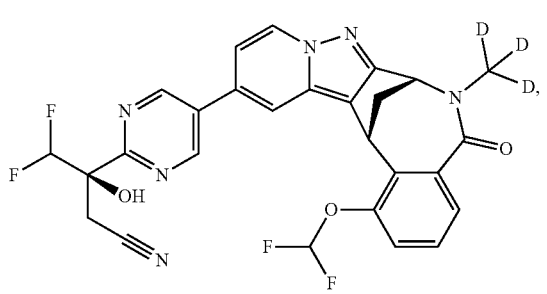
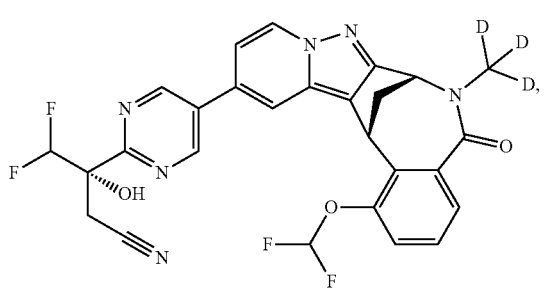
516
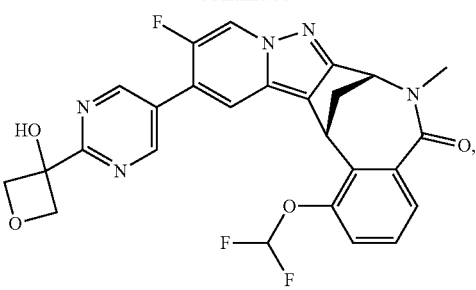
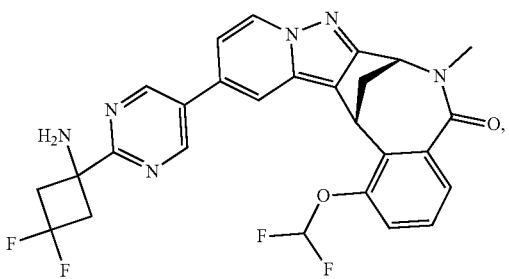
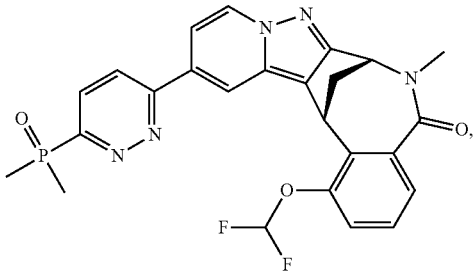
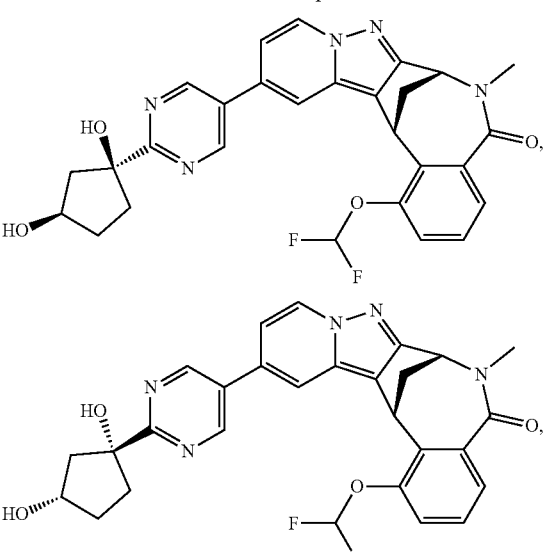
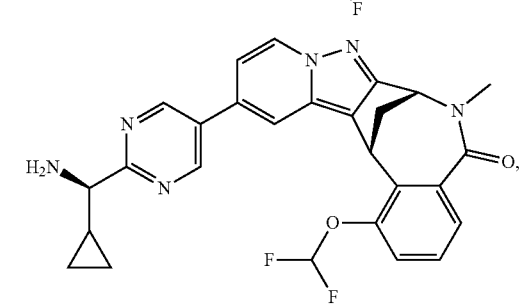

517
-continued
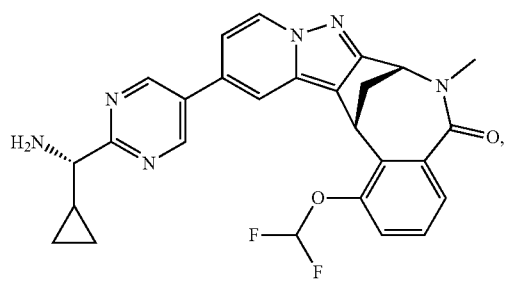
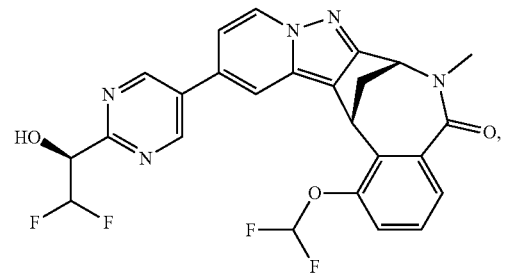
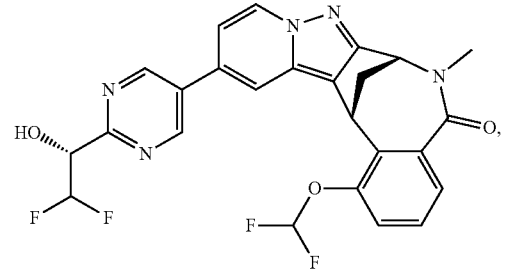
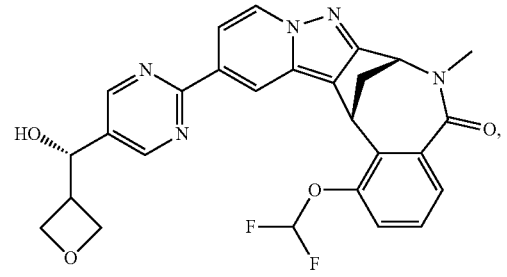
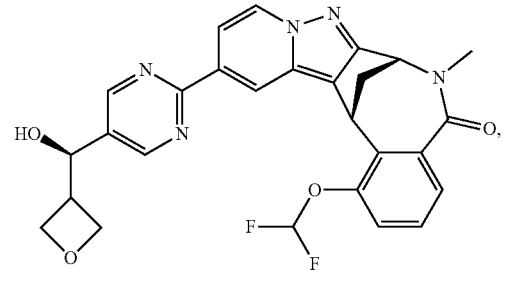
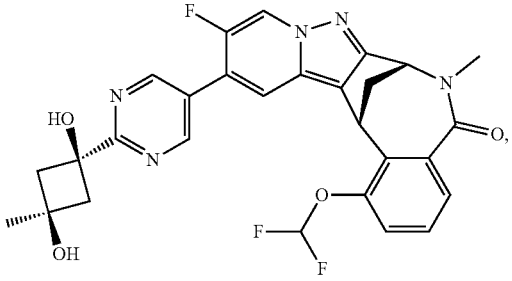
518
-continued
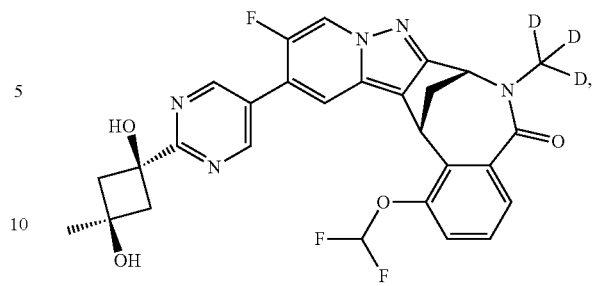
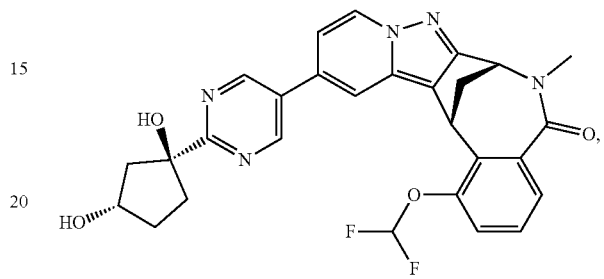
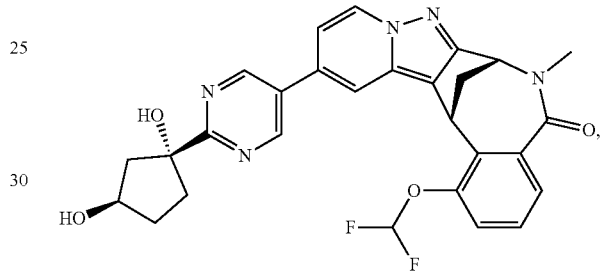
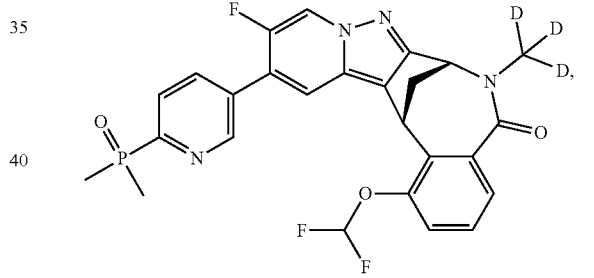
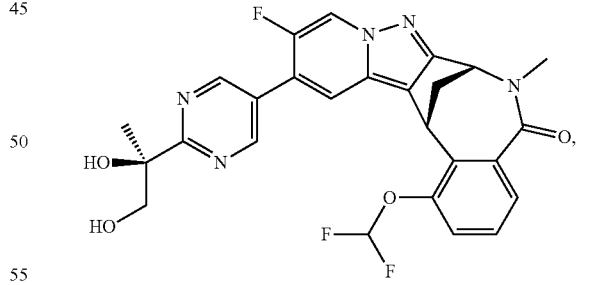
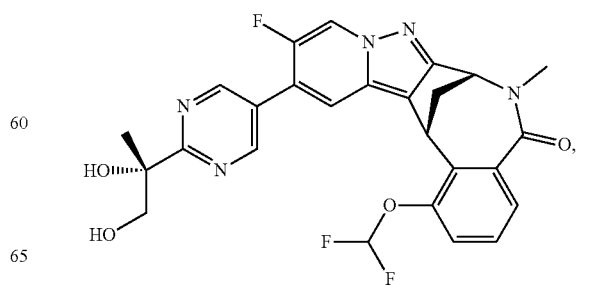

519
-continued
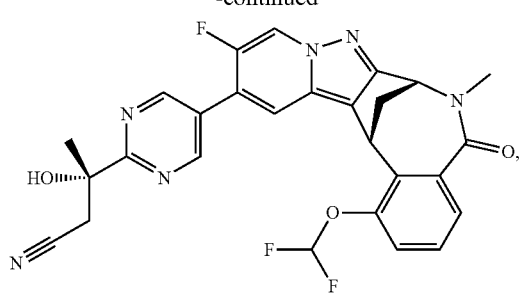
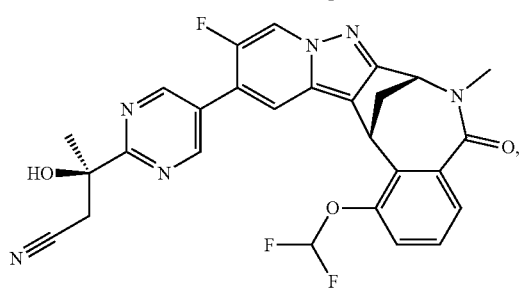
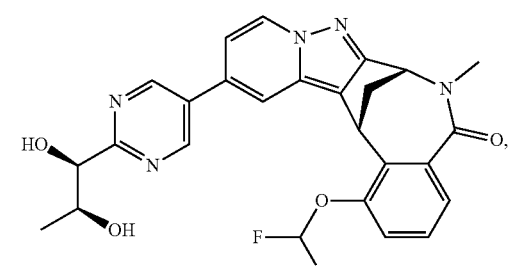
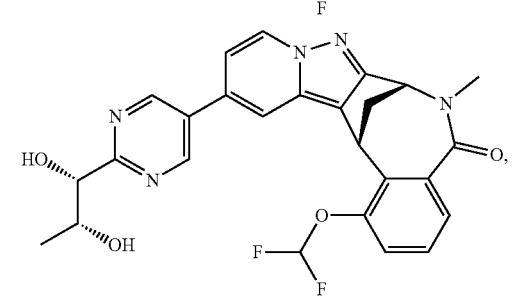
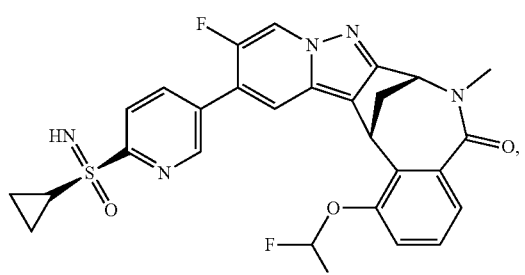
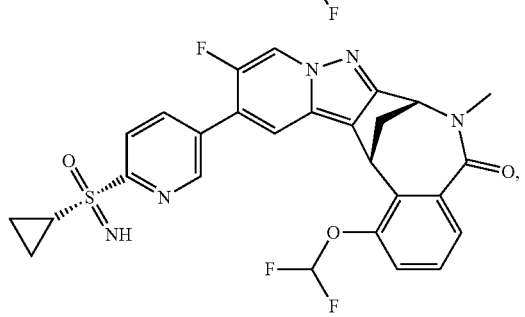
520
-continued
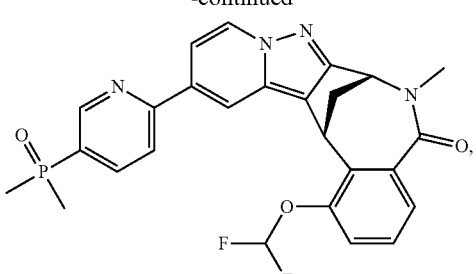
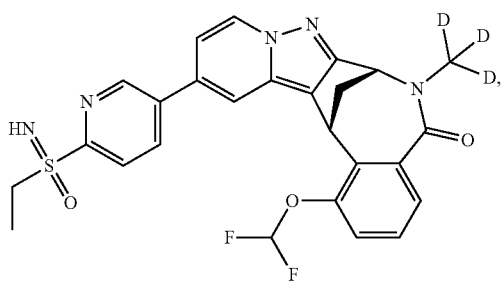
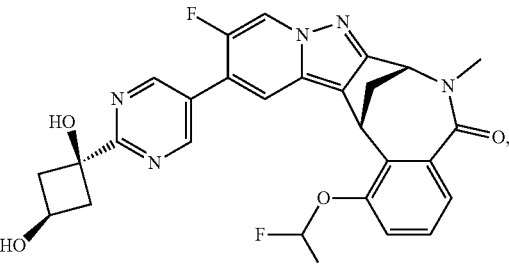
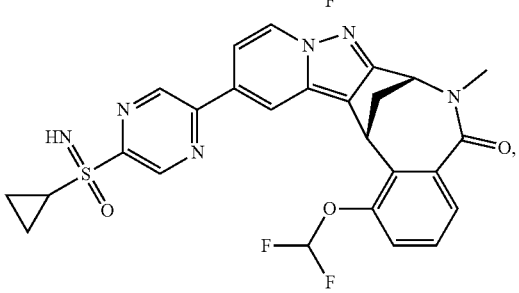
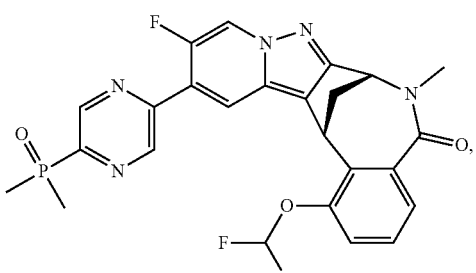
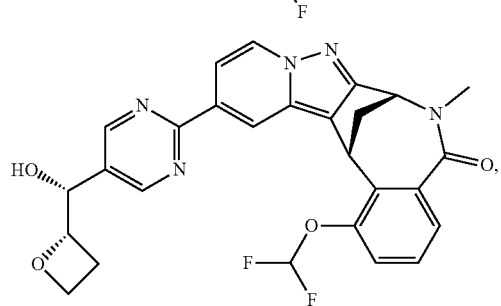

521
-continued
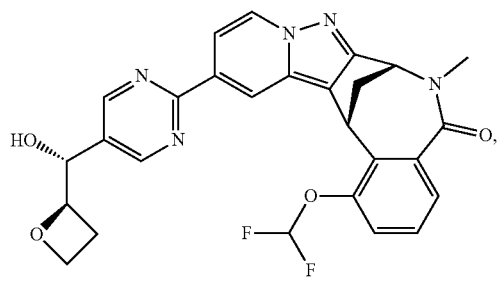
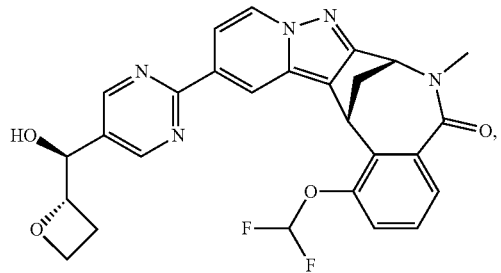
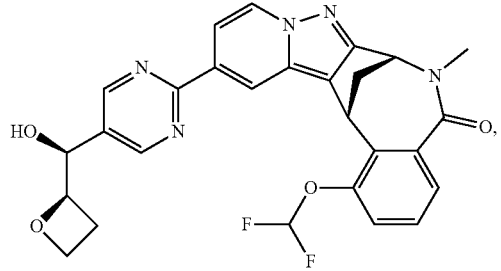
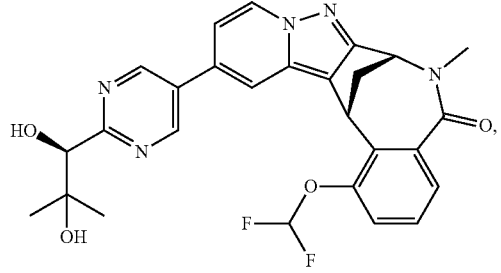
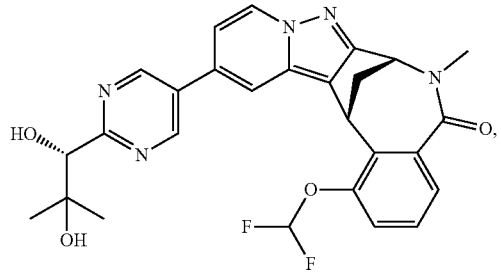
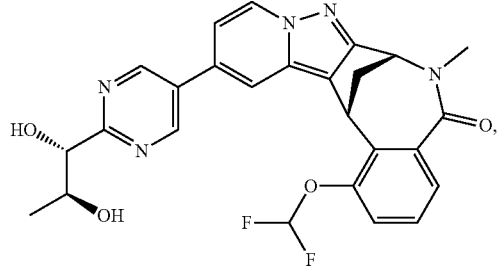
522
-continued
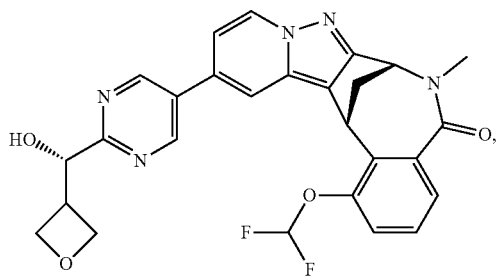
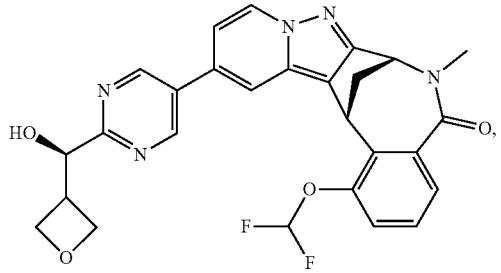
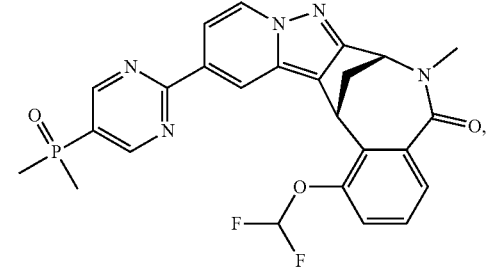
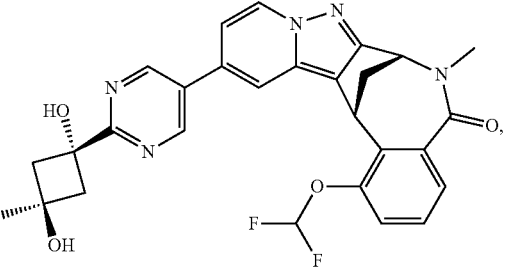
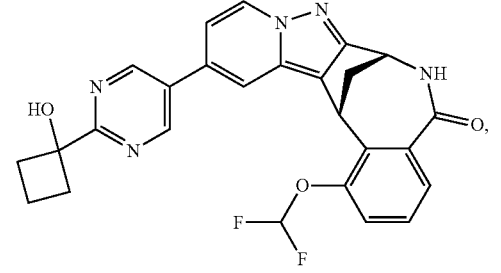
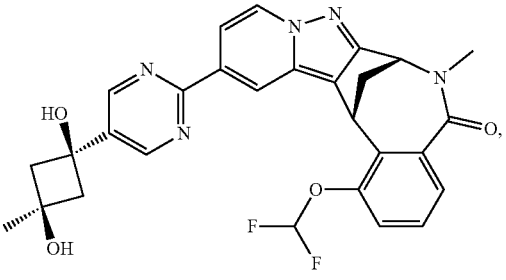

523
-continued
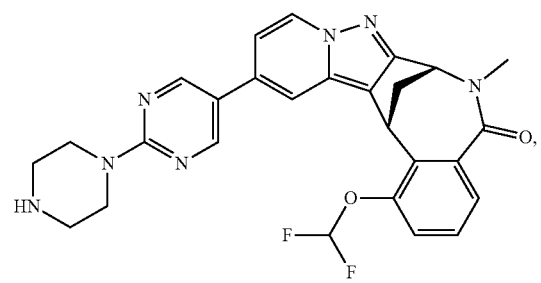
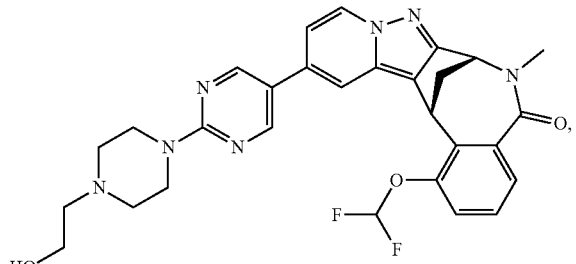
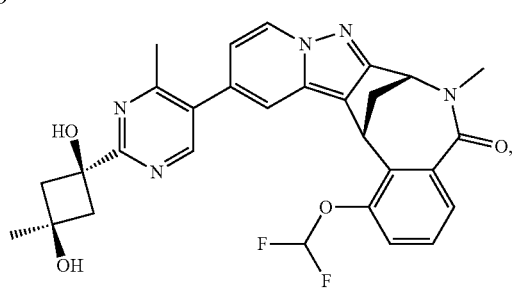
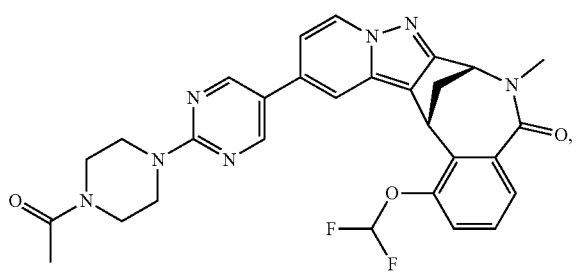
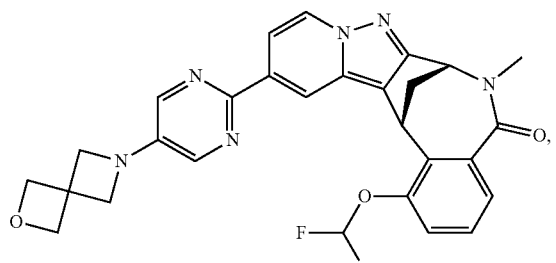
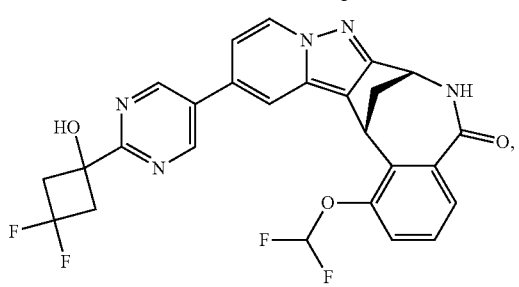
524
-continued
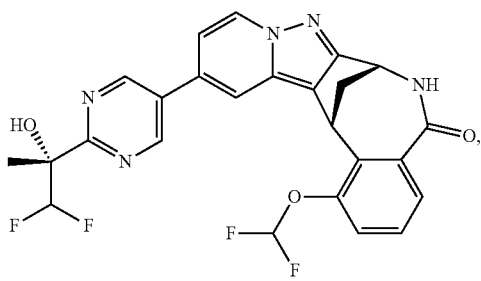
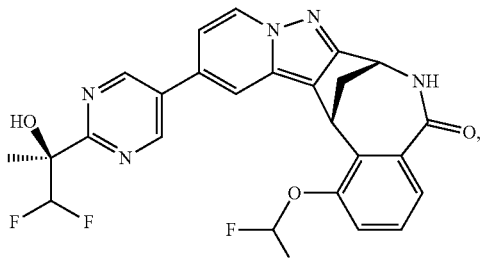
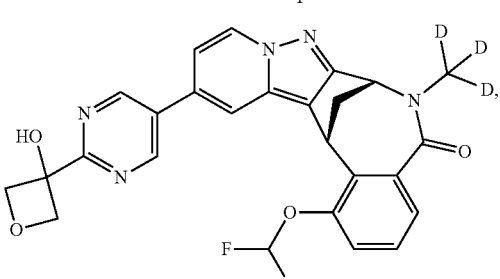
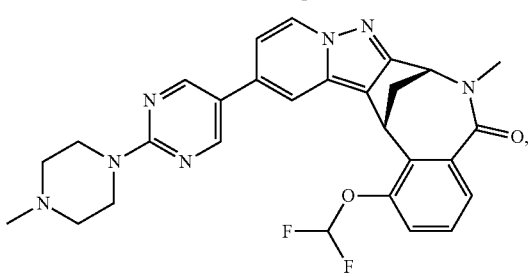
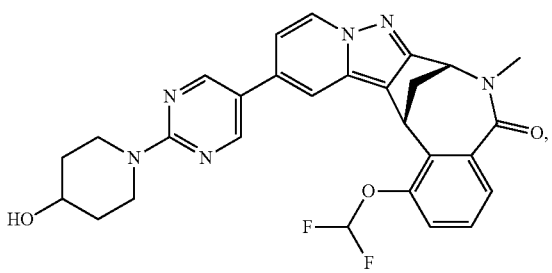
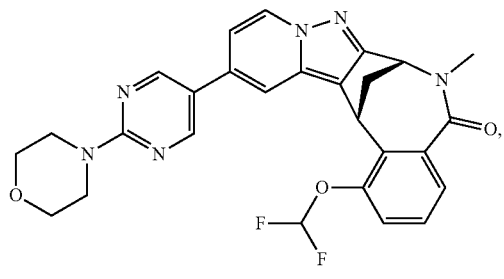

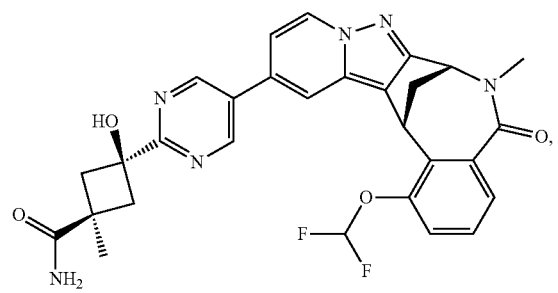
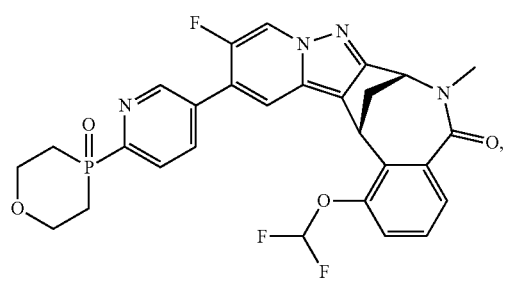
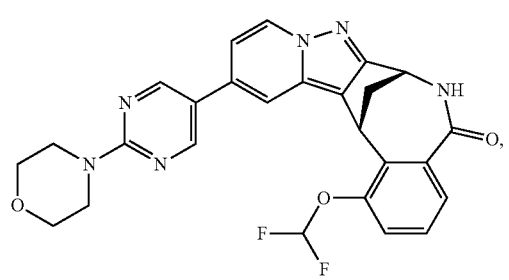
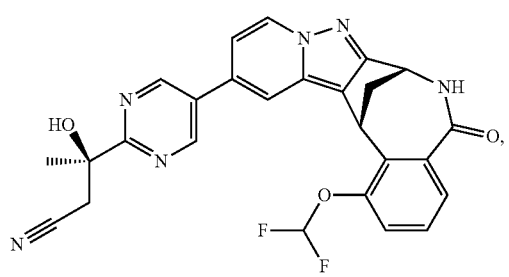
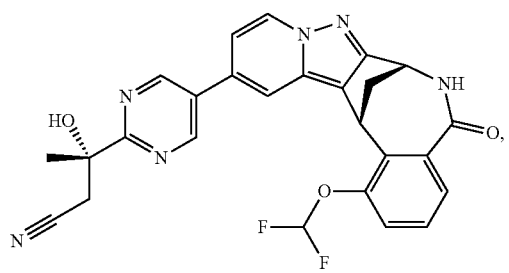
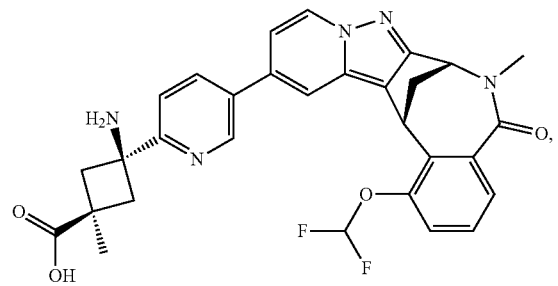
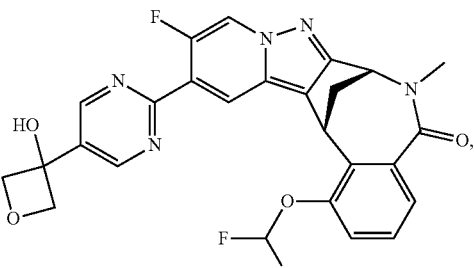
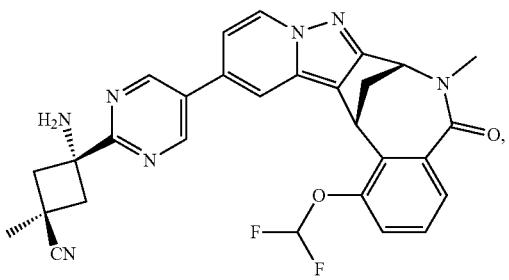
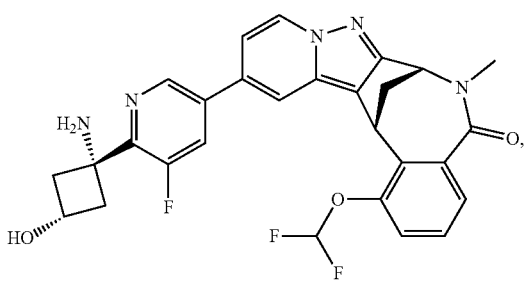
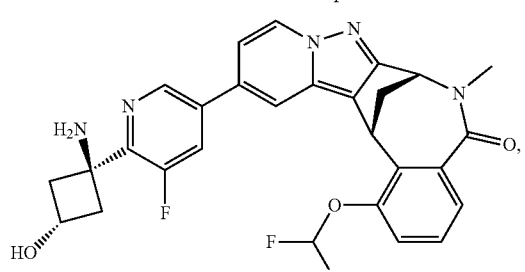
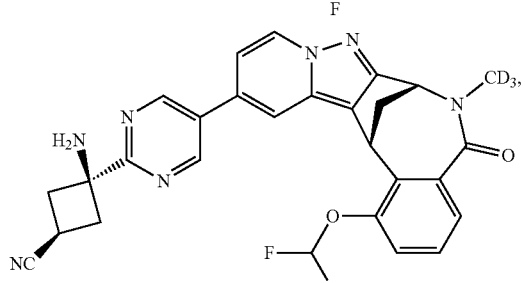
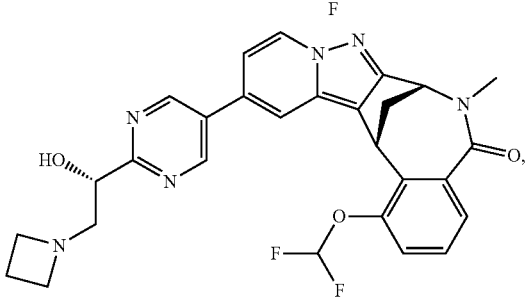

| 527 -continued | 528 -continued |
|---|---|
| 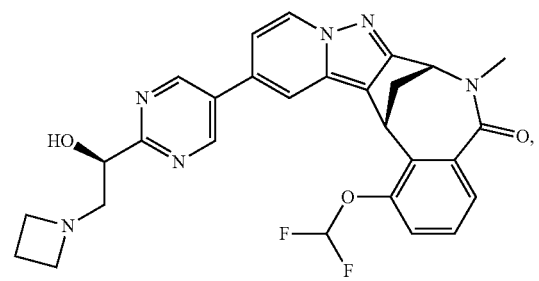 | 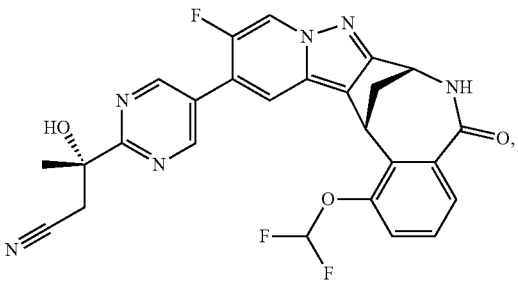 |
| 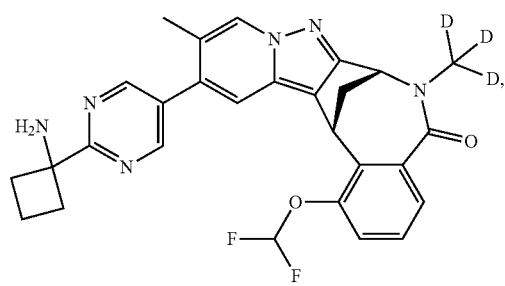 | 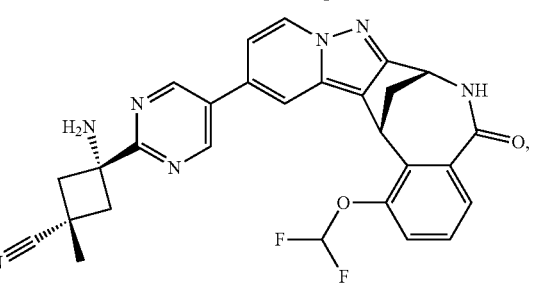 |
| 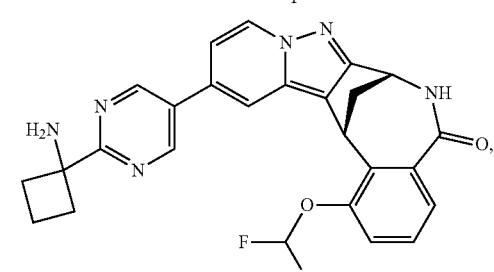 | 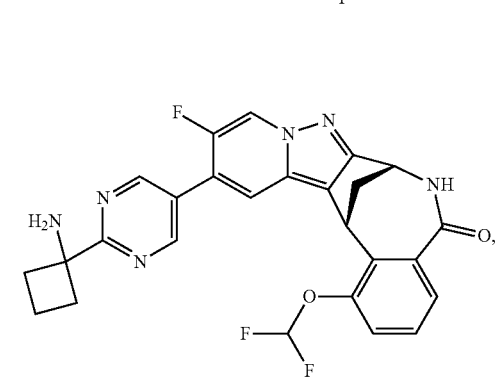 |
| 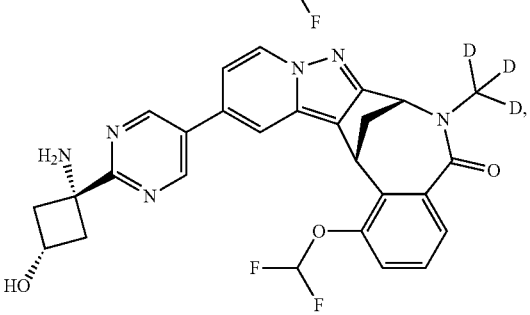 | |
| 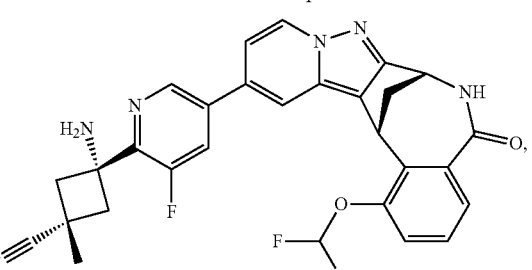 | 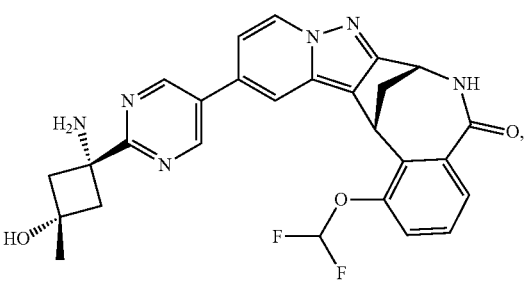 |
| 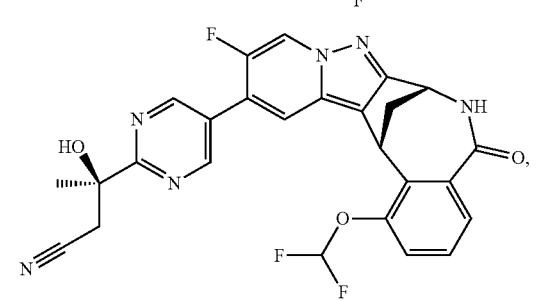 | 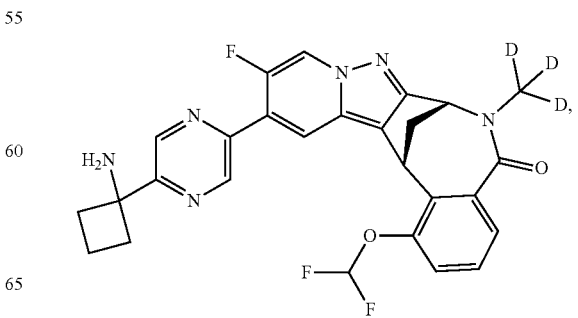 |

529
-continued
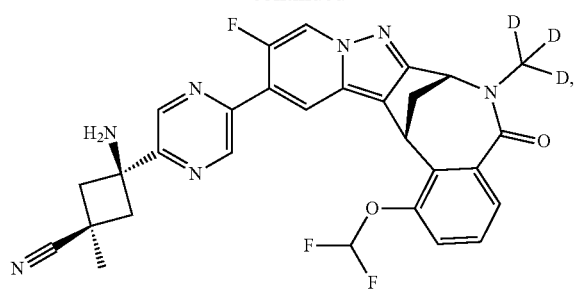
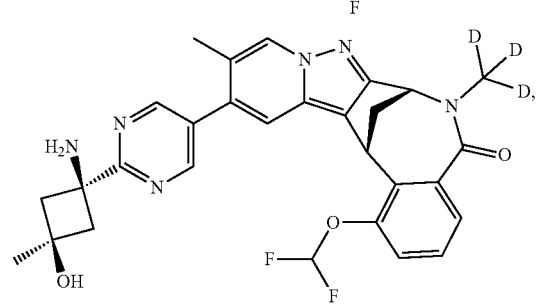
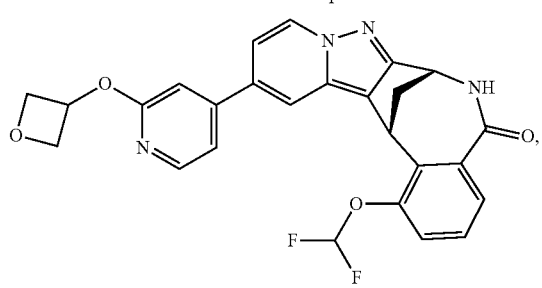
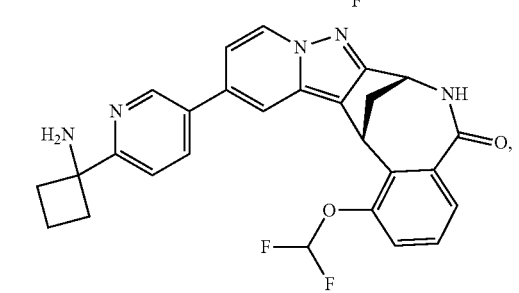
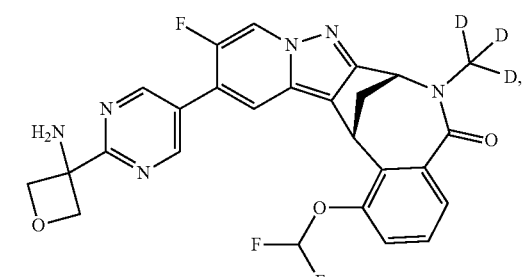
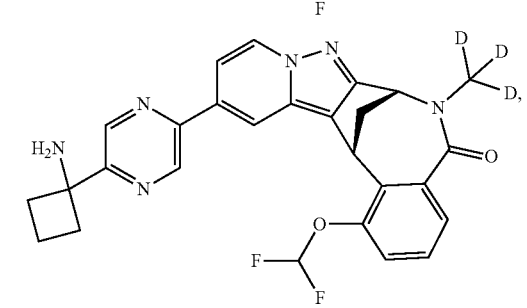
530
-continued
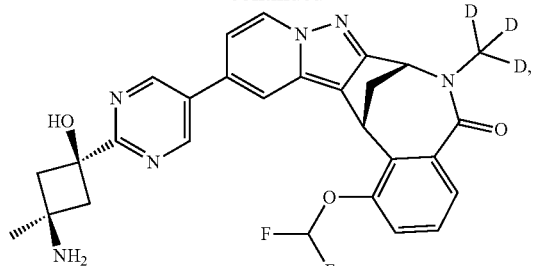
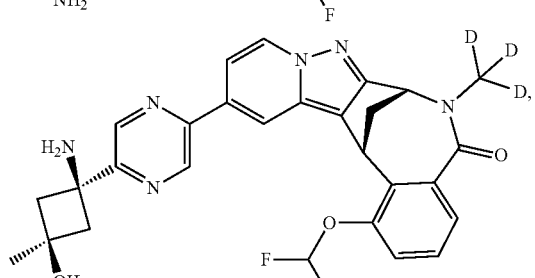
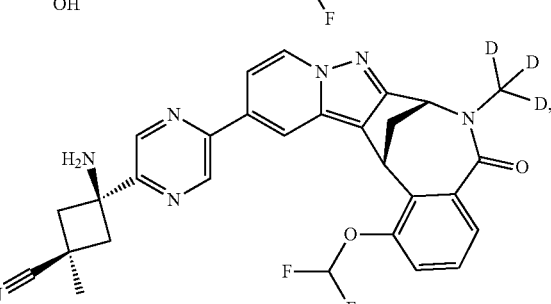
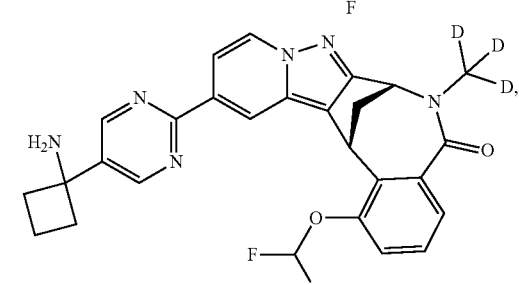
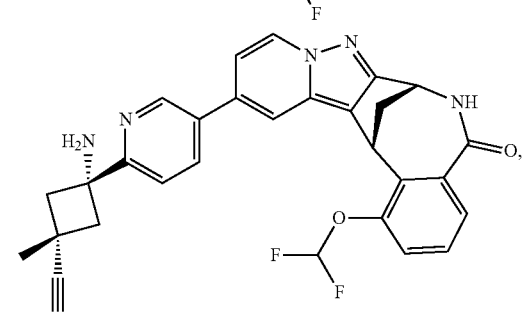
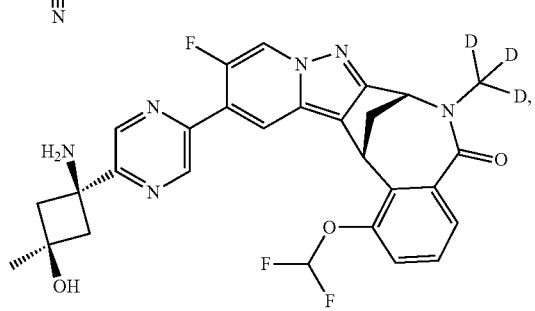

531
-continued
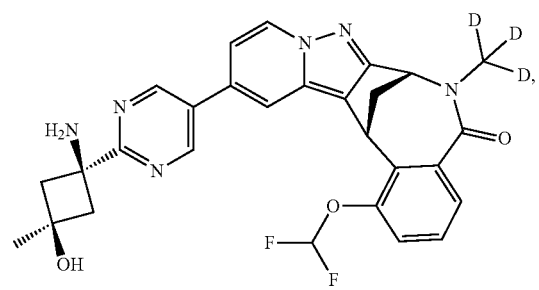
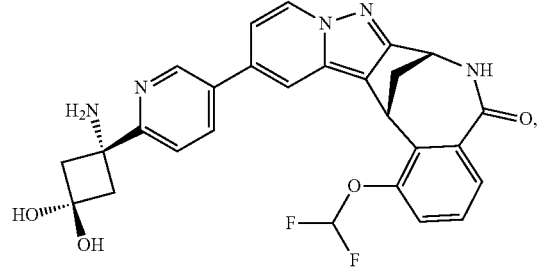
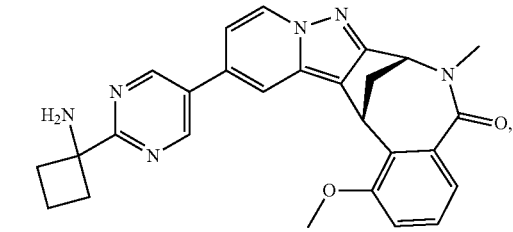
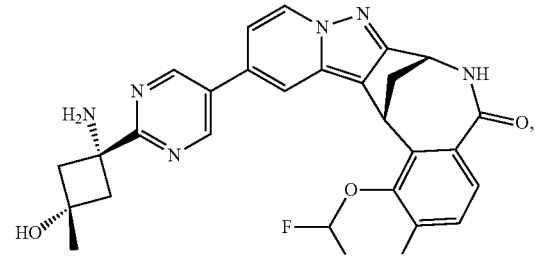
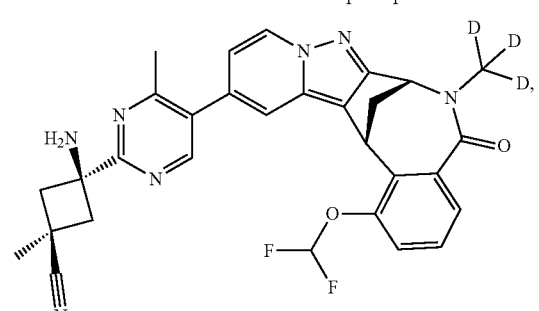
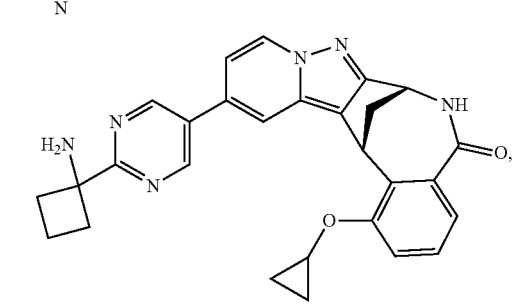
532
-continued
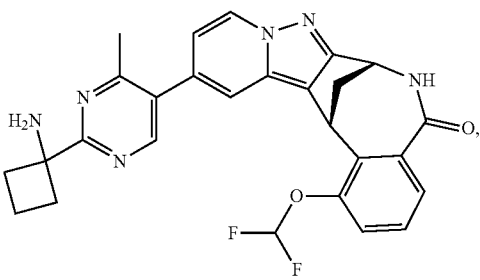
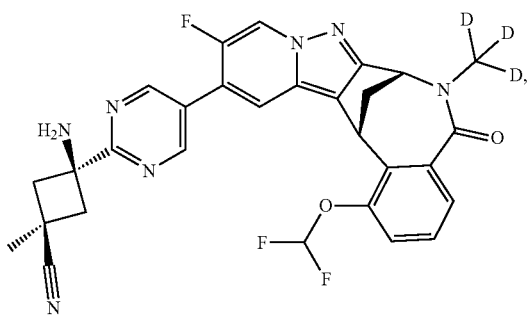
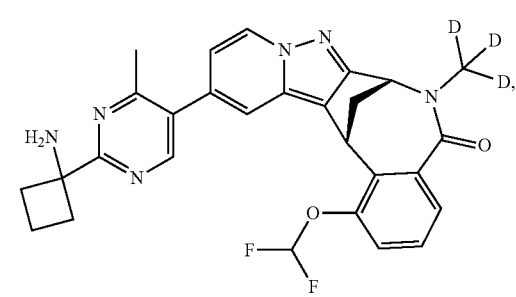
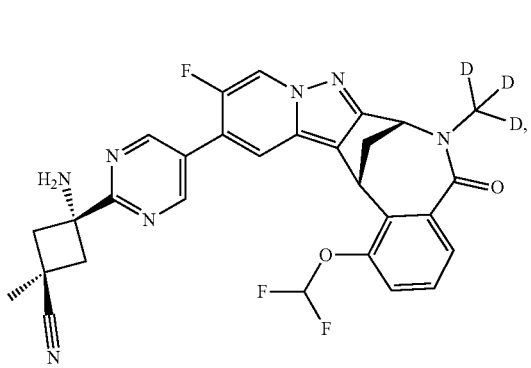
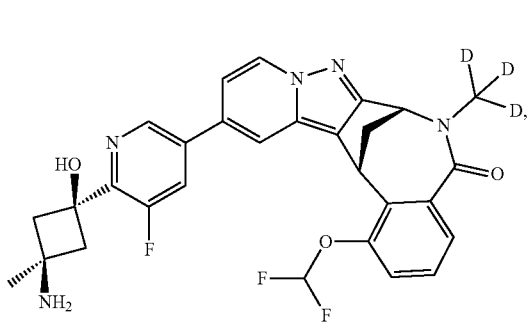

| 533 -continued | 534 -continued |
|---|---|
| 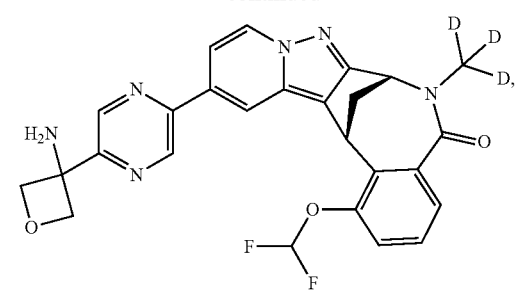 | 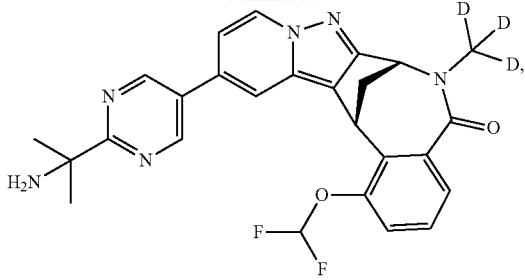 |
| 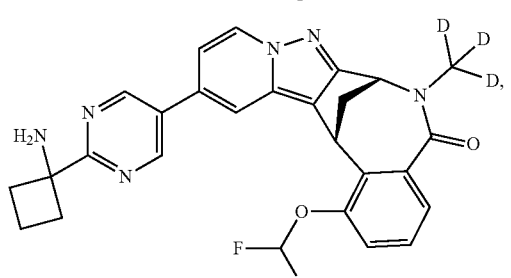 | 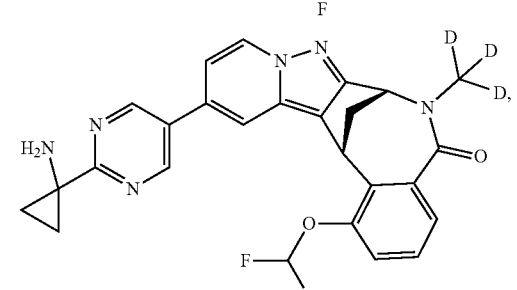 |
| 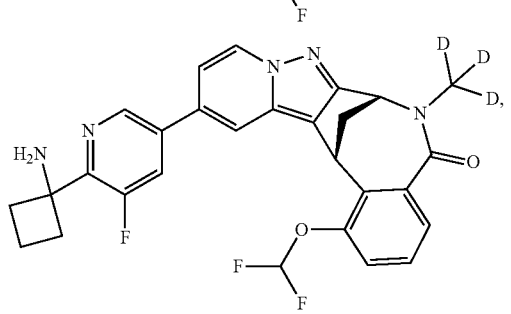 | 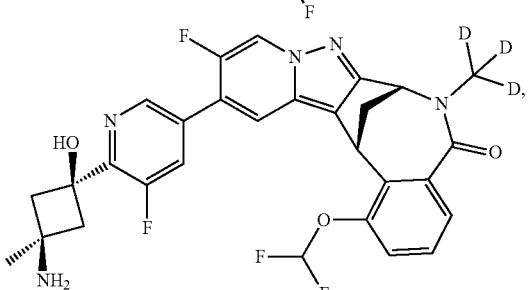 |
| 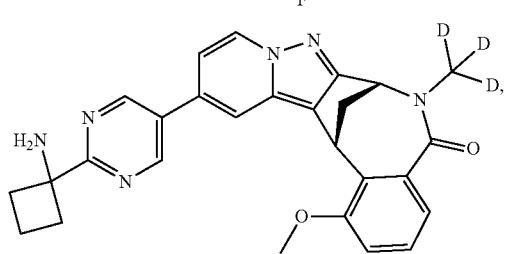 | 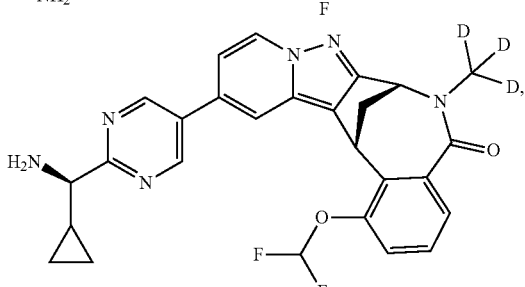 |
| 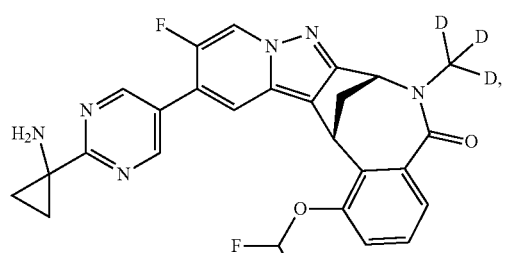 | 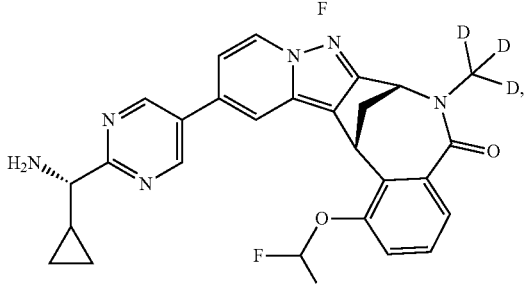 |
| 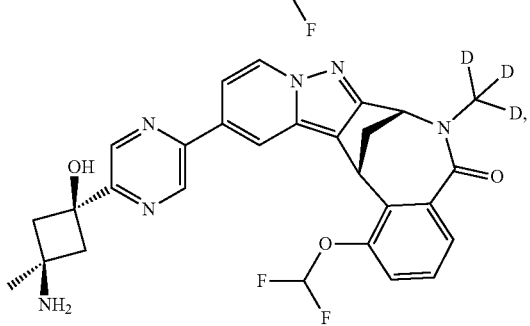 | 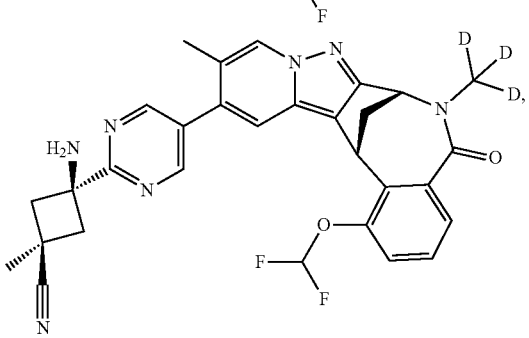 |

535
-continued
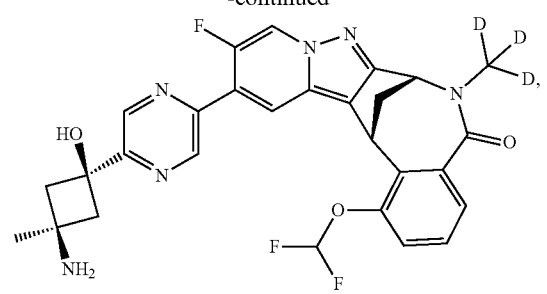
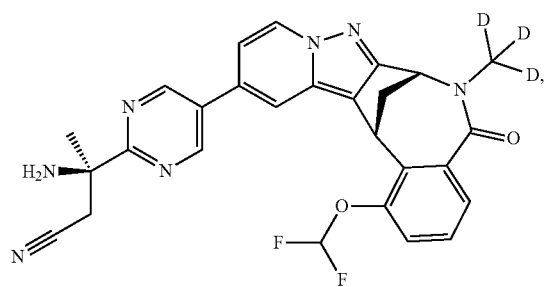
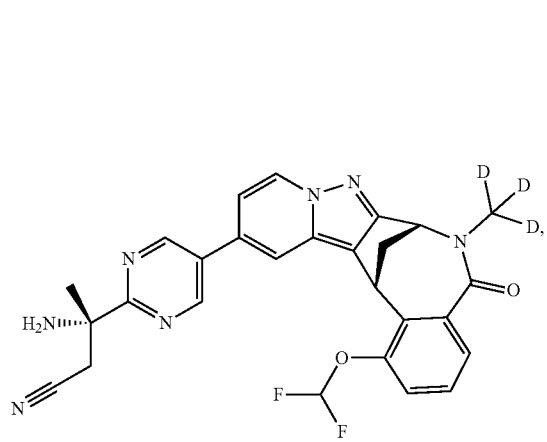
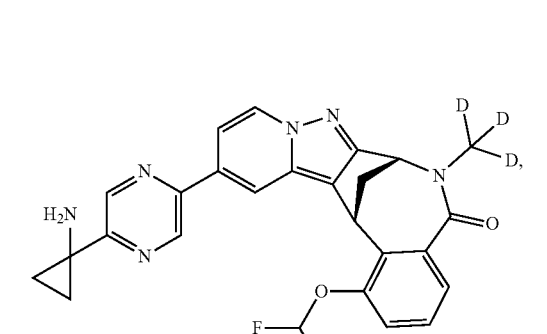
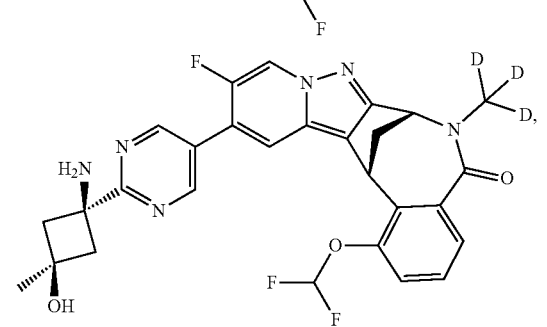
536
-continued
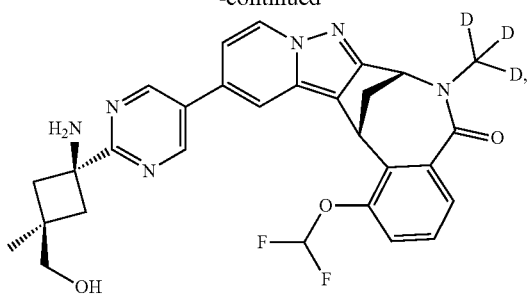
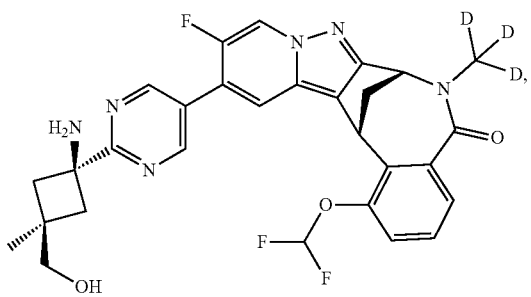
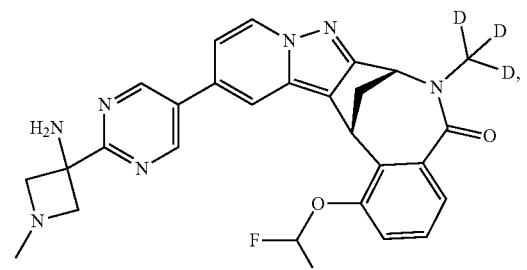
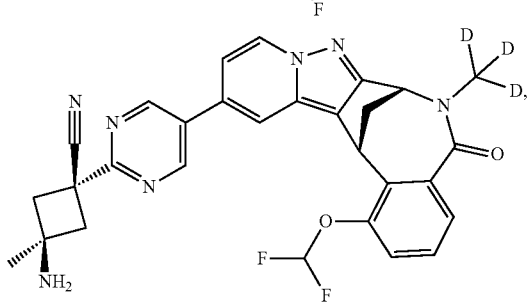
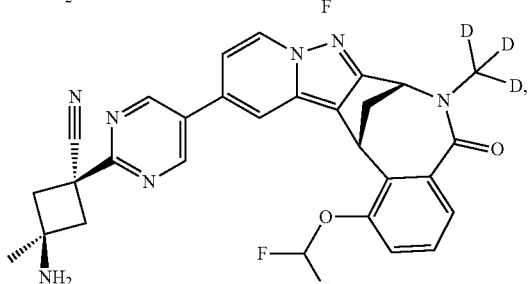
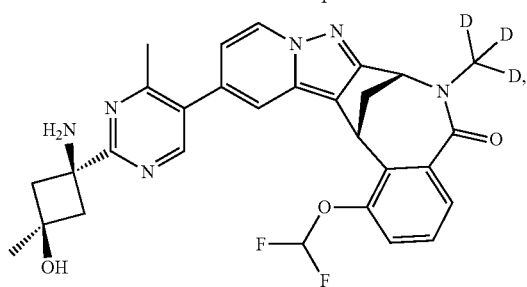

537
-continued
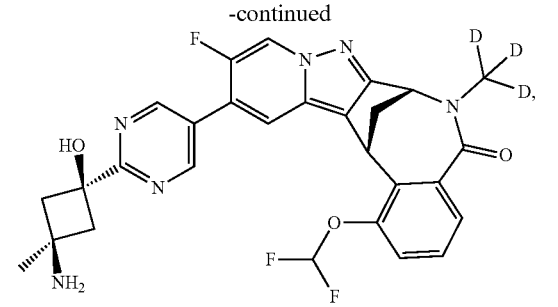
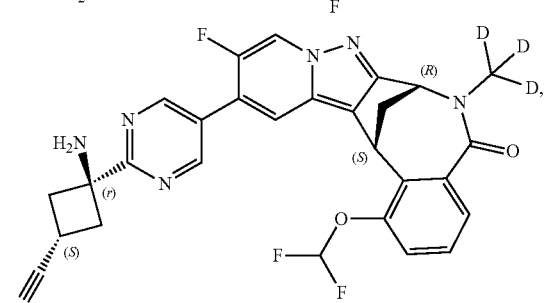
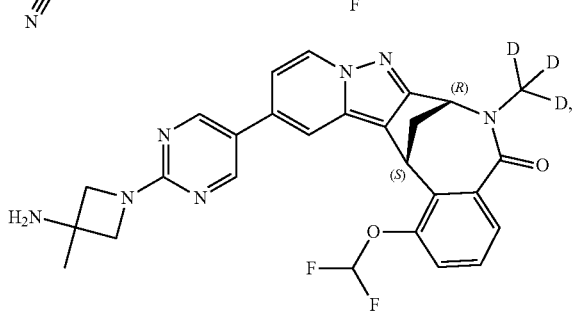
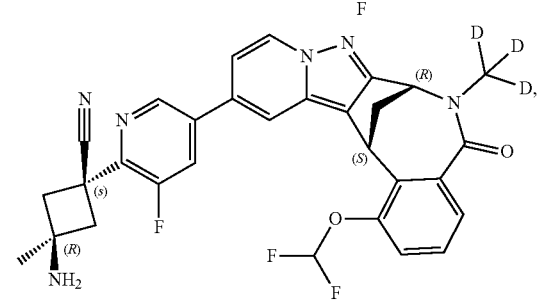
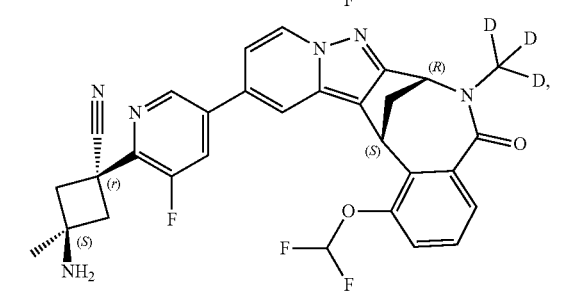
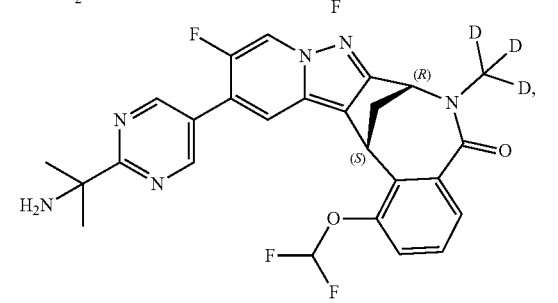
538
-continued
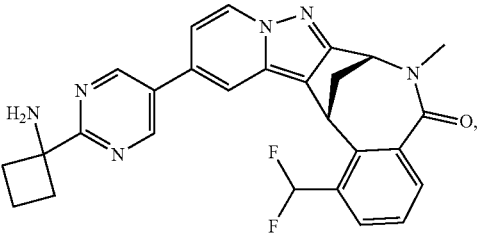
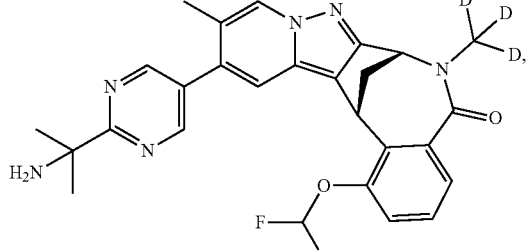
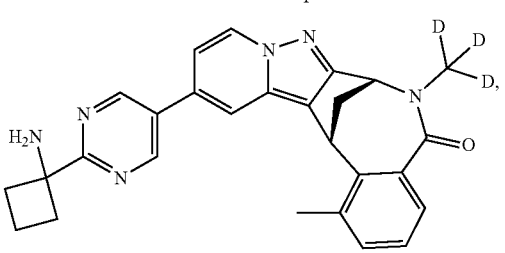
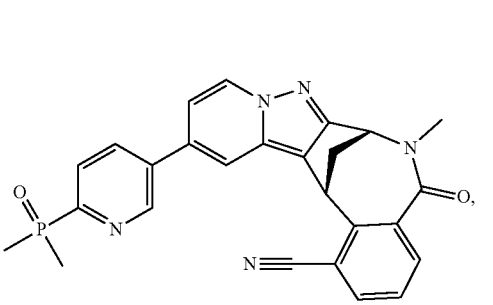
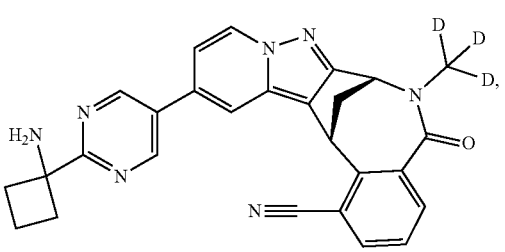
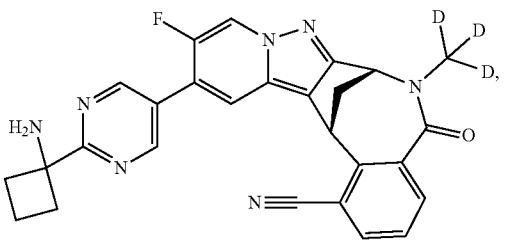

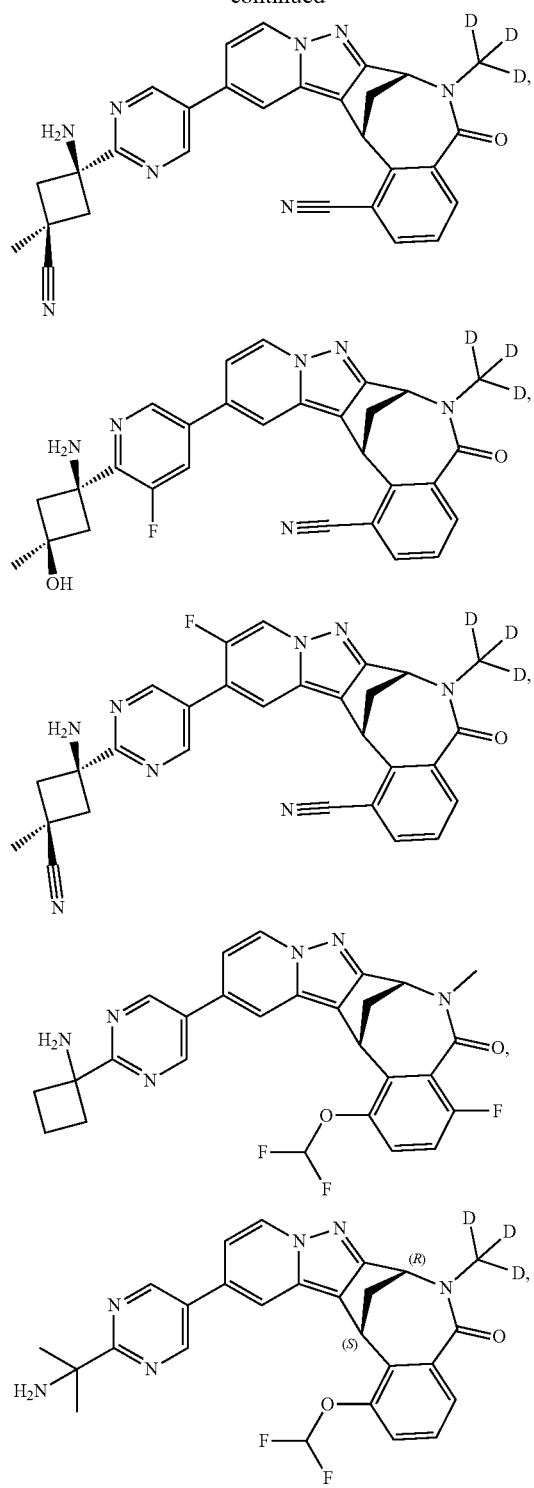

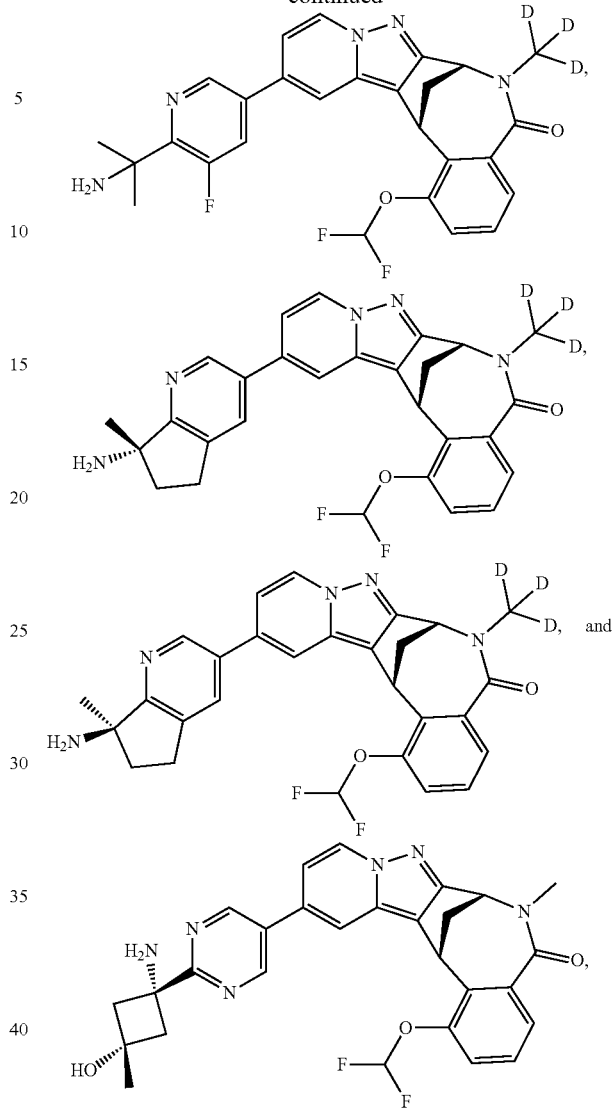

or a pharmaceutically acceptable salt or solvate thereof.

15. A pharmaceutical composition comprising the compound of claim 1, or a pharmaceutically acceptable salt or solvate thereof, and at least one pharmaceutically acceptable excipient.

16. A method for the treatment of an inflammatory disorder, an autoimmune disorder, a neurological disorder, a neuro-degenerative disorder, pain, a nociceptive disorder, a cardiovascular disorder, a metabolic disorder, an ocular disorder, or an oncological disorder, which comprises administering to a patient in need of such treatment an effective amount of a compound of claim 1, or a pharmaceutically acceptable salt or solvate thereof.

* * * * *

UNITED STATES PATENT AND TRADEMARK OFFICE
CERTIFICATE OF CORRECTION

PATENT NO. : 12,410,179 B2  
APPLICATION NO. : 18/812527  
DATED : September 9, 2025  
INVENTOR(S) : Pengyu Yang et al.

Page 1 of 2

It is certified that error appears in the above-identified patent and that said Letters Patent is hereby corrected as shown below:

In the Claims

Column 509, Lines 55-65:
In Claim 14, replace

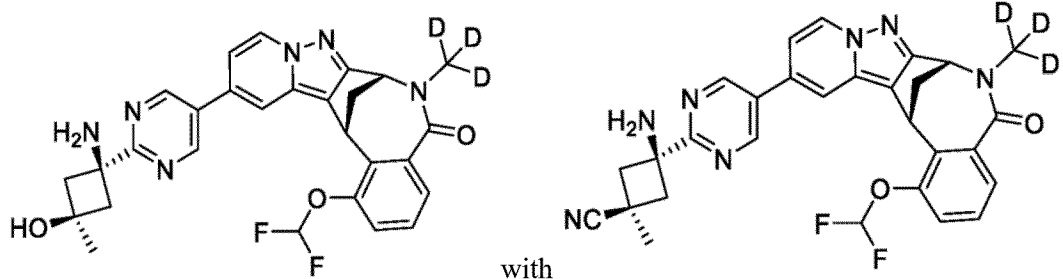

with

Column 510, Lines 12-22:
In Claim 14, replace

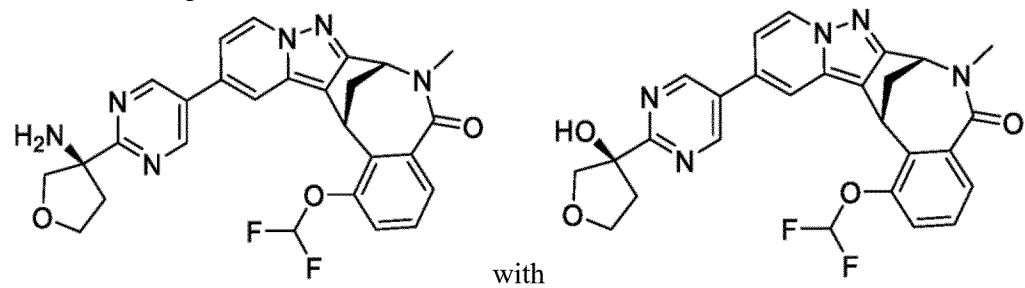

with

Signed and Sealed this
Twenty-eighth Day of October, 2025

John A. Squires
*Director of the United States Patent and Trademark Office*

CERTIFICATE OF CORRECTION (continued)  Page 2 of 2
U.S. Pat. No. 12,410,179 B2

Column 531, Lines 12-22:
In Claim 14, replace

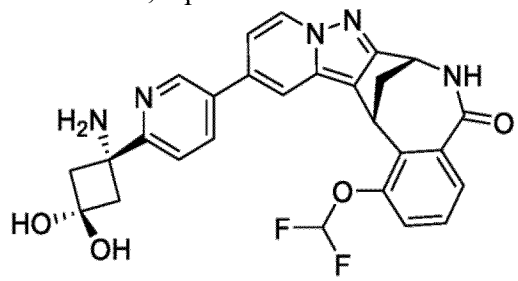

with

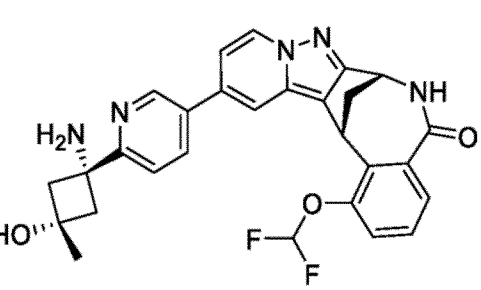

Column 536, Lines 25-35:
In Claim 14, replace

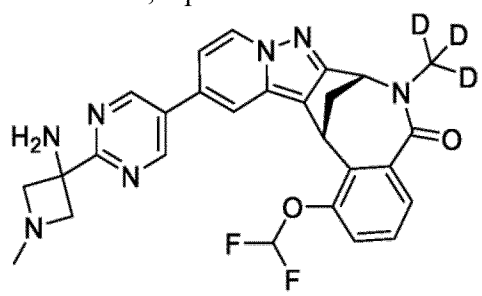

with

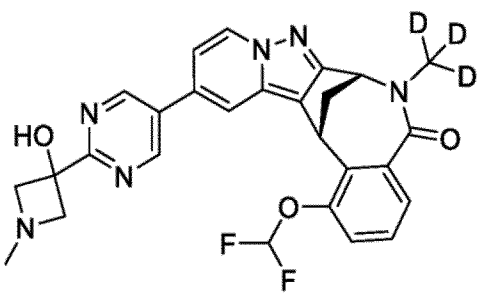

Column 539, Lines 47-57:
In Claim 14, replace

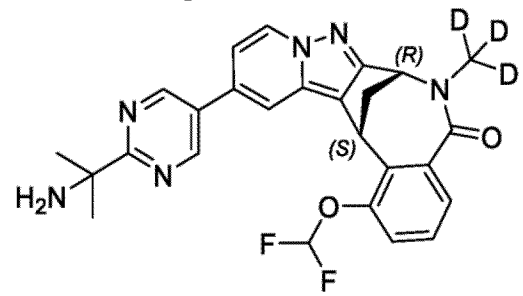

with

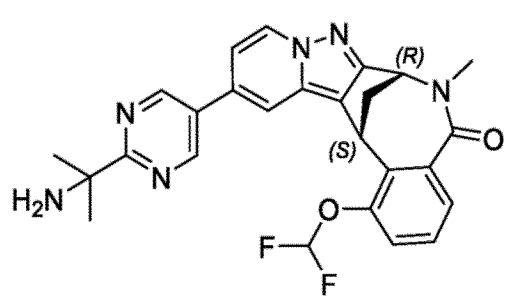

Column 540, Lines 32-42:
In Claim 14, replace

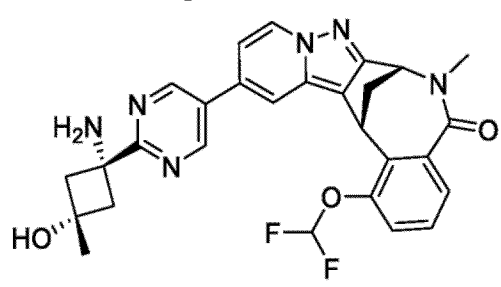

with